US008629274B2

(12) United States Patent  (10) Patent No.: US 8,629,274 B2
Hartman et al.  (45) Date of Patent: Jan. 14, 2014

(54) HEPATITIS B ANTIVIRAL AGENTS

(71) Applicants: George D. Hartman, Radnor, PA (US); Osvaldo A. Flores, Radnor, PA (US)

(72) Inventors: George D. Hartman, Radnor, PA (US); Osvaldo A. Flores, Radnor, PA (US)

(73) Assignee: Novira Therapeutics, Inc., Radnor, PA (US)

( * ) Notice: Subject to any disclaimer, the term of this patent is extended or adjusted under 35 U.S.C. 154(b) by 0 days.

(21) Appl. No.: 13/723,869

(22) Filed: Dec. 21, 2012

(65) Prior Publication Data

US 2013/0251673 A1 Sep. 26, 2013

Related U.S. Application Data

(60) Provisional application No. 61/578,716, filed on Dec. 21, 2011, provisional application No. 61/709,331, filed on Oct. 3, 2012.

(51) Int. Cl.
*C07D 213/00* (2006.01)
*A01N 43/00* (2006.01)
*A61K 31/445* (2006.01)
*A01N 41/06* (2006.01)
*A61K 31/18* (2006.01)
*A01N 37/18* (2006.01)
*A61K 31/165* (2006.01)

(52) U.S. Cl.
USPC ............... 546/1; 514/315; 514/604; 514/618; 514/619

(58) Field of Classification Search
None
See application file for complete search history.

(56) References Cited

U.S. PATENT DOCUMENTS

| 4,569,940 | A | 2/1986 | Watts |
| 5,272,167 | A | 12/1993 | Girijavallabhan et al. |
| 5,607,929 | A | 3/1997 | Nicol |
| 5,919,970 | A | 7/1999 | Song et al. |
| 5,939,423 | A | 8/1999 | Karlin |
| 6,650,463 | B2 | 11/2003 | Obikawa et al. |
| 7,186,735 | B2 | 3/2007 | Strobel et al. |
| 7,338,956 | B2 | 3/2008 | Strobel et al. |
| 7,595,322 | B2 | 9/2009 | Morgan et al. |
| 7,888,373 | B2 | 2/2011 | Morgan et al. |
| 8,101,620 | B2 | 1/2012 | Morgan et al. |
| 8,404,747 | B2 | 3/2013 | Kazantsev et al. |
| 2004/0039009 | A1 | 2/2004 | Jagtap |
| 2005/0009871 | A1 | 1/2005 | Ramesh et al. |
| 2005/0054850 | A1 | 3/2005 | Wu et al. |
| 2005/0239833 | A1 | 10/2005 | Kazantsev et al. |
| 2007/0142440 | A1 | 6/2007 | Burgdorf et al. |
| 2009/0163545 | A1 | 6/2009 | Goldfarb |
| 2011/0009622 | A1 | 1/2011 | Jitsuoka et al. |
| 2011/0275630 | A1 | 11/2011 | Matulenko et al. |

FOREIGN PATENT DOCUMENTS

| CN | 102093320 A | 6/2011 |
| EP | 0742200 B1 | 7/1999 |
| WO | WO 8403281 A1 | 8/1984 |
| WO | WO 9938845 A1 | 8/1999 |
| WO | WO 9948492 A1 | 9/1999 |
| WO | WO 9965906 A1 | 12/1999 |
| WO | WO 0105390 A2 | 1/2001 |
| WO | WO 0119788 A2 | 3/2001 |
| WO | WO 0155121 A1 | 8/2001 |
| WO | WO 0185694 A2 | 11/2001 |
| WO | WO 02051410 A2 | 7/2002 |
| WO | WO 03007955 A2 | 1/2003 |
| WO | WO 03044016 A1 | 5/2003 |
| WO | WO 2004022060 A2 | 3/2004 |
| WO | WO 2004058709 A1 | 7/2004 |
| WO | WO 2004086865 A1 | 10/2004 |
| WO | WO 2004099192 A2 | 11/2004 |
| WO | WO 2005016922 A2 | 2/2005 |
| WO | WO 2004100947 A2 | 3/2005 |
| WO | WO 2005044797 A1 | 5/2005 |
| WO | WO 2005087217 A1 | 9/2005 |
| WO | WO 2005105785 A2 | 11/2005 |
| WO | WO 2005115374 A1 | 12/2005 |
| WO | WO 2006002133 A1 | 1/2006 |
| WO | WO 2006053109 A1 | 5/2006 |
| WO | WO 2006123257 A2 | 11/2006 |
| WO | WO 2006128129 A2 | 11/2006 |
| WO | WO 2006128172 A2 | 11/2006 |
| WO | WO 2007031791 A1 | 3/2007 |
| WO | WO 2008022171 A1 | 2/2008 |
| WO | WO 2008093614 A1 | 8/2008 |
| WO | WO 2008137794 A1 | 11/2008 |
| WO | WO 2009016088 A1 | 2/2009 |
| WO | WO 2009131065 A1 | 10/2009 |
| WO | WO 2010018113 A2 | 2/2010 |
| WO | WO 2010043592 A1 | 4/2010 |
| WO | WO 2010088000 A2 | 8/2010 |
| WO | WO 2010123139 A1 | 10/2010 |
| WO | WO 2011002635 A1 | 1/2011 |

(Continued)

OTHER PUBLICATIONS

Taylor, et al.; A Brain-Permeable Small Molecule Reduces Neuronal Cholesterol by Inhibiting Activity of Sirtuin 2 Deacetylase; ACS Chemical Biology, vol. 6, No. 6 Mar. 3, 2011, pp. 540-546.
Taylor, et al.; Arylsulfonamide CB2 receptor agonists: SAR and optimization of CB2 selectivity; Bioorganic & Medicinal Chemistry Letters, vol. 18, No. 5, Mar. 1, 2008, pp. 1725-1729.
Lambeng, et al.; Arylsulfonamides as a new class of cannabinoid CB1 receptor ligands: Identification of a lead and initial SAR studies; Bioorganic & Medicinal Chemistry Letters, vol. 17, No. 1, Jan. 1, 2007, pp. 272-277.

(Continued)

*Primary Examiner* — James D Anderson
*Assistant Examiner* — Stephanie Springer
(74) *Attorney, Agent, or Firm* — Lathrop & Gage LLP; Brian C. Trinque

(57) ABSTRACT

The present invention includes a method of inhibiting, suppressing or preventing HBV infection in an individual in need thereof, comprising administering to the individual a therapeutically effective amount of at least one compound of the invention.

22 Claims, 1 Drawing Sheet

(56) References Cited

FOREIGN PATENT DOCUMENTS

| WO | WO 2011088015 A1 | 7/2011 |
| WO | WO 2011088561 A1 | 7/2011 |
| WO | WO 2011109237 A2 | 9/2011 |
| WO | WO 2011112191 A1 | 9/2011 |
| WO | WO 2011123609 A1 | 10/2011 |
| WO | WO 2011155898 A1 | 12/2011 |
| WO | WO 2012016133 A2 | 2/2012 |
| WO | WO 2012018635 A2 | 2/2012 |
| WO | WO 2012075235 A1 | 6/2012 |
| WO | WO 2013006394 A1 | 1/2013 |

OTHER PUBLICATIONS

El-Sharief, et al.; Synthesis of different types of chlorinated sulfonamides with expected insecticidal and bactericidal activities; Proceedings of the Indian National Science Academy, Part A: Physical Sciences, vol. 53, No. 1, 1987, pp. 179-188.

Mohamed, et al.; Synthesis of different types of chlorinated sulfonamides with expected insecticidal and antimicrobial activities; Acta Pharmaceutica Jugoslavica, vol. 36, No. 3, 1986, pp. 301-310.

International Search Report for Application No. PCT/US2012/071195 dated Dec. 21, 2012.

Campagna, et al,; Sulfonamoylbenzamides derivatives inhibit the assembly of hepatitis B virus in nucleocapsids; Journal of Virology, vol. 87, No. 12, Jun. 2013, pp. 6931-6942.

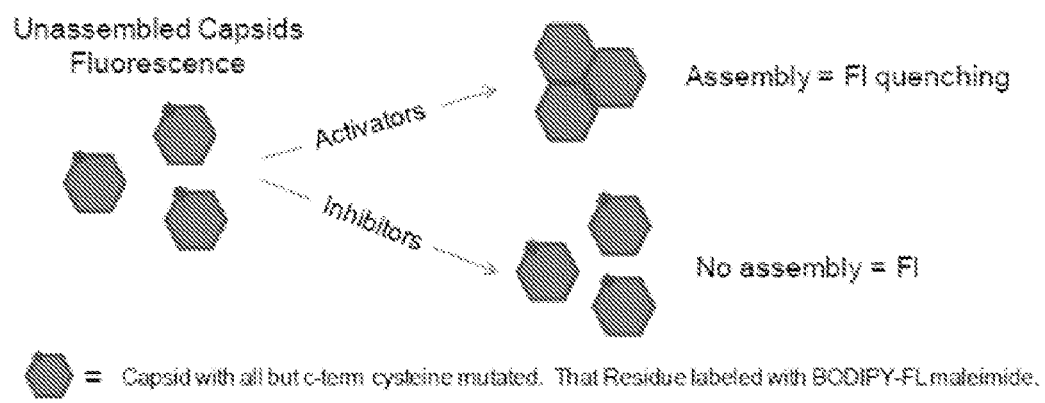
Source: Nature Protocols 2:490-498

HEPATITIS B ANTIVIRAL AGENTS

RELATED APPLICATION

This application claims priority to U.S. Provisional Patent Application Nos. 61/578,716, filed on Dec. 21, 2011 and 61/709,331, filed on Oct. 3, 2012. The entire contents of these applications are herein incorporated by reference in their entirety.

BACKGROUND OF THE INVENTION

Chronic hepatitis B virus (HBV) infection is a significant global health problem, affecting over 5% of the world population (over 350 million people worldwide and 1.25 million individuals in the U.S.).

Despite the availability of a prophylactic HBV vaccine, the burden of chronic HBV infection continues to be a significant unmet worldwide medical problem, due to suboptimal treatment options and sustained rates of new infections in most parts of the developing world. Current treatments do not provide a cure and are limited to only two classes of agents (interferon and nucleoside analogues/inhibitors of the viral polymerase); drug resistance, low efficacy, and tolerability issues limit their impact. The low cure rates of HBV are attributed at least in part to the presence and persistence of covalently closed circular DNA (cccDNA) in the nucleus of infected hepatocytes. However, persistent suppression of HBV DNA slows liver disease progression and helps to prevent hepatocellular carcinoma. Current therapy goals for HBV-infected patients are directed to reducing serum HBV DNA to low or undetectable levels, and to ultimately reducing or preventing the development of cirrhosis and hepatocellular carcinoma.

There is a need in the art for novel therapeutic agents that treat, ameliorate or prevent HBV infection. Administration of these therapeutic agents to an HBV infected patient, either as monotherapy or in combination with other HBV treatments or ancillary treatments, will lead to significantly improved prognosis, diminished progression of the disease, and enhanced seroconversion rates.

SUMMARY OF THE INVENTION

Provided herein are compounds useful for the treatment of HBV infection in man.

Accordingly, in an aspect, provided herein is a compound of formula (I), or a salt, solvate, or N-oxide thereof:

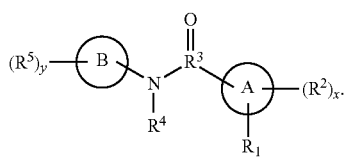

In an embodiment, compounds of formula (I) are of the formula (II):

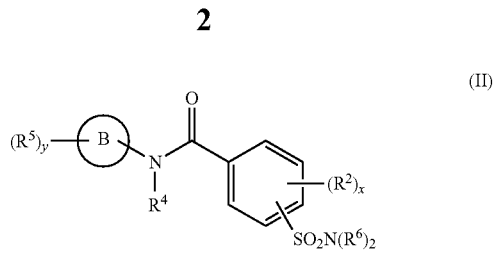

or pharmaceutically acceptable salts thereof.

In an embodiment, compounds of the formula (II) are of the formula (IIa), (IIb), and (IIc).

In another embodiment, the compound of formula (I) has the formula (III):

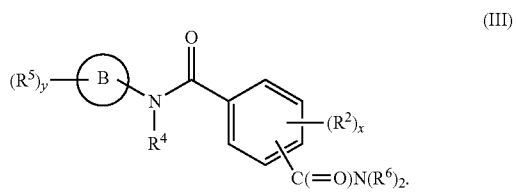

In another aspect, provided herein are compounds having the formula IV:

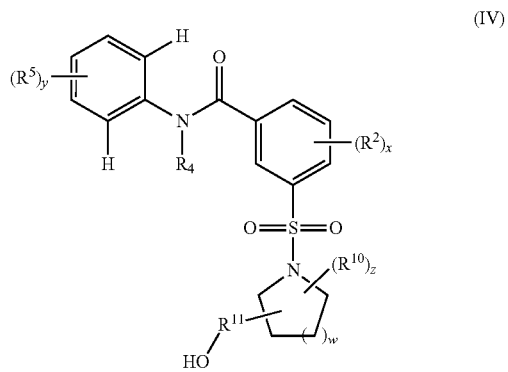

or pharmaceutically acceptable salts thereof.

In an embodiment, compounds of formula IV are of the formula IVa, IVb, and IVc, or pharmaceutically acceptable salts of those compounds.

In another aspect, provided herein are compounds of formula V:

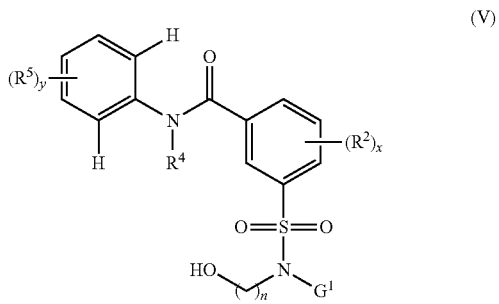

or pharmaceutically acceptable salts thereof.

In still another aspect, provided herein are compounds of formula VI:

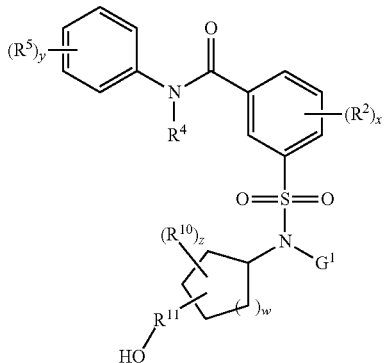

or pharmaceutically acceptable salts thereof.

In an embodiment, compounds of formula VI have the formula VIa or VIb, or pharmaceutically acceptable salts of those compounds, In another aspect, provided herein are compounds of formula VII:

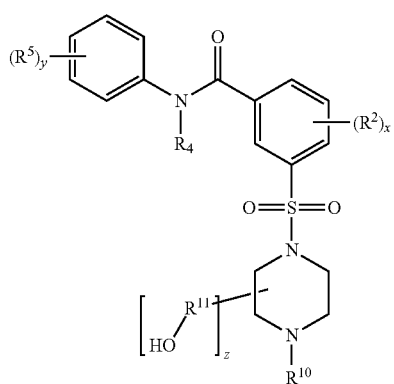

or pharmaceutically acceptable salts thereof.

Also provided herein are compositions comprising a compound provided herein (also referred to herein as "a compound of the invention"). In an embodiment, the composition is pharmaceutical and further comprises at least one pharmaceutically acceptable carrier.

In an aspect, provided herein is a method of treating, eradicating, reducing, slowing, or inhibiting an HBV infection in an individual in need thereof, comprising administering to the individual a therapeutically effective amount of a compound of the invention.

In another aspect, provided herein is a method of reducing the viral load associated with an HBV infection in an individual in need thereof, comprising administering to the individual a therapeutically effective amount of a compound of the invention.

In still another aspect, provided herein is a method of reducing reoccurrence of an HBV infection in an individual in need thereof, comprising administering to the individual a therapeutically effective amount of a compound of the invention.

In yet another aspect, provided herein is a method of reducing an adverse physiological impact of an HBV infection in an individual in need thereof, comprising administering to the individual a therapeutically effective amount of a compound of the invention.

Also provided herein are methods of inducing remission of hepatic injury from an HBV infection in an individual in need thereof, comprising administering to the individual a therapeutically effective amount of a compound of the invention.

In another aspect, provided herein is a method of reducing the physiological impact of long-term antiviral therapy for HBV infection in an individual in need thereof, comprising administering to the individual a therapeutically effective amount of a compound of the invention.

Also provided herein is a method of prophylactically treating an HBV infection in an individual in need thereof, wherein the individual is afflicted with a latent HBV infection, comprising administering to the individual a therapeutically effective amount of a compound of the invention.

In any above methods, the compound can be administered in combination with an additional therapeutic agent. In an embodiment, the additional therapeutic agent selected from the group consisting of a HBV polymerase inhibitor, interferon, viral entry inhibitor, viral maturation inhibitor, literature-described capsid assembly modulator, reverse transcriptase inhibitor, a TLR-agonist, and agents of distinct or unknown mechanism, and a combination thereof.

In another embodiment, the additional therapeutic agent selected from immune modulator or immune stimulator therapies, which includes biological agents belonging to the interferon class, such as interferon alpha 2a or 2b or modified interferons such as pegylated interferon, alpha 2a, alpha 2b, lamda; or TLR modulators such as TLR-7 agonists or TLR-9 agonists, or antiviral agents that block viral entry or maturation or target the HBV polymerase such as nucleoside or nucleotide or non-nucleos(t)ide polymerase inhibitors, and agents of distinct or unknown mechanism including agents that disrupt the function of other essential viral protein(s) or host proteins required for HBV replication or persistence.

In an embodiment of the combination therapy, the reverse transcriptase inhibitor is at least one of Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

In another embodiment of the combination therapy, the TLR-7 agonist is selected from the group consisting of SM360320 (9-benzyl-8-hydroxy-2-(2-methoxyethoxy)adenine) and AZD 8848 (methyl[3-({[3-(6-amino-2-butoxy-8-oxo-7,8-dihydro-9H-purin-9-yl)propyl][3-(4-morpholinyl) propyl]amino}methyl)phenyl]acetate).

In an embodiment of these combination therapies, the compound and the additional therapeutic agent are co-formulated. In another embodiment, the compound and the additional therapeutic agent are co-administered.

In another embodiment of the combination therapy, administering the compound of the invention allows for administering of the additional therapeutic agent at a lower dose or frequency as compared to the administering of the at least one additional therapeutic agent alone that is required to achieve similar results in prophylactically treating an HBV infection in an individual in need thereof.

In another embodiment of the combination therapy, before administering the therapeutically effective amount of the compound of the invention, the individual is known to be refractory to a compound selected from the group consisting of a HBV polymerase inhibitor, interferon, viral entry inhibitor, viral maturation inhibitor, distinct capsid assembly modulator, antiviral compounds of distinct or unknown mechanism, and combination thereof.

In still another embodiment of the method, administering the compound of the invention reduces viral load in the individual to a greater extent compared to the administering of a compound selected from the group consisting of a HBV polymerase inhibitor, interferon, viral entry inhibitor, viral maturation inhibitor, distinct capsid assembly modulator, antiviral compounds of distinct or unknown mechanism, and combination thereof.

In another embodiment, administering of the compound of the invention causes a lower incidence of viral mutation and/or viral resistance than the administering of a compound selected from the group consisting of a HBV polymerase inhibitor, interferon, viral entry inhibitor, viral maturation inhibitor, distinct capsid assembly modulator, antiviral compounds of distinct or unknown mechanism, and combination thereof.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1 is a scheme illustrating the fluorescence quenching in vitro HBV assembly assay. This assay utilizes a mutant C150 HBV capsid protein wherein all wild-type cysteines are mutated to alanines, but a C-terminal cysteine residue is preserved and is labeled with fluorescent BoDIPY-FL dye. The fluorescence signal of HBV C150Bo protein decreases during the capsid assembly process, and thus monitoring the fluorescence of the reaction provides a good readout on the extent of the capsid assembly.

DETAILED DESCRIPTION OF THE INVENTION

Provided herein are compounds that are useful in the treatment and prevention of HBV in man. In a non-limiting aspect, these compounds modulate and/or disrupt HBV assembly by interacting with HBV capsid to afford defective viral particles with greatly reduced virulence. The compounds of the invention have potent antiviral activity, exhibit favorable metabolic, tissue distribution, safety and pharmaceutical profiles, and are suitable for use in man.

The HBV capsid protein plays essential functions during the viral life cycle. HBV capsid/core proteins form metastable viral particles or protein shells that protect the viral genome during intercellular passage, and also play a central role in viral replication processes, including genome encapsidation, genome replication, and virion morphogenesis and egress. Capsid structures also respond to environmental cues to allow un-coating after viral entry. Consistently, proper capsid assembly has been found to be critical for viral infectivity.

The crucial function of HBV capsid proteins imposes stringent evolutionary constraints on the viral capsid protein sequence, leading to the observed low sequence variability and high conservation. Consistently, mutations in HBV capsid that disrupt its assembly are lethal, and mutations that perturb capsid stability severely attenuate viral replication. The more conserved a drug target is, the fewer replication-competent resistance mutations are acquired by patients. Indeed, natural mutations in HBV capsid for chronically infected patients accumulate in only four out of 183 residues in the full length protein. Thus, HBV capsid assembly inhibitors may elicit lower drug resistance emergence rates relative to existing HBV antivirals. Further, drug therapy that targets HBV capsid could be less prone to drug-resistant mutations when compared to drugs that target traditional NA enzyme active sites. Reports describing compounds that bind viral capsids and inhibit replication of HIV, rhinovirus and HBV provide strong pharmacological proof of concept for viral capsid proteins as antiviral drug targets.

In one aspect, the compounds of the invention are useful in HBV treatment by disrupting, accelerating, reducing, delaying and/or inhibiting normal viral capsid assembly and/or disassembly of immature or mature particles, thereby inducing aberrant capsid morphology and leading to antiviral effects such as disruption of virion assembly and/or disassembly, virion maturation, and/or virus egress. In one embodiment, a disruptor of capsid assembly interacts with mature or immature viral capsid to perturb the stability of the capsid, thus affecting assembly and/or disassembly. In another embodiment, a disruptor of capsid assembly perturbs protein folding and/or salt bridges required for stability, function and/or normal morphology of the viral capsid, thereby disrupting and/or accelerating capsid assembly and/or disassembly. In yet another embodiment, the compounds of the invention bind capsid and alter metabolism of cellular polyproteins and precursors, leading to abnormal accumulation of protein monomers and/or oligomers and/or abnormal particles, which causes cellular toxicity and death of infected cells. In another embodiment, the compounds of the invention cause failure of the formation of capsid of optimal stability, affecting efficient uncoating and/or disassembly of viruses (e.g., during infectivity).

In one embodiment, the compounds of the invention disrupt and/or accelerate capsid assembly and/or disassembly when the capsid protein is immature. In another embodiment, the compounds of the invention disrupt and/or accelerate capsid assembly and/or disassembly when the capsid protein is mature. In yet another embodiment, the compounds of the invention disrupt and/or accelerate capsid assembly and/or disassembly during vial infectivity. In yet another embodiment, the disruption and/or acceleration of capsid assembly and/or disassembly attenuates HBV viral infectivity and/or reduces viral load. In yet another embodiment, disruption, acceleration, inhibition, delay and/or reduction of capsid assembly and/or disassembly eradicates the virus from the host organism. In yet another embodiment, eradication of the HBV from a host advantageously obviates the need for chronic long-term therapy and/or reduces the duration of long-term therapy.

In one embodiment, the compounds described herein are suitable for monotherapy and are effective against natural or native HBV strains and against HBV strains resistant to currently known drugs. In another embodiment, the compounds described herein are suitable for use in combination therapy.

In another embodiment, the compounds of the invention can be used in methods of modulating (e.g., inhibit, disrupt or accelerate) the activity of HBV cccDNA. In yet another embodiment, the compounds of the invention can be used in methods of diminishing or preventing the formation of HBV cccDNA.

DEFINITIONS

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e. to at least one) of the grammatical object of the article. By way of example, "an element" means one element or more than one element. Furthermore, use of the term "including" as well as other forms, such as "include", "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "capsid assembly modulator" refers to a compound that disrupts and/or accelerates and/or inhibits and/or hinders and/or delays and or reduces and/or modifies normal capsid assembly (e.g., during maturation) and/or normal capsid disassembly (e.g., during infectivity) and/or perturbs capsid stability, thereby inducing aberrant capsid morphology and function. In one embodiment, a capsid assembly modulator accelerates capsid assembly and/or disassembly, thereby inducing aberrant capsid morphology. In another embodiment, a capsid assembly modulator interacts (e.g. binds at an active site, binds at an allosteric site, modifies and/or hinders folding and the like) with the major capsid assembly protein (CA), thereby disrupting capsid assembly and/or disassembly. In yet another embodiment, a capsid assembly modulator causes a perturbation in structure and/or function of CA (e.g., ability of CA to assemble, disassemble, bind to a substrate, fold into a suitable conformation, or the like), which attenuates viral infectivity and/or is lethal to the virus.

As used herein, the term "literature-described capsid assembly modulator" refers a capsid assembly modulator that is not a compound of the present invention.

As used herein, the term "treatment" or "treating," is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has HBV infection, a symptom of HBV infection or the potential to develop HBV infection, with the purpose to cure, heal, alleviate, relieve, alter, remedy, ameliorate, improve or affect HBV infection, the symptoms of HBV infection or the potential to develop HBV infection. Such treatments may be specifically tailored or modified, based on knowledge obtained from the field of pharmacogenomics.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, subject or individual is human.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof. Examples of such inorganic acids are hydrochloric, hydrobromic, hydroiodic, nitric, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-toluenesulfonic, and mesylic. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Furthermore, pharmaceutically acceptable salts include, by way of non-limiting example, alkaline earth metal salts (e.g., calcium or magnesium), alkali metal salts (e.g., sodium-dependent or potassium), and ammonium salts.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

As used herein, the term "alkyl," by itself or as part of another substituent means, unless otherwise stated, a straight or branched chain hydrocarbon having the number of carbon atoms designated (i.e., $C_{1-6}$ means one to six carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is $(C_1-C_6)$alkyl, particularly ethyl, methyl, isopropyl, isobutyl, n-pentyl, n-hexyl and cyclopropylmethyl.

As used herein, the term "substituted alkyl" means alkyl as defined above, substituted by one, two or three substituents selected from the group consisting of halogen, —OH, alkoxy, —$NH_2$, —$N(CH_3)_2$, —C(=O)OH, trifluoromethyl, —C≡N, —C(=O)O($C_1$-$C_4$)alkyl, —C(=O)$NH_2$, —$SO_2NH_2$, —C(=NH)$NH_2$, and —$NO_2$, preferably containing one or two substituents selected from halogen, —OH, alkoxy, —$NH_2$, trifluoromethyl, —$N(CH_3)_2$, and —C(=O) OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, and —$CH_2CH_2$—S(=O)—$CH_3$. Up to two heteroatoms may be consecutive, such as, for example, —$CH_2$—NH—$OCH_3$, or —$CH_2$—$CH_2$—S—S—$CH_3$. Preferred heteroalkyl groups have 1-10 carbons.

As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are $(C_1-C_3)$alkoxy, particularly ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" refers to a mono cyclic or polycyclic non-aromatic radical, wherein each of the atoms forming the ring (i.e., skeletal atoms) is a carbon atom. In one embodiment, the cycloalkyl group is saturated or partially unsaturated. In another embodiment, the cycloalkyl group is fused with an aromatic ring. Cycloalkyl groups include groups having from 3 to 10 ring atoms. Illustrative examples of cycloalkyl groups include, but are not limited to, the following moieties:

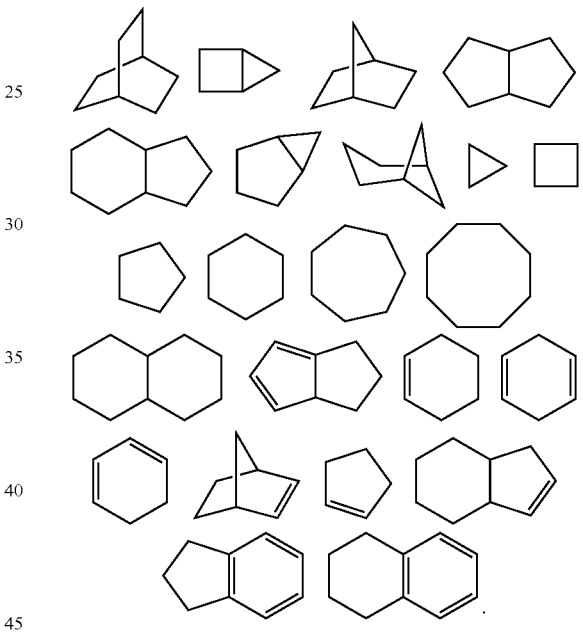

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon carbon double bond or one carbon carbon triple bond.

As used herein, the term "heterocycloalkyl" or "heterocyclyl" refers to a heteroalicyclic group containing one to four ring heteroatoms each selected from O, S and N. In one embodiment, each heterocycloalkyl group has from 4 to 10 atoms in its ring system, with the proviso that the ring of said group does not contain two adjacent O or S atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

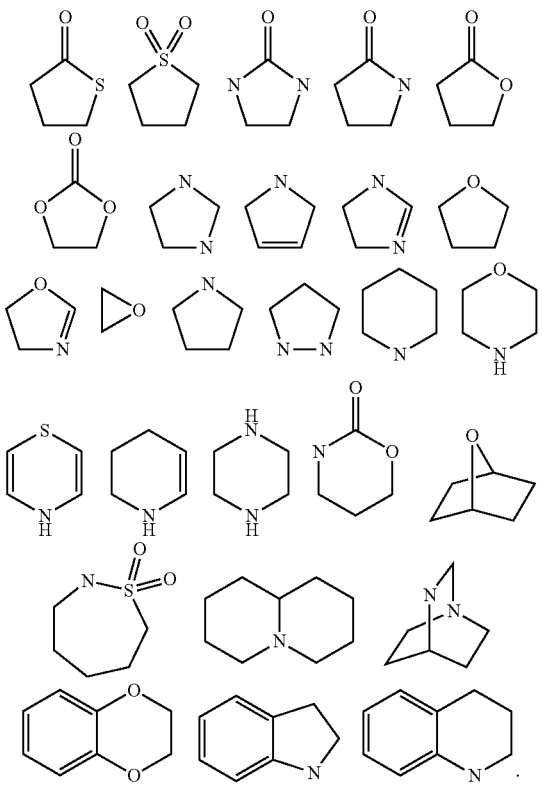

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl. Preferred examples are phenyl and naphthyl, most preferred is phenyl.

As used herein, the term "aryl-($C_1$-$C_3$)alkyl" means a functional group wherein a one- to three-carbon alkylene chain is attached to an aryl group, e.g., —$CH_2CH_2$-phenyl. Preferred is aryl-$CH_2$— and aryl-$CH(CH_3)$—. The term "substituted aryl-($C_1$-$C_3$)alkyl" means an aryl-($C_1$-$C_3$)alkyl functional group in which the aryl group is substituted. Preferred is substituted aryl($CH_2$)—. Similarly, the term "heteroaryl-($C_1$-$C_3$)alkyl" means a functional group wherein a one to three carbon alkylene chain is attached to a heteroaryl group, e.g., —$CH_2CH_2$-pyridyl. Preferred is heteroaryl-($CH_2$)—. The term "substituted heteroaryl-($C_1$-$C_3$)alkyl" means a heteroaryl-($C_1$-$C_3$)alkyl functional group in which the heteroaryl group is substituted. Preferred is substituted heteroaryl-($CH_2$)—.

As used herein, the term "heteroaryl" or "heteroaromatic" refers to a heterocycle having aromatic character. A polycyclic heteroaryl may include one or more rings that are partially saturated. Examples include the following moieties:

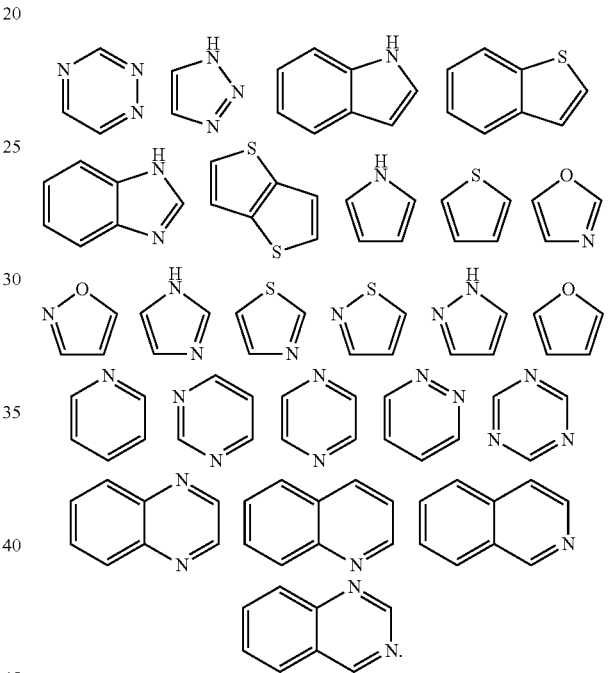

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In one embodiment, the substituents are independently selected from the group consisting of oxo, halogen, —CN, —NH$_2$, —OH, —NH(CH$_3$), —N(CH$_3$)$_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S(=O)$_2$alkyl, —C(=O)NH[substituted or unsubstituted alkyl, or substituted or unsubstituted phenyl], —C(=O)N[H or alkyl]$_2$, —OC(=O)N[substituted or unsubstituted alkyl]$_2$, —NHC(=O)NH[substituted or unsubstituted alkyl, or substituted or unsubstituted phenyl], —NHC(=O)alkyl, —N[substituted or unsubstituted alkyl]C(=O)[substituted or unsubstituted alkyl], —NHC(=O)[substituted or unsubstituted alkyl], —C(OH)[substituted or unsubstituted alkyl]$_2$, and —C(NH$_2$)[substituted or unsubstituted alkyl]$_2$. In another embodiment, by way of example, an optional substituent is selected from oxo, fluorine, chlorine, bromine, iodine, —CN, —NH$_2$, —OH, —NH(CH$_3$), —N(CH$_3$)$_2$, —CH$_3$, —CH$_2$CH$_3$, —CH(CH$_3$)$_2$, —CF$_3$, —CH$_2$CF$_3$, —OCH$_3$, —OCH$_2$CH$_3$, —OCH(CH$_3$)$_2$, —OCF$_3$, —OCH$_2$CF$_3$, —S(=O)$_2$—CH$_3$, —C(=O)NH$_2$, —C(=O)—NHCH$_3$, —NHC(=O)NHCH$_3$, —C(=O)CH$_3$, and —C(=O)OH. In yet one embodiment, the substituents are independently selected from the group consisting of C$_{1-6}$ alkyl, —OH, C$_{1-6}$ alkoxy, halo, amino, acetamido, oxo and nitro. In yet another embodiment, the substituents are independently selected from the group consisting of C$_{1-6}$ alkyl, C$_{1-6}$ alkoxy, halo, acetamido, and nitro. As used herein, where a substituent is an alkyl or alkoxy group, the carbon chain may be branched, straight or cyclic, with straight being preferred.

COMPOUNDS OF THE INVENTION

The present invention relates to the discovery of compounds that are useful in the treatment and prevention of HBV in man. In one aspect, the compounds of the invention are useful in HBV treatment by disrupting, accelerating, reducing delaying and/or inhibiting normal viral capsid assembly and/or disassembly of immature or mature particles, thereby inducing aberrant capsid morphology and leading to antiviral effects such as disruption of virion assembly and/or disassembly and/or virion maturation, and/or virus egress.

The capsid assembly disruptors disclosed herein may be used as monotherapy and/or in novel cross-class combination regimens for treating HBV infection in man. Combination therapy with drugs exhibiting different mechanism of action (MOA) that act at different steps in the virus life cycle may deliver greater efficacy due to additive or synergistic antiviral effects. Clinically evaluated HIV treatment regimens have shown that combination therapy improves the efficacy of viral load reduction, and dramatically reduces emergence of antiviral resistance. Combination therapy for the treatment of Hepatitis C (HCV) virus infection has also resulted in significant improvement in sustained antiviral response and eradication rates. Thus, use of the HBV capsid assembly inhibitors of the present invention in combination with, for example, NA drugs, is likely to deliver a more profound antiviral effect and greater disease eradication rates than current standards of care.

Capsid assembly plays a central role in HBV genome replication. HBV polymerase binds pre-genomic HBV RNA (pgRNA), and pgRNA encapsidation must occur prior to HBV DNA synthesis. Moreover, it is well established that nuclear accumulation of the cccDNA replication intermediate, which is responsible for maintenance of chronic HBV replication in the presence of nucleoside suppressive therapy, requires the capsid for shuttling HBV DNA to the nuclei. Therefore, the HBV capsid assembly disruptors of the invention have the potential to increase HBV eradication rates through synergistic or additive suppression of viral genome replication and to further reduce accumulation of cccDNA when used alone or in combination with existing nucleoside drugs. The capsid assembly disruptors of the present invention may also alter normal core protein degradation, potentially leading to altered MHC-1 antigen presentation, which may in turn increase seroconversion/eradication rates through immuno-stimulatory activity, more effectively clearing infected cells.

In one aspect, drug resistance poses a major threat to current therapies for chronic HBV infection, and cross-class combination therapy is a proven strategy for delaying emergence of drug resistance strains. The capsid assembly disruptors of the present invention can, when administered alone or in combination with other HBV therapy, offer enhanced drug resistant profiles and improved management of chronic HBV.

The compounds useful within the invention may be synthesized using techniques well-known in the art of organic synthesis. The starting materials and intermediates required for the synthesis may be obtained from commercial sources or synthesized according to methods known to those skilled in the art.

In one aspect, the compound of the invention is a compound of formula (I), or a salt, solvate, or N-oxide thereof:

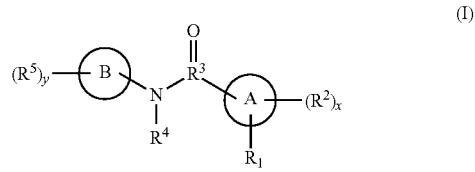

(I)

wherein:
ring A is a monocyclic or bicyclic aryl or a monocyclic or bicyclic heteroaryl ring;
ring B is a monocyclic or bicyclic aryl or a monocyclic or bicyclic heteroaryl ring;
$R^1$ is SO$_2$N(R$^6$)R$^7$ or C(=O)N(H)R$^6$;
$R^2$ and $R^5$ are independently selected at each occurrence from the group consisting of halo, —CN, —NO$_2$, -(L)$_m$-OR$^8$, -(L)$_m$-SR$^9$, -(L)$_m$-S(=O)R$^9$, -(L)$_m$-S(=O)$_2$R$^9$, -(L)$_m$-NHS(=O)$_2$R$^9$, -(L)$_m$-C(=O)R$^9$, -(L)$_m$-OC(=O)R$^9$, -(L)$_m$CO$_2$R$^8$, -(L)$_m$-OCO$_2$R$^8$, -(L)$_m$-CH(R$^8$)$_2$, -(L)$_m$-N(R$^8$)$_2$, -(L)$_m$-C(=O)N(R$^8$)$_2$, -(L)$_m$-OC(=O)N(R$^8$)$_2$, -(L)$_m$-NHC(=O)NH(R$^8$), -(L)$_m$-NHC(=O)R$^9$, -(L)$_m$-NHC(=O)OR$^9$, -(L)$_m$-C(OH)(R$^8$)$_2$, -(L)$_m$C(NH$_2$)(R$^8$)$_2$, —C$_1$-C$_6$ alkyl, —C$_1$-C$_6$ fluoroalkyl and —C$_1$-C$_6$ heteroalkyl;

R$^3$ is C or S(=O);

R$^4$ is H, C$_1$-C$_6$ alkyl, C$_1$-C$_6$ heteroalkyl, —C$_1$-C$_3$alkyl-(C$_3$-C$_6$ cycloalkyl) or -(L)$_m$-aryl, and wherein the alkyl, heteroalkyl, cycloalkyl or aryl group is optionally substituted with 0-5 substituents selected from R$^2$;

R$^6$ and R$^7$ are independently selected from the group consisting of H, C$_1$-C$_6$ alkyl, C$_1$-C$_6$ fluoroalkyl, C$_1$-C$_6$ heteroalkyl, C$_3$-C$_{10}$ cycloalkyl, C$_2$-C$_{10}$ heterocycloalkyl, aryl, heteroaryl, —C$_1$-C$_4$ alkyl-(C$_3$-C$_{10}$ cycloalkyl), —C$_1$-C$_4$ alkyl-(C$_2$-C$_{10}$ heterocycloalkyl), —C$_1$-C$_4$ alkyl-(aryl), or —C$_1$-C$_4$ alkyl(heteroaryl), and wherein the alkyl, heteroalkyl, cycloalkyl, heterocycloalkyl, aryl or heteroaryl group is optionally substituted with 0-5 substituents selected from R$^2$, or the R$^6$ and R$^7$ groups attached to the same N atom are taken together with the N atom to which they are attached to form an optionally substituted C$_2$-C$_{10}$ heterocycloalkyl ring, wherein the ring optionally comprises a moiety selected from O, C=O, S(O)$_m$, NR$^4$S(O)$_m$, NR$^4$(C=O) or N—R$^4$, and wherein the cycloalkyl or heterocycloalkyl ring is optionally substituted with 0-5 substituents selected from R$^2$;

each R$^8$ is independently, at each occurrence, H, C$_1$-C$_6$ alkyl, C$_1$-C$_6$ fluoroalkyl, C$_1$-C$_6$ heteroalkyl, C$_3$-C$_{10}$ cycloalkyl, C$_2$-C$_{10}$ heterocycloalkyl, aryl, heteroaryl, —C$_1$-C$_4$ alkyl-(C$_3$-C$_{10}$ cycloalkyl), —C$_1$-C$_4$ alkyl-(C$_2$-C$_{10}$ heterocycloalkyl), —C$_1$-C$_4$ alkyl-(aryl), or —C$_1$-C$_4$ alkyl(heteroaryl), and wherein the alkyl, heteroalkyl, cycloalkyl, heterocycloalkyl, aryl and heteroaryl is optionally substituted with 0-5 substituents selected from R$^2$; or two R$^8$ groups attached to the same N or C atom are taken together with the N or C atom to which they are attached to form an optionally substituted C$_2$-C$_{10}$ heterocycloalkyl or C$_3$-C$_{10}$ heterocycloalkyl, wherein the ring optionally comprises a moiety selected from O, C=O, S(O)$_m$, NR$^4$S(O)$_m$, NR$^4$(C=O) or N—R$^4$, and wherein the ring is optionally substituted with 0-5 substituents selected from R$^2$;

R$^9$ is C$_1$-C$_6$ alkyl, C$_1$-C$_6$ fluoroalkyl, C$_1$-C$_6$ heteroalkyl, C$_3$-C$_{10}$ cycloalkyl, a C$_2$-C$_{10}$ heterocycloalkyl, aryl, heteroaryl, —C$_1$-C$_4$ alkyl-(C$_3$-C$_{10}$ cycloalkyl), —C$_1$-C$_4$ alkyl-(C$_2$-C$_{10}$ heterocycloalkyl), —C$_1$-C$_4$ alkyl-(aryl), or —C$_1$-C$_4$ alkyl-(heteroaryl), and wherein the alkyl, heteroalkyl, cycloalkyl, heterocycloalkyl, aryl or heteroaryl ring is optionally substituted with 0-5 substituents selected from R$^2$;

each occurrence of x and y is independently selected from the group consisting of 0, 1, 2, 3 and 4;

L is independently, at each occurrence, a bivalent radical selected from —(C$_1$-C$_3$ alkylene)$_m$-, —(C$_3$-C$_7$ cycloalkylene), —(C$_1$-C$_3$ alkylene)$_m$-O—(C$_1$-C$_3$ alkylene)$_m$-, or —(C$_1$-C$_3$ alkylene)$_m$-NH—(C$_1$-C$_3$ alkylene)$_m$-; and, each occurrence of m is independently 0, 1 or 2.

In one embodiment, ring A is a monocyclic aryl ring optionally substituted with 0-3 substituents selected from R$^2$. In another embodiment, ring A is a monocyclic heteroaryl ring optionally substituted with 0-3 substituents selected from R$^2$. In yet another embodiment, ring A is a bicyclic aryl ring optionally substituted with 0-3 substituents selected from R$^2$. In yet another embodiment, ring A is a bicyclic heteroaryl ring optionally substituted with 0-3 substituents selected from R$^2$. In yet another embodiment, ring A is optionally substituted with zero substituents selected from R$^2$.

In one embodiment, ring B is a monocyclic aryl ring optionally substituted with 0-3 substituents selected from R$^5$. In another embodiment, ring B is a monocyclic heteroaryl ring optionally substituted with 0-3 substituents selected from R$^5$. In yet another embodiment, ring B is a bicyclic aryl ring optionally substituted with 0-3 substituents selected from R$^5$. In yet another embodiment, ring B is a bicyclic heteroaryl ring optionally substituted with 0-3 substituents selected from R$^5$. In yet another embodiment, ring B is optionally substituted with zero substituents selected from R$^5$.

In one embodiment, B is phenyl; A is aryl or heteroaryl; R$^1$ is SO$_2$N(R$^6$)R$^7$ or C(=O)N(H)R$^6$.

In one embodiment, A is phenyl; B is phenyl; R$^3$ is C; R$^1$ is SO$_2$N(R$^6$)R$^7$ or C(=O)N(H)R$^6$.

In one embodiment, A is phenyl; B is phenyl; x is zero; R$^3$ is C; R$^1$ is SO$_2$N(R$^6$)R$^7$ or C(=O)N(H)R$^6$; wherein substituents R$^1$ and R$^3$ are in a 1,3-position (or meta-substitution) with respect to each other.

In one embodiment, A is phenyl; B is phenyl; x is zero; R$^3$ is C; R$^1$ is SO$_2$N(R$^6$)R$^7$; wherein substituents R$^1$ and R$^3$ are in a 1,3-position (or meta-substitution) with respect to each other.

In one embodiment, A is phenyl; B is phenyl; x is zero; R$^3$ is C; R$^1$ is C(=O)N(H)R$^6$; wherein substituents R$^1$ and R$^3$ are in a 1,3-position (or meta-substitution) with respect to each other.

In one embodiment, x is zero. In another embodiment, x is 1 and R$^2$ is halo.

In one embodiment, the compound of the invention is a compound of formula (II), or a salt, solvate, or N-oxide thereof:

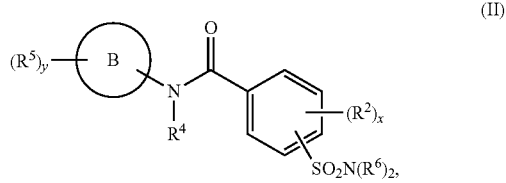

(II)

wherein ring B, R$^5$, y, R$^4$, R$^2$, x, and R$^6$ have the definitions provided above for Formula I.

In an embodiment, the compound of formula (II) is a compound of formula (IIa), or a salt, solvate, or N-oxide thereof:

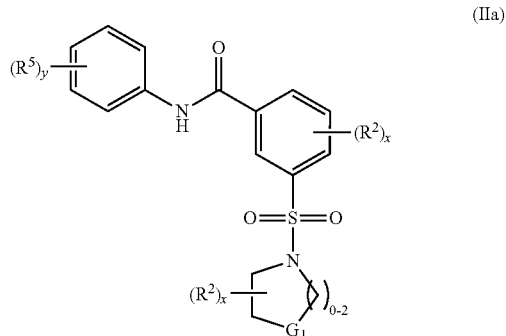

(IIa)

wherein R$^5$, y, R$^2$, individually for each occurrence, and x, individually for each occurrence, have the definitions provided above for Formula I, and G$_1$ is carbon or nitrogen.

In another embodiment, the compound of formula (II) is a compound of formula (IIb), or a salt, solvate, or N-oxide thereof:

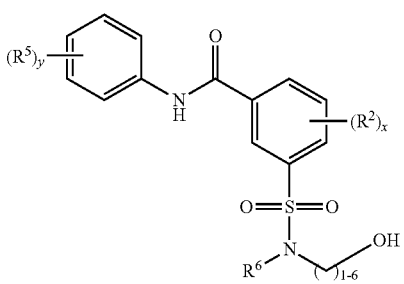

wherein $R^5$, y, $R^2$, x, and $R^6$ have the definitions provided above for Formula I, and wherein the $(CH_2)_{1-6}$ group can optionally be further substituted with OH, $C_{1-6}$ alkyl, or $OC_{1-6}$ alkyl.

In still another embodiment, the compound of formula (II) is a compound of formula (IIc), or a salt, solvate, or N-oxide thereof:

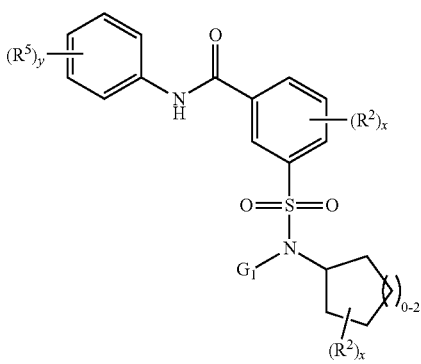

wherein $R^5$, y, $R^2$, individually for each occurrence, and x, individually for each occurrence, have the definitions provided above for Formula I, and $G_1$ is H, alkyl, or substituted alkyl.

In one embodiment, the compound of the invention is a compound of formula (III), or a salt, solvate, or N-oxide thereof:

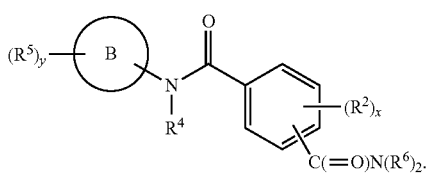

In one aspect, provided herein are compounds having the Formula IV:

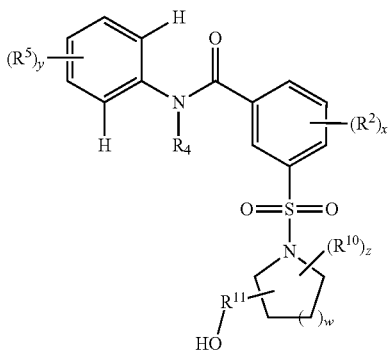

or pharmaceutically acceptable salts thereof;
wherein
$R^4$ is H or $C_1$-$C_6$ alkyl;
wherein each $R^5$ is independently selected at each occurrence from the group consisting of $CH_3$, $C_1$-$C_6$ alkoxy, halo, —CN, —$NO_2$, -(L)$_m$-$SR^9$, -(L)$_m$-S(=O)$R^9$, -(L)$_m$-S(=O)$_2$ $R^9$, -(L)$_m$-NHS(=O)$_2R^9$, -(L)$_m$-C(=O)$R^9$, -(L)$_m$-OC(=O) $R^9$, -(L)$_m$-$CO_2R^8$, -(L)$_m$-$OCO_2R^8$, -(L)$_m$-N($R^8$)$_2$, -(L)$_m$-C (=O)N($R^8$)$_2$, -(L)$_m$-OC(=O)N($R^8$)$_2$, -(L)$_m$-NHC(=O)NH ($R^8$), -(L)$_m$-NHC(=O)$R^9$, -(L)$_m$-NHC(=O)$OR^9$, -(L)$_m$-C (OH)($R^8$)$_2$, -(L)$_m$C(NH$_2$)($R^8$)$_2$, —$C_1$-$C_6$ haloalkyl, —$C_1$-$C_6$ dihaloalkyl and —$C_1$-$C_6$ trihaloalkyl;

L is independently, at each occurrence, a bivalent radical selected from —($C_1$-$C_3$ alkylene)-, —($C_3$-$C_7$ cycloalkylene)-, —($C_1$-$C_3$ alkylene)$_m$-O—($C_1$-$C_3$ alkylene)$_m$-, or —($C_1$-$C_3$ alkylene)$_m$-NH—($C_1$-$C_3$ alkylene)$_m$-;

each $R^8$ is independently, at each occurrence, H, $C_1$-$C_6$ alkyl, —$C_1$-$C_6$ haloalkyl, —$C_1$-$C_6$ dihaloalkyl, —$C_1$-$C_6$ trihaloalkyl, $C_1$-$C_6$ heteroalkyl, $C_3$-$C_{10}$ cycloalkyl, $C_3$-$C_{10}$ heterocycloalkyl, aryl, heteroaryl, —$C_1$-$C_4$ alkyl-($C_3$-$C_{10}$ cycloalkyl), —$C_1$-$C_4$ alkyl-($C_3$-$C_{10}$ heterocycloalkyl), —$C_1$-$C_4$ alkyl-(aryl), or —$C_1$-$C_4$ alkyl(heteroaryl), and wherein the alkyl, heteroalkyl, cycloalkyl, heterocycloalkyl, aryl and heteroaryl is optionally substituted with 1-5 substituents selected from $R^2$;

$R^9$ is $C_1$-$C_6$ alkyl, —$C_1$-$C_6$ haloalkyl, —$C_1$-$C_6$ dihaloalkyl, —$C_1$-$C_6$ trihaloalkyl, $C_1$-$C_6$ heteroalkyl, $C_3$-$C_{10}$ cycloalkyl, a $C_3$-$C_{10}$ heterocycloalkyl, aryl, heteroaryl, —$C_1$-$C_4$ alkyl-($C_3$-$C_{10}$ cycloalkyl), —$C_1$-$C_4$ alkyl-($C_3$-$C_{10}$ heterocycloalkyl), —$C_1$-$C_4$ alkyl-(aryl), or —$C_1$-$C_4$ alkyl-(heteroaryl), and wherein the alkyl, heteroalkyl, cycloalkyl, heterocycloalkyl, aryl or heteroaryl ring is optionally substituted with 0-5 substituents selected from $R^2$;

$R^{10}$ is OH, $C_1$-$C_6$ alkyl, $C_1$-$C_6$ alkyl-OH, —$C_1$-$C_6$ haloalkyl, —$C_1$-$C_6$ dihaloalkyl, —$C_1$-$C_6$ trihaloalkyl, $C_1$-$C_6$ heteroalkyl, $C_3$-$C_{10}$ cycloalkyl, a $C_3$-$C_{10}$ heterocycloalkyl, aryl, heteroaryl, —$C_1$-$C_4$ alkyl-($C_3$-$C_{10}$ cycloalkyl), —$C_1$-$C_4$ alkyl-($C_3$-$C_{10}$ heterocycloalkyl), —$C_1$-$C_4$ alkyl-(aryl), or —$C_1$-$C_4$ alkyl-(heteroaryl), and wherein the alkyl, heteroalkyl, cycloalkyl, heterocycloalkyl, aryl or heteroaryl ring is optionally substituted with 1-5 substituents selected from $R^2$;

$R^{11}$ is a bond or $C_1$-$C_3$ alkylene, wherein the $C_1$-$C_3$ alkylene is optionally substituted with 1-3 substituents selected from $R^2$;

$R^2$ is independently selected at each occurrence from the group consisting of OH, halo, —CN, —$NO_2$, —$C_1$-$C_6$ alkyl, —$C_1$-$C_6$ alkoxy, —$C_1$-$C_6$ haloalkyl, —$C_1$-$C_6$ dihaloalkyl, —$C_1$-$C_6$ trihaloalkyl, —$C_1$-$C_6$ heteroalkyl, and C(O)—$C_1$-$C_6$ alkyl;

w is 0, 1 or 2;

each occurrence of x is independently selected from the group consisting of 0, 1, 2, 3 and 4;

each occurrence of y is independently selected from the group consisting of 1, 2, and 3;

each occurrence of z is independently selected from the group consisting of 0, 1, 2, and 3;

each occurrence of m is independently 0, 1 or 2.

In one embodiment of Formula IV, $R^2$ is independently selected at each occurrence from the group consisting of halo, —CN, —NO$_2$, —C$_1$-C$_6$ alkyl, —C$_1$-C$_6$ alkoxy, —C$_1$-C$_6$ haloalkyl, —C$_1$-C$_6$ dihaloalkyl, —C$_1$-C$_6$ trihaloalkyl, —C$_1$-C$_6$ heteroalkyl, and C(O)—C$_1$-C$_6$ alkyl;

In one embodiment, compounds of Formula IV are of the Formula IVa:

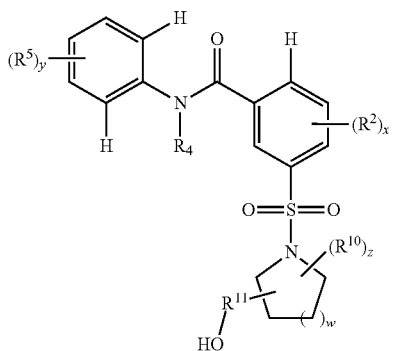

(IVa)

or pharmaceutically acceptable salts thereof.

In embodiments of Formulae IV or IVa, each $R^5$ is independently selected at each occurrence from the group consisting of CH$_3$, C$_1$-C$_6$ alkoxy, halo, —CN, —NO$_2$, —C$_1$-C$_6$ haloalkyl, —C$_1$-C$_6$ dihaloalkyl, —C$_1$-C$_6$ and trihaloalkyl;

$R^{10}$ is OH, halo, C$_1$-C$_6$ alkyl, C$_1$-C$_6$ alkyl-OH, —C$_1$-C$_6$ chloroalkyl, —C$_1$-C$_6$ dichloroalkyl, —C$_1$-C$_6$ trichloroalkyl, —C$_1$-C$_6$ fluoroalkyl, —C$_1$-C$_6$ difluoroalkyl, —C$_1$-C$_6$ trifluoroalkyl, C$_1$-C$_6$ heteroalkyl, C$_3$-C$_{10}$ cycloalkyl, a C$_3$-C$_{10}$ heterocycloalkyl, aryl, heteroaryl, —C$_1$-C$_4$ alkyl-(C$_3$-C$_{10}$ cycloalkyl), —C$_1$-C$_4$ alkyl-(C$_3$-C$_{10}$ heterocycloalkyl), —C$_1$-C$_4$ alkyl-(aryl), or —C$_1$-C$_4$ alkyl-(heteroaryl), and wherein the alkyl, heteroalkyl, cycloalkyl, heterocycloalkyl, aryl or heteroaryl ring is optionally substituted with 1-5 substituents selected from $R^2$;

$R^{11}$ is a bond or C$_1$-C$_3$ alkylene, wherein the C$_1$-C$_3$ alkylene is optionally substituted with 1-3 substituents selected from $R^2$;

$R^2$ is independently selected at each occurrence from the group consisting of halo, —CN, —NO$_2$, —C$_1$-C$_6$ alkyl, —C$_1$-C$_6$ alkoxy, —C$_1$-C$_6$ fluoroalkyl, —C$_1$-C$_6$ heteroalkyl, C(O)—C$_1$-C$_6$ alkyl, and C(O)—C$_1$-C$_6$ alkoxy.

In other embodiments of Formulae IV or IVa, each $R^5$ is independently selected at each occurrence from the group consisting of CH$_3$, C$_1$-C$_6$ alkoxy, halo, fluoromethyl, difluoromethyl, trifluoromethyl, chloromethyl, dichloromethyl, and trichloromethyl;

$R^{10}$ is OH, halo, C$_1$-C$_6$ alkyl, C$_1$-C$_6$ alkyl-OH, C$_1$-C$_6$ fluoroalkyl, C$_1$-C$_6$ difluoroalkyl, C$_1$-C$_6$ trifluoroalkyl, C$_1$-C$_6$ heteroalkyl, C$_3$-C$_{10}$ cycloalkyl, C$_3$-C$_{10}$ heterocycloalkyl, aryl, heteroaryl, —C$_1$-C$_4$ alkyl-(C$_3$-C$_{10}$ cycloalkyl), —C$_1$-C$_4$ alkyl-(C$_3$-C$_{10}$ heterocycloalkyl), —C$_1$-C$_4$ alkyl-(aryl), or —C$_1$-C$_4$ alkyl-(heteroaryl), and wherein the alkyl, heteroalkyl, cycloalkyl, heterocycloalkyl, aryl or heteroaryl ring is optionally substituted with 1-5 substituents selected from $R^2$;

$R^{11}$ is a bond or C$_1$-C$_3$ alkylene;

$R^2$ is independently selected at each occurrence from the group consisting of halo, —CN, —NO$_2$, —C$_1$-C$_6$ alkyl, —C$_1$-C$_6$ alkoxy, —C$_1$-C$_6$ fluoroalkyl, —C$_1$-C$_6$ heteroalkyl, and C(O)—C$_1$-C$_6$ alkyl, and C(O)—C$_1$-C$_6$ alkoxy.

In other embodiments of Formulae IV and IVa, $R^5$ (i.e., $(R^5)_y$) is 3-F, 3-Cl, 3-CH$_3$, 3-CH$_2$F, 3-CHF$_2$, 4-F, 3-CH$_3$-4-F, 3-Cl-4-F, 3-Br-4-F, 3,4,5-trifluoro, 3,4,5-trichloro, or 3-chloro-4,5-difluoro. In another embodiment, w is 1 or 2.

In yet other embodiments of Formulae IV and IVa, $R^{11}$ is a bond or C$_1$-C$_3$ alkylene;

$R^{10}$ is OH, halo, C$_1$-C$_6$ alkyl, C$_1$-C$_6$ alkyl-OH, —C$_1$-C$_6$ chloroalkyl, —C$_1$-C$_6$ dichloroalkyl, —C$_1$-C$_6$ trichloroalkyl, —C$_1$-C$_6$ fluoroalkyl, —C$_1$-C$_6$ difluoroalkyl, —C$_1$-C$_6$ trifluoroalkyl, C$_3$-C$_{10}$ cycloalkyl, C$_3$-C$_{10}$ heterocycloalkyl, or phenyl, wherein the C$_3$-C$_{10}$ cycloalkyl, a C$_3$-C$_{10}$ heterocycloalkyl, or phenyl groups are optionally substituted with 1-5 substituents selected from halo, —C$_1$-C$_6$ alkyl, and —C$_1$-C$_6$ alkoxy; and z is 0 or 1.

In another embodiment, compounds of Formula IV are of the Formula IVb:

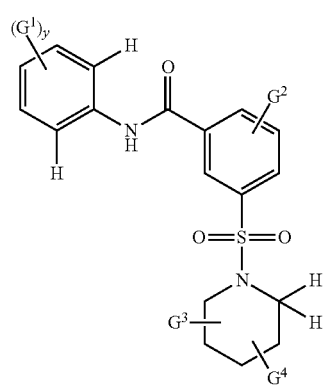

(IVb)

or pharmaceutically acceptable salts thereof;

wherein $G^1$ is independently selected at each occurrence from CH$_3$, OCH$_3$, halo, CF$_3$, CCl$_3$, CH$_2$Cl, CCl$_2$H, CF$_2$H, CH$_2$F, and CF$_3$;

$G^2$ is H, C$_1$-C$_4$ alkyl, or halo;

$G^3$ is OH, CH$_2$OH, or CH$_2$CH$_2$OH;

$G^4$ is H, OH, halo, C$_1$-C$_6$ alkyl, C$_1$-C$_6$ alkyl-OH, —C$_1$-C$_6$ chloroalkyl, —C$_1$-C$_6$ dichloroalkyl, —C$_1$-C$_6$ trichloroalkyl, —C$_1$-C$_6$ fluoroalkyl, —C$_1$-C$_6$ difluoroalkyl, —C$_1$-C$_6$ trifluoroalkyl, or phenyl, wherein the phenyl group is optionally independently substituted with 1-5 substituents selected from halo, —C$_1$-C$_6$ alkyl, and —C$_1$-C$_6$ alkoxy; and y is 1, 2, or 3.

In an embodiment of Formula IVb, wherein $G^1$ is independently selected at each occurrence from halo, CF$_3$, CCl$_3$, CH$_2$Cl, CCl$_2$H, CF$_2$H, CH$_2$F, and CF$_3$;

In another embodiment, compounds of Formula IV are of the Formula IVc:

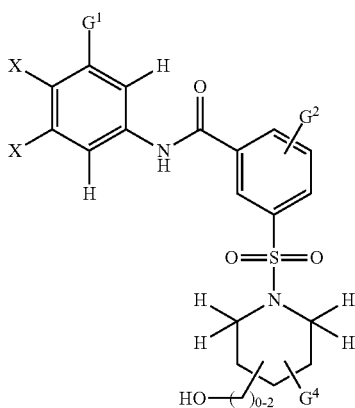

or pharmaceutically acceptable salts thereof;
wherein X is halo;
G¹ is hydrogen or halo;
G² is H, $C_1$-$C_4$ alkyl, or halo; and
G⁴ is H, halo, $C_1$-$C_4$ alkyl, or OH.

In one embodiment of Formula IVc, G² is $C_1$-$C_4$ alkyl or halo, and wherein G² is in the 2, 3, or 4 position of the phenyl ring.

In another aspect, provided herein are compounds of the Formula V:

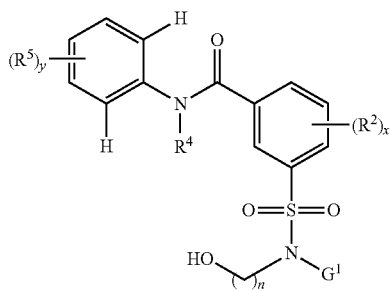

or pharmaceutically acceptable salts thereof;
wherein
$R^4$ is H or $C_1$-$C_6$ alkyl;
$G^1$ is H or $C_1$-$C_6$ alkyl;
wherein each $R^5$ is independently selected at each occurrence from the group consisting of —$C_1$-$C_6$ alkyl, halo, —CN, —$NO_2$, -(L)$_m$-OR⁸, -(L)$_m$-SR⁹, -(L)$_m$-S(=O)R⁹, -(L)$_m$-S(=O)$_2$R⁹, -(L)$_m$-NHS(=O)$_2$R⁹, -(L)$_m$C(=O)R⁹, -(L)$_m$-OC(=O)R⁹, -(L)$_m$CO$_2$R⁸, -(L)$_m$-OCO$_2$R⁸, -(L)$_m$-CH(R⁸)$_2$, -(L)$_m$-N(R⁸)$_2$, -(L)$_m$C(=O)N(R⁸)$_2$, -(L)$_m$-OC(=O)N(R⁸)$_2$, -(L)$_m$-NHC(=O)NH(R⁸), -(L)$_m$-NHC(=O)R⁹, -(L)$_m$-NHC(=O)OR⁹, -(L)$_m$OC(OH)(R⁸)$_2$, -(L)$_m$C(NH$_2$)(R⁸)$_2$, —$C_1$-$C_6$ haloalkyl, —$C_1$-$C_6$ dihaloalkyl and —$C_1$-$C_6$ trihaloalkyl;
L is independently, at each occurrence, a bivalent radical selected from —($C_1$-$C_3$ alkylene)-, —($C_3$-$C_7$ cycloalkylene)-, —($C_1$-$C_3$ alkylene)$_m$-O—($C_1$-$C_3$ alkylene)$_m$-, or —($C_1$-$C_3$ alkylene)$_m$-NH—($C_1$-$C_3$ alkylene)$_m$-;
each $R^8$ is independently, at each occurrence, H, $C_1$-$C_6$ alkyl, —$C_1$-$C_6$ haloalkyl, —$C_1$-$C_6$ dihaloalkyl, —$C_1$-$C_6$ trihaloalkyl, $C_1$-$C_6$ heteroalkyl, $C_3$-$C_{10}$ cycloalkyl, $C_3$-$C_{10}$ heterocycloalkyl, aryl, heteroaryl, —$C_1$-$C_4$ alkyl-($C_3$-$C_{10}$ cycloalkyl), —$C_1$-$C_4$ alkyl-($C_3$-$C_{10}$ heterocycloalkyl), —$C_1$-$C_4$ alkyl-(aryl), or —$C_1$-$C_4$ alkyl(heteroaryl), and wherein the alkyl, heteroalkyl, cycloalkyl, heterocycloalkyl, aryl and heteroaryl is optionally substituted with 1-5 substituents selected from $R^2$;
$R^9$ is $C_1$-$C_6$ alkyl, —$C_1$-$C_6$ haloalkyl, —$C_1$-$C_6$ dihaloalkyl, —$C_1$-$C_6$ trihaloalkyl, $C_1$-$C_6$ heteroalkyl, $C_3$-$C_{10}$ cycloalkyl, a $C_3$-$C_{10}$ heterocycloalkyl, aryl, heteroaryl, —$C_1$-$C_4$ alkyl-($C_3$-$C_{10}$ cycloalkyl), —$C_1$-$C_4$ alkyl-($C_3$-$C_{10}$ heterocycloalkyl), —$C_1$-$C_4$ alkyl-(aryl), or —$C_1$-$C_4$ alkyl-(heteroaryl), and wherein the alkyl, heteroalkyl, cycloalkyl, heterocycloalkyl, aryl or heteroaryl ring is optionally substituted with 1-5 substituents selected from $R^2$;
$R^2$ is independently selected at each occurrence from the group consisting of halo, —OH, —CN, —$NO_2$, —$C_1$-$C_6$ alkyl, —$C_1$-$C_6$ alkoxy, —$C_1$-$C_6$ fluoroalkyl, —$C_1$-$C_6$ heteroalkyl, and C(O)—$C_1$-$C_6$ alkyl;
n is 1, 2, 3, 4, 5, or 6;
each occurrence of x is independently selected from the group consisting of 0, 1, 2, 3 and 4;
each occurrence of y is independently selected from the group consisting of 1, 2, and 3; and
each occurrence of m is independently 0, 1 or 2.

In one embodiment of Formula (V),
each $R^5$ is independently selected at each occurrence from the group consisting of OH, $C_1$-$C_6$ alkyl, $C_1$-$C_6$ alkoxy, halo, —CN, —$NO_2$, $C_1$-$C_6$ chloroalkyl, —$C_1$-$C_6$ dichloroalkyl, —$C_1$-$C_6$ trichloroalkyl, —$C_1$-$C_6$ fluoroalkyl, —$C_1$-$C_6$ difluoroalkyl and —$C_1$-$C_6$ trifluoroalkyl; and
$R^2$ is independently selected at each occurrence from the group consisting of halo, —OH, —CN, —$NO_2$, —$C_1$-$C_6$ alkyl, —$C_1$-$C_6$ alkoxy, —$C_1$-$C_6$ fluoroalkyl, —$C_1$-$C_6$ heteroalkyl, and C(O)—$C_1$-$C_6$ alkyl.

In another embodiment of Formula (V),
each $R^5$ is independently selected at each occurrence from the group consisting of —OH, $C_1$-$C_6$ alkyl, $C_1$-$C_6$ alkoxy, halo, fluoromethyl, difluoromethyl, trifluoromethyl, chloromethyl, dichloromethyl, and trichloromethyl;
$R^2$ is independently selected at each occurrence from the group consisting of —OH, halo, —CN, —$NO_2$, —$C_1$-$C_6$ alkyl, —$C_1$-$C_6$ alkoxy, —$C_1$-$C_6$ fluoroalkyl, —$C_1$-$C_6$ heteroalkyl, and C(O)—$C_1$-$C_6$ alkyl.

In still another embodiment of Formula (V),
each $R^5$ is independently selected at each occurrence from the group consisting of —OH, $C_1$-$C_6$ alkyl, halo, fluoromethyl, difluoromethyl, trifluoromethyl, chloromethyl, dichloromethyl, and trichloromethyl; and
each $R^2$ is independently selected at each occurrence from the group consisting of halo, —$C_1$-$C_6$ alkyl, or —$C_1$-$C_6$ alkoxy.

In another aspect, provided herein are compounds of Formula VI:

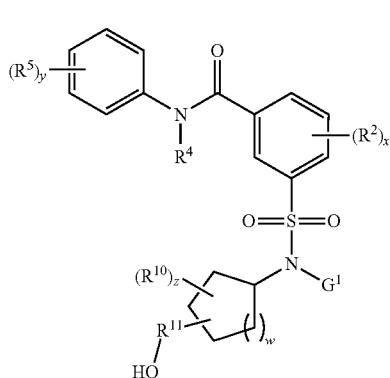

or pharmaceutically acceptable salts thereof;

wherein $R^4$ is H or $C_1$-$C_6$ alkyl;

$G^1$ is H or $C_1$-$C_6$ alkyl;

wherein each $R^5$ is independently selected at each occurrence from the group consisting of $C_1$-$C_6$ alkyl, $C_1$-$C_6$ alkoxy, halo, —CN, —NO$_2$, -(L)$_m$-SR$^9$, -(L)$_m$-S(=O)R$^9$, -(L)$_m$-S(=O)$_2$R$^9$, -(L)$_m$-NHS(=O)$_2$R$^9$, -(L)$_m$-C(=O)R$^9$, -(L)$_m$-OC(=O)R$^9$, -(L)$_m$CO$_2$R$^8$, -(L)$_m$-OCO$_2$R$^8$, -(L)$_m$-CH(R$^8$)$_2$, -(L)$_m$-N(R$^8$)$_2$, -(L)$_m$-C(=O)N(R$^8$)$_2$, -(L)$_m$-OC(=O)N(R$^8$)$_2$, -(L)$_m$-NHC(=O)NH(R$^8$), -(L)$_m$-NHC(=O)R$^9$, -(L)$_m$-NHC(=O)OR$^9$, -(L)$_m$-C(OH)(R$^8$)$_2$, -(L)$_m$C(NH$_2$)(R$^8$)$_2$, —C$_1$-C$_6$ haloalkyl, —C$_1$-C$_6$ dihaloalkyl and —C$_1$-C$_6$ trihaloalkyl;

L is independently, at each occurrence, a bivalent radical selected from —(C$_1$-C$_3$ alkylene)-, —(C$_3$-C$_7$ cycloalkylene)-, —(C$_1$-C$_3$ alkylene)$_m$-O—(C$_1$-C$_3$ alkylene)$_m$-, or —(C$_1$-C$_3$ alkylene)$_m$-NH—(C$_1$-C$_3$ alkylene)$_m$-;

each $R^8$ is independently, at each occurrence, H, $C_1$-$C_6$ alkyl, —C$_1$-C$_6$ haloalkyl, —C$_1$-C$_6$ dihaloalkyl, —C$_1$-C$_6$ trihaloalkyl, C$_1$-C$_6$ heteroalkyl, C$_3$-C$_{10}$ cycloalkyl, C$_3$-C$_{10}$ heterocycloalkyl, aryl, heteroaryl, —C$_1$-C$_4$ alkyl-(C$_3$-C$_{10}$ cycloalkyl), —C$_1$-C$_4$ alkyl-(C$_3$-C$_{10}$ heterocycloalkyl), —C$_1$-C$_4$ alkyl-(aryl), or —C$_1$-C$_4$ alkyl(heteroaryl), and wherein the alkyl, heteroalkyl, cycloalkyl, heterocycloalkyl, aryl and heteroaryl is optionally substituted with 1-5 substituents selected from $R^2$;

$R^9$ is $C_1$-$C_6$ alkyl, —C$_1$-C$_6$ haloalkyl, —C$_1$-C$_6$ dihaloalkyl, —C$_1$-C$_6$ trihaloalkyl, C$_1$-C$_6$ heteroalkyl, C$_3$-C$_{10}$ cycloalkyl, a C$_3$-C$_{10}$ heterocycloalkyl, aryl, heteroaryl, —C$_1$-C$_4$ alkyl-(C$_3$-C$_{10}$ cycloalkyl), —C$_1$-C$_4$ alkyl-(C$_3$-C$_{10}$ heterocycloalkyl), —C$_1$-C$_4$ alkyl-(aryl), or —C$_1$-C$_4$ alkyl-(heteroaryl), and wherein the alkyl, heteroalkyl, cycloalkyl, heterocycloalkyl, aryl or heteroaryl ring is optionally substituted with 1-5 substituents selected from $R^2$;

$R^{10}$ is OH, $C_1$-$C_6$ alkyl, $C_1$-$C_6$ alkyl-OH, $C_1$-$C_6$ fluoroalkyl, C$_1$-C$_6$ heteroalkyl, C$_3$-C$_{10}$ cycloalkyl, a C$_3$-C$_{10}$ heterocycloalkyl, aryl, heteroaryl, —C$_1$-C$_4$ alkyl-(C$_3$-C$_{10}$ cycloalkyl), —C$_1$-C$_4$ alkyl-(C$_3$-C$_{10}$ heterocycloalkyl), —C$_1$-C$_4$ alkyl-(aryl), or —C$_1$-C$_4$ alkyl-(heteroaryl), and wherein the alkyl, heteroalkyl, cycloalkyl, heterocycloalkyl, aryl or heteroaryl ring is optionally substituted with 1-5 substituents selected from $R^2$;

$R^{11}$ is a bond or $C_1$-$C_3$ alkylene, wherein the $C_1$-$C_3$ alkylene is optionally substituted with 1-3 substituents selected from $R^2$;

$R^2$ is independently selected at each occurrence from the group consisting of halo, —CN, —NO$_2$, —C$_1$-C$_6$ alkyl, —C$_1$-C$_6$ alkoxy, —C$_1$-C$_6$ fluoroalkyl, —C$_1$-C$_6$ heteroalkyl, and C(O)—C$_1$-C$_6$ alkyl;

w is 0, 1 or 2;

each occurrence of x is independently selected from the group consisting of 0, 1, 2, 3 and 4;

each occurrence of y is independently selected from the group consisting of 0, 1, 2, 3 and 4;

each occurrence of z is independently selected from the group consisting of 0, 1, 2, and 3;

each occurrence of m is independently 0, 1 or 2.

In certain embodiments of Formula VI, each $R^5$ is independently selected at each occurrence from the group consisting of $C_1$-$C_6$ alkyl, $C_1$-$C_6$ alkoxy, halo, —CN, —NO$_2$, —C$_1$-C$_6$ haloalkyl, —C$_1$-C$_6$ dihaloalkyl, and —C$_1$-C$_6$ trihaloalkyl;

$R^{10}$ is OH, halo, $C_1$-$C_6$ alkyl, $C_1$-$C_6$ alkyl-OH, —C$_1$-C$_6$ haloalkyl, —C$_1$-C$_6$ dihaloalkyl, —C$_1$-C$_6$ trihaloalkyl, C$_1$-C$_6$ heteroalkyl, C$_3$-C$_{10}$ cycloalkyl, a C$_3$-C$_{10}$ heterocycloalkyl, aryl, heteroaryl, —C$_1$-C$_4$ alkyl-(C$_3$-C$_{10}$ cycloalkyl), —C$_1$-C$_4$ alkyl-(C$_3$-C$_{10}$ heterocycloalkyl), —C$_1$-C$_4$ alkyl-(aryl), or —C$_1$-C$_4$ alkyl-(heteroaryl), and wherein the alkyl, heteroalkyl, cycloalkyl, heterocycloalkyl, aryl or heteroaryl ring is optionally substituted with 1-5 substituents selected from $R^2$;

$R^{11}$ is a bond or $C_1$-$C_3$ alkylene, wherein the $C_1$-$C_3$ alkylene is optionally substituted with 1-3 substituents selected from $R^2$;

$R^2$ is independently selected at each occurrence from the group consisting of halo, —CN, —NO$_2$, —C$_1$-C$_6$ alkyl, —C$_1$-C$_6$ alkoxy, —C$_1$-C$_6$ fluoroalkyl, —C$_1$-C$_6$ heteroalkyl, C(O)—C$_1$-C$_6$ alkyl, and C(O)—C$_1$-C$_6$ alkoxy.

In another embodiment of Formula VI, each $R^5$ is independently selected at each occurrence from the group consisting of $C_1$-$C_6$ alkyl, $C_1$-$C_6$ alkoxy, halo, fluoromethyl, difluoromethyl, trifluoromethyl, chloromethyl, dichloromethyl, and trichloromethyl;

$R^{10}$ is OH, halo, $C_1$-$C_6$ alkyl, $C_1$-$C_6$ alkyl-OH, $C_1$-$C_6$ fluoroalkyl, $C_1$-$C_6$ difluoroalkyl, $C_1$-$C_6$ trifluoroalkyl, $C_1$-$C_6$ heteroalkyl, C$_3$-C$_{10}$ cycloalkyl, a C$_3$-C$_{10}$ heterocycloalkyl, aryl, heteroaryl, —C$_1$-C$_4$ alkyl-(C$_3$-C$_{10}$ cycloalkyl), —C$_1$-C$_4$ alkyl-(C$_3$-C$_{10}$ heterocycloalkyl), —C$_1$-C$_4$ alkyl-(aryl), or —C$_1$-C$_4$ alkyl-(heteroaryl), and wherein the alkyl, heteroalkyl, cycloalkyl, heterocycloalkyl, aryl or heteroaryl ring is optionally substituted with 1-5 substituents selected from $R^2$;

$R^{11}$ is a bond or $C_1$-$C_3$ alkylene;

$R^2$ is independently selected at each occurrence from the group consisting of halo, —CN, —NO$_2$, —C$_1$-C$_6$ alkyl, —C$_1$-C$_6$ alkoxy, —C$_1$-C$_6$ fluoroalkyl, —C$_1$-C$_6$ heteroalkyl, and C(O)—C$_1$-C$_6$ alkyl, and C(O)—C$_1$-C$_6$ alkoxy.

In other embodiments of Formula VI, $R^5$ is 3-F, 3-Cl, 3-CH$_3$, 3-CH$_2$F, 3-CHF$_2$, 4-F, 3-CH$_3$-4-F, 3-Cl-4-F, 3-Br-4-F, 3,4,5-trifluoro, 3,4,5-trichloro, or 3-chloro-4,5-difluoro. In another embodiment, w is 1 or 2.

In still another embodiment of Formula VI, $R^{11}$ is a bond or $C_1$-$C_3$ alkylene;

$R^{10}$ is OH, halo, $C_1$-$C_6$ alkyl, $C_1$-$C_6$ alkyl-OH, —C$_1$-C$_6$ chloroalkyl, —C$_1$-C$_6$ dichloroalkyl, —C$_1$-C$_6$ trichloroalkyl, —C$_1$-C$_6$ fluoroalkyl, —C$_1$-C$_6$ difluoroalkyl, —C$_1$-C$_6$ trifluoroalkyl, C$_3$-C$_{10}$ cycloalkyl, a C$_3$-C$_{10}$ heterocycloalkyl, or phenyl, wherein the C$_3$-C$_{10}$ cycloalkyl, a C$_3$-C$_{10}$ heterocycloalkyl, or phenyl groups are optionally substituted with 1-5 substituents selected from halo, —C$_1$-C$_6$ alkyl, and —C$_1$-C$_6$ alkoxy; and z is 0 or 1.

In an embodiment, compounds of Formula VI are of the Formula VIa:

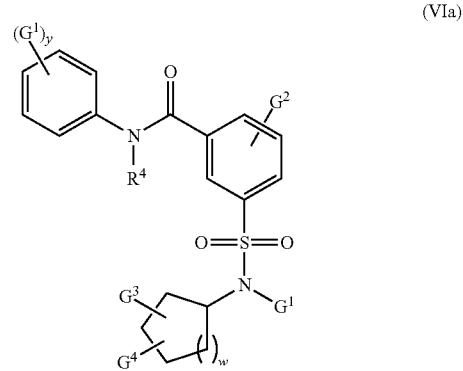

(VIa)

or pharmaceutically acceptable salts thereof;

wherein G¹ is independently selected at each occurrence from CH₃, OCH₃, halo, CF₃, CCl₃, CH₂Cl, CCl₂H, CF₂H, CH₂F, and CF₃;
G² is H, C₁-C₄ alkyl, or halo;
G³ is OH, CH₂OH, or CH₂CH₂OH;
G⁴ is H, OH, halo, C₁-C₆ alkyl, C₁-C₆ alkyl-OH, —C₁-C₆ chloroalkyl, —C₁-C₆ dichloroalkyl, —C₁-C₆ trichloroalkyl, —C₁-C₆ fluoroalkyl, —C₁-C₆ difluoroalkyl, —C₁-C₆ trifluoroalkyl, or phenyl, wherein the phenyl group is optionally independently substituted with 1-5 substituents selected from halo, —C₁-C₆ alkyl, and —C₁-C₆ alkoxy; and
y is 1, 2, or 3.

In an embodiment, compounds of Formula VI are of the Formula VIaa:

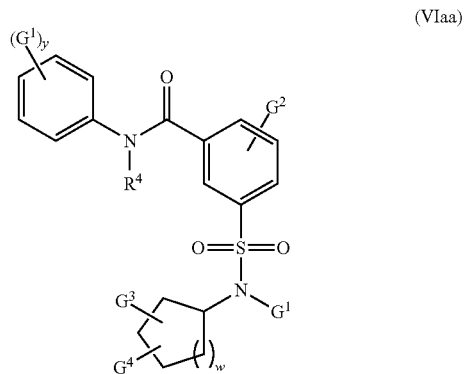

(VIaa)

or pharmaceutically acceptable salts thereof;
wherein G¹ is independently selected at each occurrence from C₁-C₆alkyl, OC₁-C₆alkyl, halo, CF₃, CCl₃, CH₂Cl, CCl₂H, CF₂H, CH₂F, and CF₃;
G² is H, C₁-C₄ alkyl, or halo;
G³ is OH, CH₂OH, or CH₂CH₂OH;
G⁴ is H, OH, halo, C₁-C₆ alkyl, C₁-C₆ alkyl-OH, —C₁-C₆ chloroalkyl, —C₁-C₆ dichloroalkyl, —C₁-C₆ trichloroalkyl, —C₁-C₆ fluoroalkyl, —C₁-C₆ difluoroalkyl, —C₁-C₆ trifluoroalkyl, or phenyl, wherein the phenyl group is optionally independently substituted with 1-5 substituents selected from halo, —C₁-C₆ alkyl, and —C₁-C₆ alkoxy; and
y is 1, 2, or 3.

In another embodiment, compounds of Formula VI are of the Formula VIb:

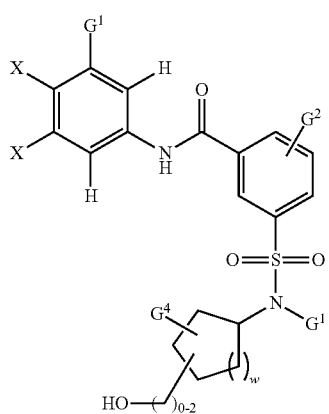

(VIb)

or pharmaceutically acceptable salts thereof;
wherein X is halo;
G¹ is hydrogen or halo;
G² is H, C₁-C₄ alkyl, or halo; and
G⁴ is H, halo, C₁-C₄ alkyl, or OH.

In another aspect, provided herein is a compound of Formula VII:

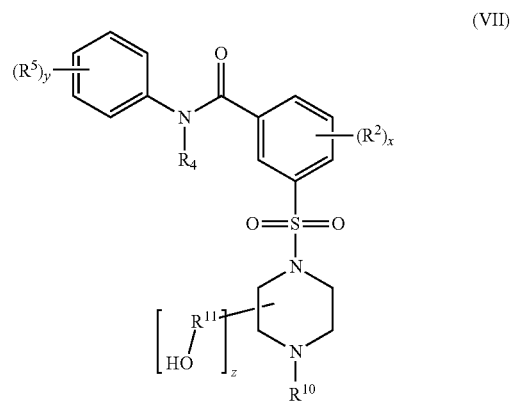

(VII)

or pharmaceutically acceptable salts thereof;
wherein
R⁴ is H or C₁-C₆ alkyl;
wherein each R⁵ is independently selected at each occurrence from the group consisting of C₁-C₆ alkyl, C₁-C₆ alkoxy, halo, —CN, —NO₂, -(L)ₘ-SR⁹, -(L)ₘ-S(=O)R⁹, -(L)ₘ-S(=O)₂R⁹, -(L)ₘ-NHS(=O)₂R⁹, -(L)ₘ-C(=O)R⁹, -(L)ₘ-OC(=O)R⁹, -(L)ₘCO₂R⁸, -(L)ₘ-OCO₂R⁸, -(L)ₘ-CH(R⁸)₂, -(L)ₘ-N(R⁸)₂, -(L)ₘ-C(=O)N(R⁸)₂, -(L)ₘ-OC(=O)N(R⁸)₂, -(L)ₘ-NHC(=O)NH(R⁸), -(L)ₘ-NHC(=O)R⁹, -(L)ₘ-NHC(=O)OR⁹, -(L)ₘ-C(OH)(R⁸)₂, -(L)ₘC(NH₂)(R⁸)₂, —C₁-C₆ haloalkyl, —C₁-C₆ dihaloalkyl and —C₁-C₆ trihaloalkyl;
L is independently, at each occurrence, a bivalent radical selected from —(C₁-C₃ alkylene)-, —(C₃-C₇ cycloalkylene)-, —(C₁-C₃ alkylene)ₘ-O—(C₁-C₃ alkylene)ₘ-, or —(C₁-C₃ alkylene)ₘ-NH—(C₁-C₃ alkylene)ₘ-;
each R⁸ is independently, at each occurrence, H, C₁-C₆ alkyl, —C₁-C₆ haloalkyl, —C₁-C₆ dihaloalkyl, —C₁-C₆ trihaloalkyl, C₁-C₆ heteroalkyl, C₃-C₁₀ cycloalkyl, C₃-C₁₀ heterocycloalkyl, aryl, heteroaryl, —C₁-C₄ alkyl-(C₃-C₁₀ cycloalkyl), —C₁-C₄ alkyl-(C₃-C₁₀ heterocycloalkyl), —C₁-C₄ alkyl-(aryl), or —C₁-C₄ alkyl(heteroaryl), and wherein the alkyl, heteroalkyl, cycloalkyl, heterocycloalkyl, aryl and heteroaryl is optionally substituted with 1-5 substituents selected from R²;
R⁹ is C₁-C₆ alkyl, —C₁-C₆ haloalkyl, —C₁-C₆ dihaloalkyl, —C₁-C₆ trihaloalkyl, C₁-C₆ heteroalkyl, C₃-C₁₀ cycloalkyl, a C₃-C₁₀ heterocycloalkyl, aryl, heteroaryl, —C₁-C₄ alkyl-(C₃-C₁₀ cycloalkyl), —C₁-C₄ alkyl-(C₃-C₁₀ heterocycloalkyl), —C₁-C₄ alkyl-(aryl), or —C₁-C₄ alkyl-(heteroaryl), and wherein the alkyl, heteroalkyl, cycloalkyl, heterocycloalkyl, aryl or heteroaryl ring is optionally substituted with 1-5 substituents selected from R²;
R¹⁰ is H, C₁-C₆ alkyl, -(L)ₘ-C(=O)C₁-C₆ alkyl, -(L)ₘ-C(=O)C₃-C₁₀ cycloalkyl, -(L)ₘ-C(=O)OC₁-C₆ alkyl, -(L)ₘ-C(=O)OC₃-C₁₀ cycloalkyl wherein the alkyl or cycloalkyl groups are optionally substituted with halo, —C₁-C₆ haloalkyl, —C₁-C₆ dihaloalkyl, or —C₁-C₆ trihaloalkyl;
R¹¹ is a bond or C₁-C₃ alkylene, wherein the C₁-C₃ alkylene is optionally substituted with 0-3 substituents selected from R²;

$R^2$ is independently selected at each occurrence from the group consisting of halo, —CN, —NO$_2$, —C$_1$-C$_6$ alkyl, —C$_1$-C$_6$ alkoxy, —C$_1$-C$_6$ fluoroalkyl, —C$_1$-C$_6$ heteroalkyl, and C(O)—C$_1$-C$_6$ alkyl;

each occurrence of x is independently selected from the group consisting of 0, 1, 2, 3, or 4;

each occurrence of y is independently selected from the group consisting of 1, 2, and 3;

z is 0 or 1; and each occurrence of m is independently 0, 1 or 2.

In one embodiment of Formula VII, each $R^5$ is independently selected at each occurrence from the group consisting of C$_1$-C$_6$ alkyl, C$_1$-C$_6$ alkoxy, halo, —CN, —NO$_2$, —C$_1$-C$_6$haloalkyl, —C$_1$-C$_6$ dihaloalkyl, and —C$_1$-C$_6$ trihaloalkyl;

$R^{11}$ is a bond or C$_1$-C$_3$ alkylene, wherein the C$_1$-C$_3$ alkylene is optionally substituted with 0-3 substituents selected from $R^2$;

$R^2$ is independently selected at each occurrence from the group consisting of halo, —CN, —NO$_2$, —C$_1$-C$_6$ alkyl, —C$_1$-C$_6$ alkoxy, —C$_1$-C$_6$ fluoroalkyl, —C$_1$-C$_6$ heteroalkyl, C(O)—C$_1$-C$_6$ alkyl, and C(O)—C$_1$-C$_6$ alkoxy.

In an embodiment of Formula VII, each $R^5$ is independently selected at each occurrence from the group consisting of C$_1$-C$_6$ alkyl, C$_1$-C$_6$ alkoxy, halo, fluoromethyl, difluoromethyl, trifluoromethyl, chloromethyl, dichloromethyl, and trichloromethyl;

$R^{11}$ is a bond or C$_1$-C$_3$ alkylene;

$R^2$ is independently selected at each occurrence from the group consisting of halo, —CN, —NO$_2$, —C$_1$-C$_6$ alkyl, —C$_1$-C$_6$ alkoxy, —C$_1$-C$_6$ fluoroalkyl, —C$_1$-C$_6$ heteroalkyl, and C(O)—C$_1$-C$_6$ alkyl, and C(O)—C$_1$-C$_6$ alkoxy.

In an embodiment of Formula VII, $R^5$ is 3-F, 3-Cl, 3-CH$_3$, 3-CH$_2$F, 3-CHF$_2$, 4-F, 3-CH$_3$-4-F, 3-Cl-4-F, 3-Br-4-F, 3,4,5-trifluoro, 3,4,5-trichloro, or 3-chloro-4,5-difluoro. In another embodiment, $R^2$ is H, C$_1$-C$_4$ alkyl, or halo. In still another embodiment, $R^{10}$ is C(=O)C$_3$-C$_{10}$ cycloalkyl, wherein the or cycloalkyl group is optionally substituted with halo, —C$_1$-C$_6$ haloalkyl, —C$_1$-C$_6$ dihaloalkyl, or —C$_1$-C$_6$ trihaloalkyl.

It will be appreciated that the description of the present invention herein should be construed in congruity with the laws and principals of chemical bonding. In some instances it may be necessary to remove a hydrogen atom in order to accommodate a substitutent at any given location.

It is noted for the generic structures described herein that rings that are substituted by two or more variables (R groups, G groups, etc.) can indicate, for example, either viscinal (e.g., compounds 960D1 and 960D2) or geminal (e.g., compound 916) substitution patterns.

Preferred embodiments of Formulas I-VII, including pharmaceutically acceptable salts thereof, as well as enantiomers, stereoisomers, rotamers, tautomers, diastereomers, atropisomers or racemates thereof, and are shown below in Table 1 and are also considered to be "compounds of the invention." (Some compounds of Table 1 do not include hydrogens on hydroxyl groups; it is understood that "–0" indicates a hydroxyl substituent at these positions.)

Synthetic method codes refer to the synthesis methodologies provided in the experimental section. For example, "A19B03C15" refers the use of intermediate A19 for region A, intermediate B03 for region B, and intermediate C15 for region C, and "GA" refers to general synthesis procedures G and A.

TABLE 1

| Structure MS(M + H)$^+$ Synthetic method | Cmp. ID |
|---|---|
| [structure of 2-fluorophenyl benzamide with sulfonyl piperidine] 363 GB | 001 A01B01C01 |
| [structure of 3-fluorophenyl benzamide with sulfonyl piperidine] 363 GB | 002 A01B01C02 |
| [structure of 3-chlorophenyl benzamide with sulfonyl piperidine] 379/381 GB | 005 A01B01C05 |

TABLE 1-continued
| Structure MS(M + H)+ Synthetic method | Cmp. ID |
|---|---|
| 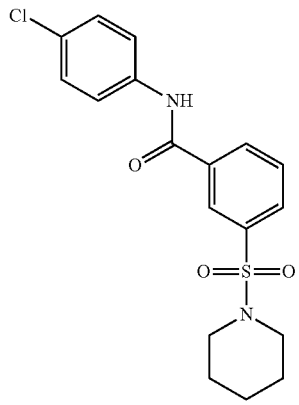<br>379/381<br>GB<br>A01B01C06 | 006 |
| 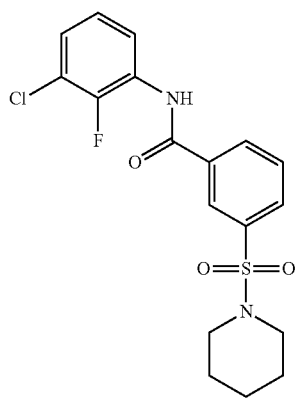<br>397/399<br>GB<br>A01B01C13<br>¹H NMR (400 MHz, DMSO-d6) δ 10.60 (br, 1H), 8.29 (m, 2H), 7.94 (m, 1 H), 7.81 (m, 1H), 7.52 (m, 1H), 7.50 (m, 1H), 7.22(m, 1H), 2.92(m, 4H), 1.53(m, 4H), 1.35(m, 2H), | 013 |
| 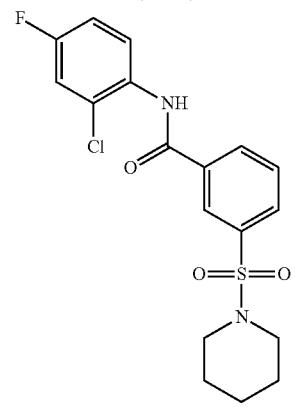<br>397/399<br>GB<br>A01B01C14 | 014 |
TABLE 1-continued
| Structure MS(M + H)+ Synthetic method | Cmp. ID |
|---|---|
| 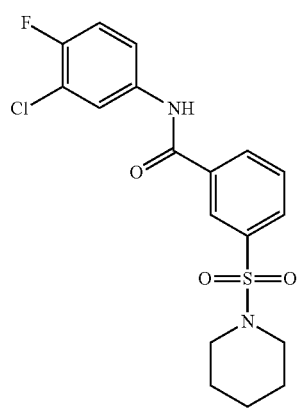<br>397/399<br>GB<br>A01B01C15 | 015 |
| 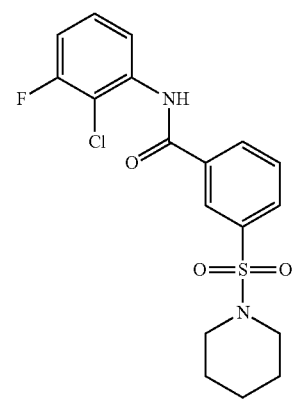<br>397/399<br>GB<br>A01B01C16 | 016 |
| 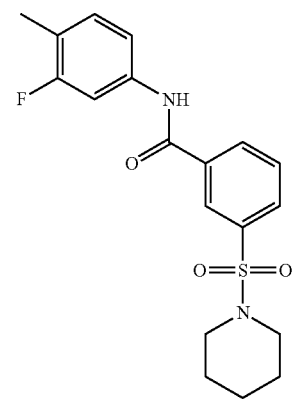<br>377<br>GB<br>A01B01C21 | 021 |

TABLE 1-continued
| Structure MS(M + H)+ Synthetic method | Cmp. ID |
|---|---|
| 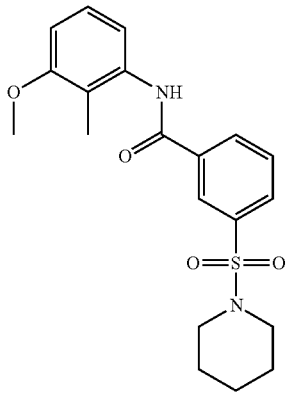<br>389<br>GB<br>A01B01C22<br>¹H NMR (400 MHz, DMSO-d6) δ 10.22 (br, 1H), 8.29 (m, 2H), 7.91 (m, 1 H), 7.78 (m, 1H), 7.18 (m, 1H), 6.89 (m, 2H), 3.79(s, 3H), 2.92(m, 4H), 2.02(s, 3H), 1.53(m, 4H), 1.35(m, 2H). | 022 |
| 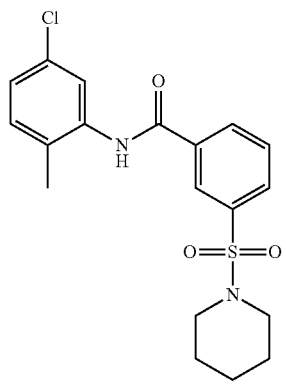<br>393/395<br>GB<br>A01B01C25 | 025 |
| 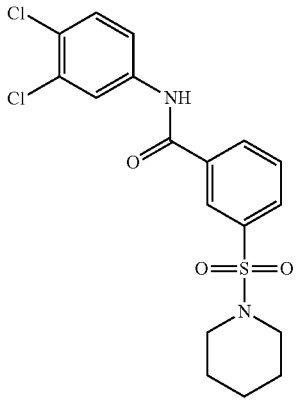<br>413/415<br>GB<br>A01B01C26 | 026 |
TABLE 1-continued
| Structure MS(M + H)+ Synthetic method | Cmp. ID |
|---|---|
| 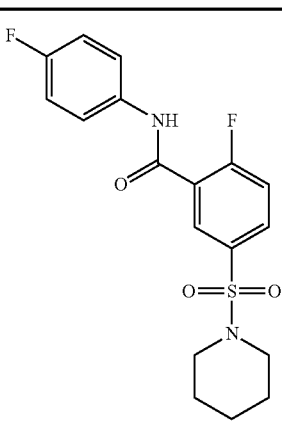<br>381<br>GB<br>A01B02C03 | 033 |
| 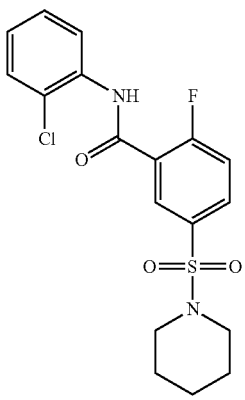<br>397/399<br>GB<br>A01B02C04 | 034 |
| 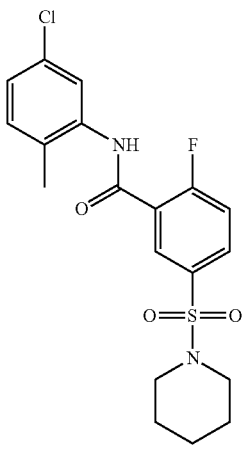<br>411/413<br>GB<br>A01B02C25 | 037 |

TABLE 1-continued
| Structure MS(M + H)+ Synthetic method | Cmp. ID |
|---|---|
| 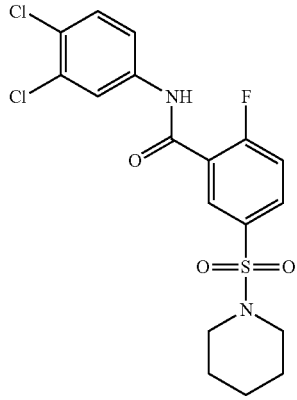<br>431/433<br>GB<br>A01B02C26<br>¹H NMR (400 MHz, CD₃OD) δ 8.11 (m, 1 H), 8.05 (m, 1H), 7.99 (m, 1H), 7.61 (m, 1H), 7.53(m, 2H), 3.05(m, 4H), 1.67(m, 4H), 1.48(m, 2H) | 038 |
| 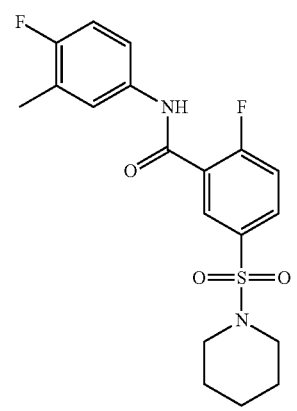<br>395<br>GB<br>A01B02C20 | 041 |
| 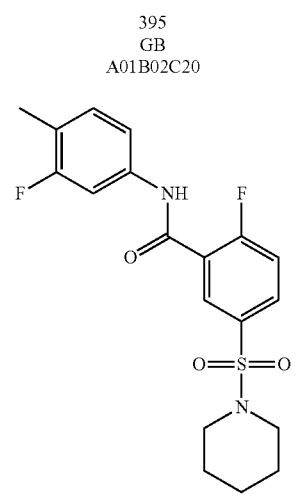<br>395<br>GB<br>A01B02C21 | 042 |
TABLE 1-continued
| Structure MS(M + H)+ Synthetic method | Cmp. ID |
|---|---|
| 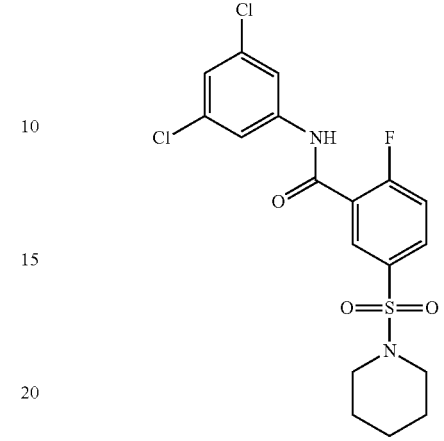<br>431/433<br>GB<br>A01B02C89 | 049 |
| 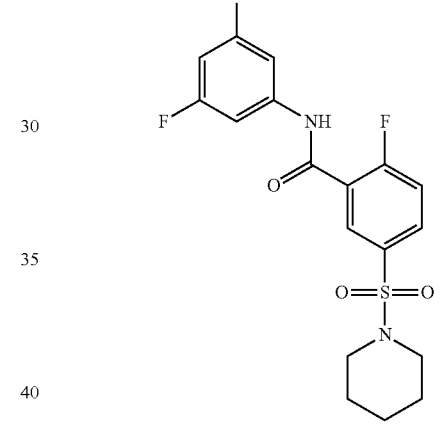<br>399<br>GB<br>A01B02C24 | 050 |
| 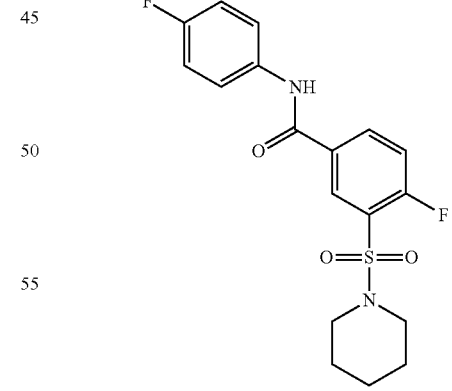<br>381<br>GB<br>A01B03C03<br>¹H NMR (400 MHz, CDCl₃) δ 8.27 (t, 1H), 8.18(m 1 H), 7.95 (s, 1H), 7.61 (q, 2H), 7.34 (t, 1H), 7.09(m, 2H), 3.21(t, 4H), 1.65(m, 4H), 1.53(q, 2H), | 053 |

TABLE 1-continued
| Structure MS(M + H)+ Synthetic method | Cmp. ID |
|---|---|
| 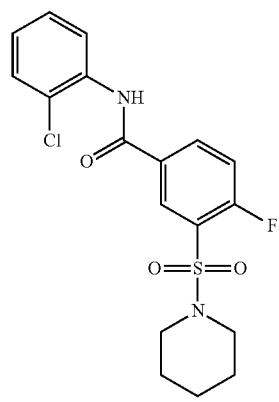<br>397/399<br>GB<br>A01B03C04 | 054 |
| 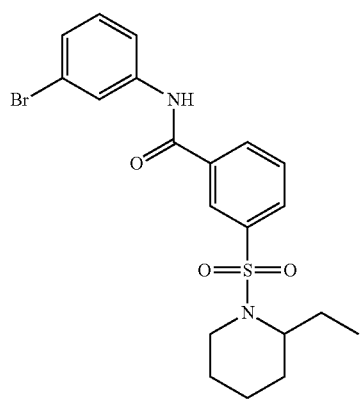<br>451/453<br>GA<br>A02B01C31 | 061 |
| 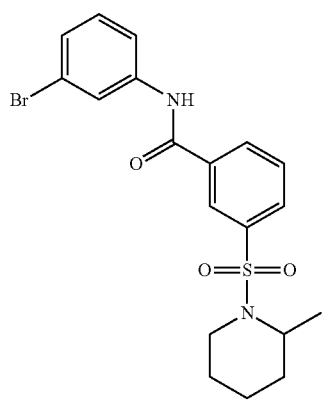<br>437/439<br>GA<br>A03B01C31 | 062 |
| 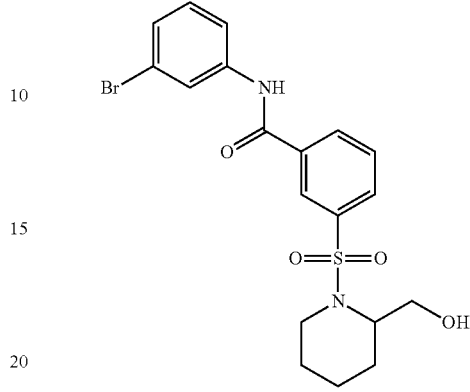<br>453/455<br>GA<br>A04B01C31 | 063 |
| 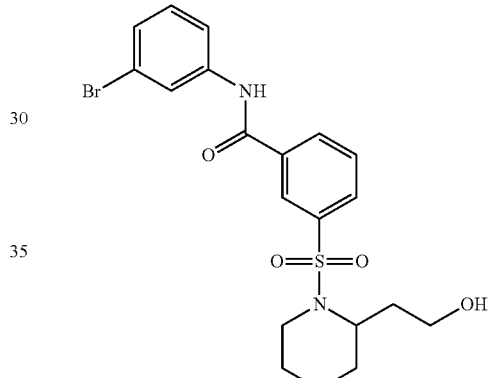<br>467/469<br>GA<br>A05B01C31 | 064 |
| 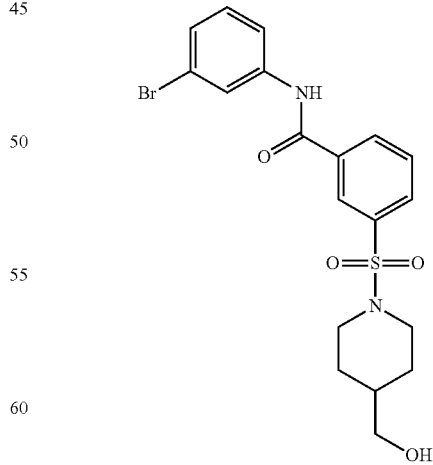<br>453/455<br>GA<br>A06B01C31 | 065 |

TABLE 1-continued

| Structure MS(M + H)+ Synthetic method | Cmp. ID |
|---|---|
| [Structure: 3-bromophenyl-NH-C(=O)-phenyl-SO2-N(piperidine-3-yl-CH2OH)] 453/455 GA A07B01C31 | 066 |
| [Structure: 3-bromophenyl-NH-C(=O)-phenyl-SO2-N(piperidine-4-carboxamide)] 466/468 GA A12B01C31 | 071 |
| [Structure: 3-bromophenyl-NH-C(=O)-phenyl-SO2-N(3,5-dimethylpiperidine)] 451/453 GA A13B01C31 | 072 |
| [Structure: 3-bromophenyl-NH-C(=O)-phenyl-SO2-N(2,6-dimethylmorpholine)] 453/455 GA A14B01C31 | 073 |
| [Structure: 3-bromophenyl-NH-C(=O)-phenyl-SO2-N(piperazine-N-C(=O)-cyclopropyl)] 492/494 GA A15B01C31 | 074 |
| [Structure: 3-bromophenyl-NH-C(=O)-phenyl-SO2-N(piperazine-N-C(=O)-phenyl)] 528/530 GA A16B01C31 | 075 |

TABLE 1-continued
| Structure MS(M + H)+ Synthetic method | Cmp. ID |
|---|---|
| 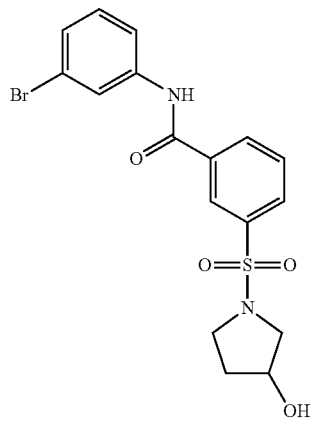<br>425/427<br>GA<br>A17B01C31 | 076 |
| 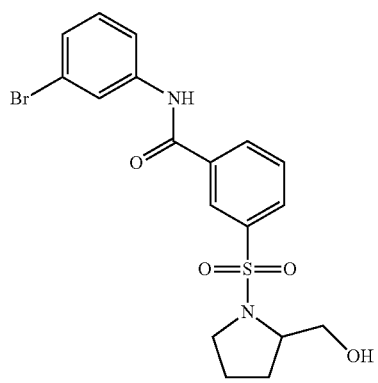<br>439/441<br>GA<br>A18B01C31 | 077 |
| 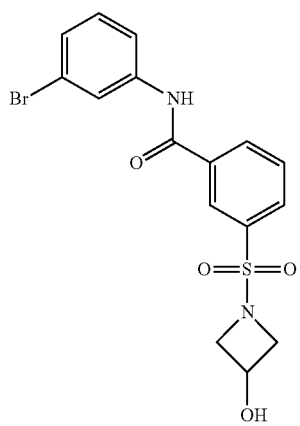<br>411/413<br>GA<br>A19B01C31 | 078 |
| Structure MS(M + H)+ Synthetic method | Cmp. ID |
|---|---|
| 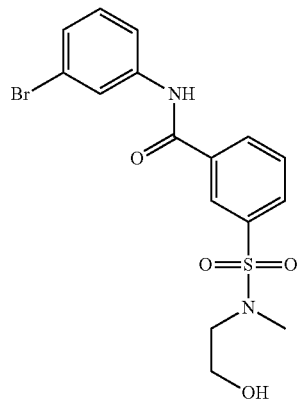<br>413/415<br>GA<br>A20B01C31 | 079 |
| 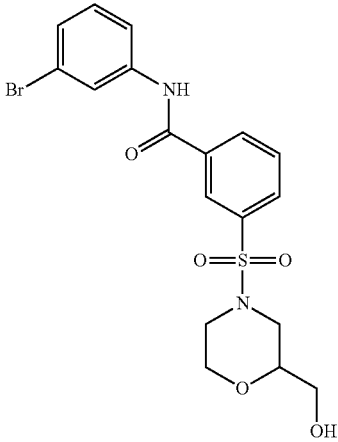<br>455/457<br>GA<br>A21B01C31 | 080 |
| 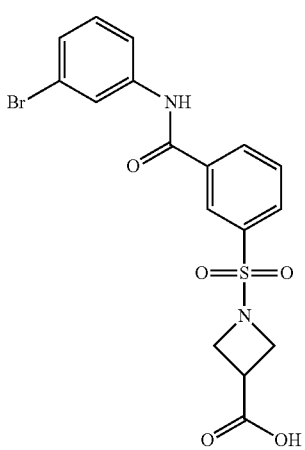<br>439/441<br>GA<br>A22B01C31 | 081 |

TABLE 1-continued
| Structure MS(M + H)+ Synthetic method | Cmp. ID |
|---|---|
| 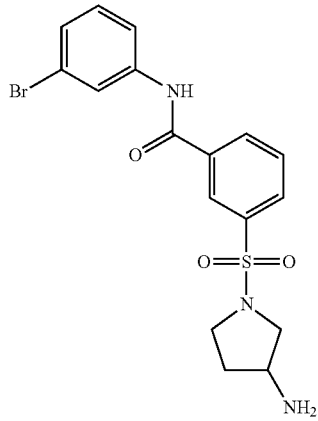 424/426 GA A23B01C31 | 082 |
| 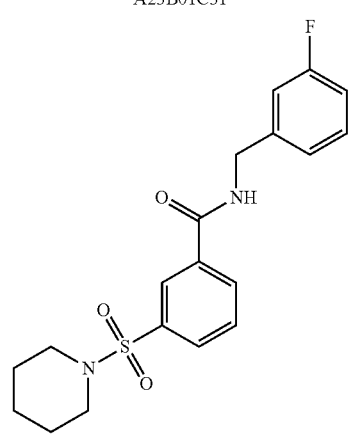 377 GB A01B01C66 | 083 |
| 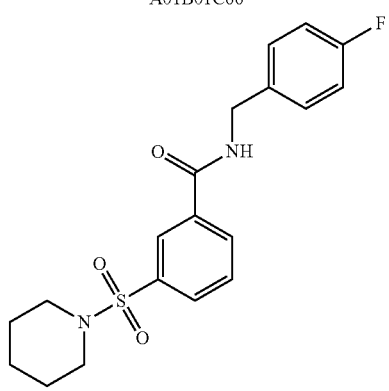 377 GB A01B01C66 $^1$H-NMR (400 MHz, CDCl3): δ ppm: 8.19 (m, 2H), 7.87 (m, 1H), 7.62 (t, 1H), 7.30 (m, 1H), 7.08 (m, 3H), 6.87 (s, 1H), 4.65 (d, 2H), 2.98 (t, 4H), 1.62 (m, 4H), 1.42 (m, 2H). | 084 |
TABLE 1-continued
| Structure MS(M + H)+ Synthetic method | Cmp. ID |
|---|---|
| 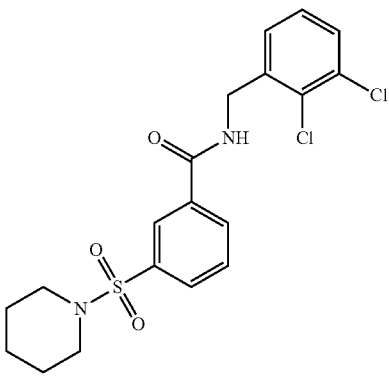 427/429 GB A01B01C77 | 097 |
| 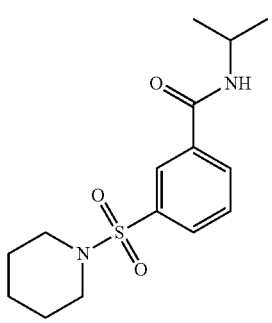 311 GB A01B01C32 | 098 |
| 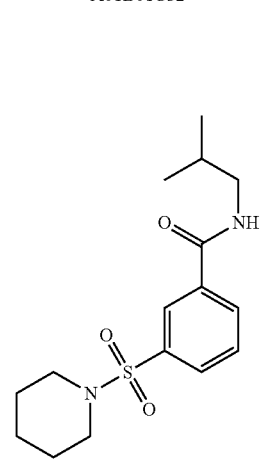 325 GB A01B01C33 | 099 |

TABLE 1-continued

| Structure MS(M + H)+ Synthetic method | Cmp. ID |
|---|---|
| [Structure: N-phenethyl 3-(piperidin-1-ylsulfonyl)benzamide]<br>373<br>GB<br>A01B01C34<br>¹H-NMR (400 MHz, CDCl3): δ ppm: 7.98 (m, 2H), 7.84 (m, 1H), 7.59 (t, 1H), 7.31 (m, 2H), 7.24 (m, 3H), 6.42 (d, 1H), 3.72 (m, 2H), 2.95 (m, 6H), 1.62 (m, 4H), 1.40 (m, 2H). | 100 |
| [Structure: N-(biphenyl-4-yl) 3-(piperidin-1-ylsulfonyl)benzamide]<br>421<br>GB<br>A01B01C36 | 103 |

TABLE 1-continued

| Structure MS(M + H)+ Synthetic method | Cmp. ID |
|---|---|
| [Structure: N-(4-(piperidin-1-yl)benzyl) 3-(piperidin-1-ylsulfonyl)benzamide]<br>442<br>GB<br>A01B01C37 | 104 |
| [Structure: N-(3,5-difluorophenyl)-3-(piperidine-1-carbonyl)benzamide]<br>345<br>GB<br>A01B13C24 | 115 |
| [Structure: N-(3-bromophenyl) 3-(piperazin-1-ylsulfonyl)benzamide]<br>424/426<br>GA<br>A24B01C31 | 116 |

TABLE 1-continued
| Structure MS(M + H)+ Synthetic method | Cmp. ID |
|---|---|
| 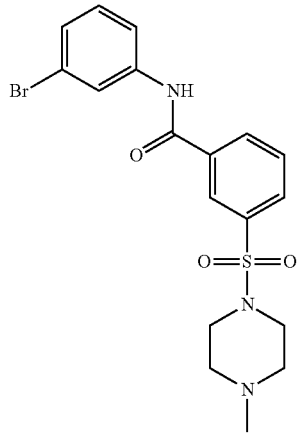<br>438/440<br>GA<br>A25B01C31 | 117 |
| 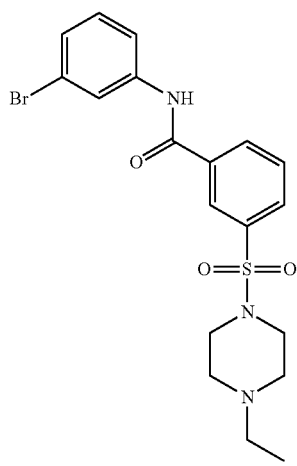<br>452/454<br>GA<br>A26B01C31 | 118 |
| 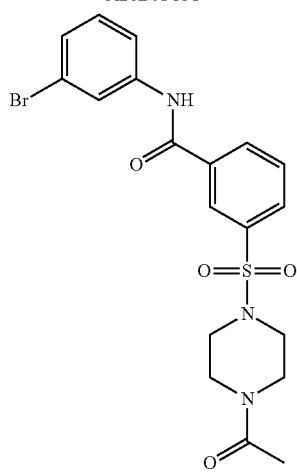<br>466/468<br>GA<br>A27B01C31 | 119 |
TABLE 1-continued
| Structure MS(M + H)+ Synthetic method | Cmp. ID |
|---|---|
| 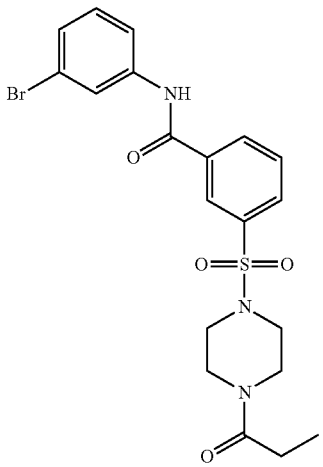<br>480/482<br>GA<br>A28B01C31 | 120 |
| 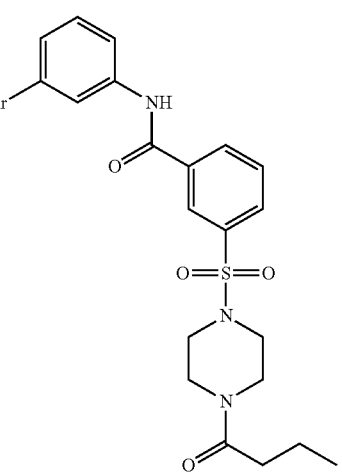<br>494/496<br>GA<br>A29B01C31 | 121 |

TABLE 1-continued
| Structure MS(M + H)+ Synthetic method | Cmp. ID |
|---|---|
| 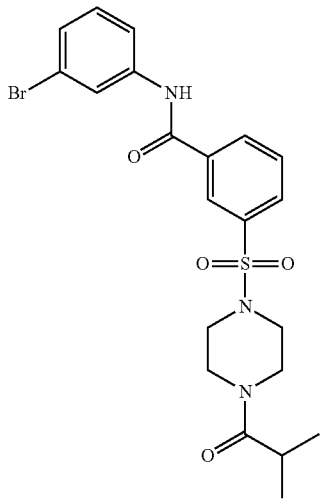<br>494/496<br>GA<br>A30B01C31 | 122 |
| 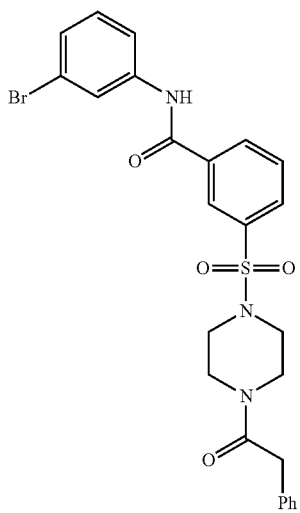<br>542/544<br>GA<br>A31B01C31 | 123 |
TABLE 1-continued
| Structure MS(M + H)+ Synthetic method | Cmp. ID |
|---|---|
| 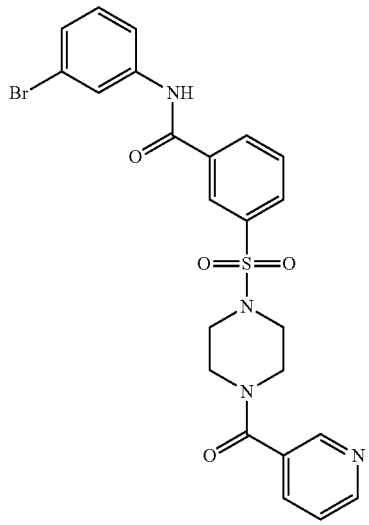<br>529/531<br>GA<br>A32B01C31 | 124 |
| <br>500/502<br>GA<br>A33B01C31 | 125 |

TABLE 1-continued
| Structure MS(M + H)+ Synthetic method | Cmp. ID |
|---|---|
| 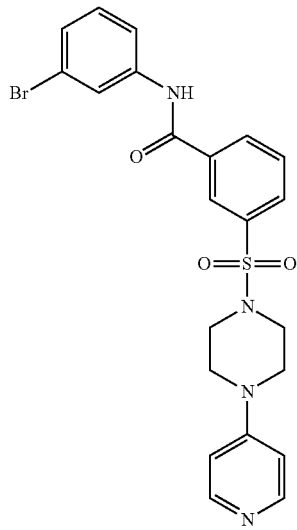<br>501/503<br>GA<br>A34B01C31 | 126 |
| 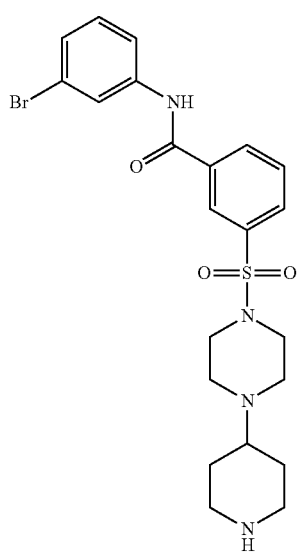<br>507/509<br>GA<br>A35B01C31 | 127 |
TABLE 1-continued
| Structure MS(M + H)+ Synthetic method | Cmp. ID |
|---|---|
| 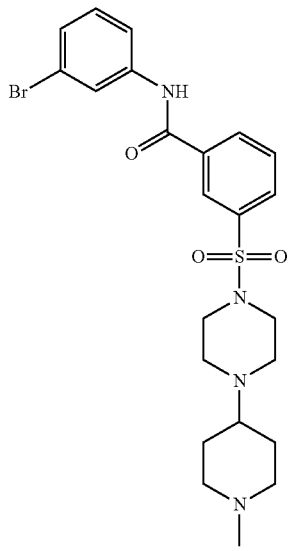<br>521/523<br>GA<br>A36B01C31 | 128 |
| 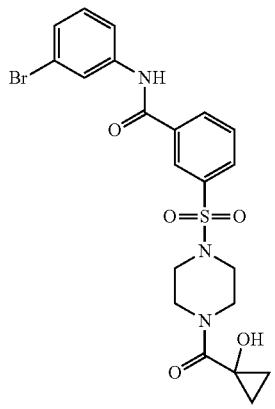<br>508/510<br>GA<br>A37B01C31<br>$^1$H NMR (400 MHz, CD$_3$OD) δ 8.18 (m, 2H), 8.06(br, 1 H), 7.94 (d, 2H), 7.72 (t, 1H), 7.54 (m, 1H), 7.34 (m, 1H), 3.80(m, 4H), 3.08(m, 4H), 2.87(m, 1H), 1.25 (m, 2H), 1.06 (m, 1H), 0.94 (m, 1H). | 129 |

TABLE 1-continued
| Structure MS(M + H)+ Synthetic method | Cmp. ID |
|---|---|
| 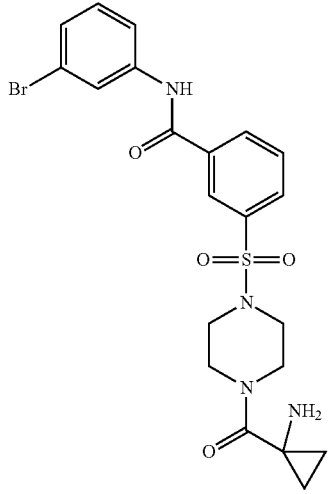<br>507/509<br>GA<br>A38B01C31 | 130 |
| 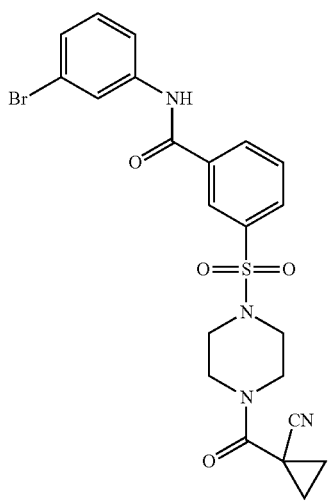<br>517/519<br>GA<br>A39B01C31 | 131 |
TABLE 1-continued
| Structure MS(M + H)+ Synthetic method | Cmp. ID |
|---|---|
| 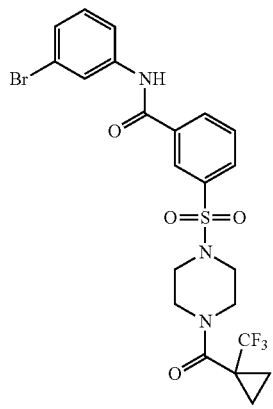<br>560/562<br>GA<br>A40B01C31<br>$^1$H NMR (400 MHz, CD$_3$OD) δ 8.33 (s, 1H), 8.16(m, 2 H), 7.88 (m, 2H), 7.69 (t, 1H), 7.62 (d, 1H), 7.32 (m, 1H), 3.71(m, 4H), 3.04(m, 4H), 1.29(m, 2H), 1.07 (m, 2H). | 132 |
| 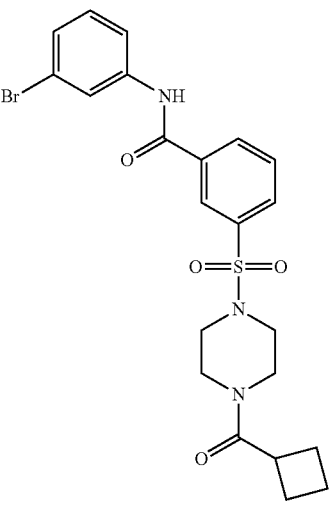<br>506/508<br>GA<br>A45B01C31 | 135 |

TABLE 1-continued
| Structure MS(M + H)+ Synthetic method | Cmp. ID |
|---|---|
| 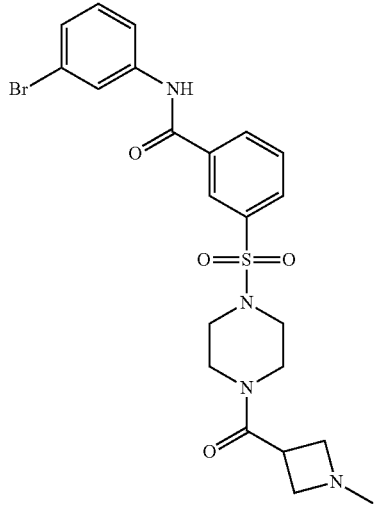 521/523 GA A43B01C31 | 136 |
| 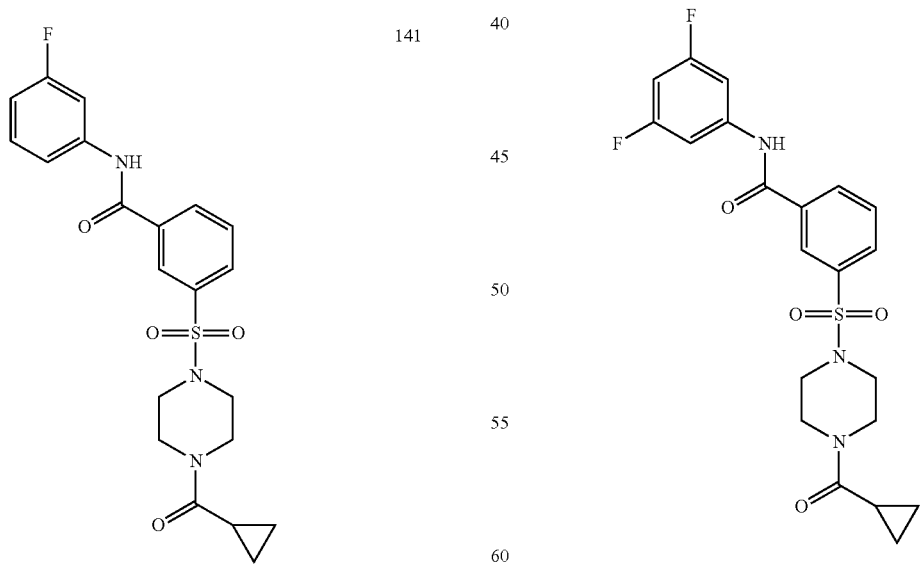 432 GB A15B01C02 | 141 |
TABLE 1-continued
| Structure MS(M + H)+ Synthetic method | Cmp. ID |
|---|---|
| 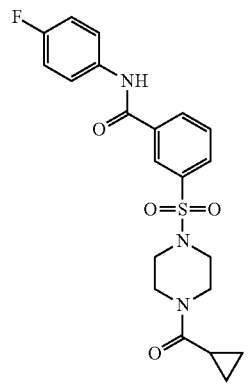 432 GB A15B01C03 $^1$H NMR (400 MHz, CDCl$_3$) δ 8.19 (s, 1H), 8.14 (d, 1H), 7.93 (m, 1 H), 7.85 (s, 1H), 7.72(m, 1H), 7.62(m, 2H), 7.10(t, 2H), 3.76(br, 4H), 3.07 (br, 4H), 1.62(m, 1H), 1.62 (m, 1H), 0.93 (m, 2H), 0.75(m, 2H) | 142 |
| 450 GB A15B01C24 | 147 |

TABLE 1-continued

| Structure MS(M + H)+ Synthetic method | Cmp. ID |
|---|---|
| [structure: N-(4-fluoro-3-methylphenyl)-3-(4-(cyclopropanecarbonyl)piperazin-1-ylsulfonyl)benzamide]<br>446 GB A15B01C20<br>$^1$H NMR (400 MHz, CDCl$_3$) δ 8.18 (s, 1H), 8.13 (d, 1H), 7.91 (m, 1 H), 7.83(d, 1H), 7.70(t, 1H), 7.50(m, 1H), 7.40(m, 1H), 7.02(t, 1H), 3.75 (br, 4H), 3.05 (br, 4H) 1.62(m, 1H), 0.93 (m, 2H), 0.75(m, 2H) | 148 |
| [structure: N-(3-chloro-4-fluorophenyl)-3-(4-(cyclopropanecarbonyl)piperazin-1-ylsulfonyl)benzamide]<br>466/468 GB A15B01C15<br>$^1$H NMR (400 MHz, CDCl$_3$) δ 8.18 (s, 1H), 8.17(m, 1H), 8.13 (s, 1 H), 7.91(m, 1H), 7.86(m, 1H), 7.71(t, 1H), 7.50(m, 1H), 7.16(t, 1H), 3.75 (br, 4H), 3.04 (br, 4H) 1.62(m, 1H), 0.93 (m, 2H), 0.75(m, 2H) | 151 |

TABLE 1-continued

| Structure MS(M + H)+ Synthetic method | Cmp. ID |
|---|---|
| [structure: N-(2,4-difluorophenyl)-3-(4-(cyclopropanecarbonyl)piperazin-1-ylsulfonyl)benzamide]<br>450 GB A15B01C82 | 152 |
| [structure: N-(3-bromophenyl)-3-(4-(2-methylpropanoyl)piperidin-4-ylsulfonyl)benzamide]<br>493/495 GA A48B01C31 | 159 |

TABLE 1-continued
| Structure MS(M + H)+ Synthetic method | Cmp. ID |
|---|---|
| 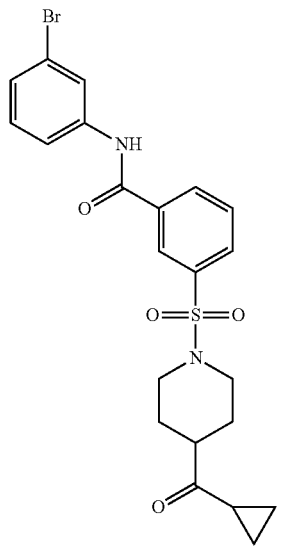 491/493 GA A15B01C31 | 160 |
| 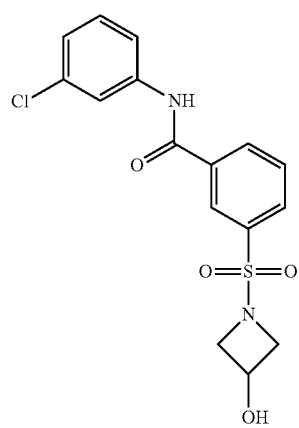 367/369 GB A19B01C05 | 168 |
TABLE 1-continued
| Structure MS(M + H)+ Synthetic method | Cmp. ID |
|---|---|
| 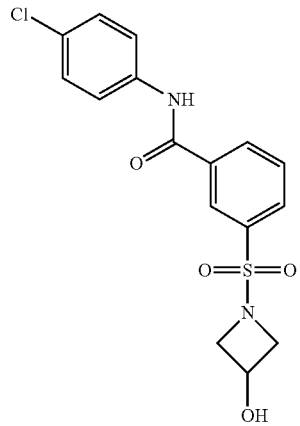 367/369 GB A19B01C06 | 169 |
| 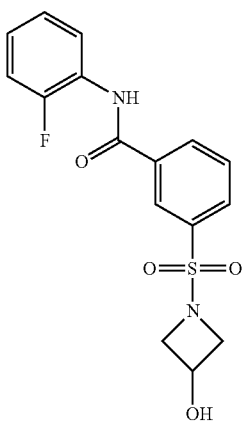 351 GB A19B01C01 | 170 |
| 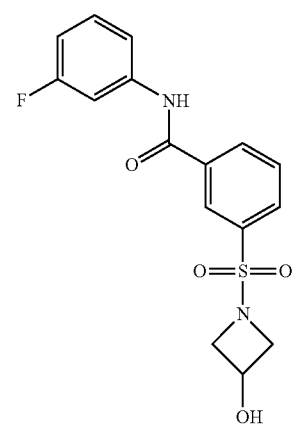 351 GB A19B01C02 | 171 |

TABLE 1-continued
| Structure MS(M + H)+ Synthetic method | Cmp. ID |
|---|---|
| 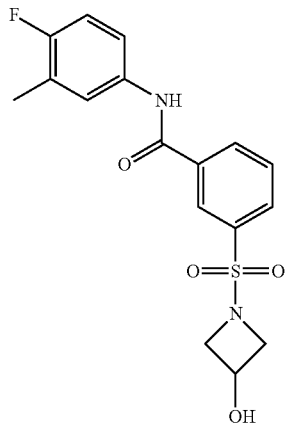<br>365<br>GB<br>A19B01C20 | 174 |
| 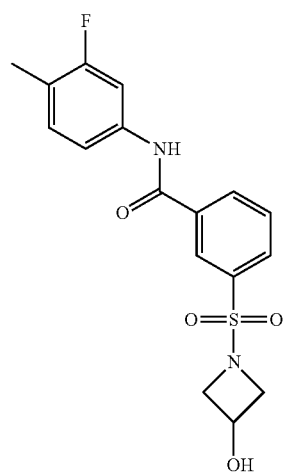<br>365<br>GB<br>A19B01C21 | 175 |
TABLE 1-continued
| Structure MS(M + H)+ Synthetic method | Cmp. ID |
|---|---|
| 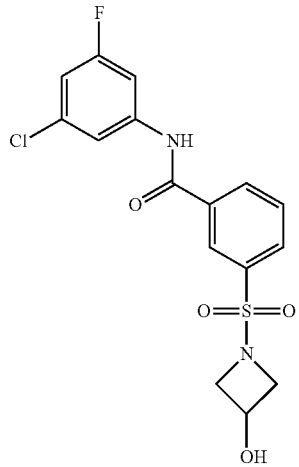<br>385/387<br>GB<br>A19B01C17 | 176 |
| 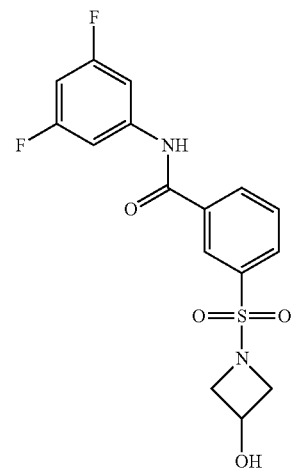<br>369<br>GB<br>A19B01C24 | 177 |

TABLE 1-continued
| Structure MS(M + H)+ Synthetic method | Cmp. ID |
|---|---|
| 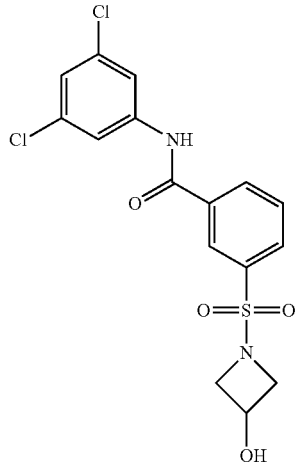<br>401/403<br>GB<br>A19B01C79 | 178 |
| 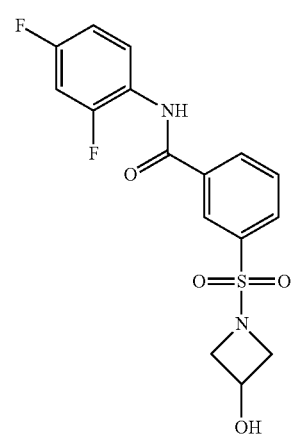<br>369<br>GB<br>A19B01C24 | 179 |
| 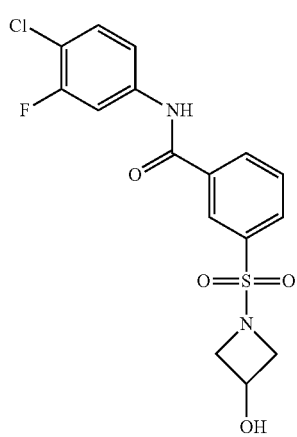<br>385/387<br>GB<br>A149B01C15 | 180 |
TABLE 1-continued
| Structure MS(M + H)+ Synthetic method | Cmp. ID |
|---|---|
| 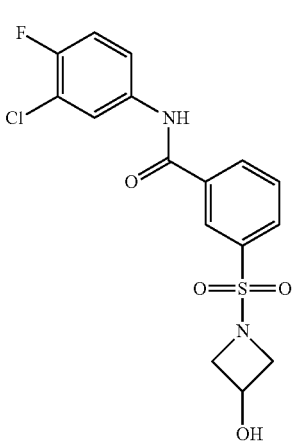<br>385/387<br>GB<br>A19B01C15 | 181 |
| 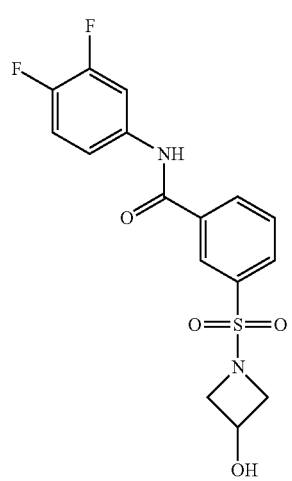<br>369<br>GB<br>A19B01C63 | 182 |
| 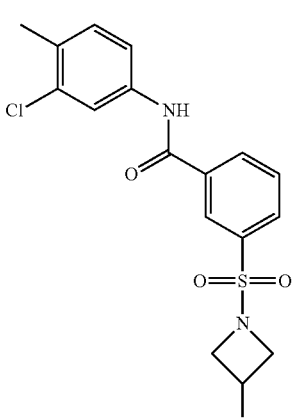<br>381/383<br>A19B01C27 | 183 |

TABLE 1-continued
| Structure MS(M + H)+ Synthetic method | Cmp. ID |
|---|---|
| 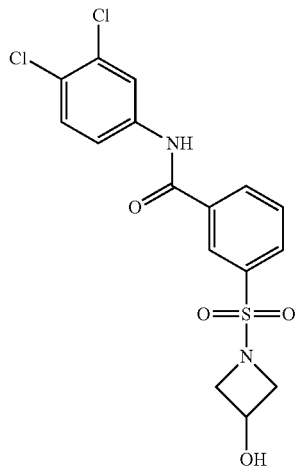 401/403 GB A19B01C26 | 184 |
| 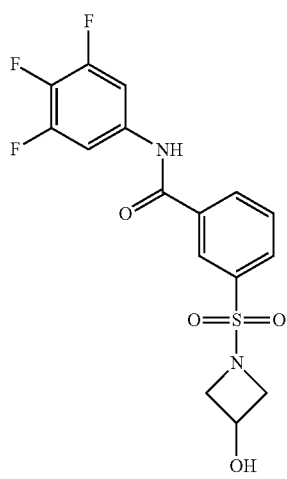 387 GB A19B01C40 | 186 |
TABLE 1-continued
| Structure MS(M + H)+ Synthetic method | Cmp. ID |
|---|---|
| 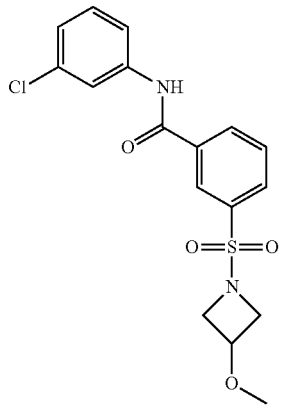 381/383 GB A108B01C05 $^1$H NMR (400 MHz, CD$_3$OD) δ 8.34 (m, 2H), 8.024(d, 1 H), 7.98 (d, 2H), 7.83 (s, 1H), 7.74 (m, 2H), 7.55 (m, 1H), 7.32 (m, 1H), 7.14(m, 1H), 4.02(m, 3H), 3.60(m, 2H), 3.16(s, 3H) | 191 |
| 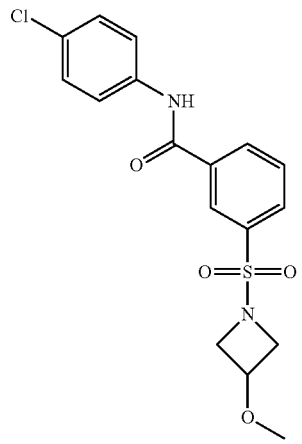 381/383 GB A108B01C06 | 192 |

TABLE 1-continued
| Structure MS(M + H)+ Synthetic method | Cmp. ID |
|---|---|
| 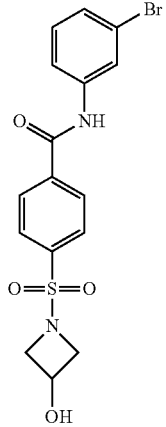<br>411/413<br>GA<br>A108B16C31<br><sup>1</sup>H NMR (400 MHz, CD<sub>3</sub>OD) δ 8.16 (d, 2H), 8.04(br, 1 H), 7.97 (d, 2H), 7.67 (q, 1H), 7.30 (m, 2H), 4.34(m, 1H), 4.00(m, 2H), 3.50(m, 2H). | 201 |
| 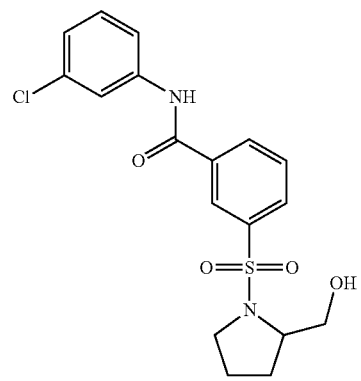<br>395/397<br>GB<br>A18B01C05 | 206 |
| 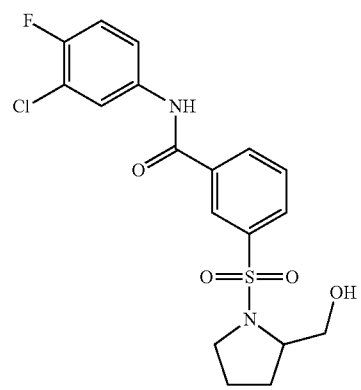<br>413/415<br>GB<br>A18B01C15 | 208 |
TABLE 1-continued
| Structure MS(M + H)+ Synthetic method | Cmp. ID |
|---|---|
| 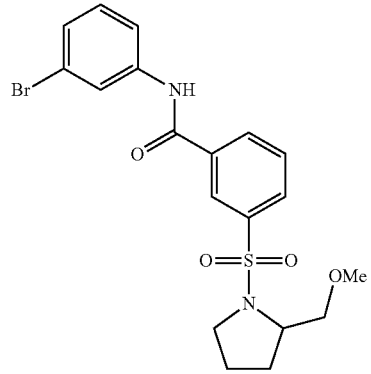<br>453/455<br>GB<br>A109B01C31 | 210 |
| 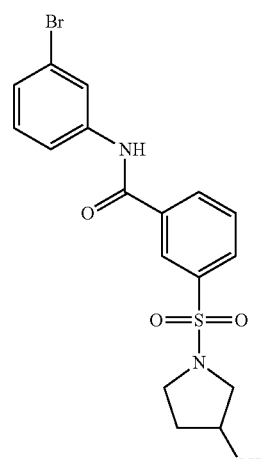<br>425/427<br>GA<br>A17B01C31 | 212 |
| 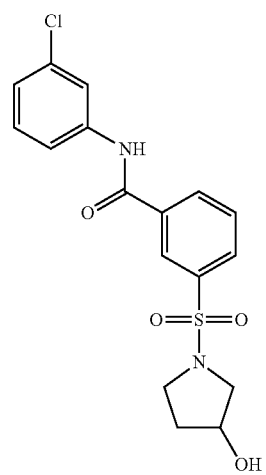<br>381/383<br>GB<br>A17B01C05 | 215 |

TABLE 1-continued
| Structure MS(M + H)+ Synthetic method | Cmp. ID |
|---|---|
| 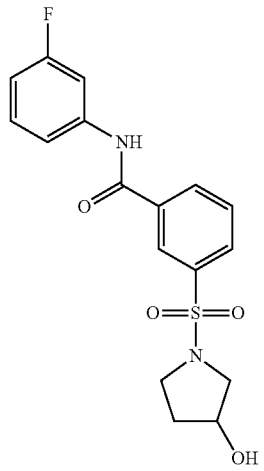<br>365<br>GB<br>A17B01C02 | 216 |
| 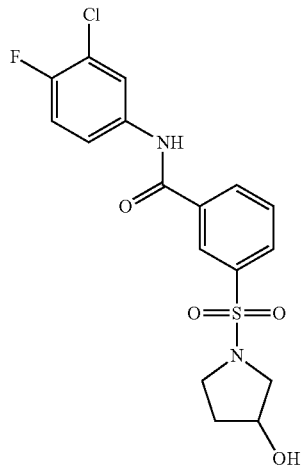<br>399/411<br>GB<br>A17B01C15 | 217 |
TABLE 1-continued
| Structure MS(M + H)+ Synthetic method | Cmp. ID |
|---|---|
| 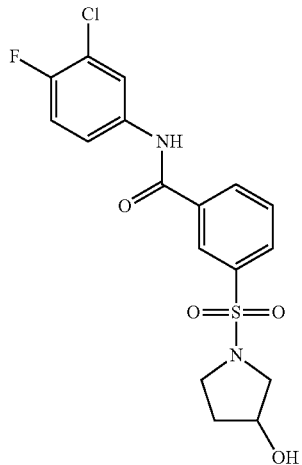<br>399/411<br>GB<br>A17B01C15 | 217_R |
| 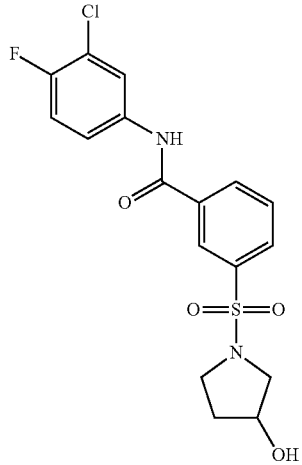<br>399/411<br>GB<br>A17B01C15 | 217_S |

TABLE 1-continued
| Structure MS(M + H)+ Synthetic method | Cmp. ID |
|---|---|
| 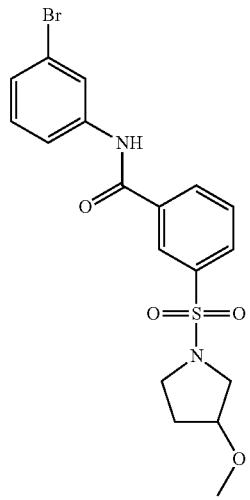<br>439/441<br>GB<br>A130B01C31 | 219 |
| 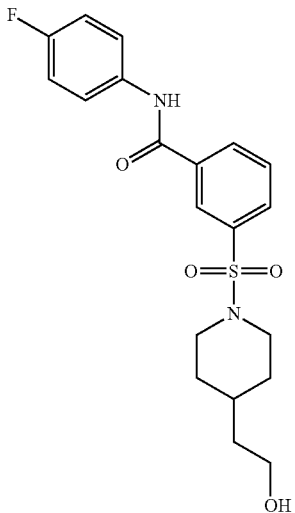<br>407<br>GB<br>A09B01C03 | 225 |
| 407<br>GB<br>A09B01C02 | 224 |
| 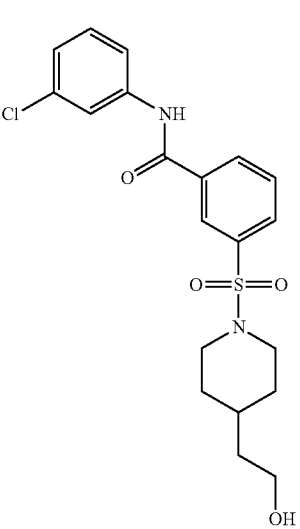<br>423/425<br>GB<br>A09B01C05 | 226 |

TABLE 1-continued
| Structure MS(M + H)+ Synthetic method | Cmp. ID |
|---|---|
| 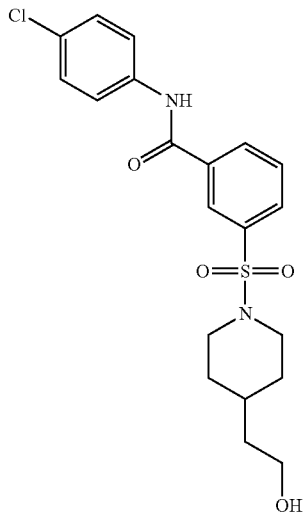<br>423/425<br>GB<br>A09B01C06 | 227 |
| 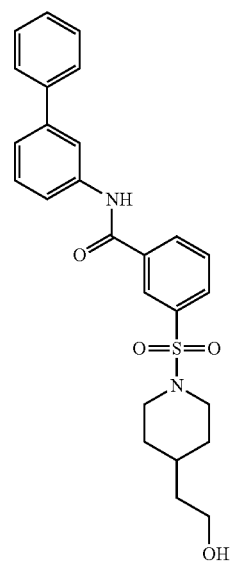<br>465<br>GB<br>A09B01C36 | 228 |
TABLE 1-continued
| Structure MS(M + H)+ Synthetic method | Cmp. ID |
|---|---|
| 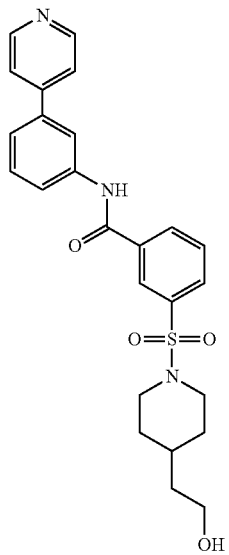<br>466<br>GB<br>A09B01C45 | 229 |
| 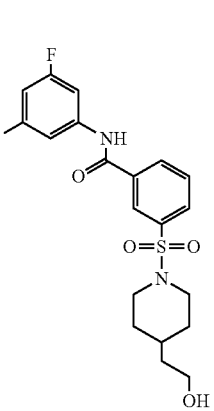<br>425 GB A09B01C24<br>$^1$H NMR (400 MHz, CD$_3$OD) δ 8.39 (s, 1H), 8.16(m, 2 H), 7.90 (d, 1H), 7.68 (t, 1H), 7.36 (m, 2H), 6.64(m, 1H), 3.78 (m, 2H), 3.64 (m, 2H), 2.28 (m, 2H), 1.73 (m, 2H), 1.47 (m, 2H), 1.37 (m, 1H), 1.28 (m, 3H). | 230 |

TABLE 1-continued
| Structure MS(M + H)+ Synthetic method | Cmp. ID |
|---|---|
| 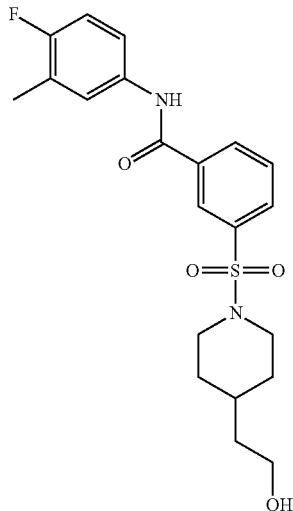 421 GB A09B01C20 | 231 |
| 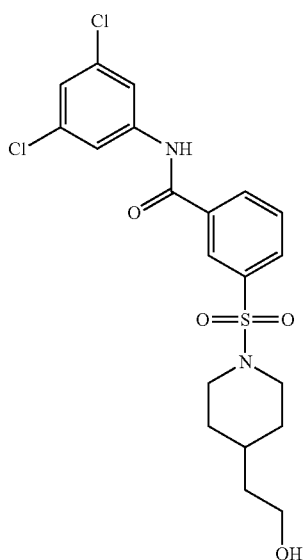 457/459 GB A09B01C79 | 233 |
TABLE 1-continued
| Structure MS(M + H)+ Synthetic method | Cmp. ID |
|---|---|
| 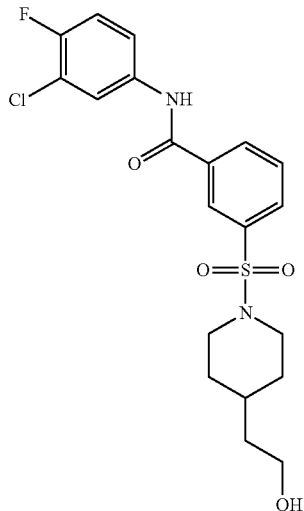 441/443 GB A09B01C15 | 234 |
| 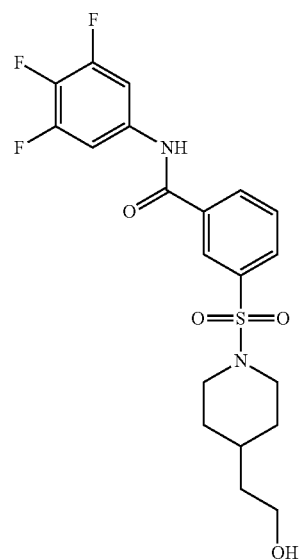 443 GB A09B01C40 | 238 |

TABLE 1-continued
| Structure MS(M + H)+ Synthetic method | Cmp. ID |
|---|---|
| 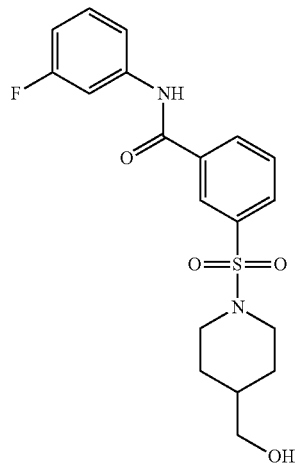<br>393<br>GB<br>A06B01C02 | 244 |
| 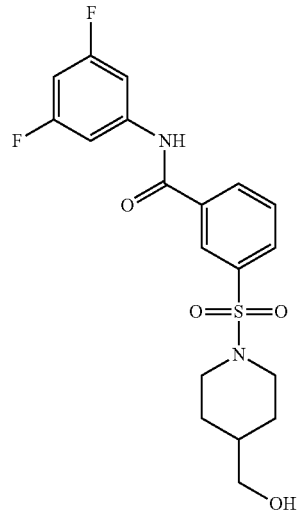<br>411<br>GB<br>A06B01C24 | 250 |
| 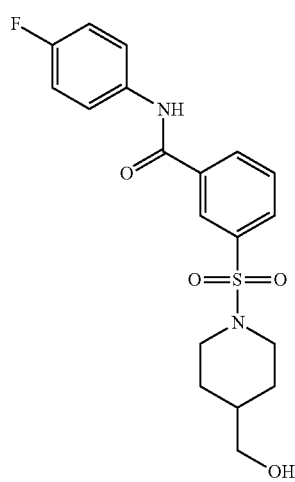<br>393<br>GB<br>A06B01C03 | 245 |
| 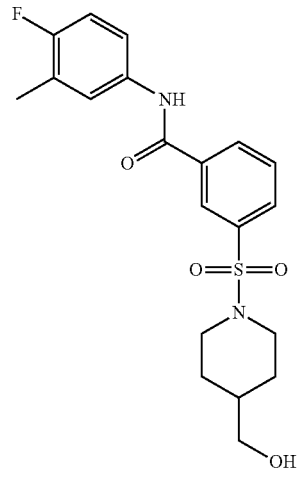<br>407<br>GB<br>A06B01C20 | 251 |

TABLE 1-continued
| Structure MS(M + H)+ Synthetic method | Cmp. ID |
|---|---|
| 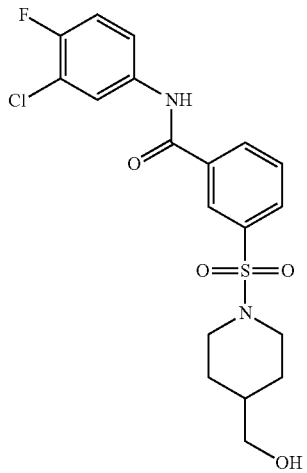 427/429 GB A06B01C15 | 254 |
| 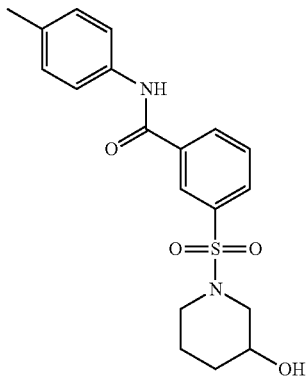 375 GB A08B01C09 ¹H NMR (400 MHz, CD₃OD) δ 8.33 (s, 1H), 8.23 (d, 1H), 7.98 (t, 1H), 7.78 (t, 1H), 7.59 (d, 2H), 7.21(d, 2H), 3.72 (m, 1H), 3.57 (m, 1H), 3.42 (m, 1H), 2.61 (t, 1H), 2.47 (m, 1H), 2.36 (s, 3H), 1.85 (t, 2H), 1.61 (m, 1H), 1.27 (m, 1H) | 263 |
| 429 GB A06B01C40 | 258 |
| 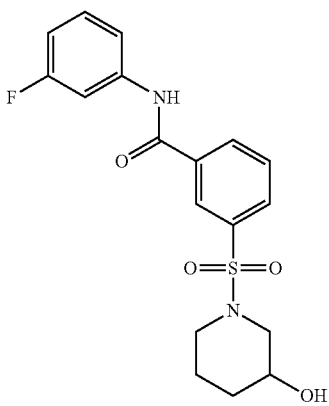 379 GB A08B01C02 | 264 |

TABLE 1-continued

| Structure MS(M + H)+ Synthetic method | Cmp. ID |
|---|---|
| (structure) 438 GB A08B01C45 | 269 |
| (structure) 397 GB A08B01C24 | 270 |

TABLE 1-continued

| Structure MS(M + H)+ Synthetic method | Cmp. ID |
|---|---|
| (structure) 393 GB A08B01C20 $^1$H NMR (400 MHz, CD$_3$OD) δ 8.33 (s, 1H), 8.23 (d, 1H), 8.00 (m, 1H), 7.79 (t, 1H), 7.59 (m, 1H), 7.53 (m, 1H), 7.06(t, 1H), 3.72 (m, 1H), 3.59 (m, 1H), 3.43 (m, 1H), 2.60 (m, 1H), 2.45 (m, 1H), 3.31 (d, 3H), 1.84 (m, 2H), 1.60 (m, 1H), 1.26 (m, 1H) | 271 |
| (structure) 413/415 GB A08B01C15 | 274 |

TABLE 1-continued
| Structure MS(M + H)+ Synthetic method | Cmp. ID |
|---|---|
| 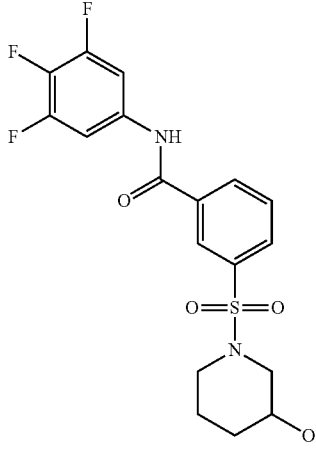 415 GB A08B01C40 | 278 |
| 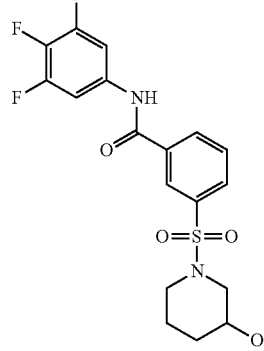 415 GB A08B01C40 $^1$H NMR (400 MHz, MeOD) δ 8.33 (s, 1H), 8.23 (d, J = 8.0 Hz, 1H), 8.00 (d, J = 8.0 Hz, 1H), 7.80 (t, J = 8.0 Hz, 1H), 7.63 (m, 2H), 3.73 (m, 1H), 3.58 (m, 1H), 3.42 (m, 1H), 2.63 (m, 1H), 2.45 (m, 1H), 1.85 (m, 2H), 1.61 (m, 1H), 1.28 (m, 1H). | 278_E1 |
|  415 GB A08B01C40 1H NMR (400 MHz, MeOD) δ 8.33 (s, 1H), 8.23 (d, J = 8.0 Hz, 1H), 8.00 (d, J = 8.0 Hz, 1H), 7.80 (t, J = 8.0 Hz, 1H), 7.63 (m, 2H), 3.73 (m, 1H), 3.57 (m, 1H), 3.42 (m, 1H), 2.63 (m, 1H), 2.45 (m, 1H), 1.85 (m, 2H), 1.61 (m, 1H), 1.28 (m, 1H). | 278_E2 |
| 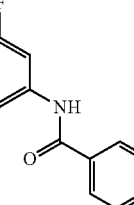 393 GB A04B01C02 | 284 |
| 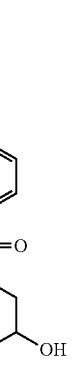 393 GB A04B01C03 | 285 |

TABLE 1-continued

| Structure MS(M + H)+ Synthetic method | Cmp. ID |
|---|---|
| (3,5-difluorophenyl)-NH-C(O)-[3-sulfonyl-phenyl]-SO2-N(piperidin-2-yl-CH2OH) 411 GB A04B01C24 | 290 |
| (4-fluoro-3-methylphenyl)-NH-C(O)-[3-sulfonyl-phenyl]-SO2-N(piperidin-2-yl-CH2OH) 407 GB A04B01C20 | 291 |
| (4-fluoro-3-methylphenyl)-NH-C(O)-[3-sulfonyl-phenyl]-SO2-N(piperidin-2-yl-CH2OH) 407 GB A04B01C20 | 291_E1 |
| (4-fluoro-3-methylphenyl)-NH-C(O)-[3-sulfonyl-phenyl]-SO2-N(piperidin-2-yl-CH2OH) 407 GB A04B01C20 | 291_E2 |
| (3-chloro-4-fluorophenyl)-NH-C(O)-[3-sulfonyl-phenyl]-SO2-N(piperidin-2-yl-CH2OH) 427/429 GB A04B01C15 | 294 |
| (3,4,5-trifluorophenyl)-NH-C(O)-[3-sulfonyl-phenyl]-SO2-N(piperidin-2-yl-CH2OH) 429 GB A04B01C40 | 298 |

TABLE 1-continued
| Structure MS(M + H)+ Synthetic method | Cmp. ID |
|---|---|
| 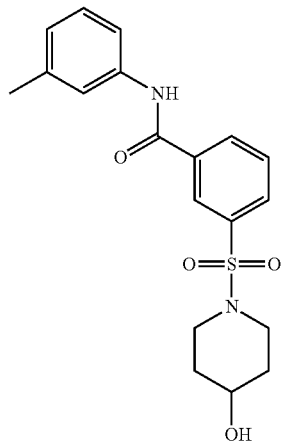<br>375<br>GB<br>A10B01C08 | 302 |
| 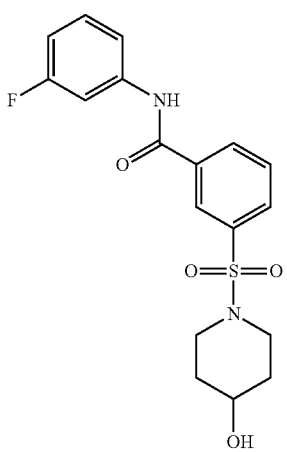<br>379<br>GB<br>A10B01C02 | 304 |
TABLE 1-continued
| Structure MS(M + H)+ Synthetic method | Cmp. ID |
|---|---|
| 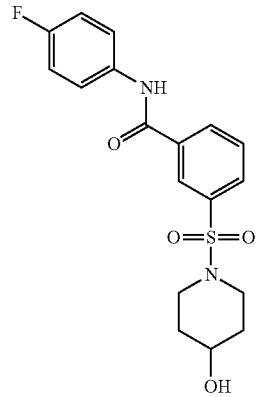<br>379<br>GB<br>A10B01C03<br>$^1$H NMR (400 MHz, DMSO-d6) δ 10.57(s, 1H), 8.26 (m, 2H), 7.94 (m, 1 H), 7.81 (m, 3H), 7.23 (m, 2H), 4.70(s, 1H), 3.47(d, 1H), 3.20(m, 2H), 2.78(m, 2H), 1.76(m, 2H), 1.45(m, 2H) | 305 |
| 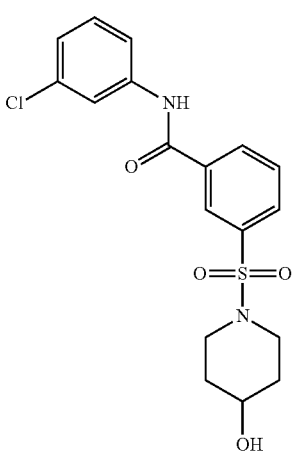<br>395/397<br>GB<br>A10B01C05 | 306 |

TABLE 1-continued
| Structure MS(M + H)+ Synthetic method | Cmp. ID |
|---|---|
| 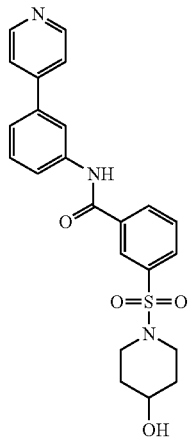 438 GB A10B01C45 ¹H NMR (400 MHz, DMSO-d6) δ 10.69(s, 1H), 8.67 (m, 1H), 8.33 (m, 2H), 8.21 (m, 1H), 7.96 (m, 1H), 7.87(m, 2H), 7.68 (m, 2H), 7.57(m, 2H), 3.53(m, 2H), 3.18(m, 3H), 2.68(m, 2H), 1.77(m, 2H), 1.45(m, 2H) | 309 |
TABLE 1-continued
| Structure MS(M + H)+ Synthetic method | Cmp. ID |
|---|---|
| 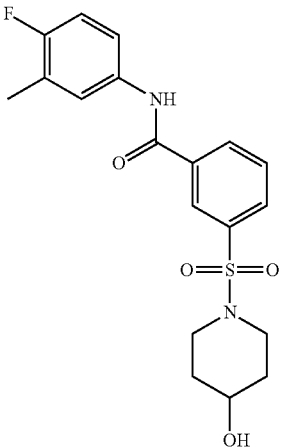 393 GB A10B01C20 | 311 |
| 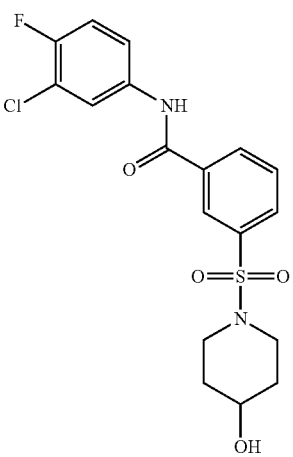 413/415 GB A10B01C15 | 314 |
| Structure MS(M + H)+ Synthetic method | Cmp. ID |
|---|---|
| 397 GB A10B01C24 ¹H NMR (400 MHz, DMSO-d6) δ 10.83(s, 1H), 8.25 (m, 2H), 7.96 (m, 1 H), 7.83 (m, 1H), 7.56 (m, 2H), 7.01(m, 1H), 4.68 (d, 1H), 4.54(m, 1H), 3.17(m, 2H), 1.76(m, 2H), 1.44(m, 2H) | 310 |

TABLE 1-continued

| Structure MS(M + H)+ Synthetic method | Cmp. ID |
|---|---|
| [3,4,5-trifluorophenyl amide of 3-(4-hydroxypiperidin-1-ylsulfonyl)benzoic acid]  415  GB  A10B01C40  ¹H NMR (400 MHz, DMSO-d6) δ 10.81(s, 1H), 8.28 (m, 2H), 7.98 (d, 1 H), 7.85 (t, 1H), 7.74 (m, 2H), 4.68(d, 1H), 3.54(m, 2H), 3.15(m, 2H), 2.81(m, 2H), 1.74(m, 2H), 1.42(m, 2H). | 318 |
| [4-chloro-3-fluorophenyl amide of 3-(4-(cyclopropylcarbonyl)piperazin-1-ylsulfonyl)benzoic acid]  466/468  GA  A15B01C83 | 321 |

TABLE 1-continued

| Structure MS(M + H)+ Synthetic method | Cmp. ID |
|---|---|
| [4-chloro-3-fluorophenyl amide of 3-(2-(hydroxymethyl)pyrrolidin-1-ylsulfonyl)benzoic acid]  413/415  GA  A04B01C83 | 322 |
| [4-chloro-3-fluorophenyl amide of 3-(4-hydroxypiperidin-1-ylsulfonyl)benzoic acid]  413/415  GA  A10B01C83  ¹H NMR (400 MHz, DMSO-d6) δ 10.79(s, 1H), 8.27(d, 1H), 7.95 (m, 2 H), 7.83 (m, 1H), 7.59 (d, 2H), 3.16(d, 2H), 2.77 (m, 2H), 1.73(m, 2H), 1.43(m, 2H), 1.17 (m, 1H) | 328 |
| [3-methylphenyl amide of 3-(N-methyl-N-(2-hydroxyethyl)sulfamoyl)benzoic acid]  349  GB  A20B01C08 | 329 |

TABLE 1-continued
| Structure MS(M + H)+ Synthetic method | Cmp. ID |
|---|---|
| 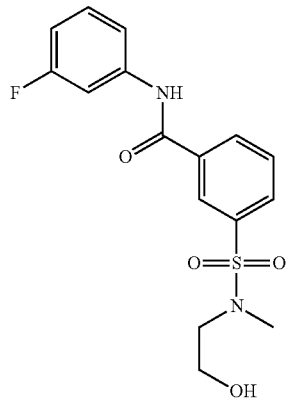<br>353<br>GB<br>A20B01C02 | 331 |
| 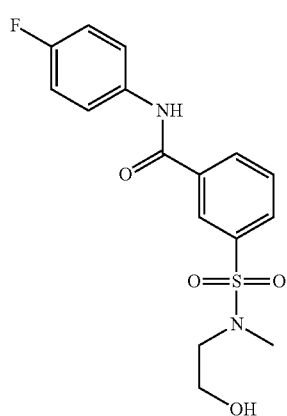<br>353<br>GB<br>A20B01C03 | 332 |
| 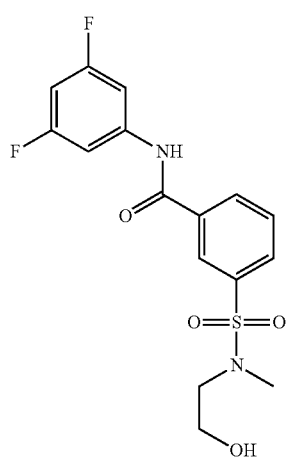<br>371<br>GB<br>A20B01C24 | 335 |
TABLE 1-continued
| Structure MS(M + H)+ Synthetic method | Cmp. ID |
|---|---|
| 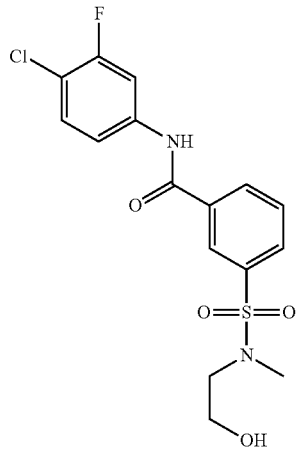<br>387/389<br>GB<br>A20B01C83 | 336 |
| 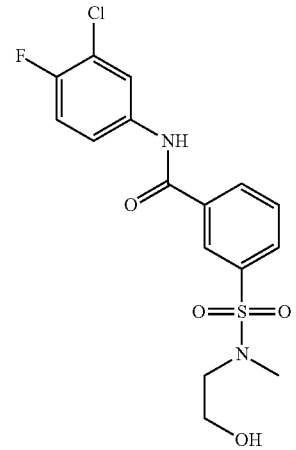<br>387/389<br>GB<br>A20B01C15 | 337 |

TABLE 1-continued

| Structure MS(M + H)⁺ Synthetic method | Cmp. ID |
|---|---|
| *[structure: 4-fluoro-3-methylphenyl benzamide with sulfonamide N(Me)CH₂CH₂OH]*<br>367<br>GB<br>A20B01C20 | 338 |
| *[structure: 3-fluorophenyl benzamide with sulfonamide N(Et)CH₂CH₂OH]*<br>367<br>GB<br>A50B01C02 | 341 |
| *[structure: 4-fluorophenyl benzamide with sulfonamide N(Et)CH₂CH₂OH]*<br>367<br>GB<br>A50B01C03 | 342 |
| *[structure: 3-chlorophenyl benzamide with sulfonamide N(Et)CH₂CH₂OH]*<br>383/385<br>GB<br>A50B01C05 | 343 |
| *[structure: 3,5-difluorophenyl benzamide with sulfonamide N(Et)CH₂CH₂OH]*<br>385<br>GB<br>A50B01C24 | 345 |
| *[structure: 3-chloro-4-fluorophenyl benzamide with sulfonamide N(Et)CH₂CH₂OH]*<br>401/403<br>GB<br>A50B01C15 | 347 |

TABLE 1-continued
| Structure MS(M + H)+ Synthetic method | Cmp. ID |
|---|---|
| 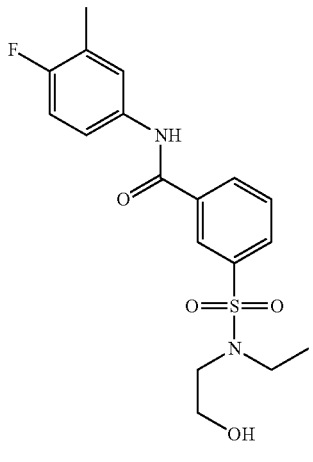 381 GB A50B01C20 | 348 |
| 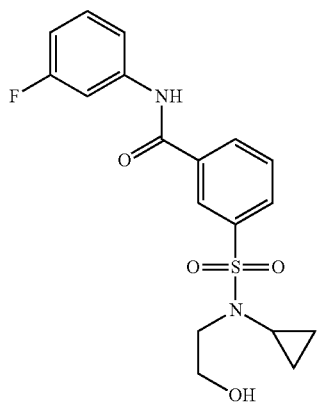 379 GB A51B01C02 | 351 |
| 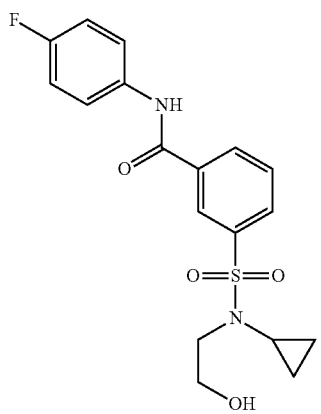 379 GB A51B01C02 | 352 |
TABLE 1-continued
| Structure MS(M + H)+ Synthetic method | Cmp. ID |
|---|---|
| 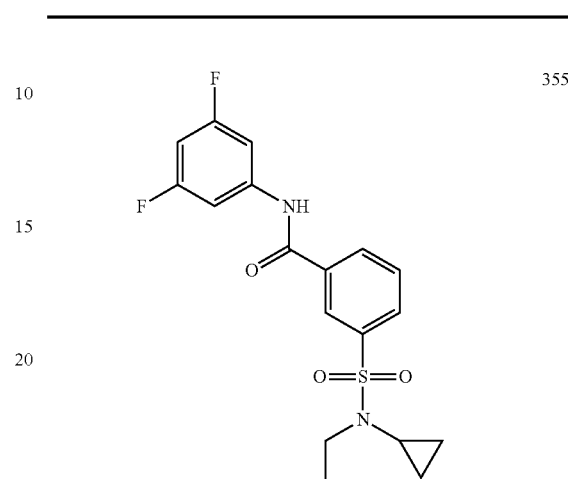 397 GB A51B01C24 | 355 |
| 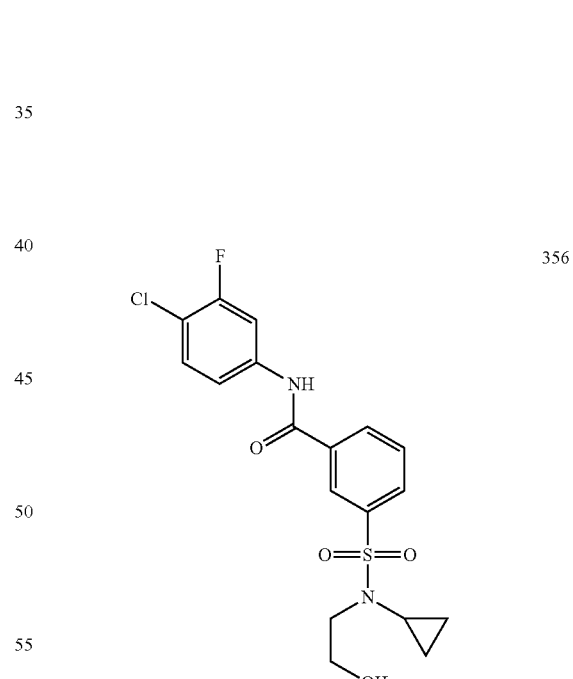 413/415 GB A51B01C83 | 356 |

TABLE 1-continued

| Structure MS(M + H)+ Synthetic method | Cmp. ID |
|---|---|
| [Structure: 3-chloro-4-fluorophenyl benzamide with sulfonamide N-cyclopropyl-N-(2-hydroxyethyl)] 413/415 GB A51B01C15 | 357 |
| [Structure: 4-fluoro-3-methylphenyl benzamide with sulfonamide N-cyclopropyl-N-(2-hydroxyethyl)] 393 GB A51B01C20 | 358 |
| [Structure: 3-bromophenyl benzamide with sulfonamide N-methyl-N-(2,3-dihydroxypropyl)] 444/446 GA A52B01C31 | 359 |
| [Structure: 3-bromophenyl benzamide with sulfonamide N-methyl-N-(2-hydroxy-3-methoxypropyl)] 457/459 GA A58B01C31 | 360 |
| [Structure: 3-bromophenyl benzamide with sulfonamide N-methyl-N-(2-hydroxypropyl)] 427/429 GA A53B01C31 | 361 |

TABLE 1-continued
| Structure MS(M + H)+ Synthetic method | Cmp. ID |
|---|---|
| 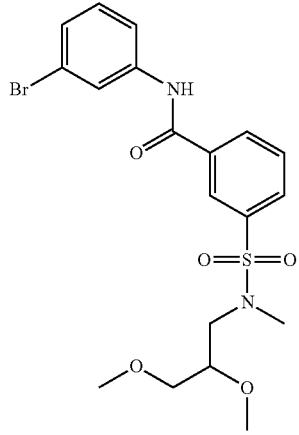<br>471/473<br>GA<br>A55B01C31 | 363 |
| 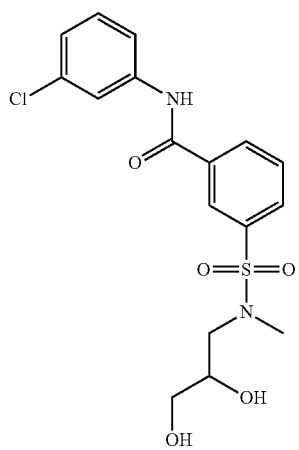<br>399/411<br>GA<br>A52B01C05 | 366 |
| 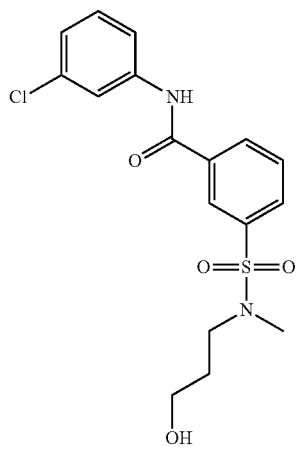<br>383/385<br>GA<br>A56B01C05 | 371 |
TABLE 1-continued
| Structure MS(M + H)+ Synthetic method | Cmp. ID |
|---|---|
| 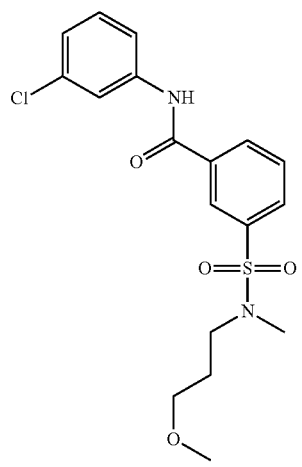<br>397/399<br>GA<br>A57B01C05 | 372 |
| 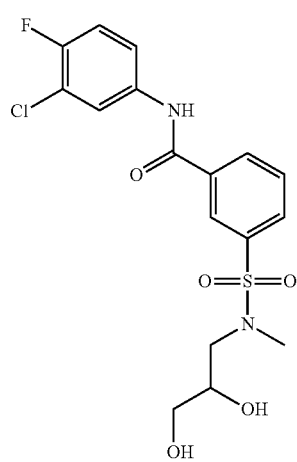<br>417/419<br>GA<br>A52B01C15 | 373 |

TABLE 1-continued

| Structure MS(M + H)+ Synthetic method | Cmp. ID |
|---|---|
| (3-chloro-4-fluorophenyl)-NHC(O)-C6H4-SO2-N(CH3)-CH2-CH(OH)-CH2-OCH3<br>431/433<br>GA<br>A58B01C15 | 374 |
| (3-chloro-4-fluorophenyl)-NHC(O)-C6H4-SO2-N(CH3)-CH2-CH(OH)-CH3<br>401/403<br>GA<br>A53B01C15 | 375 |
| (3-chloro-4-fluorophenyl)-NHC(O)-C6H4-SO2-N(CH3)-CH2-CH2-OCH3<br>401/403<br>GA<br>A54B01C15 | 376 |
| (4-fluoro-3-nitrophenyl)-NHC(O)-C6H4-SO2-N(azetidine-3-ol)<br>396<br>GA<br>A19B01C46 | 380 |
| (4-fluoro-3-nitrophenyl)-NHC(O)-C6H4-SO2-N(piperidin-4-ol)<br>424<br>GA<br>A10B01C46 | 383 |

TABLE 1-continued

| Structure MS(M + H)+ Synthetic method | Cmp. ID |
|---|---|
| *[4-fluoro-3-nitrophenyl benzamide with 3-sulfonyl-(4-hydroxymethyl)piperidine]*<br>392<br>GA<br>A06B01C46<br>¹H NMR (400 MHz, CD₃OD) δ 10.91 (s, 1H), 8.68(d, 1 H), 8.32 (d, 1H), 8.26 (m, 1H), 798 (m, 2H), 7.75(t, 1H), 7.64(m, 1H), 4.48(s, 1H) 3.62(m, 2H), 3.28(m, 2H), 2.25(m, 2H), 1.72(m, 2H), 1.32(m, 1H), 1.16(m, 2H). | 386 |
| *[4-fluoro-3-nitrophenyl benzamide with 3-sulfonyl-(3-hydroxy)pyrrolidine]*<br>364<br>GA<br>A17B01C46 | 387 |
| *[4-fluoro-3-nitrophenyl benzamide with 3-sulfonyl-(3-hydroxy)piperidine]*<br>378<br>GA<br>A08B01C46 | 388 |
| *[4-fluoro-3-(trifluoromethyl)phenyl benzamide with 3-sulfonyl-(2-hydroxymethyl)pyrrolidine]*<br>378<br>GA<br>A18B01C47 | 390 |
| *[4-fluoro-3-(trifluoromethyl)phenyl benzamide with 3-sulfonyl-N-methyl-N-(2-hydroxyethyl)amine]*<br>352<br>GA<br>A20B01C47 | 391 |

TABLE 1-continued
| Structure MS(M + H)+ Synthetic method | Cmp. ID |
|---|---|
| 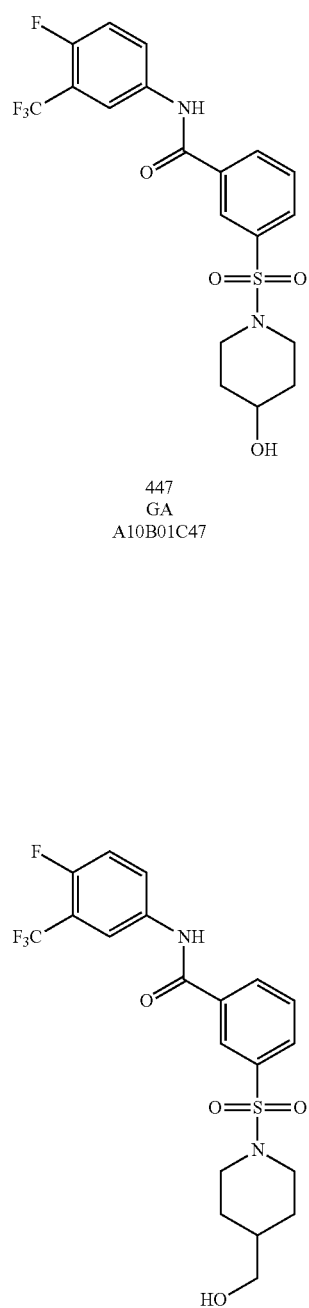 447 GA A10B01C47 | 392 |
| 461 GA A06B01C47 | 395 |
TABLE 1-continued
| Structure MS(M + H)+ Synthetic method | Cmp. ID |
|---|---|
| 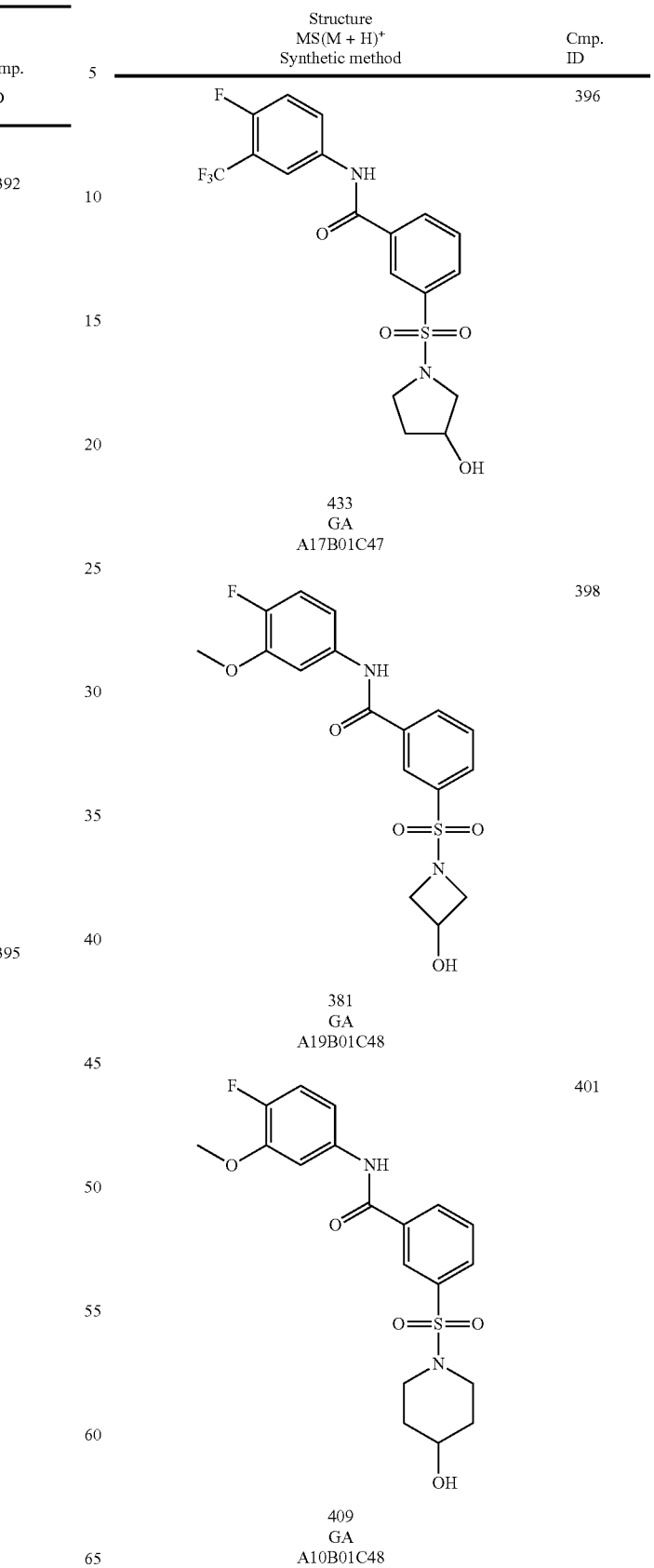 433 GA A17B01C47 | 396 |
| 381 GA A19B01C48 | 398 |
| 409 GA A10B01C48 | 401 |

TABLE 1-continued

| Structure MS(M + H)+ Synthetic method | Cmp. ID |
|---|---|
| [Structure: 4-fluoro-3-methoxyphenyl amide of 3-(4-(hydroxymethyl)piperidin-1-ylsulfonyl)benzoic acid]<br>423<br>GA<br>A06B01C48<br>¹H NMR (400 MHz, CD₃OD) δ 10.91 (s, 1H), 8.68(d, 1 H), 8.32 (d, 1H), 8.26 (m, 1H), 798 (m, 2H), 7.75(t, 1H), 7.64(m, 1H), 4.48(s, 1H), 3.85(s, 3H), 3.62(m, 2H), 3.28(m, 2H), 2.25(m, 2H), 1.72(m, 2H), 1.32(m, 1H), 1.16(m, 2H). | 404 |
| [Structure: 4-fluoro-3-methoxyphenyl amide of 3-(3-hydroxypyrrolidin-1-ylsulfonyl)benzoic acid]<br>395<br>GA<br>A17B01C48 | 405 |

TABLE 1-continued

| Structure MS(M + H)+ Synthetic method | Cmp. ID |
|---|---|
| [Structure: 4-fluoro-3-methoxyphenyl amide of 3-(3-hydroxypiperidin-1-ylsulfonyl)benzoic acid]<br>409<br>GA<br>A08B01C48 | 406 |
| [Structure: 3-bromo-4-fluorophenyl amide of 3-(3-hydroxyazetidin-1-ylsulfonyl)benzoic acid]<br>429/431<br>GA<br>A19B01C49 | 407 |
| [Structure: 3-bromo-4-fluorophenyl amide of 3-(2-(hydroxymethyl)pyrrolidin-1-ylsulfonyl)benzoic acid]<br>457/459<br>GA<br>A18B01C49 | 408 |

TABLE 1-continued

| Structure MS(M + H)+ Synthetic method | Cmp. ID |
|---|---|
| [Structure of N-(3-bromo-4-fluorophenyl)-3-((4-hydroxypiperidin-1-yl)sulfonyl)benzamide]<br>457/459<br>GA<br>A10B01C49 | 410 |
| [Structure of N-(3-bromo-4-fluorophenyl)-3-((2-(hydroxymethyl)piperidin-1-yl)sulfonyl)benzamide]<br>471/473<br>GA<br>A04B01C49 | 411 |
| [Structure of N-(3-bromo-4-fluorophenyl)-3-((4-(2-hydroxyethyl)piperidin-1-yl)sulfonyl)benzamide]<br>48/487<br>GA<br>A09B01C49 | 412 |
| [Structure of N-(3-bromo-4-fluorophenyl)-3-((3-hydroxypiperidin-1-yl)sulfonyl)benzamide]<br>457/459<br>GA<br>A08B01C49 | 415 |
| [Structure of N-(3-cyano-4-fluorophenyl)-3-((2-(hydroxymethyl)pyrrolidin-1-yl)sulfonyl)benzamide]<br>404<br>GA<br>A18B01C52 | 417 |

TABLE 1-continued

| Structure MS(M + H)+ Synthetic method | Cmp. ID |
|---|---|
| [Structure of compound 378] | 418 |
| 378 GA A20B01C52 | |
| [Structure of compound 404] | 419 |
| 404 GA A10B01C52 ¹H NMR (400 MHz, CD₃OD) δ 10.84 (s, 1H), 8.68(d, 1 H), 8.32 (d, 1H), 8.26 (m, 1H), 798 (m, 2H), 7.75(t, 1H), 7.64(m, 1H), 4.68(s, 1H), 3.52(m, 2H), 3.14(m, 2H), 2.79(m, 2H), 1.74(m, 2H), 1.42(m, 2H). | |

TABLE 1-continued

| Structure MS(M + H)+ Synthetic method | Cmp. ID |
|---|---|
| [Structure of compound 418] | 420 |
| 418 GA A04B01C52 | |
| [Structure of compound 381] | 425 |
| 381 GA A19B01C51 | |
| [Structure of compound 383] | 427 |
| 383 GA A20B01C51 | |

TABLE 1-continued
| Structure MS(M + H)+ Synthetic method | Cmp. ID |
|---|---|
| 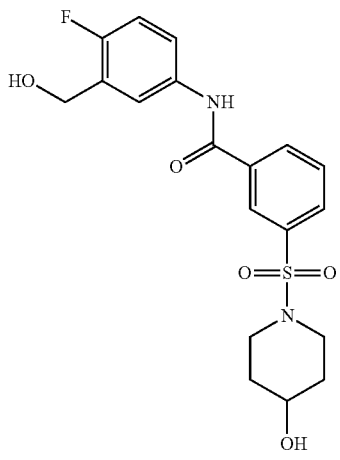<br>409<br>GA<br>A10B01C51 | 428 |
| 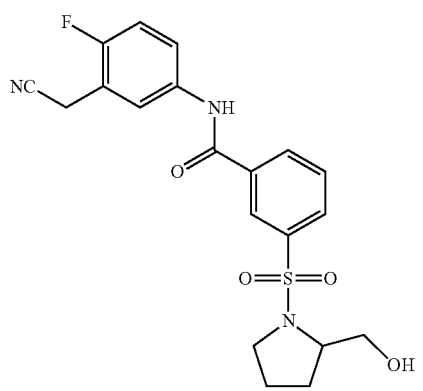<br>418<br>GA<br>A18B01C52 | 435 |
| 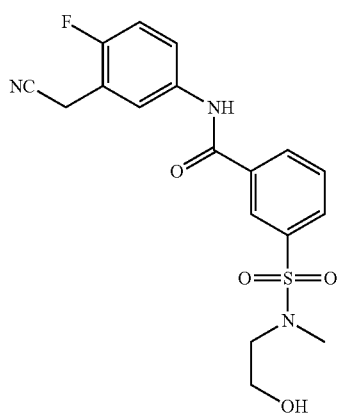<br>392<br>GA<br>A20B01C52 | 436 |
TABLE 1-continued
| Structure MS(M + H)+ Synthetic method | Cmp. ID |
|---|---|
| 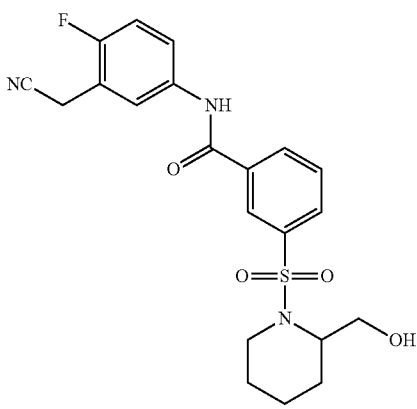<br>406<br>GA<br>A04B01C52 | 438 |
| 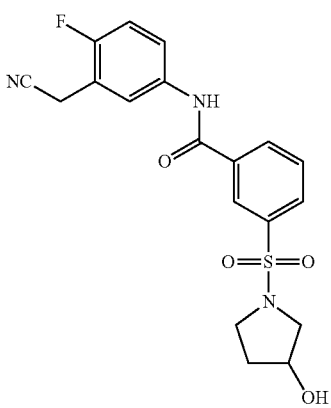<br>378<br>GA<br>A17B01A52<br>¹H NMR (400 MHz, CD₃OD) δ 8.37 (s, 1H), 8.21(d, 1 H), 8.04 (d, 1H), 7.88 (m, 1H), 7.76 (m, 2H), 7.18(t, 1H), 4.28(m, 1H), 3.92(s, 2H) 3.40(m, 3H), 3.24(m, 1H), 1.88(m, 1H), 1.76(m, 1H). | 441 |

TABLE 1-continued
| Structure MS(M + H)+ Synthetic method | Cmp. ID |
|---|---|
| 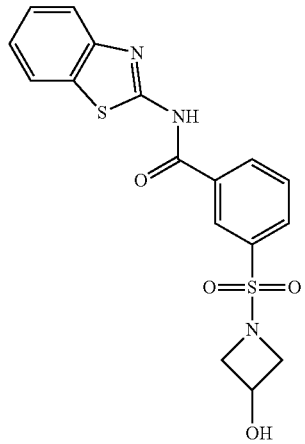<br>390<br>GA<br>A19B01C55 | 447 |
| 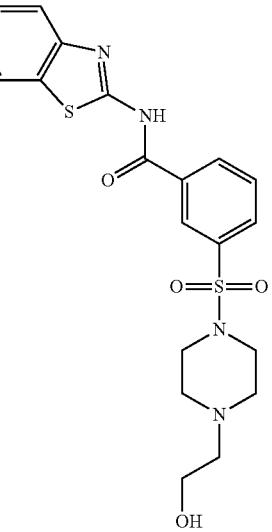<br>446<br>GA<br>A09B01C55 | 448 |
TABLE 1-continued
| Structure MS(M + H)+ Synthetic method | Cmp. ID |
|---|---|
| 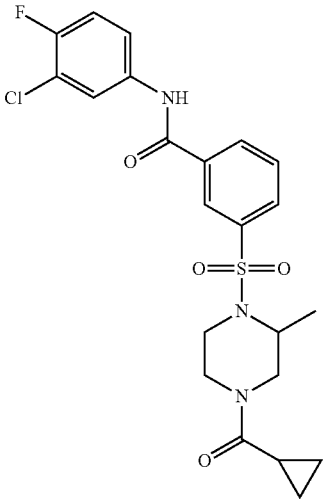<br>480/482<br>GA<br>A61B01C15 | 455 |
| 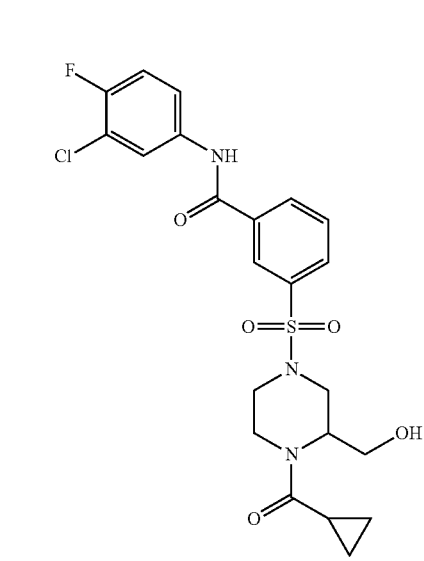<br>496/498<br>GA<br>A64B01C15 | 458 |

TABLE 1-continued
| Structure MS(M + H)+ Synthetic method | Cmp. ID |
|---|---|
| 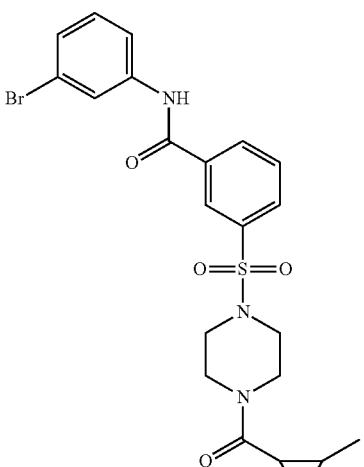 506/508 GA A65B01C31 | 463 |
| 460 GA A65B01C20 | 467 |
TABLE 1-continued
| Structure MS(M + H)+ Synthetic method | Cmp. ID |
|---|---|
| 460 GA A66B01C20 | 468 |
| 379 GA A17B01C20 | 471 |

TABLE 1-continued

| Structure MS(M + H)+ Synthetic method | Cmp. ID |
|---|---|
| (structure) 393 GA A49B01C20 | 472 |
| (structure) 393 GA A18B01C20 | 473 |
| (structure) 376 GA A109B01C20 | 474 |
| (structure) 441/443 GA A67B01C15 | 477 |
| (structure) 421 GA A67B01C20 | 478 |

TABLE 1-continued
| Structure MS(M + H)+ Synthetic method | Cmp. ID |
|---|---|
| 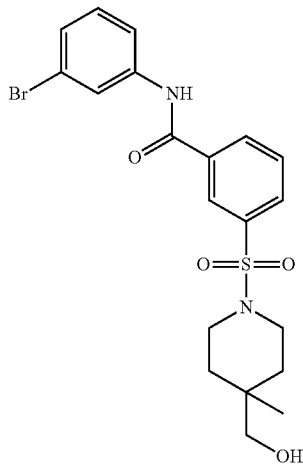 467/469 GA A67B01C31 | 479 |
| 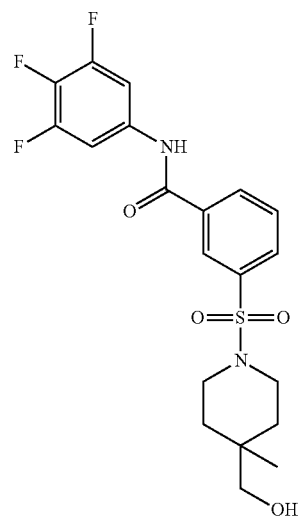 443 GA A67B01C40 | 482 |
TABLE 1-continued
| Structure MS(M + H)+ Synthetic method | Cmp. ID |
|---|---|
| 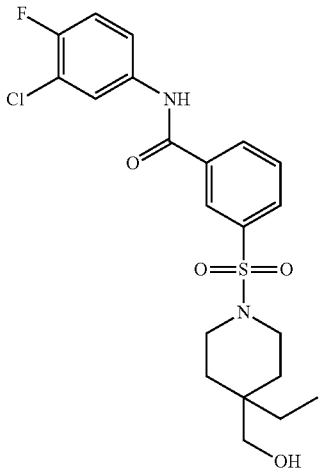 455/457 GA A68B01C15 | 489 |
| 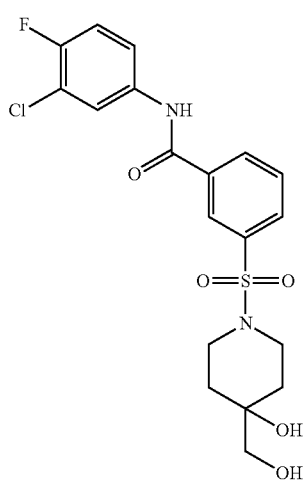 443/445 GA A81B01C15 | 501 |

TABLE 1-continued
| Structure MS(M + H)+ Synthetic method | Cmp. ID |
|---|---|
| 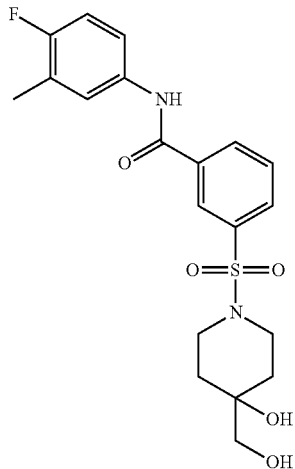<br>423<br>GA<br>A81B01C20 | 502 |
| 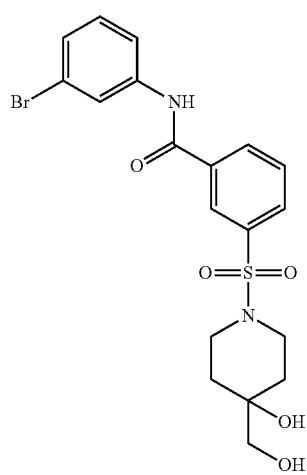<br>469/471<br>GA<br>A81B01C31 | 503 |
TABLE 1-continued
| Structure MS(M + H)+ Synthetic method | Cmp. ID |
|---|---|
| 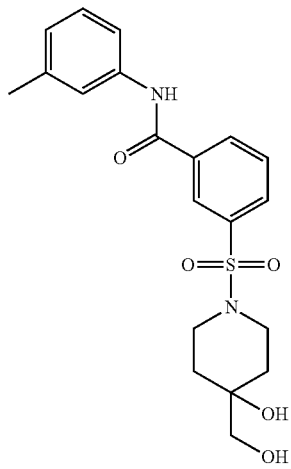<br>405<br>GA<br>A81B01C08 | 505 |
| 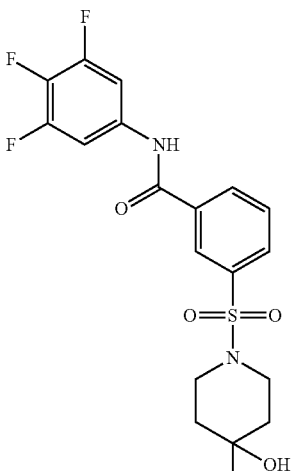<br>445<br>GA<br>A81B01C40 | 506 |

TABLE 1-continued
| Structure MS(M + H)+ Synthetic method | Cmp. ID |
|---|---|
| 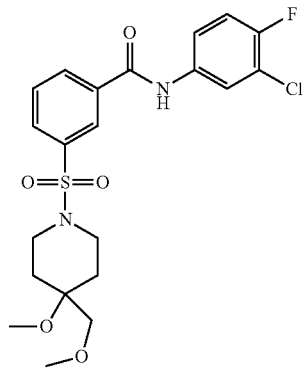 471 GA A82B011C15 <br> $^1$H NMR (400 MHz, CDCl$_3$) δ 8.21 (s, 1H), 8.19 (d, 1 H), 8.07 (s, 1H), 7.96 (d, 1H), 7.91 (m, 1H), 7.72 (t, 1H), 7.51 (m, 1H), 7.19 (t, 1H), 3.62(d, 2H), 3.36 (s, 3H), 3.28(s, 2H), 3.18 (s, 3H), 2.62 (t, 2H), 1.87(d, 2H), 1.65(d, 2H). | 507 |
| 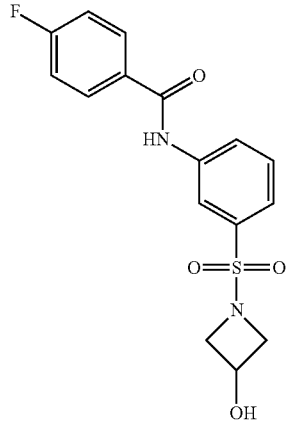 351 GB A19B05C93 | 520 |
TABLE 1-continued
| Structure MS(M + H)+ Synthetic method | Cmp. ID |
|---|---|
| 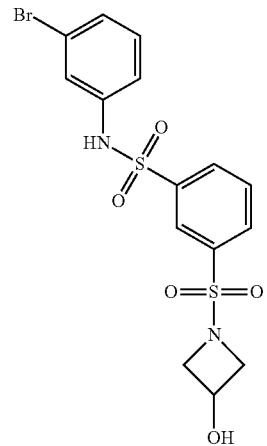 448/450 GE A19B10C31 | 521 |
| 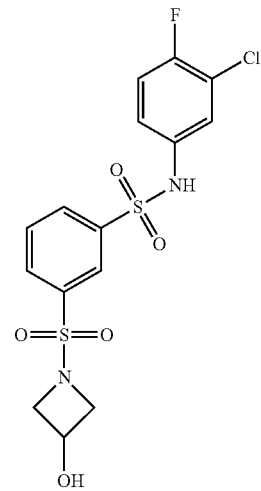 421/423 GE A19B10C15 | 522 |

TABLE 1-continued
| Structure MS(M + H)+ Synthetic method | Cmp. ID |
|---|---|
| 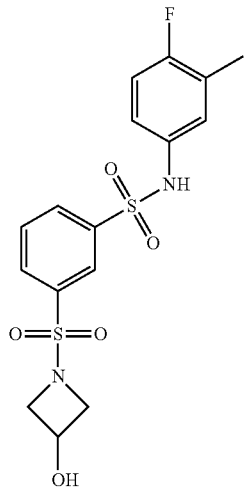<br>401<br>GE<br>A19B10C20 | 523 |
| 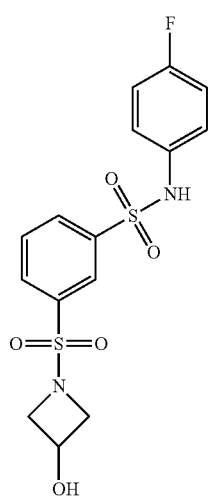<br>387<br>GE<br>A19B10C03 | 524 |
TABLE 1-continued
| Structure MS(M + H)+ Synthetic method | Cmp. ID |
|---|---|
| 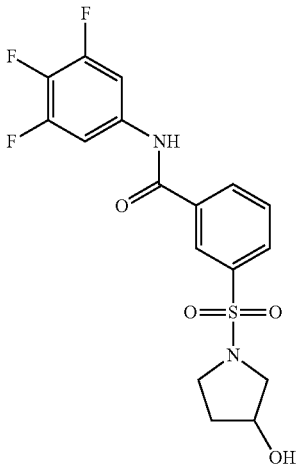<br>401<br>GA<br>A17B01C40 | 526 |
| 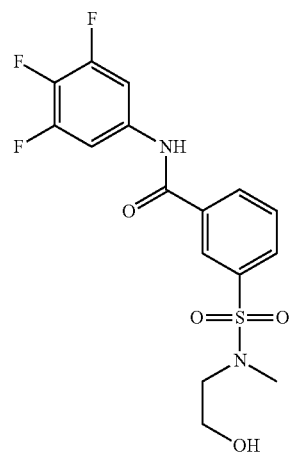<br>389<br>GA<br>A20B01C40 | 527 |

TABLE 1-continued

| Structure MS(M + H)+ Synthetic method | Cmp. ID |
|---|---|
| (3,4,5-trifluorophenyl-NH-C(O)-phenyl-SO2-N(Et)-CH2CH2OH) 403 GA A50B01C40 | 528 |
| (3-Cl-4-F-phenyl-NH-C(O)-phenyl-SO2-N(4-methyl-4-hydroxypiperidine)) 427/429 GA A73B01C15 | 529 |
| (4-F-3-methylphenyl-NH-C(O)-phenyl-SO2-N(4-methyl-4-hydroxypiperidine)) 407 GA A73B01C20 | 530 |
| (3,4,5-trifluorophenyl-NH-C(O)-phenyl-SO2-N(4-methyl-4-hydroxypiperidine)) 429 GA A73B01C40 $^1$H NMR (400 MHz, CD$_3$OD) δ 8.30 (s, 1H), 8.23(d, 1 H), 7.98 (d, 1H), 7.76 (t, 1H), 7.58 (m, 2H), 3.48(m, 2H), 2.74 (m, 2H), 1.61(m, 4H), 1.16 (s, 3H). | 531 |

TABLE 1-continued
| Structure MS(M + H)+ Synthetic method | Cmp. ID |
|---|---|
| 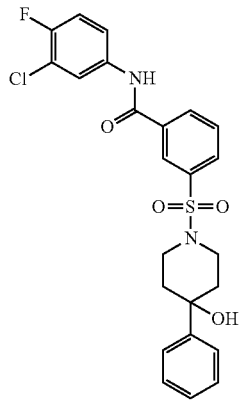 489/491 GA A75B01C15 <br> 1H NMR (400 MHz, CD3OD) δ 10.73 (s, 1H), 8.33(m, 2 H), 8.04 (d, 2H), 7.38 (t, 1H), 7.24 (m, 1H), 7.46(m, 3H), 7.33 (m, 2H), 7.19(m, 1H), 4.85 (s, 1H), 3.63 (m, 2H), 2.63 (m, 2H), 1.95 (m, 2H), 1.63 (m, 2H) | 541 |
| 471/473 GA A75B01C05 | 544 |
TABLE 1-continued
| Structure MS(M + H)+ Synthetic method | Cmp. ID |
|---|---|
| 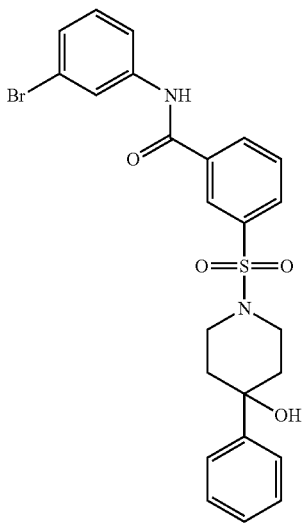 515/517 GA A75B01C31 | 545 |
| 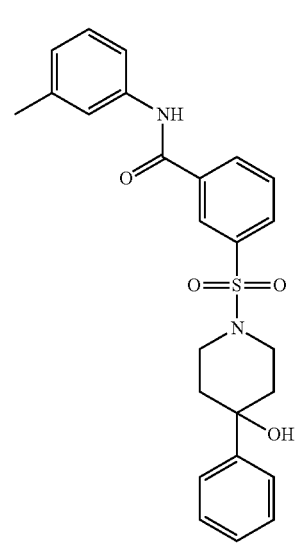 451 GA A75B01C05 | 546 |

TABLE 1-continued
| Structure MS(M + H)+ Synthetic method | Cmp. ID |
|---|---|
| 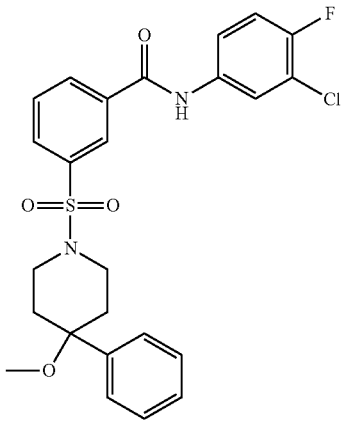 503/505 GA A79B01C15 | 547 |
| 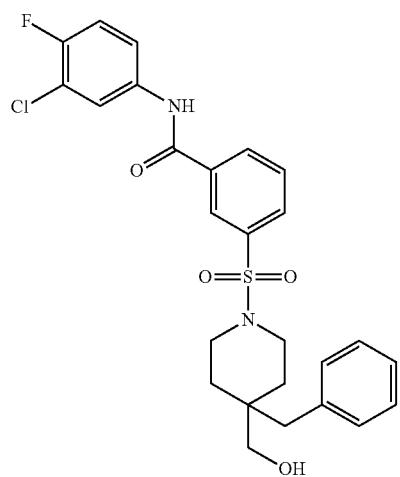 517/519 GA A69B01C15 | 553 |
TABLE 1-continued
| Structure MS(M + H)+ Synthetic method | Cmp. ID |
|---|---|
| 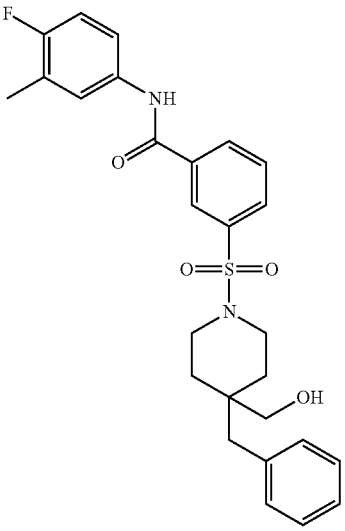 497 GA A69B01C20 | 554 |
| 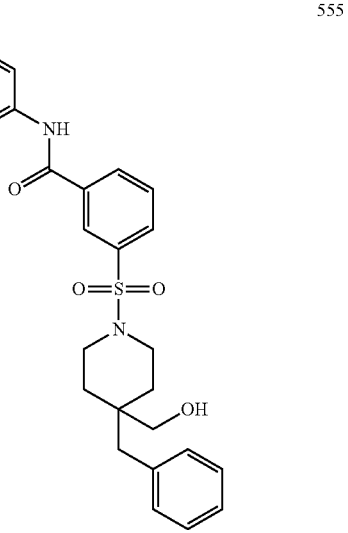 519 GA A69B01C40 | 555 |

TABLE 1-continued
| Structure MS(M + H)+ Synthetic method | Cmp. ID |
|---|---|
| 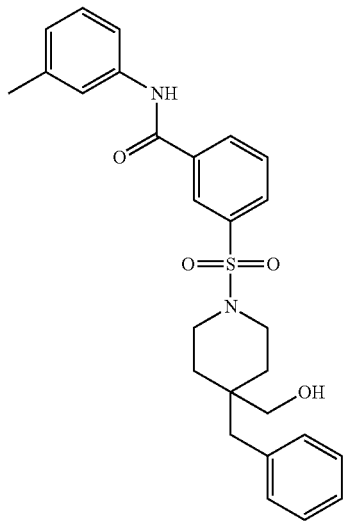 479 GA A69B01C08 | 558 |
| 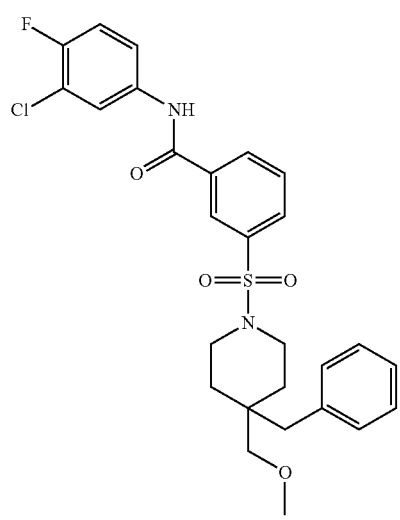 531/532 GA A72B01C15 | 559 |
TABLE 1-continued
| Structure MS(M + H)+ Synthetic method | Cmp. ID |
|---|---|
| 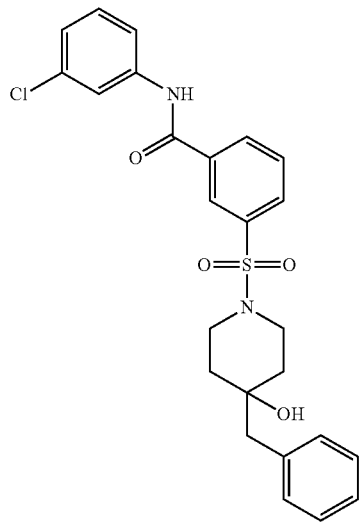 485/487 GA A76B01C05 | 568 |
| 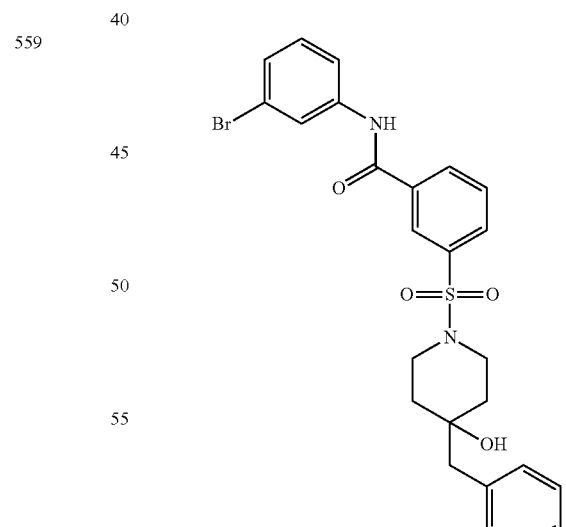 529/531 GA A76B01C31 | 569 |

TABLE 1-continued
| Structure MS(M + H)+ Synthetic method | Cmp. ID |
|---|---|
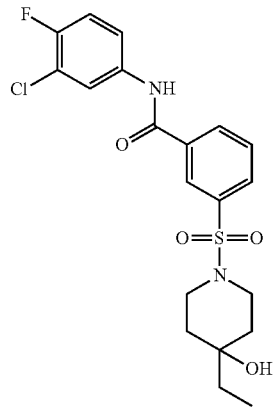
577
441/443
GA
A74B01C15
¹H NMR (400 MHz, CD₃OD) δ 8.32 (s, 1H), 8.19(d, 1 H), 7.98 (m, 2H), 7.76 (t, 1H), 7.53(m, 1H), 7.23 (t, 1H), 3.55 (m, 2H), 2.68 (m, 2H), 1.58 (m, 4H), 1.42 (q, 2H), 0.84 (t, 3H).
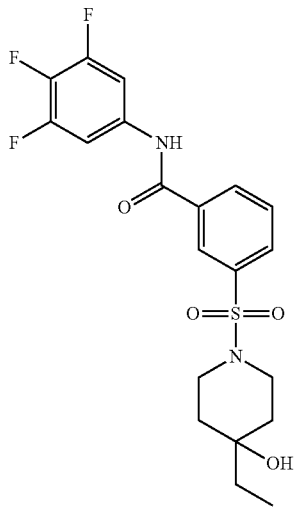
579
443
GA
A74B01C40
578
421
GA
A74B01C20
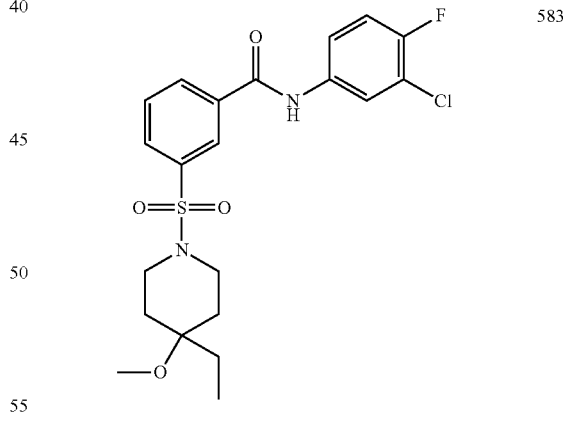
583
455/457
GA
A78B01C15
¹H NMR (400 MHz, CD₃OD) δ 8.33 (s, 1H), 8.25(d, 1 H), 8.00 (d, 2H), 7.80 (t, 1H), 7.68(m, 1H), 7.30 (t, 1H), 3.58 (d, 2H), 3.01 (s, 3H), 2.62 (t, 2H), 1.85 (d, 2H), 1.55 (m, 4H), 0.84 (t, 3H).

TABLE 1-continued
| Structure MS(M + H)+ Synthetic method | Cmp. ID |
|---|---|
| 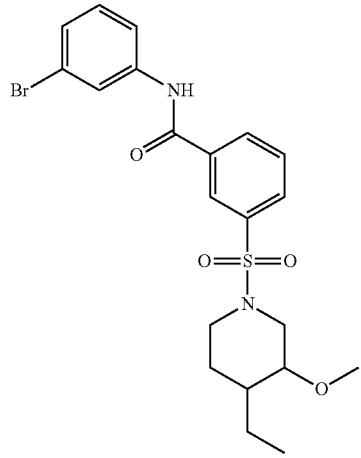 481/483 GA A78B01C31 | 587 |
| 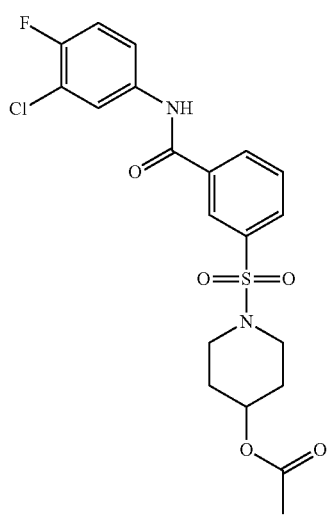 455/457 GA A83B01C15 | 589 |
TABLE 1-continued
| Structure MS(M + H)+ Synthetic method | Cmp. ID |
|---|---|
| 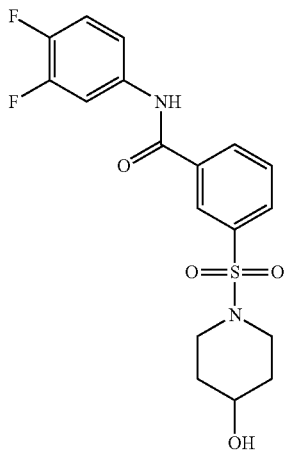 397 GB A10B01C63 | 593 |
| 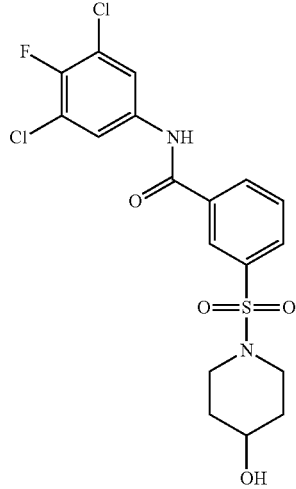 447/449 GB A10B01C57 | 594 |

TABLE 1-continued

| Structure MS(M + H)+ Synthetic method | Cmp. ID |
|---|---|
| [Structure: 3,5-difluoro-4-chlorophenyl amide of 3-((4-hydroxypiperidin-1-yl)sulfonyl)benzamide] 431/432 GB A10B01C58 | 595 |
| [Structure: 3-chloro-4-fluorophenyl amide of 3-((3-ethyl-4-hydroxypiperidin-1-yl)sulfonyl)benzamide] 441/443 GA A85B01C15 | 596-D1 |

TABLE 1-continued

| Structure MS(M + H)+ Synthetic method | Cmp. ID |
|---|---|
| [Structure: 3-chloro-4-fluorophenyl amide of 3-((3-ethyl-4-hydroxypiperidin-1-yl)sulfonyl)benzamide] 441/443 GA A85B01C15 | 596-D2 |
| [Structure: 4-fluoro-3-methylphenyl amide of 3-((3-ethyl-4-hydroxypiperidin-1-yl)sulfonyl)benzamide] 421 GA A85B01C20 <br> 1H NMR (400 MHz, CD3OD) δ 8.29 (s, 1H), 8.20(m, 1 H), 7.94 (m, 1H), 7.72 (m, 1H), 7.50(m, 2H), 7.01 (t, 1H), 3.57 (m, 2H), 3.23 (m, 1H), 2.68 (m, 1H), 2.39 (m, 1H), 2.26 (s, 3H), 1.92 (m, 1H), 1.73 (m, 1H), 1.53 (m, 1H), 1.42 (m, 1H), 1.19 (m, 1H), 0.91 (t, 3H). | 597_D1 |

TABLE 1-continued
| Structure MS(M + H)+ Synthetic method | Cmp. ID |
|---|---|
| 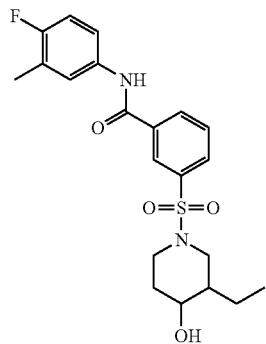 421 GA A85B01C20 ¹H NMR (400 MHz, CD₃OD) δ 8.29 (s, 1H), 8.20(m, 1 H), 7.94 (m, 1H), 7.72 (m, 1H), 7.50(m, 1H), 7.48 (m, 1H), 7.01 (t, 1H), 3.82 (m, 1H), 3.37 (m, 1H), 3.30 (m, 1H), 2.80 (m, 1H), 2.54 (m, 1H), 2.26 (s, 3H), 1.76 (m, 2H), 1.56 (m, 1H), 1.39 (m, 1H), 1.27 (m, 1H), 0.91 (t, 3H). | 597_D2 |
| 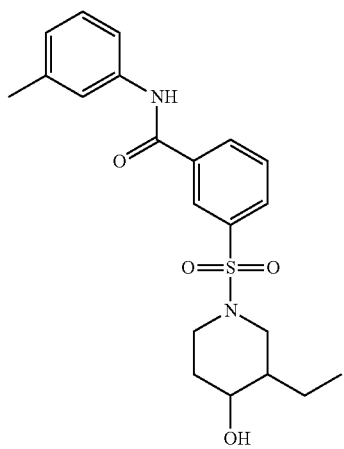 403 GA A85B01C08 | 601_D1 |
TABLE 1-continued
| Structure MS(M + H)+ Synthetic method | Cmp. ID |
|---|---|
| 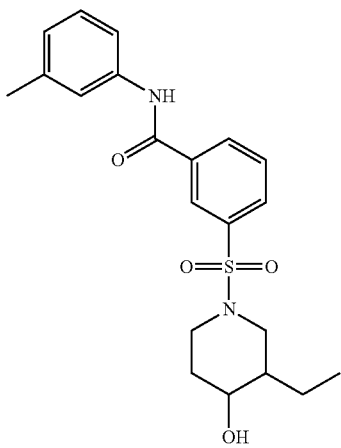 403 GA A85B01C08 | 601_D2 |
| 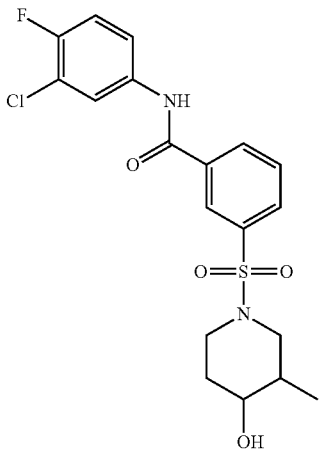 427/429 GA A84B01C15 | 608_D1 |

TABLE 1-continued
| Structure MS(M + H)+ Synthetic method | Cmp. ID |
|---|---|
| 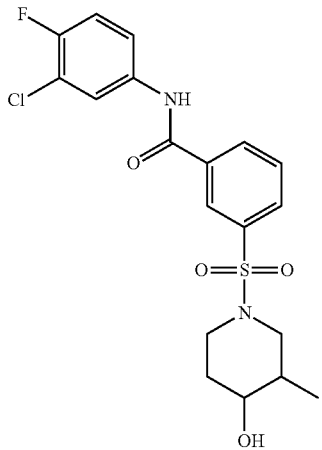<br>427/429<br>GA<br>A84B01C15 | 608_D2 |
| <br>429<br>GA<br>A84B01C40 | 610_D1 |
TABLE 1-continued
| Structure MS(M + H)+ Synthetic method | Cmp. ID |
|---|---|
| 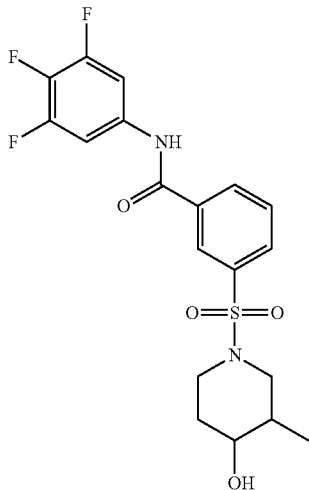<br>429<br>GA<br>A84B01C40 | 610_D2 |
| 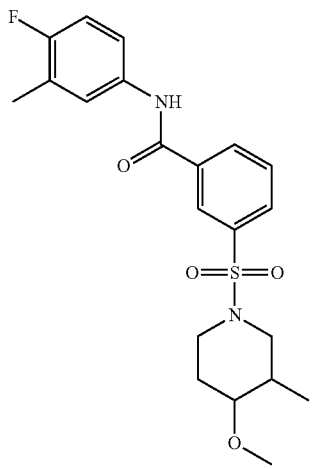<br>421<br>GA<br>A87B01C20 | 615_D1 |

TABLE 1-continued
| Structure MS(M + H)+ Synthetic method | Cmp. ID |
|---|---|
| 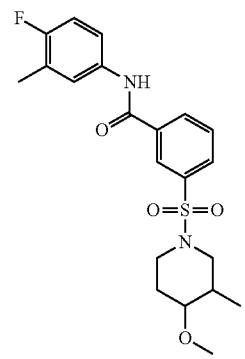 421 GA A87B01C20 $^1$H NMR (400 MHz, CDCl3): δppm: 8.17-8.13 (m, 2H), 7.99 (s, 1H), 7.90 (d, 1H), 7.70-7.66 (m, 1H), 7.54 (d, 1H), 7.42 (t, 1H), 7.00 (t, 1H), 3.46-3.42(m, 2H), 3.38 (s, 3H), 2.80-2.70 (m, 2H), 2.45-2.40 (m, 1H), 2.40 (s, 1H), 2.07-2.00 (m, 1H), 1.85-1.81 (m, 1H), 1.57-1.54 (m, 1H), 1.00-0.99 (m, 3H). | 615_D2 |
| 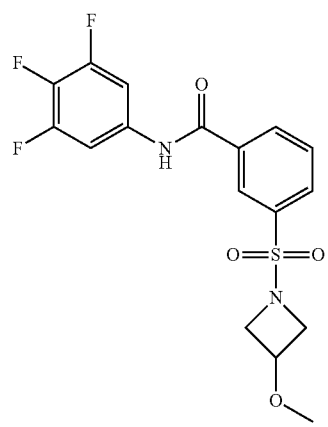 401 GA A108B01C40 | 620 |
TABLE 1-continued
| Structure MS(M + H)+ Synthetic method | Cmp. ID |
|---|---|
| 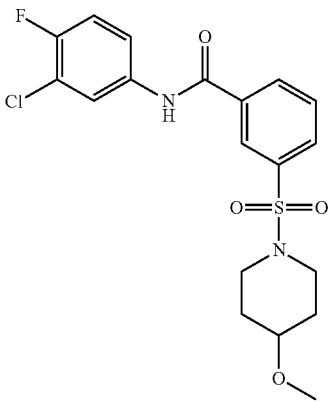 427/429 GA A131B01C15 | 621 |
| 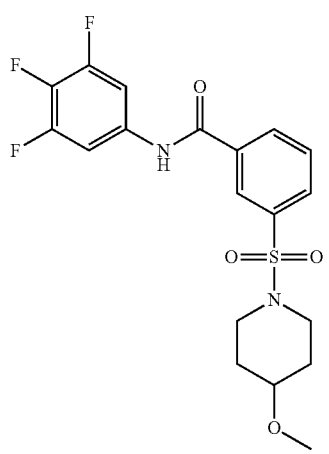 429 GA A131B01C40 | 622 |
| 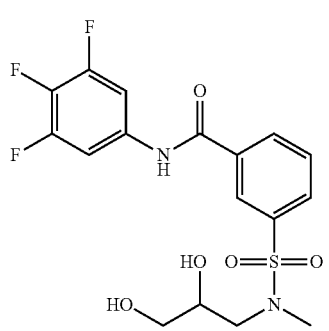 419 GA A52B01C40 | 623 |

TABLE 1-continued
| Structure MS(M + H)+ Synthetic method | Cmp. ID |
|---|---|
| 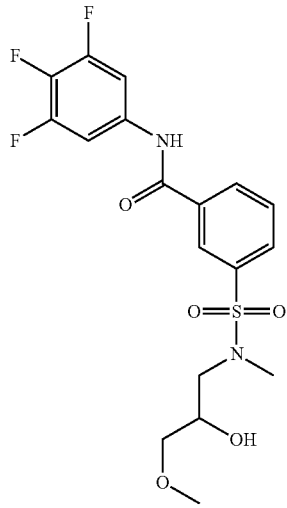 433 GA A58B01C40 | 624 |
| 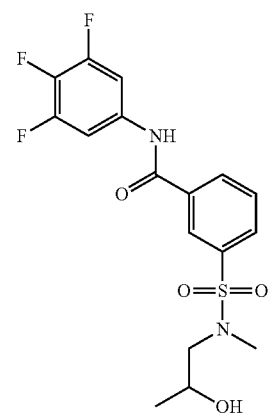 403 GA A53B01C40 1H NMR (400 MHz, CDCl3) δ 8.25 (s, 1H), 8.14 (d, J = 7.6 Hz, 1H), 7.91 (d, J = 7.6 Hz, 1H), 7.64 (t, J = 7.6 Hz, 1H), 7.49 (m, 1H), 7.29 (s, 1H) 3.94 (m, 1H), 3.33 (s, 1H), 3.04 (m, 1H), 2.92 (m, 1H), 2.83 (s, 3H), 1.16 (m, 3H). | 625 |
TABLE 1-continued
| Structure MS(M + H)+ Synthetic method | Cmp. ID |
|---|---|
| 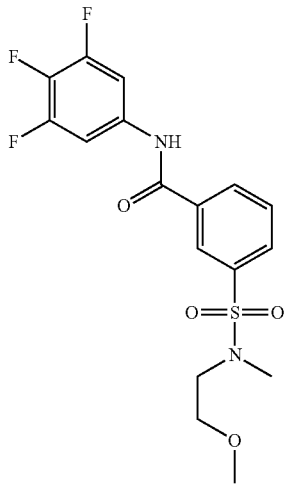 403 GA A54B01C40 | 626 |
| 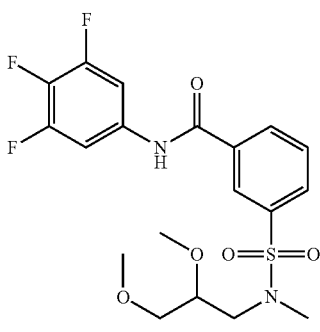 447 GA A55B01C40 | 627 |
| 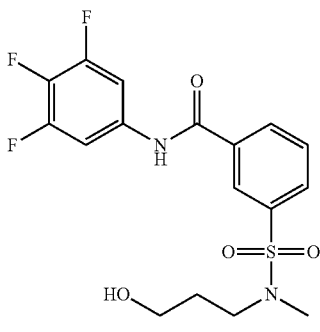 403 A GA 56B01C40 | 628 |

TABLE 1-continued
| Structure MS(M + H)+ Synthetic method | Cmp. ID |
|---|---|
| 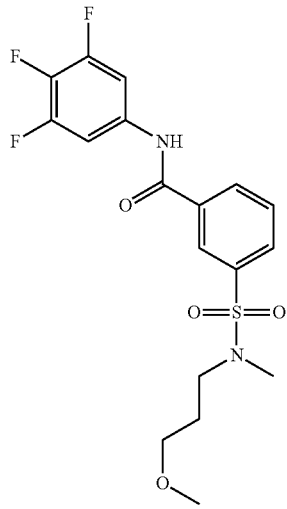<br>417<br>GA<br>A57B01C40 | 629 |
| 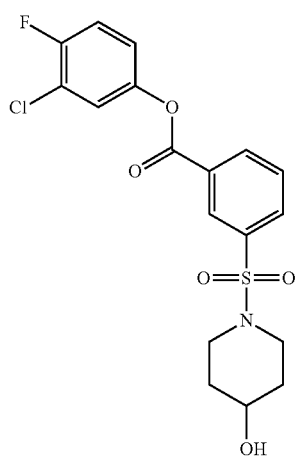<br>414/416<br>GA<br>A10B01C15 | 630 |
TABLE 1-continued
| Structure MS(M + H)+ Synthetic method | Cmp. ID |
|---|---|
| 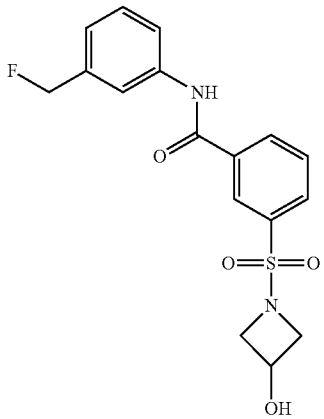<br>365<br>GA<br>A49B01C59 | 631 |
| 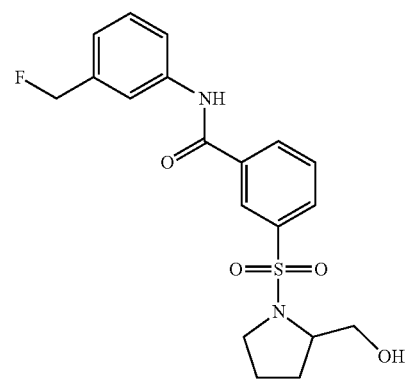<br>393<br>GA<br>A18B01C59 | 632_R |
| 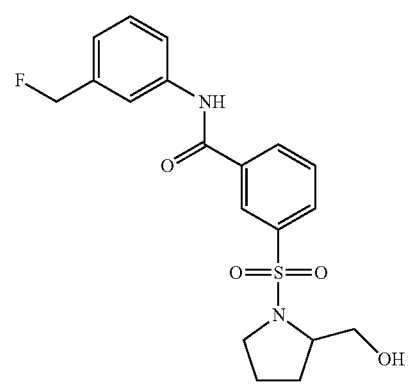<br>393<br>GA<br>A18B01C59 | 632_S |

TABLE 1-continued
| Structure MS(M + H)+ Synthetic method | Cmp. ID |
|---|---|
| 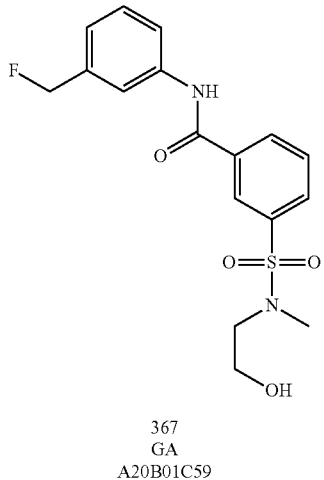 [SMILES: CN(CCO)S(=O)(=O)c1cccc(C(=O)Nc2cccc(CF)c2)c1]<br>367<br>GA<br>A20B01C59 | 633 |
| 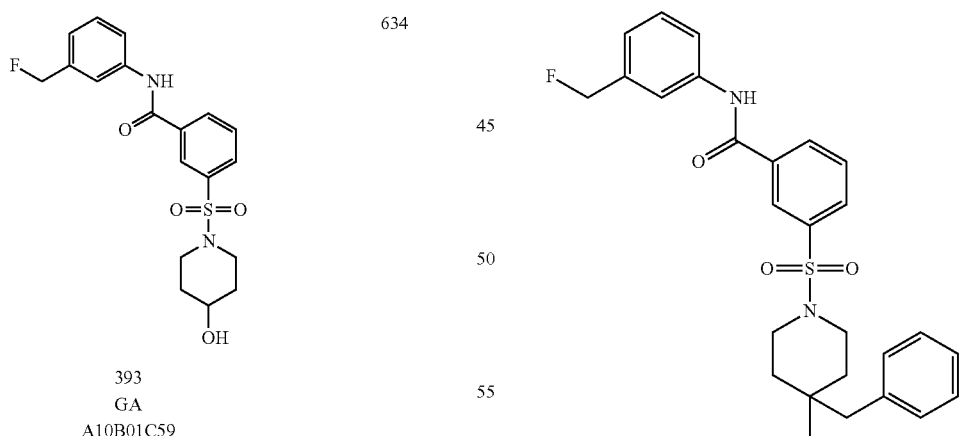<br>393<br>GA<br>A10B01C59<br>¹H NMR (400 MHz, CDCl3): δppm: 8.20 (s, 1H), 8.15-8.13 (m, 1H), 8.07 (s, 1H), 7.94-7.92 (m, 1H), 7.74-7.63 (m, 3H), 7.44-7.41 (m, 1H), 7.21-7.19 (m, 1H), 5.42 (d, 2H), 3.81 (m, 1H), 3.34-3.29 (m, 2H), 2.98-2.92 (m, 2H), 1.96-1.89 (m, 2H), 1.71-1.62 (m, 2H), 1.42 (m, 1H). | 634 |
TABLE 1-continued
| Structure MS(M + H)+ Synthetic method | Cmp. ID |
|---|---|
| 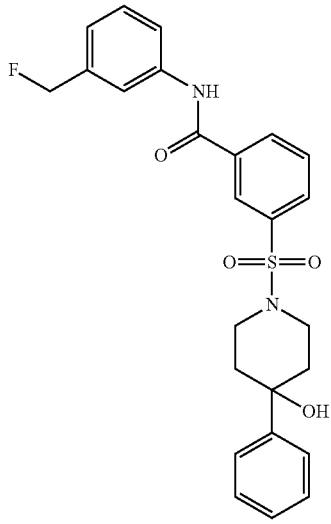<br>469<br>GA<br>A75B01C59 | 641 |
| 497<br>GA<br>A69B01C59 | 642 |

TABLE 1-continued
| Structure MS(M + H)+ Synthetic method | Cmp. ID |
|---|---|
| 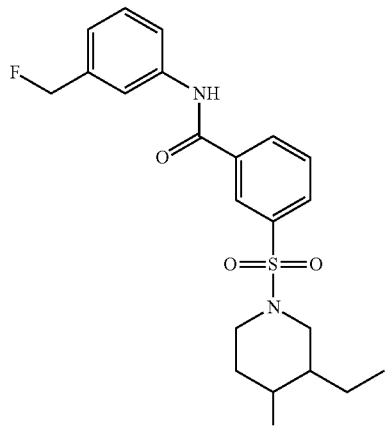<br>421<br>GA<br>A85B01C59 | 644_D2 |
| 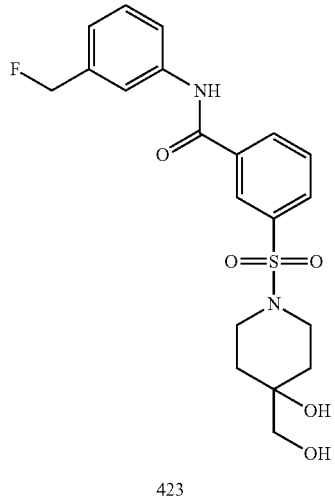<br>423<br>GA<br>A81B01C59 | 645 |
TABLE 1-continued
| Structure MS(M + H)+ Synthetic method | Cmp. ID |
|---|---|
| 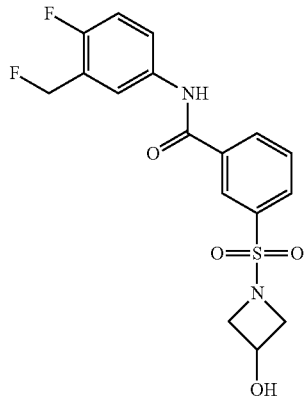<br>383<br>GA<br>A19B01C60<br>$^1$H NMR (400 MHz, CDCl3): δ ppm 8.34 (s, 1H), 8.27 (s, 1H), 8.18 (d, 1H), 7.98 (d, 1H), 7.73-7.67 (m, 3H), 7.11 (t, 1H), 5.47 (d, 2H), 4.49 (m, 1H), 4.06-4.02 (m, 2H), 3.63-3.59 (m, 2H), 2.51 (br, 2H). | 646 |
| 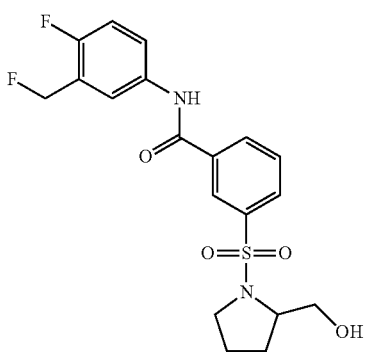<br>411<br>GA<br>A18B01C60<br>$^1$H NMR (400 MHz, CDCl3): δ ppm: 8.64 (s, 1H), 8.31 (s, 1H), 8.17 (d, 1H), 7.96 (d, 1H), 7.74-7.64 (m, 3H), 7.10-7.05 (m, 1H), 7.42-7.38 (m, 1H), 5.45 (d, 2H), 3.68-3.65 (m, 3H), 3.47-3.41 (m, 1H), 3.27-3.21 (m, 1H), 2.88 (br, 1H), 1.85-1.76 (m, 2H), 1.74-1.64 (m, 2H). | 647_R |

TABLE 1-continued
| Structure MS(M + H)+ Synthetic method | Cmp. ID |
|---|---|
| 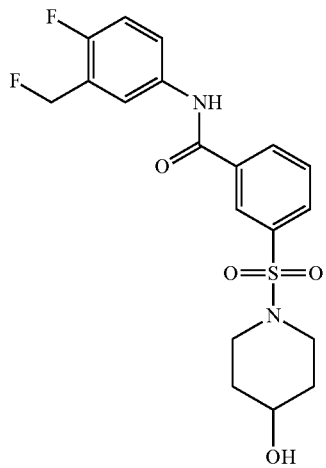 411 GA A10B01C60 | 649 |
| 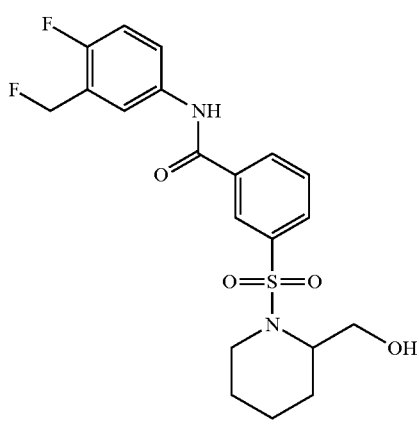 425 GA A04B01C60 | 650 |
TABLE 1-continued
| Structure MS(M + H)+ Synthetic method | Cmp. ID |
|---|---|
| 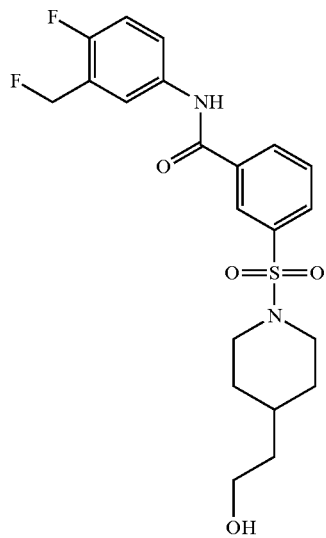 439 GA A09B01C60 | 651 |
| 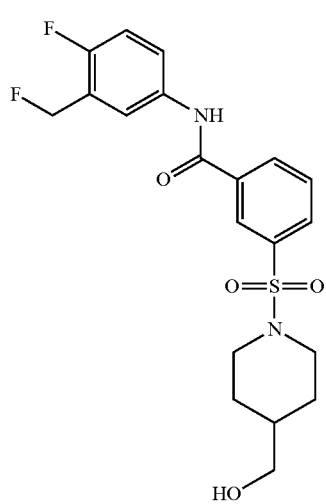 425 GA A06B01C60 | 652 |

TABLE 1-continued
| Structure MS(M + H)+ Synthetic method | Cmp. ID |
|---|---|
| 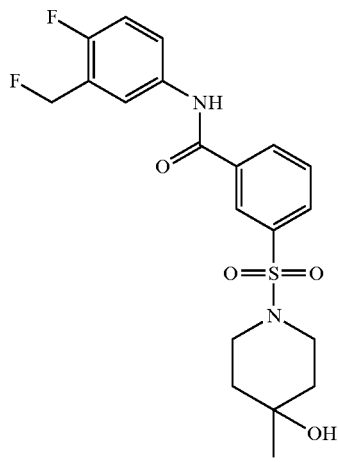 425 GA A73B01C60 | 655 |
| 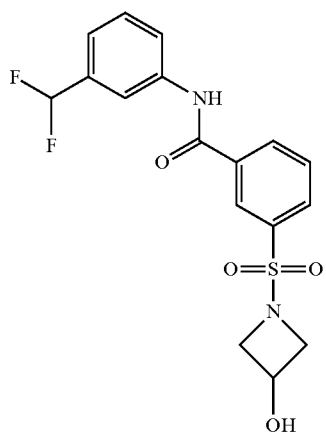 383 GA A19B01C61 | 661 |
TABLE 1-continued
| Structure MS(M + H)+ Synthetic method | Cmp. ID |
|---|---|
| 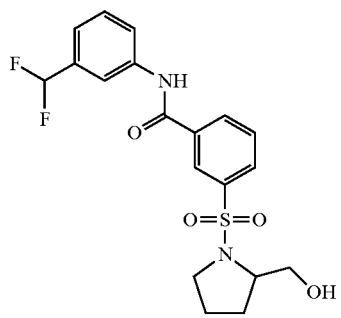 411 GA A18B01C61 $^1$H NMR (400 MHz, CDCl3): δ ppm: 8.38-8.35 (m, 1H), 8.23-8.21 (m, 1H), 8.17 (d, 1H), 8.05-8.03 (m, 1H), 7.92 (s, 1H), 7.82 (d, 1H), 7.75-7.51 (m, 1H), 7.74-7.64 (m, 3H), 7.10-7.05 (m, 1H), 7.42-7.38 (m, 1H), 5.45 (d, 2H), 3.68-3.65 (m, 3H), 3.47-3.41 (m, 1H), 3.27-3.21 (m, 1H), 2.88 (br, 1H), 1.85-1.76 (m, 2H), 1.74-1.64 (m, 2H). | 662_R |
| 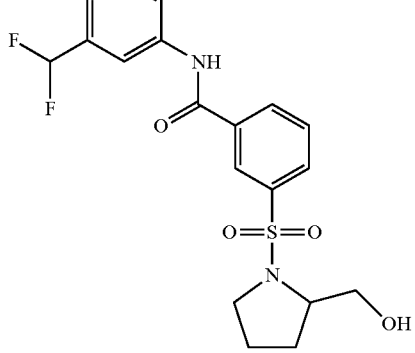 411 GA A18B01C61 | 662_S |

TABLE 1-continued
| Structure MS(M + H)+ Synthetic method | Cmp. ID |
|---|---|
| 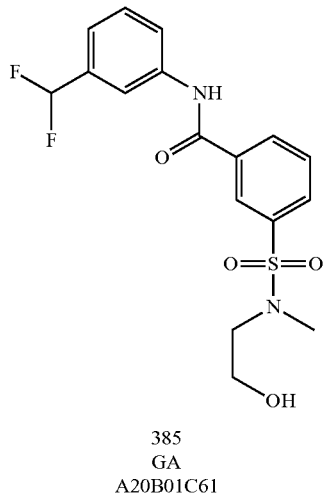 [SMILES: CN(CCO)S(=O)(=O)c1cccc(C(=O)Nc2cccc(C(F)F)c2)c1]<br>385<br>GA<br>A20B01C61 | 663 |
| 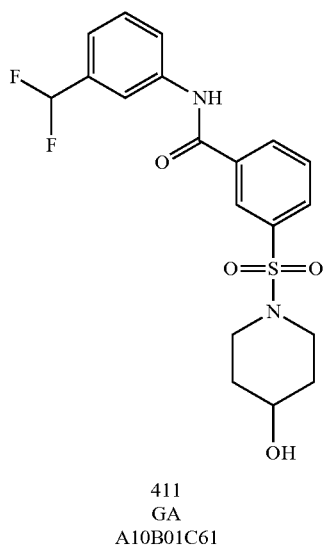 [SMILES: O=C(Nc1cccc(C(F)F)c1)c1cccc(S(=O)(=O)N2CCC(O)CC2)c1]<br>411<br>GA<br>A10B01C61 | 664 |
TABLE 1-continued
| Structure MS(M + H)+ Synthetic method | Cmp. ID |
|---|---|
| 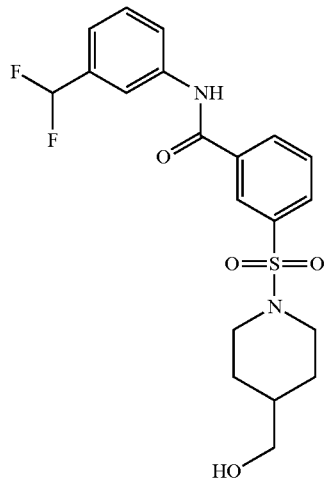<br>425<br>GA<br>A06B01C61 | 667 |
| 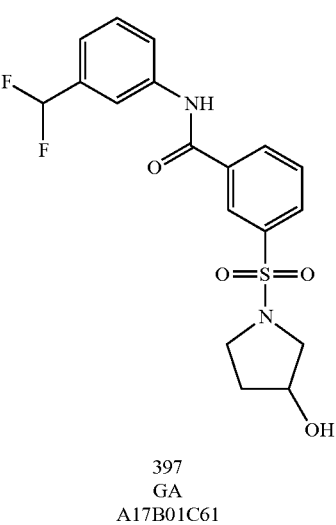 [SMILES: O=C(Nc1cccc(C(F)F)c1)c1cccc(S(=O)(=O)N2CCC(O)C2)c1]<br>397<br>GA<br>A17B01C61 | 668 |

TABLE 1-continued

| Structure MS(M + H)+ Synthetic method | Cmp. ID |
|---|---|
| (structure) | 675 |
| 441 GA A81B01C61 | |
| (structure) | 676 |
| 401 GA A19B01C62 | |
| (structure) | 677_R |
| 429 GA A19B01C62 | |
| (structure) | 677_S |
| 429 GA A18B01C62 | |
| (structure) | 678 |
| 403 GA A20B01C62 | |

TABLE 1-continued
| Structure MS(M + H)+ Synthetic method | Cmp. ID |
|---|---|
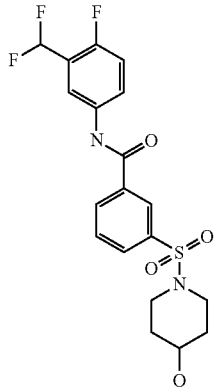
429 GA A10B01C62
$^1$H NMR (400 MHz, CDCl$_3$) 8.23 (s, 1H), 8.17-8.18 (d, 2H), 7.95-7.97 (d, J = 8.0 Hz, 1H), 7.88-7.89 (d, J = 5.2 Hz, 2H), 7.40-7.74 (m, 1H), 7.18-7.23 (t, J = 18.8 Hz, 1H), 6.79-7.07 (t, J = 29.6 Hz 1H), 3.82-3.85 (m, 1H), 3.30-3.35 (m, 2H), 2.96-3.02 (m, 2H), 1.92-1.98 (m, 2H), 1.61-1.73 (m, 2H), 1.42 (s, 1H).
679
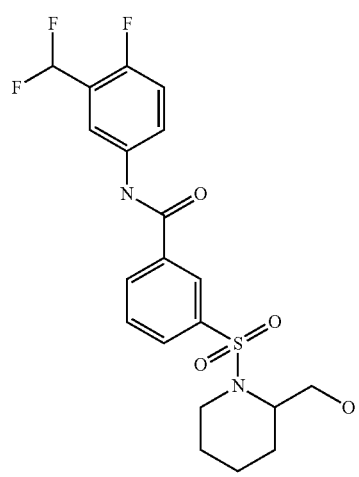
443
GA
A04B01C62
680
TABLE 1-continued
| Structure MS(M + H)+ Synthetic method | Cmp. ID |
|---|---|
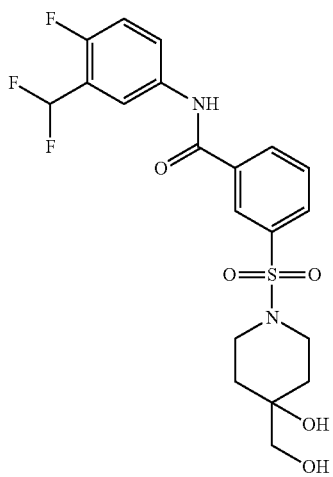
459
GA
A81B01C62
690
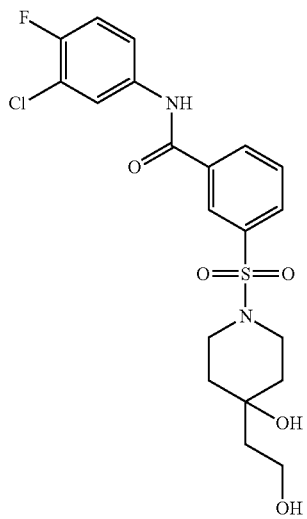
457/459
GA
A90B01C15
694

TABLE 1-continued

| Structure MS(M + H)+ Synthetic method | Cmp. ID |
|---|---|
| (structure) 437 GA A90B01C20 | 695 |
| (structure) 459 GA A90B01C40 | 696 |
| (structure) 397 GA A18B01C63 | 700_R |
| (structure) 397 GA A18B01C63 | 700_S |
| (structure) 383 GA A17B01C63 | 705 |

TABLE 1-continued
| Structure MS(M + H)+ Synthetic method | Cmp. ID |
|---|---|
| 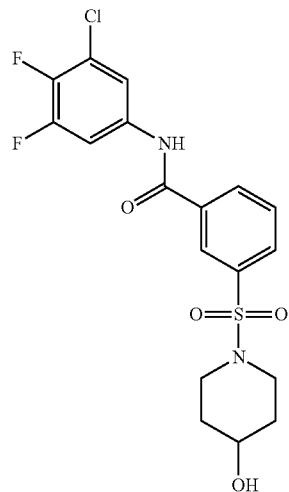<br>397/399<br>GA<br>A10B01C58 | 706 |
| 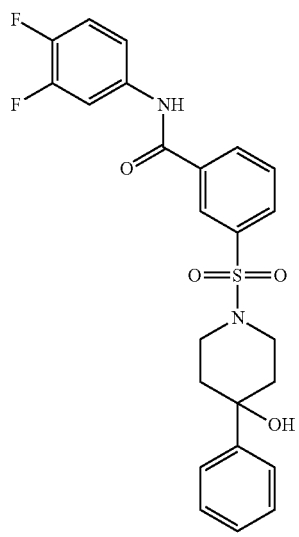<br>473<br>GA<br>A75B01C63 | 708 |
TABLE 1-continued
| Structure MS(M + H)+ Synthetic method | Cmp. ID |
|---|---|
| 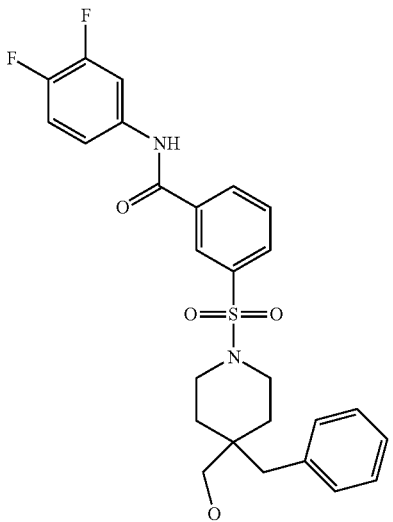<br>501<br>GA<br>A69B01C63 | 709 |
| 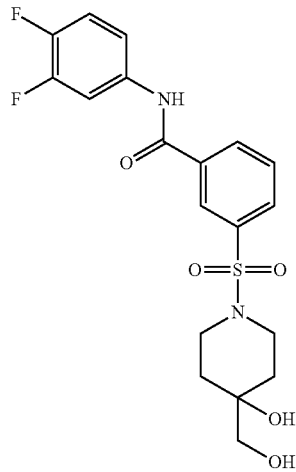<br>427<br>GA<br>A81B01C63 | 712 |

TABLE 1-continued
| Structure MS(M + H)+ Synthetic method | Cmp. ID |
|---|---|
| 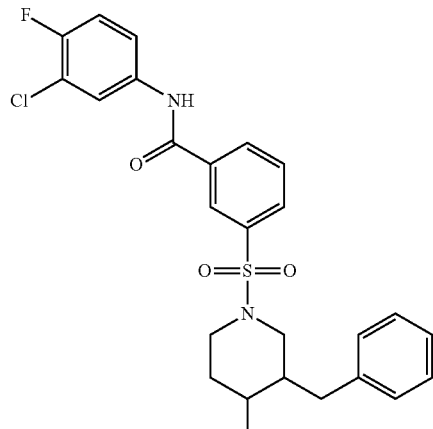 503/505 GA A86B01C15 | 713_D1 |
| 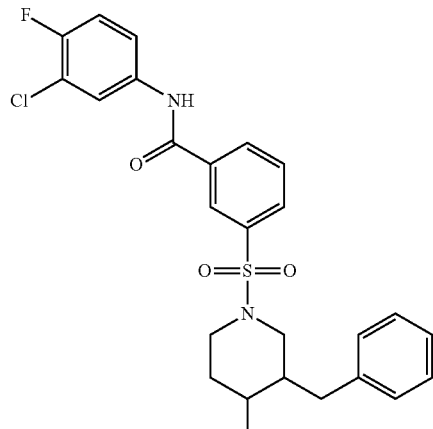 503/505 GA A86B01C15 | 713-D2 |
TABLE 1-continued
| Structure MS(M + H)+ Synthetic method | Cmp. ID |
|---|---|
| 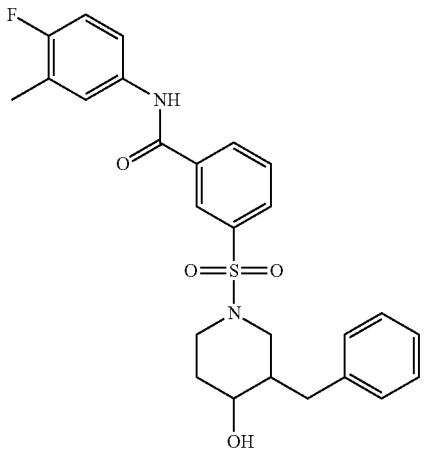 483 GA A86B01C20 | 714_D1 |
| 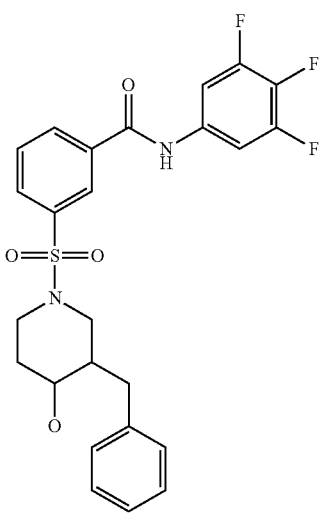 505 GA A86B01C40 | 715_D2 |

TABLE 1-continued
| Structure MS(M + H)+ Synthetic method | Cmp. ID |
|---|---|
| 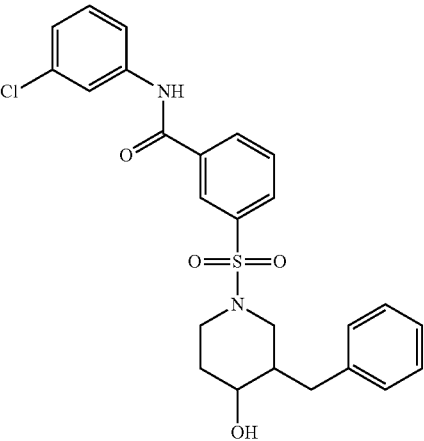 485/487 GA A86B01C05 | 716_D1 |
| 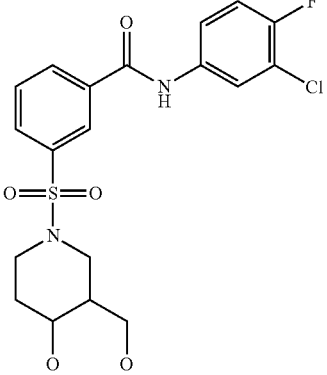 443/445 GA A103B01C15 | 719_D1 |
| 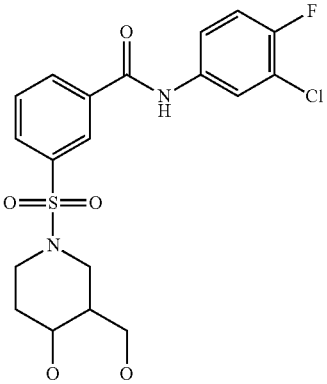 443/445 GA A103B01C15 | 719_D2 |
| 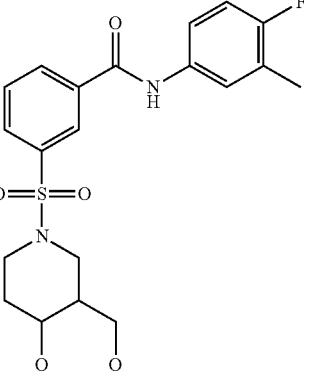 423 GA A103B01C20 | 720_D1 |
| 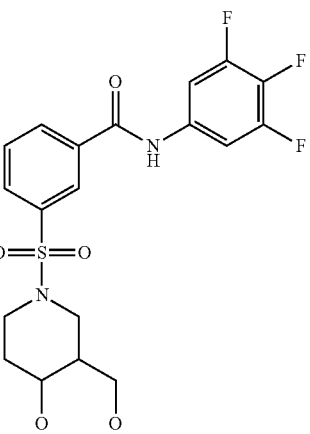 423 GA A103B01C20 | 720_D2 |
| 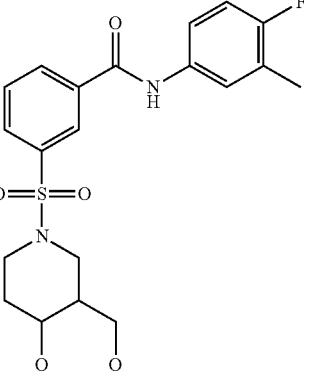 445 GA A103B01C40 | 721_D1 |

TABLE 1-continued

| Structure MS(M + H)+ Synthetic method | Cmp. ID |
|---|---|
| *[structure: 3-methylphenyl benzamide with piperidine sulfonamide bearing 4-OH and 3-CH2OH]* <br> 405 <br> GA <br> A103B01C08 <br> ¹H NMR (400 MHz, CD₃OD) δ 8.33 (s, 1H), 8.24(d, 1 H), 8.02 (d, 1H), 7.80 (t, 1H), 7.58 (m, 2H), 7.29 (t, 1H), 7.03 (d, 1H), 4.61 (s, 2H), 3.91 (s, 1H), 3.67 (m, 1H), 3.60 (m, 1H), 3.53 (m, 2H), 2.80 (m, 1H), 2.61 (t, 1H), 2.38 (s, 3H), 1.91 (m, 1H), 1.76 (m, 2H). | 724_D2 |
| *[structure: 3-chloro-4-fluorophenyl benzamide with piperidine sulfonamide bearing 3-OH and 4-CH2OH]* <br> 443/445 <br> GA <br> A104B01C15 <br> ¹H NMR (400 MHz, CD₃OD) δ 8.34 (s, 1H), 8.25(d, 1 H), 8.00 (m, 2H), 7.78 (t, 1H), 7.67 (m, 1H), 7.27 (t, 1H), 3.88 (m, 1H), 3.80 (m, 1H), 3.75 (m, 1H), 3.56 (m, 2H), 2.34 (t, 1H), 2.13 (t, 1H), 1.90 (m, 1H), 1.48 (m, 1H), 1.33 (m, 1H). | 725_D2 |
| *[structure: 3-chloro-4-fluorophenyl benzamide with piperidine sulfonamide bearing 3-OH and 4-CH2OH]* <br> 443/445 <br> GA <br> A104B01C15 | 725_D1 |
| *[structure: 3-methyl-4-fluorophenyl benzamide with piperidine sulfonamide bearing 3-OH and 4-CH2OH]* <br> 423 <br> GA <br> A104B01C20 | 726_D1 |

TABLE 1-continued
| Structure MS(M + H)+ Synthetic method | Cmp. ID |
|---|---|
| 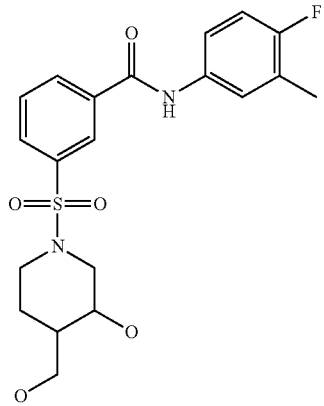<br>423<br>GA<br>A104B01C20 | 726_D2 |
| 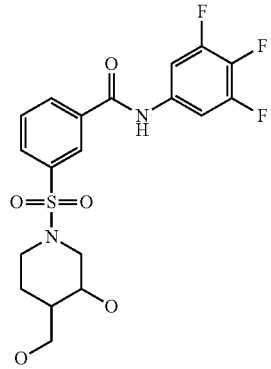<br>445<br>GA<br>A104B01C40<br>¹H NMR (400 MHz, CD₃OD) δ 8.34 (s, 1H), 8.25(d, 1 H), 8.03 (d, 1H), 7.82 (t, 1H), 7.65 (m, 2H), 3.91 (m, 1H), 3.82 (m, 1H), 3.73 (m, 1H), 3.57 (m, 2H), 2.35 (t, 1H), 2.13 (m, 1H), 1.89 (m, 1H), 1.47 (m, 1H), 1.31 (m, 1H). | 727_D2 |
| 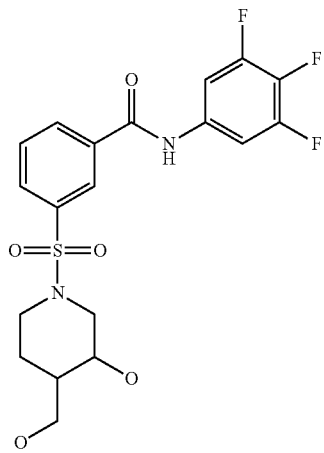<br>445<br>GA<br>A104B01C40 | 727_D1 |
| 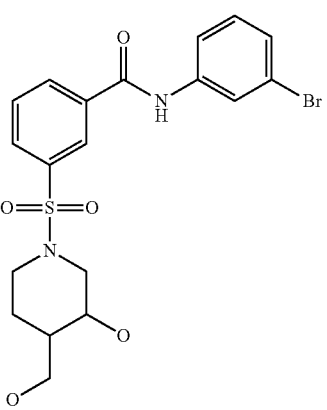<br>469/471<br>GA<br>A104B01C31 | 729_D2 |

TABLE 1-continued
| Structure MS(M + H)+ Synthetic method | Cmp. ID |
|---|---|
| 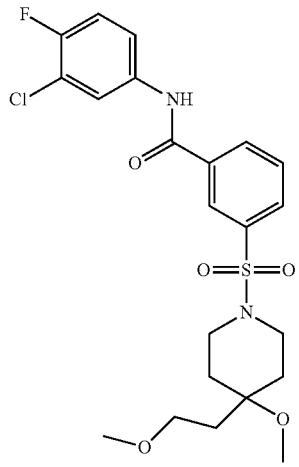<br>485/487<br>GA<br>A92B01C15 | 731 |
| 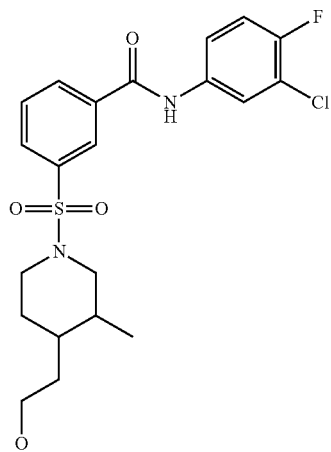<br>455/457<br>GA<br>A93B01C15 | 741 |
TABLE 1-continued
| Structure MS(M + H)+ Synthetic method | Cmp. ID |
|---|---|
| 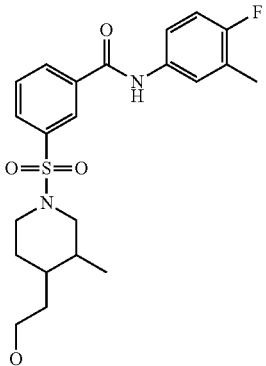<br>435<br>GA<br>A93B01C20<br>$^1$H NMR (400 MHz, CD$_3$OD) δ 8.31 (m, 1H), 8.22 (d, 1H), 7.98 (m, 1H), 7.76 (m, 1H), 7.61 (d, 1H), 7.55 (m, 1H), 7.03 (t, 1H), 3.70 (m, 4H), 2.52 (d, 1H), 2.31 (s, 3H), 1.92 (m, 2H), 1.50 (m, 4H), 1.10 (m, 4H). | 742 |
| 457<br>GA<br>A93B01C40 | 743_D1 |

TABLE 1-continued
| Structure MS(M + H)+ Synthetic method | Cmp. ID |
|---|---|
| 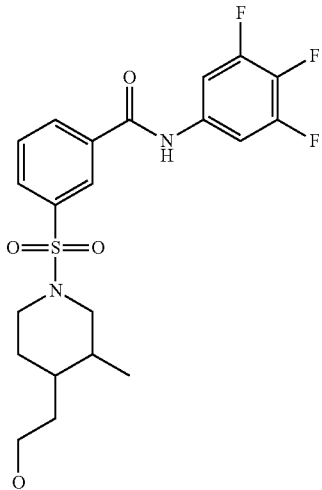<br>457<br>GA<br>A93B01C40 | 743_D2 |
| 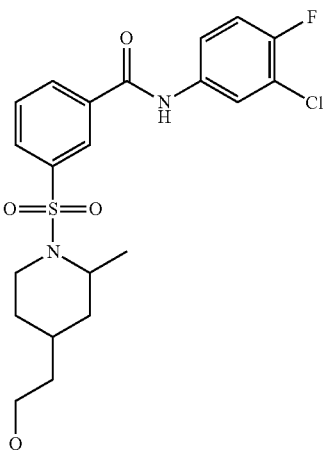<br>455/457<br>GA<br>A95B01C15 | 747_D1 |
TABLE 1-continued
| Structure MS(M + H)+ Synthetic method | Cmp. ID |
|---|---|
| 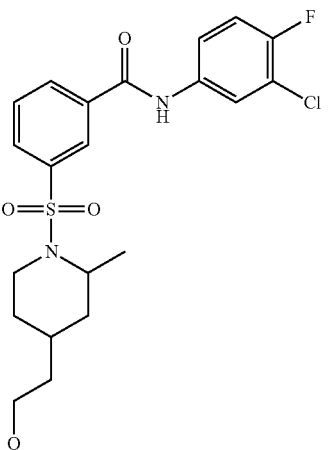<br>455/457<br>GA<br>A95B01C15 | 747_D2 |
| 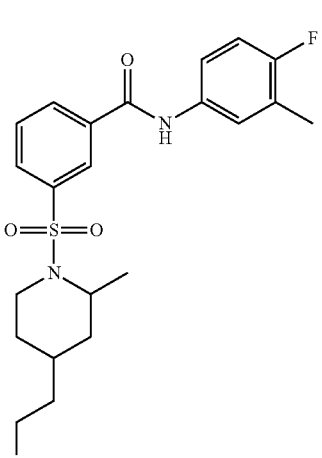<br>435<br>GA<br>A95B01C20 | 748_D1 |

TABLE 1-continued
| Structure MS(M + H)+ Synthetic method | Cmp. ID |
|---|---|
| 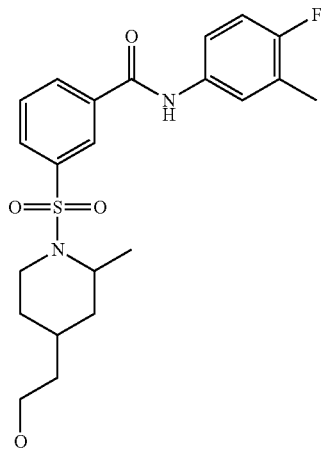<br>435<br>GA<br>A95B01C20 | 748_D2 |
| 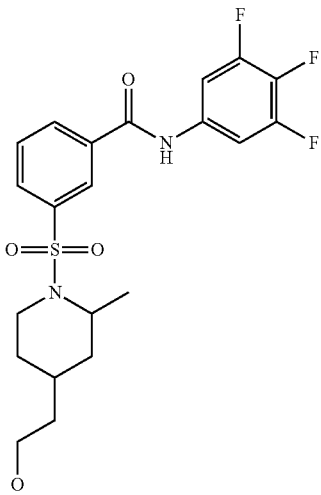<br>457<br>GA<br>A95B01C40 | 749_D2 |
| 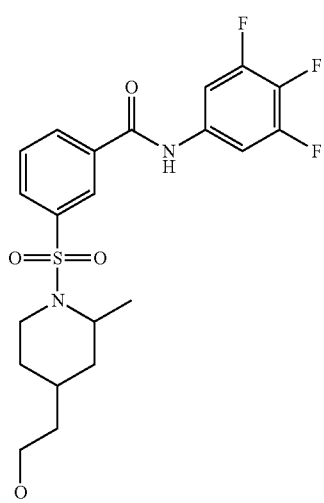<br>457<br>GA<br>A95B01C40 | 749_D1 |
| 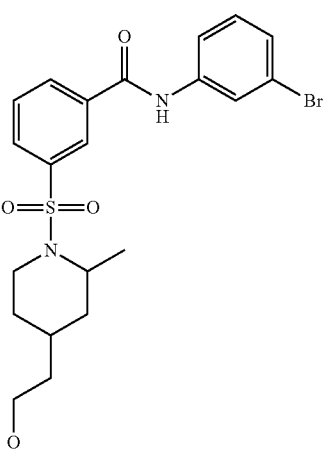<br>481/483<br>GA<br>A95B01C31 | 751_D1 |

TABLE 1-continued
| Structure MS(M + H)+ Synthetic method | Cmp. ID |
|---|---|
| 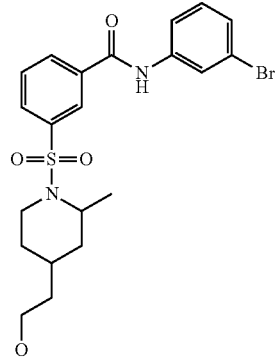<br>481/483<br>GA<br>A95B01C31<br>¹H NMR (400 MHz, CD₃OD) δ 8.37 (s, 1H), 8.22 (d, 1H), 8.06 (m, 2H), 7.78 (t, 1H), 7.68 (d, 1H), 7.33 (m, 2H), 3.86 (m, 1H), 3.55 (m, 2H), 3.22 (m, 1H), 3.05 (m, 1H), 1.82 (m, 1H), 1.75 (d, 1H), 1.47 (m, 3H), 1.36 (d, 3H), 1.23 (m, 2H). | 751_D2 |
| 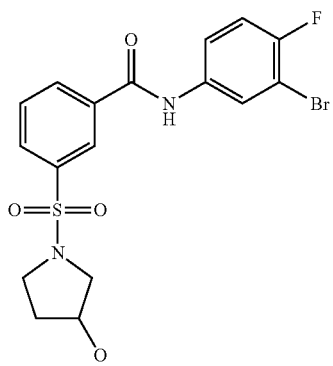<br>443/445<br>GA<br>A17B01C49 | 753 |
TABLE 1-continued
| Structure MS(M + H)+ Synthetic method | Cmp. ID |
|---|---|
| 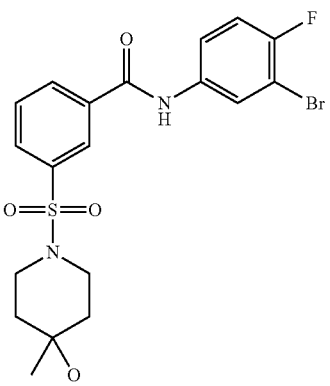<br>471/473<br>GA<br>A73B01C49<br>¹H NMR (400 MHz, CD₃OD) δ 8.34 (s, 1H), 8.25(d, 1H), 8.14 (m, 1H), 8.02 (d, 1H), 7.79 (t, 1H), 7.70 (m, 1H), 7.27 (t, 1H), 3.53 (m, 2H), 2.77 (m, 2H), 1.68 (m, 4H), 1.19 (s, 3H). | 754 |
| 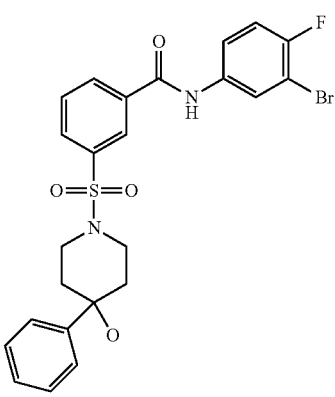<br>533/535<br>GA<br>A75B01C49<br>¹H NMR (400 MHz, CD₃OD) δ 8.39 (s, 1H), 8.26(d, 1H), 8.15 (m, 1H), 8.07 (d, 1H), 7.84 (t, 1H), 7.74 (m, 1H), 7.47 (m, 2H), 7.28 (t, 2H), 7.25 (m, 2H), 3.77 (m, 2H), 2.87 (t, 2H), 2.19 (m, 2H), 1.77 (d, 2H). | 755 |

TABLE 1-continued

| Structure MS(M + H)+ Synthetic method | Cmp. ID |
|---|---|
| (structure) 471/473 GA A84B01C49 | 756_D1 |
| (structure) 471/473 GA A84B01C49 | 756_D2 |
| (structure) 485/487 GA A67B01C49 | 757 |
| (structure) 487/489 GA A81B01C49 | 758 |
| (structure) 533/535 GA A97B01C31 | 759 |

TABLE 1-continued
| Structure MS(M + H)+ Synthetic method | Cmp. ID |
|---|---|
| 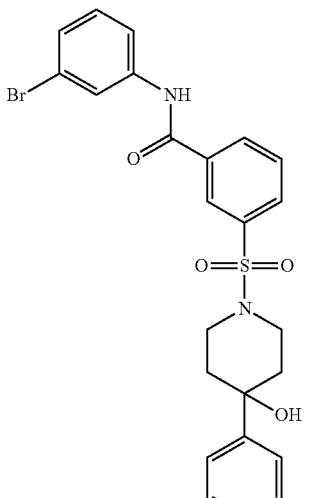 533/535 GA A98B01C31 | 760 |
| 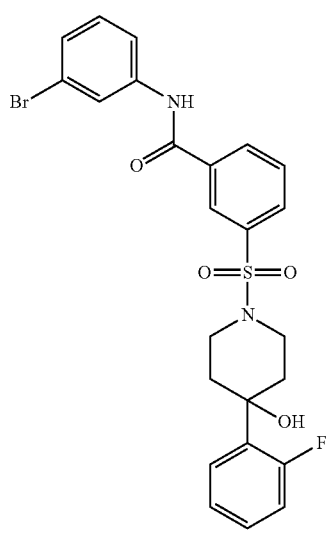 533/535 GA A99B01C31 | 761 |
TABLE 1-continued
| Structure MS(M + H)+ Synthetic method | Cmp. ID |
|---|---|
| 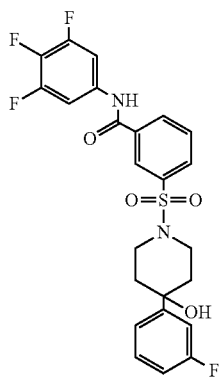 509 GA A97B01C40 1H NMR (400 MHz, DMSO) δ 10.85 (s, 1H), 8.31 (t, J = 2 Hz, 2H), 8.04 (d, J = 8.0 Hz, 1H), 7.90 (t, J = 8.0 Hz, 1H), 7.74 (dd, J = 6.8, 10.4 Hz, 2H), 7.47 (m, 2H), 7.13 (t, J = 8.8 Hz, 2H), 5.03 (s, 1H), 3.62 (d, J = 10.8 Hz, 2H), 2.62 (t, J = 10.8 Hz, 2H), 1.99 (m, 2H), 1.66 (d, J = 13.2 Hz, 2H). | 765 |
| 509 GA A98B01C40 1H NMR (400 MHz, DMSO) δ 1H NMR (400 MHz, DMSO) δ 8.31 (m, 2H), 8.04 (d, J = 7.4 Hz, 1H), 7.90 (t, J = 8.0 Hz, 1H), 7.74 (dd, J = 6.8, 10.4 Hz, 2H), 7.47 (m, 2H), 7.03 (m, 1H), 5.11 (s, 1H), 3.62 (d, J = 11.2 Hz, 2H), 2.62 (t, J = 11.2 Hz, 2H), 2.03 (dt, J = 4.0, 12.8 Hz, 2H), 1.66 (d, J = 12.8 Hz, 2H). | 766 |

TABLE 1-continued
| Structure MS(M + H)+ Synthetic method | Cmp. ID |
|---|---|
| 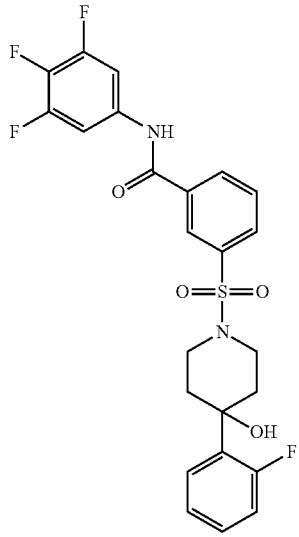 | 767 |
| 509 GA A99B01C40 | |
| <br><br> | 768 |
| 527 GA A100B01C40<br>1H NMR (400 MHz, MeOD) δ 10.38 (m, 1H), 8.26 (d, J = 7.6 Hz, 1H), 8.06 (d, J = 8.4 Hz, 1H), 7.83 (t, J = 8.0 Hz, 1H), 7.65 (m, 2H), 7.38 (m, 1H), 7.26 (m, 2H), 3.76 (dd, J = 2, 9.2 Hz, 2H), 2.62 (dt, J = 2, 12 Hz, 2H), 2.23 (dt, J = 4.8, 9.2 Hz, 2H), 1.66 (d, J = 12.4 Hz, 2H). | |
TABLE 1-continued
| Structure MS(M + H)+ Synthetic method | Cmp. ID |
|---|---|
| 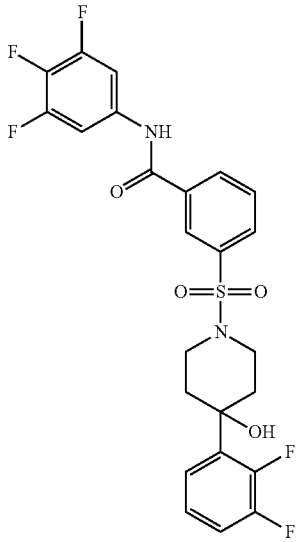 | 769 |
| 527 GA A101B01C40 | |
| 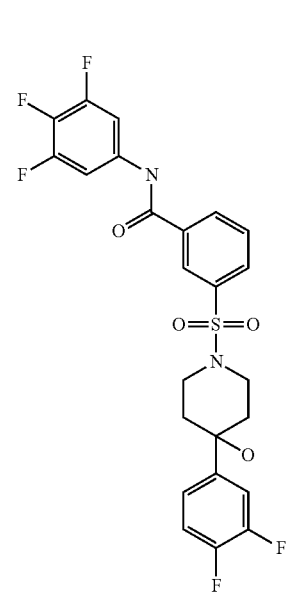 | 770 |
| 527 GA A102B01C40 | |

TABLE 1-continued
| Structure MS(M + H)+ Synthetic method | Cmp. ID |
|---|---|
| 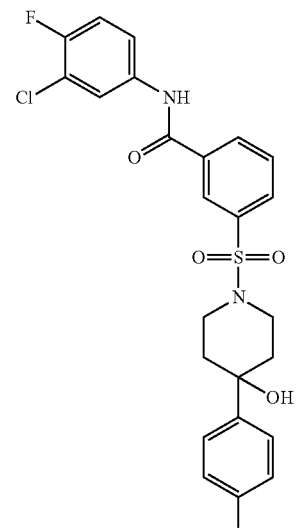 507/509 GA A97B01C15 | 771 |
| 507/509 GA A98B01C15 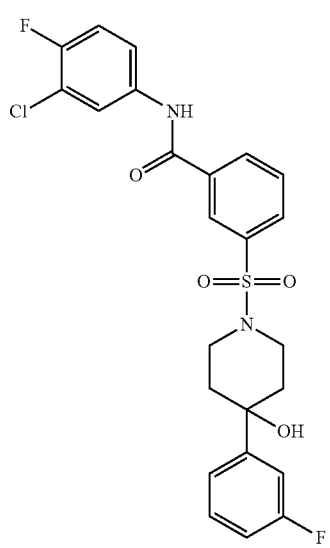 | 772 |
| 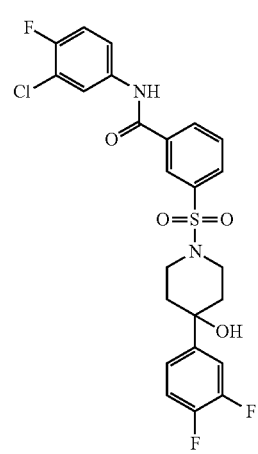 507/509 GA A99B01C15 1H NMR (400 MHz, DMSO) δ 10.73 (s, 1H), 8.33 (m, 2H), 8.08 (dd, J = 2.8, 6.8 Hz, 1H), 8.03 (d, J = 6.8 Hz, 1H), 7.90 (t, J = 8.0 Hz, 1H), 7.75 (m, 1H), 7.57 (m, 1H), 7.46 (t, J = 9.2 Hz, 1 H), 7.29 (m, 1H), 7.16 (m, 2H), 5.23 (s, 1H), 3.62 (d, J = 10.8 Hz, 2H), 2.62 (t, J = 10.8 Hz, 2H), 2.23 (m, 2H), 1.66 (d, J = 13.2 Hz, 2H). | 773 |
| 525/527 GA A100B01C15 1H NMR (400 MHz, MeOD) δ 8.46 (s, 1H), 8.27 (d, J = 8.0 Hz, 1H), 8.03 (m, 2H), 7.82 (t, J = 8.0 Hz, 1H), 7.68 (m, 1H), 7.37 (m, 1H), 7.24 (m, 3H), 3.76 (dd, J = 2, 8.8 Hz, 2H), 2.62 (dt, J = 2, 12 Hz, 2H), 2.13 (dt, J = 4.4, 13.2 Hz, 2H), 1.77 (d, J = 12.4 Hz, 2H). | 774 |

TABLE 1-continued
| Structure MS(M + H)+ Synthetic method | Cmp. ID |
|---|---|
| 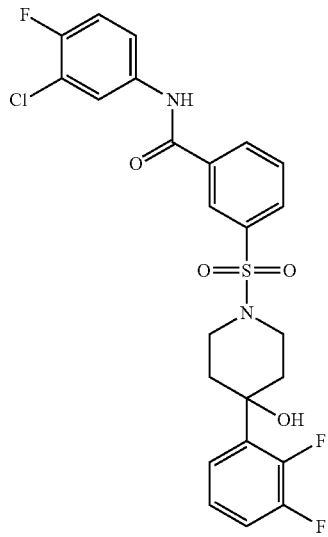<br>525/527<br>GA<br>A101B01C15 | 775 |
| 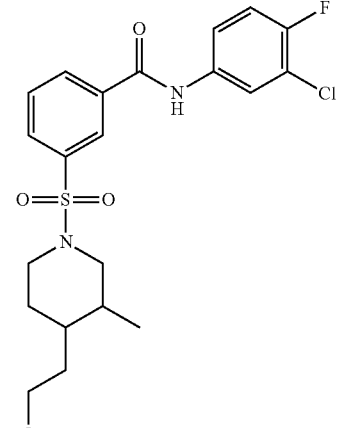 (left structure)<br>525/527<br>GA<br>A102B01C15 | 776 |
TABLE 1-continued
| Structure MS(M + H)+ Synthetic method | Cmp. ID |
|---|---|
| 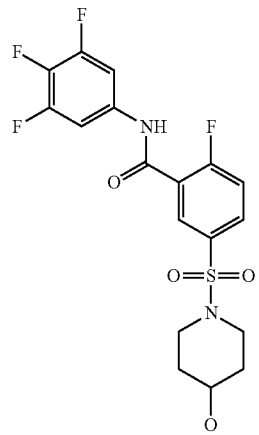<br>433<br>GA<br>A10B02C40<br>$^1$H NMR (400 MHz, MeOD) δ 8.13 (m, 1H), 8.01 (m, 1H), 7.56 (m, 3H), 3.68 (m, 1H), 3.40 (m, 2H), 2.89 (m, 2H), 1.91 (m, 2H), 1.61 (m, 2H). | 777 |
| <br>469/471<br>GA<br>A94B01C15 | 785 |

TABLE 1-continued
| Structure MS(M + H)+ Synthetic method | Cmp. ID |
|---|---|
| 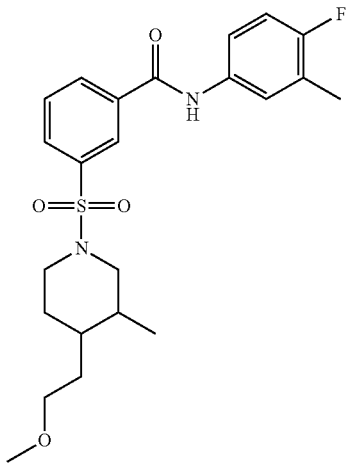<br>449<br>GA<br>A94B01C20 | 786 |
| 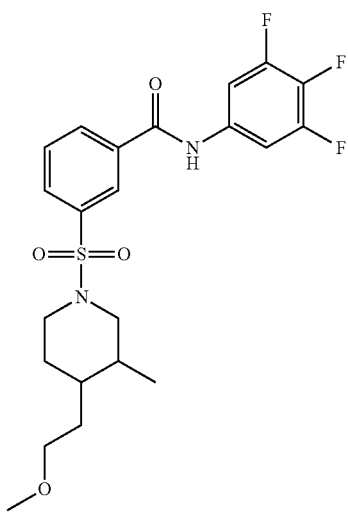<br>471<br>GA<br>A94B01C40 | 787_D1 |
TABLE 1-continued
| Structure MS(M + H)+ Synthetic method | Cmp. ID |
|---|---|
| 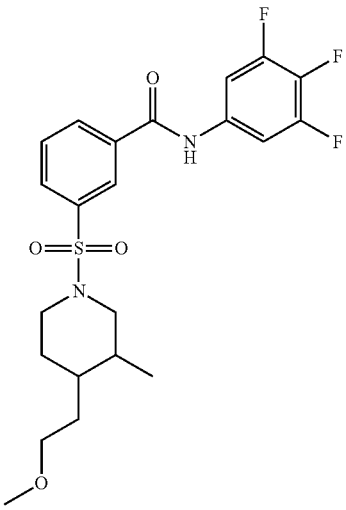<br>471<br>GA<br>A94B01C40 | 787_D2 |
| 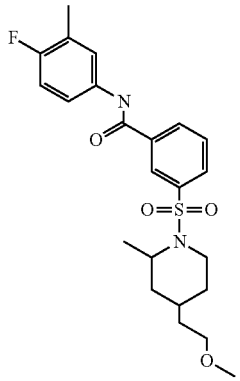<br>449 GA A96B01C20<br>$^1$H NMR (400 MHz, CDCl$_3$) 8.25 (s, 1H), 8.00-8.12 (m, 1H), 7.94-7.98 (m, 2H), 7.66-7.70 (m, 1H), 7.55-7.56 (m, 1H), 7.42-7.44 (m, 1H), 7.02-7.07 (t, J = 17.6 Hz, 1H), 3.86-3.92 (m, 1H), 3.18-3.38 (m, 2H), 3.16 (s, 3H), 3.12-3.20 (m, 1H), 2.93-2.99 (m, 1 H), 2.33-2.35 (d, J = 1.6 Hz, 3H), 1.72-1.82 (m, 2H), 1.50-1.55 (m, 3H), 1.49-1.58 (m, 5H). | 792 |

| Structure MS(M + H)+ Synthetic method | Cmp. ID |
|---|---|
| 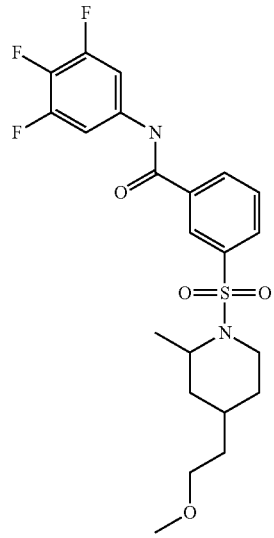 471 GA A96B01C40 | 793 |
| 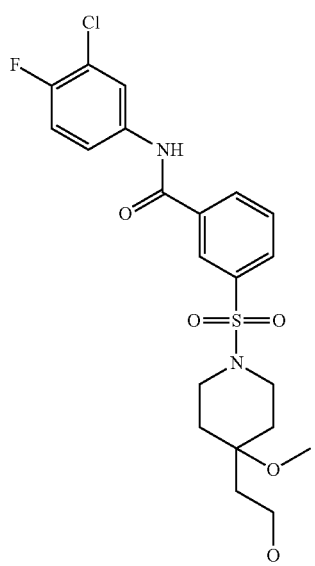 471/473 GA A91B01C15 | 797 |
| Structure MS(M + H)+ Synthetic method | Cmp. ID |
|---|---|
| 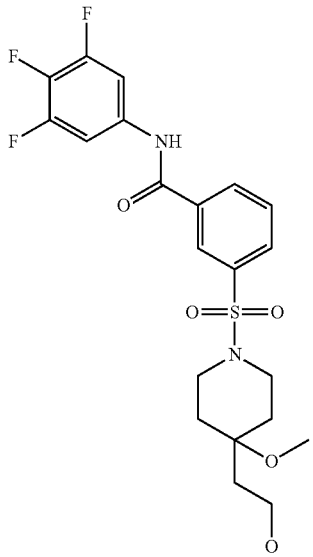 473 GA A91B01C40 | 799 |
| 401 GA A19B01C65 $^1$H NMR (400 MHz, MeOD) δ 8.41 (m, 1H), 8.31-8.30 (m, 1H), 8.09-8.07 (m, 1H), 7.92-7.91 (m, 1H), 7.83 (m, 1H), 7.63-7.62 (m, 1H), 5.58 (s, 1H), 5.46 (s, 1H), 4.45-4.39 (m, 1H), 4.05-4.03 (m, 2H), 3.56 (m, 2H). | 803 |

TABLE 1-continued
| Structure MS(M + H)+ Synthetic method | Cmp. ID |
|---|---|
| 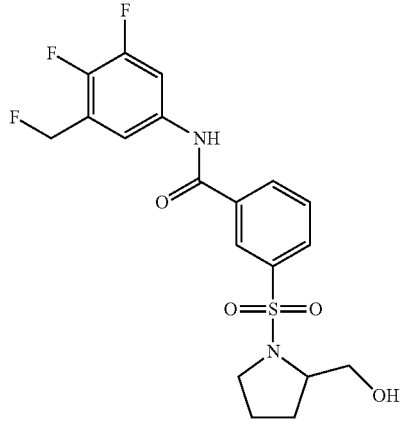<br>429<br>GA<br>A18B01C65 | 804_R |
| 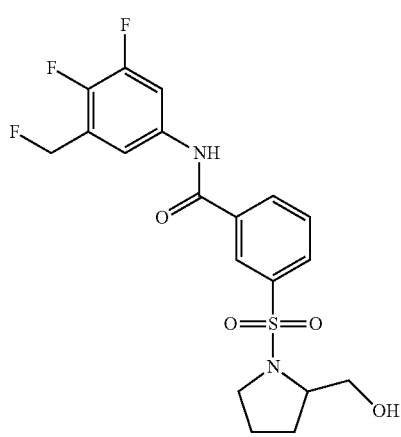<br>429<br>GA<br>A18B01C65 | 804_S |
| 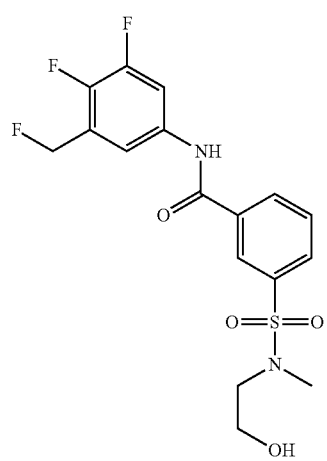<br>403<br>GA<br>A20B01C65 | 805 |
TABLE 1-continued
| Structure MS(M + H)+ Synthetic method | Cmp. ID |
|---|---|
| 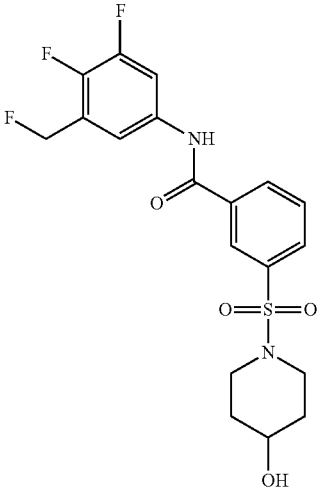<br>429<br>GA<br>A10B01C65 | 806 |
| 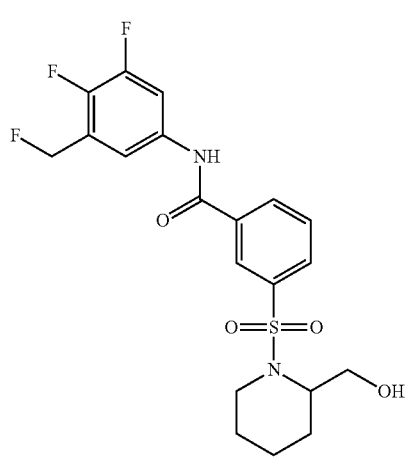<br>443<br>GA<br>A04B01C65 | 807 |

TABLE 1-continued
| Structure MS(M + H)+ Synthetic method | Cmp. ID |
|---|---|
| 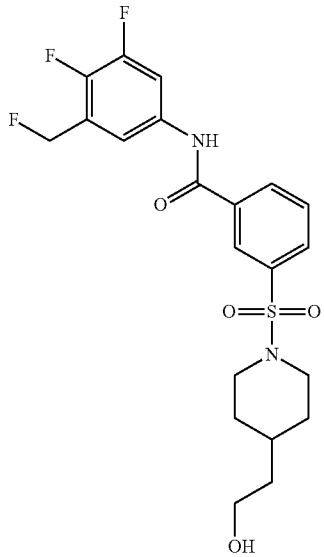 457 GA A09B01C65 | 808 |
| 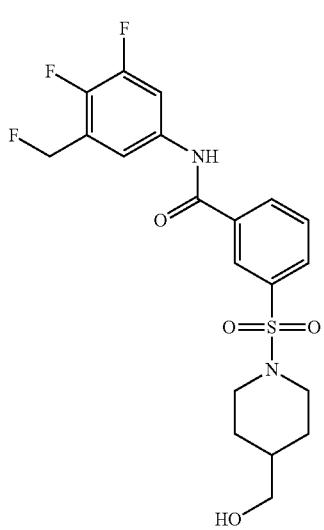 443 GA A06B01C65 | 809 |
| 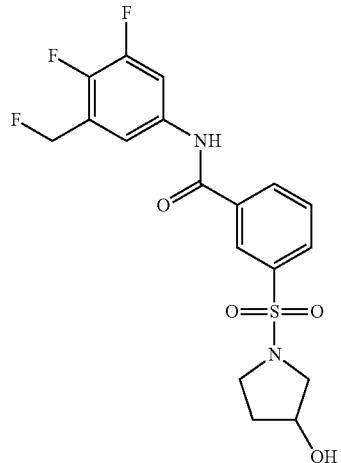 415 GA A17B01C65 | 810 |
| 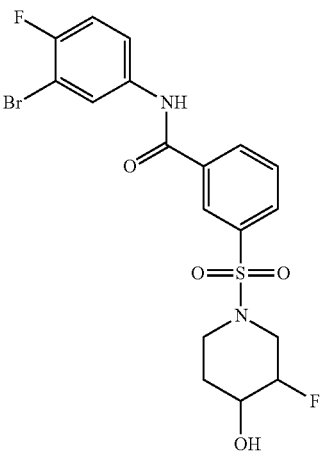 475/477 GA A111B01C49 | 818_D2 |

TABLE 1-continued
| Structure MS(M + H)+ Synthetic method | Cmp. ID |
|---|---|
| 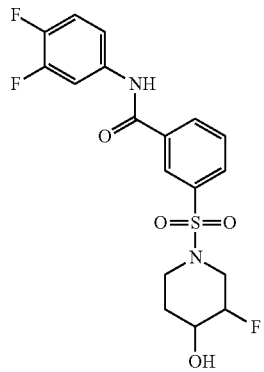  415  GA  A111B01C63  ¹H NMR (400 MHz, CD₃OD) δ 8.38 (s, 1H), 8.25 (d, J = 8 Hz, 1H), 8.05 (d, J = 2.4 Hz, 1H), 7.79 (m, 1H), 7.69 (s, 1H), 7.45 (m, 1H), 7.25 (m, 1H), 4.71 (m, 1H), 3.70 (m, 2H), 3.45 (m, 1H), 3.15 (m, 1H), 2.93 (m, 1H), 1.86 (m, 2H) | 819_D1 |
| 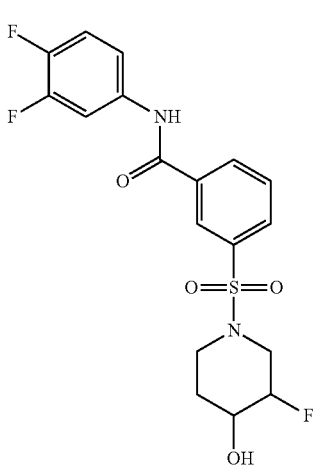  415  GA  A111B01C63 | 819_D2 |
TABLE 1-continued
| Structure MS(M + H)+ Synthetic method | Cmp. ID |
|---|---|
| 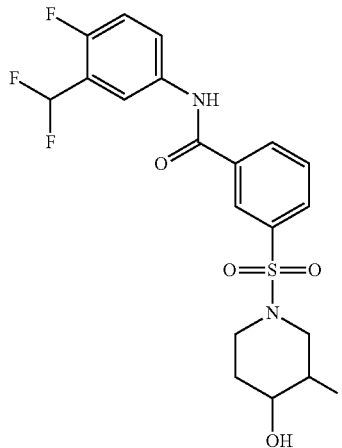  447  GA  A111B01C62 | 820_D1 |
| 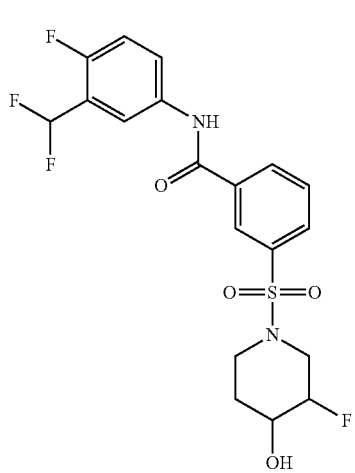  447  GA  A111B01C62 | 820_D2 |

TABLE 1-continued
| Structure MS(M + H)+ Synthetic method | Cmp. ID |
|---|---|
| 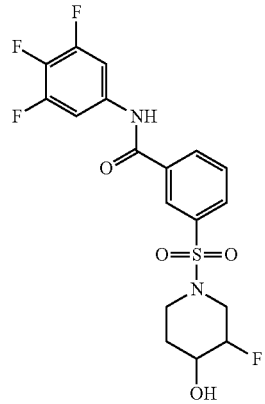<br>433<br>GA<br>A111B01C40<br>$^1$H NMR (400 MHz, CD$_3$OD) δ 8.40 (s, 1H), 8.25 (d, J = 7.6 Hz, 1H), 8.08 (d, J = 7.6 Hz, 1H), 7.80 (m, 1H), 7.65 (m, 2H), 4.70 (m, 1H), 3.75 (m, 2H), 3.45 (m, 1H), 3.15 (m, 1H), 2.90 (m, 1H), 1.78 (m, 2H) | 821_D1 |
| 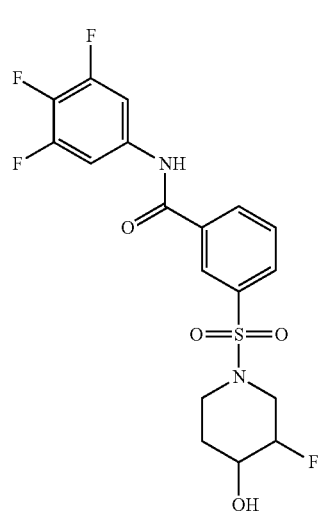<br>433<br>GA<br>A111B01C40 | 821_D2 |
TABLE 1-continued
| Structure MS(M + H)+ Synthetic method | Cmp. ID |
|---|---|
| 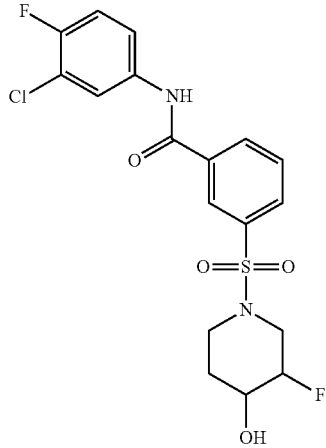<br>431/433<br>GA<br>A111B01C15 | 822_D1 |
| 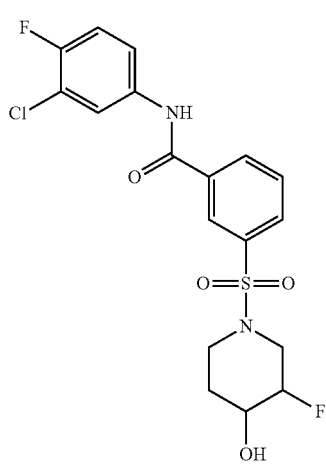<br>431/433<br>GA<br>A111B01C15 | 822_D2 |

TABLE 1-continued
| Structure MS(M + H)+ Synthetic method | Cmp. ID |
|---|---|
| 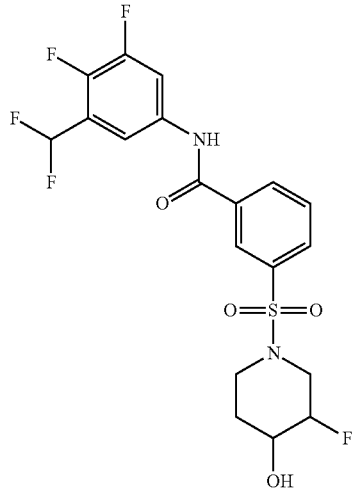 465 GA A111B01C64 | 824_D1 |
| 465 GA A111B01C64 | 824_D2 |
TABLE 1-continued
| Structure MS(M + H)+ Synthetic method | Cmp. ID |
|---|---|
| 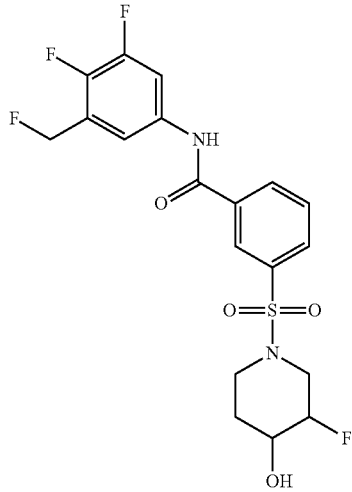 447 GA A111B01C64 | 825_D1 |
| 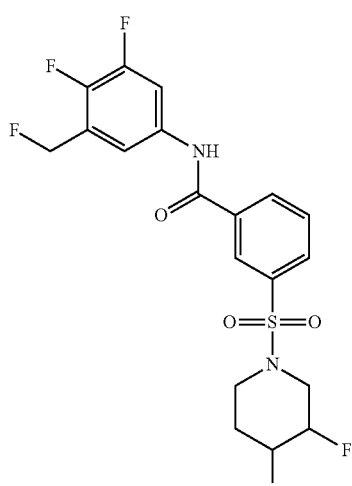 447 GA A111B01C64 | 825_D2 |

TABLE 1-continued
| Structure MS(M + H)+ Synthetic method | Cmp. ID |
|---|---|
| 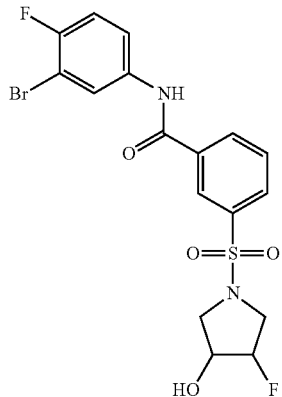<br>461/463<br>GA<br>A110B01C49<br>¹H NMR (400 MHz, CD₃OD) δ 8.30 (s, 1H), 8.14 (d, J = 7.6 Hz, 1H), 8.05 (m, 2H), 7.65 (m, 2H), 7.15 (m, 1H), 4.65 (m, 1H), 4.15 (m, 1H), 3.55 (s, 1H), 3.48 (m, 1H), 3.36 (m, 1H), 3.28 (s, 1H). | 826 |
| 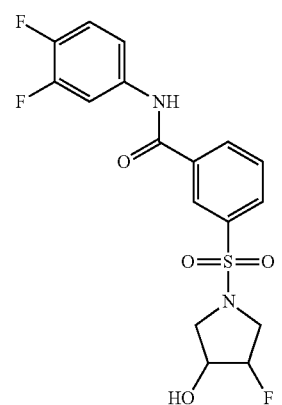<br>401<br>GA<br>A110B01C63<br>¹H NMR (400 MHz, CD₃OD) δ 8.41 (d, J = 2 Hz, 1H), 8.25 (m, 1H), 8.05 (m, 1H), 7.60 (m, 2H), 7.45 (m, 1H), 7.25 (m, 1H), 4.75 (m, 1H), 4.25 (m, 1H), 3.60 (m, 2H), 3.51 (m, 1H), 3.40 (m, 1H) | 827 |
TABLE 1-continued
| Structure MS(M + H)+ Synthetic method | Cmp. ID |
|---|---|
| 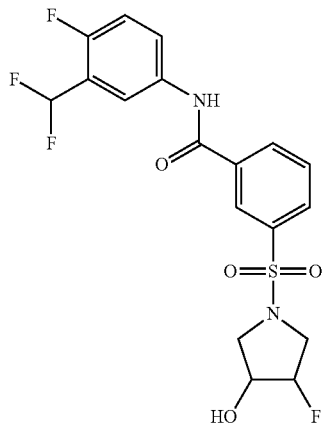<br>433<br>GA<br>A110B01C62 | 828 |
| 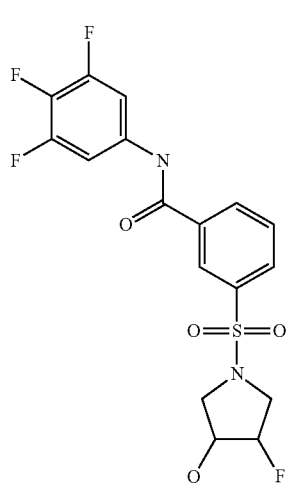<br>419<br>GA<br>A110B01C40 | 829 |

TABLE 1-continued

| Structure MS(M + H)+ Synthetic method | Cmp. ID |
|---|---|
| (structure) 417/419 GA A110B01C15 ¹H NMR (400 MHz, CD₃OD) δ 8.41 (s, 1H), 8.25 (d, J = 8 Hz, 1H), 8.01 (m, 2H), 7.75 (m, 1H), 7.60 (m, 1H), 7.21 (m, 1H), 4.75 (m, 1H), 4.24 (m, 1H), 3.66 (m, 1H), 3.57 (m, 1H), 3.45 (m, 1H), 3.36 (m, 1H). | 830 |
| (structure) 487/485 GA A85B01C49 | 834_D1 |
| (structure) 443/441 GA A112B01C49 | 835 |
| (structure) 457/459 GA A113B01C49 | 843 |
| (structure) 397 GA A113B01C63 | 844 |

TABLE 1-continued

| Structure MS(M + H)+ Synthetic method | Cmp. ID |
|---|---|
| (3,4,5-trifluorophenyl amide; cyclopentanol sulfonamide structure) 415 GA A113B01C40 | 846 |
| (3-chloro-4-fluorophenyl amide; cyclopentanol sulfonamide structure) 413/415 GA A113B01C15 ¹H NMR (400 MHz, CD₃OD) δ 8.45 (s, 1H), 8.18 (d, 1H), 8.12 (d, 1H), 8.01 (d, 1H), 7.72 (t, 1H), 7.65 (m, 1H), 7.27 (t, 1H), 3.95 (m, 1H), 3.33 (m, 1H), 1.86 (m, 2H), 1.66 (m, 2H), 1.52 (m, 1H), 1.36 (m, 1H). | 847 |

TABLE 1-continued

| Structure MS(M + H)+ Synthetic method | Cmp. ID |
|---|---|
| (4-fluoro-3-methylphenyl amide; cyclopentanol sulfonamide structure) 393 GA A113B01C20 | 848 |
| (3,4-difluoro-5-(difluoromethyl)phenyl amide; cyclopentanol sulfonamide structure) 447 GA A113B01C64 ¹H NMR (400 MHz, MeOD) δ 8.47 (s, 1H), 8.20-8.03 (m, 3H), 7.77-7.73 (m, 2H), 7.20-6.93 (t, 1H), 3.97-3.93 (m, 1H), 3.40-3.39 (m, 1H), 1.94-1.84(m, 2H), 1.68-1.63(m, 2H), 1.55-1.49 (m, 1H), 1.40-1.34(m, 1H). | 849 |

TABLE 1-continued
| Structure MS(M + H)+ Synthetic method | Cmp. ID |
|---|---|
| 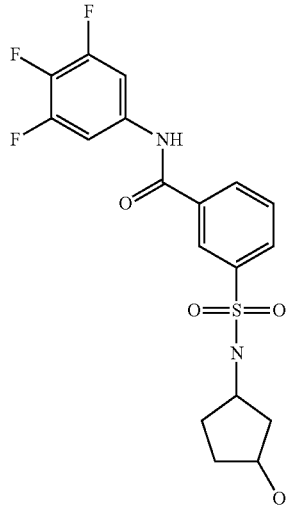<br>415<br>GA<br>A114B01C40 | 854 |
| 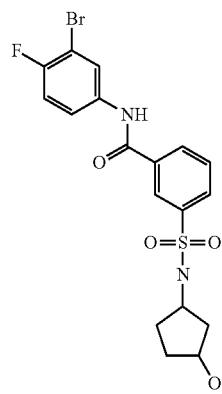<br>459/457<br>GA<br>A114B01C49<br>¹H NMR (400 MHz, CD₃OD) δ 8.42 (m, 1H), 8.19 (m, 1H), 8.13 (m, 1H), 8.08 (m, 1H), 7.76 (t, 1H), 7.70 (m, 1H), 7.25 (t, 1H), 4.13 (m, 1H), 3.65 (m, 1H), 2.08 (m, 1H), 1.69 (m, 4H), 1.36 (m, 1H). | 851 |
TABLE 1-continued
| Structure MS(M + H)+ Synthetic method | Cmp. ID |
|---|---|
| 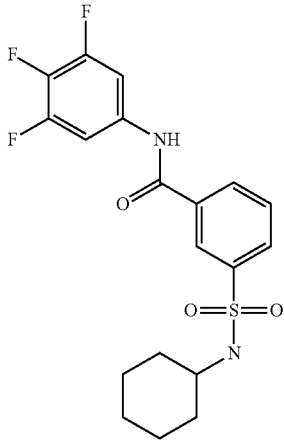<br>413<br>GA<br>A115B01C40 | 862 |
| 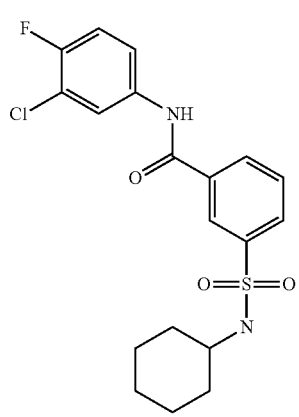<br>411/413<br>GA<br>A115B01C15 | 863 |

TABLE 1-continued
| Structure MS(M + H)+ Synthetic method | Cmp. ID |
|---|---|
| 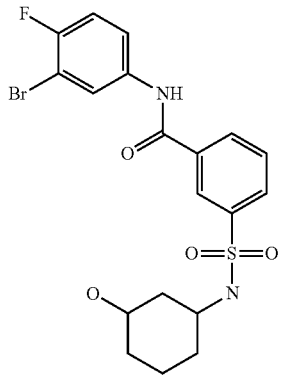<br>473, 471<br>GA<br>A116B01C49<br>¹H NMR (400 MHz, CD₃OD) δ 8.45 (m, 1H), 8.18 (d, 1H), 8.14 (m, 1H), 8.10 (m, 1H), 7.76 (t, 1H), 7.69 (m, 1H), 7.27 (t, 1H), 3.46 (m, 1H), 3.17 (m, 1H), 1.98 (m, 1H), 1.85 (m, 1H), 1.69 (m, 2H), 1.20 (m, 4H). | 867_D1 |
| 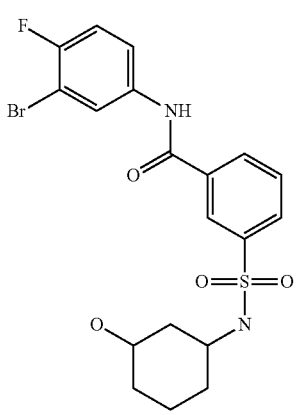<br>473, 471<br>GA<br>A116B01C49<br>¹H NMR (400 MHz, CD₃OD) δ 8.46 (m, 1H), 8.18 (m, 1H), 8.14 (m, 1H), 8.11 (m, 1H), 7.76 (t, 1H), 7.70 (m, 1H), 7.27 (t, 1H), 3.96 (m, 1H), 3.55 (m, 1H), 1.68 (m, 3H), 1.50 (m, 4H), 1.29 (m, 1H). | 867_D2 |
TABLE 1-continued
| Structure MS(M + H)+ Synthetic method | Cmp. ID |
|---|---|
| 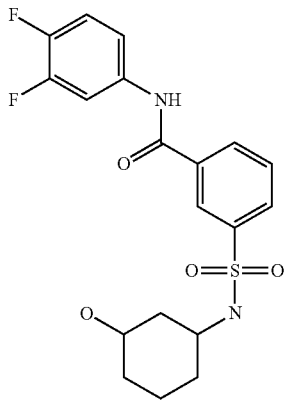<br>411<br>GA<br>A116B01C63 | 868_D1 |
| 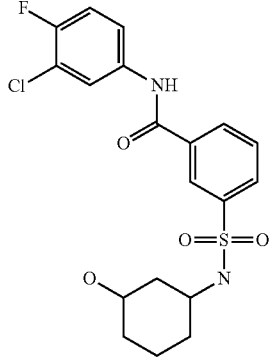<br>427/429<br>GA<br>A116B01C15<br>¹H NMR (400 MHz, CD₃OD) δ 8.44 (s, 1H), 8.18 (d, 1H), 8.08 (d, 1H), 8.00 (m, 1H), 7.76 (t, 1H), 7.65 (m, 1H), 7.30 (t, 1H), 3.47 (m, 1H), 3.16 (m, 1H), 1.94 (m, 1H), 1.82 (m, 1H), 1.69 (m, 1H), 1.16 (m, 4H). | 871_D1 |

TABLE 1-continued
| Structure MS(M + H)+ Synthetic method | Cmp. ID |
|---|---|
| 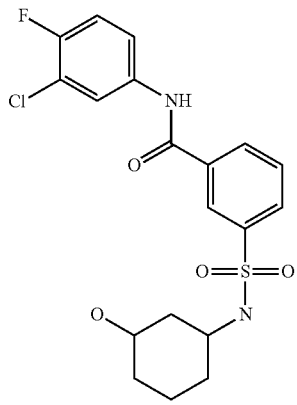<br>427/429<br>GA<br>A116B01C15<br>¹H NMR (400 MHz, CD₃OD) δ 8.45 (s, 1H), 8.18 (d, 1H), 8.11 (d, 1H), 8.01 (m, 1H), 7.76 (t, 1H), 7.65 (m, 1H), 7.30 (t, 1H), 3.96 (m, 1H), 3.53 (m, 1H), 1.59 (m, 3H), 1.48 (m, 4H), 1.29 (m, 1H). | 871_D2 |
| 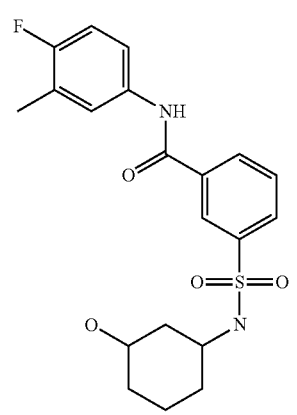<br>407<br>GA<br>A116B01C20 | 872_D1 |
TABLE 1-continued
| Structure MS(M + H)+ Synthetic method | Cmp. ID |
|---|---|
| 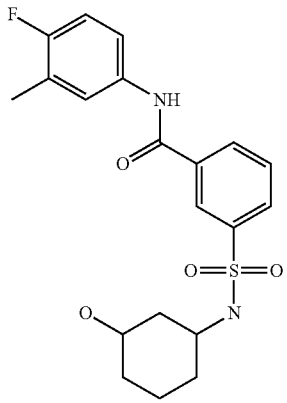<br>407<br>GA<br>A116B01C20 | 872_D2 |
| 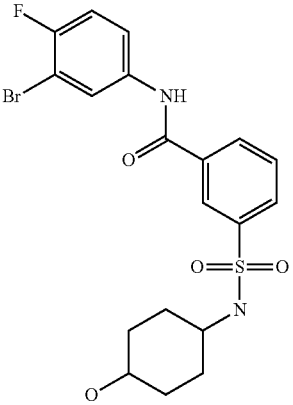<br>473/471<br>GA<br>A117B01C49<br>¹H NMR (400 MHz, CD₃OD) δ 8.43 (s, 1H), 8.18 (d, 1H), 8.14 (m, 1H), 8.08 (d, 1H), 7.76 (m, 2H), 7.27 (t, 1H), 3.46 (m, 1H), 3.07 (m, 1H), 1.87 (m, 2H), 1.76 (m, 2H), 1.27 (m, 4H). | 875 |

TABLE 1-continued
| Structure MS(M + H)+ Synthetic method | Cmp. ID |
|---|---|
| 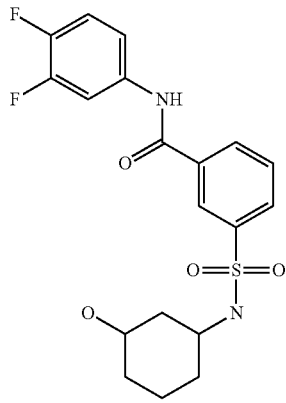<br>411<br>GA<br>A117B01C63<br>¹H NMR (400 MHz, CD₃OD) δ 8.43 (s, 1H), 8.18 (d, 1H), 8.08(d, 1H), 7.87 (m, 1H), 7.76 (t, 1H), 7.48 (m, 1H), 7.30 (m, 1H), 3.47 (m, 1H), 3.07 (m, 1H), 1.87 (m, 2H), 1.77 (m, 2H), 1.27 (m, 4H). | 876 |
| 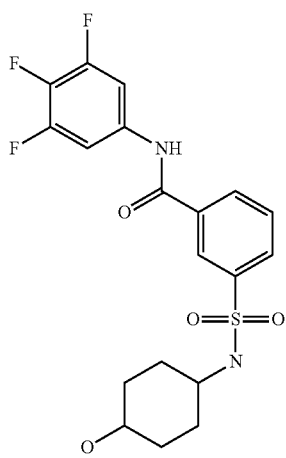<br>429<br>GA<br>A117B01C40 | 878 |
TABLE 1-continued
| Structure MS(M + H)+ Synthetic method | Cmp. ID |
|---|---|
| 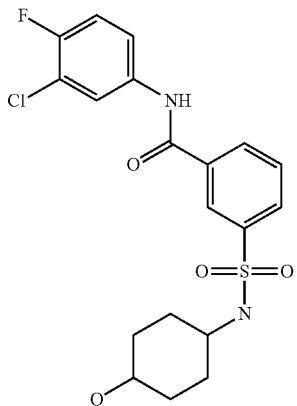<br>427/429<br>GA<br>A117B01C15 | 879 |
| 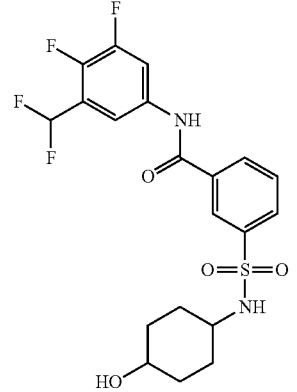<br>461<br>GA<br>A117B01C64<br>¹H NMR (400 MHz, MeOD) δ8.45 (s, 1H), 8.20-8.02 (m, 3H), 7.77-7.73 (m, 2H), 7.20-6.92 (t, 1H), 3.49-3.44 (m, 1H), 3.11-3.05 (m, 1H), 1.87-1.75 (m, 4H), 1.34-1.22(m, 4H). | 881 |

TABLE 1-continued
| Structure MS(M + H)+ Synthetic method | Cmp. ID |
|---|---|
| 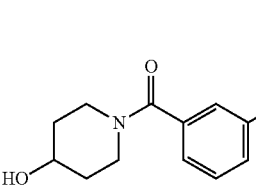<br>443<br>GA<br>A117B01C65<br>¹H NMR (400 MHz, MeOD) δ8.44 (s, 1H), 8.19-8.17 (m, 1H), 8.11-8.09 (m, 1H), 7.93-7.89 (m, 1H), 7.77-7.73 (m, 1H), 7.61 (m, 1H), 5.58(s, 1H), 5.46(s, 1H), 3.49-3.44 (m, 1H), 3.11-3.05 (m, 1H), 1.88-1.75(m, 4H), 1.34-1.19(m, 4H). | 882 |
| 379<br>GA<br>A10B13C40 | 883 |
| 385<br>GA<br>A10B01C87 | 884 |
TABLE 1-continued
| Structure MS(M + H)+ Synthetic method | Cmp. ID |
|---|---|
| 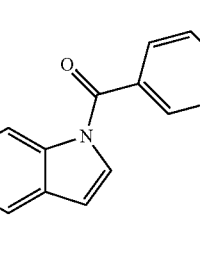<br>431/433<br>GA<br>A10B02V15<br>¹H NMR (400 MHz, CD₃OD) δ 8.14 (m, 1H), 8.02 (m, 2H), 7.62 (m, 1H), 7.53 (t, 1H), 7.27 (t, 1H), 3.67 (m, 1H), 3.39 (m, 2H), 2.88 (m, 2H), 1.92 (m, 2H), 1.63 (m, 2H). | 885 |
| 475/477<br>GA<br>A10B02C49 | 886 |

TABLE 1-continued
| Structure MS(M + H)+ Synthetic method | Cmp. ID |
|---|---|
| 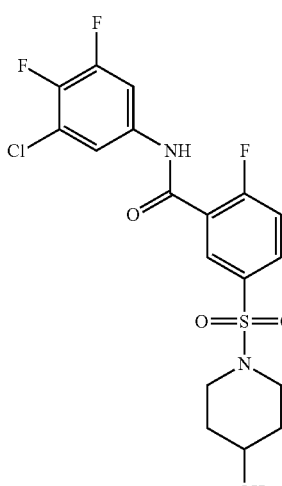  449/451  GA  A10B02C58 | 887 |
| 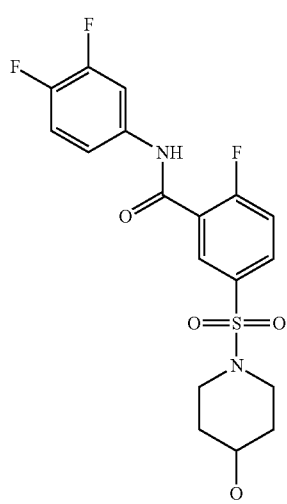  415  GA  A10B02C63 | 888 |
TABLE 1-continued
| Structure MS(M + H)+ Synthetic method | Cmp. ID |
|---|---|
| 465  GA  A10B02C64 | 889 |
| 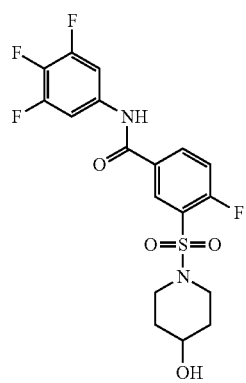  433  GA  A10B03C40  $^1$H NMR (400 MHz, CDCl$_3$) δ 9.71 (s, 1H), 8.31 (dd, J = 2.0, 6.4 Hz, 1H), 8.21 (m, 1H), 7.49 (dd, J = 6.4, 9.6 Hz, 1H), 7.35 (t, J = 8.8 Hz, 1H), 3.82 (m, 1H), 3.49 (m, 2H), 3.12 (m, 2H), 1.92 (m, 2H), 1.66 (m, 2H). | 890 |

TABLE 1-continued
| Structure MS(M + H)+ Synthetic method | Cmp. ID |
|---|---|
| 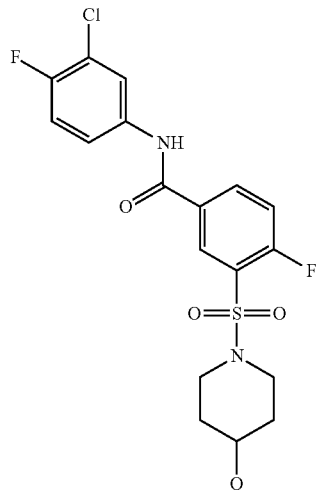<br>431/433<br>GA<br>A10B03C15 | 891 |
| 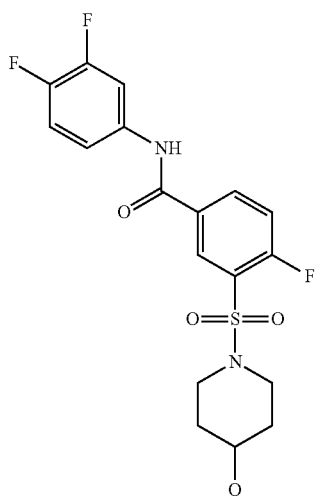<br>475/477<br>GA<br>A10B03C49 | 892 |
TABLE 1-continued
| Structure MS(M + H)+ Synthetic method | Cmp. ID |
|---|---|
| 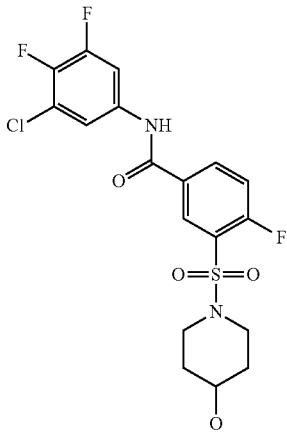<br>449/451<br>GA<br>A10B03C58<br>¹H NMR (400 MHz, CD₃OD) δ 8.44 (m, 1H), 8.27 (m, 1H), 7.74 (m, 2H), 7.55 (t, 1H), 3.76 (m, 1H), 3.58 (s, 2H), 3.06 (m, 2H), 1.93 (m, 2H), 1.60 (m, 2H). | 893 |
| 415<br>GA<br>A10B03C63 | 894 |

TABLE 1-continued

| Structure MS(M + H)+ Synthetic method | Cmp. ID |
|---|---|
| (structure) | 895 |
| 465 GA A10B03C64 1H NMR (400 MHz, MeOD) δ 8.46-8.44 (m, 1H), 8.30-8.27 (m, 1H), 8.05-8.01 (m, 1H), 7.76 (m, 1H), 7.54-7.50 (m, 1H), 7.19-6.92(t, 1H), 3.77-3.73 (m, 1H), 3.59-3.56 (m, 2H), 3.10-3.04(m, 2H), 1.94-1.90(m, 2H), 1.64-1.56(m, 2H). | |
| (structure) | 896 |
| 447 GA A10B03C65 | |

TABLE 1-continued

| Structure MS(M + H)+ Synthetic method | Cmp. ID |
|---|---|
| (structure) | 898_D1 |
| 447 GA A84B03C40 | |
| (structure) | 898_D2 |
| 447 GA A84B03C40 | |

TABLE 1-continued
| Structure MS(M + H)+ Synthetic method | Cmp. ID |
|---|---|
| 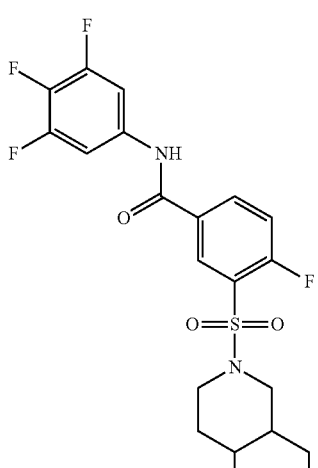 461 GA A85B03C40 | 899_D1 |
| 461 GA A85B03C40 | 899_D2 |
| 461 GA A09B03C40 | 900 |
| 405 GA A19B03C40 | 901 |

TABLE 1-continued
| Structure MS(M + H)+ Synthetic method | Cmp. ID |
|---|---|
| 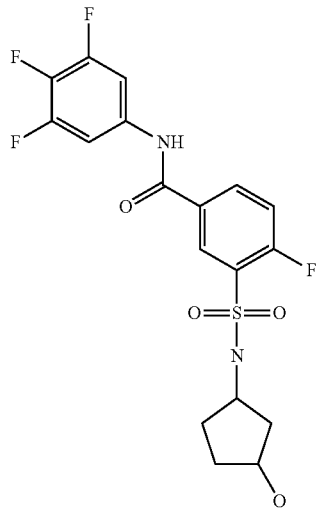 433 GA A114B03C40 | 902 |
| 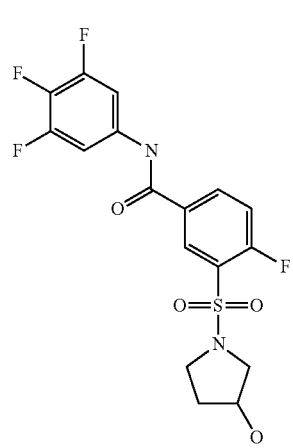 419 GA A17B03C40 ¹H NMR (400 MHz, CD₃OD) δ 8.37 (m, 1H), 8.14 (m, 1H), 7.50 (m, 2H), 7.37 (t, 1H), 4.27 (m, 1H), 3.43 (m, 3H), 3.28 (m, 1H), 1.92 (m, 1H), 1.78 (m, 1H). | 903 |
TABLE 1-continued
| Structure MS(M + H)+ Synthetic method | Cmp. ID |
|---|---|
| 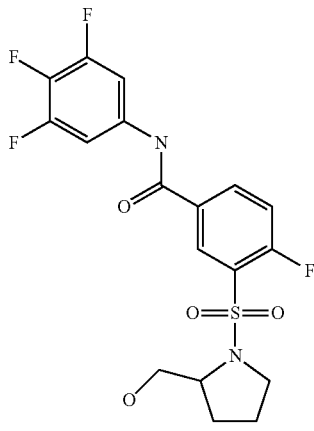 433 GA A18B03C40 | 904_R |
| 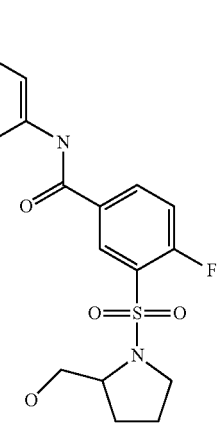 433 GA A18B03C40 | 904_S |

TABLE 1-continued

| Structure MS(M + H)+ Synthetic method | Cmp. ID |
|---|---|
| [Structure with 3,4,5-trifluorophenyl, amide, fluoro-benzene, sulfonyl, 4-phenyl-4-hydroxypiperidine]<br>509<br>GA<br>A75B03C40<br>$^1$H NMR (400 MHz, CD$_3$OD) δ 8.48 (m, 1H), 8.31 (m, 1H), 7.64 (m, 3H), 7.49 (m, 2H), 7.36 (m, 2H), 7.26 (m, 1H), 3.83 (m, 2H), 3.14 (m, 2H), 2.18 (m, 2H), 1.83 (m, H). | 907 |
| [Structure with 3,4,5-trifluorophenyl, amide, fluoro-benzene, sulfonyl, 3-hydroxy-4-fluoropyrrolidine]<br>437<br>GA<br>A110B03C40 | 908 |

TABLE 1-continued

| Structure MS(M + H)+ Synthetic method | Cmp. ID |
|---|---|
| [Structure with 3,4,5-trifluorophenyl, amide, fluoro-benzene, sulfonyl, 4-hydroxy-4-(hydroxymethyl)piperidine]<br>463<br>GA<br>A81B03C40<br>$^1$H NMR (400 MHz, CD$_3$OD) δ 8.44 (m, 1H), 8.26 (m, 1H), 7.63 (m, 2H), 7.52 (t, 1H), 3.72 (m, 2H), 3.35 (s, 2H), 3.01 (t, 2H), 1.73 (m, 2H), 1.63 (m, 2H). | 916 |
| [Structure with 3-chloro-4-fluorophenyl, amide, fluoro-benzene, sulfonyl, 3-hydroxypyrrolidine]<br>417/419<br>GA<br>A17B03C15<br>$^1$H NMR (400 MHz, DMSO): δ ppm: 10.65(s, 1H), 8.40(dd, J = 2.0, 6.4 Hz, 1H), 8.27(m, 1H), 8.04 (dd, J = 2.4, 7.2 Hz, 1H), 7.68(m, 2H), 7.44(t, J = 9.0 Hz, 1H), 4.94(d, J = 3.2 Hz, 1H), 4.23(s, 1H), 3.40(m, 2H), 3.18(m, 1H), 1.85(m, 2H). | 917 |

TABLE 1-continued
| Structure MS(M + H)+ Synthetic method | Cmp. ID |
|---|---|
| 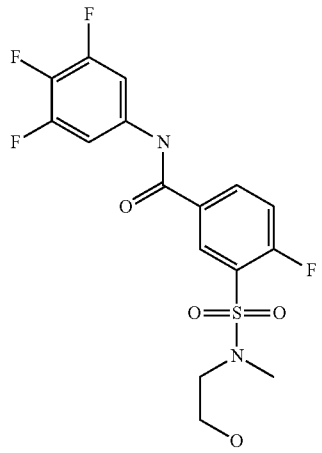 407 GA A20B03C40 | 910 |
| 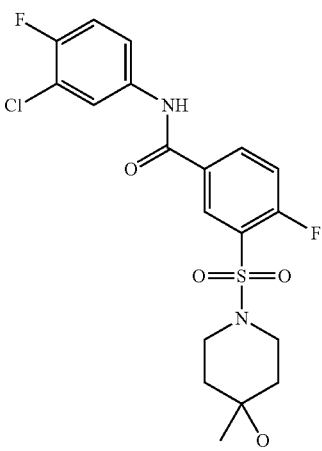 445/447 GA A73B03C15 | 911 |
TABLE 1-continued
| Structure MS(M + H)+ Synthetic method | Cmp. ID |
|---|---|
| 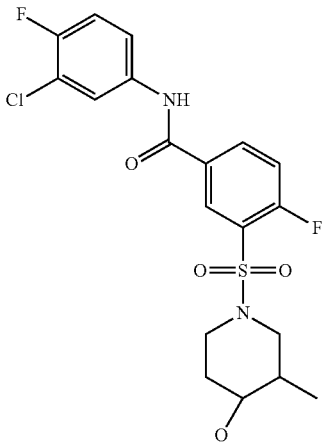 445/447 GA A84B03C15 | 912_D1 |
| 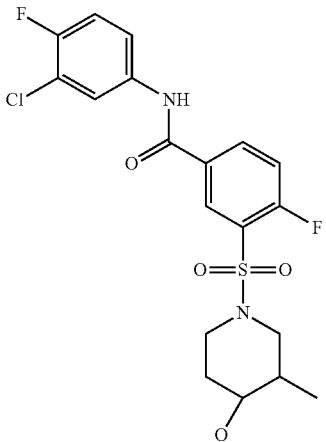 445/447 GA A84B03C15 | 912_D2 |

TABLE 1-continued
| Structure MS(M + H)+ Synthetic method | Cmp. ID |
|---|---|
| 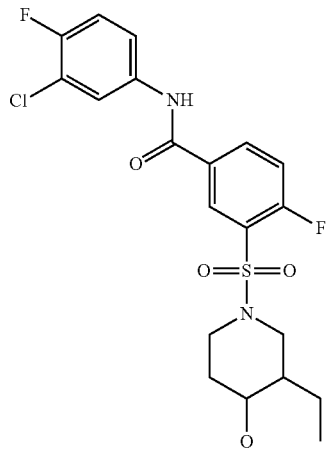 459/461 GA A85B03C15 | 913_D1 |
| 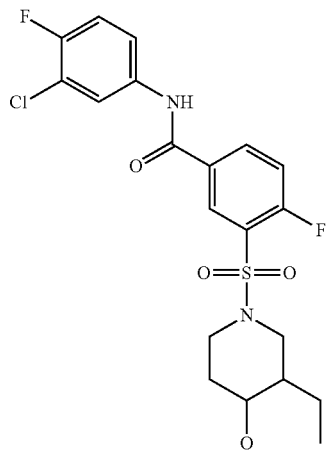 459/461 GA A58B03C15 | 913_D2 |
TABLE 1-continued
| Structure MS(M + H)+ Synthetic method | Cmp. ID |
|---|---|
| 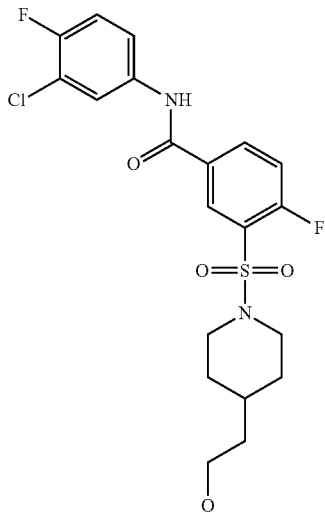 459/461 GA A09B03C15 | 914 |
| 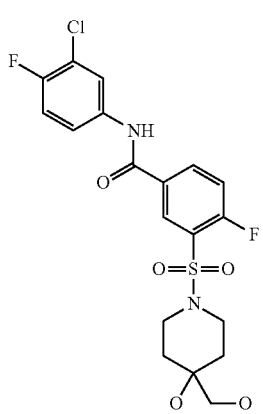 461/463 GA A81B03C15 <br> ¹H NMR (400 MHz, CD₃OD) δ 8.44 (m, 1H), 8.27 (m, 1H), 7.99 (m, 1H), 7.64 (m, 1H), 7.55(t, 1H), 7.29 (t, 1H), 3.72 (m, 2H), 3.35 (s, 2H), 2.98 (t, 2H), 1.72 (m, 2H), 1.63 (m, 2H). | 919 |

TABLE 1-continued
| Structure MS(M + H)+ Synthetic method | Cmp. ID |
|---|---|
| 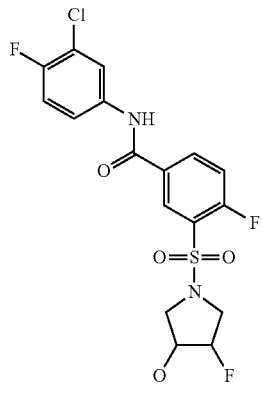<br>435/437<br>GA<br>A110B03C15<br>¹H NMR (400 MHz, CD₃OD) δ 8.46 (m, 1H), 8.26 (m, 1H), 7.98 (m, 1H), 7.65 (m, 1H), 7.49 (t, 1H), 7.29 (t, 1H), 4.28 (m, 1H), 3.76 (s, 1H), 3.69 (s, 1H), 3.62 (t, 1H), 3.58 (t, 1H), 3.52 (m, 1H), 3.32 (d, 1H). | 922 |
| <br>449/451<br>GA<br>A111B03C15 | 923_D1 |
TABLE 1-continued
| Structure MS(M + H)+ Synthetic method | Cmp. ID |
|---|---|
| 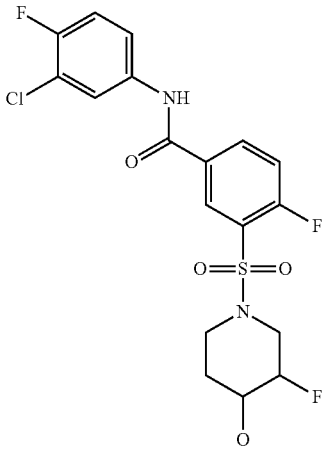<br>449/451<br>GA<br>A111B03C15 | 923_D2 |
| 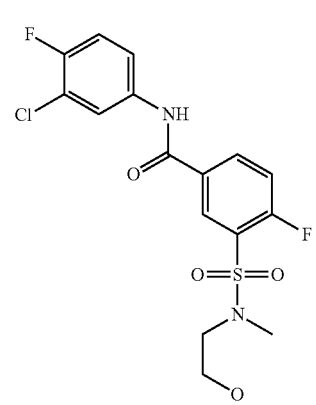<br>405/407<br>GA<br>A20B03C15<br>¹H NMR (400 MHz, CD₃OD): δ ppm: 8.44(dd, J = 2.4, 7.2 Hz, 1H), 8.21(m, 1H), 7.95(dd, J = 2.4, 6.4 Hz, 1H), 7.63 (m, 1H), 7.48(t, J = 9.2 Hz, 1H), 7.24(t, J = 9.0 Hz, 1H), 3.70(t, J = 5.8 Hz, 2H), 3.31(m, 2H), 2.97(d, J = 1.6 Hz, 3H). | 924 |

TABLE 1-continued
| Structure MS(M + H)+ Synthetic method | Cmp. ID |
|---|---|
| 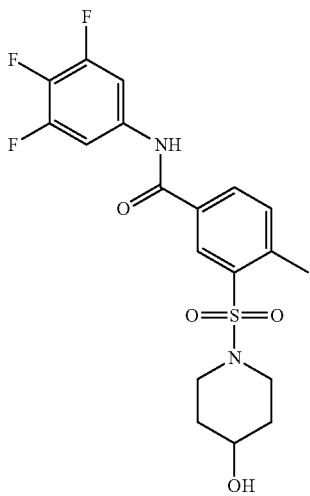<br>429<br>GA<br>A10B18C40 | 925 |
| 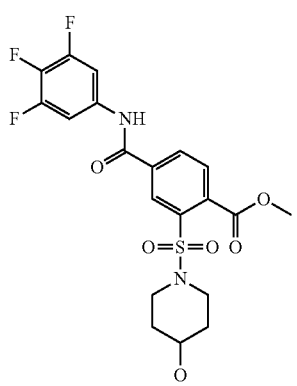<br>473<br>GG<br>A10B17C40<br>¹H NMR (400 MHz, DMSO): δ ppm:<br>10.86(s, 1H), 8.31(s, 1H), 8.29(s, 1H), 7.85<br>(d, J = 7.6 Hz, 1H), 7.72(t, J = 5.0 Hz,<br>2H), 4.73(d, J = 4.0 Hz, 1H), 3.86(s, 3H),<br>3.61(m, 1H), 3.35(m, 2H), 2.95(m, 2H),<br>1.75(m, 2H), 1.38(m, 2H),. | 927 |
TABLE 1-continued
| Structure MS(M + H)+ Synthetic method | Cmp. ID |
|---|---|
| 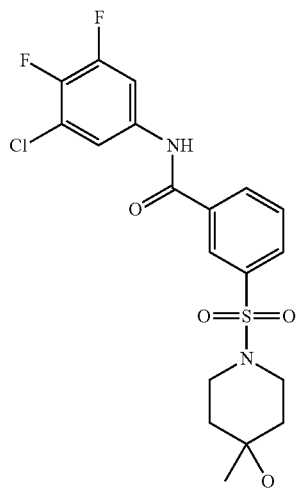<br>445/447<br>GA<br>A73B01C58 | 931 |
| 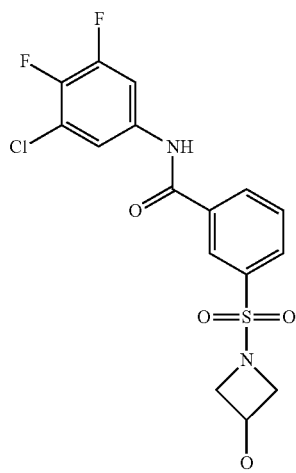<br>403/405<br>GA<br>A19B01C58 | 935 |

TABLE 1-continued
| Structure MS(M + H)+ Synthetic method | Cmp. ID |
|---|---|
| 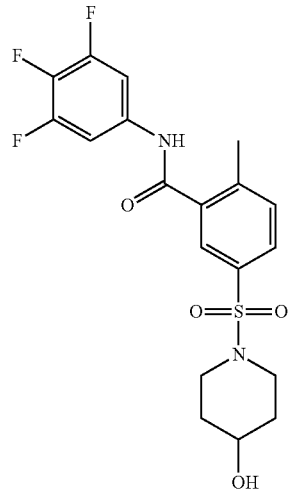<br>429<br>GA<br>A10B17C40 | 928 |
| 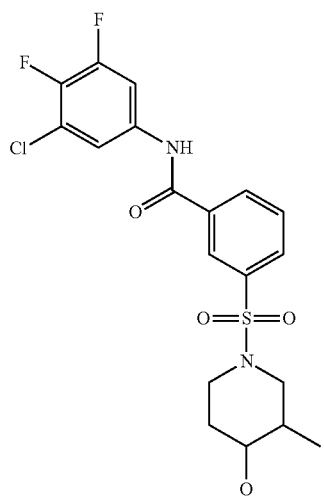<br>445/447<br>GA AGA<br>A84B01C58 | 932_D1 |
TABLE 1-continued
| Structure MS(M + H)+ Synthetic method | Cmp. ID |
|---|---|
| 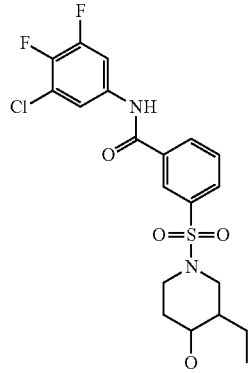<br>459/461<br>GA<br>A85B01C58<br>¹H NMR (400 MHz, CD₃OD) δ 8.34 (s, 1H), 8.24 (d, 1H), 8.03 (d, 1H), 7.80 (m, 2H), 7.75 (m, 1H), 3.60 (m, 2H), 3.27 (m, 1H), 2.74 (m, 1H), 2.47 (m, 1H), 1.96 (m, 1H), 1.75 (m, 1H), 1.59 (m, 1H), 1.44 (m, 1H), 1.27 (m, 1H), 0.99 (t, 3H). | 933_D1 |
| 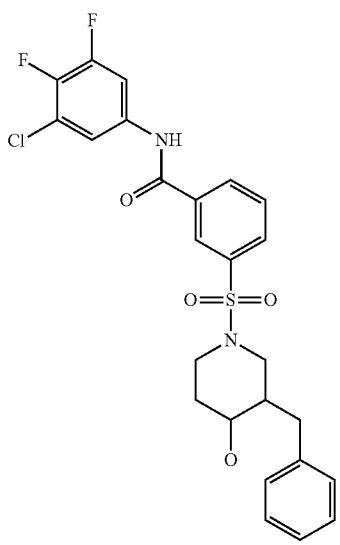<br>521/523<br>GA<br>A86B01C58 | 940_D1 |

TABLE 1-continued
| Structure MS(M + H)+ Synthetic method | Cmp. ID |
|---|---|
| 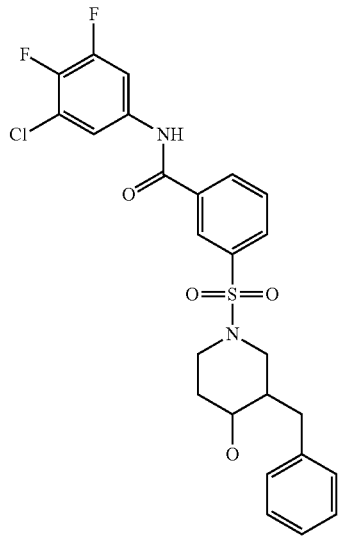 521/523 GA A86B01C58 | 940_D2 |
| 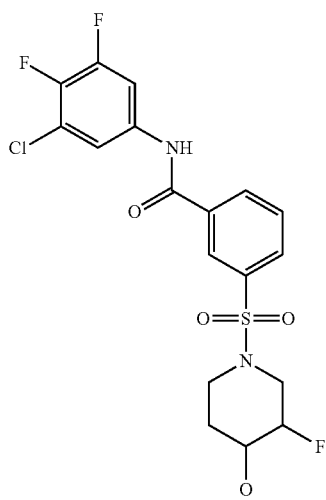 449/451 GA A111B01C58 | 943_D1 |
TABLE 1-continued
| Structure MS(M + H)+ Synthetic method | Cmp. ID |
|---|---|
| 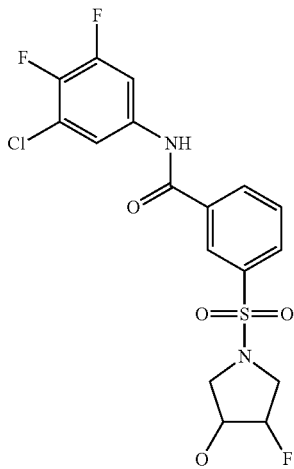 435/439 GA A110B01C58 | 942 |
| 449/451 GA A111B01C58 | 943_D2 |

TABLE 1-continued
| Structure MS(M + H)+ Synthetic method | Cmp. ID |
|---|---|
| 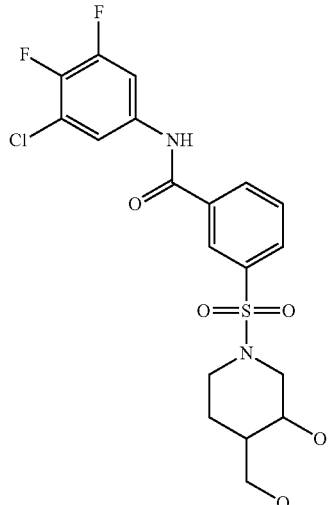<br>461/463<br>GA<br>A104B01C58 | 945_D2 |
| 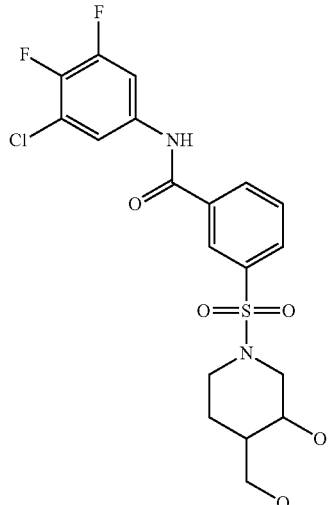<br>463<br>GA<br>A104B01C40 | 946_D1 |
TABLE 1-continued
| Structure MS(M + H)+ Synthetic method | Cmp. ID |
|---|---|
| 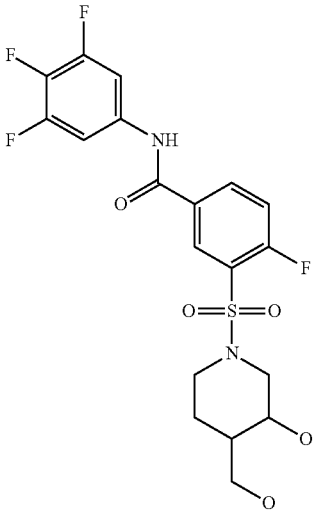 [SMILES: O=C(Nc1cc(F)c(F)c(F)c1)c1ccc(F)c(S(=O)(=O)N2CCC(CO)C(O)C2)c1] | 946_D2 |
| 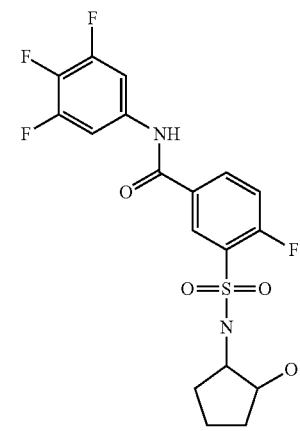<br>433<br>GA<br>A113B03C40<br>¹H NMR (400 MHz, CD₃OD) δ 8.50 (m, 1H), 8.23 (m, 1H), 7.63 (m, 2H), 7.45 (m, 1H), 3.96 (m, 1H), 3.45 (m, 1H), 1.91 (m, 2H), 1.68 (m, 2H), 1.48 (m, 2H). | 952 |

TABLE 1-continued

| Structure MS(M + H)+ Synthetic method | Cmp. ID |
|---|---|
| 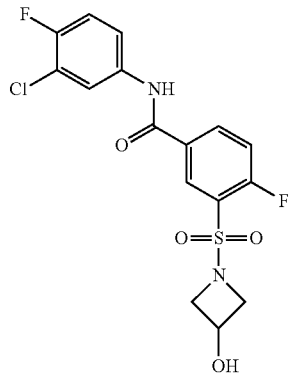<br>403/405<br>GA<br>A19B03C15<br>$^1$H NMR (400 MHz, CD$_3$OD): δ ppm: 8.42(dd, J = 2.0, 6.4 Hz, 1H), 8.26(m, 1H), 7.96(dd, J = 2.4, 6.8 Hz, 1H), 7.62 (m, 1H), 7.54(t, J = 9.2 Hz, 1H), 7.25(t, J = 9.0 Hz, 1H), 4.45(m, 1H), 4.12(t, J = 7.8 Hz, 2H), 3.72(t, J = 6.8 Hz, 2H). | 953 |
| 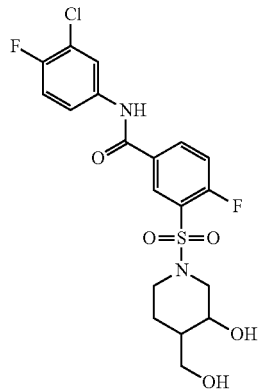<br>475/477<br>GA<br>A113B03C49<br>$^1$H NMR (400 MHz, CD$_3$OD) δ 8.49 (m, 1H), 8.25 (m, 1H), 8.13 (m, 1H), 7.69 (m, 1H), 7.47 (t, 1H), 7.25 (t, 1H), 3.96 (m, 1H), 3.46 (m, 1H), 1.93 (m, 2H), 1.69 (m, 2H), 1.47 (m, 2H). | 954 |

TABLE 1-continued

| Structure MS(M + H)+ Synthetic method | Cmp. ID |
|---|---|
| 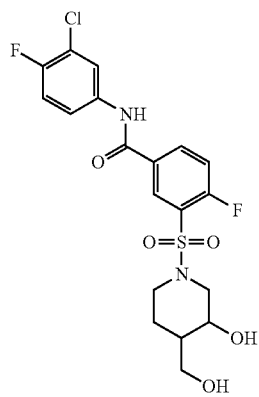<br>461/463<br>GA<br>A104B01C15<br>$^1$H NMR (400 MHz, CD$_3$OD) δ 8.42 (m, 1H), 8.25 (m, 1H), 7.95 (m, 1H), 7.61 (m, 1H), 7.51 (t, 1H), 7.25 (t, 1H), 3.94 (m, 1H), 3.86 (d, 1H), 3.75 (m, 1H), 3.57 (m, 1H), 3.48 (m, 1H), 2.59 (t, 1H), 2.47 (t, 1H), 1.87 (m, 1H), 1.42 (m, 2H). | 955_D1 |
| 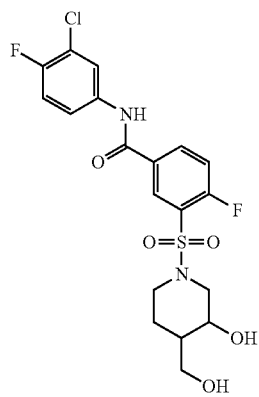<br>461/463<br>GA<br>A104B01C15<br>$^1$H NMR (400 MHz, CD$_3$OD) δ 8.42 (m, 1H), 8.25 (m, 1H), 7.95 (m, 1H), 7.61 (m, 1H), 7.51 (t, 1H), 7.25 (t, 1H), 3.94 (m, 1H), 3.86 (d, 1H), 3.75 (m, 1H), 3.57 (m, 1H), 3.48 (m, 1H), 2.59 (t, 1H), 2.47 (t, 1H), 1.87 (m, 1H), 1.42 (m, 2H). | 955_D2 |

TABLE 1-continued

| Structure MS(M + H)+ Synthetic method | Cmp. ID |
|---|---|
| (3,4-difluorophenyl amide with 4-fluoro-3-(N-(2-hydroxycyclopentyl)sulfamoyl)benzamide structure) 415 GA A113B03C63 | 956 |
| (3,4,5-trifluorophenyl amide with 4-fluoro-3-(N-(3-hydroxycyclopentyl)sulfamoyl)benzamide structure) 433 GA A114B03C40 ¹H NMR (400 MHz, CD₃OD) δ 8.48 (m, 1H), 8.23 (m, 1H), 7.63 (m, 1H), 7.52 (t, 1H), 4.13 (m, 1H), 3.71 (m, 1H), 2.09 (m, 1H), 1.68 (m, 4H), 1.44 (m, 1H). | 957 |
| (3-chloro-4-fluorophenyl amide with 4-fluoro-3-(N-(3-hydroxycyclopentyl)sulfamoyl)benzamide structure) 431/433 GA A114B03C15 | 958 |
| (3-bromo-4-fluorophenyl amide with 4-fluoro-3-(N-(3-hydroxycyclopentyl)sulfamoyl)benzamide structure) 475/477 GA A114B03C49 | 959 |

TABLE 1-continued
| Structure MS(M + H)+ Synthetic method | Cmp. ID |
|---|---|
|  451 GA A111B03C40 | 960_D1 |
| 451 GA A111B03C40 | 960_D2 |
TABLE 1-continued
| Structure MS(M + H)+ Synthetic method | Cmp. ID |
|---|---|
| 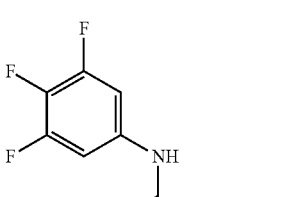 415 GA A114B03C63 | 961 |
| 447 GA A116B03C40 $^1$H NMR (400 MHz, CD$_3$OD) δ 8.48 (m, 1H), 8.25 (m, 1H), 7.63 (m, 1H), 7.52 (t, 1H), 3.46 (m, 1H), 3.24 (m, 1H), 2.05 (m, 1H), 1.84 (m, 1H), 1.73 (m, 2H), 1.24 (m, 4H). | 962_D1 |

TABLE 1-continued
| Structure MS(M + H)+ Synthetic method | Cmp. ID |
|---|---|
| 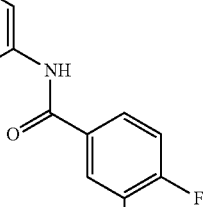 447 GA A116B03C40 | 962_D2 |
| 445/447 GA A116B03C15 | 963_D1 |
TABLE 1-continued
| Structure MS(M + H)+ Synthetic method | Cmp. ID |
|---|---|
| 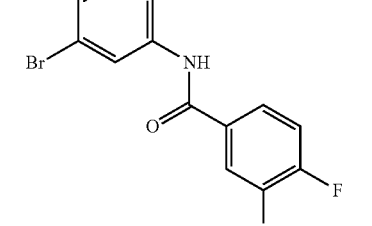 445/447 GA A116B03C15 | 963_D2 |
| 489/491 GA A116B03C15 | 964_D1 |

TABLE 1-continued
| Structure MS(M + H)+ Synthetic method | Cmp. ID |
|---|---|
| 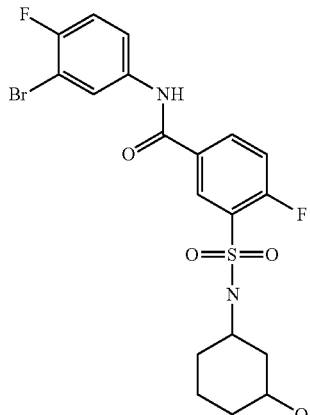<br>489/491<br>GA<br>A116B03C49<br>$^1$H NMR (400 MHz, CD$_3$OD) δ 8.49 (m, 1H), 8.23 (m, 1H), 8.13 (m, 1H), 7.68 (m, 1H), 7.48 (m, 1H), 7.25 (t, 1H), 3.99 (m, 1H), 3.61 (m, 1H), 1.57 (m, 8H). | 964_D2 |
| 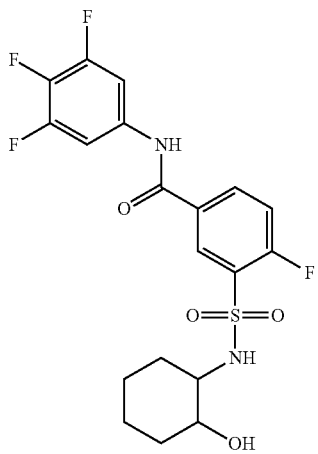<br>447<br>GA<br>A118B03C40 | 972_D1 |
TABLE 1-continued
| Structure MS(M + H)+ Synthetic method | Cmp. ID |
|---|---|
| <br>447<br>GA<br>A118B03C40 | 972_D2 |
| 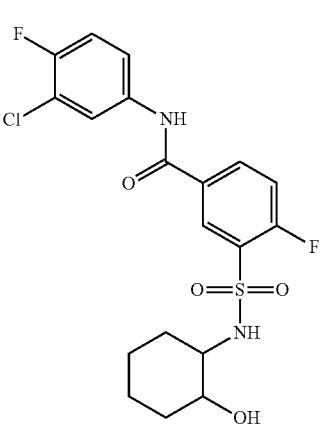<br>445/447<br>GA<br>A118B03C15 | 973_D1 |

TABLE 1-continued

| Structure MS(M + H)+ Synthetic method | Cmp. ID |
|---|---|
| [Structure: N-(3-chloro-4-fluorophenyl)-4-fluoro-3-[(2-hydroxycyclohexyl)sulfamoyl]benzamide] 445/447 GA A118B03C15 $^1$H NMR (400 MHz, CD$_3$OD) δ 8.49 (m, 1H), 8.23 (m, 1H), 7.98 (m, 1H), 7.63 (m, 1H), 7.48 (m, 1H), 7.27 (t, 1H), 3.78 (m, 1H), 1.58 (m, 9H). | 973_D2 |
| [Structure: N-(3,4-difluorophenyl)-4-fluoro-3-[(2-hydroxycyclohexyl)sulfamoyl]benzamide] 429 GA A118B03C63 $^1$H NMR (400 MHz, CD$_3$OD) δ 8.49 (m, 1H), 8.21 (m, 1H), 7.83 (m, 1H), 7.42 (t, 2H), 7.27 (m, 1H), 3.00 (m, 1H), 1.91 (m, 2H), 1.67 (m, 2H), 1.27 (m, 5H). | 976_D1 |
| [Structure: 4-fluoro-3-[(3-hydroxycyclobutyl)sulfamoyl]-N-(3,4,5-trifluorophenyl)benzamide] 419 GA A119B03C40 | 977_D2 |
| [Structure: N-(3-chloro-4-fluorophenyl)-4-fluoro-3-[(3-hydroxycyclobutyl)sulfamoyl]benzamide] 417/419 GA A119B03C15 | 978_CT1 |
| [Structure: N-(3-chloro-4-fluorophenyl)-4-fluoro-3-[(3-hydroxycyclobutyl)sulfamoyl]benzamide] 417 GA A119B03C15 | 978_CT2 |

| Structure MS(M + H)+ Synthetic method | Cmp. ID |
|---|---|
| 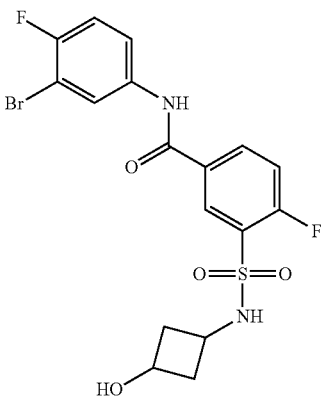<br>462/464<br>GA<br>A119B03C49 | 979_CT1 |
| 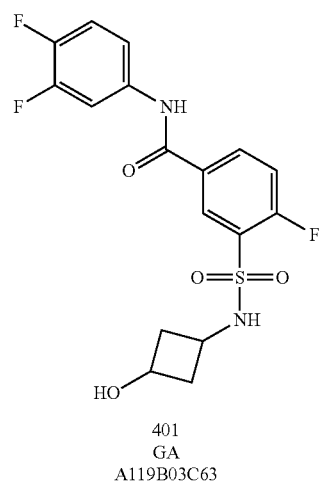 [SMILES: O=C(Nc1ccc(F)c(F)c1)c1ccc(F)c(S(=O)(=O)NC2CC(O)C2)c1]<br>401<br>GA<br>A119B03C63 | 981_CT2 |
| 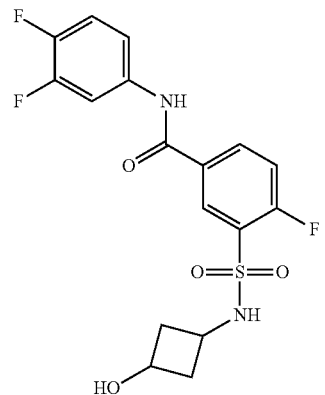<br>401<br>GA<br>A119B03C63 | 981_D1 |
| Structure MS(M + H)+ Synthetic method | Cmp. ID |
|---|---|
| 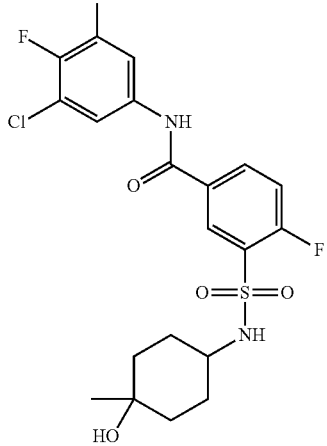<br>477/479<br>GA<br>A121B03C58 | 990_D1 |
| 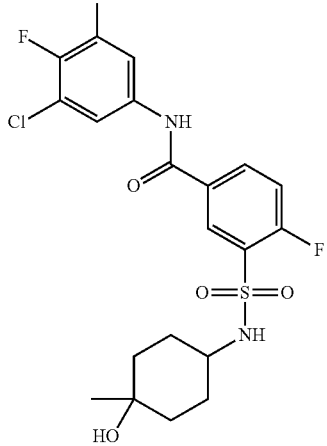<br>459/461<br>GA<br>A121B03C15 | 988_D1 |
| 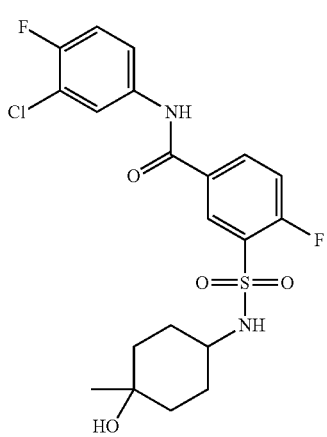<br>459/461<br>GA<br>A121B03C15 | 988_D2 |

TABLE 1-continued
| Structure MS(M + H)+ Synthetic method | Cmp. ID |
|---|---|
| 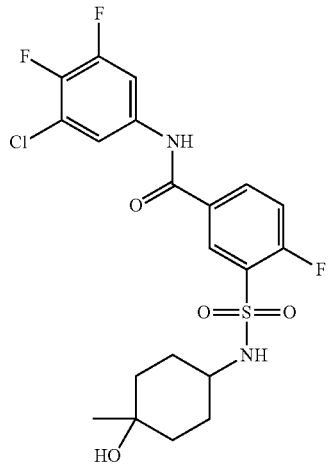<br>477/479<br>GA<br>A121B03C58 | 990_D2 |
| 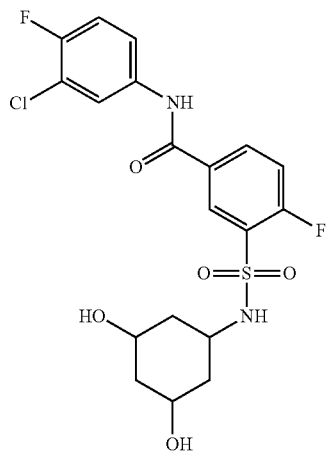<br>461/463<br>GA<br>A123B03C15 | 998_D1 |
TABLE 1-continued
| Structure MS(M + H)+ Synthetic method | Cmp. ID |
|---|---|
| 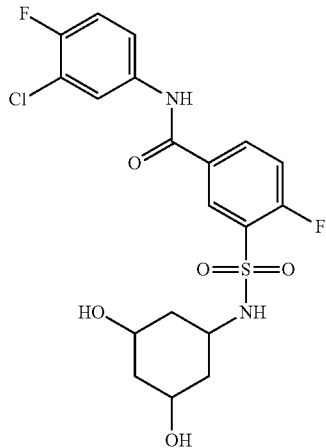<br>461/463<br>GA<br>A123B03C15 | 998_D2 |
| 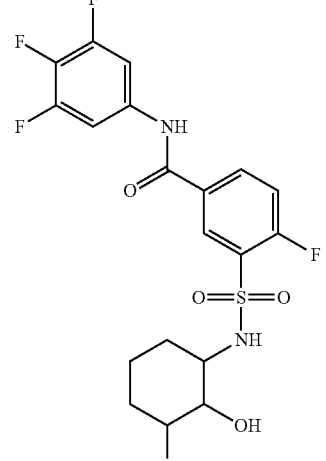<br>463<br>GA<br>A125B03C40 | 1007 |

TABLE 1-continued

| Structure MS(M + H)+ Synthetic method | Cmp. ID |
|---|---|
| (structure) 461/463 GA A125B03C15 ¹H NMR (400 MHz, MeOD) δ 8.51-8.49 (m, 2H), 7.99-7.96 (m, 1H), 7.63-7.62 (m, 1H), 7.50-7.45 (m, 1H), 7.28-7.24 (m, 1H), 3.77-3.76 (m, 1H), 3.65-3.62 (m, 1H), 3.56-3.54 (m, 1H), 1.79-1.73 (m, 2H), 1.49-1.42 (m, 2H), 1.41-1.38 (m, 2H). | 1008 |
| (structure) 433/435 GA A112B07C40 | 1017 |
| (structure) 431/435 GA A112B07C15 | 1018 |
| (structure) 476/478 GA A112B07C49 | 1019 |
| (structure) 449/451 GA A113B07C40 | 1021 |

TABLE 1-continued
| Structure MS(M + H)+ Synthetic method | Cmp. ID |
|---|---|
| 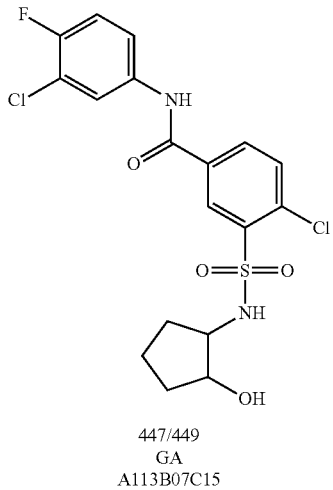 [SMILES: O=C(Nc1ccc(F)c(Cl)c1)c1ccc(Cl)c(S(=O)(=O)NC2CCCC2O)c1]<br>447/449<br>GA<br>A113B07C15 | 1022 |
| 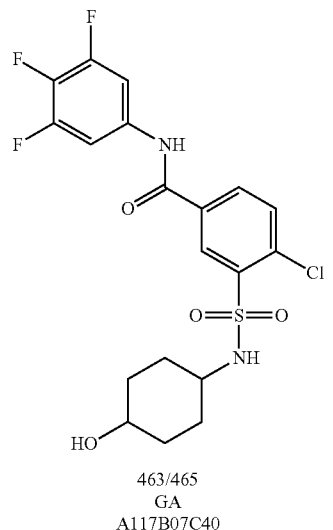 [SMILES: O=C(Nc1cc(F)c(F)c(F)c1)c1ccc(Cl)c(S(=O)(=O)NC2CCC(O)CC2)c1]<br>463/465<br>GA<br>A117B07C40 | 1033 |
TABLE 1-continued
| Structure MS(M + H)+ Synthetic method | Cmp. ID |
|---|---|
| 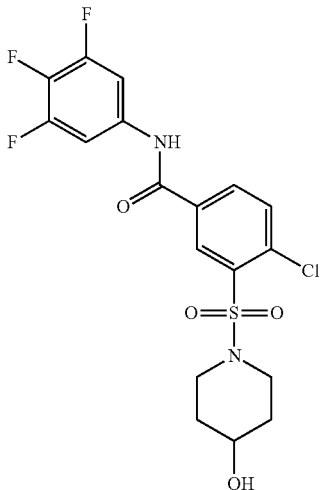<br>449/451<br>GA<br>A10B07C40 | 1057 |
| 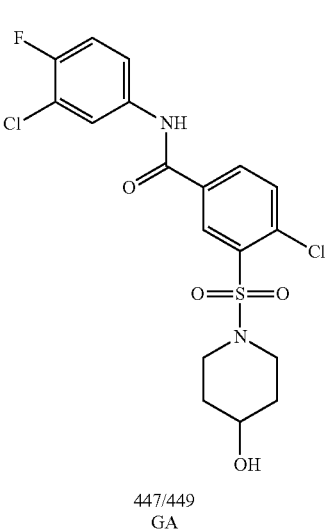<br>447/449<br>GA<br>A10B07C15 | 1058 |

TABLE 1-continued
| Structure MS(M + H)+ Synthetic method | Cmp. ID |
|---|---|
| 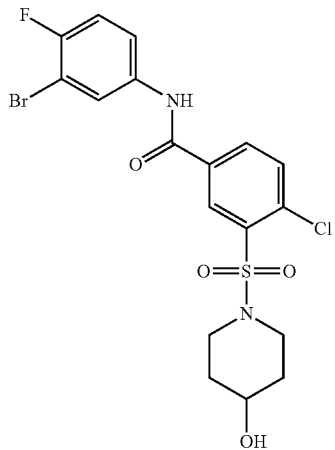<br>492/494<br>GA<br>A10B07C49 | 1059 |
| 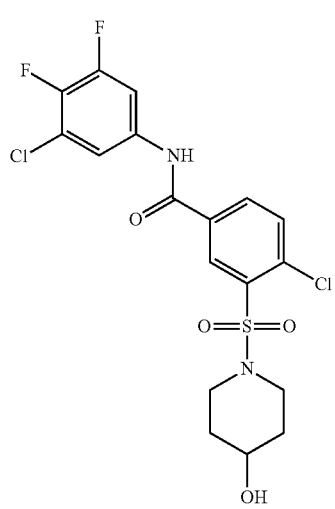<br>465/467<br>GA<br>A10B07C58 | 1060 |
TABLE 1-continued
| Structure MS(M + H)+ Synthetic method | Cmp. ID |
|---|---|
| 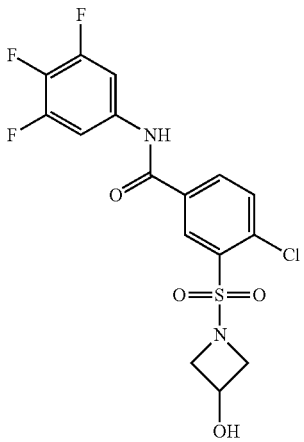<br>421/423<br>GA<br>A19B07C40<br>$^1$H NMR (400 MHz, CD$_3$OD) δ 8.56 (d, 1 H), 8.15 (m, 1H), 7.81 (d, 1H), 7.61 (m, 2H), 4.53 (m, 1H), 4.16 (m, 2H), 3.89 (m, 2H). | 1061 |
| 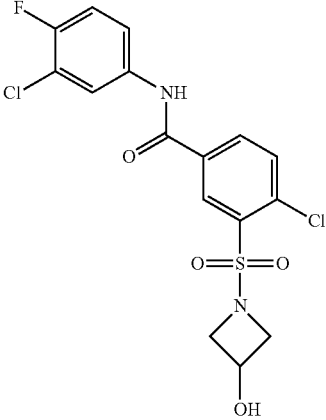<br>419/421<br>GA<br>A19B07C15<br>$^1$H NMR (400 MHz, CD$_3$OD) δ 8.56 (d, 1 H), 8.15 (d, 1H), 7.99 (m, 1H), 7.82 (m, 1H), 7.63 (m, 1H), 7.25 (m, 1H), 4.53 (m, 1H), 4.17 (m, 2H), 3.89 (m, 2H). | 1062 |

TABLE 1-continued
| Structure MS(M + H)+ Synthetic method | Cmp. ID |
|---|---|
| 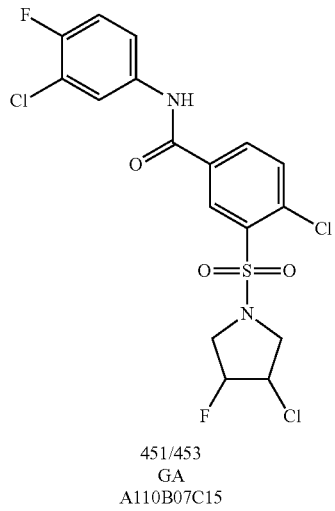 [SMILES: O=C(Nc1ccc(F)c(Cl)c1)c1ccc(Cl)c(S(=O)(=O)N2CC(F)C(Cl)C2)c1]<br>451/453<br>GA<br>A110B07C15 | 1070 |
| 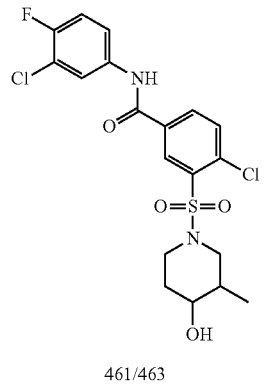<br>461/463<br>GA<br>A84B07C15<br>¹H NMR (400 MHz, CD₃OD) δ 8.48 (d, J = 2 Hz, 1H), 8.08 (m, 1H), 8.01 (s, 1H), 7.88 (d, J = 6.4 Hz, 1H), 7.68 (m, 1H), 7.50 (m, 1H), 7.17 (m, 1H), 3.75 (m, 2H), 3.30 (m, 1H), 3.01 (m, 1H), 2.65 (m, 1H), 2.01 (m, 1H), 1.68 (m, 2H), 1.10 (d, J = 6.4 Hz, 3H) | 1078_D1 |
TABLE 1-continued
| Structure MS(M + H)+ Synthetic method | Cmp. ID |
|---|---|
| 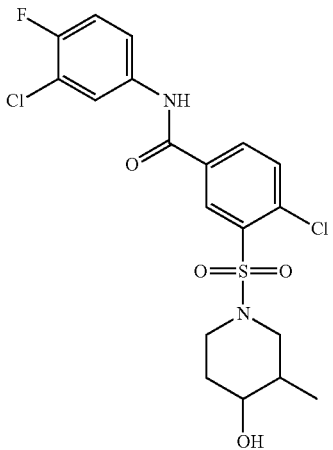<br>461/463<br>GA<br>A84B07C15 | 1078_D2 |
| 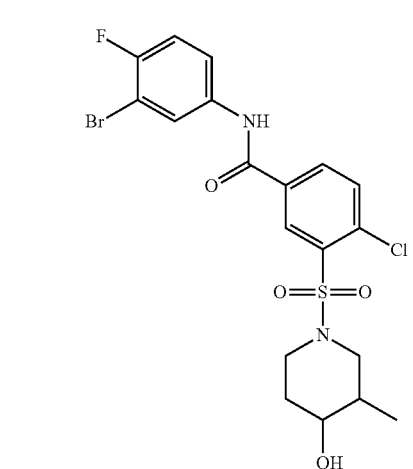<br>506/508<br>GA<br>A84B07C49 | 1079 |

TABLE 1-continued
| Structure MS(M + H)+ Synthetic method | Cmp. ID |
|---|---|
| 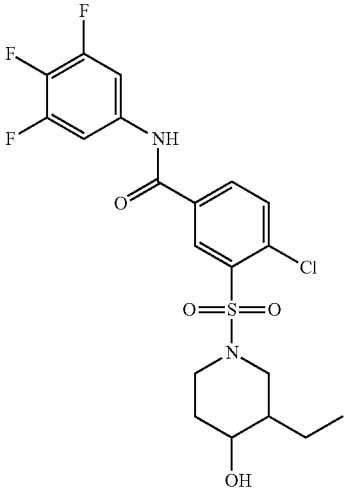 477/479 GA A85B07C40 | 1081_D1 |
| 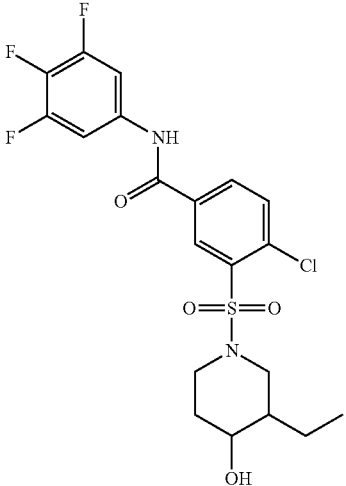 477/479 GA A85B07C40 | 1081_D2 |
TABLE 1-continued
| Structure MS(M + H)+ Synthetic method | Cmp. ID |
|---|---|
| 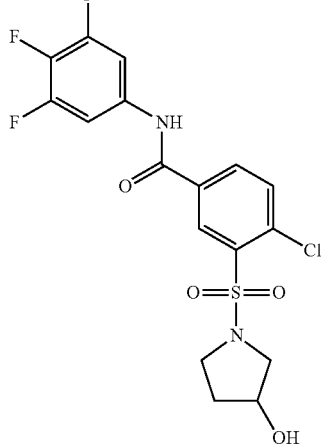 435/437 GA A17B07C40 | 1089 |
| 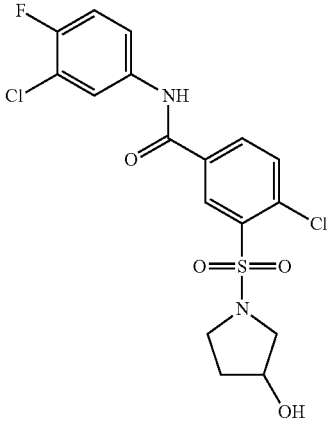 433/435 GA A17B07C15 | 1090 |
| 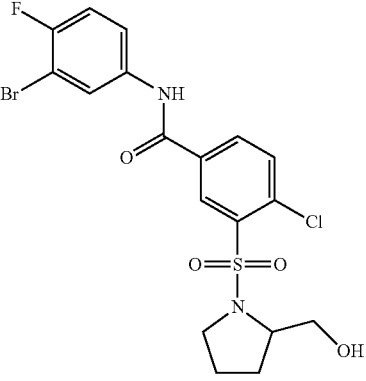 492/494 GA A18B07C49 | 1095_R |

TABLE 1-continued

| Structure MS(M + H)+ Synthetic method | Cmp. ID |
|---|---|
| (structure) 491/493 GA A18B07C49 | 1095_S |
| (structure) 465/467 GA A18B07C58 | 1096_R |
| (structure) 465/467 GA A18B07C58 | 1096_S |
| (structure) 477/479 GA A81B07C15 | 1098 |
| (structure) 523/521 GA A81B07C49 | 1099 |

TABLE 1-continued
| Structure MS(M + H)+ Synthetic method | Cmp. ID |
|---|---|
| 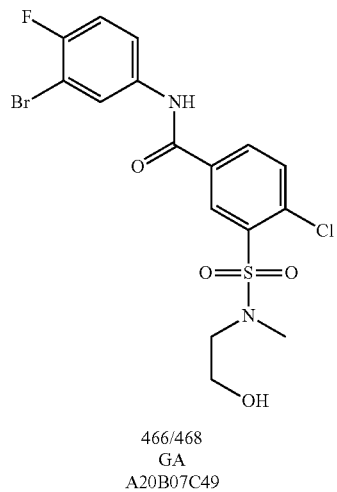<br>466/468<br>GA<br>A20B07C49 | 1107 |
| 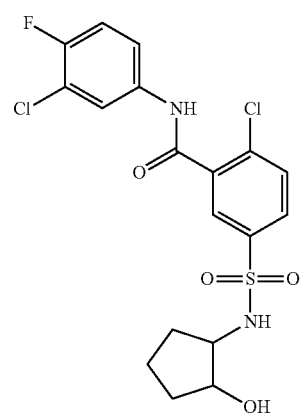<br>447/449<br>GA<br>A113B06C15<br>¹H NMR (400 MHz, CD₃OD) δ 8.06 (d, J = 2 Hz, 1 H), 7.99 (m, 2 H), 7.75 (m, 1 H), 7.30 (m, 1 H), 7.25 (m, 1 H), 3.93 (m, 1 H), 3.35 (m, 1 H), 1.93 (m, 2 H), 1.88 (m, 2 H), 1.68 (m, 1 H), 1.52 (m, 1 H). | 1114 |
TABLE 1-continued
| Structure MS(M + H)+ Synthetic method | Cmp. ID |
|---|---|
| 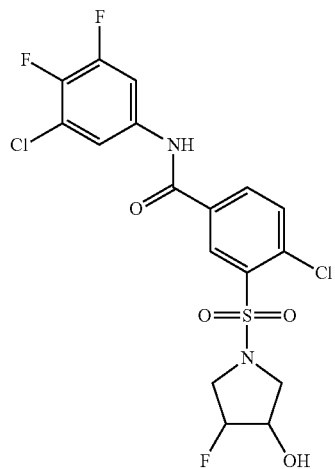<br>469/471<br>GA<br>A110B07C58 | 1116 |
| 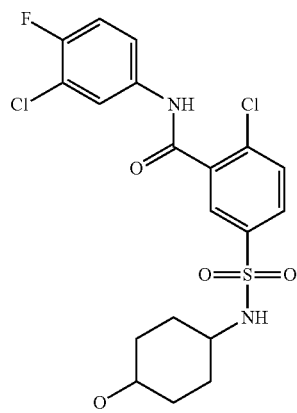<br>461/463<br>GA<br>A117B06C15 | 1126 |

TABLE 1-continued
| Structure MS(M + H)+ Synthetic method | Cmp. ID |
|---|---|
| 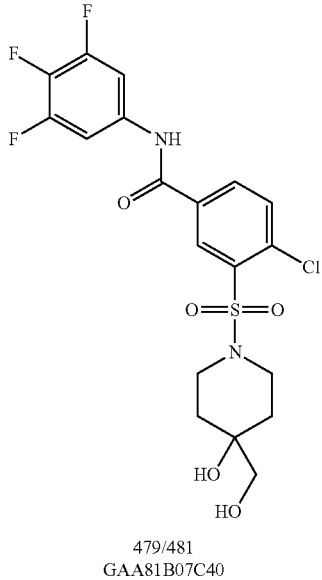 [SMILES: O=C(Nc1cc(F)c(F)c(F)c1)c1ccc(Cl)c(S(=O)(=O)N2CCC(O)(CO)CC2)c1] 479/481 GAA81B07C40 | 1130 |
| 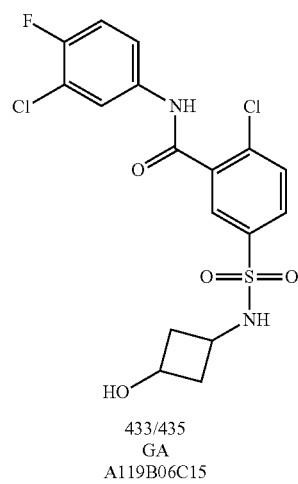 [SMILES: O=C(Nc1ccc(F)c(Cl)c1)c1cc(S(=O)(=O)NC2CC(O)C2)ccc1Cl] 433/435 GA A119B06C15 | 1134_CT1 |
| 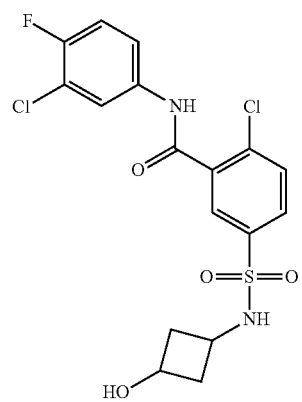 433/435 GA A119B06C15 | 1134_CT2 |
TABLE 1-continued
| Structure MS(M + H)+ Synthetic method | Cmp. ID |
|---|---|
| 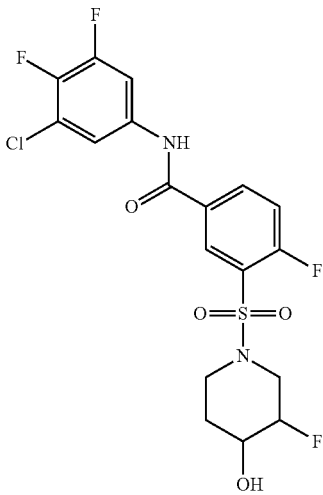 467/469 GA A111B03C58 | 1135_D1 |
| 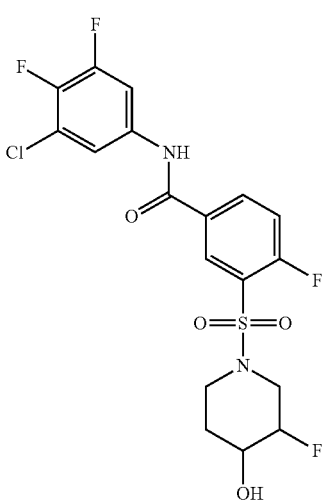 467/469 GA A111B03C58 | 1135_D2 |

TABLE 1-continued

| Structure MS(M + H)+ Synthetic method | Cmp. ID |
|---|---|
| [Structure: N-(3,4,5-trifluorophenyl)-2-chloro-5-((4-hydroxypiperidin-1-yl)sulfonyl)benzamide] 449/451 GA A10B06C40 $^1$H NMR (400 MHz, CD$_3$OD) δ 7.95 (s, 1 H), 7.88 (d, J = 2 Hz, 1 H), 7.81 (d, J = 4.4 Hz, 1 H), 7.53 (m, 2 H), 3.69 (m, 1 H), 3.40 (m, 2 H), 2.91 (m, 2 H), 1.88 (m, 2 H), 1.60 (m, 2 H). | 1149 |
| [Structure: N-(3-chloro-4-fluorophenyl)-2-chloro-5-((4-hydroxypiperidin-1-yl)sulfonyl)benzamide] 447/449 GA A10B06C15 | 1150 |
| [Structure: N-(3-chloro-4-fluorophenyl)-2-chloro-5-((3-hydroxyazetidin-1-yl)sulfonyl)benzamide] 419/421 GA A19B06C15 | 1154 |
| [Structure: N-(3-chloro-4-fluorophenyl)-3-((3-hydroxycyclopentyl)sulfamoyl)benzamide] 413/415 GA A114B01C15 | 1157 |

TABLE 1-continued

| Structure MS(M + H)+ Synthetic method | Cmp. ID |
|---|---|
| (structure) 447 GA A73B03C40 | 1161 |
| (structure) 461/463 GA A84B06C15 | 1170_D1 |
| (structure) 461/463 GA A84B06C15 | 1170_D2 |
| (structure) 475/477 GA A09B06C15 | 1178 |

TABLE 1-continued

| Structure MS(M + H)+ Synthetic method | Cmp. ID |
|---|---|
| [Structure: N-(3-chloro-4-fluorophenyl)-2-chloro-5-((3-hydroxypyrrolidin-1-yl)sulfonyl)benzamide] 433/435 GA A17B06C15 | 1182 |
| [Structure: N-(3-chloro-4-fluorophenyl)-2-chloro-5-(N-(2-hydroxyethyl)-N-methylsulfamoyl)benzamide] 421/423 GA A20B06C15 | 1198 |
| [Structure: N-(3-chloro-4-fluorophenyl)-2-chloro-5-((4-hydroxy-4-phenylpiperidin-1-yl)sulfonyl)benzamide] 523/525 GA A75B06C15 | 1194 |
| [Structure: 2,4-difluoro-5-((4-hydroxypiperidin-1-yl)sulfonyl)-N-(3,4,5-trifluorophenyl)benzamide] 451 GA A10B08C40 ¹HNMR (400 MHz, CD₃OD) δ 8.24 (t, 1H), 7.57 (m, 2H), 7.42 (t, 1H), 3.76 (m, 1H), 3.53 (m, 1H), 3.08 (m, 2H), 1.92 (m, 2H), 1.60 (m, 2H). | 1201 |

TABLE 1-continued
| Structure MS(M + H)+ Synthetic method | Cmp. ID |
|---|---|
| 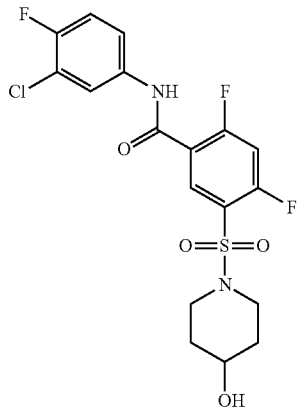<br>449/451<br>GA<br>A10B08C15<br>¹H NMR (400 MHz, CD₃OD) d 8.25 (t, 1H), 7.97 (m, 1H), 7.58(m, 1H), 7.47 (t, 1H), 7.27 (t, 1H), 3.75 (m, 1H), 3.55 (m, 1H), 3.06 (m, 1H), 1.91(m, 2H), 1.60 (m, 2H). | 1202 |
| 423<br>GA<br>A19B08C40 | 1205 |
TABLE 1-continued
| Structure MS(M + H)+ Synthetic method | Cmp. ID |
|---|---|
| 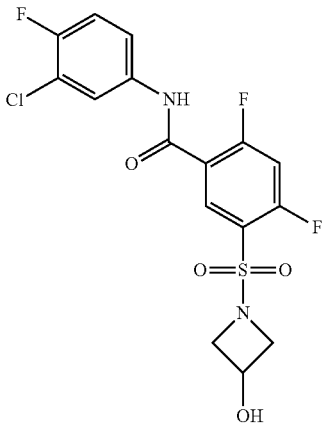<br>421/423<br>GA<br>A19B08C15 | 1206 |
| 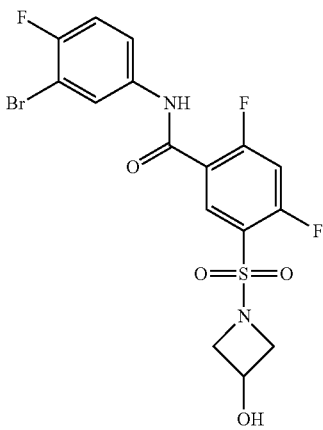<br>466/468<br>GA<br>A19B08C49 | 1207 |

TABLE 1-continued
| Structure MS(M + H)+ Synthetic method | Cmp. ID |
|---|---|
| 439/441<br>GA<br>A19B08C58<br>¹H NMR (400 MHz, CD₃OD) δ 8.26 (t, 1H), 7.74 (m, 1H), 7.66 (m, 1H), 7.51 (t, 1H), 4.49 (m, 1H), 4.13 (m, 2H), 3.73 (m, 2H). | 1208 |
| 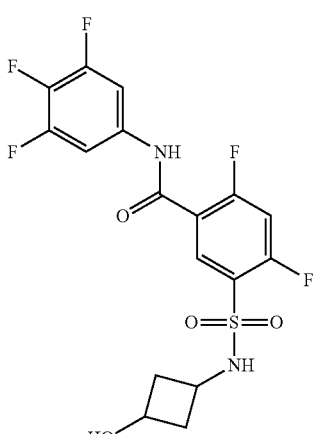<br>437<br>GA<br>A119B08C40<br>¹H NMR (400 MHz, CD₃OD) δ 8.24 (t, 1H), 7.58 (m, 2H), 7.44 (m, 1H), 4.34 (m, 1H), 4.05 (m, 1H), 2.20 (m, 4H). | 1209_CT1 |
| Structure MS(M + H)+ Synthetic method | Cmp. ID |
|---|---|
| 437<br>GA<br>A119B08C40 | 1209_CT2 |
| 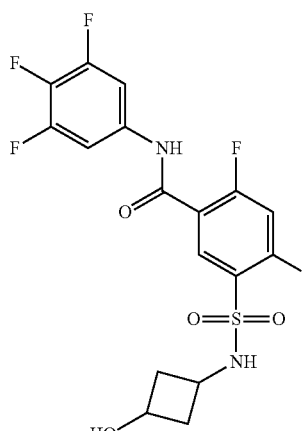507/509<br>GA<br>A84B08C49 | 1231 |

TABLE 1-continued
| Structure MS(M + H)+ Synthetic method | Cmp. ID |
|---|---|
| <br>437<br>GA<br>A17B08C40 | 1241 |
| 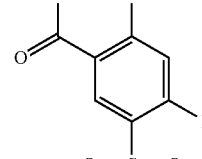<br>435/437<br>GA<br>A17B08C15 | 1242 |
| 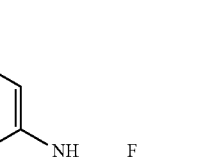<br>481<br>GA<br>A81B08C40 | 1249 |
| 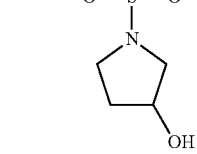<br>479/481<br>GA<br>A81B08C15 | 1250 |

TABLE 1-continued
| Structure MS(M + H)+ Synthetic method | Cmp. ID |
|---|---|
| 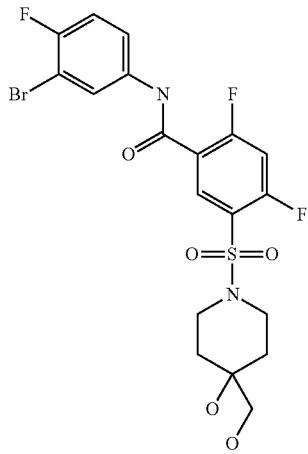<br>GA A81B08C49<br>¹H NMR (400 MHz, CD₃OD) δ 8.25 (t, 1H), 8.08 (m, 1H), 7.65 (m, 1H), 7.43 (t, 1H), 7.27 (t, 1H), 3.66 (m, 2H), 3.38 (s, 2H), 2.97 (t, 2H), 1.75 (m, 2H), 1.60 (m, 2H). | 1251 |
| 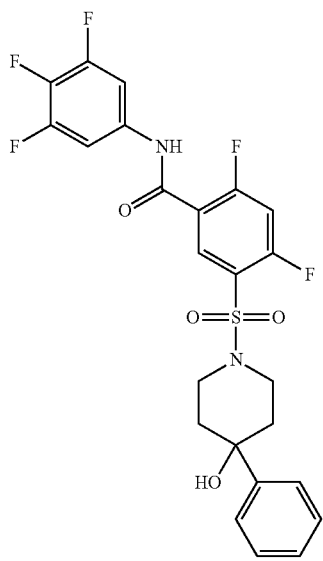<br>527<br>GA<br>A75B08C40 | 1253 |
TABLE 1-continued
| Structure MS(M + H)+ Synthetic method | Cmp. ID |
|---|---|
| 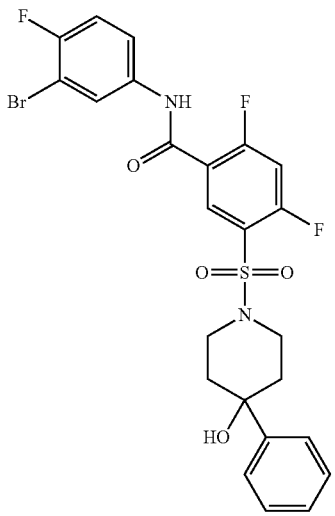<br>569/571<br>GA<br>A75B08C49 | 1255 |
| 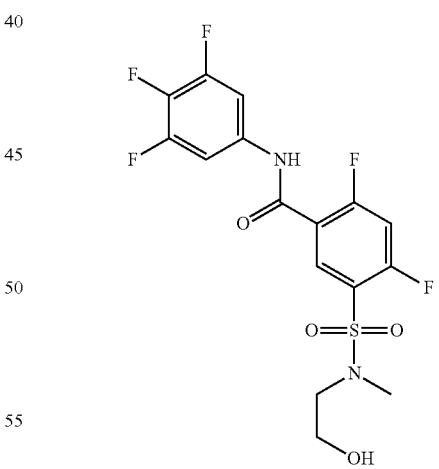<br>425<br>GA<br>A20B08C40 | 1257 |

TABLE 1-continued
| Structure MS(M + H)+ Synthetic method | Cmp. ID |
|---|---|
| 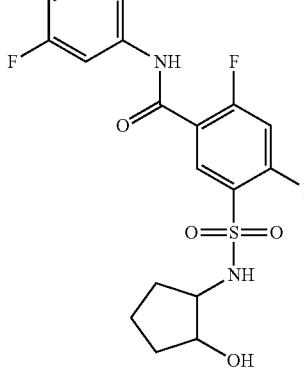<br>451<br>GA<br>A113B08C40 | 1261 |
| 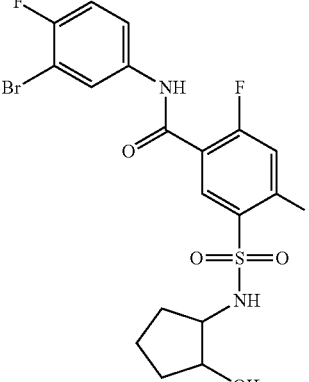<br>493/495<br>GA<br>A113B08C49 | 1263 |
| 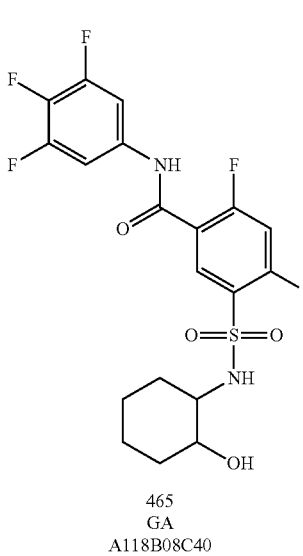<br>465<br>GA<br>A118B08C40 | 1273_D1 |
TABLE 1-continued
| Structure MS(M + H)+ Synthetic method | Cmp. ID |
|---|---|
| 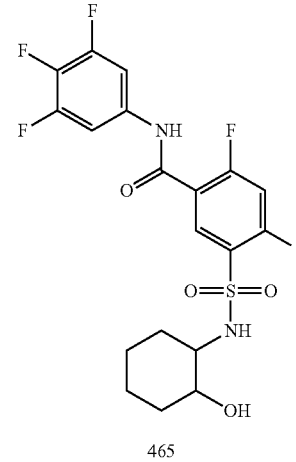<br>465<br>GA<br>A118B08C40<br>$^1$H NMR (400 MHz, CD$_3$OD) δ 8.29 (t, 1H), 7.57 (m, 2H), 7.35 (t, 1H), 2.98 (m, 1H), 1.91 (m, 2H), 1.67 (m, 2H), 1.25 (m, 5H). | 1273_D2 |
| 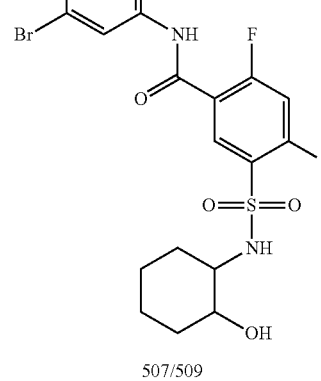<br>507/509<br>GA<br>A118B08C49 | 1275 |

TABLE 1-continued
| Structure MS(M + H)+ Synthetic method | Cmp. ID |
|---|---|
| 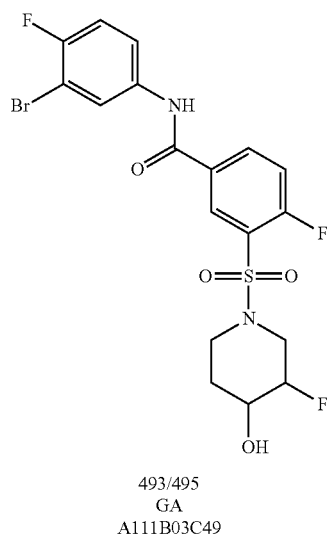 [SMILES: O=C(Nc1ccc(F)c(Br)c1)c1ccc(F)c(S(=O)(=O)N2CCC(O)C(F)C2)c1]<br>493/495<br>GA<br>A111B03C49 | 1281_D1 |
| <br>493/495<br>GA<br>A111B03C49 | 1281_D2 |
| 445<br>GA A123B03C63 | 1001_D1 |
TABLE 1-continued
| Structure MS(M + H)+ Synthetic method | Cmp. ID |
|---|---|
| 445<br>GA A123B03C63 | 1001_D2 |
| 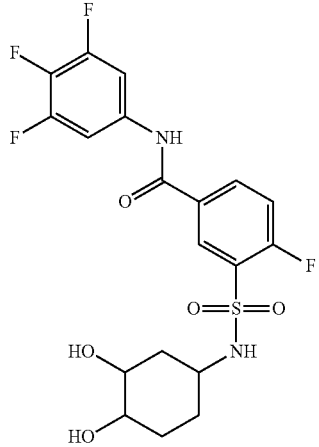<br>463<br>GA A12B03C40 | 1002_D1 |

TABLE 1-continued

| Structure MS(M + H)+ Synthetic method | Cmp. ID |
|---|---|
| [Structure: 3,4,5-trifluorophenyl-NH-C(=O)-benzene(4-F)-SO2-NH-cyclohexane(3-OH,4-OH)]<br>463<br>GA A124B03C40<br>1H NMR (400 MHz, METHANOL-d4) = 8.47 (m, 1H), 8.23 (m, 1H), 7.61 (m, 2H), 7.49 (m, 1H), 3.78-3.72 (m, 1H), 3.58-3.49 (m, 1H), 3.32-3.27 (m, 1H), 1.83-1.75 (m, 1H), 1.74-1.56 (m, 3H), 1.51-1.36 (m, 2H) | 1002_D2 |
| [Structure: 3-Cl-4-F-phenyl-NH-C(=O)-benzene(4-F)-SO2-NH-cyclohexane(3-OH,4-OH)]<br>461/463<br>GA A124B03C15 | 1003_D1 |
| [Structure: 3-Cl-4-F-phenyl-NH-C(=O)-benzene(4-F)-SO2-NH-cyclohexane(3-OH,4-OH)]<br>461/163<br>GA<br>A124B03C15 | 1003_D2 |
| [Structure: 3-Br-4-F-phenyl-NH-C(=O)-benzene(4-F)-SO2-NH-cyclohexane(3-OH,4-OH)]<br>505/507<br>GA<br>A124B03C49 | 1004_D1 |
| [Structure: 3-Br-4-F-phenyl-NH-C(=O)-benzene(4-F)-SO2-NH-cyclohexane(3-OH,4-OH)]<br>505/507<br>GA<br>A124B03C49 | 1004_D2 |
| [Structure: 3-Cl-4,5-diF-phenyl-NH-C(=O)-benzene(4-F)-SO2-NH-cyclohexane(3-OH,4-OH)]<br>479/481<br>GA<br>A124B03C58 | 1005_D1 |

TABLE 1-continued
| Structure MS(M + H)+ Synthetic method | Cmp. ID |
|---|---|
| 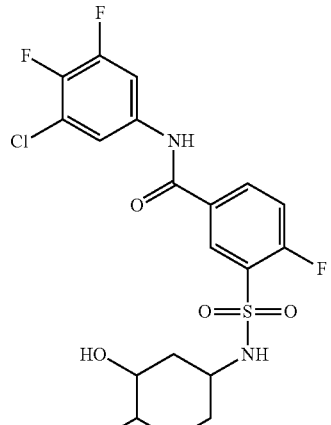 479/481 GA A124B03C58 | 1005_D2 |
| 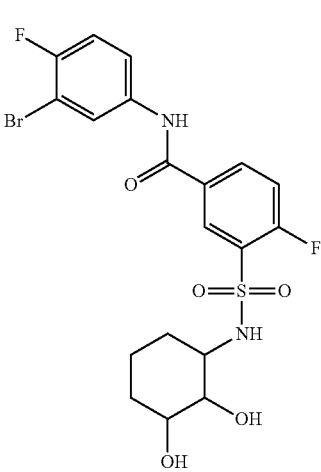 445/446 GA A121B06C40 | 1006_D1 |
TABLE 1-continued
| Structure MS(M + H)+ Synthetic method | Cmp. ID |
|---|---|
| 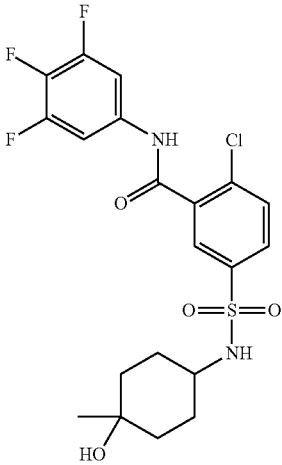 445/446 GA A121B06C40 | 1006_D2 |
| 505/507 GA A125B03C49 | 1009 |

TABLE 1-continued

| Structure MS(M + H)+ Synthetic method | Cmp. ID |
|---|---|
| [Structure of 3-chloro-4,5-difluoro-phenyl benzamide with 4-F and sulfonamide linked to 2,3-dihydroxycyclohexyl] 479/481 GA A125B03C58 ¹H NMR (400 MHz, METHANOL-d4) = 8.58-8.48 (m, 1H), 8.26-8.17 (m, 1H), 7.83-7.71 (m, 2H), 7.48-7.43 (m, 1H), 3.98-3.91 (m, 1H), 3.45 (m, 1H), 3.36-3.34 (m, 1H), 1.89-1.71 (m, 2H), 1.68-1.55 (m, 1H), 1.44 (m, 2H), 1.37-1.26 (m, 1H) | 1010 |
| [Structure of 3,4-difluorophenyl benzamide with 4-F and sulfonamide linked to 2,3-dihydroxycyclohexyl] 445 GA A125B03C63 | 1011 |

TABLE 1-continued

| Structure MS(M + H)+ Synthetic method | Cmp. ID |
|---|---|
| [Structure of 3-chloro-4,5-difluorophenyl benzamide with 4-Cl and sulfonamide linked to cyclopentyl] 449/451 GA A112B07C49 | 1020 |
| [Structure of 3-bromo-4-fluorophenyl benzamide with 4-Cl and sulfonamide linked to 2-hydroxycyclopentyl] 491/493 GA A113B07C49 | 1023 |
| [Structure of 3-chloro-4,5-difluorophenyl benzamide with 4-Cl and sulfonamide linked to 2-hydroxycyclopentyl] 465/467 GA A113B07C58 | 1024 |

TABLE 1-continued

| Structure MS(M + H)+ Synthetic method | Cmp. ID |
|---|---|
| [structure: N-(3,4,5-trifluorophenyl)-4-chloro-3-(N-cyclohexylsulfamoyl)benzamide] 447/449 GA A115B07C40 $^1$H NMR (400 MHz, CD$_3$OD) δ 8.62 (d, J = 2 Hz, 1H), 8.11 (d, J = 2.4 Hz, 1H), 7.66 (d, J = 8 Hz, 1H), 7.61 (m, 2H), 3.10 (m, 1H), 1.67 (m, 4H), 1.55 (m, 1H), 1.26 (m, 5H). | 1025 |
| [structure: N-(3-chloro-4-fluorophenyl)-4-chloro-3-(N-cyclohexylsulfamoyl)benzamide] 445/447 GA A115B07C15 | 1026 |
| [structure: N-(3-bromo-4-fluorophenyl)-4-chloro-3-(N-cyclohexylsulfamoyl)benzamide] 489/491 GA A115B07C49 | 1027 |
| [structure: N-(3-chloro-4,5-difluorophenyl)-4-chloro-3-(N-cyclohexylsulfamoyl)benzamide] 463/465 GA A115B07C58 | 1028 |
| [structure: N-(3,4,5-trifluorophenyl)-4-chloro-3-(N-(3-hydroxycyclohexyl)sulfamoyl)benzamide] 463/465 GA A116B07C40 | 1029_D1 |

TABLE 1-continued

| Structure MS(M + H)+ Synthetic method | Cmp. ID |
|---|---|
| [Structure: N-(3,4,5-trifluorophenyl)-4-chloro-3-(N-(3-hydroxycyclohexyl)sulfamoyl)benzamide] 463/465 GA A116B07C40 | 1029_D2 |
| [Structure: N-(3-chloro-4-fluorophenyl)-4-chloro-3-(N-(3-hydroxycyclohexyl)sulfamoyl)benzamide] 461/463 GA A116B07C15 | 1030_D1 |
| [Structure: N-(3-chloro-4-fluorophenyl)-4-chloro-3-(N-(3-hydroxycyclohexyl)sulfamoyl)benzamide] 461/463 GA A116B07C15 | 1030_D2 |

TABLE 1-continued

| Structure MS(M + H)+ Synthetic method | Cmp. ID |
|---|---|
| [Structure: N-(3-bromo-4-fluorophenyl)-4-chloro-3-(N-(3-hydroxycyclohexyl)sulfamoyl)benzamide] 507/505 GA A116B07C49 $^1$H NMR (400 MHz, CD$_3$OD) δ 8.62 (d, 1 H), 8.12 (m, 1H), 7.76 (m, 1H), 7.68 (m, 1H), 7.25 (m, 1H), 3.47 (m, 1H), 3.15 (m, 1H), 1.96 (m, 1H), 1.80 (m, 1H), 1.73 (m, 2H), 1.25 (m, 4H). | 1031_D1 |
| [Structure: N-(3-bromo-4-fluorophenyl)-4-chloro-3-(N-(3-hydroxycyclohexyl)sulfamoyl)benzamide] 507/505 GA A116B07C49 | 1031_D2 |

TABLE 1-continued
| Structure MS(M + H)+ Synthetic method | Cmp. ID |
|---|---|
| 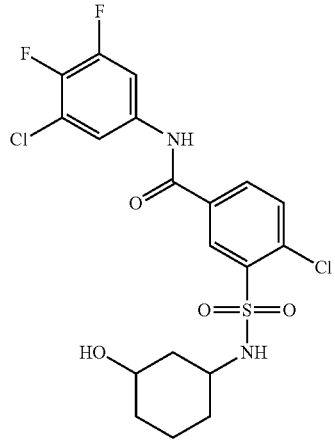 479/481 GA A116B07C58 | 1032_D1 |
| 479/481 GA A116B07C58 | 1032_D2 |
TABLE 1-continued
| Structure MS(M + H)+ Synthetic method | Cmp. ID |
|---|---|
| 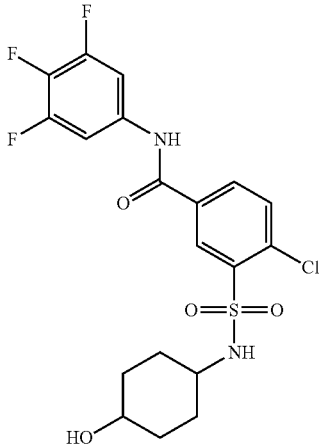 463/465 GA A117B07C40 | 1033 |
| 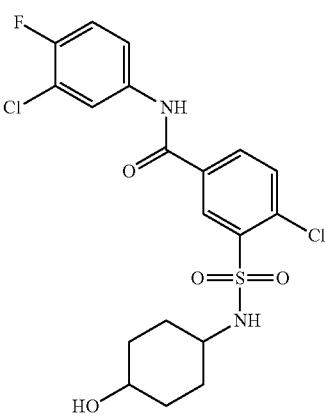 461/463 GA A117B07C15 | 1034 |

TABLE 1-continued

| Structure MS(M + H)+ Synthetic method | Cmp. ID |
|---|---|

[Structure: N-(3-bromo-4-fluorophenyl) benzamide with 4-chloro and sulfonamide linked to 4-hydroxycyclohexyl]

506/508
GA
A117B07C49

1035

¹H NMR (400 MHz, CD₃OD) δ 8.63 (d, J = 2 Hz, 1H), 8.12 (m, 2H), 7.76 (d, J = 8.4 Hz, 1H), 7.60 (m, 1H), 7.25 (m, 1H), 3.48 (m, 1H), 3.12 (m, 1H), 1.79 (m, 4H), 1.36 (m, 2H), 1.24 (m, 2H).

[Structure: N-(3-chloro-4,5-difluorophenyl) benzamide with 4-chloro and sulfonamide linked to 4-hydroxycyclohexyl]

479/481
GA
A117B07C58

1036

[Structure: N-(3,4,5-trifluorophenyl) benzamide with 4-chloro and sulfonamide linked to 2-hydroxycyclohexyl]

463/465
GA
A118B07C40

1037

[Structure: N-(3-chloro-4-fluorophenyl) benzamide with 4-chloro and sulfonamide linked to 2-hydroxycyclohexyl]

461/463
GA
A118B07C15

1038

[Structure: N-(3-bromo-4-fluorophenyl) benzamide with 4-chloro and sulfonamide linked to 2-hydroxycyclohexyl]

506/508
GA
A118B07C49

1039

TABLE 1-continued

| Structure MS(M + H)+ Synthetic method | Cmp. ID |
|---|---|
| [Structure: 3-chloro-4,5-difluoro-N-phenyl group; benzamide with 4-Cl and sulfonamide to 2-hydroxycyclohexyl] 479/481 GA A118B07C58 | 1040 |
| [Structure: 3,4,5-trifluorophenyl-NH-C(O)-benzene(4-Cl)-SO2NH-(3-hydroxycyclobutyl)] 452/454 GA A119B07C40 | 1041 |
| [Structure: 3-chloro-4-fluorophenyl-NH-C(O)-benzene(4-Cl)-SO2NH-(3-hydroxycyclobutyl)] 433/435 GA A119B07C15 | 1042 |

TABLE 1-continued

| Structure MS(M + H)+ Synthetic method | Cmp. ID |
|---|---|
| [Structure: 3-bromo-4-fluorophenyl-NH-C(O)-benzene(4-Cl)-SO2NH-(3-hydroxycyclobutyl)] 479/481 GA A119B07C49 | 1043 |
| [Structure: 3-chloro-4,5-difluorophenyl-NH-C(O)-benzene(4-Cl)-SO2NH-(3-hydroxycyclobutyl)] 451/453 GA A119B07C58 | 1044 |

TABLE 1-continued
| Structure MS(M + H)+ Synthetic method | Cmp. ID |
|---|---|
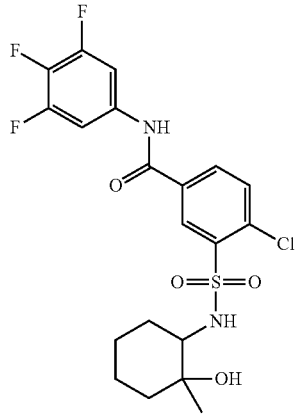
459/461
GA
A122B07C40
$^1$H NMR (400 MHz, CD$_3$OD) δ 8.62 (d, 1 H), 8.05 (m, 1H), 7.75 (d, 1H), 7.61 (m, 2H), 7.53(m, 2H), 3.18(m, 1H), 1.76(m, 1H), 1.64(m, 3H), 1.40 (m, 4H), 1.15 (s, 3H).
1049
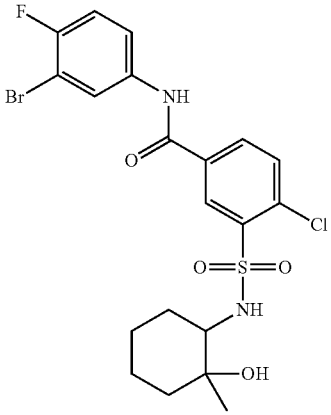
503/501
GA
A122B07C49
$^1$H NMR (400 MHz, CD$_3$OD) δ 8.62 (d, 1 H), 8.11 (m, 2H), 7.75 (m, 2H), 7.25 (m, 1H), 3.18(m, 1H), 1.64(m, 4H), 1.37 (m, 4H), 1.15 (s, 3H).
1051
457/459
GA
A122B07C15
1050
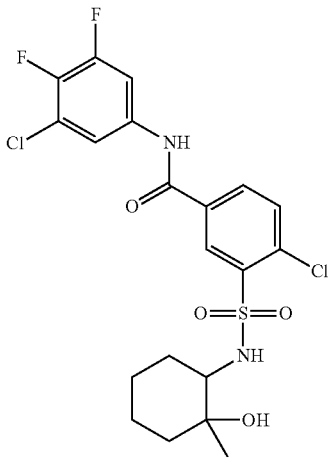
475/477
GA
A122B07C58
1052

TABLE 1-continued
| Structure MS(M + H)+ Synthetic method | Cmp. ID |
|---|---|
| 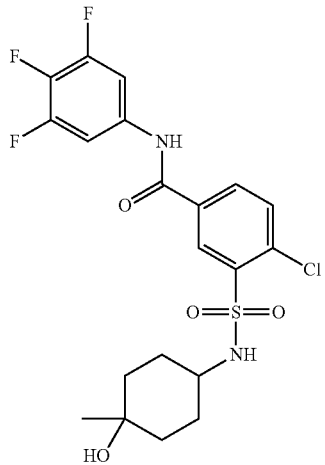<br>459/461<br>GA<br>A121B07C40 | 1053 |
| 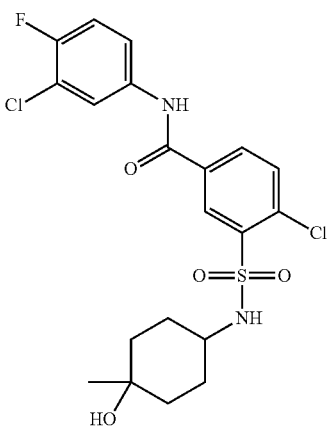<br>457/459<br>GA<br>A121B07C15 | 1054 |
TABLE 1-continued
| Structure MS(M + H)+ Synthetic method | Cmp. ID |
|---|---|
| 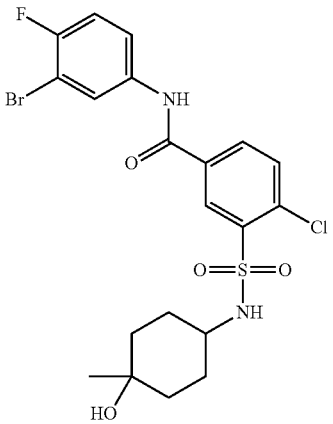<br>503/501<br>GA<br>A121B07C49<br>¹H NMR (400 MHz, CD₃OD) δ 8.63 (d, 1 H), 8.13 (m, 1H), 7.68 (m, 2H), 7.25 (m, 1H), 3.25 (m, 1H), 1.73 (m, 2H), 1.64 (m, 2H), 1.48 (m, 4H), 1.20 (s, 3H). | 1055 |
| 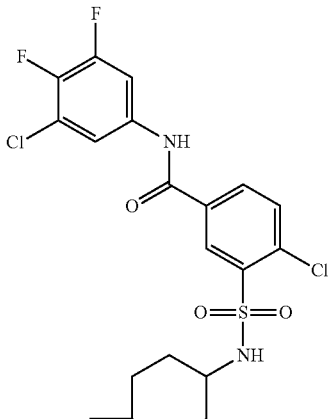<br>475/477<br>GA<br>A121B07C58 | 1056_D2 |

TABLE 1-continued
| Structure MS(M + H)+ Synthetic method | Cmp. ID |
|---|---|
| 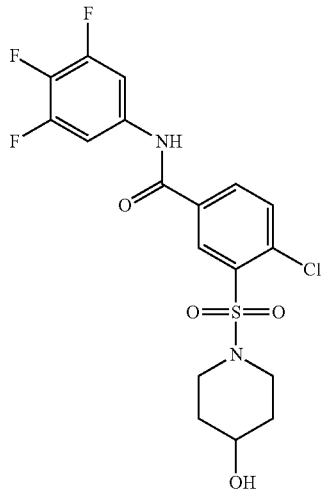<br>449/451<br>GA<br>A10B07C40 | 1057 |
| 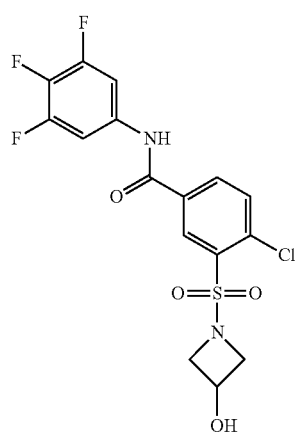<br>421/423<br>GA<br>A19B07C40<br>¹H NMR (400 MHz, CD₃OD) δ 8.56 (d, 1 H), 8.15 (m, 1H), 7.81 (d, 1H), 7.61 (m, 2H), 4.53 (m, 1H), 4.16 (m, 2H), 3.89 (m, 2H). | 1061 |
TABLE 1-continued
| Structure MS(M + H)+ Synthetic method | Cmp. ID |
|---|---|
| 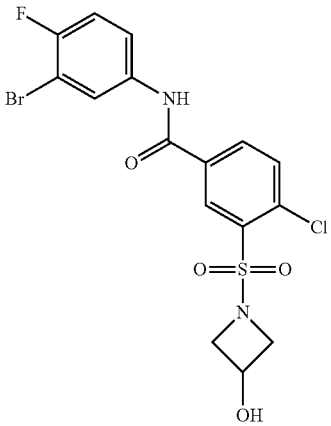<br>465/463<br>GA<br>A19B07C49<br>¹H NMR (400 MHz, CD₃OD) δ 8.56 (d, 1 H), 8.15 (m, 2H), 7.82 (m, 1H), 7.68 (m, 1H), 7.25 (m, 1H), 4.53 (m, 1H), 4.17 (m, 2H), 3.89 (m, 2H). | 1063 |
| 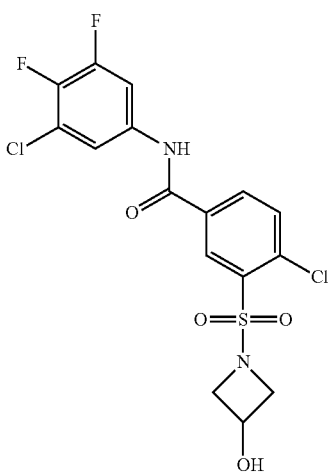<br>437/439<br>GA<br>A19B07C58 | 1064 |

TABLE 1-continued
| Structure MS(M + H)+ Synthetic method | Cmp. ID |
|---|---|
| 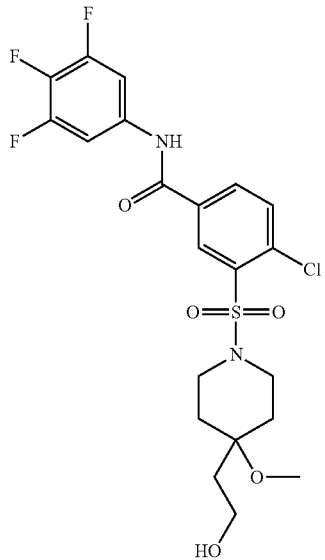<br>475/477<br>GA<br>A91B07C40 | 1065 |
| 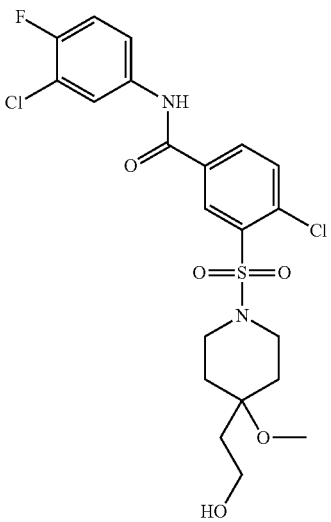<br>473/475<br>GA<br>A91B07C15 | 1066 |
TABLE 1-continued
| Structure MS(M + H)+ Synthetic method | Cmp. ID |
|---|---|
| 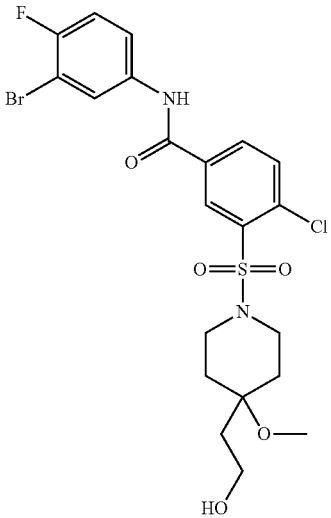<br>519/517<br>GA<br>A91B07C49 | 1067 |
| 491/493<br>GA<br>A91B07C58 | 1068 |

TABLE 1-continued
| Structure MS(M + H)+ Synthetic method | Cmp. ID |
|---|---|
| 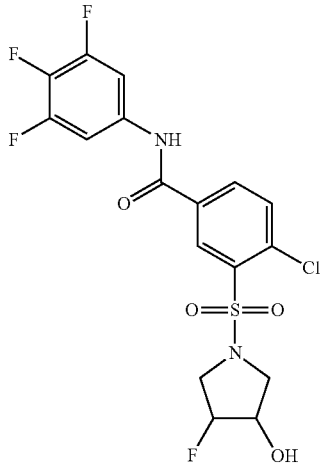 453/455 GA A110B07C40 | 1069 |
| 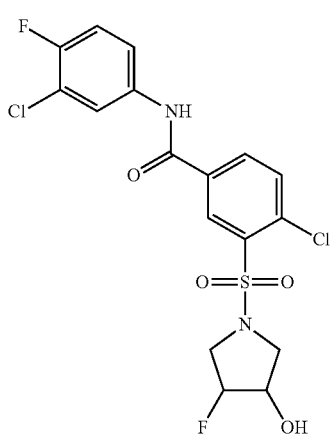 451/455 GA A110B07C15 | 1070 |
| 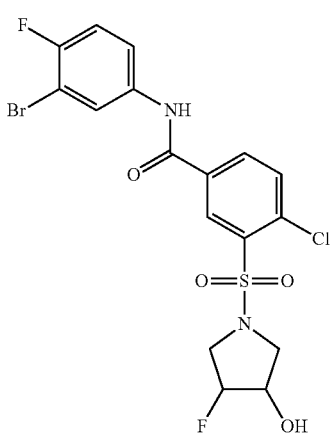 497/495 GA A110B07C49 | 1071 |
TABLE 1-continued
| Structure MS(M + H)+ Synthetic method | Cmp. ID |
|---|---|
| 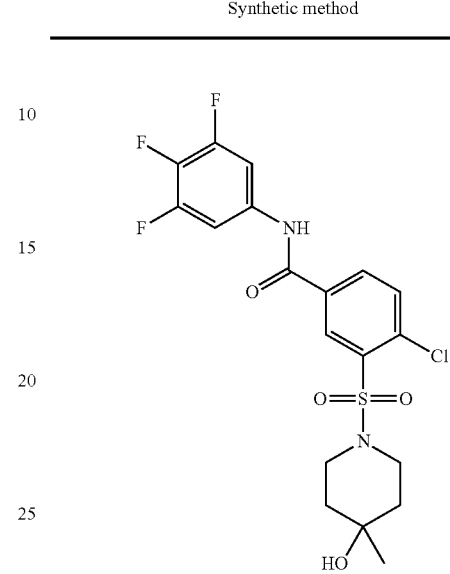 463/465 GA A73B07C40 | 1073 |
| 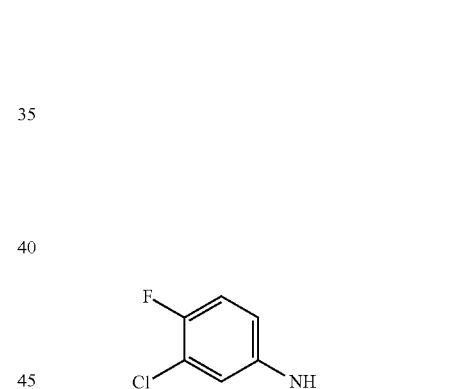 461/463 GA A73B07C15 | 1074 |

TABLE 1-continued
| Structure MS(M + H)+ Synthetic method | Cmp. ID |
|---|---|
| 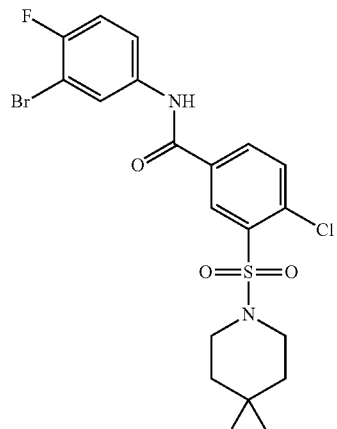<br>506/508<br>GA<br>A73B07C49 | 1075 |
| 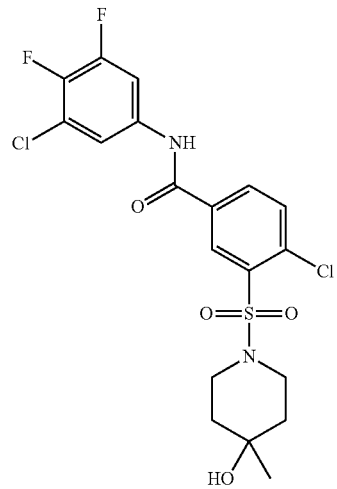<br>461/463<br>GA<br>A73B07C58 | 1076 |
TABLE 1-continued
| Structure MS(M + H)+ Synthetic method | Cmp. ID |
|---|---|
| 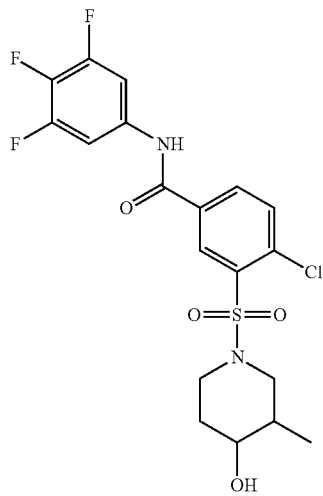<br>463/465<br>GA<br>A84B07C40 | 1077_D1 |
| 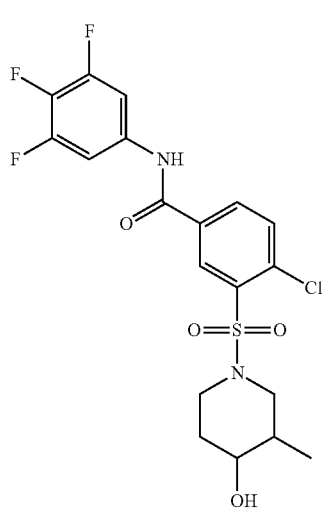<br>463/465<br>GA<br>A84B07C40 | 1077_D2 |

TABLE 1-continued

| Structure MS(M + H)+ Synthetic method | Cmp. ID |
|---|---|
| [Structure: N-(3-chloro-4,5-difluorophenyl)-4-chloro-3-((4-hydroxy-3-methylpiperidin-1-yl)sulfonyl)benzamide]<br>479/481<br>GA<br>A84B07C58 | 1080 |
| [Structure: N-(3-chloro-4-fluorophenyl)-4-chloro-3-((3-ethyl-4-hydroxypiperidin-1-yl)sulfonyl)benzamide]<br>475/477<br>GA<br>A85B07C15<br>$^1$H NMR (400 MHz, CD$_3$OD) δ 8.59 (d, J = 2.4 Hz, 1H), 8.15 (m, 1H), 7.99 (d, J = 8.4 Hz, 1H), 7.78 (m, 1 H), 7.63 (m, 1H), 7.27 (m, 1H), 3.81 (m, 1H), 3.78 (m, 1 H), 3.39 (m, 1 H), 3.07 (m, 1H), 2.77 (m, 1H), 1.95 (m, 1 H), 1.75 (m, 1 H), 1.56 (m, 1H), 1.43 (m, 1 H), 1.24 (m, 1 H), 0.93 (m, 3 H). | 1082_D1 |

| Structure MS(M + H)+ Synthetic method | Cmp. ID |
|---|---|
| [Structure: N-(3-chloro-4-fluorophenyl)-4-chloro-3-((3-ethyl-4-hydroxypiperidin-1-yl)sulfonyl)benzamide]<br>475/479<br>GA<br>A85B07C15 | 1082_D2 |
| [Structure: N-(3-bromo-4-fluorophenyl)-4-chloro-3-((3-ethyl-4-hydroxypiperidin-1-yl)sulfonyl)benzamide]<br>520/522<br>GA<br>A85B07C49 | 1083_D1 |

TABLE 1-continued
| Structure MS(M + H)+ Synthetic method | Cmp. ID |
|---|---|
| 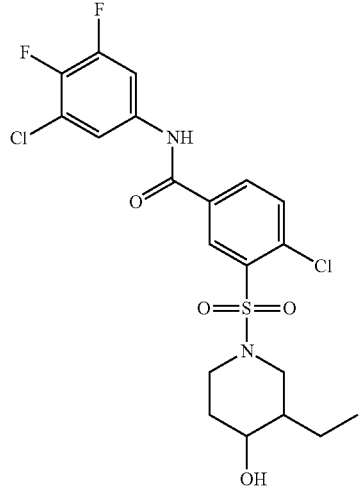 493/495 GA A85B07C58 | 1084_D1 |
| 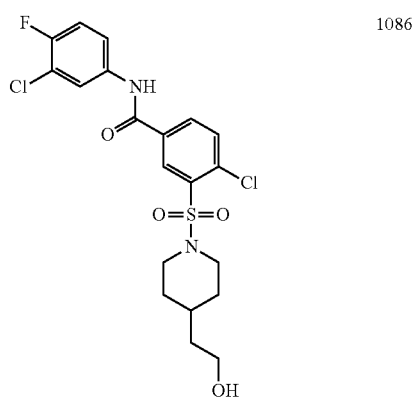 493/495 GA A85B07C58 | 1084_D2 |
TABLE 1-continued
| Structure MS(M + H)+ Synthetic method | Cmp. ID |
|---|---|
| 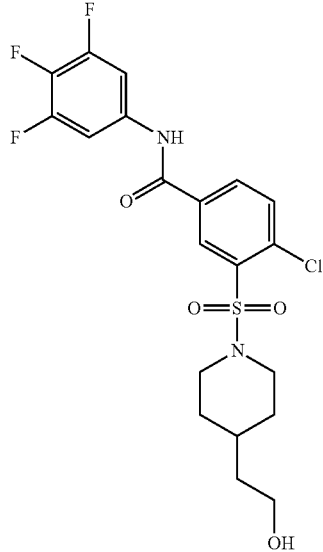 477/479 GA A09B07C40 | 1085 |
| 475/477 GA A09B07C15<br>$^1$H NMR (400 MHz, CD$_3$OD) δ 8.57 (d, J = 6.4 Hz, 1 H), 8.14 (m, 1 H), 8.12 (m, 1 H), 7.99 (m, 1 H), 7.63 (m, 1 H), 7.27 (m, 1H), 3.84 (m, 2H), 3.64 (m, 2 H), 2.82 (m, 2H), 1.79 (m, 2H), 1.60 (m, 1 H), 1.50 (m, 2H), 1.26 (m, 2H). | 1086 |

TABLE 1-continued
| Structure MS(M + H)+ Synthetic method | Cmp. ID |
|---|---|
| 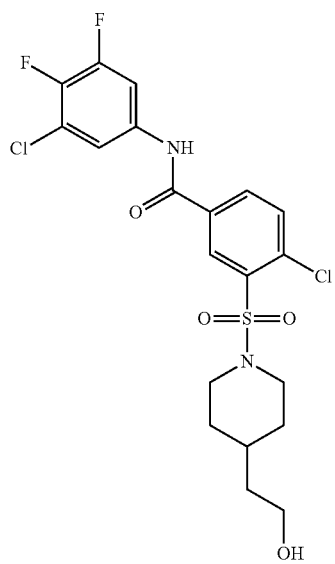<br>519/521<br>GA<br>A09B07C49 | 1087 |
| 493/495<br>GA<br>A09B07C58 | 1088 |
| 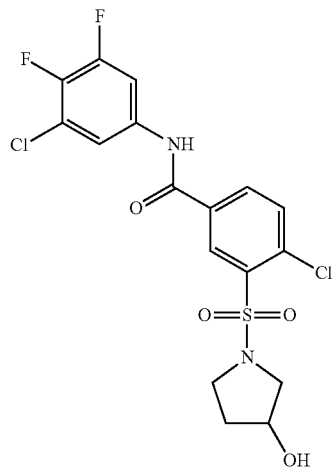<br>477/479<br>GA<br>A17B07C49<br>¹H NMR (400 MHz, CD₃OD) δ 8.61 (d, J = 2.4 Hz, 1 H), 8.14 (m, 2 H), 7.80 (m, 1H), 7.68 (m, 1 H), 7.22 (m, 1 H), 4.45 (m, 1 H), 3.59 (m, 3H), 3.38 (m, 1 H), 2.05 (m, 2H). | 1091 |
| 451/453<br>GA<br>A17B07C58 | 1092 |

TABLE 1-continued
| Structure MS(M + H)+ Synthetic method | Cmp. ID |
|---|---|
| 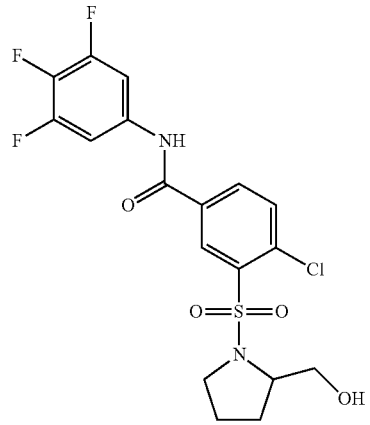  449/451  GA  A18B07C40 | 1093_R |
| 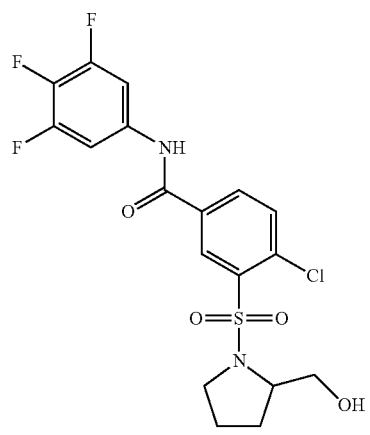  449/451  GA  A18B07C40 | 1093_S |
| 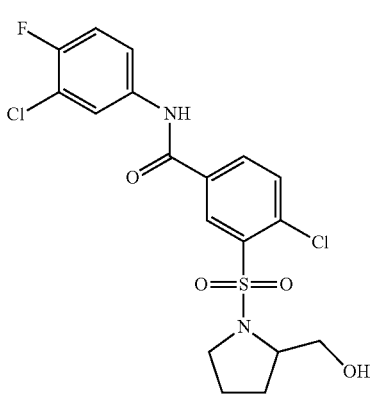  447/449  GA  A18B07C15 | 1094_R |
TABLE 1-continued
| Structure MS(M + H)+ Synthetic method | Cmp. ID |
|---|---|
| 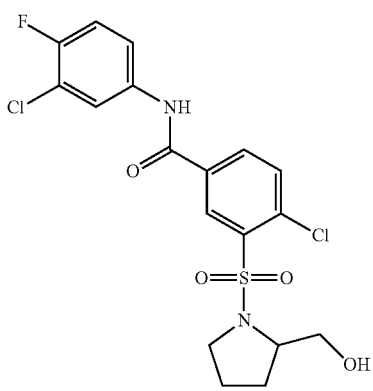  447/449  GA  A18B07C15 | 1094_S |
| 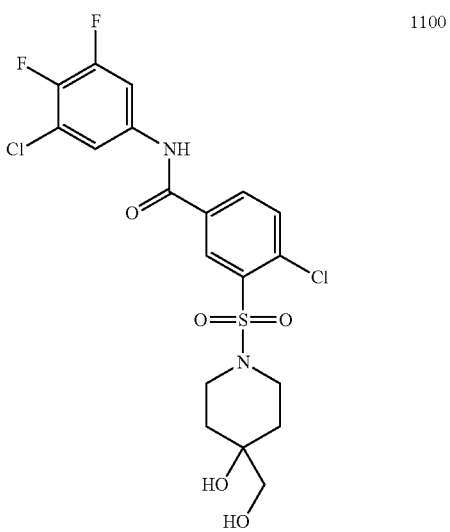  495/497  GA  A81B07C58 | 1100 |

TABLE 1-continued
| Structure MS(M + H)+ Synthetic method | Cmp. ID |
|---|---|
| 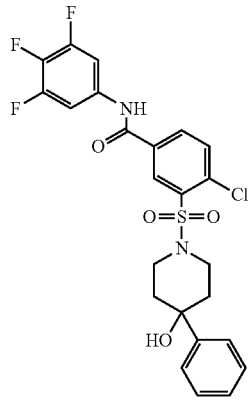<br>525/527<br>GA<br>A75B07C40<br>¹H NMR (400 MHz, CD₃OD) δ 8.62 (d, J = 2 Hz, 1 H), 8.15 (m, 1H), 7.82 (d, J = 8.4 Hz, 1 H), 7.62 (m, 2 H), 7.49 (m, 2 H), 7.35 (m, 2 H), 7.25 (m, 1 H), 3.84 (m, 2 H), 2.15 (m, 4H), 1.82 (m, 2 H). | 1101 |
| 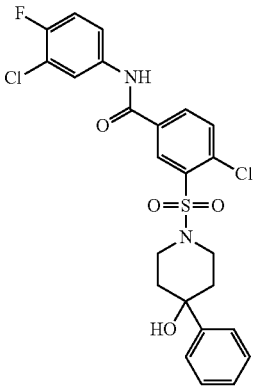<br>523/525 GA A75B07C15<br>¹H NMR (400 MHz, CD₃OD) δ 8.63 (d, J = 2.4 Hz, 1H), 8.17 (m, 1H), 7.98 (m, 1 H), 7.82 (d, J = 8 Hz, 1 H), 7.49 (m, 1H), 7.47 (m, 1 H), 7.35 (m, 2 H), 7.25 (m, 2 H), 7.22 (m, 2 H), 3.81 (m, 2 H), 3.31 (m, 2 H), 2.21 (m, 2 H), 1.81 (m, 2 H). | 1102 |
TABLE 1-continued
| Structure MS(M + H)+ Synthetic method | Cmp. ID |
|---|---|
| 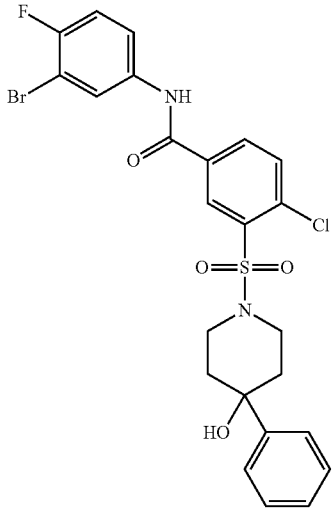<br>567/569<br>GA<br>A75B07C49 | 1103 |
| 523/525<br>GA<br>A75B07C58 | 1104 |

TABLE 1-continued
| Structure MS(M + H)+ Synthetic method | Cmp. ID |
|---|---|
| 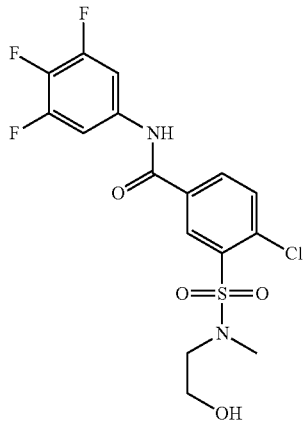<br>423/425<br>GA<br>A20B07C40<br>¹H NMR (400 MHz, CD₃OD δ 8.60 (d, J = 2 Hz, 1 H), 8.12 (m, 1 H), 7.98 (d, J = 8 Hz, 1 H), 7.61 (m, 2 H), 3.71 (m, 2 H), 3.42 (m, 2 H), 3.02 (s, 3 H). | 1105 |
| 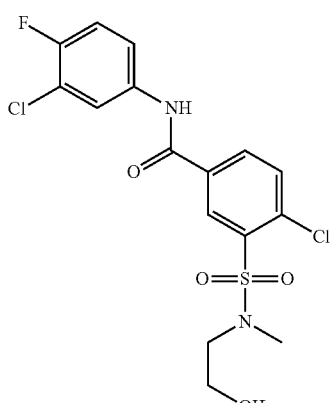<br>421/423<br>GA<br>A20B07C15 | 1106 |
TABLE 1-continued
| Structure MS(M + H)+ Synthetic method | Cmp. ID |
|---|---|
| 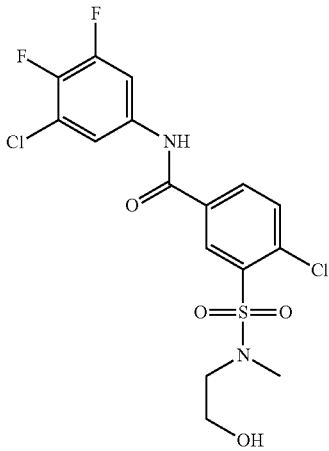<br>439/441<br>GA<br>A20B07C58 | 1108 |
| 433/435<br>GA<br>A112B07C40 | 1109 |

TABLE 1-continued

| Structure MS(M + H)+ Synthetic method | Cmp. ID |
|---|---|
| [structure of compound 1110: N-(3-chloro-4-fluorophenyl)-2-chloro-5-(N-cyclopentylsulfamoyl)benzamide]<br>431/433<br>GA<br>A112B06C15<br>¹H NMR (400 MHz, CD₃OD) δ 8.03 (d, J = 2 Hz, 1 H), 7.92 (m, 2 H), 7.84 (m, 1 H), 7.75 (m, 1 H), 7.25 (m, 1 H), 3.58 (m, 1 H), 1.80 (m, 2 H), 1.66 (m, 2 H), 1.51 (m, 4 H). | 1110 |
| [structure of compound 1111: N-(3-bromo-4-fluorophenyl)-2-chloro-5-(N-cyclopentylsulfamoyl)benzamide]<br>477/475<br>GA<br>A112B07C49 | 1111 |

TABLE 1-continued

| Structure MS(M + H)+ Synthetic method | Cmp. ID |
|---|---|
| [structure of compound 1112]<br>449/451<br>GA<br>A112B07C58 | 1112 |
| [structure of compound 1113]<br>449/451<br>GA<br>A113B07C40 | 1113 |
| [structure of compound 1115]<br>493/491<br>GA<br>A113B07C49 | 1115 |

TABLE 1-continued

| Structure MS(M + H)+ Synthetic method | Cmp. ID |
|---|---|
| [3,4-difluoro-5-chlorophenyl-NH-C(O)- benzene(2-Cl)-SO2NH-(2-hydroxycyclopentyl)] 465/467 GA A113B07C58 | 1433 |
| [3,4,5-trifluorophenyl-NH-C(O)- benzene(2-Cl)-SO2NH-cyclohexyl] 447/449 GA A115B07C40 | 1117 |
| [3-chloro-4-fluorophenyl-NH-C(O)- benzene(2-Cl)-SO2NH-cyclohexyl] 445/447 GA A115B06C15 | 1118 |
| [3-bromo-4-fluorophenyl-NH-C(O)- benzene(2-Cl)-SO2NH-cyclohexyl] 491/489 GA A115B07C49 | 1119 |
| [3-chloro-4,5-difluorophenyl-NH-C(O)- benzene(2-Cl)-SO2NH-cyclohexyl] 463/465 GA A115B07C58 | 1120 |

TABLE 1-continued

| Structure MS(M + H)+ Synthetic method | Cmp. ID |
|---|---|
| (structure) 463/465 GA A116B07C40 ¹H NMR (400 MHz, CD₃OD) δ 8.03 (d, 1 H), 7.96 (m, 1H), 7.76 (d, 1H), 7.54 (m, 2H), 3.47 (m, 1H), 3.15 (m, 1H), 2.17 (m, 1H), 1.86 (m, 1H), 1.73 (m, 2H), 1.15 (m, 4H). | 1121_D1 |
| (structure) 463/465 GA A116B07C40 | 1121_D2 |
| (structure) 461/463 GA A116B07C15 | 1122_D1 |
| (structure) 461/463 GA A116B07C15 | 1122_D2 |
| (structure) 507/505 GA A116B07C49 | 1123_D1 |

TABLE 1-continued

| Structure MS(M + H)+ Synthetic method | Cmp. ID |
|---|---|
| (structure: N-(3-bromo-4-fluorophenyl)-2-chloro-5-[(3-hydroxycyclohexyl)sulfamoyl]benzamide) 507/505 GA A116B07C49 | 1123_D2 |
| (structure: N-(3-chloro-4,5-difluorophenyl)-2-chloro-5-[(3-hydroxycyclohexyl)sulfamoyl]benzamide) 479/481 GA A116B07C58 | 1124_D1 |
| (structure: N-(3-chloro-4,5-difluorophenyl)-2-chloro-5-[(3-hydroxycyclohexyl)sulfamoyl]benzamide) 479/481 GA A116B07C58 | 1124_D2 |
| (structure: N-(3,4,5-trifluorophenyl)-2-chloro-5-[(4-hydroxycyclohexyl)sulfamoyl]benzamide) 445/447 GA A117B07C40 <br> $^{1}$H NMR (400 MHz, CD$_3$OD) δ 8.03 (d, 1 H), 7.95 (m, 1H), 7.74 (m, 1H), 7.54 (m, 2H), 3.47 (m, 2H), 3.06 (m, 1H), 1.86 (m, 4H), 1.26 (m, 4H). | 1125 |
| (structure: N-(3-chloro-4-fluorophenyl)-2-chloro-5-[(4-hydroxycyclohexyl)sulfamoyl]benzamide) 461/463 GA A117B06C15 | 1126 |

TABLE 1-continued
| Structure MS(M + H)+ Synthetic method | Cmp. ID |
|---|---|
| 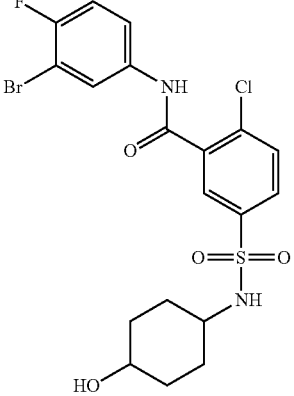 507/505 GA A117B07C49 | 1127 |
| 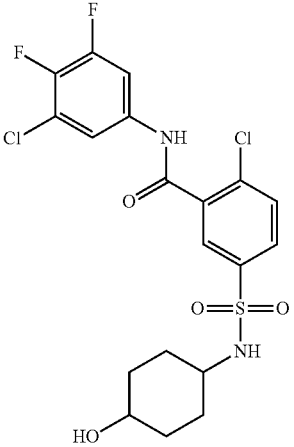 461/463 GA A117B07C58 | 1128 |
| 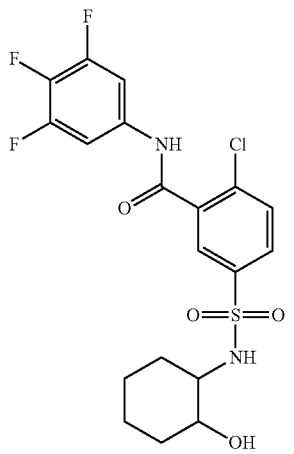 463/465 GA A117B07C40 | 1129 |
TABLE 1-continued
| Structure MS(M + H)+ Synthetic method | Cmp. ID |
|---|---|
| 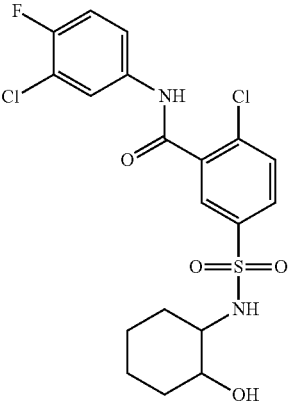 461/463 GA A118B06C15 | 1444 |
| 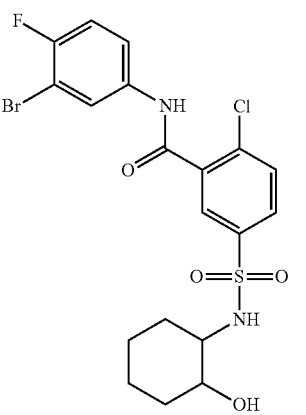 507/505 GA A118B07C49 | 1131_D1 |
| 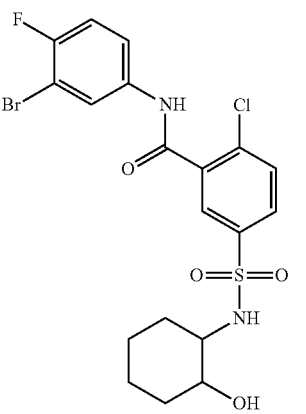 507/505 GA A118B07C49 | 1131_D2 |

TABLE 1-continued

| Structure MS(M + H)+ Synthetic method | Cmp. ID |
|---|---|
| (structure) 479/481 GA A118B07C58 | 1132_D1 |
| (structure) 479/481 GA A118B07C58 | 1132_D2 |

TABLE 1-continued

| Structure MS(M + H)+ Synthetic method | Cmp. ID |
|---|---|
| (structure) 345/347 GA A19B07C40 | 1133 |
| (structure) 479/481 GA A119B07C49 | 1445 |
| (structure) 451/453 GA A119B07C58 | 1136_CT1 |

TABLE 1-continued
| Structure MS(M + H)+ Synthetic method | Cmp. ID |
|---|---|
| 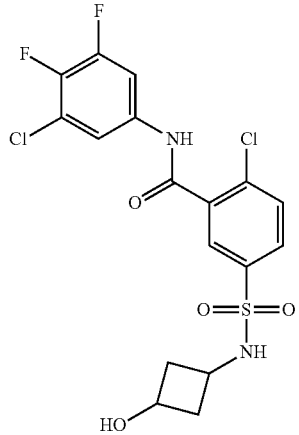<br>451/453<br>GA<br>A119B07C58 | 1136_CT2 |
| 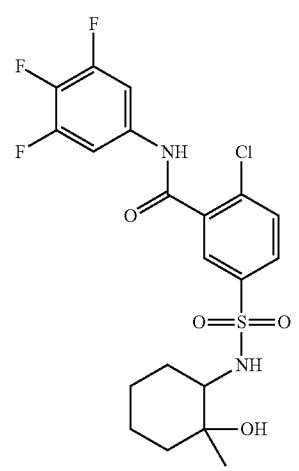<br>459/461<br>GA<br>A122B07C40 | 1141 |
| 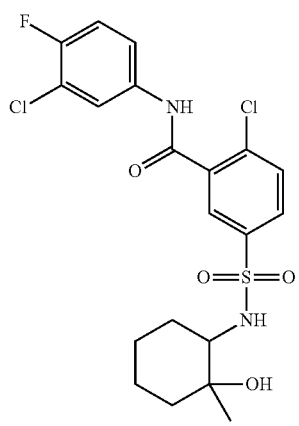<br>457/459<br>GA<br>A112B07C15 | 1142 |
TABLE 1-continued
| Structure MS(M + H)+ Synthetic method | Cmp. ID |
|---|---|
| 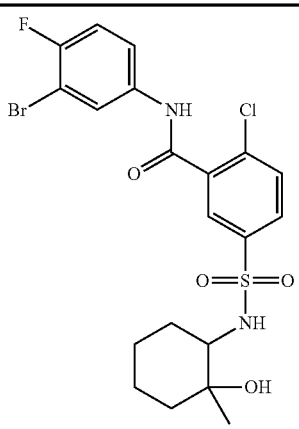<br>503/501<br>GA<br>A122B07C49 | 1143 |
| 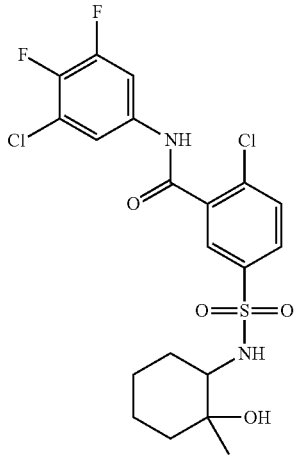<br>475/477<br>GA<br>A122B07C58 | 1144 |
| 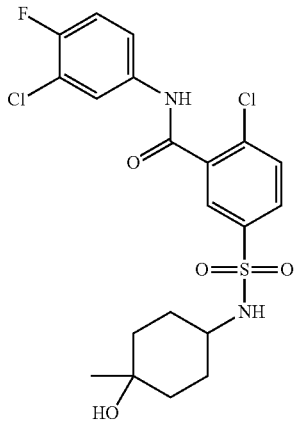<br>457/459<br>GA<br>A121B07C15 | 1146 |

TABLE 1-continued

| Structure MS(M + H)+ Synthetic method | Cmp. ID |
|---|---|
| [Structure: N-(3-bromo-4-fluorophenyl)-2-chloro-5-[(4-hydroxy-4-methylcyclohexyl)sulfamoyl]benzamide] 521/519 GA A121B07C49 | 1147 |
| [Structure: 3-chloro-N-(3,4-difluoro-5-chlorophenyl)... 4-hydroxy-4-methylcyclohexyl sulfonamide] 475/477 GA A121B07C58 $^1$H NMR (400 MHz, CD$_3$OD) δ 8.05 (d, 1H), 7.99 (m, 1H), 7.76 (m, 2H), 7.64 (m, 1H), 3.20 (m, 1H), 1.73 (m, 2H), 1.64 (m, 2H), 1.44 (m, 4H), 1.20 (s, 3H). | 1148 |
| [Structure: N-(3-bromo-4-fluorophenyl)-2-chloro-5-[(4-hydroxypiperidin-1-yl)sulfonyl]benzamide] 492/494 GA A10B07C49 | 1151 |
| [Structure: N-(3-chloro-4,5-difluorophenyl)-2-chloro-5-[(4-hydroxypiperidin-1-yl)sulfonyl]benzamide] 465/467 GA A10B07C58 | 1152 |

TABLE 1-continued
| Structure MS(M + H)+ Synthetic method | Cmp. ID |
|---|---|
| 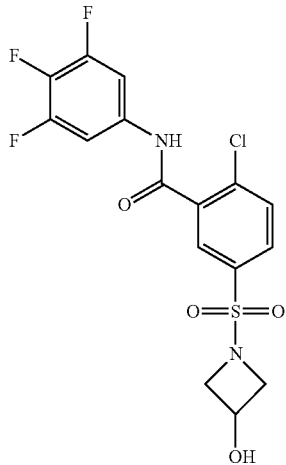 421/423 GA A19B07C40 | 1153 |
| 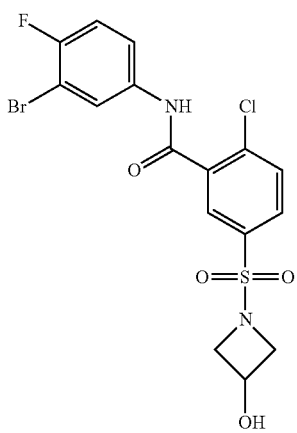 465/463 GA A19B07C49 | 1155 |
TABLE 1-continued
| Structure MS(M + H)+ Synthetic method | Cmp. ID |
|---|---|
| 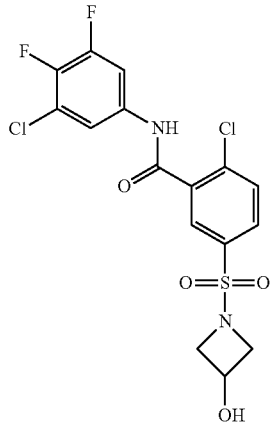 437/439 GA A19B07C58 $^1$H NMR (400 MHz, CD$_3$OD) δ 8.03 (d, 1 H), 7.97 (m, 1H), 7.84(m, 1H), 7.75 (m, 1H), 7.66 (m, 1H), 3.55(m, 2H), 4.45 (m, 1H), 4.03 (m, 2H), 3.57 (m, 2H). | 1156 |
| 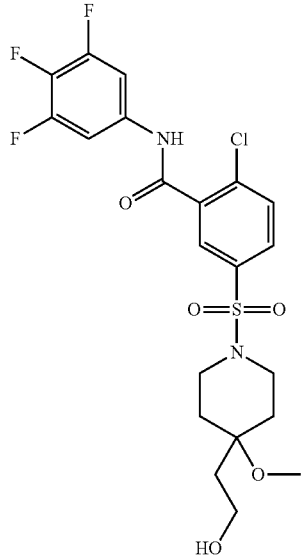 475/477 GA A91B07C40 | 1421 |

TABLE 1-continued
| Structure MS(M + H)+ Synthetic method | Cmp. ID |
|---|---|
| 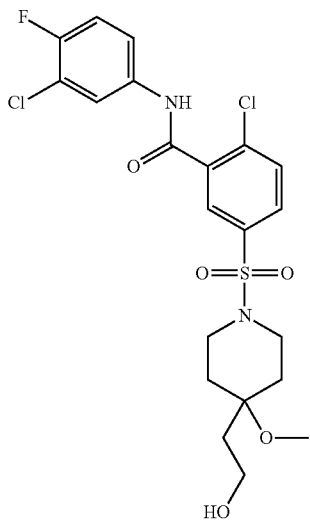<br>473/475<br>GA<br>A91B07C15 | 1158 |
| 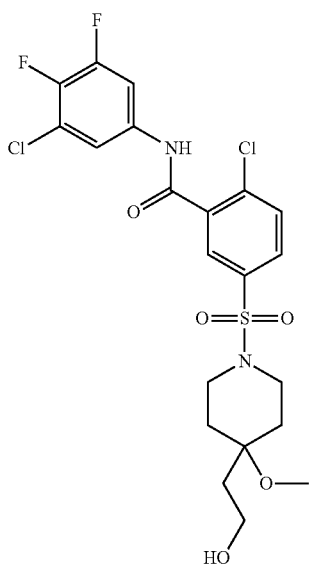<br>491/493<br>GA<br>A91B07C58 | 1160 |
| 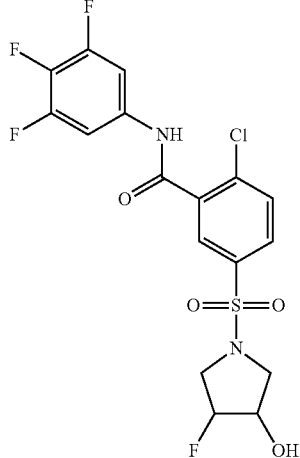<br>453/455<br>GA<br>A110B07C40 | 1422 |
| 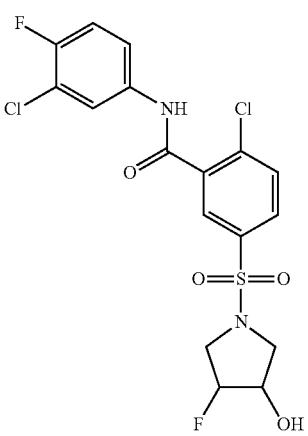<br>451/453<br>GA<br>A110B07C15 | 1162 |
| 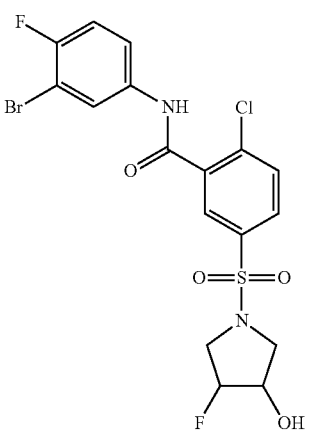<br>497/495<br>GA<br>A110B07C49 | 1163 |

TABLE 1-continued
| Structure MS(M + H)+ Synthetic method | Cmp. ID |
|---|---|
| 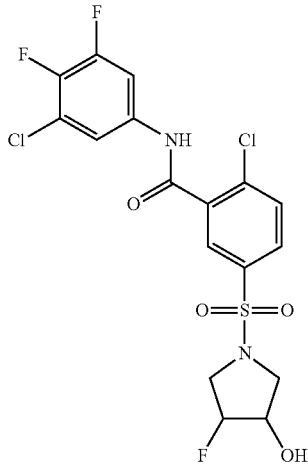<br>469/471<br>GA<br>A110B07C58 | 1164 |
| 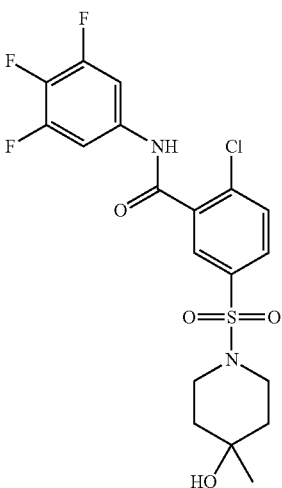<br>445/447<br>GA<br>A73B07C40 | 1165 |
TABLE 1-continued
| Structure MS(M + H)+ Synthetic method | Cmp. ID |
|---|---|
| 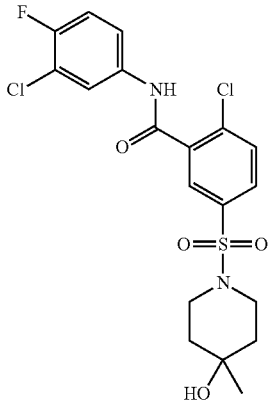<br>443/445<br>GA<br>A73B07C15<br>$^1$H NMR (400 MHz, CD$_3$OD) δ 8.10 (d, 1 H), 8.01 (d, 1H), 7.95 (m, 1H), 7.88 (m, 1H), 7.63 (m, 1H), 7.22 (m, 1H), 3.50 (m, 2H), 2.77 (m, 2H), 1.68 (m, 4H), 1.21 (s, 3H). | 1166 |
| 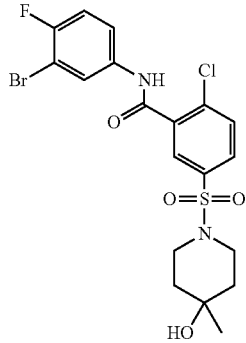<br>489/487 GA A73B07C49<br>$^1$H NMR (400 MHz, CD$_3$OD) δ 7.97 (d, 1 H), 7.95 (d, 1H), 7.90 (m, 1H), 7.88 (m, 1H), 7.57 (m, 1H), 7.27 (m, 1H), 3.49 (m, 2H), 2.77 (m, 2H), 1.68 (m, 4H), 1.21 (s, 3H). | 1167 |

TABLE 1-continued
| Structure MS(M + H)+ Synthetic method | Cmp. ID |
|---|---|
| 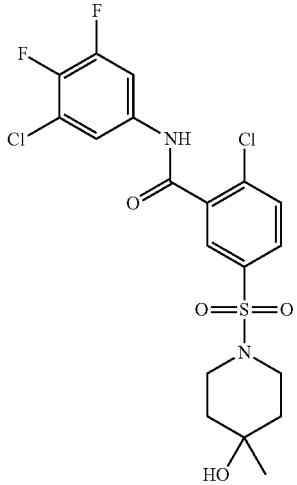 461/463 GA A73B07C58 | 1168 |
| 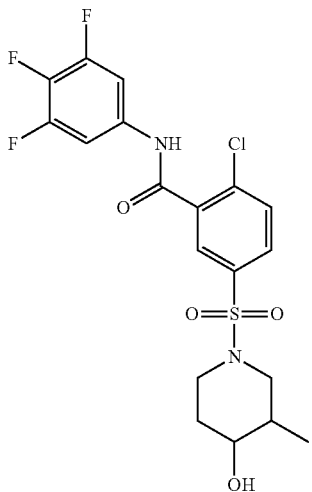 463/465 GA A84B07C40 | 1169_D1 |
TABLE 1-continued
| Structure MS(M + H)+ Synthetic method | Cmp. ID |
|---|---|
| 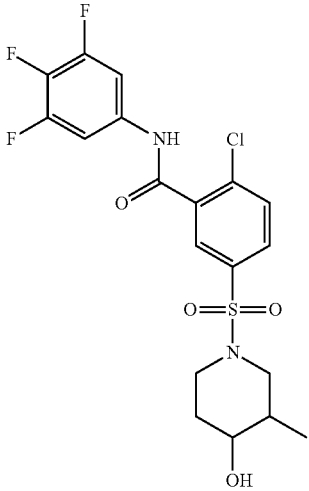 463/465 GA A84B07C40 | 1169_D2 |
| 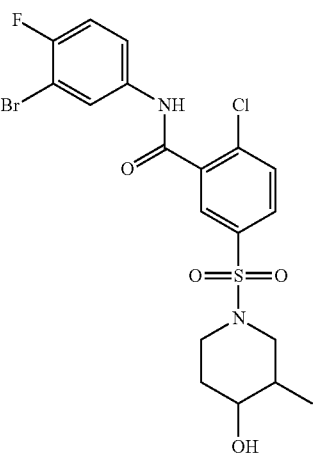 507/505 GA A84B07C49 | 1171_D1 |

TABLE 1-continued
| Structure MS(M + H)+ Synthetic method | Cmp. ID |
|---|---|
| 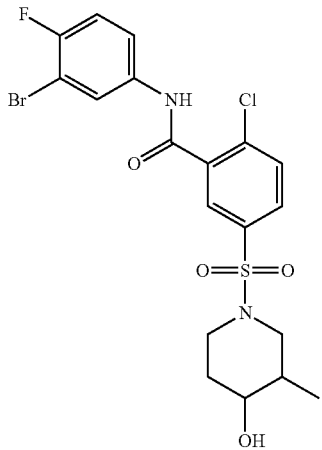<br>507/505<br>GA<br>A84B07C49 | 1171_D2 |
| 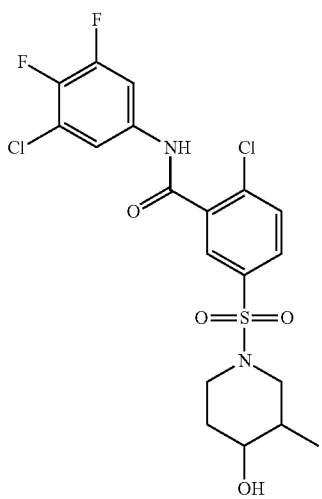<br>479/481<br>GA<br>A84B07C58 | 1172_D1 |
TABLE 1-continued
| Structure MS(M + H)+ Synthetic method | Cmp. ID |
|---|---|
| 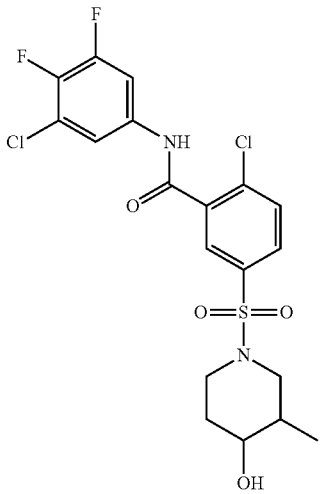<br>479/481<br>GA<br>A84B07C5 | 1172_D2 |
| 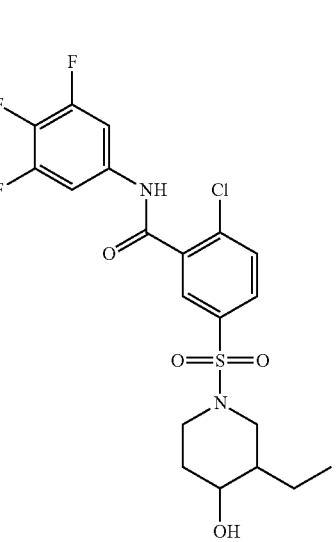<br>477/479<br>GA<br>A85B07C40 | 1173_D1 |

TABLE 1-continued
| Structure MS(M + H)+ Synthetic method | Cmp. ID |
|---|---|
| 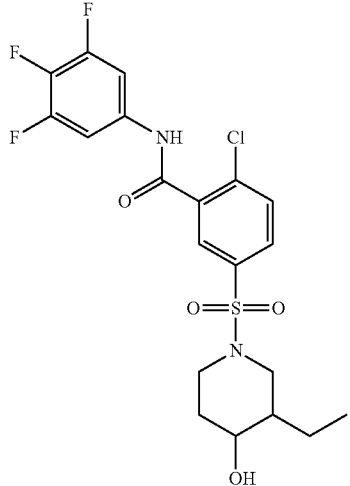<br>477/479<br>GA<br>A85B07C40 | 1173_D2 |
| 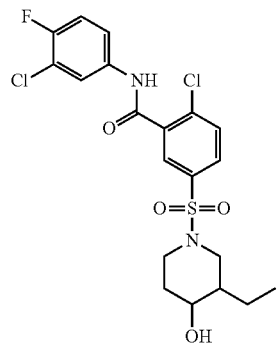<br>475/477<br>GA<br>A85B06C15<br>¹H NMR (400 MHz, CD₃OD) δ 7.97 (m, 2 H), 7.89 (d, J = 4.4 Hz, 1 H), 7.80 (m, 1 H), 7.57 (m, 1 H), 7.27 (m, 1 H), 3.60 (m, 2 H), 3.30 (m, 1 H), 2.75 (m, 1 H), 2.47 (m, 1 H), 1.95 (m, 1 H), 1.75 (m, 1 H), 1.58 (m, 1 H), 1.44 (m, 1 H), 1.21 (m, 1 H), 0.93 (m, 3 H). | 1174_D1 |
TABLE 1-continued
| Structure MS(M + H)+ Synthetic method | Cmp. ID |
|---|---|
| 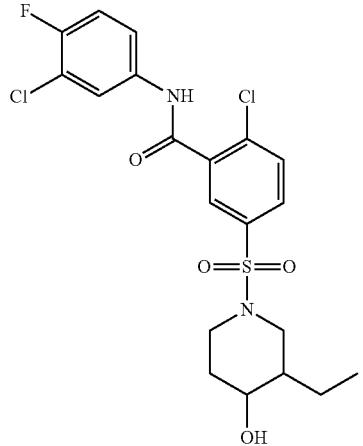<br>475/477<br>GA<br>A85B06C15 | 1174_D2 |
| 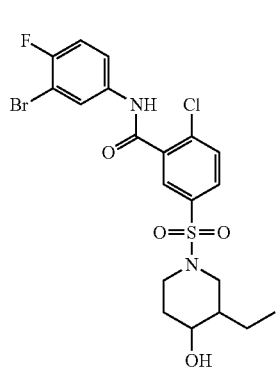<br>521/519<br>GA<br>A85B07C49<br>¹H NMR (400 MHz, CD₃OD) δ 8.10 (d, 1 H), 7.95 (m, 1H), 7.88 (m, 1H), 7.78 (m, 1H), 7.68 (m, 1H), 7.25 (m, 1H), 3.55 (m, 2H), 3.29 (m, 1H), 2.76 (m, 1H), 2.45 (m, 1H), 1.96 (m, 1H), 1.74 (m, 1H), 1.55 (m, 2H), 1.24 (m, 1H), 0.98 (m, 3H). | 1175_D1 |

TABLE 1-continued
| Structure MS(M + H)+ Synthetic method | Cmp. ID |
|---|---|
| 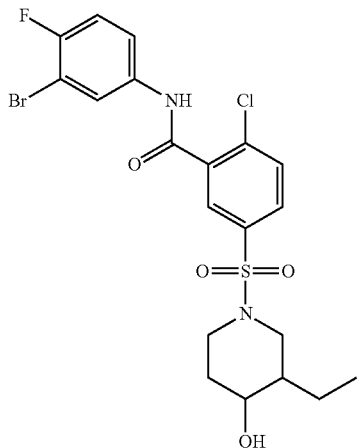<br>521/519<br>GA<br>A85B07C49 | 1175_D2 |
| 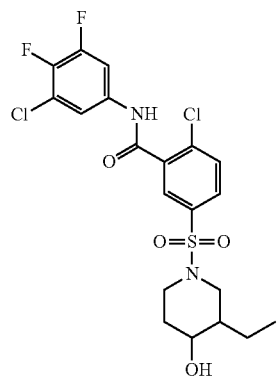<br>493/495<br>GA<br>A85B07C58<br>¹H NMR (400 MHz, CD₃OD) δ 7.97 (d, 1 H), 7.93 (m, 1H), 7.81(m, 1H), 7.75 (m, 1H), 7.68(m, 1H), 3.55(m, 2H), 3.41(m, 1H), 2.76(m, 1H), 2.45 (m, 1H), 1.96(m, 1H), 1.74 (m, 1H), 1.55(m, 2H), 1.24 (m, 1H), 0.98 (m, 3H). | 1176_D1 |
TABLE 1-continued
| Structure MS(M + H)+ Synthetic method | Cmp. ID |
|---|---|
| 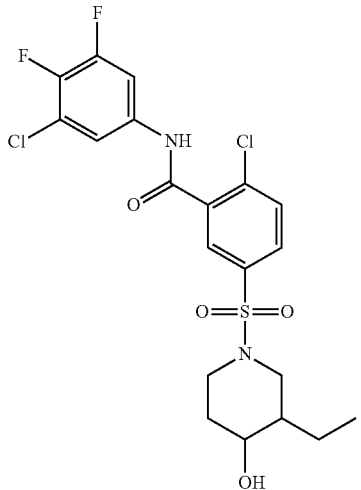<br>493/495<br>GA<br>A85B07C58 | 1176_D2 |
| 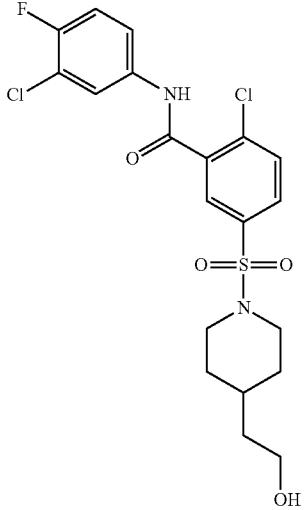<br>475/477<br>GA<br>A09B06C15 | 1178 |

TABLE 1-continued
| Structure MS(M + H)+ Synthetic method | Cmp. ID |
|---|---|
| 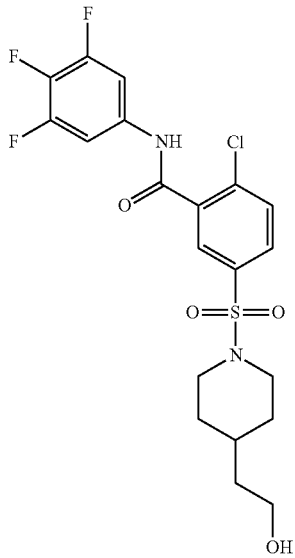<br>477/479<br>GA<br>A09B07C40 | 1177 |
| 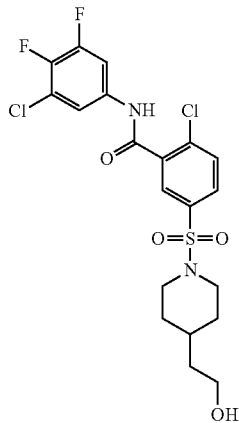<br>493/495 GA A09B07C58<br>$^1$H NMR (400 MHz, CD$_3$OD) δ 7.95 (d, 1 H), 7.87 (m, 1H), 7.81 (m, 1H), 7.79 (m, H), 7.78 (m, 1H), 3.77 (m, 2H), 3.59 (m, 2H), 2.38 (m, 2H), 1.83 (m, 2H), 1.47 (m, 2H), 1.38 (m, 2H) | 1180 |
| 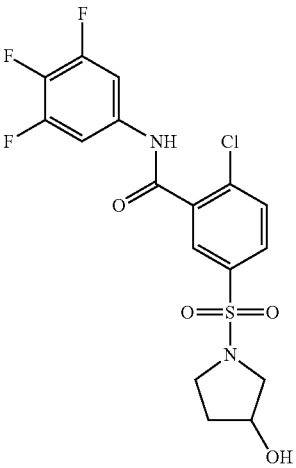<br>521/519<br>GA<br>A09B07C49 | 1179 |
| 435/437<br>GA<br>A17B07C40 | 1181 |

TABLE 1-continued
| Structure MS(M + H)+ Synthetic method | Cmp. ID |
|---|---|
| 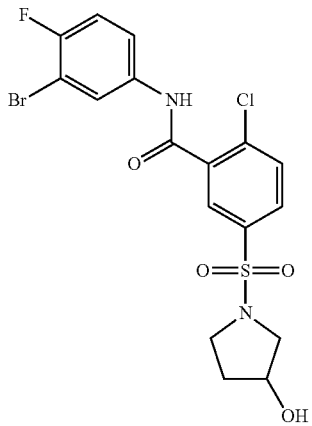<br>479/477<br>GA<br>A17B07C49 | 1183 |
| 451/453<br>GA<br>A17B07C58 | 1184 |
TABLE 1-continued
| Structure MS(M + H)+ Synthetic method | Cmp. ID |
|---|---|
| 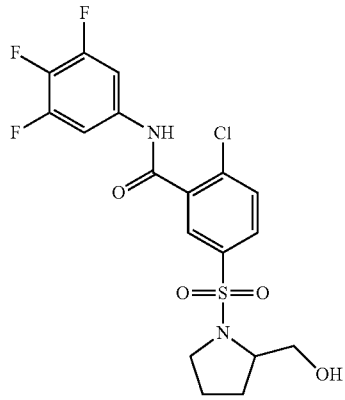<br>449/451<br>GA<br>A18B07C40<br>$^1$H NMR (400 MHz, CD$_3$OD) δ 8.05 (m, 1 H), 7.97 (d, 1H), 8.01 (m, 1H), 7.79 (d, 1H), 7.54 (m, 2H), 3.73 (m, 2H), 3.69 (m, 1H), 3.48 (m, 1H), 3.25 (m, 1H), 1.83 (m, 2H), 1.64 (m, 2H). | 1185_R |
| 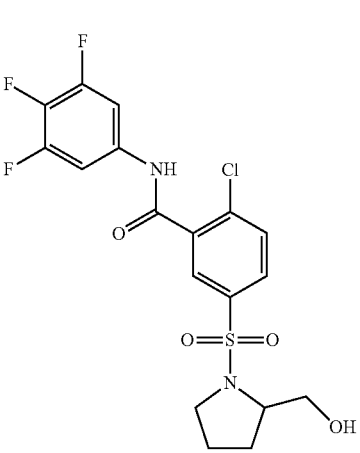<br>449/451<br>GA<br>A18B07C40 | 1185_S |

| Structure MS(M + H)+ Synthetic method | Cmp. ID |
|---|---|
| 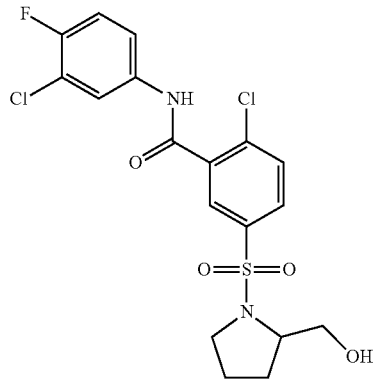<br>447/449<br>GA<br>A18B06C15<br>$^1$H NMR (400 MHz, CD$_3$OD) δ 8.04 (d, J = 2.0 Hz, 1 H), 7.98 (m, 2 H), 7.80 (m, 1 H), 7.57 (m, 1 H), 7.28 (m, 1 H), 3.75 (m, 2 H), 3.60 (m, 1 H), 3.48 (m, 1 H), 3.27 (m, 1 H), 1.93 (m, 2 H), 1.60 (m, 2 H). | 1186_R |
| 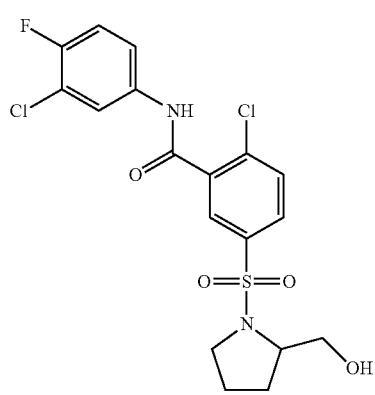<br>447/449<br>GA<br>A18B06C15 | 1186_S |
| Structure MS(M + H)+ Synthetic method | Cmp. ID |
|---|---|
| 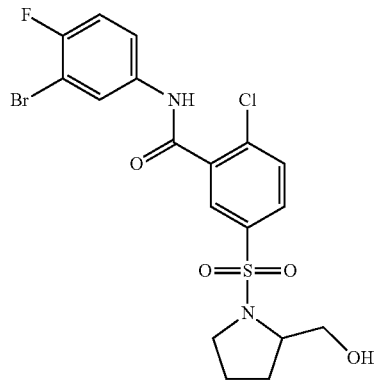<br>493/491<br>GA<br>A18B07C49<br>$^1$H NMR (400 MHz, CD$_3$OD) δ 8.11 (d, 1 H), 8.08 (d, 1H), 8.01 (m, 1H), 7.78 (m, 1H), 7.68 (m, 1H), 7.25 (m, 1H), 3.73 (m, 2H), 3.69 (m, 1H), 3.48 (m, 1H), 3.25 (m, 1H), 1.83 (m, 2H), 1.68 (m, 2H). | 1187_R |
| 493/491<br>GA<br>A18B07C49 | 1187_S |

TABLE 1-continued
| Structure MS(M + H)+ Synthetic method | Cmp. ID |
|---|---|
| 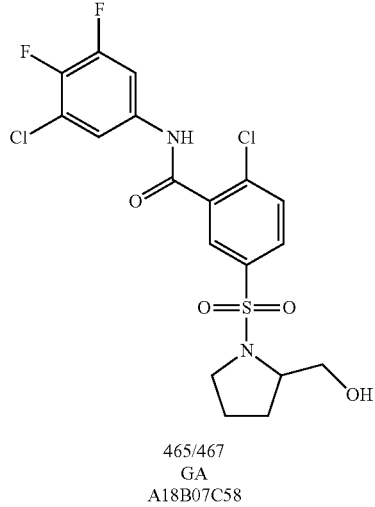 [SMILES: O=C(Nc1cc(F)c(F)c(Cl)c1)c1cc(S(=O)(=O)N2CCCC2CO)ccc1Cl] 465/467 GA A18B07C58 | 1188_R |
| 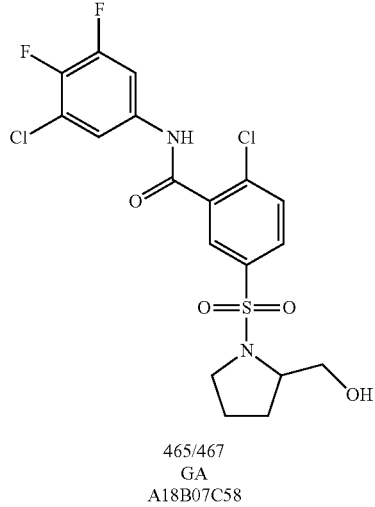 [SMILES: O=C(Nc1cc(F)c(F)c(Cl)c1)c1cc(S(=O)(=O)N2CCCC2CO)ccc1Cl] 465/467 GA A18B07C58 | 1188_S |
TABLE 1-continued
| Structure MS(M + H)+ Synthetic method | Cmp. ID |
|---|---|
| 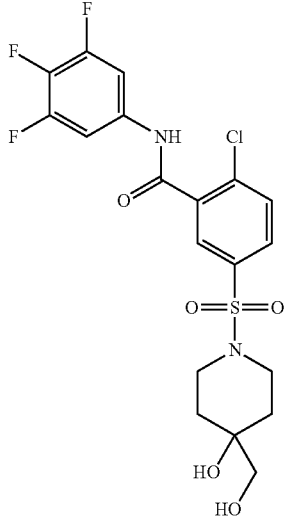 479/481 GA A81B07C40 | 1189 |
| 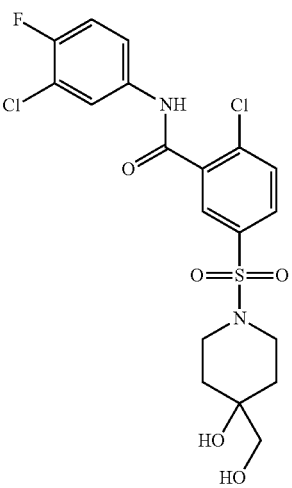 477/479 GA A81B07C15 | 1190 |

TABLE 1-continued
| Structure MS(M + H)+ Synthetic method | Cmp. ID |
|---|---|
| 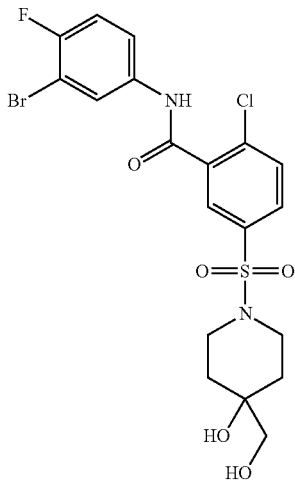 505/503 GA A81B07C49 | 1191 |
| 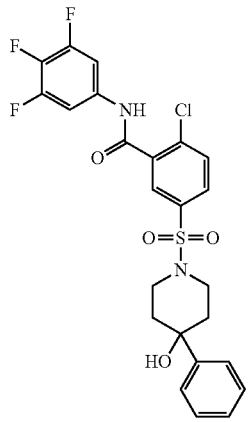 507/509 GA A75B07C40  ¹H NMR (400 MHz, CD₃OD) δ 8.01 (d, 1 H), 7.84 (m, 1H), 7.82 (m, 1H), 7.55 (m, 2H), 7.46 (m, 2H), 7.32 (m, 2H), 7.24 (m, 1H), 3.72 (m, 2H), 2.86 (m, 2H), 2.17 (m, 2H), 1.79 (m, 2H). | 1193 |
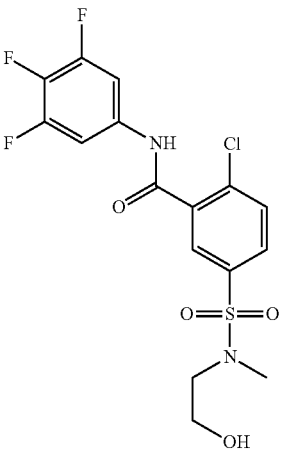
477/479
GA
A81B07C58
Cmp. ID: 1192
423/425
GA
A20B07C40
Cmp. ID: 1197

TABLE 1-continued
| Structure MS(M + H)+ Synthetic method | Cmp. ID |
|---|---|
| 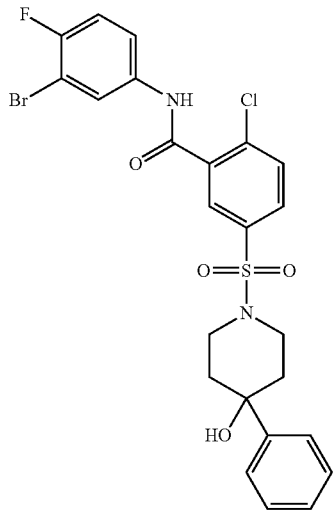<br>551/549<br>GA<br>A75B07C49 | 1195 |
| 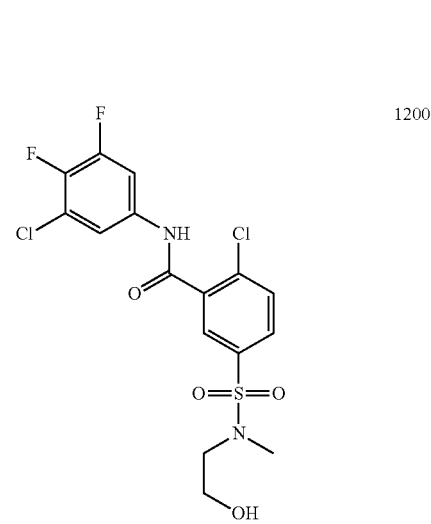<br>523/525<br>GA<br>A75B07C58 | 1196 |
TABLE 1-continued
| Structure MS(M + H)+ Synthetic method | Cmp. ID |
|---|---|
| 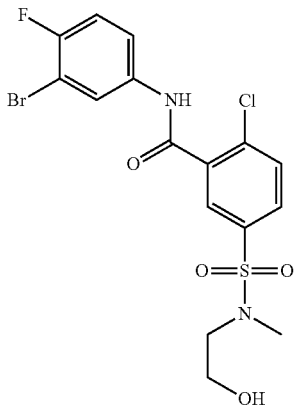<br>467/465<br>GA<br>A20B07C49<br>$^1$H NMR (400 MHz, CD$_3$OD) δ 8.09 (d, 1 H), 7.99 (m, 1H), 7.91 (m, 1H), 7.77 (m, 1H), 7.25 (m, 1H), 3.70 (m, 2H), 3.22 (m, 2H), 2.89 (s, 3H) | 1199 |
| 439/441<br>GA<br>A20B07C58<br>$^1$H NMR (400 MHz, CD$_3$OD) δ 8.01 (d, 1 H), 7.93 (m, 1H), 7.77 (m, 1H), 7.66 (m, 1H), 7.64(m, 1H), 3.70 (m, 2H), 3.22 (m, 2H), 2.89(s, 3H) | 1200 |

TABLE 1-continued

| Structure MS(M + H)+ Synthetic method | Cmp. ID |
|---|---|
| [Structure: 3-bromo-4-fluorophenyl amide of 2,4-difluoro-5-(4-hydroxypiperidin-1-ylsulfonyl)benzoic acid]<br>494/496<br>GA<br>A10B08C49<br>$^1$H NMR (400 MHz, CD$_3$OD) δ 8.25 (t, 1H), 8.10 (m, 1H), 7.64 (m, 1H), 7.47 (t, 1H), 7.25 (t, 1H), 3.75 (m, 1H), 3.54 (m, 2H), 3.08 (m, 2H), 1.92 (m, 2H), 1.60 (m, 2H). | 1203 |
| [Structure: 3-chloro-4,5-difluorophenyl amide of 2,4-difluoro-5-(4-hydroxypiperidin-1-ylsulfonyl)benzoic acid]<br>467/469<br>GA<br>A10B08C58<br>$^1$H NMR (400 MHz, CD$_3$OD) δ 8.25 (t, 1H), 7.75 (m, 1H), 7.67 (m, 1H), 7.48 (t, 1H), 3.76 (m, 1H), 3.52 (m, 2H), 3.08 (m, 2H), 1.91 (m, 2H), 1.60 (m, 2H). | 1204 |

TABLE 1-continued

| Structure MS(M + H)+ Synthetic method | Cmp. ID |
|---|---|
| [Structure: 3-bromo-4-fluorophenyl amide with cis-3-hydroxycyclobutylsulfonamide]<br>479/481<br>GA<br>A119B08C49 | 1211_CT1 |
| [Structure: 3-bromo-4-fluorophenyl amide with trans-3-hydroxycyclobutylsulfonamide]<br>479/481<br>GA<br>A119B08C49 | 1211_CT2 |
| [Structure: 3,4,5-trifluorophenyl amide with cyclopentylsulfonamide]<br>435<br>GA<br>A112B08C40 | 1217 |

TABLE 1-continued
| Structure MS(M + H)+ Synthetic method | Cmp. ID |
|---|---|
| 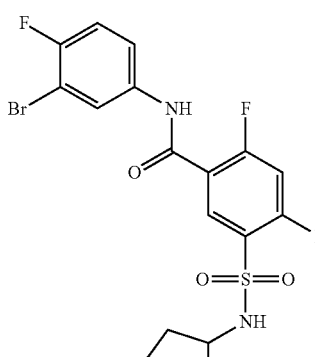<br>477/479<br>GA<br>A112B08C4 | 1219 |
| 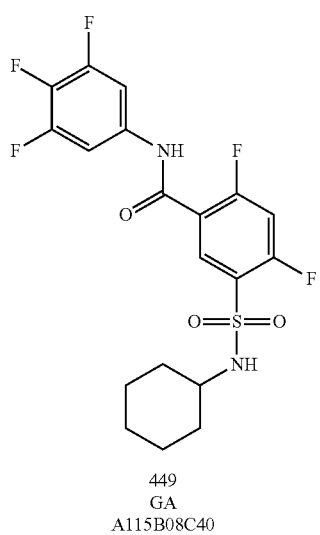 [SMILES: O=C(Nc1cc(F)c(F)c(F)c1)c1cc(S(=O)(=O)NC2CCCCC2)c(F)cc1F]<br>449<br>GA<br>A115B08C40 | 1221 |
TABLE 1-continued
| Structure MS(M + H)+ Synthetic method | Cmp. ID |
|---|---|
| 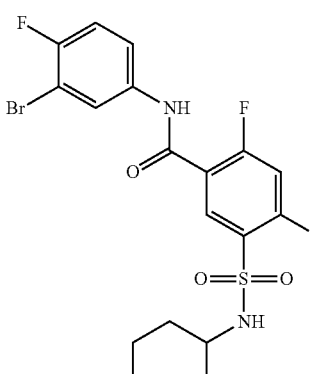<br>491/493<br>GA<br>A115B08C49<br>$^1$H NMR (400 MHz, CD$_3$OD) δ 8.29 (t, 1H), 8.10 (m, 1H), 7.63 (m, 1H), 7.43 (t, 1H), 7.27 (t, 1H), 3.17 (m, 1H), 1.76 (m, 4H), 1.59 (m, 1H), 1.30 (m, 4H), 1.16 (m, 1H). | 1223 |
| 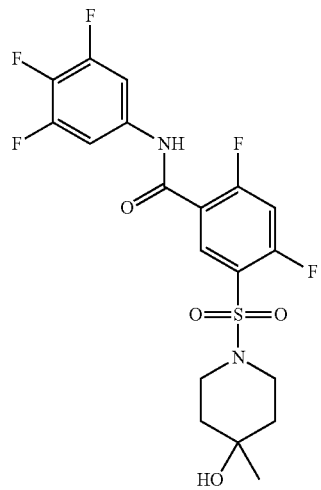<br>465<br>GA<br>A73B08C40 | 1225 |

TABLE 1-continued
| Structure MS(M + H)+ Synthetic method | Cmp. ID |
|---|---|
| 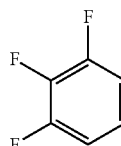<br>463/465<br>GA<br>A73B08C15 | 1226 |
| 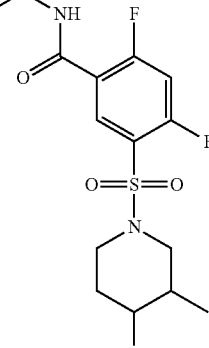<br>507/509<br>GA<br>A73B08C49 | 1227 |
TABLE 1-continued
| Structure MS(M + H)+ Synthetic method | Cmp. ID |
|---|---|
| 465<br>GA<br>A84B08C40 | 1229_D1 |
| 465<br>GA<br>A84B08C40 | 1229_D2 |

TABLE 1-continued
| Structure MS(M + H)+ Synthetic method | Cmp. ID |
|---|---|
| 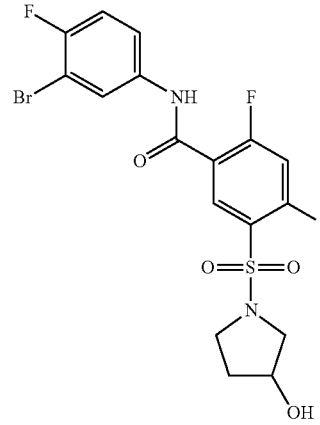<br>479<br>GA<br>A09B08C40 | 1237 |
| 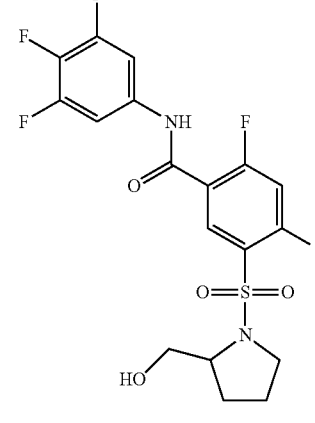<br>521/523<br>GA<br>A09B08C49 | 1239 |
TABLE 1-continued
| Structure MS(M + H)+ Synthetic method | Cmp. ID |
|---|---|
| 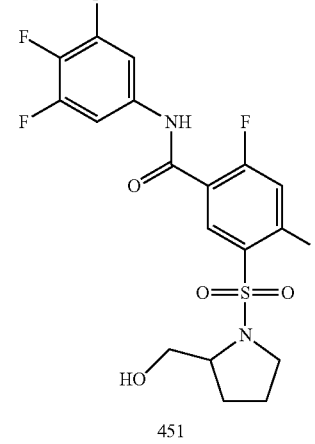<br>479/481<br>GA<br>A17B08C49 | 1243 |
| 451<br>GA<br>A18B08C40 | 1245_R |
| 451<br>GA<br>A18B08C40 | 1245_S |

TABLE 1-continued
| Structure MS(M + H)+ Synthetic method | Cmp. ID |
|---|---|
| 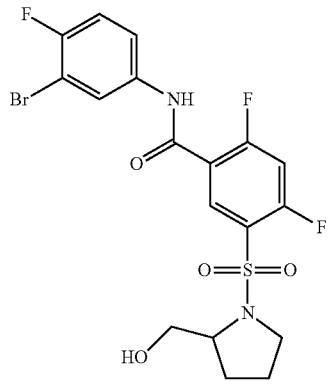<br>493/495<br>GA<br>A18B08C49 | 1247_R |
| 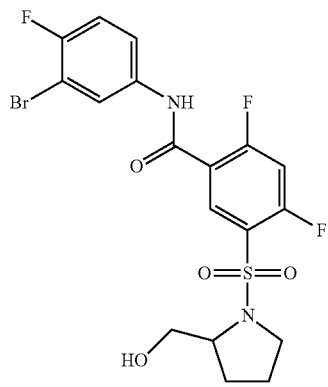<br>493/495<br>GA<br>A18B08C49<br>¹H NMR (400 MHz, CD₃OD) δ 8.31 (t, 1H), 8.10 (m, 1H), 7.65 (m, 1H), 7.45 (t, 1H), 7.25 (t, 1H), 3.87 (m, 1H), 3.70 (m, 1H), 3.57 (m, 1H), 3.48 (m, 1H), 3.38 (m, 1H), 1.98 (m, 4H). | 1247_S |
| 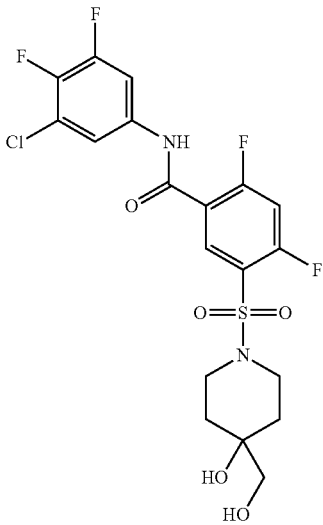<br>497/499<br>GA<br>A81B08C58 | 1252 |
| 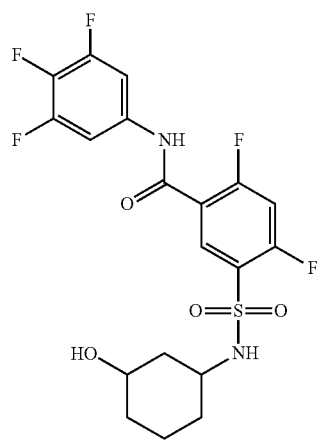<br>465<br>GA<br>A116B08C40<br>¹H NMR (400 MHz, CD₃OD) δ 8.25 (t, 1H), 7.57 (m, 2H), 7.40 (t, 1H), 3.48 (m, 1H), 3.22 (m, 1H), 1.99 (m, 1H), 1.83 (m, 1H), 1.71 (m, 2H), 1.27 (m, 4H). | 1265 |

TABLE 1-continued

| Structure MS(M + H)+ Synthetic method | Cmp. ID |
|---|---|
| [Structure: N-(3-bromo-4-fluorophenyl)-2,4-difluoro-5-[(3-hydroxycyclohexyl)sulfamoyl]benzamide]<br>507/509<br>GA<br>A116B08C49 | 1267 |
| [Structure: N-(3,4,5-trifluorophenyl)-2,4-difluoro-5-[(4-hydroxycyclohexyl)sulfamoyl]benzamide]<br>465<br>GA<br>A117B08C40 | 1269 |

TABLE 1-continued

| Structure MS(M + H)+ Synthetic method | Cmp. ID |
|---|---|
| [Structure: N-(3-bromo-4-fluorophenyl)-2,4-difluoro-5-[(4-hydroxycyclohexyl)sulfamoyl]benzamide]<br>507/509<br>GA<br>A117B08C49<br>¹H NMR (400 MHz, CD₃OD) δ 8.29 (t, 1H), 8.10 (m, 1H), 7.65 (m, 1H), 7.41 (t, 1H), 7.25 (t, 1H), 3.48 (m, 1H), 3.16 (m, 1H), 1.87 (m, 4H), 1.30 (m, 4H). | 1271 |
| [Structure: N-(3,4,5-trifluorophenyl)-4-fluoro-3-{[3-(fluoromethyl)-4-hydroxypiperidin-1-yl]sulfonyl}benzamide]<br>465<br>GA<br>A127B03C40<br>¹H NMR (400 MHz, MeOD) δ 8.45-8.43 (m, 1H), 8.29-8.26 (m, 1H), 7.64-7.61 (m, 2H), 7.59-7.51 (m, 1H), 3.78-3.73 (m, 3H), 3.62-3.52 (m, 1H), 3.01-2.98 (m, 1H), 2.88-2.85 (m, 1H), 2.14-1.98 (m, 1H), 1.87-1.82 (m, 1H). | 1283 |

| Structure MS(M + H)+ Synthetic method | Cmp. ID |
|---|---|
| 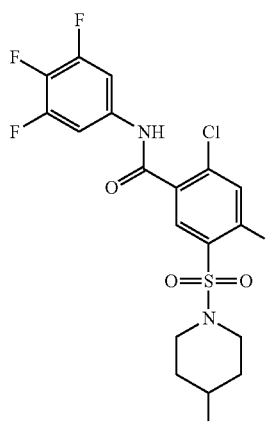 467/469 GA A10B09C40 <sup>1</sup>H NMR (400 MHz, CD3OD) δ 8.05 (d, 1H), 7.70 (d, 1H), 7.55 (dd, 1H), 3.77 (m, 1H), 3.56 (m, 2H), 3.09 (td, 2H), 1.94 (m, 2H), 1.60 (m, 2H). | 1334 |
| 465/467 GA A10B09C15 | 1335 |
| 509/512 GA A10B09C49 | 1336 |
| 483/485 GA A10B09C58 | 1337 |

TABLE 1-continued

| Structure MS(M + H)+ Synthetic method | Cmp. ID |
|---|---|
| (structure) 449/451 GA A10B09C63 | 1338 |
| (structure) 439/441 GA A19B09C40 ¹H NMR (400 MHz, CD3OD) δ 8.06 (d, 1H), 7.75 (d, 1H), 7.54 (dd, 2H), 4.50 (t, 1H), 4.13 (t, 2H), 3.73 (t, 2H). | 1339 |

TABLE 1-continued

| Structure MS(M + H)+ Synthetic method | Cmp. ID |
|---|---|
| (structure) 437/439 GA A19B09C15 | 1340 |
| (structure) 439/441 GA A20B09C15 | 1345 |
| (structure) 457/459 GA A20B09C58 | 1347 |

TABLE 1-continued
| Structure MS(M + H)+ Synthetic method | Cmp. ID |
|---|---|
| 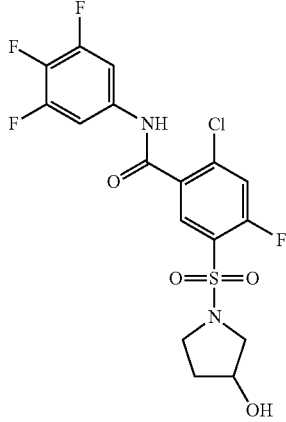 453/455 GA A17B09C40 $^1$H NMR (400 MHz, CD$_3$OD) δ 8.09 (d, 1H), 7.67 (d, 1H), 7.53 (dd, 2H), 4.38 (d, 1H), 3.51 (m, 3H), 3.39 (m, 1H), 2.02 (m, 2H). | 1349 |
| 469/471 GA A17B09C58 | 1352 |
TABLE 1-continued
| Structure MS(M + H)+ Synthetic method | Cmp. ID |
|---|---|
| 467/469 GA A18B09C40 | 1354_R |
| 467/469 GA A18B09C40 | 1354_S |
| 465/467 GA A18B09C15 | 1355_R |

TABLE 1-continued

| Structure MS(M + H)+ Synthetic method | Cmp. ID |
|---|---|
| [Structure: N-(3,4,5-trifluorophenyl)-2-chloro-4-fluoro-5-[(4-(2-hydroxyethyl)piperidin-1-yl)sulfonyl]benzamide]<br>495/497<br>GA<br>A09B09C40 | 1359 |
| [Structure: N-(3-bromo-4-fluorophenyl)-2-chloro-4-fluoro-5-[(4-(2-hydroxyethyl)piperidin-1-yl)sulfonyl]benzamide]<br>537/539<br>GA<br>A09B09C49<br>$^1$H NMR (400 MHz, CD3OD) δ 8.09 (dd, 1H), 8.03 (d, 1H), 7.67 (d, 1H), 7.61 (m, 1H), 7.27 (t, 1H), 3.83 (d, 2H), 3.62 (t, 2H), 2.66 (t, 2H), 1.83 (d, 2H), 1.51 (m, 3H), 1.28 (m, 2H). | 1361 |

TABLE 1-continued

| Structure MS(M + H)+ Synthetic method | Cmp. ID |
|---|---|
| [Structure: N-(3,4-difluorophenyl)-2-chloro-4-fluoro-5-[(4-(2-hydroxyethyl)piperidin-1-yl)sulfonyl]benzamide]<br>477/479<br>GA<br>A09B09C63<br>$^1$H NMR (400 MHz, CD3OD) d 8.03 (d, 1H), 7.84 (m, 1H), 7.68 (d, 1H), 7.36 (m, 1H), 7.30 (q, 1H), 3.86 (d, 2H), 3.62 (t, 2H), 2.67 (t, 2H), 1.83 (d, 2H), 1.50 (m, 3H), 1.28 (m, 2H). | 1363 |
| [Structure: N-(3,4,5-trifluorophenyl)-2-chloro-4-fluoro-5-[(4-hydroxy-4-methylpiperidin-1-yl)sulfonyl]benzamide]<br>481/483<br>GA<br>A73B09C40 | 1364 |

TABLE 1-continued

| Structure MS(M + H)+ Synthetic method | Cmp. ID |
|---|---|
| (structure) 479/481 GA A73B09C15 | 1365 |
| (structure) 453/455 GA A119B09C40 | 1374_CT1 |
| (structure) 453/455 GA A119B09C40 | 1374_CT2 |
| (structure) 451/453 GA A119B09C15 | 1375 |
| (structure) 497/499 GA A81B09C40 <br> ¹H NMR (400 MHz, CD3OD-d4) δ8.02-8.04 (m, 1H), 7.65-7.69 (m, 1H), 7.49-7.53 (m, 2H), 3.64-3.68 (m, 2H), 3.34 (s, 2H), 2.93-2.99 (m, 2H), 1.57-1.71(m, 4H). | 1379 |

TABLE 1-continued
| Structure MS(M + H)+ Synthetic method | Cmp. ID |
|---|---|
| 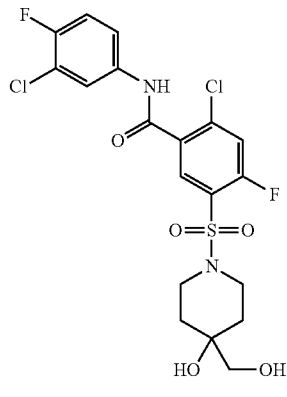  495/497  GA  A81B09C15  ¹H NMR (400 MHz, CD3OD-d4) δ8.02-8.04 (m, 1H), 7.92-7.95 (m, 1H), 7.65-7.68 (m, 1 H), 7.54-7.56 (m, 1H), 7.23-7.28 (m, 1H), 3.65-3.68 (m, 2H), 3.34 (s, 2H), 2.94-3.00(m, 2H), 1.57-1.71(m, 4H). | 1380 |
| 509/511  GA  A113B09C49 | 1386 |
TABLE 1-continued
| Structure MS(M + H)+ Synthetic method | Cmp. ID |
|---|---|
| 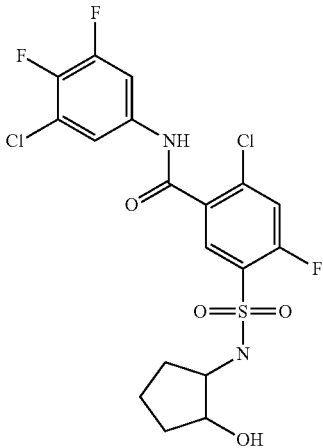  483/485  GA  A113B09C58 | 1387 |
| 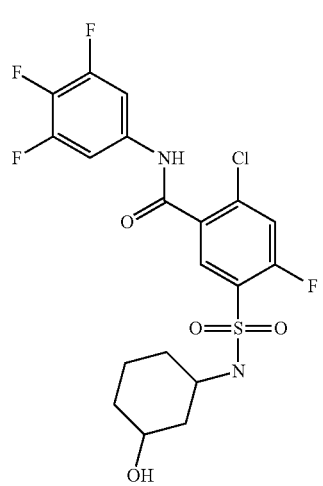  481/483  GA  A116B09C40 | 1389_D2 |

| Structure MS(M + H)+ Synthetic method | Cmp. ID |
|---|---|
| 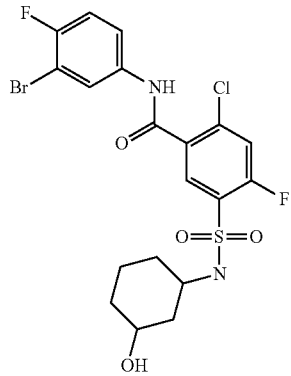<br>525/523<br>GA<br>A116B09C49<br>¹H NMR (400 MHz, METHANOL-d4) = 8.13-8.04 (m, 2H), 7.68-7.59 (m, 2H), 7.30-7.21 (m, 1H), 3.53-3.44 (m, 1H), 3.28-3.20 (m, 1H), 2.08-1.97 (m, 1H), 1.91-1.81 (m, 1H), 1.77-1.70 (m, 2H), 1.22 (s, 4H) | 1391_D1 |
| 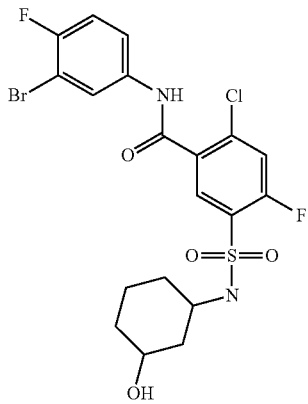<br>525/523<br>GA<br>A116B09C49<br>¹H NMR (400 MHz, METHANOL-d4) = 8.11-8.06 (m, 2H), 7.63 (d, J = 9.7 Hz, 2H), 7.25 (m, 1H), 4.01 (m, 1H), 3.65-3.55 (m, 1H), 1.80-1.61 (m, 3H), 1.61-1.05 (m, 5H) | 1391_D2 |
| Structure MS(M + H)+ Synthetic method | Cmp. ID |
|---|---|
| 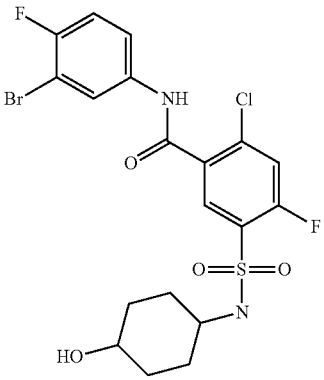<br>523/525<br>GA<br>A117B09C49<br>¹H NMR (400 MHz, CD3OD-d4) δ8.04-8.08 (m, 2H), 7.60-7.64 (m, 2H), 7.21-7.26 (m, 1H), 3.40-3.50 (m, 1H), 3.10-3.20 (m, 1H), 1.75-1.92 (m, 4H), 1.20-1.37(m, 4H). | 1396 |
| 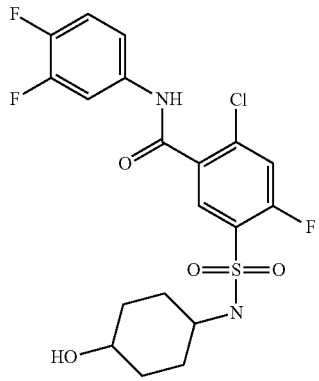<br>463/465<br>GA<br>A117B09C63 | 1398 |

TABLE 1-continued
| Structure<br>MS(M + H)+<br>Synthetic method | Cmp.<br>ID |
|---|---|
| 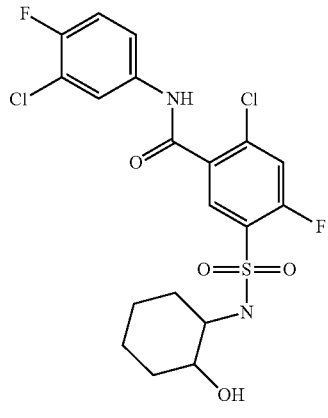<br>479/481<br>GA<br>A118B09C15<br>¹H NMR (400 MHz, CD3OD-d4) δ8.06-8.08 (m, 1H), 7.92-7.95 (m, 1H), 7.54-7.62 (m, 2 H), 7.23-7.28 (m, 1H), 3.74-3.76 (m, 1H), 3.30-3.34 (m, 1H), 1.23-1.73(m, 8H). | 1400 |
| 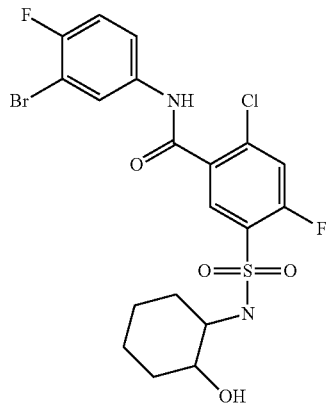<br>523/525<br>GA<br>A118B09C49<br>¹H NMR (400 MHz, CD3OD-d4) δ8.06-8.08 (m, 1H), 7.59-7.63 (m, 2H), 7.21-7.26 (m, 1 H), 3.74-3.76 (m, 1H), 3.30-3.34 (m, 1H), 1.23-1.73(m, 8H). | 1401 |
TABLE 1-continued
| Structure<br>MS(M + H)+<br>Synthetic method | Cmp.<br>ID |
|---|---|
| 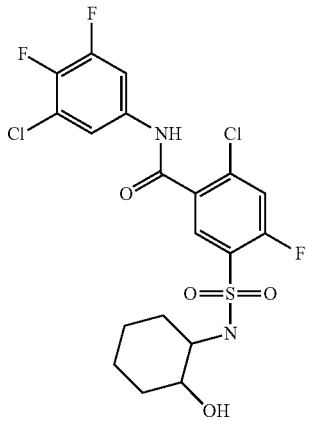<br>497/499<br>GA<br>A118B09C58<br>¹H NMR (400 MHz, CD3OD-d4) δ8.07-8.09 (m, 1H), 7.68-7.71 (m, 1H), 7.60-7.64 (m, 2 H), 3.74-3.76 (m, 1H), 3.30-3.34 (m, 1H), 1.23-1.73(m, 8H). | 1402 |
| 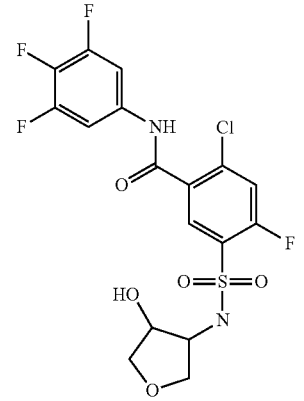<br>469/471<br>GA<br>A129B09C40<br>¹H NMR (400 MHz, CD3OD-d4) δ8.07-8.10 (m, 1H), 7.63-7.66 (m, 1H), 7.49-7.54(m, 2 H), 4.16-4.18 (m, 1H), 3.91-3.96 (m, 2H), 3.65-3.70 (m, 1H), 3.50-3.60 (m, 2H). | 1404 |

TABLE 1-continued

| Structure MS(M + H)+ Synthetic method | Cmp. ID |
|---|---|
| [Structure of compound 1405: 3-chloro-4-fluorophenyl amide with chloro, fluoro-substituted benzamide bearing sulfonamide linked to 4-hydroxytetrahydrofuran-3-yl] 467/469 GA A129B09C15 | 1405 |
| [Structure of compound 1410: 3-chloro-4-fluorophenyl amide with chloro, fluoro-substituted benzene bearing sulfonyl-pyrrolidine with hydroxy and fluoro substituents] 469/471 GA A110B09C15 | 1410 |
| [Structure of compound 1413: 3,4-difluorophenyl amide with chloro, fluoro-substituted benzene bearing sulfonyl-pyrrolidine with hydroxy and fluoro substituents] 453/455 GA A110B09C63 | 1413 |

TABLE 1-continued

| Structure MS(M + H)+ Synthetic method | Cmp. ID |
|---|---|
| [Structure of compound 1419: 3-chloro-4-fluorophenyl amide with fluoro-substituted benzamide bearing sulfonamide linked to 2-hydroxyethyl] 391/393 GA A128B03C15 <br> 1H NMR (400 MHz, CD3OD-d4) δ 8.44-8.46 (m, 1H), 8.20-8.30 (m, 1H), 7.94-7.97 (m, 1 H), 7.60-7.62 (m, 1H), 7.44-7.49 (m, 1H), 7.22-7.26 (m, 1H), 3.55-3.58 (m, 2H), 3.09-3.12 (m, 2H). | 1419 |
| [Structure of compound 1420: 3,4,5-trifluorophenyl amide with hydroxymethyl-substituted benzamide bearing sulfonyl-4-hydroxypiperidine] 445 GG A01B21C40 <br> 1H NMR (400 MHz, CD3OD-d4) δ8.41-8.42 (m, 1H), 8.21-8.23 (m, 1H), 8.05-8.07 (m, 1 H), 7.61-7.65 (m, 2H), 5.06 (s, 2H), 3.74-3.77 (m, 1H), 3.52-3.56 (m, 2H), 3.03-3.06 (m, 2H), 1.87-1.92 (m, 2H), 1.57-1.62 (m, 2H). | 1420 |

TABLE 1-continued

| Structure MS(M + H)+ Synthetic method | Cmp. ID |
|---|---|
| 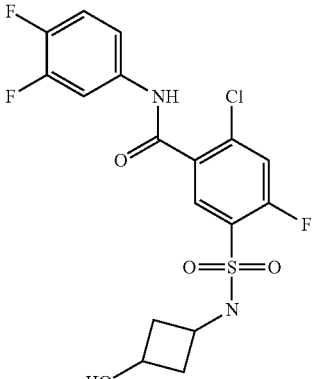 435/437 GA A119B09C63 | 1378_CT2 |

The invention further includes a composition comprising a compound of formula (I), or a salt, solvate, or N-oxide thereof. In one embodiment, the composition is pharmaceutical and further comprises at least one pharmaceutically acceptable carrier.

Preparation of the Compounds of the Invention

Compounds of formula (II) may be prepared by the reaction sequence that is illustrated in Scheme 1.

The compound of formula (IV) may be reacted with chlorosulfonic acid to yield the sulfonyl chloride of formula (V). The compound of formula (V) may be reacted with a secondary or primary amine of formula $HNR^6R^6$, in a solvent such as but not limited to tetrahydrofuran, dichloromethane, ethyl ether or a mixture thereof, preferably in the presence of a tertiary base such as but not limited to triethylamine, diisopropylethylamine or pyridine, to yield the compound of formula (VI), which may be coupled to an amine via an amide bond, yielding the compound of formula (II). The amide coupling may be performed in the presence of a coupling agent, such as but not limited to DCC (N,N'-dicyclohexyl carbodiimide), DIC (N,N'-diisopropylcarbodiimide), EDC (1-ethyl-3-(3-dimethylaminopropyl)carbodiimide), HBTU (O-benzotriazole-N,N,N',N'-tetramethyl-uronium-hexafluoro-phosphate), HATU (2-(1H-7-azabenzotriazol-1-yl)-1,1,3,3-tetramethyl uronium hexafluorophosphate methanaminium), HCTU ((2-(6-chloro-1H-benzotriazole-1-yl)-1,1,3,3-tetramethylaminium hexafluorophosphate), TBTU (O-(benzotriazol-1-yl)-N,N,N',N'-tetramethyluronium tetrafluoroborate), or PyBOP (benzotriazol-1-yl-oxytripyrrolidinophosphonium hexafluorophosphate), in a solvent such as but not limited to tetrahydrofuran, dichloromethane, or a mixture thereof, and in the optional presence of a tertiary base, such as but not limited to triethylamine, diisopropylethylamine or pyridine. Alternatively, the sulfonyl chloride of formula (V) may be reacted with a chlorinating reagent, such as but not limited to thionyl chloride, phosgene, diphosgene or triphosgene, to yield the acyl chloride of formula (VII). The compound of formula (VII) may then be reacted with an amine in a solvent such as but not limited to tetrahydrofuran, dichloromethane, ethyl ether or a Scheme 1.

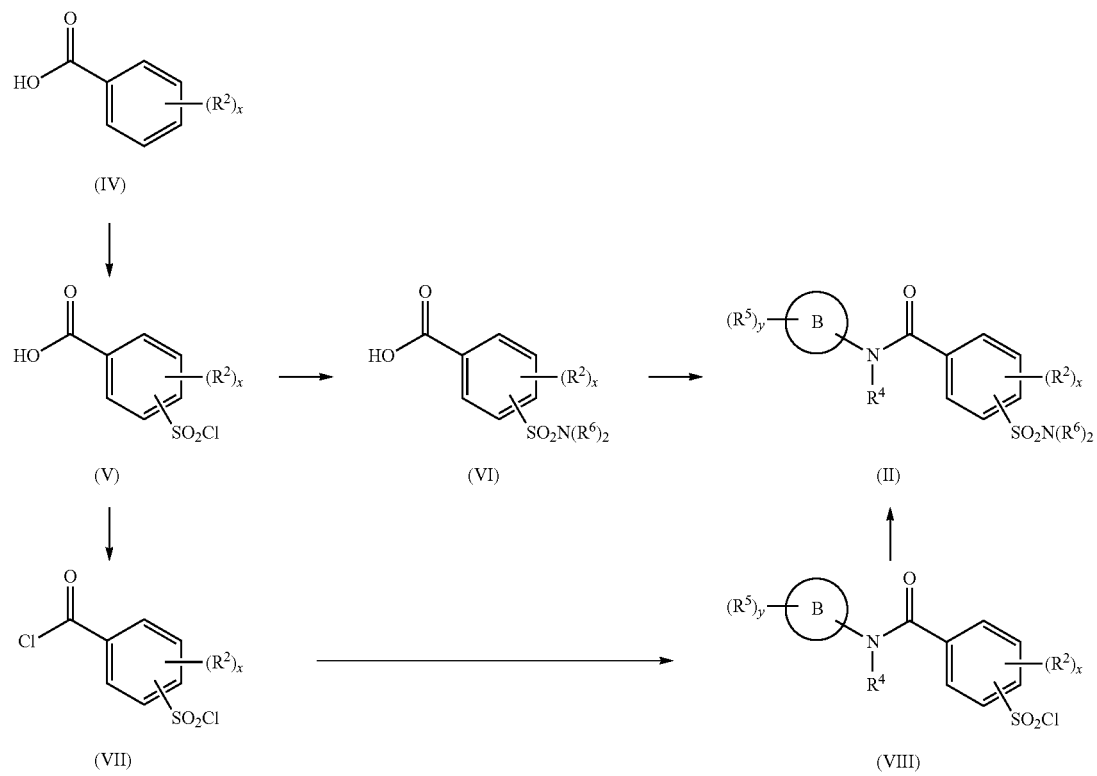

mixture thereof, under conditions that do not promote the reaction of the sulfonyl chloride group with the amine, to yield the compound of formula (VIII), which may then be reacted with the amine HNR⁶R⁶ in a solvent such as but not limited to tetrahydrofuran, toluene, dichloromethane, or a mixture thereof, and in the presence of a tertiary base, such as but not limited to triethylamine, diisopropylethylamine or pyridine, to yield the compound of formula (II).

Compounds of formula (III) may be prepared by the reaction scheme that is illustrated in Scheme 2.

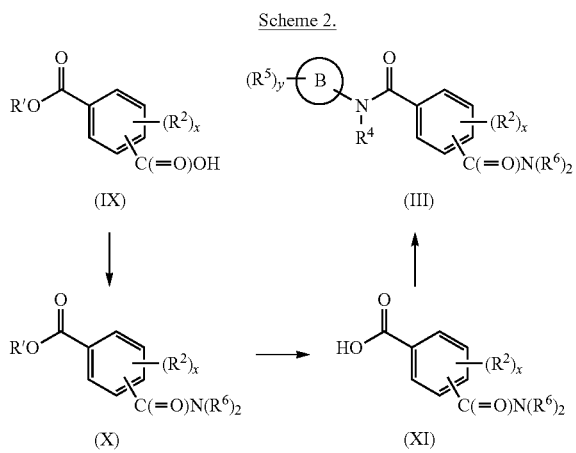

The compound of formula (IX) may be reacted with a secondary or primary amine of formula HNR⁶R⁶, in a solvent such as but not limited to tetrahydrofuran, dichloromethane, ethyl ether or a mixture thereof, in the presence of a coupling agent, such as but not limited to DCC, EDC, HBTU, HATU, HCTU, TBTU, or PyBOP, in a solvent such as but not limited to tetrahydrofuran, dichloromethane, or a mixture thereof, and in the optional presence of a tertiary base, such as but not limited to triethylamine, diisopropylethylamine or pyridine, to yield the compound of formula (X). The compound of formula (X) may be treated with a base, such as but not limited to lithium hydroxide, sodium hydroxide or potassium hydroxide, to yield the compound of formula (XI). The compound of formula (XI) may be reacted with a secondary or primary amine, in a solvent such as but not limited to tetrahydrofuran, dichloromethane, ethyl ether or a mixture thereof, in the presence of a coupling agent, such as but not limited to DCC, EDC, HBTU, HATU, HCTU, TBTU, or PyBOP, in a solvent such as but not limited to tetrahydrofuran, dichloromethane, or a mixture thereof, and in the optional presence of a tertiary base, such as but not limited to triethylamine, diisopropylethylamine or pyridine, to yield the compound of formula (III).

The compounds of the invention may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein.

Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In one embodiment, the compounds described herein exist in solvated forms with pharmaceutically acceptable solvents such as water, and ethanol. In another embodiment, the compounds described herein exist in unsolvated form.

In one embodiment, the compounds of the invention may exist as tautomers. All tautomers are included within the scope of the compounds presented herein.

In one embodiment, compounds described herein are prepared as prodrugs. A "prodrug" refers to an agent that is converted into the parent drug in vivo. In one embodiment, upon in vivo administration, a prodrug is chemically converted to the biologically, pharmaceutically or therapeutically active form of the compound. In another embodiment, a pro drug is enzymatically metabolized by one or more steps or processes to the biologically, pharmaceutically or therapeutically active form of the compound.

In one embodiment, sites on, for example, the aromatic ring portion of compounds of the invention are susceptible to various metabolic reactions. Incorporation of appropriate substituents on the aromatic ring structures may reduce, minimize or eliminate this metabolic pathway. In one embodiment, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to ²H, ³H, ¹¹C, ¹³C, ¹⁴C, ³⁶Cl, ¹⁸F, ¹²³I, ¹²⁵I, ¹³N, ¹⁵N, ¹⁵O, ¹⁷O, ¹⁸O, ³²P, and ³⁵S. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as ¹¹C, ¹⁸F, ¹⁵O and ¹³N, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In one embodiment, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In another embodiment, each protective group is removable by a different means. Protective groups that are cleaved under totally disparate reaction conditions fulfill the requirement of differential removal.

In one embodiment, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In one embodiment, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

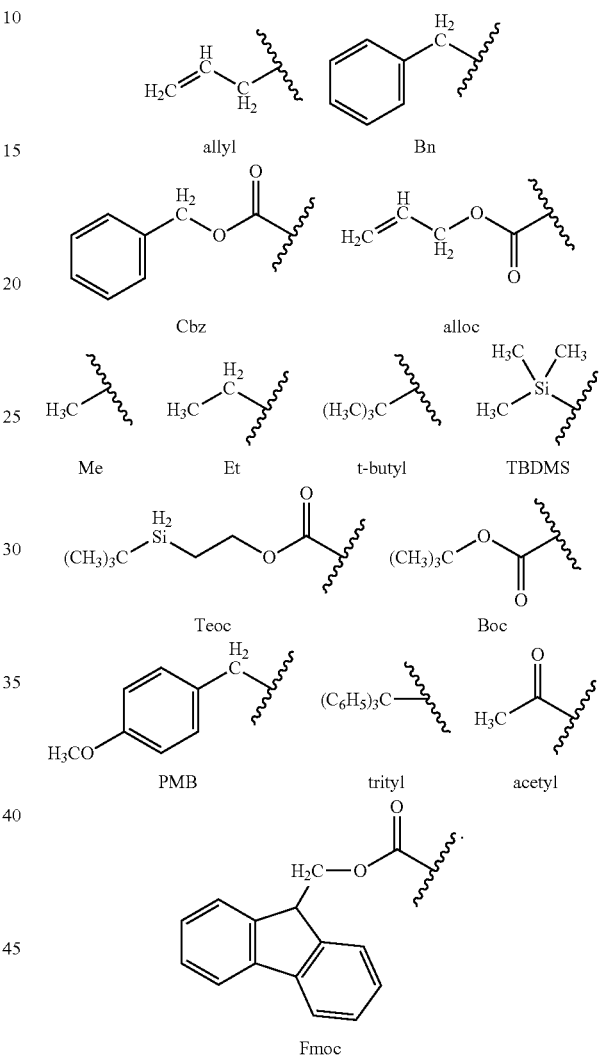

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Assays

HBV Capsid Protein Assembly Testing

The fluorescence quenching in vitro assembly HBV assay was developed according to a method described by Zlotnick and coworkers (Nature Biotechnology 2006, 24:358). The assay is based on the observation that the C-termini of the HBV core protein cluster together during capsid formation. This assay utilizes a mutant C150 HBV capsid protein where all wild-type cysteines are mutated to alanines, but a C-terminal cysteine residue is preserved and is labeled with fluorescent BoDIPY-FL dye. HBV C150Bo protein is highly fluorescent, however the fluorescence is drastically reduced during the capsid assembly process. Thus, the assay measures the ability and potency of test compounds to modulate capsid assembly by monitoring the fluorescence of the labeled capsid C150Bo protein.

In a typical assay, the mutant HBV C150 protein (amino acids 1-150, C49A, C61A, C107A, 150C) is cloned into a T7 RNA-polymerase based expression vector, expressed in *E. coli* and purified to homogeneity as a dimer. The purified HBV core protein is desalted and labeled with BODIPY-FL Dye.

In a non-limiting embodiment, the assembly assay is conducted in 96-well plate format. The assembly reactions are carried out in 50 mM Hepes buffer, pH 7.5 and 150 mM NaCl. The compounds are pre-incubated with the HBV CA protein for 15 min, and the assembly reactions are initiated by addition of NaCl. The reaction is allowed to continue for 1 hour at room temperature.

To determine the effect on capsid assembly, each test compound is initially screened at 4 different concentrations: 10 µM, 3 µM, 1 µM and 0.3 µM in duplicates. Primary hits are compounds that show activity in the assembly assay at 10 uM and a representative group of these active compounds is shown in Table 1. Identified primary hits are confirmed in follow-up studies as described elsewhere herein. Known modulators of HBV CA assembly, such as HAP-1 and BAY 41-4109, are used as control compounds in these experiments and exhibited $EC_{50}$ values consistent with the literature. $EC_{50}$ values for test compounds are determined via analysis of the dose-response curve.

HBV Antiviral Testing

Compounds active in the HBV assembly assay are tested for their activity and toxicity in cellular assay. In the first anti-viral assay, the ability of compounds to inhibit HBV replication in an HBV-producing hepatoma cell line using the dot-blot method is evaluated.

Briefly, confluent monolayers of HepG2-2.2.15 cells are incubated with complete medium containing various concentrations of a test compound. Three days later, the culture medium is replaced with fresh medium containing the appropriately diluted test compound. Six days following the initial administration of the test compound, the cell culture supernatant is collected, and cell lysis is performed. The samples are applied onto Nylos membranes and DNA is immobilized to the membrane by UV cross-linking. After pre-hybridization, the HBV probe is added and the hybridization is performed overnight. The membranes are exposed to the Kodak films; antiviral activity is calculated from the reduction in HBV DNA levels ($EC_{50}$). The $EC_{50}$ for antiviral activity is calculated from the dose response curves of active compounds. Assay performance over time is monitored by the use of the standard positive control compounds ETV, BAY 41-4109, and HAP-1.

Compound cytotoxicity ($TC_{50}$) is measured in this same HepG2-2.2.15 cell line using a CellTiter Blue-based cytotoxicity assay employed as recommended by manufacturer (Promega). To confirm and expand these results, a second antiviral assay is carried out on active compounds using the stable HBV cell line HepG2.2.15 and measuring anti-HBV potency by real-time PCR and cytotoxicity by CellTiter Blue. In this assay, 24 hours after cell seeding, HepG2-2.2.15 cells are incubated with complete medium containing various concentrations of a test compound with BAY 41-4109 and HAP-1 used as positive controls. After three days, the culture medium is replaced with fresh medium containing the appropriately diluted test compound. The cell culture is collected six days following the initial administration of the test compound, followed by HBV DNA extraction using QIAamp 96 DNA Blood Kit (Qiagen). The extracted HBV DNA is diluted and analyzed by Real-Time PCR. A standard curve is generated by plotting Ct value vs the amount of HBV plasmid standard. Cytotoxicity is determined similarly to the above described method by applying a dye uptake method (CellTiter Blue kit, Promega).

Prevention of HBV Pre-Genomic RNA (pgRNA) Incorporation.

The anti-viral activity of the compounds of the invention is assessed based on their ability to suppress both extracellular and intracellular HBV DNA production in two different cell culture models of HBV replication. To assess if these effects are due to disruption of intracellular capsid assembly, a particle-gel assay that allows quantitation of intracellular viral capsids, as well as encapsidated pre-genomic RNA and DNA, is performed. The assay relies on agarose gel separation of viral capsid from free capsid/core subunits and viral pg-RNA and DNA.

Methods of Treatment

The invention includes a method of treatment of an HBV infection in an individual in need thereof, comprising administering to the individual a therapeutically effective amount of a compound of the invention.

The invention also includes a method of reducing viral load associated with an HBV infection in an individual in need thereof, comprising administering to the individual a therapeutically effective amount of a compound of the invention.

The invention further includes a method of reducing reoccurrence of an HBV infection in an individual in need thereof, comprising administering to the individual a therapeutically effective amount of a compound of the invention.

The invention also includes a method of reducing the physiological impact of an HBV infection in an individual in need thereof, comprising administering to the individual a therapeutically effective amount of a compound of the invention.

The invention further includes a method of reducing, slowing, or inhibiting an HBV infection in an individual in need thereof, comprising administering to the individual a therapeutically effective amount of a compound of the invention.

The invention also includes a method of inducing remission of hepatic injury from an HBV infection in an individual in need thereof, comprising administering to the individual a therapeutically effective amount of a compound of the invention.

The invention further includes a method of reducing the physiological impact of long-term antiviral therapy for HBV infection in an individual in need thereof, comprising administering to the individual a therapeutically effective amount of a compound of the invention.

The invention also includes a method of eradicating an HBV infection in an individual in need thereof, comprising administering to the individual a therapeutically effective amount of a compound of the invention.

The invention further includes a method of prophylactically treating an HBV infection in an individual in need thereof, wherein the individual is afflicted with a latent HBV infection, comprising administering to the individual a therapeutically effective amount of a compound of the invention.

In one embodiment, the methods described herein further comprise administering at least one therapeutic agent selected from the group consisting of nucleotide/nucleoside analogs, entry inhibitors, fusion inhibitors, and any combination of these or other antiviral mechanisms. In another embodiment, the compound of the invention and the at least one additional therapeutic agent are co-formulated. In yet another embodiment, the compound of the invention and the at least one additional therapeutic agent are co-administered.

In one embodiment, the individual is refractory to other therapeutic classes of HBV drugs (e.g., HBV polymerase inhibitors, interferons, viral entry inhibitors, viral maturation inhibitors, literature-described capsid assembly modulators, antiviral compounds of distinct or unknown mechanism, and the like, or combinations thereof). In another embodiment, the method of the invention reduces viral load in an individual suffering from an HBV infection to a greater extent compared to the extent that other therapeutic classes of HBV drugs reduce viral load in the individual.

In one embodiment, the method of the invention reduces viral load in an individual suffering from an HBV infection, thus allowing lower doses or varying regimens of combination therapies to be used.

In one embodiment, the method of the invention causes a lower incidence of viral mutation and/or viral resistance compared to other classes of HBV drugs, thereby allowing for long term therapy and minimizing the need for changes in treatment regimens.

In one embodiment, the method of the invention increases the seroconversion rate beyond that of current treatment regimens.

In one embodiment, the method of the invention increases and/or normalizes and/or restores normal health, elicits full recovery of normal health, restores life expectancy, and/or resolves the viral infection in the individual in need thereof.

In one embodiment, the method of the invention eradicates HBV from an individual infected with HBV, thereby obviating the need for long term and/or life-long treatment, or shortening the duration of treatment, and/or allowing for reduction in dosing of other antiviral agents.

Accordingly, in one embodiment, provided herein is a method of treating an HBV infection in an individual in need thereof, comprising administering to the individual a therapeutically effective amount of a compound of formula I, or a pharmaceutically acceptable salt thereof.

In another embodiment, provided herein is a method of treating an HBV infection in an individual in need thereof, comprising administering to the individual a therapeutically effective amount of compound of formula II, or a pharmaceutically acceptable salt thereof.

In another embodiment, provided herein is a method of treating an HBV infection in an individual in need thereof, comprising administering to the individual a therapeutically effective amount of compound of formula IIa, or a pharmaceutically acceptable salt thereof. In another embodiment, provided herein is a method of treating an HBV infection in an individual in need thereof, comprising administering to the individual a therapeutically effective amount of compound of formula IIb, or a pharmaceutically acceptable salt thereof.

In another embodiment, provided herein is a method of treating an HBV infection in an individual in need thereof, comprising administering to the individual a therapeutically effective amount of compound of formula IIc, or a pharmaceutically acceptable salt thereof.

In another embodiment, provided herein is a method of treating an HBV infection in an individual in need thereof, comprising administering to the individual a therapeutically effective amount of compound of formula III, or a pharmaceutically acceptable salt thereof.

In another embodiment, provided herein is a method of treating an HBV infection in an individual in need thereof, comprising administering to the individual a therapeutically effective amount of compound of formula IV, or a pharmaceutically acceptable salt thereof.

In another embodiment, provided herein is a method of treating an HBV infection in an individual in need thereof, comprising administering to the individual a therapeutically effective amount of compound of formula IVa, or a pharmaceutically acceptable salt thereof.

In another embodiment, provided herein is a method of treating an HBV infection in an individual in need thereof, comprising administering to the individual a therapeutically effective amount of compound of formula IVb, or a pharmaceutically acceptable salt thereof.

In another embodiment, provided herein is a method of treating an HBV infection in an individual in need thereof, comprising administering to the individual a therapeutically effective amount of compound of formula IVc, or a pharmaceutically acceptable salt thereof.

In another embodiment, provided herein is a method of treating an HBV infection in an individual in need thereof, comprising administering to the individual a therapeutically effective amount of compound of formula V, or a pharmaceutically acceptable salt thereof.

In another embodiment, provided herein is a method of treating an HBV infection in an individual in need thereof, comprising administering to the individual a therapeutically effective amount of compound of formula VI, or a pharmaceutically acceptable salt thereof.

In another embodiment, provided herein is a method of treating an HBV infection in an individual in need thereof, comprising administering to the individual a therapeutically effective amount of compound of formula VIa, or a pharmaceutically acceptable salt thereof.

In another embodiment, provided herein is a method of treating an HBV infection in an individual in need thereof, comprising administering to the individual a therapeutically effective amount of compound of formula VIb, or a pharmaceutically acceptable salt thereof.

In another embodiment, provided herein is a method of treating an HBV infection in an individual in need thereof, comprising administering to the individual a therapeutically effective amount of compound of formula VII, or a pharmaceutically acceptable salt thereof.

Accordingly, in one embodiment, provided herein is a method of treating an HBV infection in an individual in need thereof, comprising administering to the individual a therapeutically effective amount of compound 318.

In another embodiment, provided herein is a method of treating an HBV infection in an individual in need thereof, comprising administering to the individual a therapeutically effective amount of compound 890.

In another embodiment, provided herein is a method of treating an HBV infection in an individual in need thereof, comprising administering to the individual a therapeutically effective amount of compound 826.

In another embodiment, provided herein is a method of treating an HBV infection in an individual in need thereof, comprising administering to the individual a therapeutically effective amount of compound 891.

In another embodiment, provided herein is a method of treating an HBV infection in an individual in need thereof, comprising administering to the individual a therapeutically effective amount of compound 903.

In another embodiment, provided herein is a method of treating an HBV infection in an individual in need thereof, comprising administering to the individual a therapeutically effective amount of compound 917.

In another embodiment, provided herein is a method of treating an HBV infection in an individual in need thereof, comprising administering to the individual a therapeutically effective amount of compound 924.

In another embodiment, provided herein is a method of treating an HBV infection in an individual in need thereof, comprising administering to the individual a therapeutically effective amount of compound 922

In another embodiment, provided herein is a method of treating an HBV infection in an individual in need thereof, comprising administering to the individual a therapeutically effective amount of compound 955D1.

In another embodiment, provided herein is a method of treating an HBV infection in an individual in need thereof, comprising administering to the individual a therapeutically effective amount of compound 955D2

In another embodiment, provided herein is a method of treating an HBV infection in an individual in need thereof, comprising administering to the individual a therapeutically effective amount of compound 129.

In another embodiment, provided herein is a method of treating an HBV infection in an individual in need thereof, comprising administering to the individual a therapeutically effective amount of compound 132.

In another embodiment, provided herein is a method of treating an HBV infection in an individual in need thereof, comprising administering to the individual a therapeutically effective amount of compound 142.

In another embodiment, provided herein is a method of treating an HBV infection in an individual in need thereof, comprising administering to the individual a therapeutically effective amount of compound 278.

In another embodiment, provided herein is a method of treating an HBV infection in an individual in need thereof, comprising administering to the individual a therapeutically effective amount of compound 305.

In another embodiment, provided herein is a method of treating an HBV infection in an individual in need thereof, comprising administering to the individual a therapeutically effective amount of compound 318.

In another embodiment, provided herein is a method of treating an HBV infection in an individual in need thereof, comprising administering to the individual a therapeutically effective amount of compound 404.

In another embodiment, provided herein is a method of treating an HBV infection in an individual in need thereof, comprising administering to the individual a therapeutically effective amount of compound 507.

In another embodiment, provided herein is a method of treating an HBV infection in an individual in need thereof, comprising administering to the individual a therapeutically effective amount of compound 531.

In another embodiment, provided herein is a method of treating an HBV infection in an individual in need thereof, comprising administering to the individual a therapeutically effective amount of compound 597D1.

In another embodiment, provided herein is a method of treating an HBV infection in an individual in need thereof, comprising administering to the individual a therapeutically effective amount of compound 634.

In another embodiment, provided herein is a method of treating an HBV infection in an individual in need thereof, comprising administering to the individual a therapeutically effective amount of compound 694.

In another embodiment, provided herein is a method of treating an HBV infection in an individual in need thereof, comprising administering to the individual a therapeutically effective amount of compound 754.

In another embodiment, provided herein is a method of treating an HBV infection in an individual in need thereof, comprising administering to the individual a therapeutically effective amount of compound 758.

In another embodiment, provided herein is a method of treating an HBV infection in an individual in need thereof, comprising administering to the individual a therapeutically effective amount of compound 768.

In another embodiment, provided herein is a method of treating an HBV infection in an individual in need thereof, comprising administering to the individual a therapeutically effective amount of compound 803.

In another embodiment, provided herein is a method of treating an HBV infection in an individual in need thereof, comprising administering to the individual a therapeutically effective amount of compound 820.

In another embodiment, provided herein is a method of treating an HBV infection in an individual in need thereof, comprising administering to the individual a therapeutically effective amount of compound 919.

In another embodiment, provided herein is a method of treating an HBV infection in an individual in need thereof, comprising administering to the individual a therapeutically effective amount of compound 824_D1.

In another embodiment, provided herein is a method of treating an HBV infection in an individual in need thereof, comprising administering to the individual a therapeutically effective amount of compound 824_D2.

In another embodiment, provided herein is a method of treating an HBV infection in an individual in need thereof, comprising administering to the individual a therapeutically effective amount of compound 825_D1.

In another embodiment, provided herein is a method of treating an HBV infection in an individual in need thereof, comprising administering to the individual a therapeutically effective amount of compound 825_D2.

In another embodiment, provided herein is a method of treating an HBV infection in an individual in need thereof, comprising administering to the individual a therapeutically effective amount of compound 826.

In another embodiment, provided herein is a method of treating an HBV infection in an individual in need thereof, comprising administering to the individual a therapeutically effective amount of compound 843.

In another embodiment, provided herein is a method of treating an HBV infection in an individual in need thereof, comprising administering to the individual a therapeutically effective amount of compound 851.

In another embodiment, provided herein is a method of treating an HBV infection in an individual in need thereof, comprising administering to the individual a therapeutically effective amount of compound 1157.

In another embodiment, provided herein is a method of treating an HBV infection in an individual in need thereof, comprising administering to the individual a therapeutically effective amount of compound 867_D1.

In another embodiment, provided herein is a method of treating an HBV infection in an individual in need thereof, comprising administering to the individual a therapeutically effective amount of compound 867_D2.

In another embodiment, provided herein is a method of treating an HBV infection in an individual in need thereof, comprising administering to the individual a therapeutically effective amount of compound 875.

In another embodiment, provided herein is a method of treating an HBV infection in an individual in need thereof, comprising administering to the individual a therapeutically effective amount of compound 1161.

In another embodiment, provided herein is a method of treating an HBV infection in an individual in need thereof, comprising administering to the individual a therapeutically effective amount of compound 901.

In another embodiment, provided herein is a method of treating an HBV infection in an individual in need thereof, comprising administering to the individual a therapeutically effective amount of compound 903.

In another embodiment, provided herein is a method of treating an HBV infection in an individual in need thereof, comprising administering to the individual a therapeutically effective amount of compound 916.

In another embodiment, provided herein is a method of treating an HBV infection in an individual in need thereof, comprising administering to the individual a therapeutically effective amount of compound 960D1.

In another embodiment, provided herein is a method of treating an HBV infection in an individual in need thereof, comprising administering to the individual a therapeutically effective amount of compound 960D2.

In another embodiment, provided herein is a method of treating an HBV infection in an individual in need thereof, comprising administering to the individual a therapeutically effective amount of compound 953.

In another embodiment, provided herein is a method of treating an HBV infection in an individual in need thereof, comprising administering to the individual a therapeutically effective amount of compound 922.

In another embodiment, provided herein is a method of treating an HBV infection in an individual in need thereof, comprising administering to the individual a therapeutically effective amount of compound 924.

In another embodiment, provided herein is a method of treating an HBV infection in an individual in need thereof, comprising administering to the individual a therapeutically effective amount of compound 927.

In another embodiment, provided herein is a method of treating an HBV infection in an individual in need thereof, comprising administering to the individual a therapeutically effective amount of compound 931.

In another embodiment, provided herein is a method of treating an HBV infection in an individual in need thereof, comprising administering to the individual a therapeutically effective amount of compound 935.

In another embodiment, provided herein is a method of treating an HBV infection in an individual in need thereof, comprising administering to the individual a therapeutically effective amount of compound 942.

In another embodiment, provided herein is a method of treating an HBV infection in an individual in need thereof, comprising administering to the individual a therapeutically effective amount of compound 946D1.

In another embodiment, provided herein is a method of treating an HBV infection in an individual in need thereof, comprising administering to the individual a therapeutically effective amount of compound 946D2.

In another embodiment, provided herein is a method of treating an HBV infection in an individual in need thereof, comprising administering to the individual a therapeutically effective amount of compound 955D1.

In another embodiment, provided herein is a method of treating an HBV infection in an individual in need thereof, comprising administering to the individual a therapeutically effective amount of compound 955D2.

In another embodiment, provided herein is a method of treating an HBV infection in an individual in need thereof, comprising administering to the individual a therapeutically effective amount of compound 952.

In another embodiment, provided herein is a method of treating an HBV infection in an individual in need thereof, comprising administering to the individual a therapeutically effective amount of compound 958.

In another embodiment, provided herein is a method of treating an HBV infection in an individual in need thereof, comprising administering to the individual a therapeutically effective amount of compound 964D1.

In another embodiment, provided herein is a method of treating an HBV infection in an individual in need thereof, comprising administering to the individual a therapeutically effective amount of compound 964D2.

In another embodiment, provided herein is a method of treating an HBV infection in an individual in need thereof, comprising administering to the individual a therapeutically effective amount of compound 976D1.

In another embodiment, provided herein is a method of treating an HBV infection in an individual in need thereof, comprising administering to the individual a therapeutically effective amount of compound 988.

In another embodiment, provided herein is a method of treating an HBV infection in an individual in need thereof, comprising administering to the individual a therapeutically effective amount of compound 1008.

In another embodiment, provided herein is a method of treating an HBV infection in an individual in need thereof, comprising administering to the individual a therapeutically effective amount of compound 1021.

In another embodiment, provided herein is a method of treating an HBV infection in an individual in need thereof, comprising administering to the individual a therapeutically effective amount of compound 1022.

In another embodiment, provided herein is a method of treating an HBV infection in an individual in need thereof, comprising administering to the individual a therapeutically effective amount of compound 1035.

In another embodiment, provided herein is a method of treating an HBV infection in an individual in need thereof, comprising administering to the individual a therapeutically effective amount of compound 1078D1.

In another embodiment, provided herein is a method of treating an HBV infection in an individual in need thereof, comprising administering to the individual a therapeutically effective amount of compound 1086.

In another embodiment, provided herein is a method of treating an HBV infection in an individual in need thereof, comprising administering to the individual a therapeutically effective amount of compound 1091.

In another embodiment, provided herein is a method of treating an HBV infection in an individual in need thereof, comprising administering to the individual a therapeutically effective amount of compound 1105.

In another embodiment, provided herein is a method of treating an HBV infection in an individual in need thereof, comprising administering to the individual a therapeutically effective amount of compound 1114.

In another embodiment, provided herein is a method of treating an HBV infection in an individual in need thereof, comprising administering to the individual a therapeutically effective amount of compound 1126.

In another embodiment, provided herein is a method of treating an HBV infection in an individual in need thereof, comprising administering to the individual a therapeutically effective amount of compound 1134CT1.

In another embodiment, provided herein is a method of treating an HBV infection in an individual in need thereof, comprising administering to the individual a therapeutically effective amount of compound 1134CT2.

In another embodiment, provided herein is a method of treating an HBV infection in an individual in need thereof, comprising administering to the individual a therapeutically effective amount of compound 1149.

In another embodiment, provided herein is a method of treating an HBV infection in an individual in need thereof, comprising administering to the individual a therapeutically effective amount of compound 1281D1.

In another embodiment, provided herein is a method of treating an HBV infection in an individual in need thereof, comprising administering to the individual a therapeutically effective amount of compound 1281D2.

In another embodiment, provided herein is a method of treating an HBV infection in an individual in need thereof, comprising administering to the individual a therapeutically effective amount of compound 1116.

In another embodiment, provided herein is a method of treating an HBV infection in an individual in need thereof, comprising administering to the individual a therapeutically effective amount of compound 1130.

In another embodiment, provided herein is a method of treating an HBV infection in an individual in need thereof, comprising administering to the individual a therapeutically effective amount of compound 1135D1.

Combination Therapies

The compounds of the present invention are intended to be useful in combination with one or more additional compounds useful for treating HBV infection. These additional compounds may comprise compounds of the present invention or compounds known to treat, prevent, or reduce the symptoms or effects of HBV infection. Such compounds include but are not limited to HBV polymerase inhibitors, interferons, viral entry inhibitors, viral maturation inhibitors, literature-described capsid assembly modulators, and other agents with distinct or unknown mechanisms that affect the HBV life cycle and/or affect the consequences of HBV infection.

In non-limiting examples, the compounds of the invention may be used in combination with one or more drugs (or a salt, solvate or prodrug thereof) selected from the group consisting of HBV reverse transcriptase inhibitors, and DNA and RNA polymerase inhibitors, including but are not limited to: lamivudine (3TC, Zeffix, Heptovir, Epivir, and Epivir-HBV), entecavir (Baraclude, Entavir), adefovir dipivoxil (Hepsara, Preveon, bis-POM PMEA), tenofovir disoproxil fumarate (Viread, TDF or PMPA);

interferons, including but not limited to interferon alpha (IFN-α), interferon lambda (IFN-λ), and interferon gamma (IFN-γ);

viral entry inhibitors;

viral maturation inhibitors;

literature-described capsid assembly modulators, such as but not limited to BAY 41-4109;

compounds of distinct or unknown mechanism, such as but not limited to AT-61 ((E)-N-(1-chloro-3-oxo-1-phenyl-3-(piperidin-1-yl)prop-1-en-2-yl)benzamide), AT-130 ((E)-N-(1-bromo-1-(2-methoxyphenyl)-3-oxo-3-(piperidin-1-yl)prop-1-en-2-yl)-4-nitrobenzamide), and similar analogs.

In another embodiment, the additional therapeutic agent selected from immune modulator or immune stimulator therapies, which includes biological agents belonging to the interferon class, such as interferon alpha 2a or 2b or modified interferons such as pegylated interferon, alpha 2a, alpha 2b, lamda; or TLR modulators such as TLR-7 agonists or TLR-9 agonists, or antiviral agents that block viral entry or maturation or target the HBV polymerase such as nucleoside or nucleotide or non-nucleos(t)ide polymerase inhibitors, and agents of distinct or unknown mechanism including agents that disrupt the function of other essential viral protein(s) or host proteins required for HBV replication or persistence.

In an embodiment of the combination therapy, the reverse transcriptase inhibitor and/or DNA and/or RNA polymerase inhibitor Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, PMPA, cidofovir, Efavirenz, Nevirapine, Delavirdine, or Etravirine.

In another embodiment of the combination therapy, the TLR-7 agonist is selected from the group consisting of SM360320 (9-benzyl-8-hydroxy-2-(2-methoxyethoxy)adenine) and AZD 8848 (methyl[3-({[3-(6-amino-2-butoxy-8-oxo-7,8-dihydro-9H-purin-9-yl)propyl][3-(4-morpholinyl)propyl]amino}methyl)phenyl]acetate).

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the patient either prior to or after the onset of a HBV infection. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat HBV infection in the patient. An effective amount of the therapeutic compound necessary to achieve a therapeutic effect may vary according to factors such as the state of the disease or disorder in the patient; the age, sex, and weight of the patient; and the ability of the therapeutic compound to treat HBV infection in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of HBV infection in a patient.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin. In one embodiment, the pharmaceutically acceptable carrier is not DMSO alone.

In one embodiment, the compositions of the invention are administered to the patient in dosages that range from one to five times per day or more. In another embodiment, the compositions of the invention are administered to the patient in a range of dosages that include, but are not limited to, once every day, every two, days, every three days to once a week, and once every two weeks. It will be readily apparent to one skilled in the art that the frequency of administration of the various combination compositions of the invention will vary from individual to individual depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physical taking all other factors about the patient into account.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating Parkinson's Disease) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of HBV infection in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds of the invention, and a further layer providing for the immediate release of a medication for treatment of Parkinson's Disease. Using a wax/pH-sensitive polymer mix, a gastric insoluble composition may be obtained in which the active ingredient is entrapped, ensuring its delayed release.

Parenteral Administration

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In one embodiment, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention will depend on the age, sex and weight of the patient, the current medical condition of the patient and the progression of HBV infection in the patient being treated. The skilled artisan will be able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the viral load, to a level at which the improved disease is retained. In one embodiment, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. Capsid assembly inhibitors exhibiting high therapeutic indices are preferred. The data obtained from cell culture assays and animal studies is optionally used in formulating a range of dosage for use in human. The dosage of such capsid assembly inhibitors lies preferably within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials:

Unless otherwise noted, all starting materials and resins were obtained from commercial suppliers and used without purification.

Library General Design

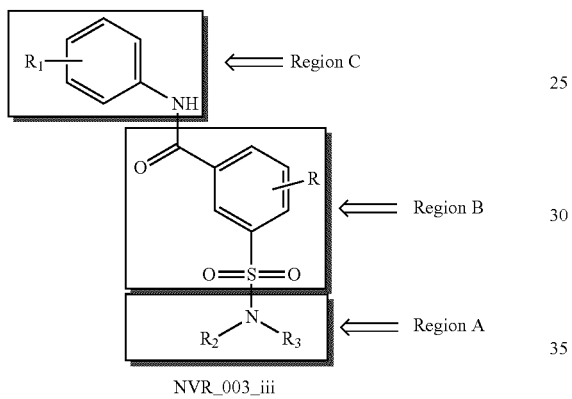

NVR_003_iii

Region A (Amines and Amino Alcohols):

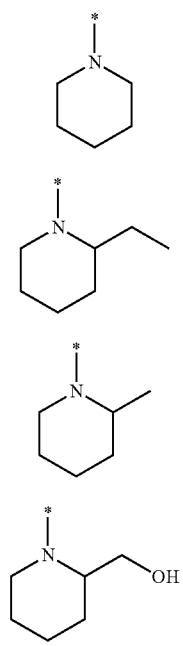

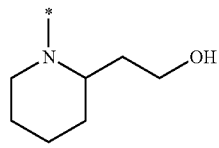
A05

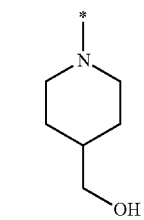
A06

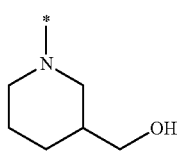
A07

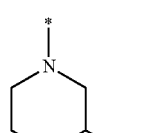
A08

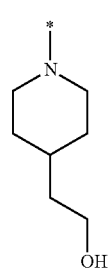
A09

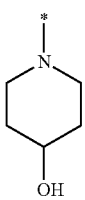
A10

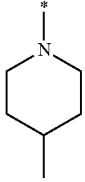
A11

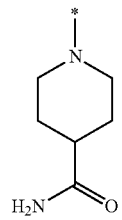
A12

-continued
| | |
|---|---|
| 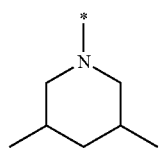 | A13 |
| 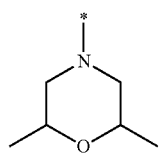 | A14 |
| 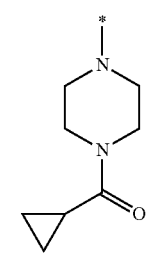 | A15 |
| 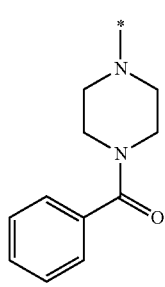 | A16 |
| 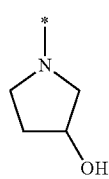 | A17 |
| 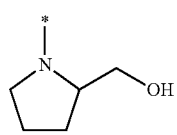 | A18 |
| 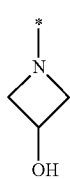 | A19 |
| 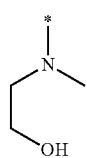 | A20 |
-continued
| | |
|---|---|
| 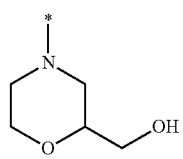 | A21 |
| 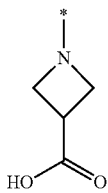 | A22 |
| 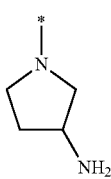 | A23 |
| 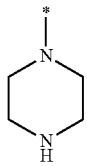 | A24 |
| 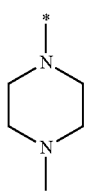 | A25 |
| 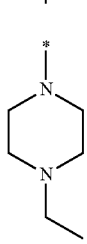 | A26 |
| 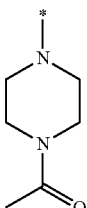 | A27 |
| 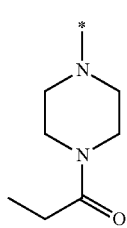 | A28 |

441
-continued
A29
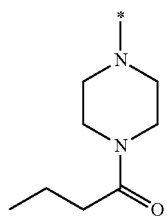
A30
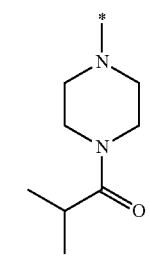
A31
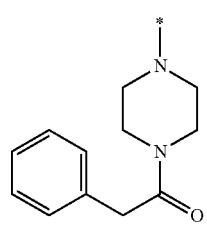
A32
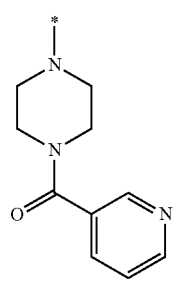
A33
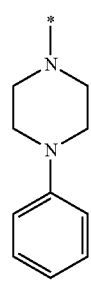
A34
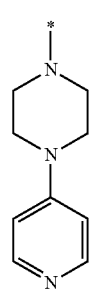
442
-continued
A35
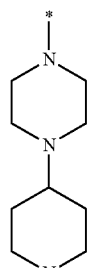
A36
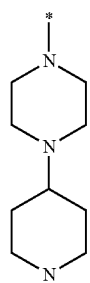
A37
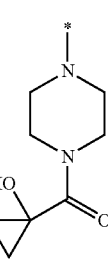
A38
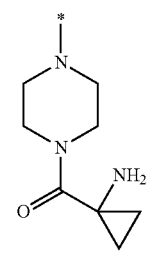
A39
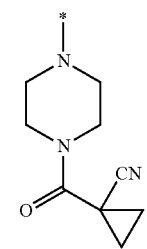
A40
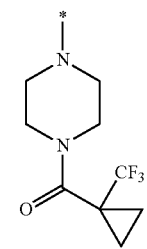

| | |
|---|---|
| A41 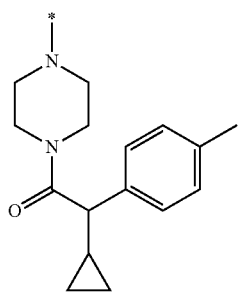 | A47 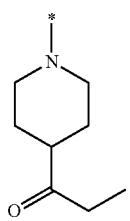 |
| A42 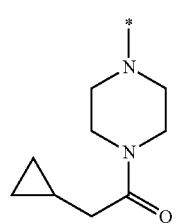 | A48 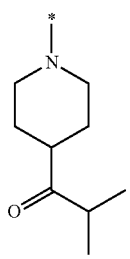 |
| A43 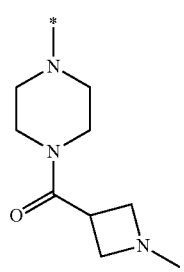 | A49 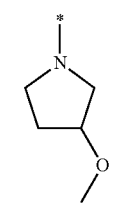 |
| A44 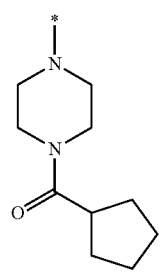 | A50 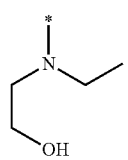 |
| A45 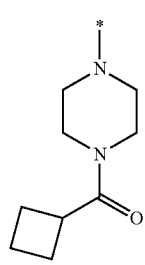 | A51 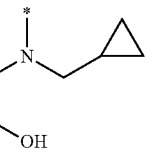 |
| A46 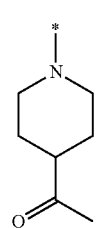 | A52 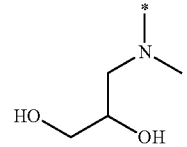 |
| | A53 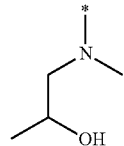 |
| | A54 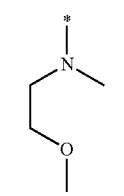 |

| | |
|---|---|
| A55 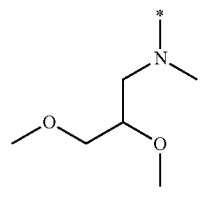 | A62 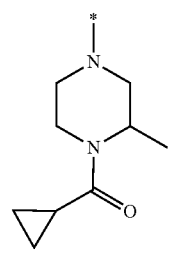 |
| A56 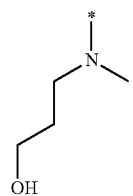 | A63 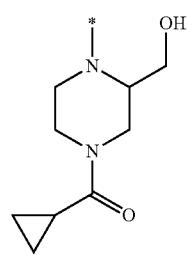 |
| A57 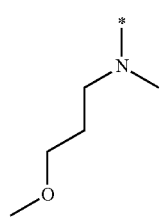 | A64 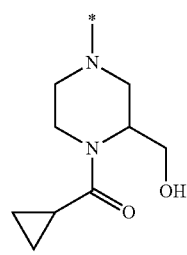 |
| A58 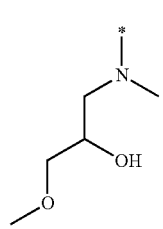 | A65 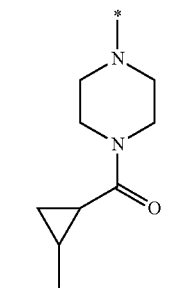 |
| A59 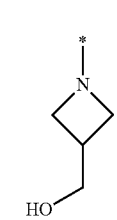 | A66 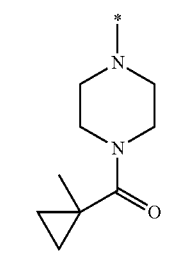 |
| A60 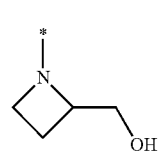 | A67 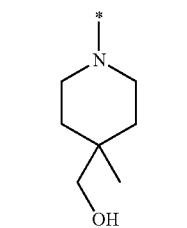 |
| A61 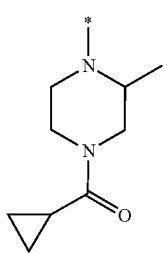 | |

A68 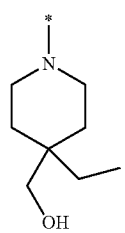
A69 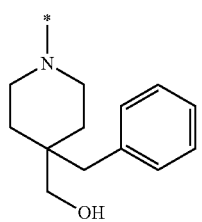
A70 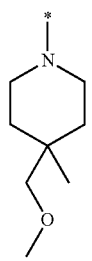
A71 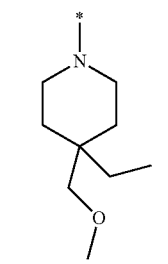
A72 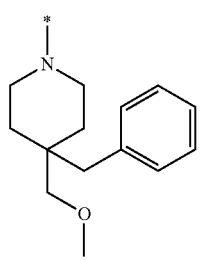
A73 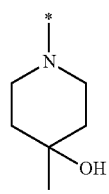
A74 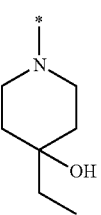
A75 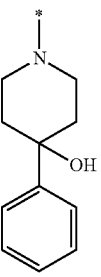
A76 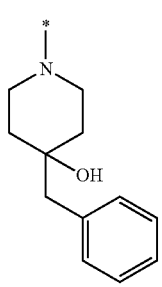
A77 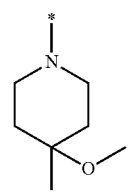
A78 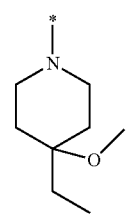
A79 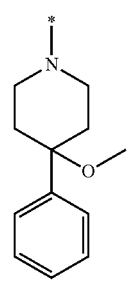

| 449 -continued | | 450 -continued | |
|---|---|---|---|
| 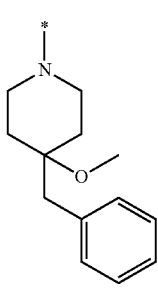 | A80 | 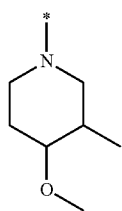 | A87 |
| 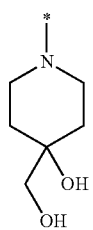 | A81 | 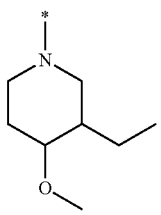 | A88 |
| 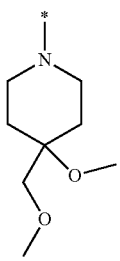 | A82 | 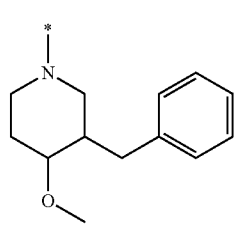 | A89 |
| 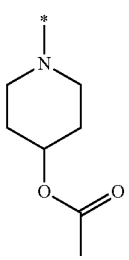 | A83 | 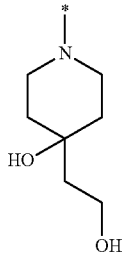 | A90 |
| 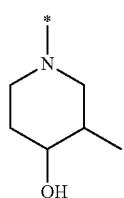 | A84 | 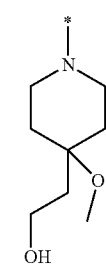 | A91 |
| 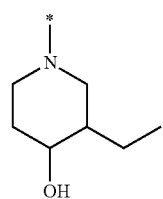 | A85 | 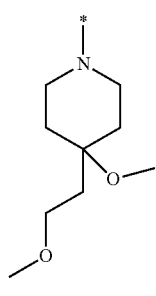 | A92 |
| 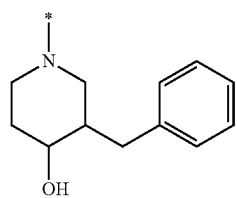 | A86 | | |

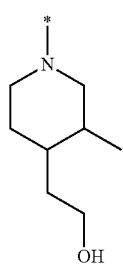 A93
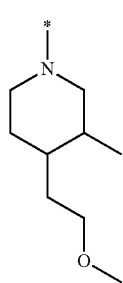 A94
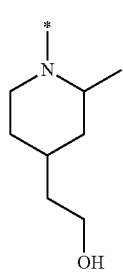 A95
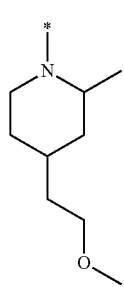 A96
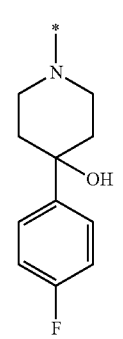 A97
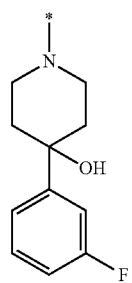 A98
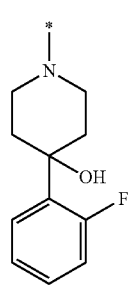 A99
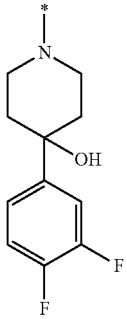 A100
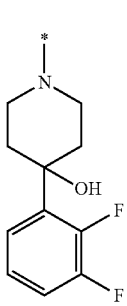 A101
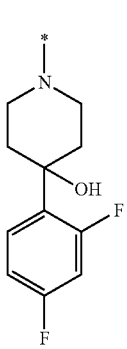 A102

453
-continued
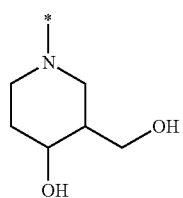 A103
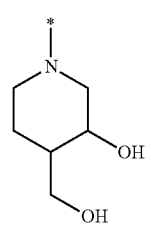 A104
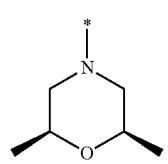 A105
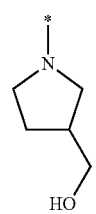 A106
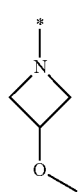 A108
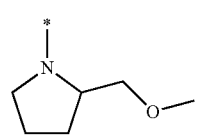 A108
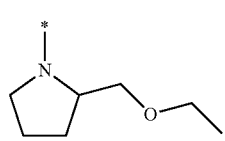 A109
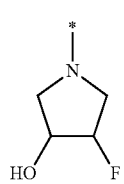 A110
454
-continued
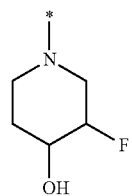 A111
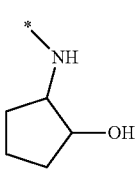 A112
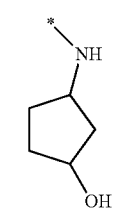 A113
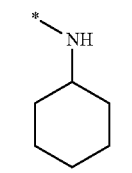 A114
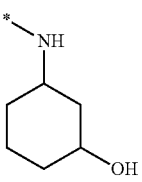 A115
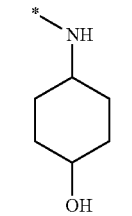 A116
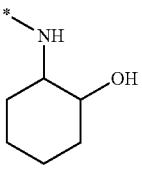 A117
A118

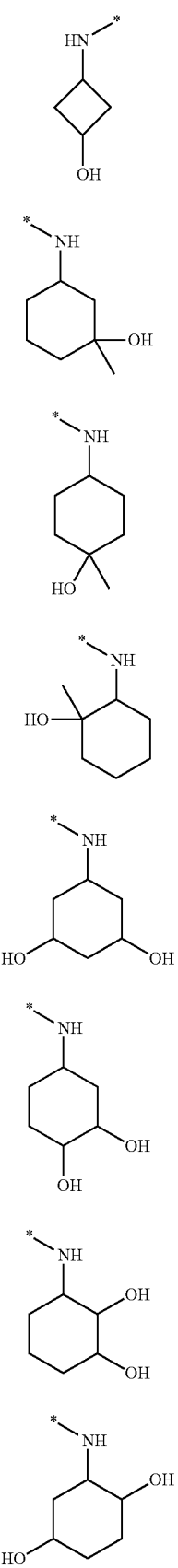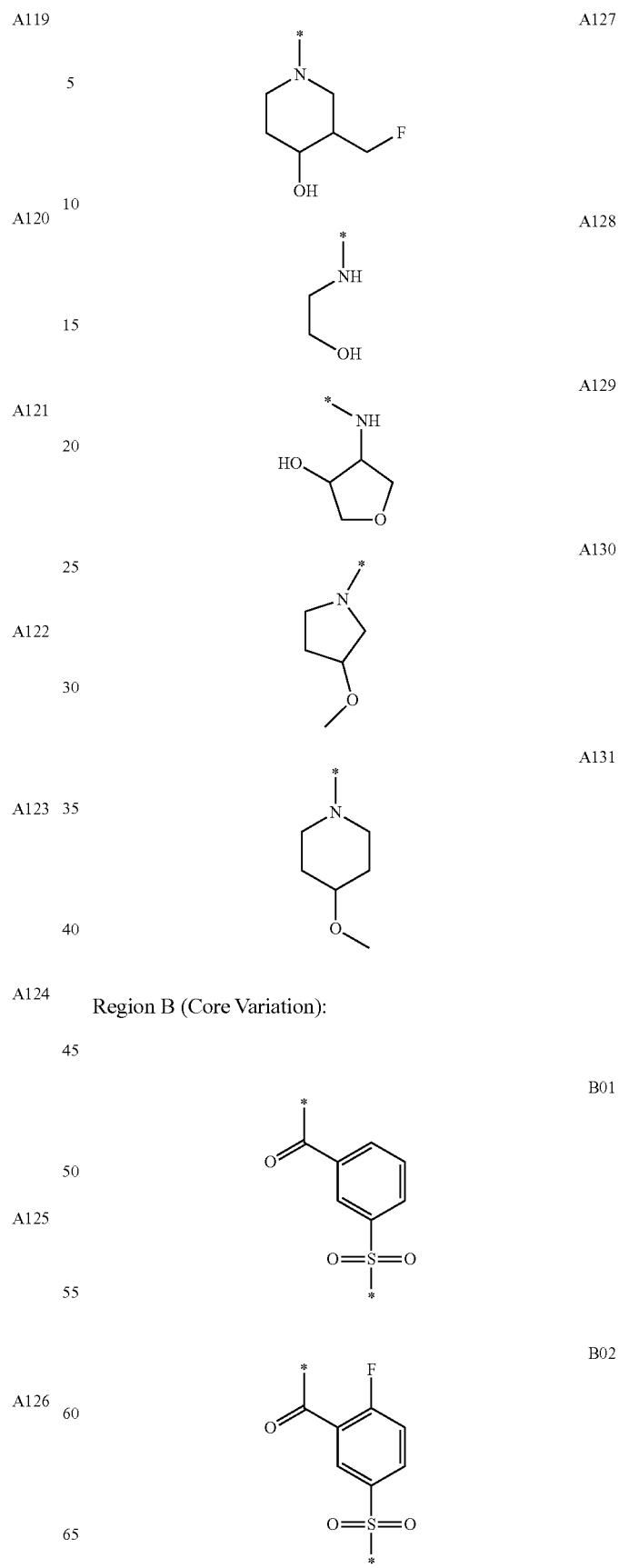

B03 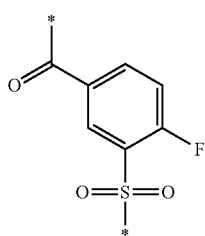
B04 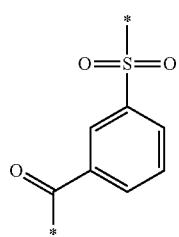
B05 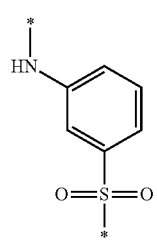
B06 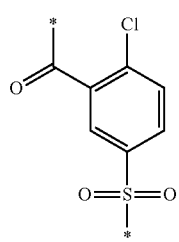
B07 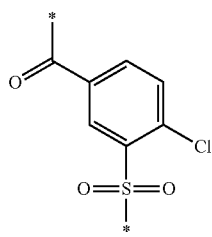
B08 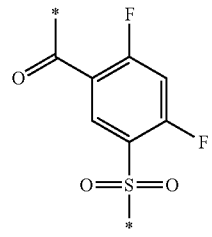
B09 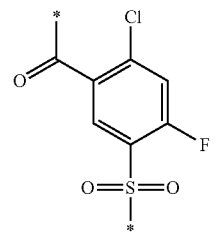
B10 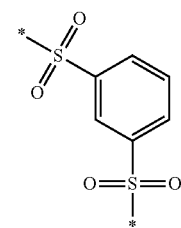
B11 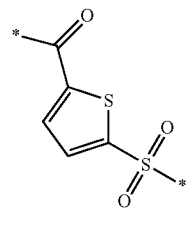
B12 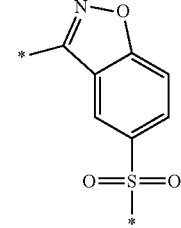
B13 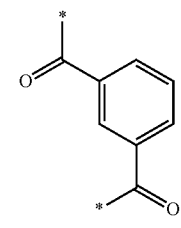
B14 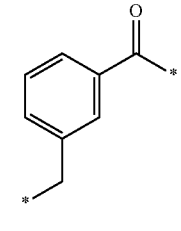
B15 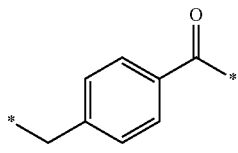

Region C (Anilines, Amines and Aryl Carboxylic Acids):
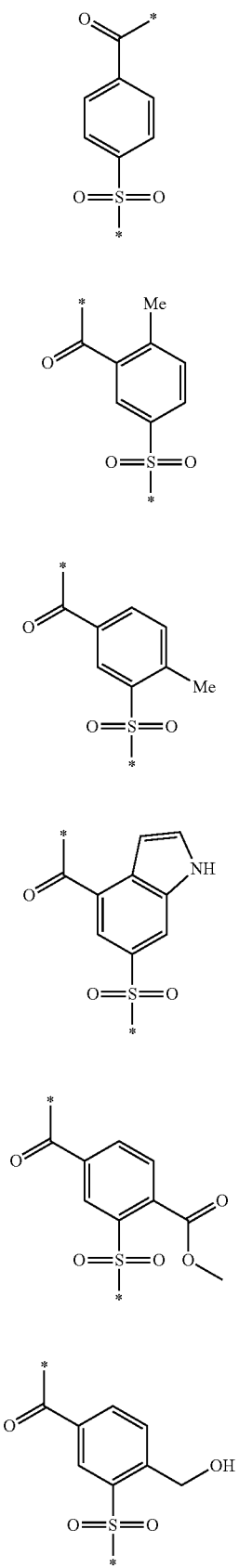

-continued
| | | |
|---|---|---|
| 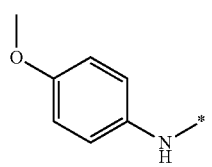 | C12 | |
| 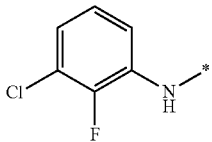 | C13 | |
| 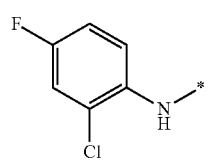 | C14 | |
| 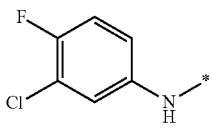 | C15 | |
| 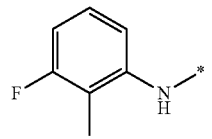 | C16 | |
| 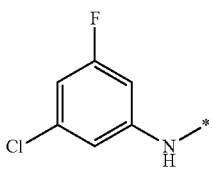 | C17 | |
| 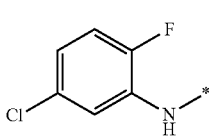 | C18 | |
| 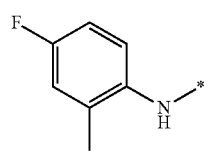 | C19 | |
| 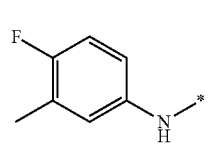 | C20 | |
| 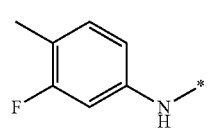 | C21 | |
-continued
| | | |
|---|---|---|
| 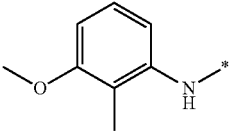 | C22 | |
| 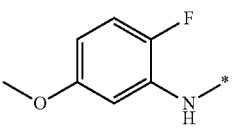 | C23 | |
| 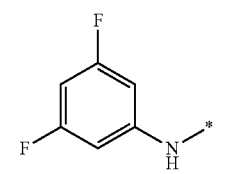 | C24 | |
| 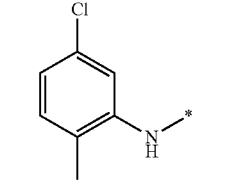 | C25 | |
| 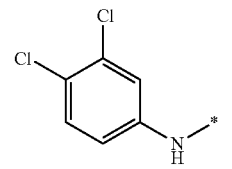 | C26 | |
| 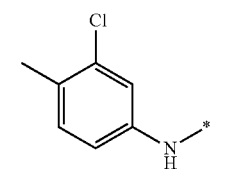 | C27 | |
| 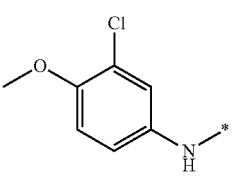 | C28 | |
| 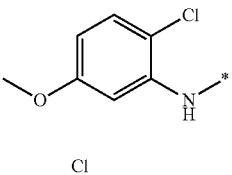 | C29 | |
| 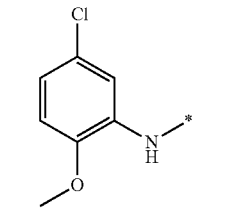 | C30 | |

-continued
| | | |
|---|---|---|
| 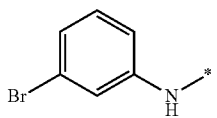 | C31 | |
| 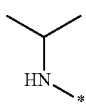 | C32 | |
| 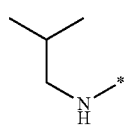 | C33 | |
| 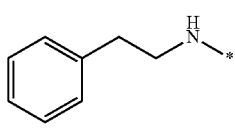 | C34 | |
| 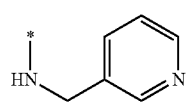 | C35 | |
| 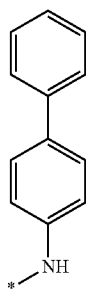 | C36 | |
| 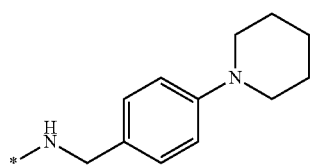 | C37 | |
| 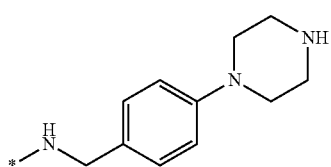 | C38 | |
| 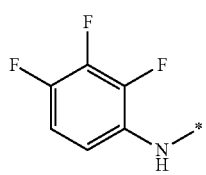 | C39 | |
| 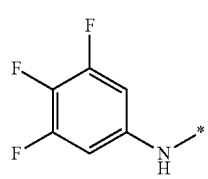 | C40 | |
-continued
| | | |
|---|---|---|
| 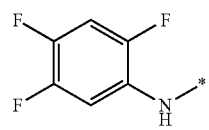 | C41 | |
| 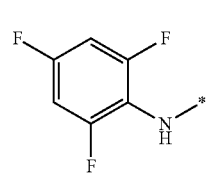 | C42 | |
| 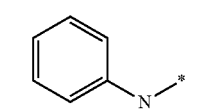 | C43 | |
| 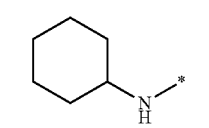 | C44 | |
| 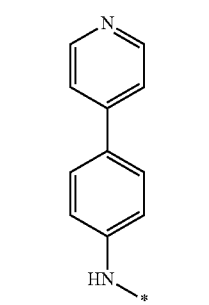 | C45 | |
| 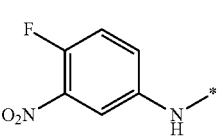 | C46 | |
| 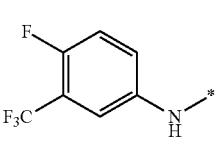 | C47 | |
| 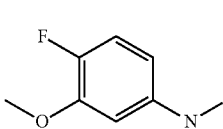 | C48 | |
| 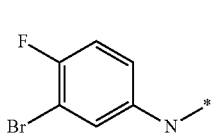 | C49 | |
| 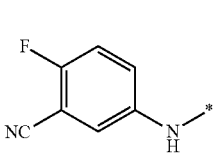 | C50 | |

-continued

| | | |
|---|---|---|
| C51 | | C61 |
| C52 | | C62 |
| C53 | | C63 |
| C54 | | C64 |
| C55 | | C65 |
| C56 | | C66 |
| C57 | | C67 |
| C58 | | C68 |
| C59 | | C69 |
| C60 | | C70 |

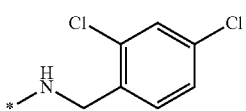 C71
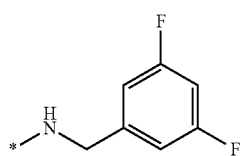 C72
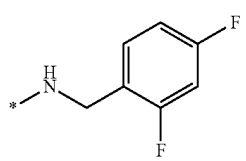 C73
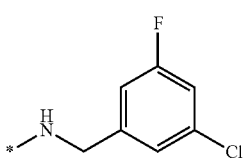 C74
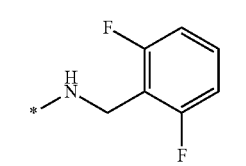 C75
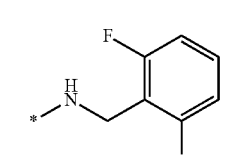 C76
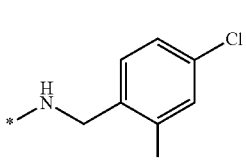 C77
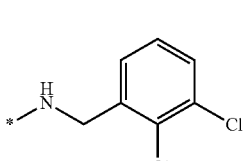 C78
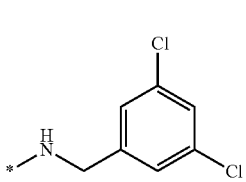 C79
 C80
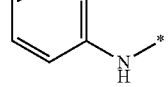 C81
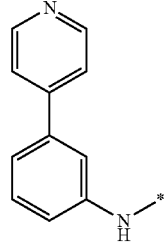 C82
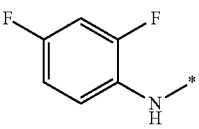 C83
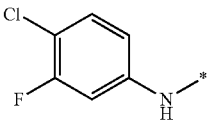 C84
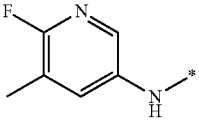 C85
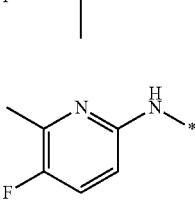 C86
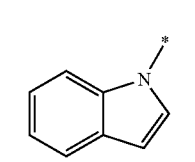 C87
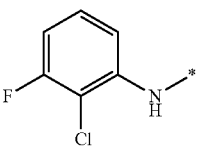 C88

C89

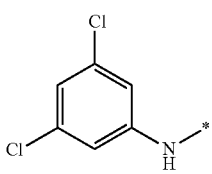

C90

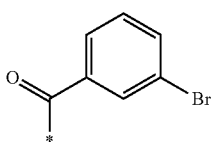

C91

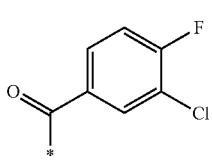

C92

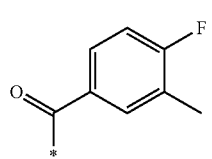

C93

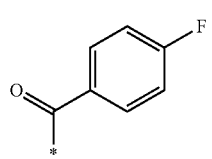

Part I Intermediate Synthesis

Regions A, B & C

1 Preparation of Region A Intermediates
1.1 Preparation of A46/47/48

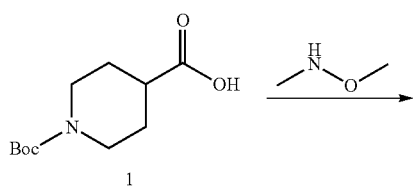

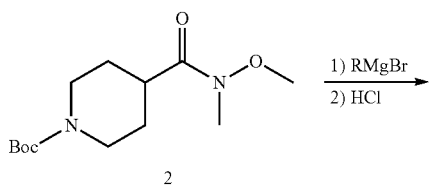

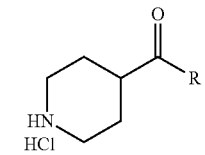

A46: R = Me
A47: R = c-Pr
A48: R = i-Pr 1.1.1 Synthetic Procedure for Preparation 2

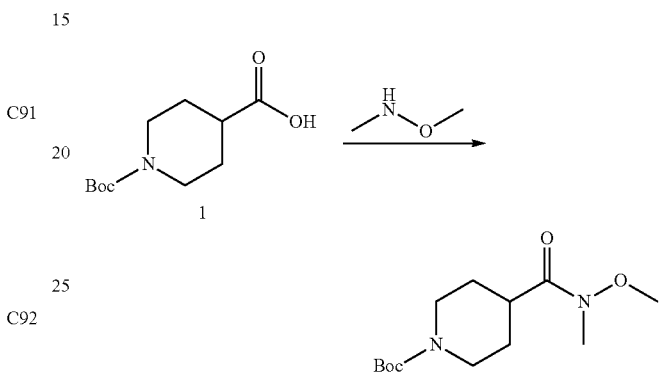

To a solution of Compound 1 (5 g, 21.8 mmol) and N,O_Dimethylhydroxylamine (1.6 g, 26.2 mmol) in DCM (50 mL) was added HATU (9.9 g, 26.2 mmol) and $Et_3N$ (2.65 g, 26.2 mmol) at rt. The formed mixture was stirred at rt overnight. The mixture was washed with water, and purified by column chromatography to give the desired product (3 g, 51%).

1.1.2 Preparation of Compound 3

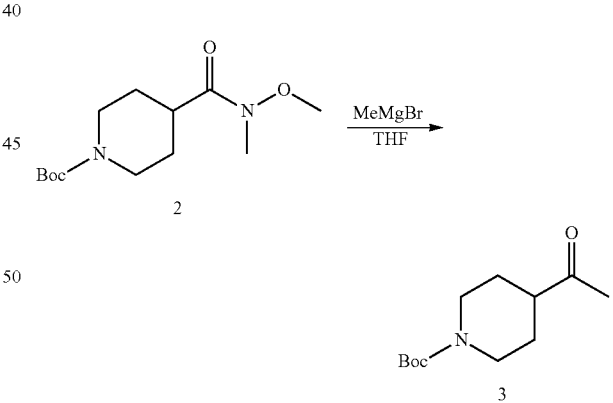

To a solution of Compound 2 (500 mg, 1.84 mmol) in anhydrous THF (5 mL) was added $CH_3MgBr$ (0.8 mL, 2.4 mmol) at 0° C. The formed mixture was allowed to warm to room temperature. The reaction was quenched with aqueous $NH_4Cl$ solution. The organic layer was separated and extracted with EtOAc (10 mL×2). The combined organic layers were concentrated to give the crude product, which was purified by column chromatography to give the desired product (300 mg, 72%). $^1H$ NMR (400 MHz, $CDCl_3$): δ ppm: 4.04 (br, 2H), 2.73 (t, 2H), 2.43 (m, 1H), 2.15 (s, 3H), 1.82 (m, 2H), 1.53 (m, 2H), 1.45 (s, 9H).

1.2.3 Preparation of A46

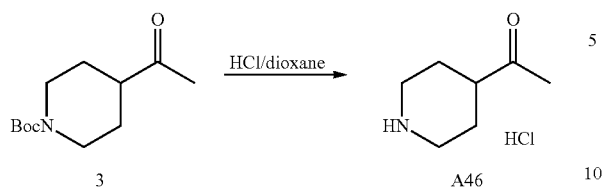

To a solution of Compound 3 (350 mg, 1.54 mmol) in anhydrous DCM (5 mL) was added HCl in dioxane (2 mL) at 0° C. The formed mixture was stirred for 2 h. The formed mixture was concentrated to give the desired product which was used for the next step (260 mg, 100%).

A47/48 were prepared following the similar procedure as A46.

1.2 Preparation of A73-80

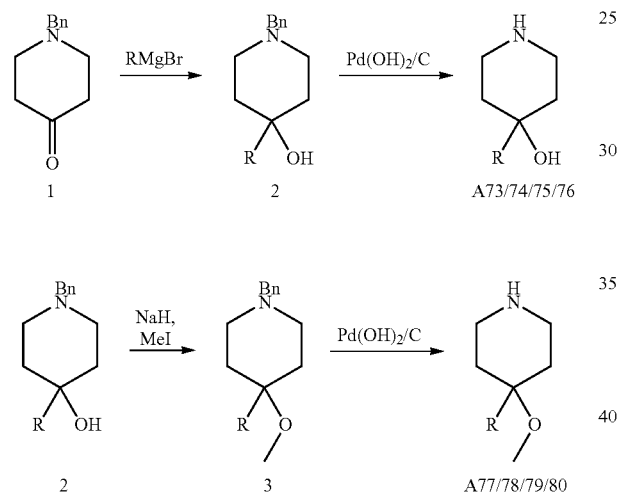

R = Me, Et, Ph, PhCH$_2$

2.1 Preparation of Compound 2

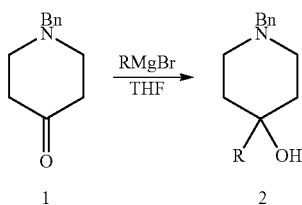

To RMgBr (0.5 M, 20 mmol) in THF was added a solution of Compound 1 (2.0 g, 10.56 mmol) in THF (20 mL) at 0-4° C. The formed mixture was stirred at rt for 3 h. The reaction was quenched by NH$_4$Cl solution, and the mixture was extracted with EtOAc (20 mL×3). The organic layer was concentrated to give the crude product, which was purified by column chromatography to give the desired product.

2.2 Preparation of Compound 3

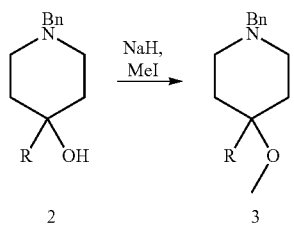

To a solution of Compound 2 (10 mmol) in DMF (40 mL) was added NaH (10 mmol) at 0° C., After stirring for 30 min, a solution of MeI (10 mmol) in DMF (5 mL) was added dropwise, and stirred at rt for 4 h. The mixture was poured into water and extracted with EA. The combined organic phase was washed with brine, dried over Na$_2$SO$_4$, and concentrated in vacuo. The residue was purified through column chromatography to give the desired product.

2.3 Preparation of A73-80

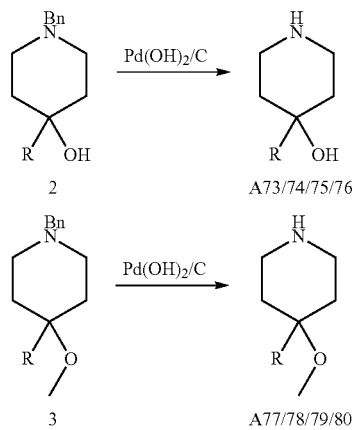

To a solution of Compound 2 or 3 in MeOH was added Pd(OH)$_2$/C (100 mg), and the formed mixture was stirred under H$_2$ at 50 psi overnight. The Pd was filtered and the filtrate was concentrated to give the desired product.

1.3 Preparation of A81/82

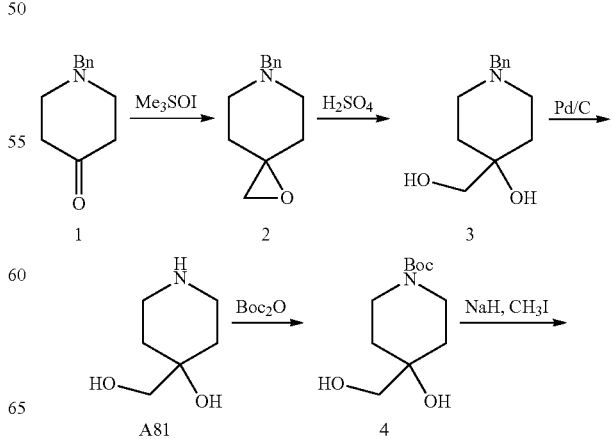

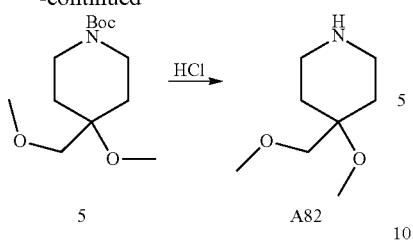

1.3.1 Preparation of Compound 2

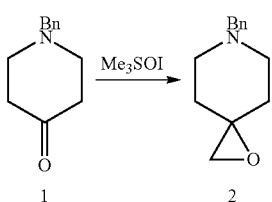 [SMILES: "Me3SOI" ; O=C1CCN(Cc2ccccc2)CC1 ; c1ccc(CN2CCC3(CC2)CO3)cc1]

To a solution of Compound 1 (1.9 g, 10 mmol) in DMSO (30 mL) was added Me₃SOI (3.3 g, 15 mmol), followed by NaH (0.6 g, 16 mmol) at 0° C. The formed mixture was stirred at rt overnight. The mixture was poured into water and extracted with EA. The combined organic phases were washed with brine, dried over Na₂SO₄, and concentrated in vacuo. The residue was purified through column chromatography to give the desired product. (0.46 g, 23%). ¹H NMR (400 MHz, CDCl₃): δ: 7.34 (m, 4H), 7.30 (m, 1H), 3.55 (s, 2H), 2.62 (s, 2H), 2.55 (m, 4H), 1.83 (m, 2H), 1.52 (m, 2H).

1.3.2 Preparation of Compound 3

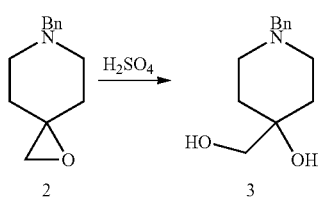

A mixture of Compound 2 (3.0 g, 14.76 mmol) in H₂SO₄ (60 mL, 0.2 M) was stirred at rt overnight. The mixture was neutralized with NaOH solution to pH8. The formed mixture was extracted with EtOAc. The combined organic layers were concentrated to give the desired product (1.5 g, 46%). ¹H NMR (400 MHz, CDCl₃): δ ppm: 7.32 (m, 4H), 7.27 (m, 1H), 3.52 (s, 2H), 3.44 (s, 2H), 2.64 (m, 2H), 2.36 (m, 2H), 2.03 (m, 2H), 1.59 (m, 4H).

1.3.3 Preparation of A81

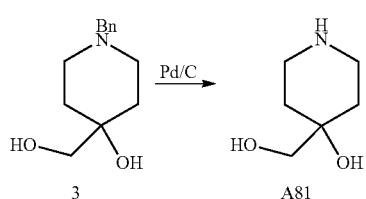

To a solution of Compound 3 (500 mg, 2 mmol) in CH₃OH (5 mL) was added Pd(OH)₂/C (50 mg). The formed mixture was hydrogenated overnight under H₂ atmosphere. The catalyst was filtered and the filtrate was concentrated to give the desired product (200 mg, 68%).

1.3.4 Preparation of Compound 4

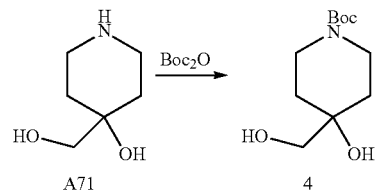

To a solution of A12 (100 mg, 0.762 mmol) and Et₃N (116 mg, 1.14 mmol) in MeOH (3 mL) was added Boc₂O (200 mg, 0.915 mmol) at rt. The formed mixture was stirred overnight. The mixture was concentrated and diluted with DCM (20 ml). The resulting mixture was washed with water. The organic layer was concentrated to give the crude product which was used for the next step (180 mg, 68%).

1.3.5 Preparation of Compound 5

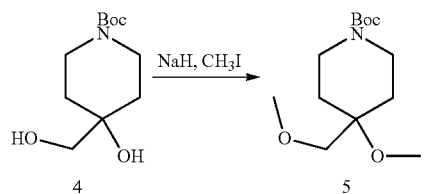

To a suspension of NaH (125 mg, 3.11 mmol) in THF (3 mL) was added a solution of compound 4 (240 mg, 1.04 mmol) at rt. The formed mixture was stirred for 10 minutes. Then CH₃I (736 mg, 5.19 mmol) was added to the above mixture. The mixture was stirred overnight. The reaction was quenched by water, and the formed mixture was concentrated to give the crude product, which was purified by column chromatography to give the desired product (200 mg, 74%). ¹H NMR (400 MHz, CDCl₃): δ ppm: 3.72 (m, 2H), 3.35 (s, 3H), 3.29 (s, 2H), 3.24 (s, 3H), 3.06 (m, 2H), 1.74 (m, 2H), 1.47 (m, 1H), 1.46 (s, 9H), 1.42 (m, 1H).

1.3.6 Preparation of A82

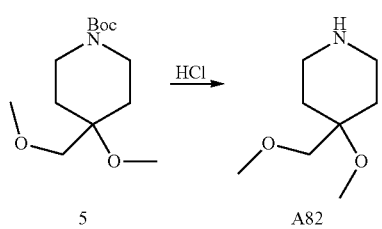

Compound 5 (200 mg, 0.77 mmol) was treated with 4 N HCl in methanol (10 mL), and stirred at rt for 20 min. The mixture was concentrated in vacuo to give a HCl salt (150 mg, 99%).

1.4 Preparation of A67-72

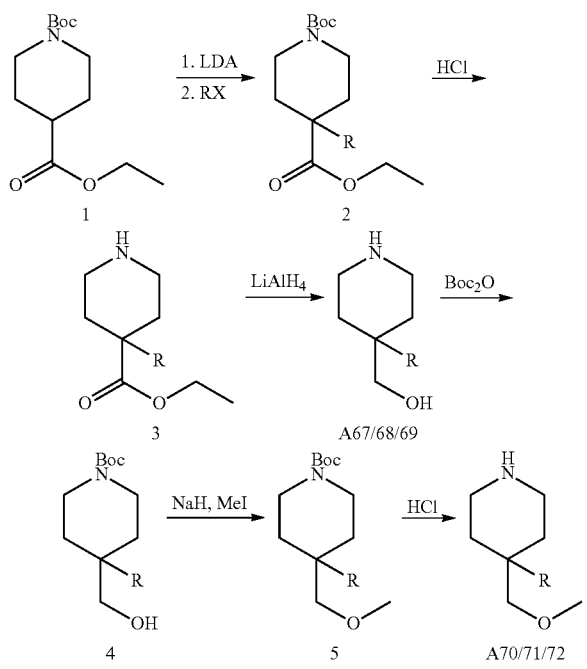

R = Me, Et, PhCH₂

1.4.1 Preparation of Compound 2

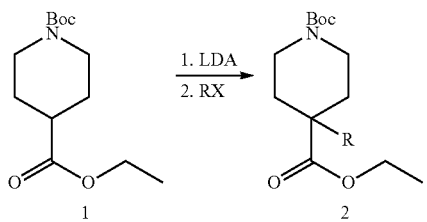

LDA (4 mmol) was added to a solution of dry THF (20 mL) slowly at −30° C. The solution was chilled to −75° C. and then Compound 1 (1.00 g, 3.89 mmol) in THF (10 mL) was added dropwise. After addition, the reaction mixture was stirred for 1 h at −30° C. RX (5 mmol) in THF (10 mL) was added dropwise. The resulted mixture was stirred at RT overnight. Aqueous NH₄Cl (30 mL) was added and the aqueous layer was extracted with ethyl acetate (20 mL 3). The organic layer was dried and concentrated to give the crude product, which was purified by column on silica gel to give the product.

1.4.2 Preparation of Compound 3

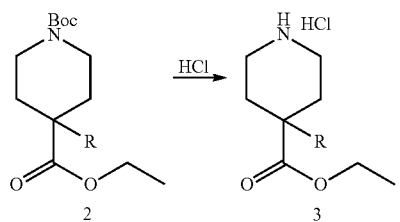

Compound 2 (4.87 mmol) was dissolved in HCl/dioxane (20 mL). The mixture was stirred at RT for 2 h. The solvent was removed to give the product.

1.4.3 Preparation of A67/68/69

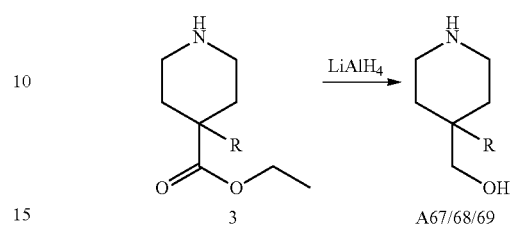

LiAlH₄ (367.80 mg, 9.93 mmol) was suspended in dry THF (30 mL) at 0. Compound 3 (4.96 mmol) in dry THF (10 mL) was added slowly. The reaction mixture was stirred at RT overnight. The reaction mixture was quenched with water (0.37 mL) and 10% NaOH (0.37 mL), then water (1.11 mL) was added. The mixture was stirred at RT for 30 min and filtered. The filtrate was concentrated to give the product.

1.4.4 Preparation of Compound 4

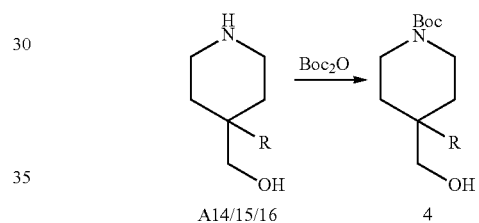

To a mixture of TEA (6 mmol) and Boc₂O (5 mmol) in DCM (40 mL) was added A14/15/16 (4.2 mmol), and stirred at rt overnight. The mixture was washed with 1N HCl, NaHCO3 and brine, dried over Na₂SO₄, and concentrated in vacuo. The residue was purified through column chromatography to give the desired product.

1.4.5 Preparation of Compound 5

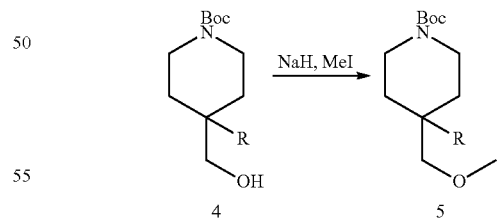

NaH (13 mmol) was suspended in dry THF (10 mL) and cooled to 0° C. A solution of compound 4 (6.55 mmol) in dry THF (10 mL) was added slowly. The reaction mixture was stirred at 0° C. for 20 min and then MeI (1.4 g, 9.8 mmol) was added dropwise. The resulted mixture was stirred at RT overnight. The reaction mixture was washed with water and concentrated. The residue was purified through column chromatography to give the desired product.

1.4.6 Preparation of A70/71/72

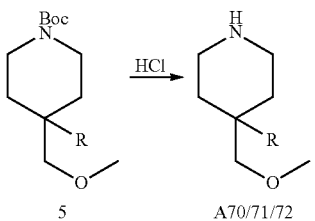

Compound 5 (3.4 mmol) was dissolved in HCl/dioxane (20 mL). The mixture was stirred at RT for 2 h. The solvent was removed to give the product.

1.5 Preparation of A84-89

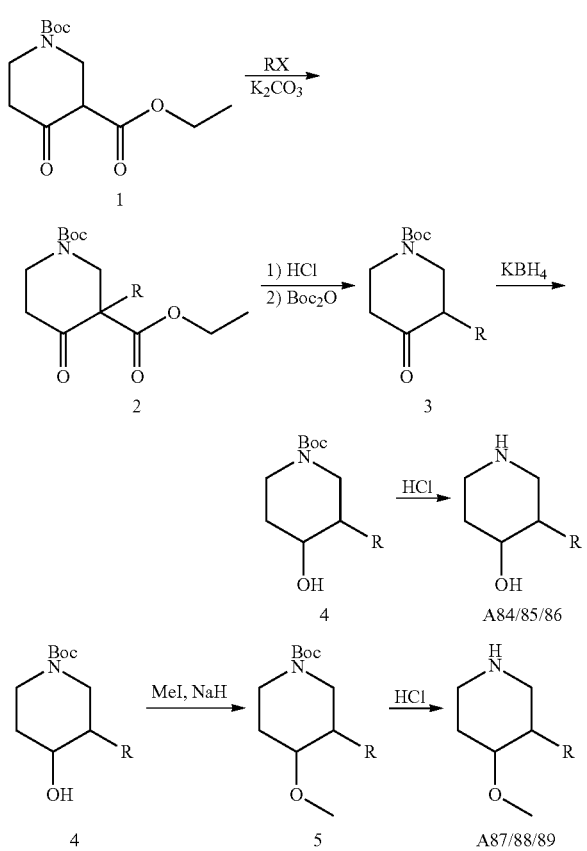

R = Me, Et, Bn

1.5.1 Preparation of Compound 2

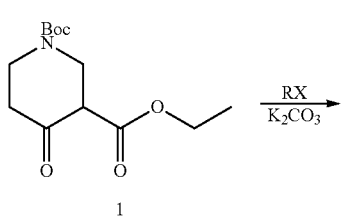

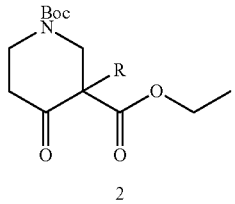

To a solution of compound 1 (2.0 g, 7.37 mmol) and $K_2CO_3$ (3.06 g, 22.11 mmol) in acetone (80 mL) was added RX (2.30 g, 14.74 mmol) slowly at RT. The reaction mixture was stirred under reflux overnight. The reaction mixture was filtered and concentrated. The residue was dissolved in water (50 mL) and extracted with ethyl acetate (50 mL2). The organic layer was dried and concentrated to give the product.

1.5.2 Preparation of Compound 3

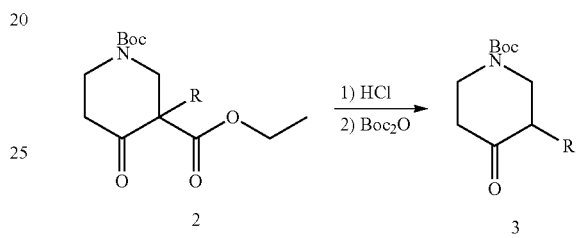

Compound 2 (13.36 mmol) was dissolved in 20% HCl (50 mL). The reaction mixture was stirred under reflux for 2 days. The solvent was removed and the crude product was dissolved in THF (100 mL) and $H_2O$ (20 mL). $Boc_2O$ (5.83 g, 26.73 mmol) and $Na_2CO_3$ (4.25 g, 40.10 mmol) was added. The reaction mixture was stirred at RT overnight. The crude product was purified by column to give the product.

1.5.3 Preparation of Compound 4

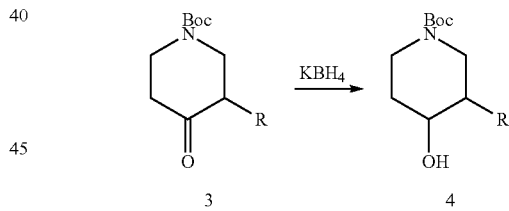

To a solution of compound 3 (11.00 mmol) in ethanol (50 mL) was added $KBH_4$ (0.712 g, 13.20 mmol) slowly at 0° C. The reaction mixture was stirred at 0° C. for 0.5 h and the stirred at RT for 2 h. The reaction mixture was pure into water (50 mL) and extracted with DCM (50 mL3). The organic layer was dried and concentrated to give the product.

1.5.4 Preparation of A84/85/86

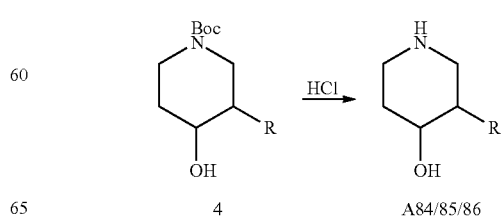

Compound 4 (4.36 mmol) was dissolved in HCl/dioxane (20 mL). The mixture was stirred at RT for 2 h. The solvent was removed to give the product.

1.5.5 Preparation of Compound 5

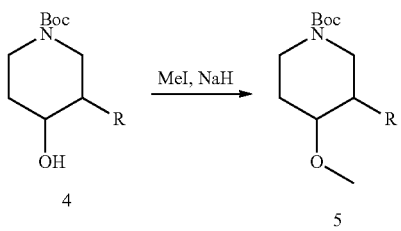

To a solution of Compound 4 (17 mmol) in dry THF (10 mL) was added NaH (20 mmol) at 0° C. slowly. The reaction mixture was stirred at 0° C. slowly, then MeI (20 mmol) was added dropwise. The resulted mixture was stirred at RT overnight. The reaction mixture was washed with water and concentrated. Purification by chromatograph gave the product.

1.5.4 Preparation of A87/88/89

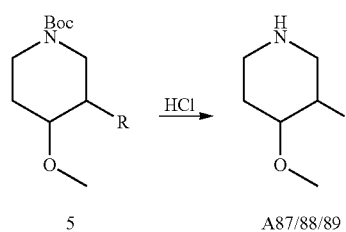

Compound 5 (5.5 mmol) was dissolved in HCl/dioxane (25 mL). The mixture was stirred at RT for 2 h. The solvent was removed to give the product.

1.6 Preparation of A103/104

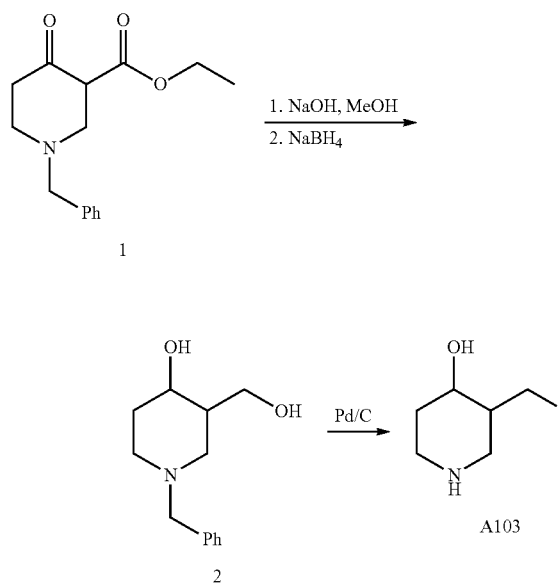

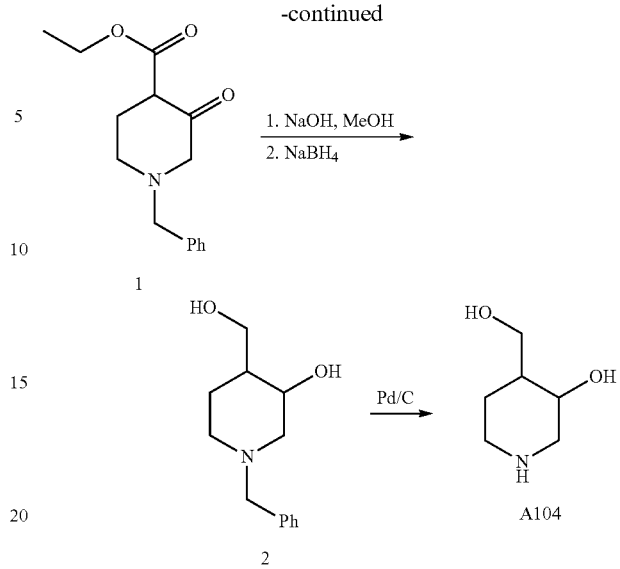

1.6.1 Preparation of Compound 2

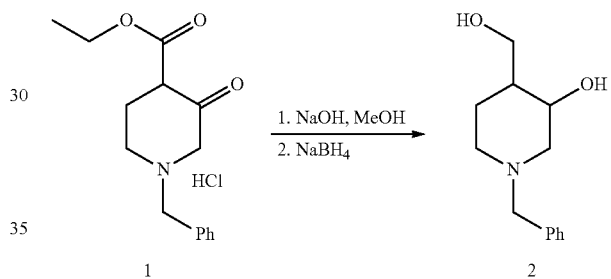

To a solution of compound 1 (1.9 mmol) was added NaOH (1.9 mmol) in MeOH (20 ml), and stirred at rt for 30 min. NaBH4 (14.4 mmol) was added in portions, and the mixture was stirred at rt overnight. Water was added slowly, and stirred at rt for 30 min. The mixture was extracted with EA. The combined organic phase was washed with brine, dried over $Na_2SO_4$, and concentrated in vacuo. The residue was purified through column chromatography to give the desired product.

1.6.2 Preparation of A104

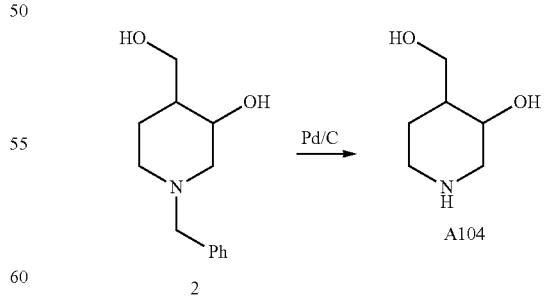

To a solution of compound 2 (450 mg, 2 mmol) in MeOH (50 mL) was added Pd(OH)$_2$/C (100 mg), and the formed mixture was stirred under $H_2$ at 50 psi overnight. The catalyst was filtered and the filtrate was concentrated to give the desired product (230 mg, 88%).

A103 was prepared following the same procedure with A104.

1.7 Preparation of A90/91/92

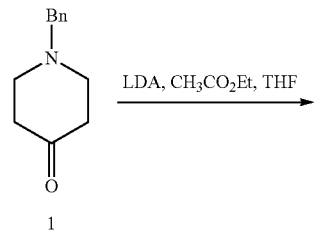

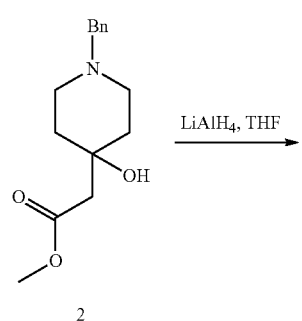

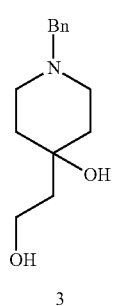

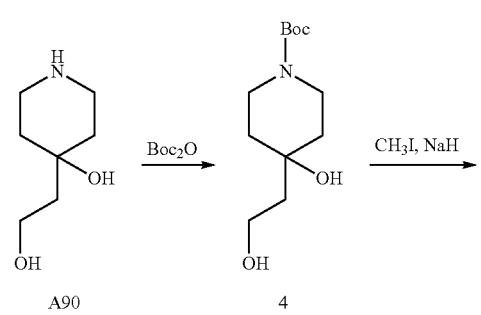

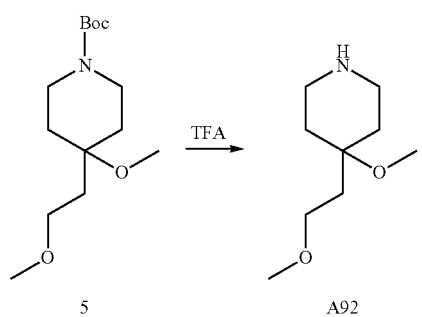

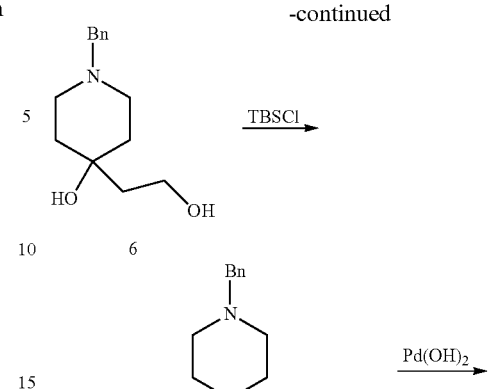

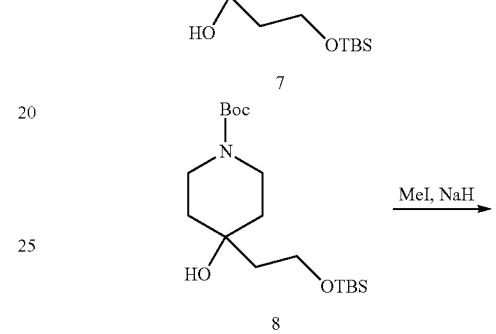

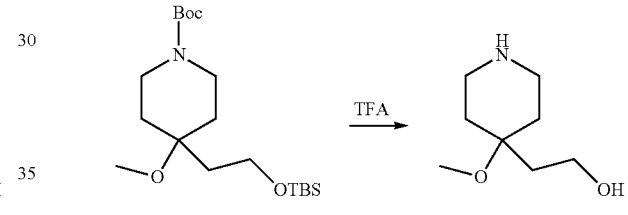

1.7.1 Preparation of Compound 2

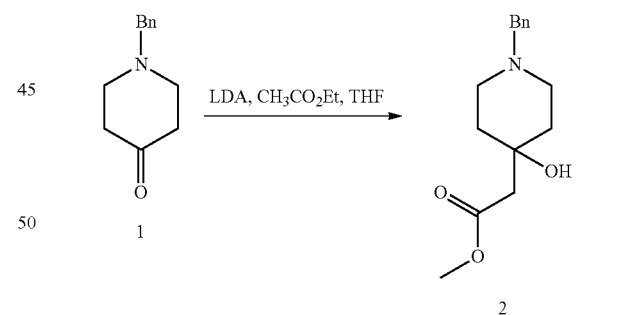

A solution of ethyl acetate (2.11 g, 24 mmol) in THF (30 mL) was added to lithium diisopropylamide solution (13 mL, 2.0 M in THF, 26 mmol) at −78° C. After stirring at the same temperature for 30 min, a solution of Compound 1 (3.8 g, 20 mmol) in THF (30 mL) was added and the mixture was stirred for 15 h at −40° C. The reaction solution was quenched with saturated NH₄Cl (100 mL) and extracted with ethyl acetate (250 mL 2). The combined organic layers were dried (Na₂SO₄) and concentrated in vacuum. Column chromatography of the residue, using petroleum ether/ethyl acetate (2:1) as eluent, gave Compound 2 as white solid. (4.2 g, yield: 80%).

1.7.2 Preparation of Compound 3

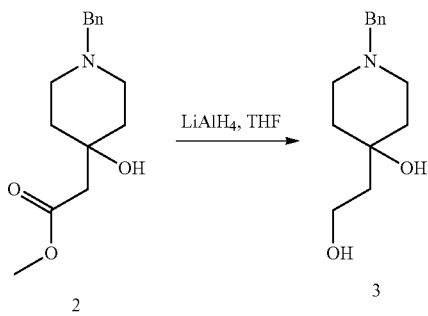 [SMILES: COC(=O)CC1(O)CCN(Cc2ccccc2)CC1 ; OCCC1(O)CCN(Cc2ccccc2)CC1]

Compound 2 (2.63 g, 10 mmol) was dissolved in THF (40 mL), then LiAlH$_4$ (380 mg, 10 mmol) was added, the mixture was stirred at rt for 1 h. Water (0.4 g) was added, then NaOH (0.4 mL, 10%) was added, the mixture was stirred for 30 min, water (1.2 mL) was added, the solid was filtered, the filtrate was concentrated and extracted with EtOAc (100 mL), the organic layer was concentrated to give desired Compound 3 (2.1 g, yield: 90%)

1.7.3 Preparation of A90

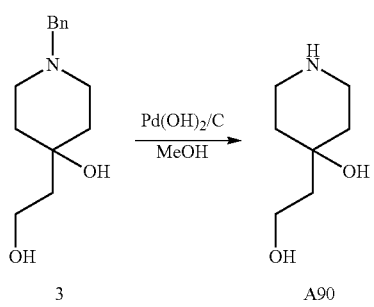

To a solution of compound 3 (460 mg, 2 mmol) in CH$_3$OH (5 mL) was added Pd(OH)$_2$/C (50 mg). The formed mixture was hydrogenated overnight under H$_2$ atmosphere. The catalyst was filtered and the filtrate was concentrated to give the desired product A90 (190 mg, 68%).

1.7.4 Preparation of Compound 4

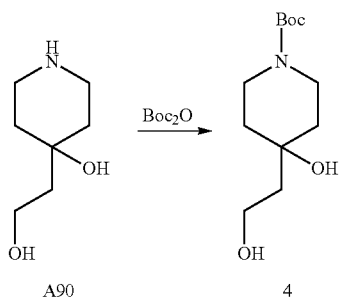

A90 (1.45 g, 10 mmol) was dissolved in MeOH (20 mL), then Boc$_2$O (2.16 g, 10 mmol) and TEA (1.5 g, 15 mmol) was added. The mixture was stirred at rt for 3 h. The solution was concentrated and dissolved with EA, washed with 1N HCl and NaHCO3, concentrated in vacuo to give desired compound 2 (2.3 g, yield: 100%).

1.7.5 Preparation of Compound 5

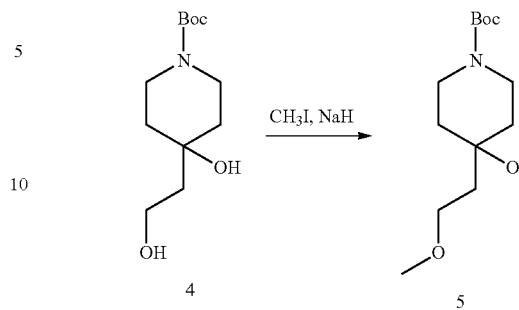

To a suspension of NaH (240 mg, 6 mmol) in THF (10 mL) was added a solution of Compound 4 (490 mg, 2 mmol) at rt. The formed mixture was stirred for 10 minutes. Then CH$_3$I (852 mg, 6 mmol) was added to the above mixture. The mixture was stirred overnight. The reaction was quenched by water, and the formed mixture was concentrated to give the crude product, which was purified by column chromatography (PE:EtOAc=10:1) to give the desired product (437 mg, 80%).

1.7.6 Preparation of A92

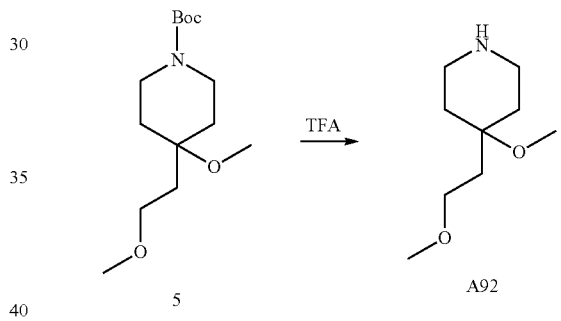

Compound 5 (2.73 g, 10 mmol) was dissolved in DCM (20 mL), Then CF$_3$COOH (20 mL) was added, the mixture stirred at room temperature for 2 hours. The solution was concentrated to give desired A92 (1.6 g, 91%).

1.7.7 Preparation of Compound 2:

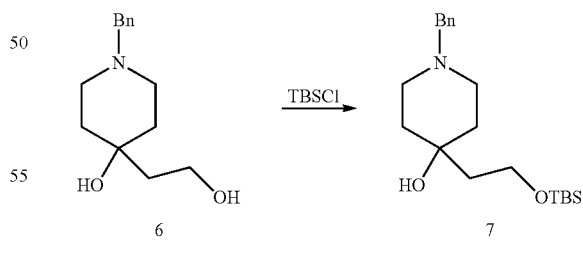

To a solution of Compound 6 (2.4 g, 10 mmol) in DMF (30 mL) was added TEA (2.02 g, 20 mmol) and TBSCl (1.5 g, 10 mmol) at rt. The formed mixture was stirred for 12 hours. The reaction was quenched by water (100 mL), and extracted by EtOAc (100 mL). The organic layer was concentrated to give the crude product, which was purified by column chromatography (PE:EtOAc=10:1) to give the desired product (2.0 g, 80%).

1.7.8 Preparation of Compound 8

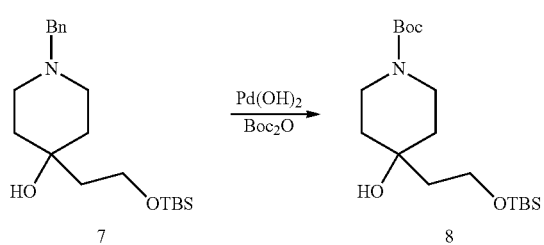 [SMILES: "Boc2O" ; CC(C)(C)[Si](C)(C)OCCC1(O)CCN(Cc2ccccc2)CC1 ; "Pd(OH)2" ; CC(C)(C)OC(=O)N1CCC(O)(CCO[Si](C)(C)C(C)(C)C)CC1]

To a solution of compound 7 (700 mg, 2 mmol) in CH₃OH (5 mL) was added Pd(OH)$_2$/C (250 mg) and Boc$_2$O (512 mg, 2 mmol). The formed mixture was hydrogenated overnight under H$_2$ atmosphere. The catalyst was filtered and the filtrate was concentrated to give the desired product 4 (575 mg, 81%).

1.7.9 Preparation of Compound 9

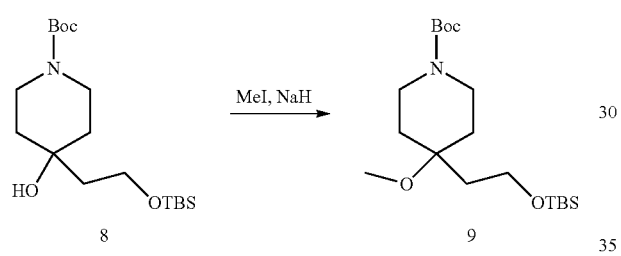

To a suspension of NaH (240 mg, 6 mmol) in THF (10 mL) was added a solution of compound 8 (720 mg, 2 mmol) at rt. The formed mixture was stirred for 10 minutes. Then CH$_3$I (852 mg, 6 mmol) was added to the above mixture. The mixture was stirred overnight. The reaction was quenched by water, and the formed mixture was concentrated to give the crude product, which was purified by column chromatography (PE:EtOAc=10:1) to give the desired product 9 (520 mg, 69%).

1.7.10 Preparation of A91

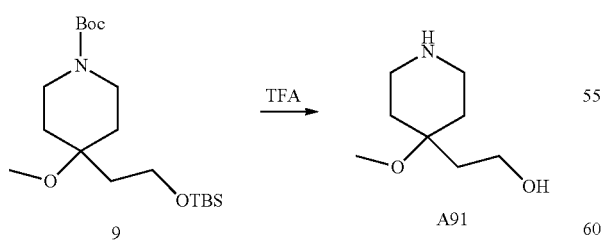

Compound 9 (373 mg, 1 mmol) was dissolved in DCM (5 mL), Then CF$_3$COOH (5 mL) was added, the mixture stirred at room temperature for 2 hours. The solution was concentrated to give desired compound A91 (273 mg, 100%).

1.8 Preparation of A93/94

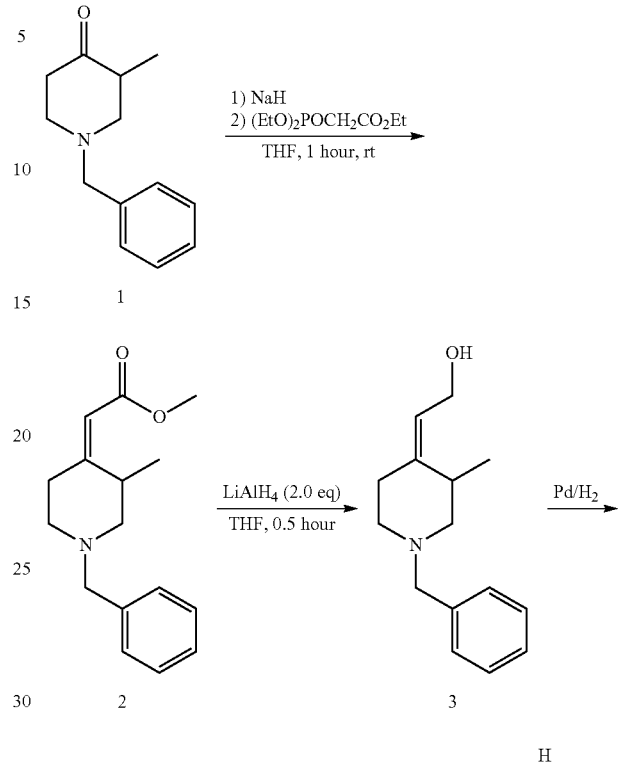

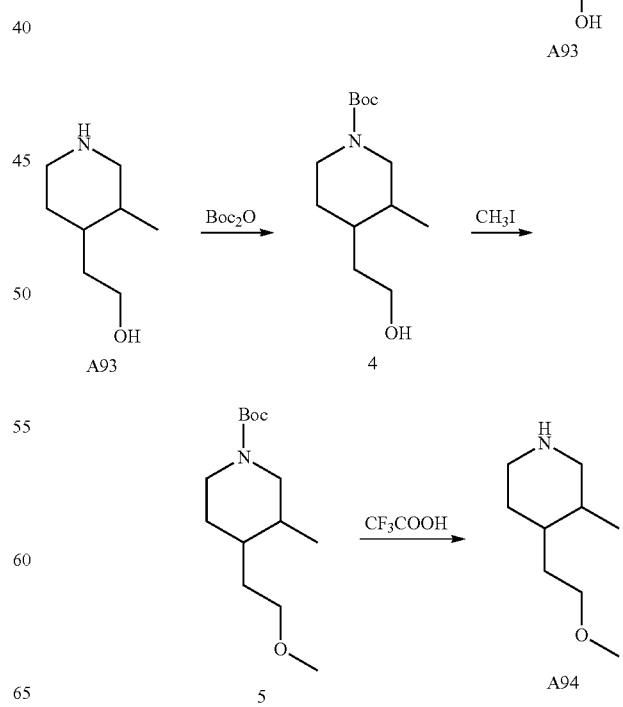

1.8.1 Preparation of Compound 2

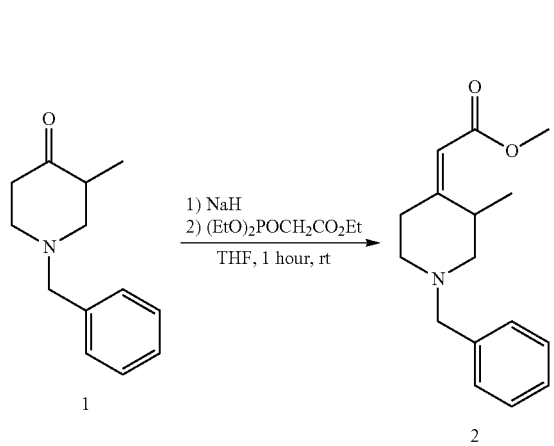 [SMILES: CC1CN(Cc2ccccc2)CCC1=O ; COC(=O)/C=C1/CCN(Cc2ccccc2)CC1C]

To a solution of (Diethoxy-phosphoryl)-acetic acid ethyl ester (4.5 g, 20 mmol) in THF (50 mL) was added NaH (960 mg, 24 mmol) at 0° C. The formed mixture was stirred for 10 minutes. Then Compound 1 (4.1 g, 20 mmol) was added to the above mixture. The mixture was stirred overnight. The reaction was quenched by water, and the formed mixture was extracted with EtOAc (200 mL). The organic layer was concentrated to give the crude product, which was purified by column chromatography (PE:EtOAc=5:1) to give the desired product 2 (3.36 g, 71%).

1.8.2 Preparation of Compound 3

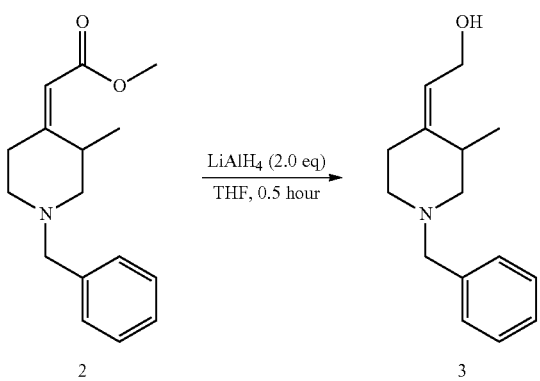 [SMILES: COC(=O)/C=C1/CCN(Cc2ccccc2)CC1C ; CC1CN(Cc2ccccc2)CC/C1=C/CO]

Compound 2 (2.59 g, 10 mmol) was dissolved in THF (40 mL), then LiAlH$_4$ (380 mg, 10 mmol) was added, the mixture was stirred at room temperature for 1 hour. Water (0.4 g) was added, then NaOH (0.4 mL, 10%) was added, the mixture was stirred for 30 min, water (1.2 mL) was added, the solid was filtered, the filtrate was concentrated and extracted with EtOAc (100 mL), the organic layer was concentrated to give desired compound 5 (2.07 g, yield: 90%).

1.8.3 Preparation of A93

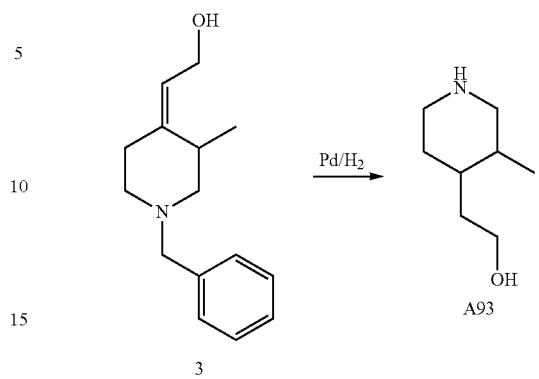

To a solution of Compound 3 (2.31 g, 10 mmol) in CH$_3$OH (30 mL) was added Pd/C (1.0 g). The formed mixture was hydrogenated overnight under H$_2$ atmosphere. The catalyst was filtered and the filtrate was concentrated to give the desired product A93 (1.28 g, 90%).

1.8.4 Preparation of Compound 4

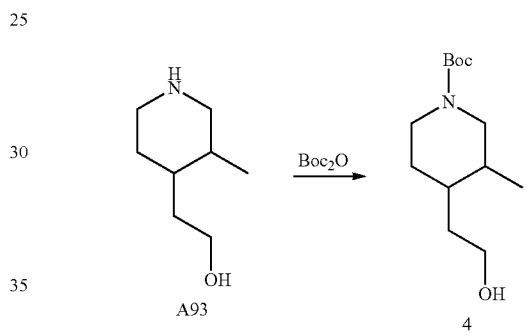

A93 (1.43 g, 10 mmol) was dissolved in MeOH (20 mL), then Boc$_2$O (2.16 g, 10 mmol) and TEA (1.5 g, 15 mmol) was added. The mixture was stirred at room temperature for 3 hours. The solution was concentrated in vacuo. The residue was dissolved with EA, washed with 1N HCl and saturated NaHCO$_3$, dried over Na$_2$SO$_4$ and concentrated in vacuo to give desired Compound 4 (2.43 g, yield: 100%).

1.8.5 Preparation of Compound 5

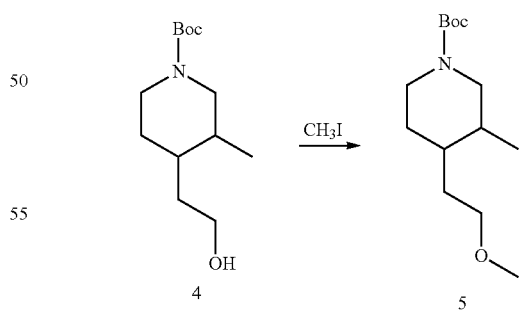

To a suspension of NaH (1.2 g, 30 mmol) in THF (50 mL) was added a solution of Compound 4 (2.43 g, 10 mmol) at rt. The formed mixture was stirred for 10 minutes. Then CH$_3$I (4.2 g, 30 mmol) was added to the above mixture. The mixture was stirred overnight. The reaction was quenched by water, and the formed mixture was concentrated to give the crude product, which was purified by column chromatography (PE: EtOAc=10:1) to give the desired product (2.05 g, 80%).

1.8.6 Preparation of A94

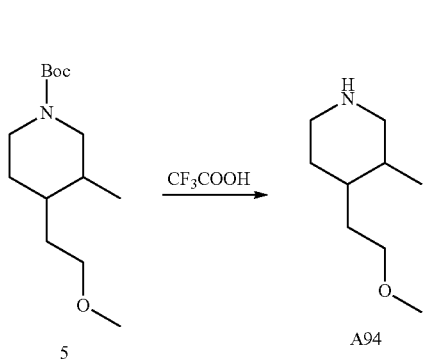

Compound 5 (2.57 g, 10 mmol) was dissolved in DCM (20 mL), Then CF$_3$COOH (20 mL) was added, the mixture stirred at room temperature for 2 hours. The solution was concentrated in vacuo to give desired A94 (1.57 g, 100%).

1.9 Preparation of A95/96

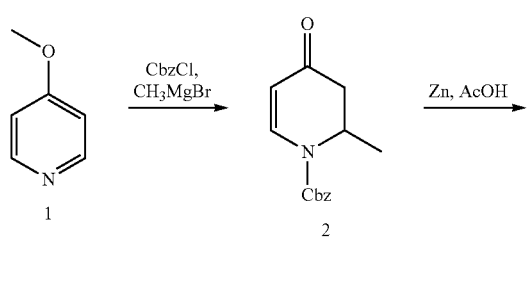

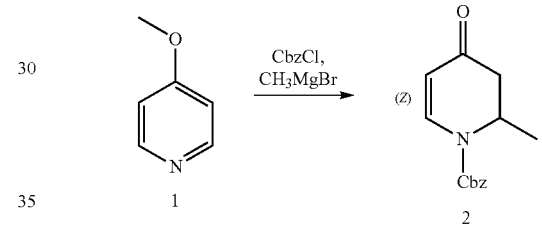

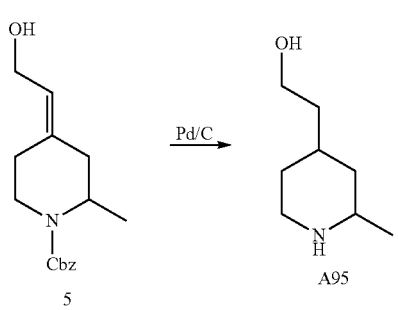

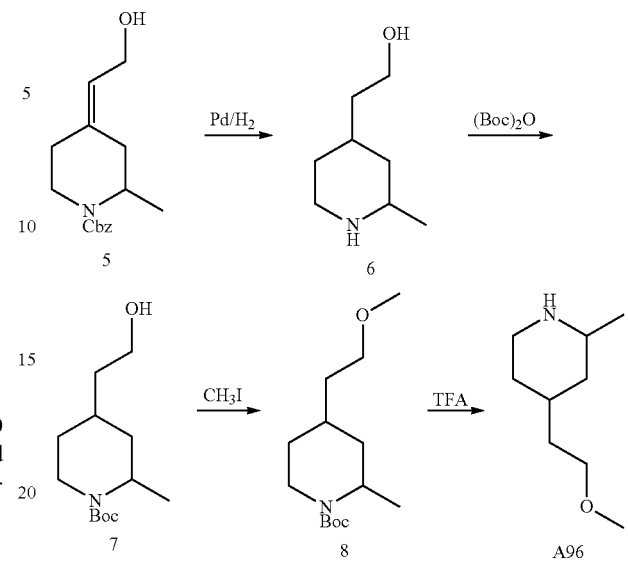

1.9.1 Preparation of Compound 2

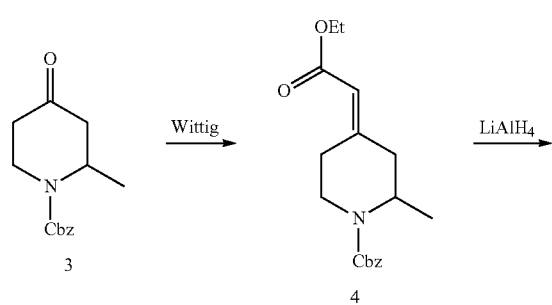

To a solution of Compound 1 (10.9 g, 100 mmol) in THF (100 mL) was added CbzCl (17.6 g, 100 mmol), at 0° C. The formed mixture was stirred for 10 minutes. Then CH$_3$MgBr (100 mL, 100 mmol) was added to the above mixture. The mixture was stirred overnight. The reaction was quenched by water, and the formed mixture was extracted with EtOAc (200 mL). The organic layer was concentrated to give the crude product, which was purified by column chromatography (PE:EtOAc=4:1) to give the desired product 2 (14.7 mg, 58%).

1.9.2 Preparation of Compound 3

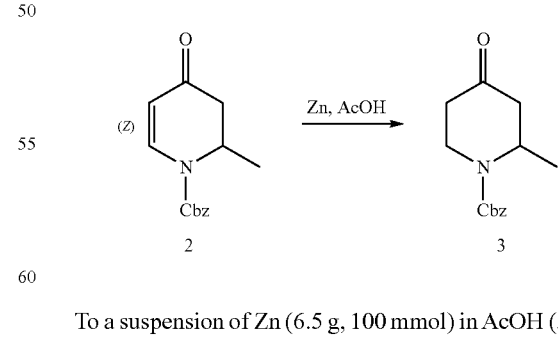

To a suspension of Zn (6.5 g, 100 mmol) in AcOH (50 mL) was added a solution of compound 2 (4.9 g, 20 mmol) at rt. The mixture was stirred overnight. The reaction was filtered and concentrated to give the crude product, which was purified by column chromatography (PE:EtOAc=5:1) to give the desired product 3 (2.9 g, 62%).

1.9.3 Preparation of Compound 4

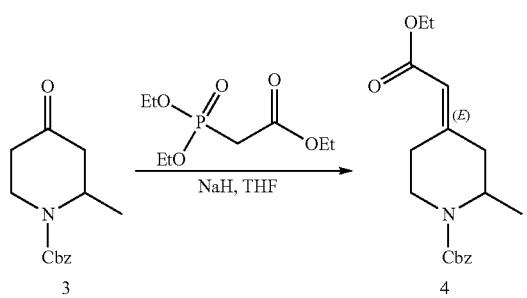 [SMILES: CC1CC(=O)CCN1C(=O)OCc1ccccc1 ; CCOC(=O)CP(=O)(OCC)OCC ; CCOC(=O)/C=C1\CCN(C(=O)OCc2ccccc2)C(C)C1]

To a solution of (Diethoxy-phosphoryl)-acetic acid ethyl ester (4.5 g, 20 mmol) in THF (50 mL) was added NaH (960 mg, 24 mmol) at 0° C. The formed mixture was stirred for 10 minutes. Then Compound 3 (4.94 g, 20 mmol) was added to the above mixture. The mixture was stirred overnight. The reaction was quenched by water, and the formed mixture was extracted with EtOAc (200 mL). The organic layer was concentrated to give the crude product, which was purified by column chromatography (PE:EtOAc=5:1) to give the desired product 4 (3.94 g, 62%).

1.9.4 Preparation of Compound 5

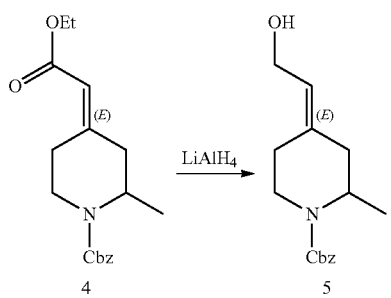 [SMILES: CCOC(=O)/C=C1\CCN(C(=O)OCc2ccccc2)C(C)C1 ; "LiAlH4" ; CC1C/C(=C/CO)CCN1C(=O)OCc1ccccc1]

Compound 4 (3.17 g, 10 mmol) was dissolved in THF (40 mL), then LiAlH$_4$ (380 mg, 10 mmol) was added, the mixture was stirred at room temperature for 1 hour. Water (0.4 g) was added, then NaOH (0.4 mL, 10%) was added, the mixture was stirred for 30 min, water (1.2 mL) was added, the solid was filtered, the filtrate was concentrated and extracted with EtOAc (100 mL), the organic layer was concentrated to give desired Compound 5 (2.47 g, yield: 90%).

1.9.5 Preparation of A95

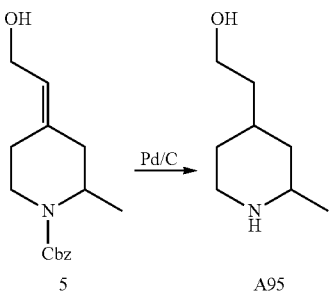

To a solution of Compound 5 (2.75 g, 10 mmol) in CH$_3$OH (30 mL) was added Pd/C (1.0 g). The formed mixture was hydrogenated overnight under H$_2$ atmosphere. The catalyst was filtered and the filtrate was concentrated to give the desired product A33 (1.28 g, 90%).

1.9.6 Preparation of Compound 6

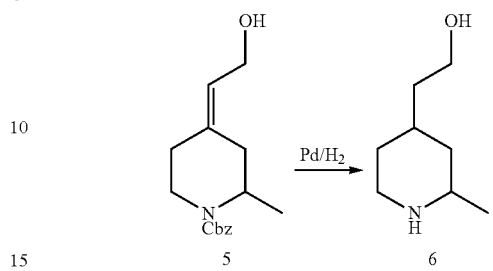

To a solution of Compound 5 (2.31 g, 10 mmol) in CH$_3$OH (30 mL) was added Pd/C (1.0 g). The formed mixture was hydrogenated overnight under H$_2$ atmosphere. The catalyst was filtered and the filtrate was concentrated to give the desired product (1.28 g, 90%).

1.9.7 Preparation of Compound 7

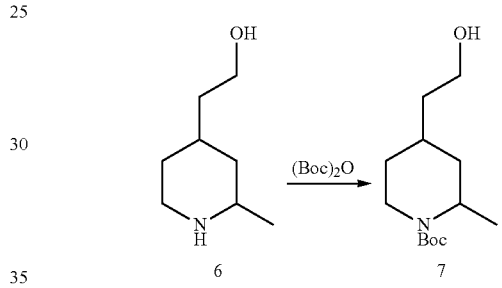

Compound 6 (1.43 g, 10 mmol) was dissolved in MeOH (20 mL), then Boc$_2$O (2.16 g, 10 mmol) and TEA (1.5 g, 15 mmol) was added. The mixture was stirred at room temperature for 3 hours. The solution was concentrated in vacuo, dissolved with EA, washed with 1N HCl and NaHCO3, dried over Na$_2$SO$_4$, and concentrated in vacuo to give desired Compound 7 (2.43 g, yield: 100%).

1.9.8 Preparation of Compound 8

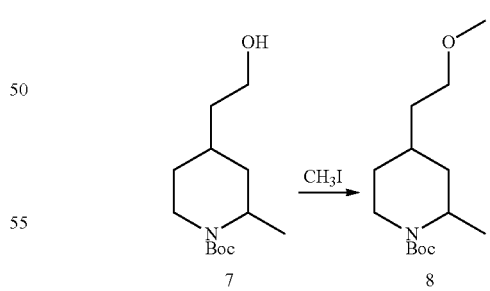

To a suspension of NaH (1.2 g, 30 mmol) in THF (50 mL) was added a solution of Compound 7 (2.43 g, 10 mmol) at rt. The formed mixture was stirred for 10 minutes. Then CH$_3$I (4.2 g, 30 mmol) was added to the above mixture. The mixture was stirred overnight. The reaction was quenched by water, and the formed mixture was concentrated to give the crude product, which was purified by column chromatography (PE: EtOAc=10:1) to give the desired product (2.05 g, 80%).

1.9.9 Preparation of A96

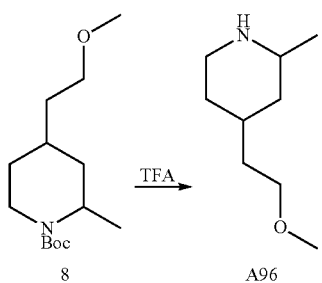

Compound 8 (2.57 g, 10 mmol) was dissolved in DCM (20 mL), Then CF₃COOH (20 mL) was added, the mixture stirred at room temperature for 2 hours. The solution was concentrated to give desired compound H (1.57 g, 100%).

1.10 Preparation of A53/58

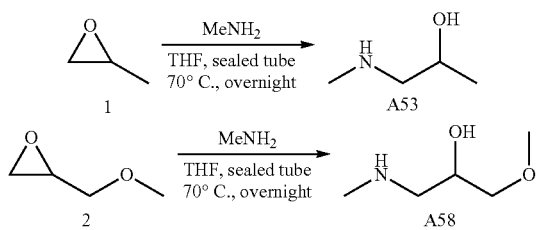

A mixture of compound 1 (1.2 g, 20 mmol) and MeNH2 in THF was heated to 70° C. in a sealed tube overnight. The mixture was concentrated in vacuo. The residue was re-dissolved in toluene, and concentrated in vacuo to give the desired product A53 (1.8 g, 98%). $^1$H NMR (400 MHz, CDCl₃): δ ppm: 3.79-3.84 (m, 1H), 2.42-2.46 (m, 2H), 3.35 (s, 3H), 1.16 (d, 2H).

A58 was prepared following the same procedure as A53.

1.11 Preparation of A98

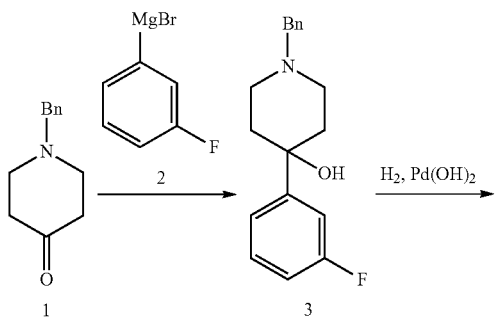

1.11.1 Preparation of Compound 3

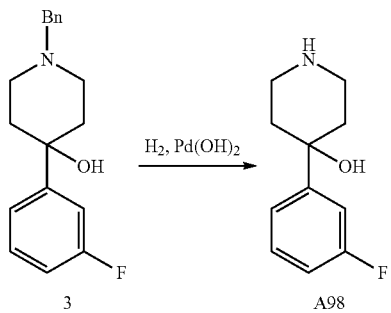

To a solution of compound 2 (10 mL, 1 M, 10 mmol) in THF was added a solution of Compound 1 (0.95 g, 5 mmol) in THF (20 mL) at 0° C. The formed mixture was stirred at rt for 3 h. The reaction was quenched by NH₄Cl solution, and the mixture was extracted with EtOAc (20 mL×3). The organic layer was concentrated to give the crude product, which was purified by column chromatography to give the desired product (1.1 g, 78%). LCMS: 286.3 [M+1].

1.11.2 Preparation of A98

To a solution of Compound 3 (1.1 g, 3.8 mmol) in MeOH was added Pd(OH)₂/C (100 mg), and the formed mixture was stirred under H₂ balloon overnight. The Pd was filtered and the filtrate was concentrated to give the desired product (680 mg, 90%). $^1$H NMR (400 MHz, CDCl₃): δ ppm: 7.24-7.38 (m, 3H), 6.95-7.00 (m, 1H), 3.10-3.17 (m, 2H), 2.98-3.01 (m, 2H), 1.99-2.06 (m, 2H), 1.72-1.79 (m, 2H).

1.12 Preparation of A97/99/101

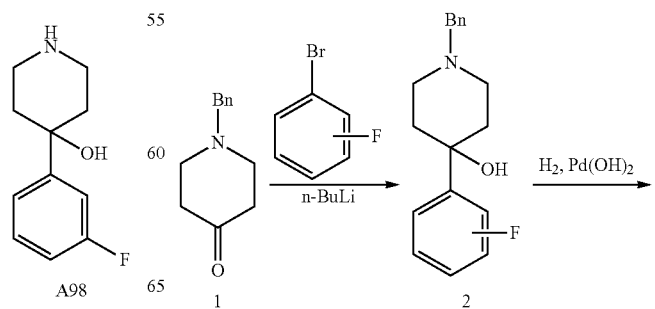

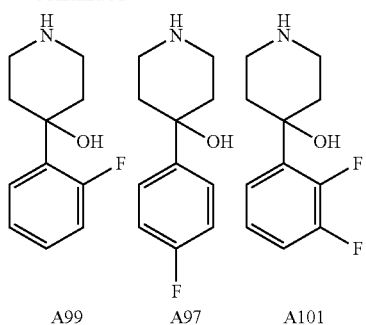

1.12.1 Preparation of Compound 2

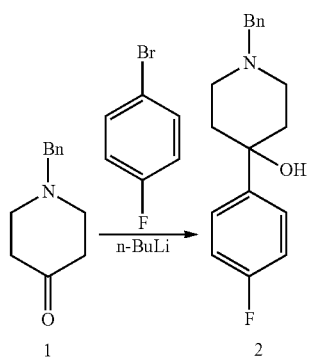

To a solution of 1-bromo-4-fluorobenzene (1.75 g, 10 mmol) in THF was added n-BuLi (4 mL, 10 mmol, 2.5 M) at −78 under N2. After stirring for 15 min, a solution of Compound 1 (0.95 g, 5 mmol) in THF (20 mL) was added dropwise at −78° C. The formed mixture was stirred at rt for 3 h. The reaction was quenched by NH₄Cl solution, and the mixture was extracted with EtOAc (20 mL×3). The organic layer was concentrated to give the crude product, which was purified by column chromatography to give the desired product (0.9 g, 64%). LCMS: 286.3 [M+1].

1.12.2 Preparation of A97

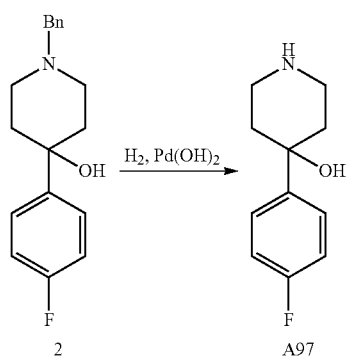

To a solution of Compound 2 (0.9 g, 3.1 mmol) in MeOH was added Pd(OH)₂/C (100 mg), and the formed mixture was stirred under H₂ balloon overnight. The Pd was filtered and the filtrate was concentrated to give the desired product (0.5 g, 82%). LCMS: 196.2 [M+1].

A99/101 were prepared following the same procedure as A97.

1.13 Preparation of A100/102

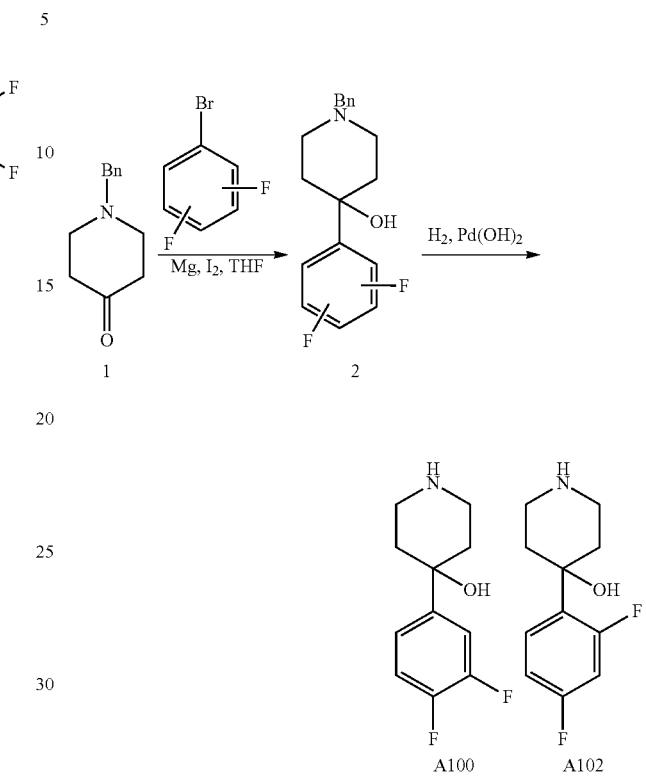

1.12.1 Preparation of Compound 2

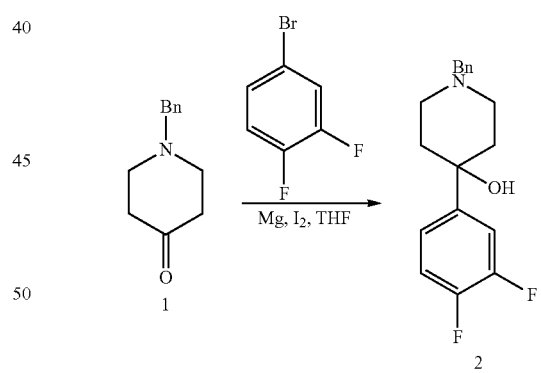

To a solution of 4-bromo-1,2-difluorobenzene (3.86 g, 20 mmol) in THF (50 mL) was added I₂ (64 mg, 0.25 mmol), followed by Mg (0.48 g, 20 mmol) at rt under N2. After stirring for 1 h, the Mg was disappeared, a solution of Compound 1 (1.9 g, 10 mmol) in THF (20 mL) was added dropwise at 0° C. The formed mixture was stirred at rt for 3 h. The reaction was quenched by NH₄Cl solution, and the mixture was extracted with EtOAc (500 mL×3). The organic layer was concentrated to give the crude product, which was purified by column chromatography to give the desired product (2.8 g, 93%). LCMS: 304.1 [M+1].

1.12.2 Preparation of A100

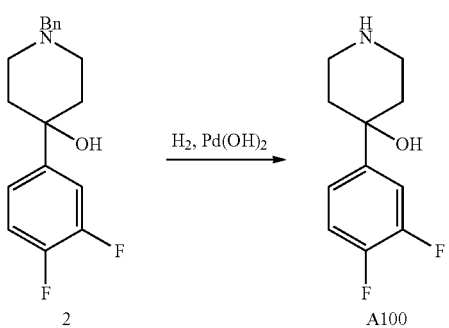

To a solution of Compound 2 (2.8 g, 9.3 mmol) in MeOH (200 mL) was added Pd(OH)$_2$/C (0.5 g), and the formed mixture was stirred under H$_2$ balloon overnight. The Pd was filtered and the filtrate was concentrated to give the desired product (1.6 g, 80%). LCMS: 214.1 [M+1].

A102 was prepared following the same procedure as A100.

1.14 Preparation of A114

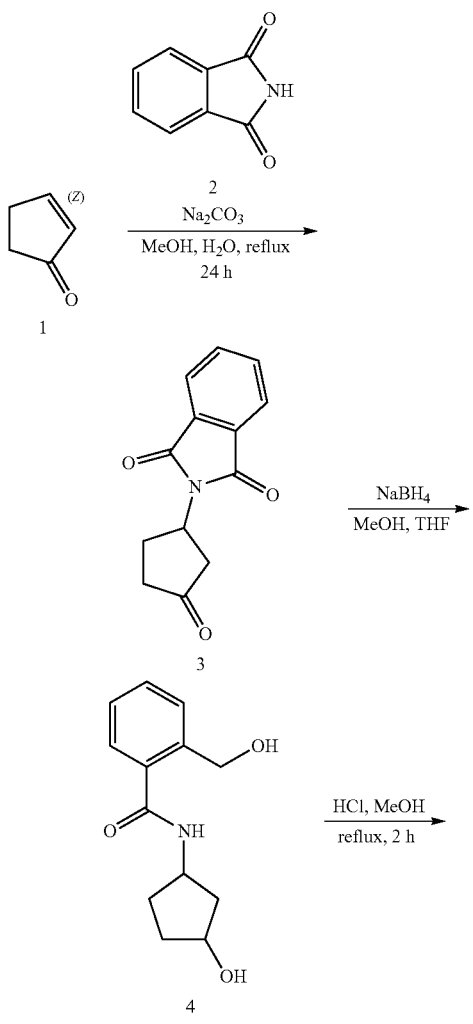

1.14.1 Preparation of Compound 2

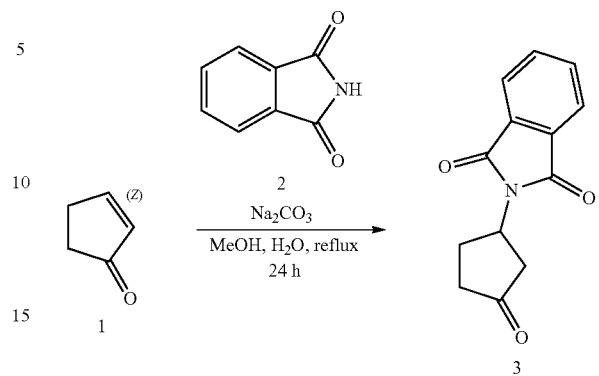

To a slurry of Compound 1 (6.5 g, 79 mmol) and Compound 2 (10.2 g, 69 mmol) in MeOH (100 mL) was added a aqueous Na2CO3 (6 mL, 2 N, 12 mmol), and stirred at rt for 24 h. The solid was collected by filteration, washed with MeoH and dried in vacuo, which was used in the next step (14 g, crude). LCMS: 230.2 [M+1].

1.14.1 Preparation of Compound 4

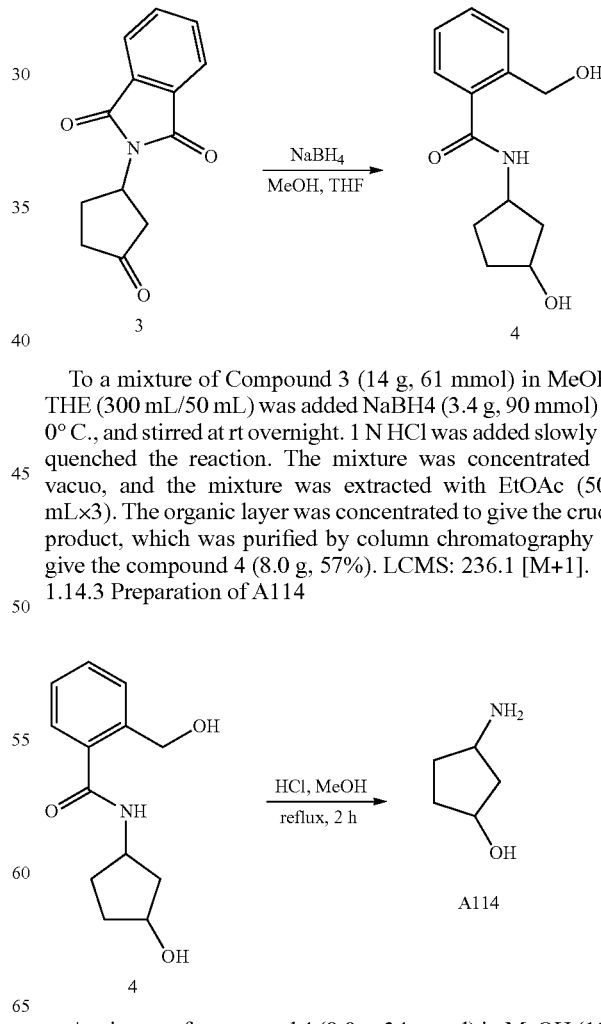

To a mixture of Compound 3 (14 g, 61 mmol) in MeOH/THE (300 mL/50 mL) was added NaBH4 (3.4 g, 90 mmol) at 0° C., and stirred at rt overnight. 1 N HCl was added slowly to quenched the reaction. The mixture was concentrated in vacuo, and the mixture was extracted with EtOAc (500 mL×3). The organic layer was concentrated to give the crude product, which was purified by column chromatography to give the compound 4 (8.0 g, 57%). LCMS: 236.1 [M+1].

1.14.3 Preparation of A114

A mixture of compound 4 (8.0 g, 34 mmol) in MeOH (100 mL) was added concentrated HCl (10 mL), and heated to reflux for 2 h. The mixture was concentrated in vacuo. The residue was dissolved with water and washed with EA. The aqueous phase was concentrated in vacuo to give the desired product with HCl salt (2.8 g, 82%). ¹H NMR (400 MHz, CDCl₃): δ ppm: 4.33 (bs, 1H), 3.66 (bs, 1H), 2.08-2.16 (m, 2H), 1.74-1.90 (m, 4H).

1.15 Preparation of A113

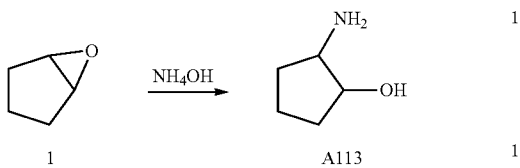

A mixture of Compound 1 (4.2 g, 50 mmol) and ammonia (25%, 20 mL) in MeOH (100 mL) was heated to 60° C. in a sealed tube overnight. The mixture was concentrated in vacuo. The residue was dissolved with 0.5 N HCl (20 mL) and washed with EA. The aqueous phase was concentrated in vacuo to give the desired product A44, which was used in the next step directly (3.0 g, 59%).

1.16 Preparation of A121

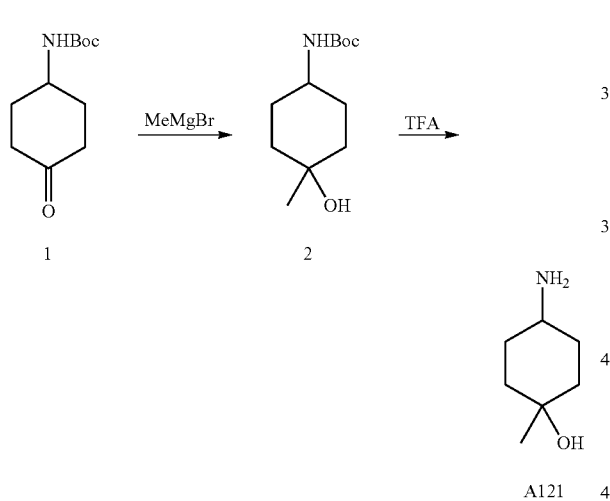

1.16.1 Preparation of Compound 2

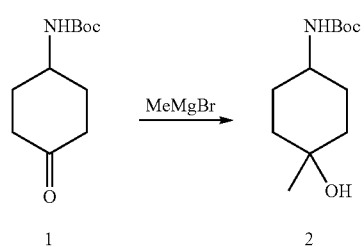 [SMILES: "MeMgBr" ; CC(C)(C)OC(=O)NC1CCC(=O)CC1 ; CC1(O)CCC(NC(=O)OC(C)(C)C)CC1]

To MeMgBr (3 mL, 12 mmol) in THF was added dropwise a solution of Compound 1 (1.0 g, 4.7 mmol) in THF (20 mL) at 0-4° C. The formed mixture was stirred at rt for 3 h. The reaction was quenched by NH₄Cl solution, and the mixture was extracted with EtOAc (20 mL×3). The organic layer was concentrated to give the desired product 2, used directly in the next step without further purification (0.97 g, 94%).

1.16.2 Preparation of A121

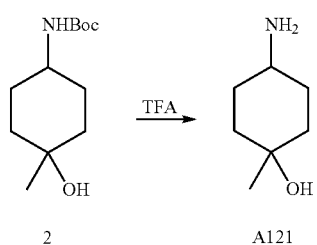

To a solution of Compound 2 (970 mg, 4.43 mmol) in DCM (10 mL) was added TFA (5 mL). The formed mixture was stirred overnight at rt. The reaction mixture was concentrated to give the product A121 (1.3 g,), which was used in the next step directly.

1.17 Preparation of A125

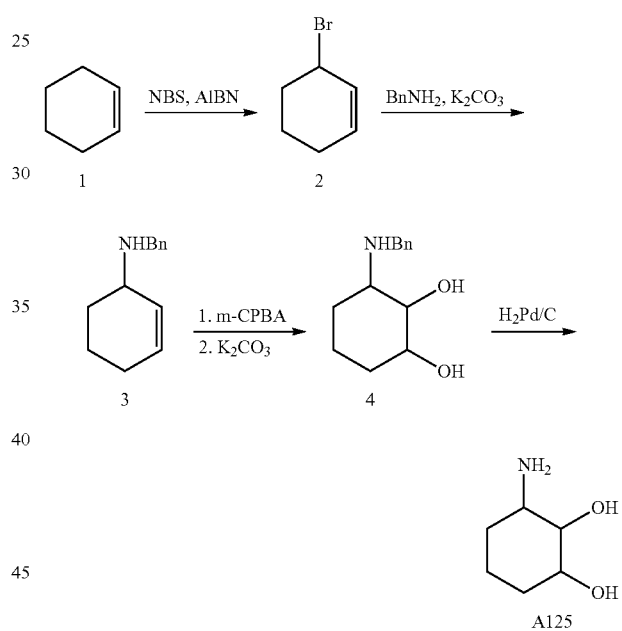

1.17.1 Preparation of Compound 2

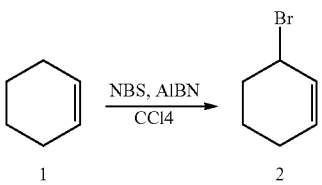

To a solution of Compound 1 (8.2 g, 0.1 mol) and NBS (21.4 g, 0.12 mol) in CCl₄ (100 mL), was added AIBN (3.3 g, 20 mmol) at rt, and heated to reflux for 3 h. The mixture was washed with Na₂SO₃, sat. NaHCO₃ and brine, dried over Na₂SO₄, and concentrated to afford desired product 2 (8.5 g, 53%), used in the next step directly.

1.17.2 Preparation of Compound 3

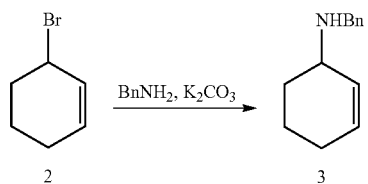

To a solution of Compound 2 (4.0 g, 24.8 mmol) and phenylmethanamine (3.2 g, 29.8 mmol) in anhydrous THF (60 mL), was added $K_2CO_3$ (5.1 g, 37.2 mmol), and heated to 60° C. for 5 h. After cooling to rt, the mixture was diluted with EA, and $H_2O$ (80 mL). The aqueous phase was extracted with EA (100 mL3). The combined organic phase was washed with brine, dried over $Na_2SO_4$, concentrated to afford crude product which was purified by silica gel column chromatography (20-50% EtOAc in PE) to afford 3 (3.1 g, 68 yield). LCMS: 187 [M+1].

1.17.3 Preparation of Compound 4

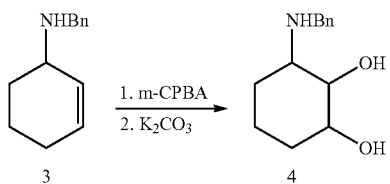

Compound 3 (1.0 g, 5.3 mmol) was dissolved in DCM (20 mL), $CF_3COOH$ (3.0 g, 26.7 mmol) was added and stirred for 30 minutes at rt. m-CPBA (1.5 g, 8.6 mmol) was added and the mixture stirred at rt overnight. Aqueous $NaHCO_3$ was added to the reaction mixture and the phases separated and extracted with DCM (3 50 mL). The combined organic extracts were dried, filtered and concentrated in vacuo to yield the crude amino diol. Purification by chromatography on $SiO_2$ (EA) gave 4 (600 mg, 51%) as a colourless oil. LCMS: 222 [M+1].

1.17.4 Preparation of A125

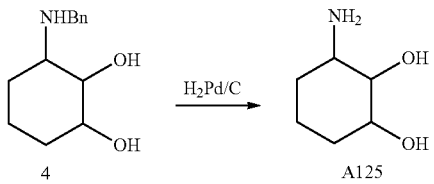

To a solution of compound 5 (600 mg, 2.7 mmol) in $CH_3OH$ (8 mL) was added $Pd(OH)_2/C$ (60 mg). The formed mixture was hydrogenated overnight under $H_2$ atmosphere. The catalyst was filtered and the filtrate was concentrated to give the desired product (340 mg, 95%).

1.18 Preparation of A127

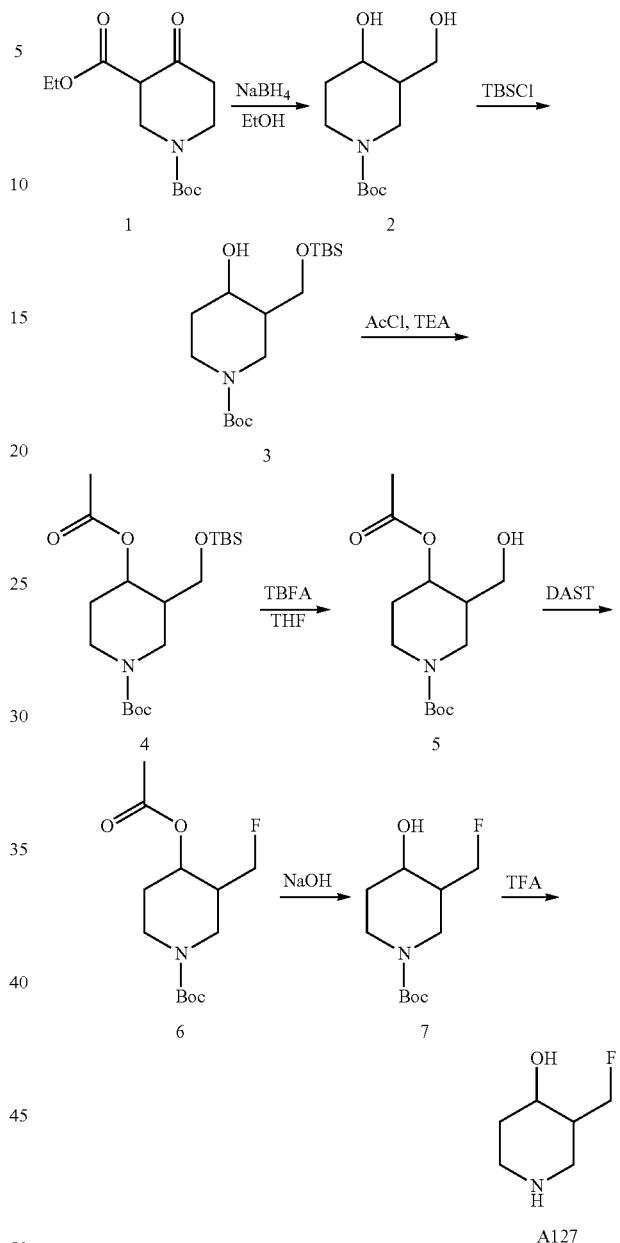

1.18.1 Preparation of Compound 2

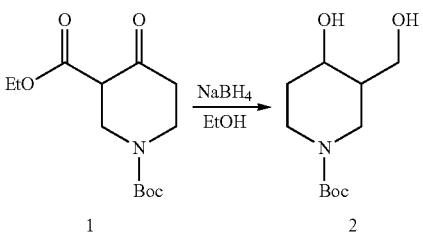

To a solution of compound 1 (7.0 g, 25.8 mmol) in EtOH (100 mL) was added NaBH4 (9.8 g, 258 mmol) in portions at 0° C. The reaction mixture was stirred at 0 for 0.5 h and then stirred at RT overnight. The reaction mixture was poured into water (100 mL) and extracted with DCM (100 mL3). The organic layer was dried and concentrated to give the product 2 (4.5 g, 75%).

1.18.3 Preparation of Compound 3

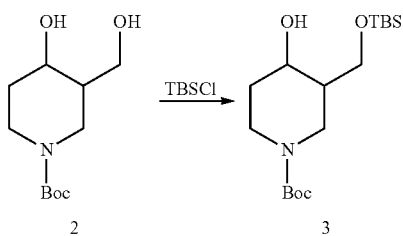

To a solution of Compound 2 (2.5 g, 10.8 mmol) and imidazole (0.9 g, 12 mmol) in anhydrous DCM (30 mL), TBSCl (1.7 g, 11.4 mmol) was added dropwise at 0° C. After complete addition, the solution was allowed to warm to rt, and stirred for 2 h. The reaction mixture was dissolved with DCM, washed with 1N HCl, saturated NaH CO3 and brine, dried over $Na_2SO_4$, and concentrated to afford desired product 3 (3.3 g, 89%). LCMS: 345 [M+1].

1.18.4 Preparation of Compound 4

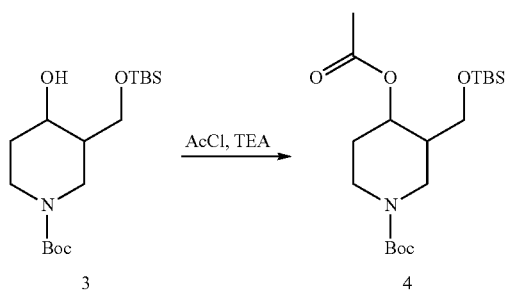 [SMILES: CC(C)(C)OC(=O)N1CCC(O)C(CO[Si](C)(C)C(C)(C)C)C1 ; "AcCl, TEA" ; CC(=O)OC1CCN(C(=O)OC(C)(C)C)CC1CO[Si](C)(C)C(C)(C)C]

To a solution of Compound 3 (3.3 g, 9.6 mmol) and TEA (1.16 g, 11.5 mmol) in anhydrous THF (30 mL), AcCl (0.83 g, 11.6 mmol) was added dropwise at 0° C. After complete addition, the solution was allowed to warm to rt, and stirred for 2 h. The reaction mixture was dissolved with DCM, washed with 1N HCl, saturated Na2CO3 and brine, dried over $Na_2SO_4$, and concentrated to afford desired product 4 (3.5 g, 95%). LCMS: 388 [M+1]

1.18.5 Preparation of Compound 5

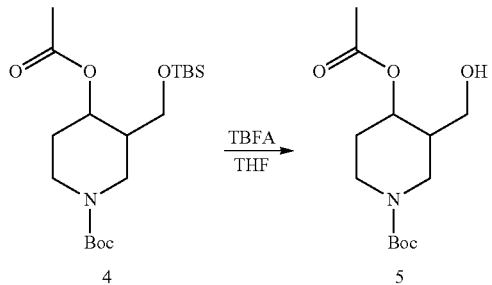

To a solution of compound 4 (3.5 g, 9.0 mmol) in THF (40 mL) was added TBAF (2.75 g, 10 mmol). The formed mixture was stirred at rt overnight. The mixture was poured into water and extracted with EA. The combined organic phase was washed with 1N HCl, saturated NaHCO3 and brine, dried over $Na_2SO_4$, and concentrated in vacuo. The residue was purified through column chromatography to give the desired product 5. (2.4 g, 96%).

1.18.6 Preparation of Compound 6

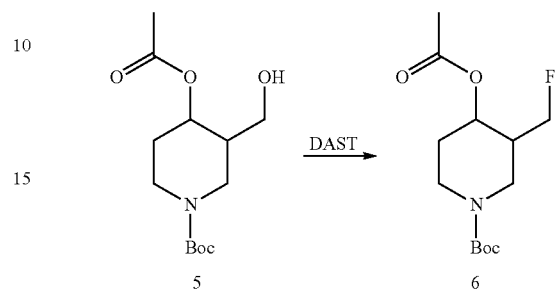

To a solution of Compound 5 (1.0 g, 3.7 mmol) in anhydrous DCM (15 mL), DAST (1.19 g, 7.4 mmol, 2.0 eq) was added dropwise at −78° C. under $N_2$. After addition the solution was warmed to rt gradually and stirred for 2 h. Quenched the reaction with sat. $NaHCO_3$ (30 mL), extracted with DCM (30 mL3), combined the organic layer, washed with brine, dried over $Na_2SO_4$, and concentrated to afford desired product 6 (870 mg, 87%).

1.18.7 Preparation of Compound 7

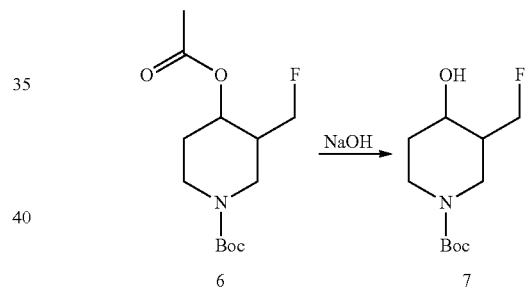

To a solution of Compound 6 (870 mg, 3.2 mmol) and NaOH (256 mg, 6.4 mmol) in MeOH/$H_2O$ (10 mL, v:v=4:1). The formed mixture was stirred overnight at rt. The reaction mixture was neutralized with 1N HCl solution and concentrated to give the crude product (720 mg, 96%).

1.18.7 Preparation of A127

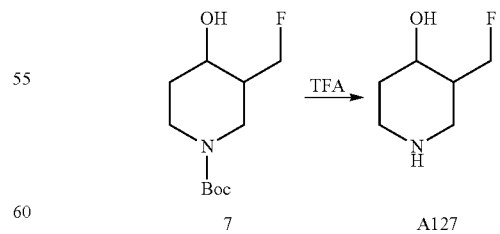

To a solution of Compound 7 (720 mg, 3.1 mmol) in DCM (6 mL) was added TFA (5 mL). The formed mixture was stirred overnight at rt. The reaction mixture was concentrated to give the crude product (800 mg, crude), used in the next step directly.

1.19 Preparation of A119

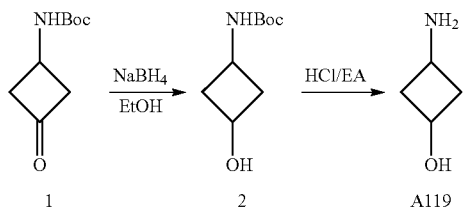

1.19.1 Preparation of Compound 2

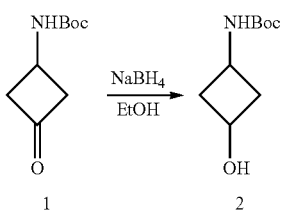

To a solution of compound 1 (4.0 g, 21.6 mmol) in ethanol (40 mL) was added NaBH$_4$ (1.64 g, 43.2 mmol) slowly at 0. The reaction mixture was stirred at RT for 5 h. The reaction mixture was quenched with NH$_4$Cl (50 mL) and extracted with ethyl acetate (50 mL3). The organic layer was dried and concentrated to give the product.

1.19.2 Preparation of A119

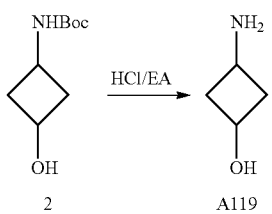

Compound 2 (4 g 21.6 mmol) was dissolved in HCl/EA (25 mL). The mixture was stirred at RT for 2 h. The solvent was removed to give the product.

1.20 Preparation of A110

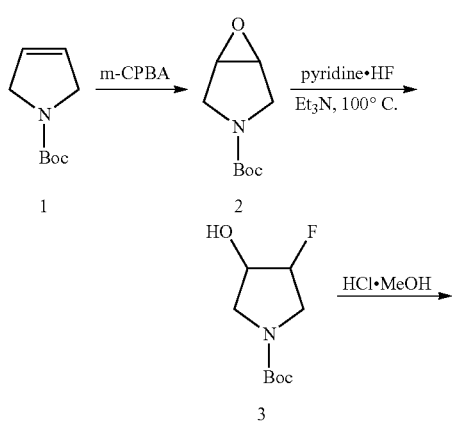

1.20.1 Preparation of Compound 2

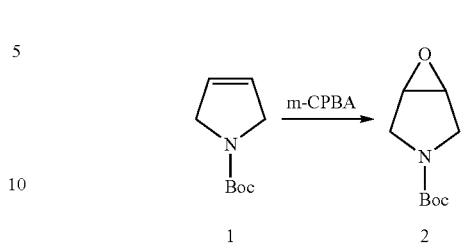

To a solution of Compound 1 (4.0 g, 0.024 mmol) in CH$_2$Cl$_2$ (40 mL) was added m-CPBA (0.3 mol) at room temperature, and the mixture was stirred at rt for 12 hours. The mixture was quenched with Na$_2$SO$_3$, washed with NaHCO$_3$, and concentrated to give the compound 2 (4.4 g, 100%). $^1$H NMR (400 MHz, CDCl$_3$): δ ppm: 3.73 (m, 2H), 3.60 (m, 2H), 3.23 (m, 2H), 1.37 (s, 9H).

1.20.2 Preparation of Compound 3

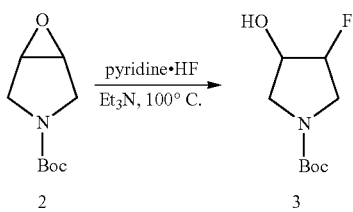 [SMILES: CC(C)(C)OC(=O)N1CC2OC2C1 ; CC(C)(C)OC(=O)N1CC(O)C(F)C1]

To a solution of Compound 2 (2.0 g, 0.01 mmol) in Et$_3$N (20 mL) was added pyridine. HF Py (3 mL) at 0° C., and the mixture was heated to 80° C. for 12 hours. Then the mixture was concentrated in vacuo. The residue was diluted with AcOEt, washed with aqueous NH$_4$Cl solution and brine, dried over Na2SO4 and concentrated in vacuo. The residue was purified by column chromatography (PE:EA=4:1) to give the desired product.

1.20.3 Preparation of A110

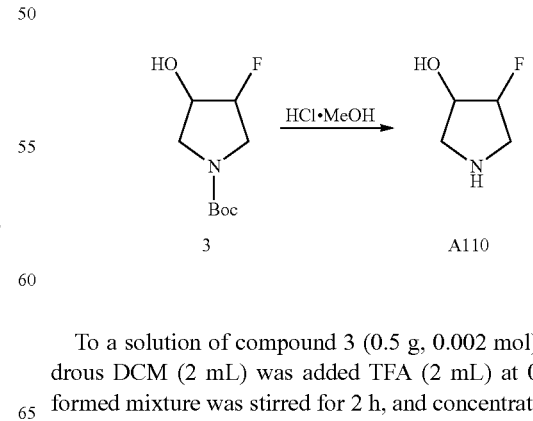

To a solution of compound 3 (0.5 g, 0.002 mol) in anhydrous DCM (2 mL) was added TFA (2 mL) at 0° C. The formed mixture was stirred for 2 h, and concentrated to give the desired product which was used for the next step (500 mg, 100%).

1.21 Preparation of A111

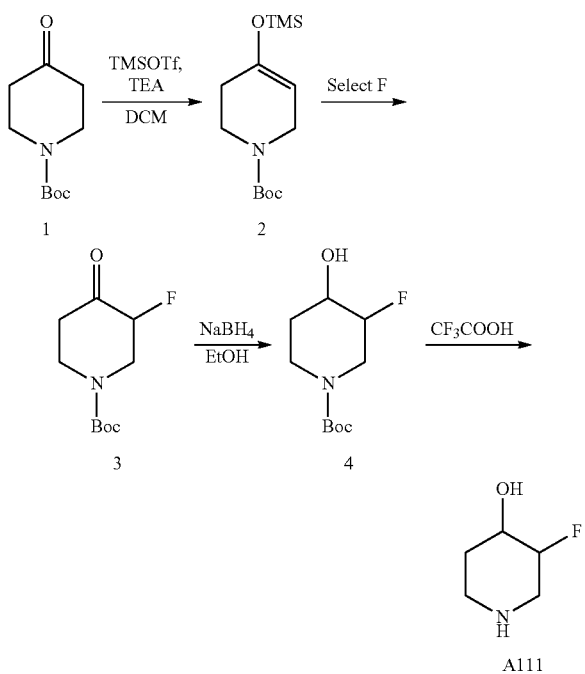

1.21.1 Preparation of Compound 2

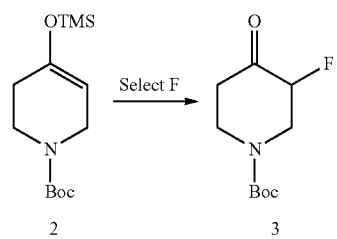

To a solution of compound 1 (4 g, 0.02 mol) in DCM (40 mL) was added TMSOTf (6.6 g, 0.03 mol), Et₃N (6.0 g, 0.06 mol) at room temperature. The reaction mixture was stirred for 1 hour. Then the mixture reaction was concentrated, purified by column chromatography (PE:AcOEt=10:1) to give the compound 2 (4.3 g, 80%). ¹H NMR (400 MHz, CDCl₃): δ ppm: 4.79 (s, 1H), 3.87 (m, 2H), 3.52 (m, 2H), 2.11 (s, 1H), 1.43 (s, 9H), 0.16 (s, 9H).

1.21.2 Preparation of Compound 3

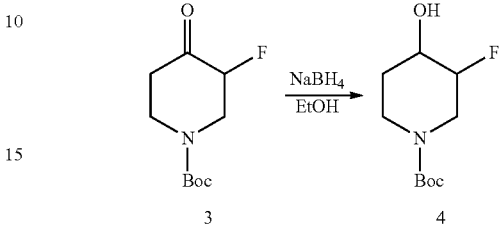

A mixture of Compound 2 (250 mg, 0.92 mmol), select F (360 mg, 0.92 mmol) in MeCN (20 mL) was stirred for 4 hours. The mixture was concentrated and purified by column chromatography (PE:AcOEt=4:1) to give the compound 3 (180 mg, 90%). ¹H NMR (400 MHz, CDCl₃): δ ppm: 4.10~4.84 (m, 1H), 3.63~3.66 (m, 1H), 3.14~3.21 (m, 1H), 2.48~2.52 (m, 1H), 2.35~2.39 (m, 2H), 1.42 (s, 9H).

1.21.3 Preparation of Compound 4

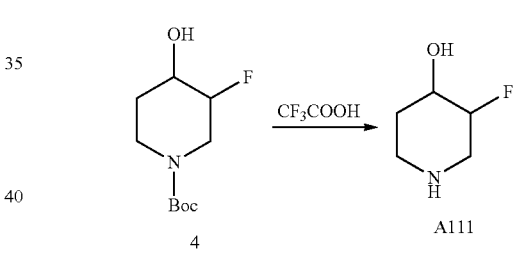

To a solution of Compound 3 (1 g, 4.6 mmol) in ethanol (10 mL) was added NaBH₄ (0.3 g, 7.8 mmol) slowly at 0° C. The reaction mixture was stirred at 0° C. for 0.5 h and the stirred at room temperature for 4 hours. The reaction mixture was quenched with aqueous NH4Cl solution and extracted with AcOEt. The organic layer was dried and concentrated to give the desired product.

1.21.4 Preparation of Compound A111

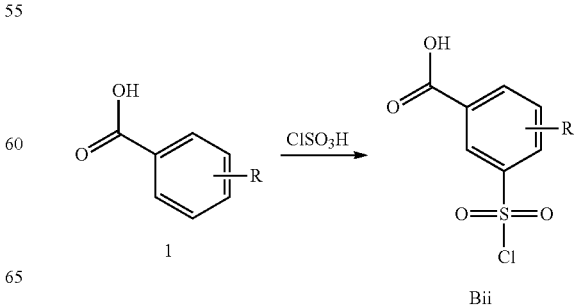

To a solution of compound 4 (0.6 g, 2.7 mmol) in anhydrous DCM (4 mL) was added TFA (4 mL) at 0° C. The formed mixture was stirred for 2 h, and concentrated to give the desired product which was used for the next step (600 mg, 100%).

2 Preparation of Region B Intermediates 2.1 Preparation of B02, 03, 06, 07, 08, 09, 17, 18

B02 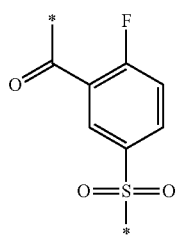

B03 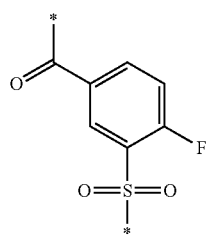

B06 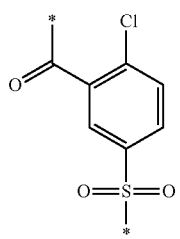

B07 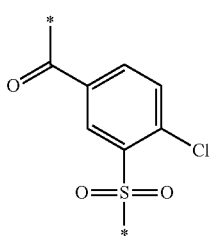

B08 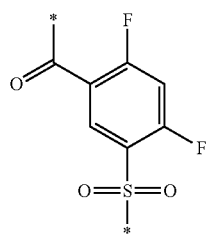

B09 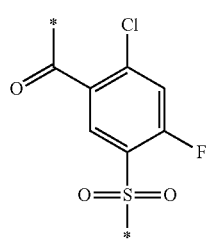

B17 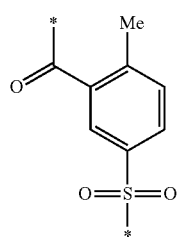

B18 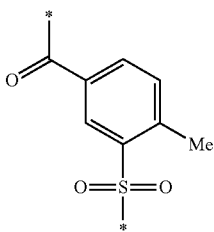

To chlorosulfonic acid (23.8 mL, 350 mmol) cooled to 0° C. was added portionwise 2-fluorobenzoic acid (5 g, 35 mmol). After complete addition, the yellow solution was allowed to warm to room temperature, then heated to 75° C. overnight. The reaction mixture was cooled to room temperature and then added dropwise to ice-water (150 mL). The white precipitate was filtered, washed with water, and dried in vacuo to afford the desired product B02 as a white solid (3.37 g, 40.4%).

B03, 06, 07, 08, 09, 17, 18 were prepared following the same procedure as B02.

B06/07/08/09 were produced under much higher temperature, such as 140-150° C., and longer reaction time, such as 6-12 h.

2.2 Preparation of B11

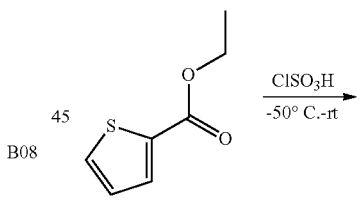

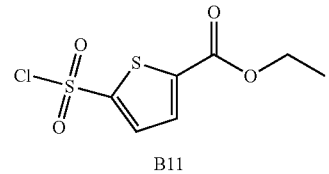

B11

Chlorosulphonic acid (8.5 mL, 130 mmol) was added to a solution of compound 1 (5.0 g, 34 mmol) in DCM (30 mL) at −50 under N2, and stirred at rt overnight. The reaction mixture was then poured into ice water, extracted with DCM, and the organic phase was dried over Na2SO4, and concentrated in vacuo. The residue was purified by chromatography to give a mixture of desired product (1.6 g, containing an 3-position isomeric side product, which was used in the next step without separation).

3 Preparation of Region C Intermediates
3.1 Preparation of C59

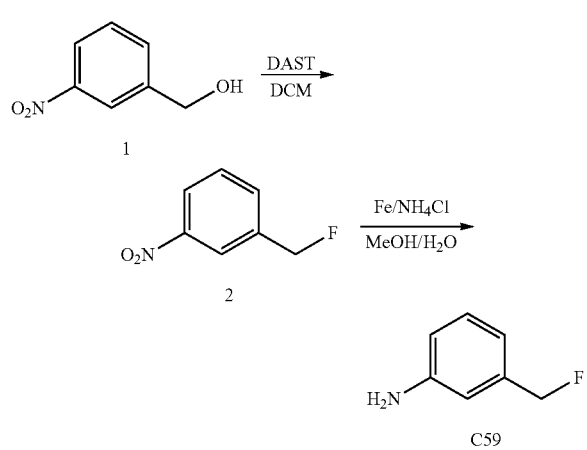

3.1.1 Preparation of Compound 2

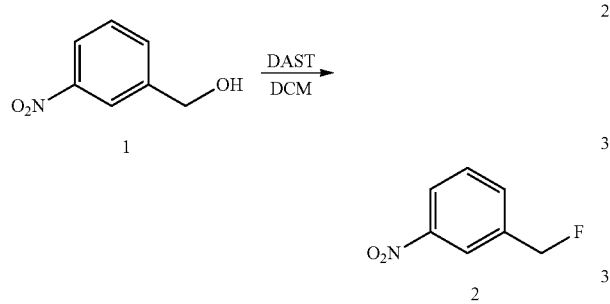

To a solution of Compound 1 (5.0 g, 32.7 mmol) in anhydrous DCM (50 mL) was added DAST (5.5 g, 34.3 mmol) drop-wise at −78° C. under $N_2$. After addition, the reaction mixture is allowed to warm back to rt and poured into a beaker containing 30 g of ice, decomposing any unreacted DAST. The organic layer is separated, and the water layer is extracted twice with 45 mL portions of DCM. The combined organic layer was washed with 50 mL of water, and dried over anhydrous magnesium sulfate. Evaporation to dryness under reduced pressure gives crude product which was purified by silica gel chromatography (eluted with PE:EA=100:1) to afford Compound 2. (3.5 g, yield: 70%)

3.1.2 Preparation of C59

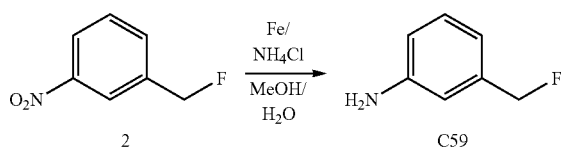 [SMILES: O=[N+]([O-])c1cccc(CF)c1 ; Nc1cccc(CF)c1 ; "C59"]

A solution of Compound 2 (3.5 g, 22.6 mmol), Fe powder (6.3 g, 0.11 mol, 5 eq.) and $NH_4Cl$ (5.9 g, 0.11 mol) in MeOH (40 mL) and water (10 mL) was heated to reflux for 3 h. The mixture was filtered. The filtrate was concentrated in vacuo, and extracted with DCM. The organic phase was concentrated in vacuo, and purified through column chromatography.

3.2 Preparation of C60

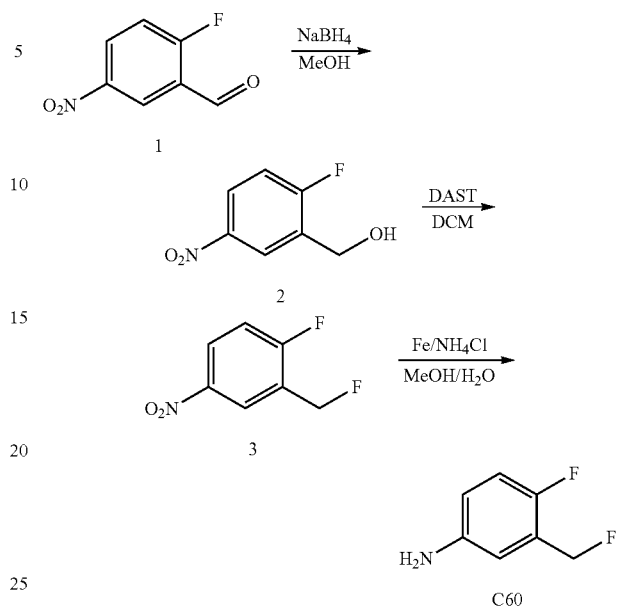

3.2.1 Preparation of Compound 2

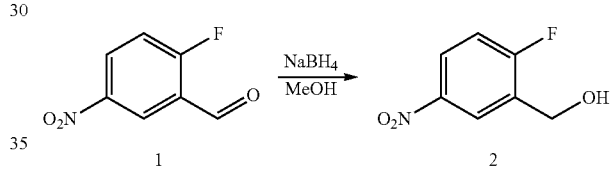

A mixture of Compound 1 (9.6 g, 56.8 mmol) in MeOH (100 mL) was added $NaBH_4$ in portions at 0° C. After addition, the reaction mixture was stirred for 1 h at rt.

The reaction mixture was quenched with 1 N HCl, and concentrated in vacuo. The residue was extracted with EtOAc (100 mL3). The organic layer was concentrated to give the crude product, which was used for the next step directly. (9.8 g, crude)

3.2.2 Preparation of Compound 3

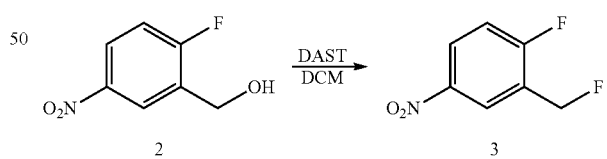

To a solution of Compound 2 (6.2 g, 36.3 mmol) in anhydrous DCM (80 mL) was added DAST (11.7 g, 34.3 mmol) drop-wise at −78° C. under $N_2$. The reaction mixture was stirred at rt for 2 h, and poured into a beaker containing 30 g of ice, decomposing any unreacted DAST. Mixture was extracted twice with 45 mL portions of DCM. The combined organic layer was washed with 50 mL of water, and dried over anhydrous magnesium sulfate. Evaporation to dryness under reduced pressure gives crude product which was purified by silica gel chromatography (eluted with PE:EA=from 100:1 to 50:1) to afford Compound 3. (4.5 g, yield: 71%)

3.2.3 Preparation of C60

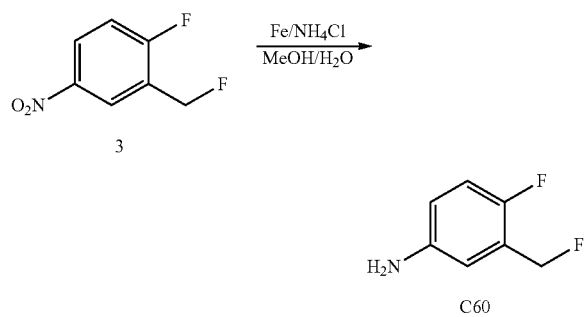

A solution of Compound 2 (4.2 g, 24.3 mmol) Fe powder (7.0 g, 0.12 mol, 5 eq.) and NH₄Cl (6.8 g, 0.12 mol) in MeOH (40 mL) and water (10 mL) was heated to reflux for 3 hours. Filtered, the filtrate concentrated in vacuo to give a solid, which was used for the next step directly.

3.3 Preparation of C61

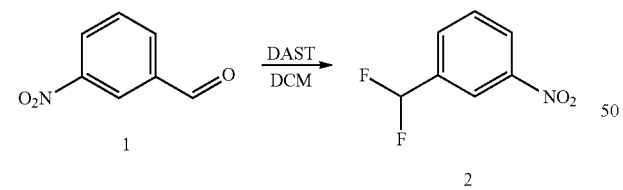

3.3.1 Preparation of Compound 2

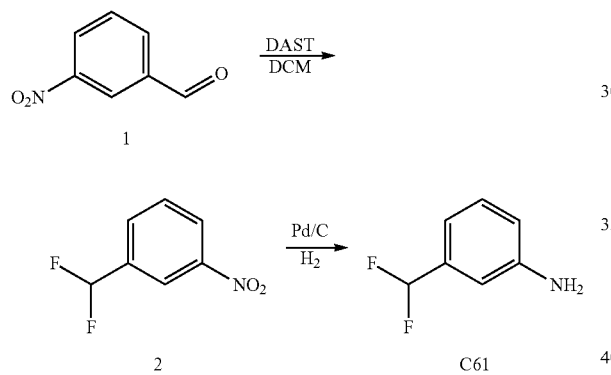

To a solution of Compound 1 (0.5 g, 3.3 mmol) in anhydrous DCM (10 mL) was added DAST (1.3 g, 7.95 mmol) drop-wise at −78° C. under N₂. The reaction mixture was stirred at rt for 2 h, and poured into a beaker containing 5 g of ice, decomposing any unreacted DAST. The mixture was extracted twice with DCM (45 mL). The combined organic layer was washed with 50 mL of water, and dried over anhydrous magnesium sulfate. Evaporation to dryness under reduced pressure gives crude product which was purified by silica gel chromatography (eluted with PE:EA=100:1) to afford Compound 2 (0.45 g, yield: 79%).

3.3.2 Preparation of C61

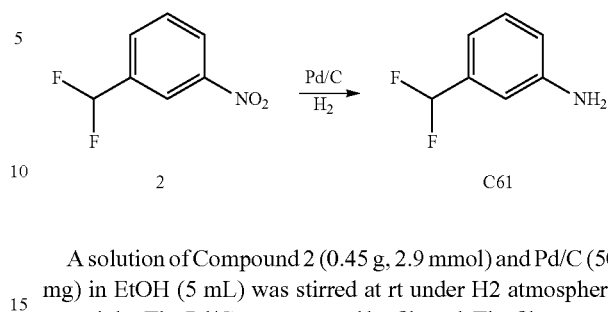

A solution of Compound 2 (0.45 g, 2.9 mmol) and Pd/C (50 mg) in EtOH (5 mL) was stirred at rt under H2 atmosphere overnight. The Pd/C was removed by filtered. The filtrate was concentrated in vacuo to give the desired product, which was used for the next step directly.

3.4 Preparation of C62

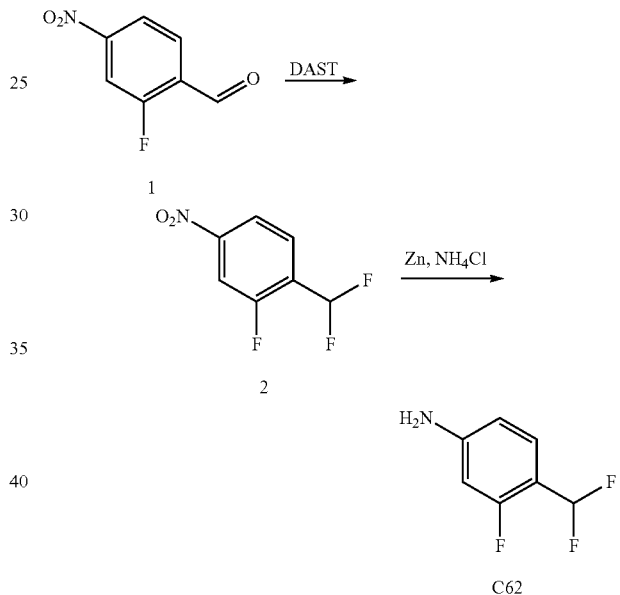

3.4.1 Preparation of Compound 2

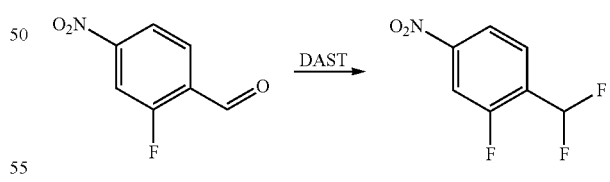

To a solution of compound 1 (3.0 g, 17.8 mmol) in anhydrous DCM (50 ml) was added DAST (6.3 g, 39.0 mmol) at 0° C. under N₂. The formed mixture was stirred at rt for 2 h, quenched by saturated NaHCO₃ solution, and diluted with EA (100 mL). The organic layer was separated, dried over Na₂SO₄ and concentrated under reduced pressure. The residue was purified by flash column chromatograph on silica gel (PE:EA 5:1 to 3:1) to give compound 2 (3.2 g, 94.1%).

3.4.2 Preparation of C62

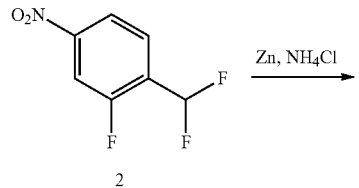

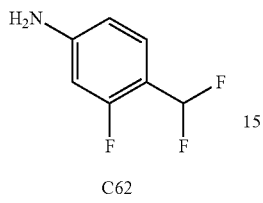

A solution of compound 2 (3.2 g, 16.8 mmol), Zn ((10.9 g, 168 mmol), and NH4Cl (9.0 g, 168 mmol) was stirred in water (20 mL) and methanol (50 mL) at 50° C. for 4 h. The mixture was filtrated, and concentrated under vacuum. The residue was purified by silica gel chromatography to give desired product (2.6 g, 96.3%). LCMS: 162 [M+1].

3.5 Preparation of C58

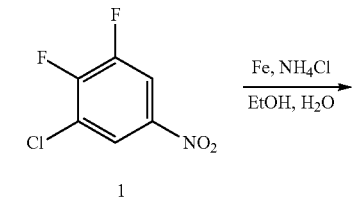

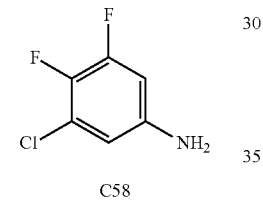

A solution of Compound 1 (5.0 g, 25.83 mmol), Fe powder (14.47 g, 258.3 mmol, 10 eq.) and NH₄Cl (13.95 g, 258.3 mmol) in EtOH (80 mL) and water (10 mL) was heated to reflux for 3 h. The reaction mixture was filtered and concentrated. The residue was dissolved in water (50 mL) and extracted with ethyl acetate (50 mL2). The organic layer was dried and concentrated to give the product used in the next step directly. LCMS: 164 [M+1].

3.6 Preparation of C64/65

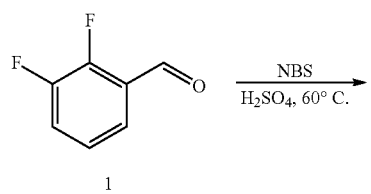

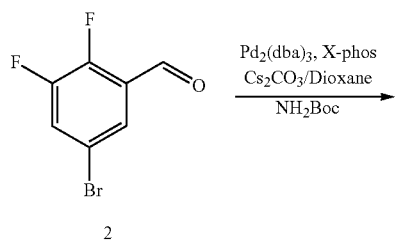

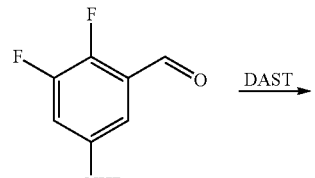

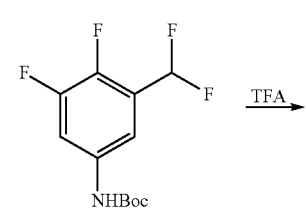

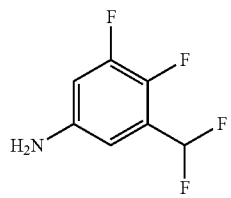

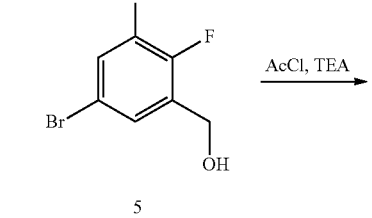

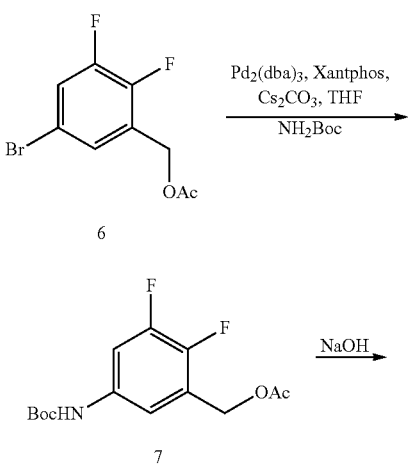

-continued

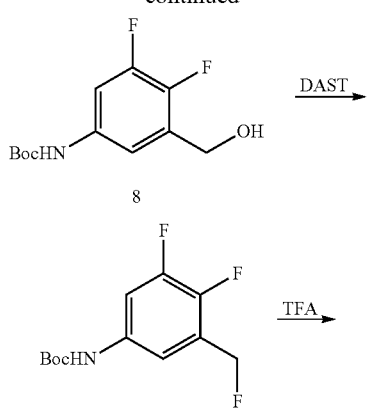

3.6.1 Preparation of Compound 2

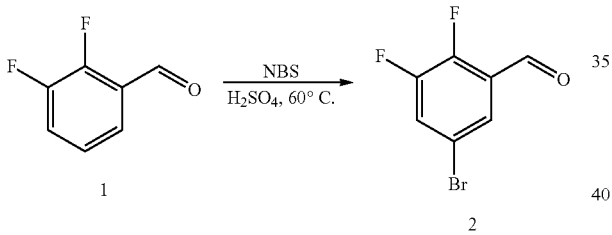

Compound 1 (5.0 g, 3.5 mmol) was dissolved in concentrated H₂SO₄ (16 mL) and heated to 60° C. N-bromosuccinimide (7.5, 4.2 mmol) was added in three portions over a period of 30 min. After being heated for 3 h under N₂, the reaction mixture was poured into ice water. The product was extracted with EtOAc, washed with water and brine, and dried over Na₂SO₄. Purification by silica gel column chromatography (0-10% EtOAc in PE) yielded an orange liquid as product 2 in 45% yield. ¹H NMR (400 MHz, CDCl₃) δ 10.31 (d, 1H, J=1.2 Hz), 7.80-7.99 (m, 1H), 7.64-7.60 (m, 1H).

3.6.2 Preparation of Compound 3

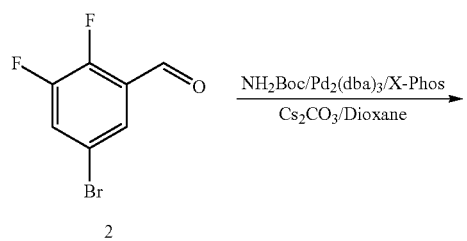

-continued

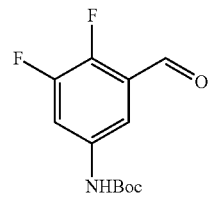

A mixture of compound 2 (1.0 g, 4.5 mmol), NH₂Boc (660 mg, 5.7 mmol), Cs₂CO₃ (2.05 g, 6.3 mmol), Pd₂(dba)₃ (124 mg, 0.135 mmol) and X-Phos (193 mg, 0.405 mmol) in 30 mL of dioxane was heated to 100° C. overnight. After cooling to rt, the aqueous was extracted with EA for three times. The organic layer was washed with water and brine, dried over Na₂SO₄, filtered and evaporated to give crude product, which was purified by silica gel column chromatography (0-10% EtOAc in PE) to give 3 (300 mg, 13%). LCMS: 258 [M+1].

3.6.3 Preparation of Compound 4

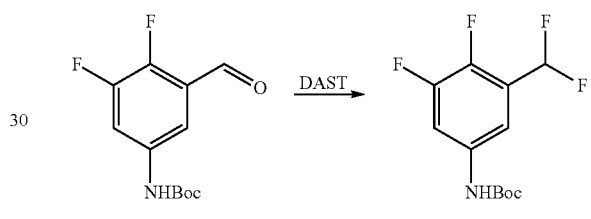

To a solution of Compound 3 (500 mg, 1.95 mmol) in anhydrous DCM (10 mL), was added DAST (1.25 g, 7.78 mmol, 4.0 eq) dropwise at −78° C. under N₂. After addition, the solution was warmed to rt gradually and stirred for 2 h. The mixture was quenched with saturated NaHCO₃ (30 mL), extracted with DCM (10 mL3). The combined the organic phase was washed with brine, dried over Na₂SO₄ and concentrated in vacuo to afford desired product 4 (380 mg, 70%). LCMS: 280.1 [M+1].

3.6.4 Preparation of C64

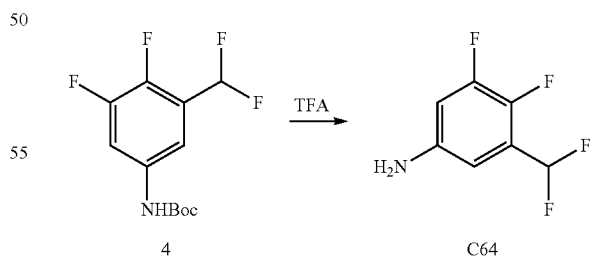

To a solution of Compound 4 (280 mg, 1.0 mmol) in DCM (5 mL) was added TFA (5 ml). The formed mixture was stirred overnight at room temperature. The reaction mixture was concentrated to give the crude product G (145 mg, 81%). ¹H NMR (400 MHz, CDCl₃) δ 6.94-6.67 (t, 1H), 5.58-6.54 (m, 2H), 3.75 (br, 2H) LCMS: 180.1 [M+1].

3.6.5 Preparation of Compound 5

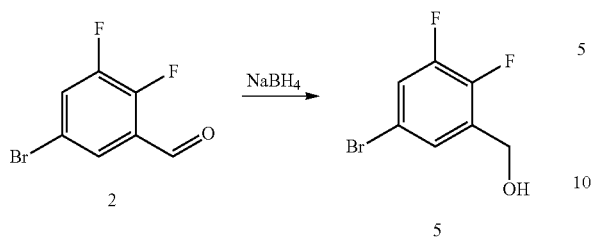

To a solution of compound 2 (1.0 g, 3.5 mmol) in MeOH (20 mL) was added NaBH$_4$ (200 mg, 5.0 mmol) slowly at 0° C. The reaction mixture was stirred at 0° C. for 0.5 h and then stirred at RT for 2 h. The reaction mixture was quenched with 1N HCl (20 mL) and concentrated in vacuo. The residue was extracted with DCM (30 mL3). The organic layer was dried and concentrated to give the product 5 (1.05 g, crude).

3.6.6 Preparation of Compound 6

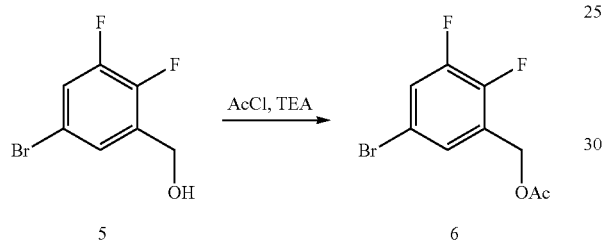

To a solution of Compound 5 (2.0 g, 9.0 mmol) and TEA (1.36 g, 13.5 mmol) in anhydrous THF (20 mL), AcCl (0.85 g, 10.8 mmol) was added dropwise at 0° C. After addition, the solution was allowed to warm to rt, and stirred for 2 h. The reaction was dissolved with EtOAc (100 mL), washed with 1 N HCl, 5% NaOH and brine, dried over Na$_2$SO$_4$ and concentrated in vacuo to afford desired product 6 (2.3 g, 96%). LCMS: 265/267 [M+1].

3.3.7 Preparation of Compound 7

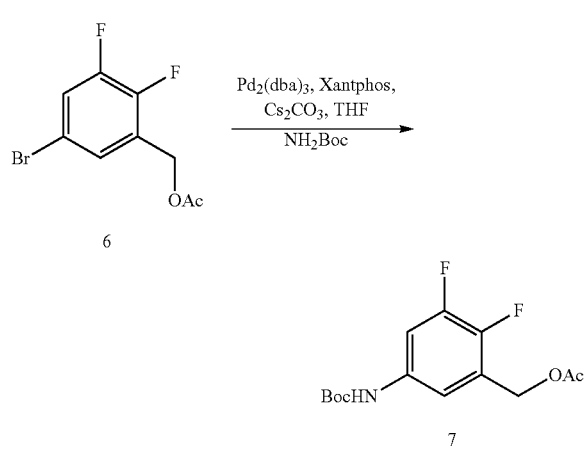

A mixture of Compound 6 (6.0 g, 22.3 mmol), NH$_2$Boc (3.3 g, 27.9 mmol, 1.2 eq.), Cs$_2$CO$_3$ (10.2 g, 31.2 mmol), Pd$_2$(dba)$_3$ (613 mg, 0.7 mmol, 3%) and Xant-Phos (955 mg, 2.01 mmol, 9%) in 200 mL of dioxane was heated to 100° C. for overnight. After cooling to rt, the mixture was filtered, and the filterate was concentrated in vacuo. The residue was purified by silica gel column chromatography (0-10% EtOAc in PE) to afford 7 (4.5 g, 66% yield). LCMS: 302 [M+1].

3.3.8 Preparation of Compound 8

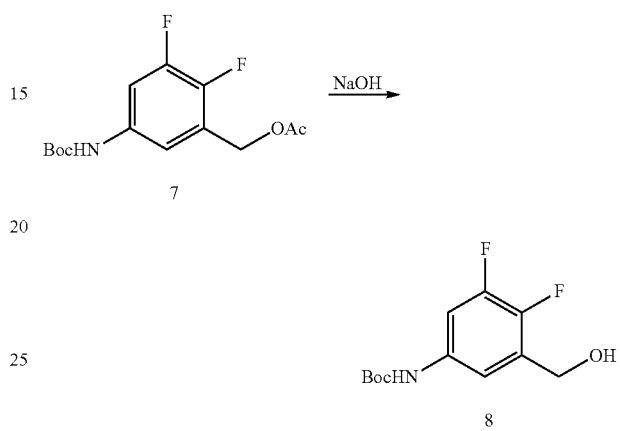

To a solution of Compound 7 (490 mg, 1.63 mmol) in THF (50 mL) was added aqueous solution of NaOH (80 mg, 2.0 mmol, 10%), and stirred overnight at rt. The reaction mixture was acidified by 1N HCl solution and concentrated in vacuo. The residue was extracted with EA. The organic layer was washed with water and brine, dried over Na$_2$SO$_4$ and concentrated in vacuo to afford desired product 8 (380 mg, 90%).

$^1$H NMR (400 MHz, CDCl$_3$) δ 7.38-7.33 (m, 1H), 7.07-7.05 (m, 1H), 4.75 (s, 2H), 1.51 (s, 9H). LCMS: 260 [M+1].

3.3.9 Preparation of Compound 9

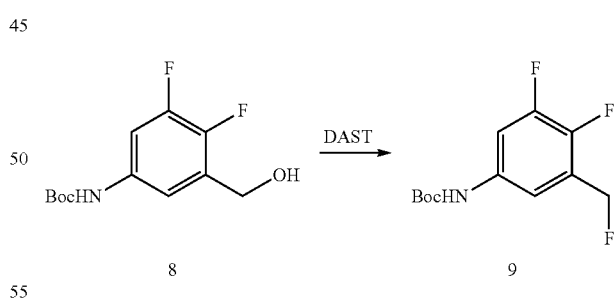

To a solution of Compound 8 (380 mg, 1.47 mmol) in anhydrous DCM (5 mL), DAST (473 mg, 2.94 mmol, 2.0 eq) was added dropwise at −78° C. under N$_2$. After addition, the solution was warmed to rt gradually and stirred for 2 h. The reaction mixture was poured into sat. NaHCO$_3$ (20 mL) at 0° C., extracted with DCM (10 mL3). The combined organic phase was washed with brine, dried over Na$_2$SO$_4$, and concentrated to afford desired product 9 (370 mg, 96%). LCMS: 262 [M+1].

3.3.10 Preparation of C65

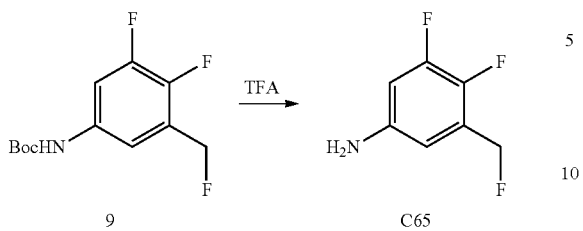

To a solution of Compound 9 (370 mg, 1.7 mmol) in DCM (5 mL) was added TFA (5 mL). The formed mixture was stirred overnight at rt. The reaction mixture was concentrated in vacuo to give the crude product C65 (130 mg, 58%). $^1$H NMR (400 MHz, CDCl$_3$) δ 6.42-6.38 (m, 2H), 5.38 (d, J=1.2 Hz, 1H), 5.26 (d, 2H, J=1.2 Hz) LCMS: 162 [M+1].

Part II General Procedure for Targets

General Procedure A

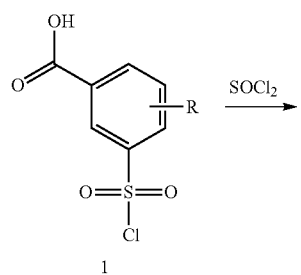

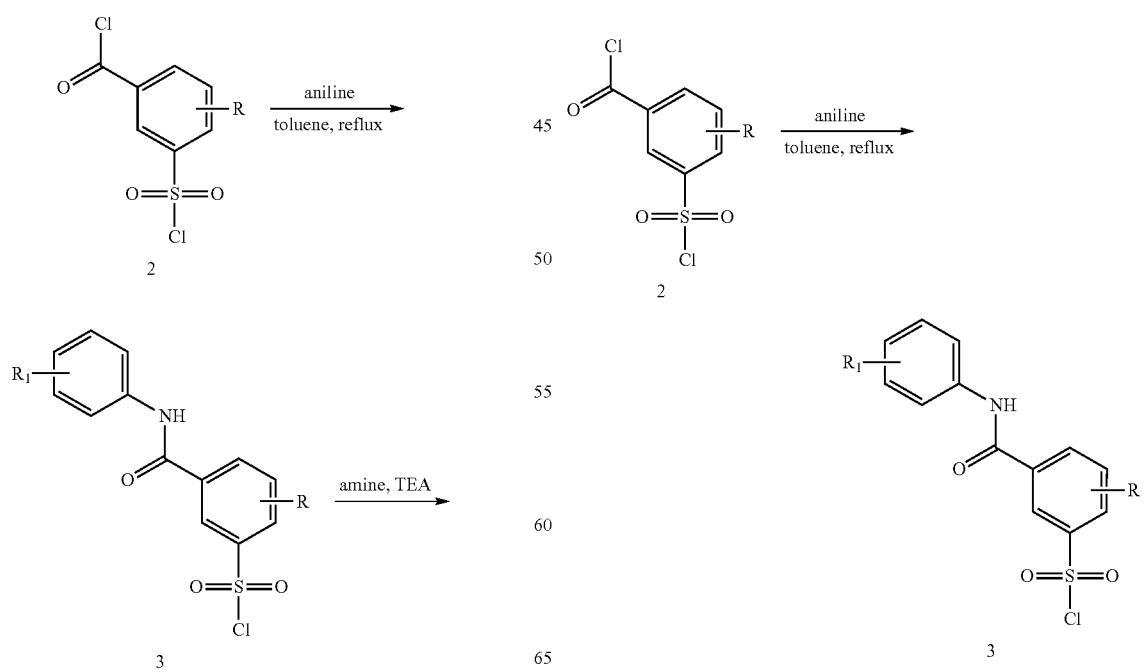

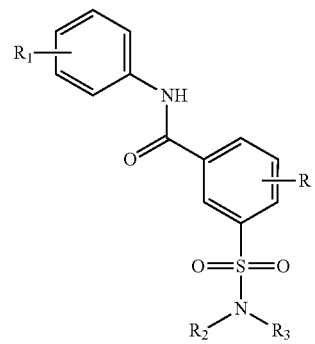

1.1 General Procedure for Preparation of Compound 2

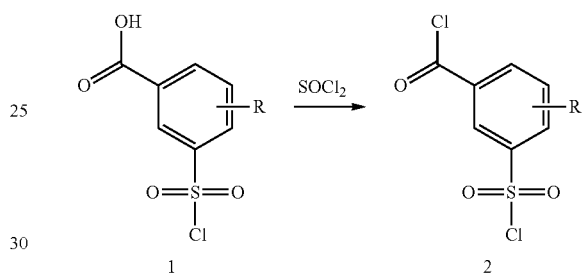

A mixture of Compound 1 (4.53 mmol) in SOCl$_2$ (10 mL) was heated to reflux overnight. The mixture was concentrated to give the crude product, which was used for the next step directly.

1.2. General Procedure for Preparation of Compound 3

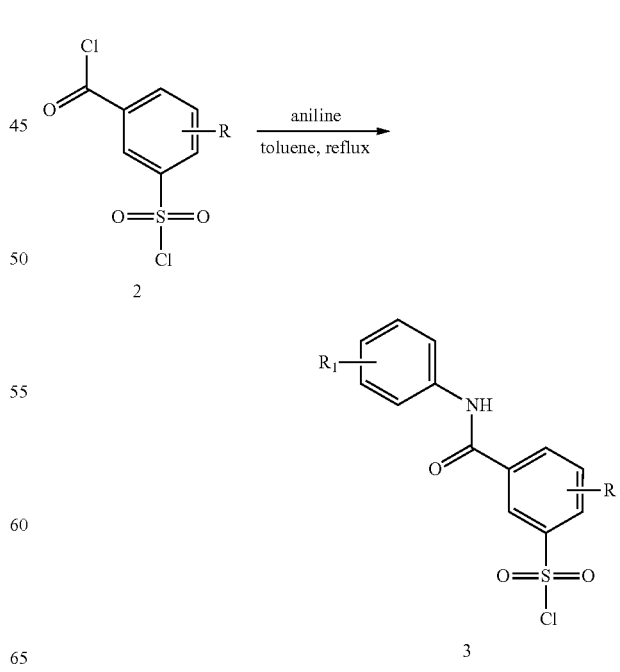

To a boiled solution of Compound 2 (1.08 g, 4.52 mmol) in toluene (10 mL) was added aniline (4.52 mmol), and refluxed for 2 h. The mixture was concentrated in vacuo to give a solid, which was used for the next step directly.

1.3 General Procedure for Preparation of iii

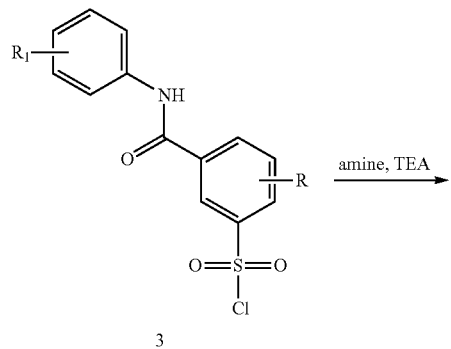

-continued

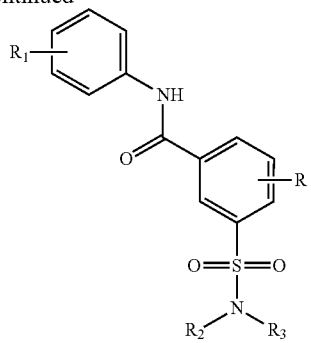

NVR_003_iii

To a solution of Compound 3 (0.3 mmol) in $CH_2Cl_2$ (3 mL) was added amine (0.3 mmol) and $Et_3N$ (30 mg, 0.33 mmol) at rt, and the mixture was stirred at rt for 2 h. The mixture was diluted with $CH_2Cl_2$ (20 mL) and washed with water. The organic phase was concentrated in vacuo to give the crude product, which was purified by prep-HPLC to give the desired product.

General Procedure B

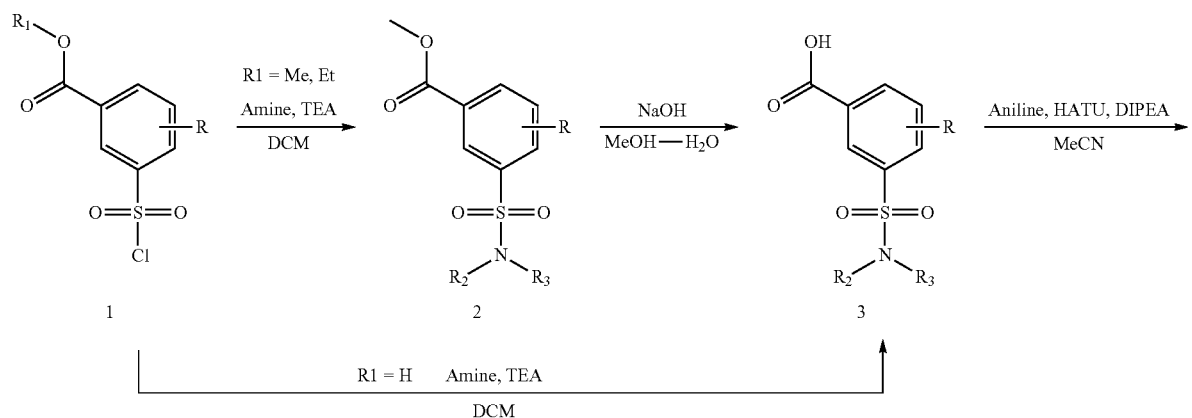

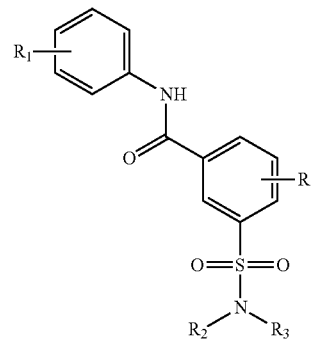

NVR_003_iii

1.1 General Procedure for Preparation of Compound 2

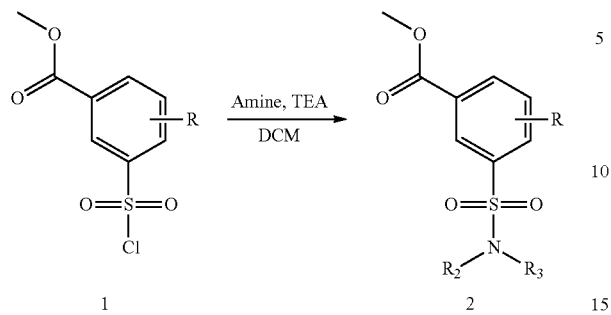

To a solution of Compound 1 (10 mmol) in $CH_2Cl_2$ (50 mL) was added amine (10 mmol) and TEA (11 mmol), and stirred at rt overnight. The mixture was washed with 1 N HCl and saturated $NaHCO_3$, and concentrated in vacuo. The residue was purified by chromatography to give the desire product.

1.2 General Procedure for Preparation of Compound 3

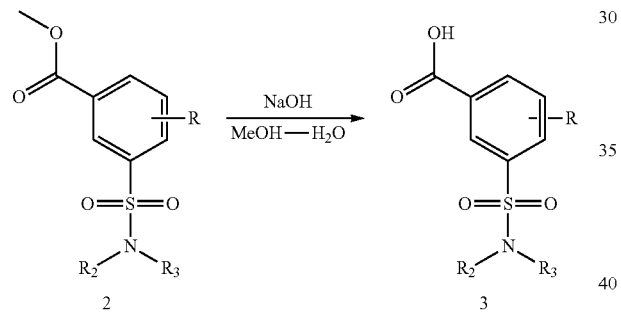

To a solution of Compound 2 (5 mmol) in MeOH (40 mL) was added an aqueous solution of NaOH (7 mmol, 1N), and stirred at rt overnight. The reaction mixture was acidified by 1N HCl solution to pH 6 and extracted with DCM. The combined organic phase was concentrated in vacuo to give the product.

1.3 General Procedure for Preparation of iii

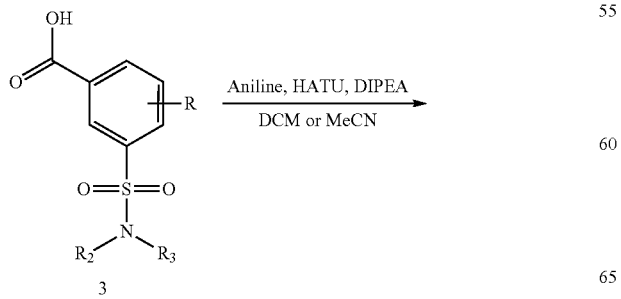

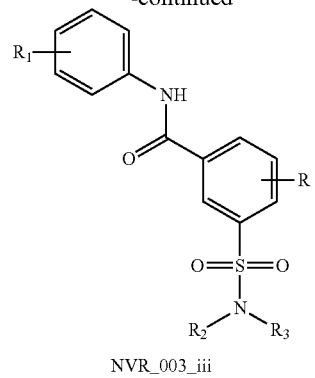

To a solution of Compound 3 (1 mmol) and aniline (1 mmol) in DCM (10 mL) was added HATU (1.1 mmol), followed by DIPEA (1.5 mmol). The formed mixture was stirred at rt overnight. The mixture was diluted with $CH_2Cl_2$ (20 mL) and washed with water. The organic layer was concentrated to give the crude product, which was purified by preparative HPLC to give the desired product.

General Procedure C

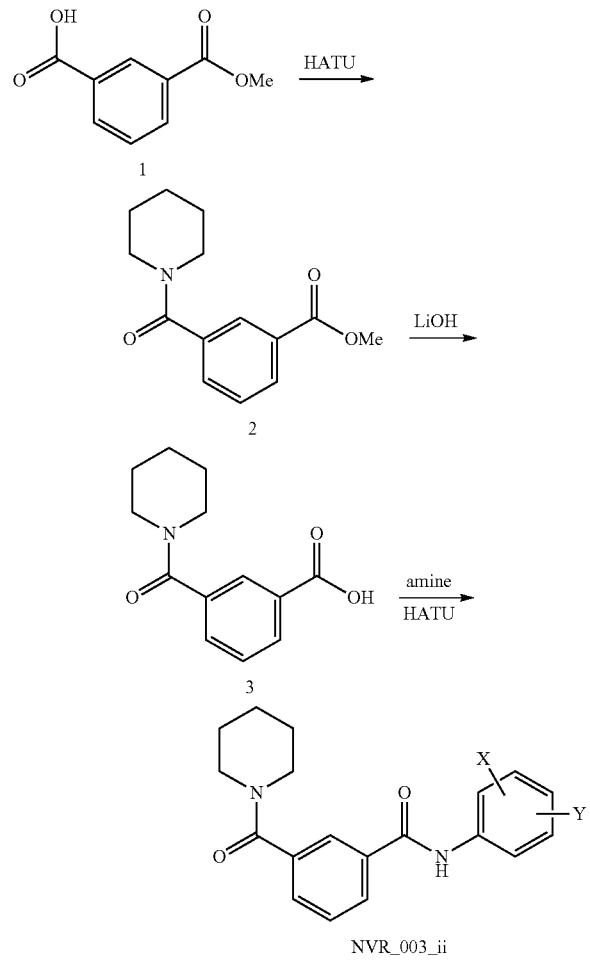

1.1 General Procedure for Preparation of Compound 2

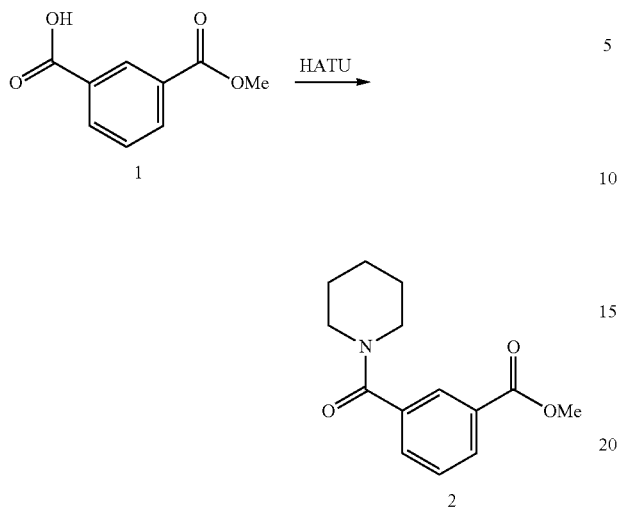

To a solution of Compound 1 (1.80 g, 10 mmol) and piperidine (2.1 g, 25 mmol) in DCM (50 mL) was added HATU (3.8 g, 10 mmol) a at rt. The formed mixture was stirred overnight. The mixture was washed with 1N HCl, NaOH (5%) and brine, and concentrated in vacuo to give the desired product (2.1 g, 85%). LCMS: 248 [M+1].

1.2 General Procedure for Preparation of Compound 3

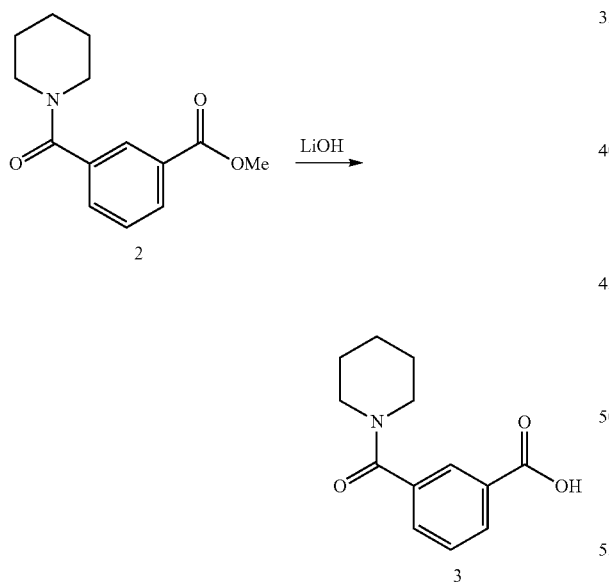

To a solution of methyl Compound 2 (2.1 g, 8.5 mmol) in CH$_3$OH (40 mL) and H2O (10 mL) was added LiOH H$_2$O (0.6 g, 15 mmol). The formed mixture was stirred overnight. The resulting mixture was acidified by 1N HCl and concentrated in vacuo. The residue was extracted DCM. The combined organic phase was concentrated in vacuo to give the crude product, which was used for the next step directly (1.7 g, 86%). LCMS: 234 [M+1].

1.3 General Procedure for Preparation of iii

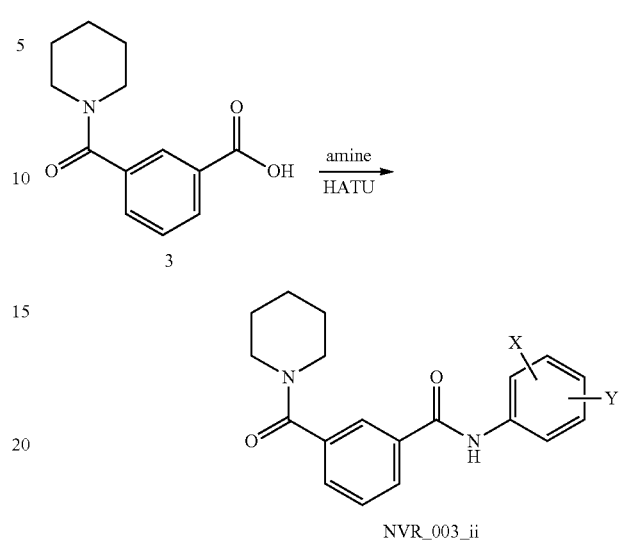

To a solution of Compound 3 (0.3 mmol), amine (0.3 mmol) and Et$_3$N (30 mg, 0.33 mmol) in CH$_2$Cl$_2$ (3 mL) was added HATU (0.33 mmol), and the mixture was stirred at rt for 2 h. The mixture was diluted with CH$_2$Cl$_2$ (20 mL) and washed with water. The organic phase was concentrated in vacuo to give the crude product, which was purified preparative HPLC to give the desired product.

General Procedure D

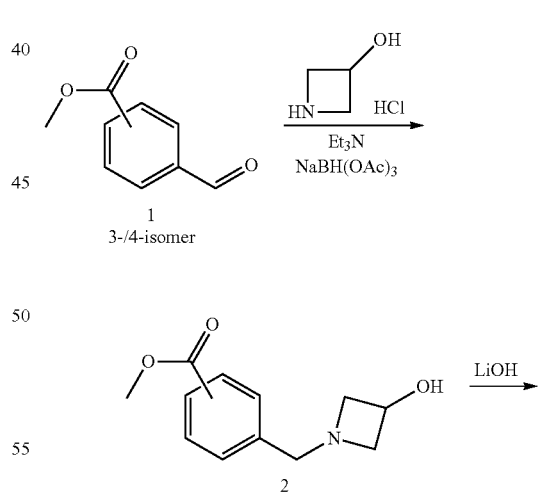

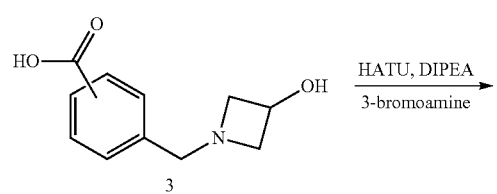

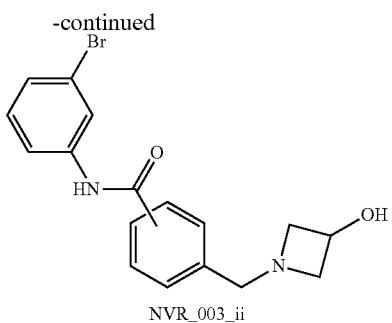

NVR_003_ii

1.1 General Procedure for Preparation of Compound 2

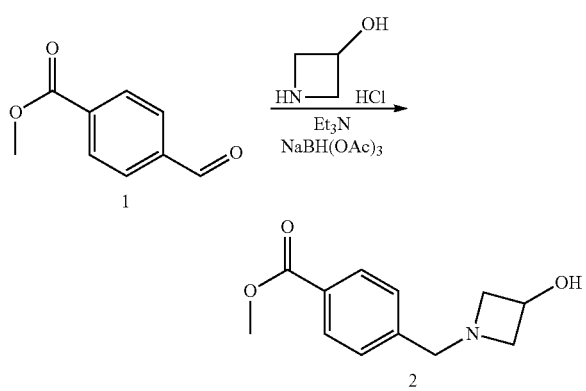

To a solution of methyl 4-formylbenzoate (150 mg, 0.914 mmol), azetidin-3-ol hydrochloride (120 mg, 1.10 mmol) and Et₃N (111 mg, 1.10 mmol) in CH₂Cl₂ (3 mL) was added NaBH(OAc)₃ (580 mg, 2.74 mmpl). The formed mixture was stirred at rt overnight. The reaction was quenched by NaHCO₃ solution, and the formed mixture was extracted with CH₂Cl₂ (10 mL×3). The organic layer was concentrated to give the crude product, which was purified preparative TLC to give the desired product (150 mg, 74%). $^1$H NMR (400 MHz, CDCl₃): δ ppm: 7.97 (d, 2H), 7.34 (d, 2H), 3.89 (s, 3H), 3.68 (s, 2H), 3.63 (m, 2H), 3.04 (m, 2H).

1.2 General Procedure for Preparation of Compound 3

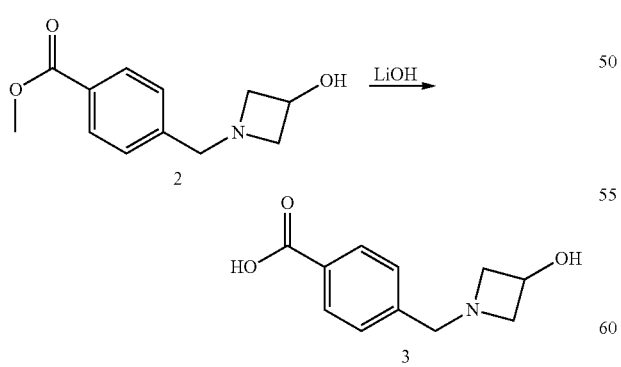

To a solution of methyl 4-((3-hydroxyazetidin-1-yl)methyl)benzoate (150 mg, 0.68 mmol) in CH₃OH (3 mL) and H₂O (1 mL) was added LiOH H₂O (57 mg, 1.36 mmpl). The formed mixture was stirred overnight. The resulting mixture was acidified by 1N HCl and concentrated in vacuo. The residue was extracted DCM. The combined organic phase was concentrated in vacuo to give the crude product, which was used for the next step directly (150 mg, crude).

1.3 General Procedure for Preparation of iii

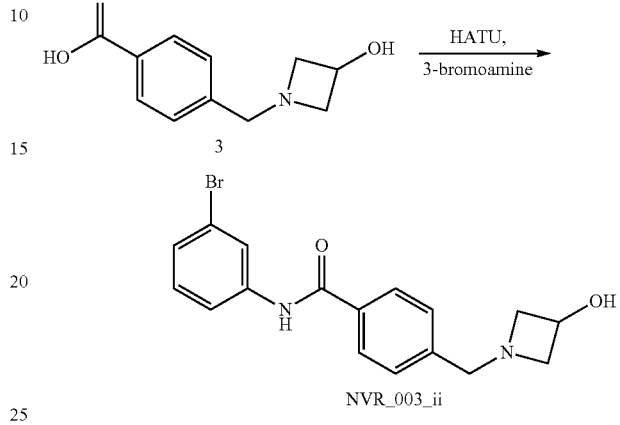

NVR_003_ii

To a solution of ((3-hydroxyazetidin-1-yl)methyl)benzoic acid (150 mg, 0.723 mmol) and 3-bromoamine (187 mg, 1.09 mmol) in DMF (3 mL) was added HATU (413 mg, 1.09 mmol) and DIEA (187 mg, 1.45 mmol) at rt. The formed mixture was stirred overnight. The mixture was diluted with CH₂Cl₂ (20 mL) and washed with water (5 mL×2). The organic layer was concentrated to give the crude product, which was purified preparative HPLC to give the desired product (15 mg, 6%). $^1$H NMR (400 MHz, CDCl₃): δ ppm: 11.03 (br, 1H), 10.49 (s, 1H), 8.11 (s, 1H), 7.98 (d, 2H), 7.75 (m, 1H), 7.67 (d, 2H), 7.29 (m, 2H), 4.45 (m, 3H), 4.16 (m, 2H), 3.87 (m, 2H). LCMS: 361/363 [M+1/M+1+2].

General Procedure E

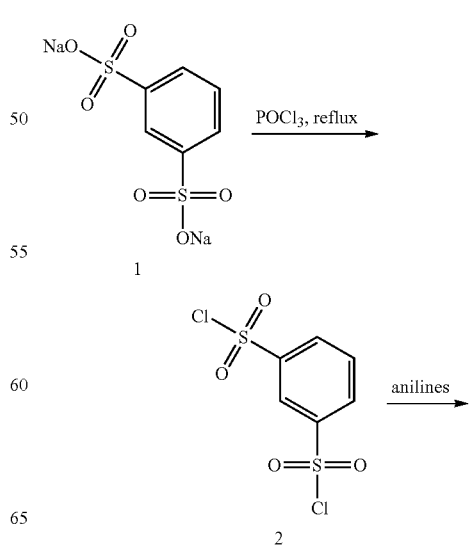

-continued

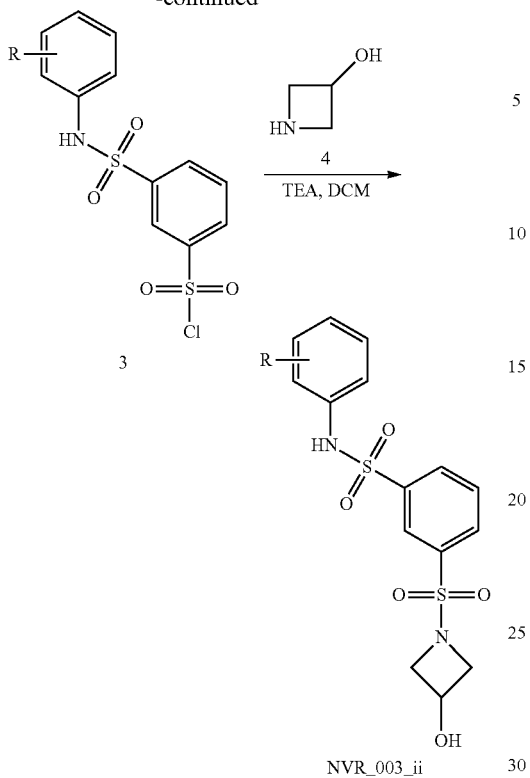

NVR_003_ii

1.1 General Procedure for Preparation of Compound 2

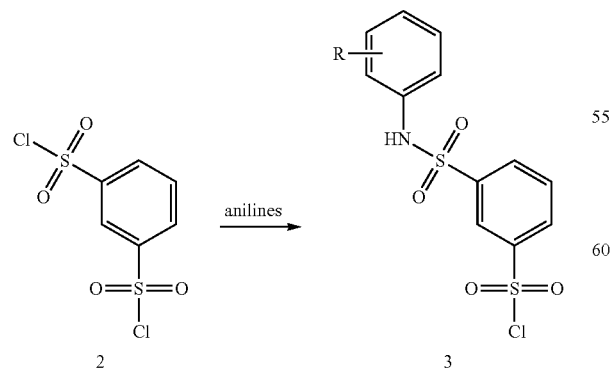

Compound 1 (1.0 g, 3.54 mmol) was dissolved in 10 g (65.22 mmol) of POCl₃, then, the mixture was warmed to 100° C. and stirred for overnight. Solvent was evaporated in vacuo and the residue was prepared for next step.

1.2 General Procedure for Preparation of Compound 3

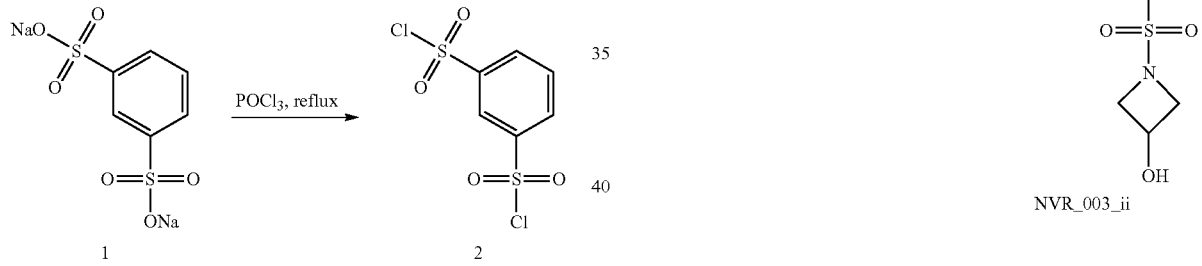

To a solution of compound 2 (138 mg, 050 mmol) in 5 mL of DCM, aniline (0.55 mmol) and Et₃N (51 mg, 050 mmol) was added. The mixture was stirred at rt for overnight. Water was added to the mixture and extracted with DCM, the organic layer was washed with brine, dried over Na₂SO₄, filtered and solvent was evaporated in vacuo. The residue was prepared for next step.

1.3 General Procedure for Preparation of iii

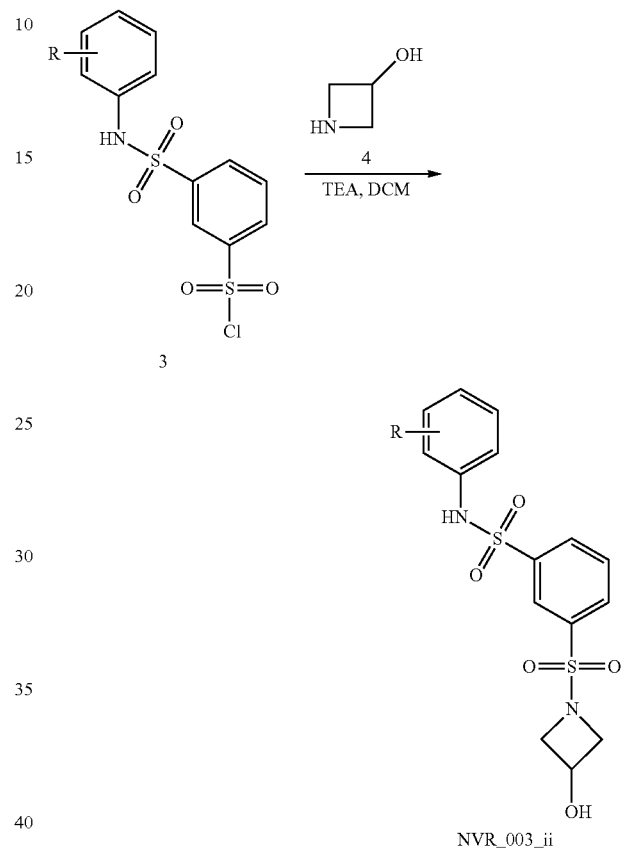

NVR_003_ii

To a solution of Compound 3 (0.3 mmol) in CH₂Cl₂ (3 mL) was added amine (0.3 mmol) and Et₃N (30 mg, 0.33 mmol) at rt, and the mixture was stirred at rt for 2 h. The mixture was diluted with CH₂Cl₂ (20 mL) and washed with water. The organic phase was concentrated in vacuo to give the crude product, which was purified preparative HPLC to give the desired product.

General Procedure F

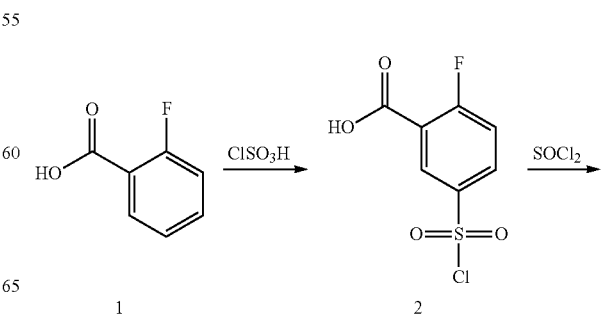

533
-continued
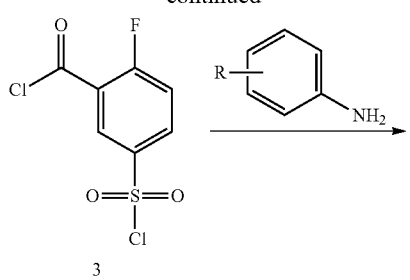
3
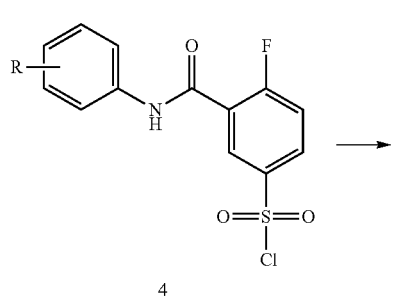
4
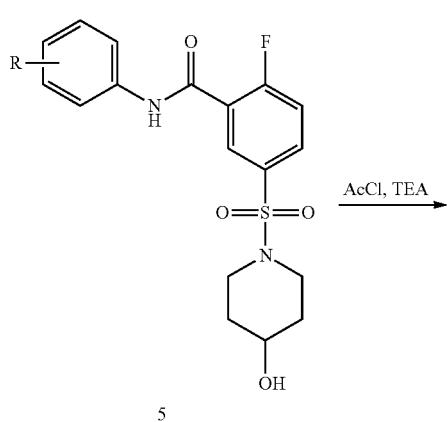
5
AcCl, TEA →
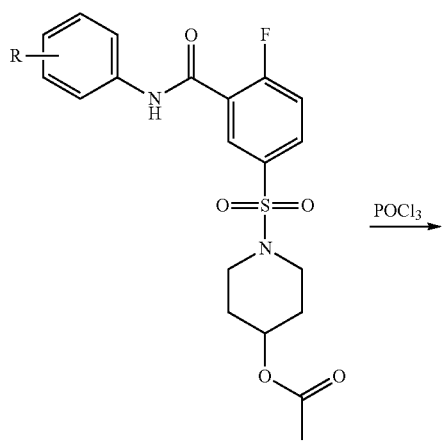
6
POCl₃ →
534
-continued
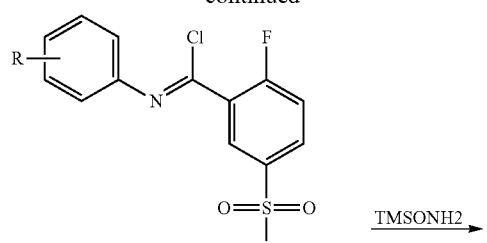
7
TMSONH2 →
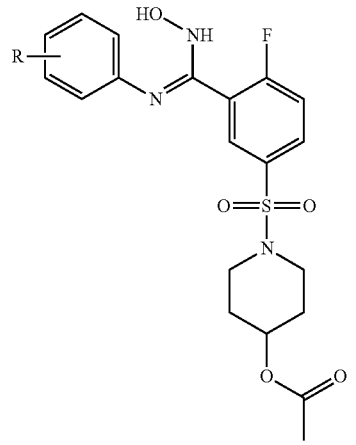
8
t-BuOK / NMP/100° C. →
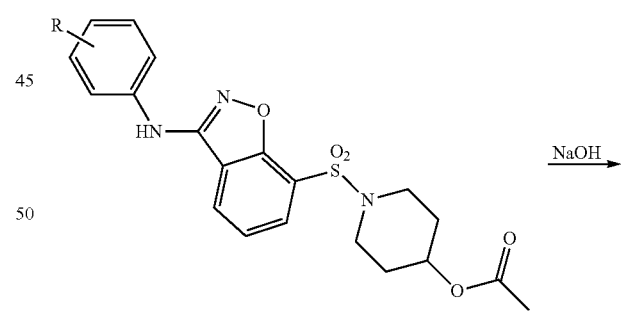
9
NaOH →
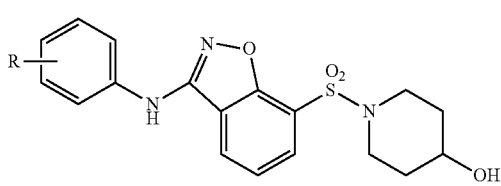
NVR_003_737/738

1.1 Preparation of Compound 2

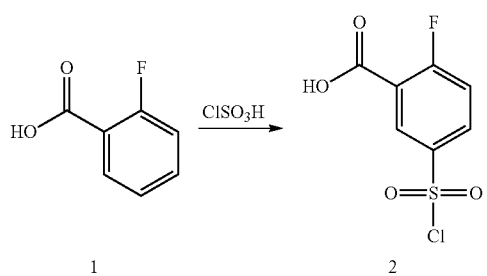

To chlorosulfonic acid (65 g, 0.56 mol) cooled to 0° C. was added portionwise Compound 1 (10.2 g, 73 mmol). After complete addition, the yellow solution was warmed to room temperature, then heated to 70° C. overnight. The reaction mixture was cooled to room temperature and then added drop-wise to ice (0.5 L). The white precipitate was filtered, washed with water, and dried in vacuo to afford the desired product as a white solid (13.7 g, 80%).

1.2 Preparation of Compound 3

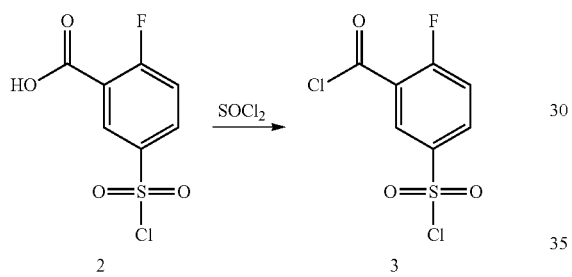

A mixture of Compound 2 (13.7 g, 57.6 mmol) in SOCl$_2$ (60 mL) was heated to reflux overnight. The mixture was concentrated to give the crude product, which was used for the next step directly.

1.3 Preparation of Compound 4

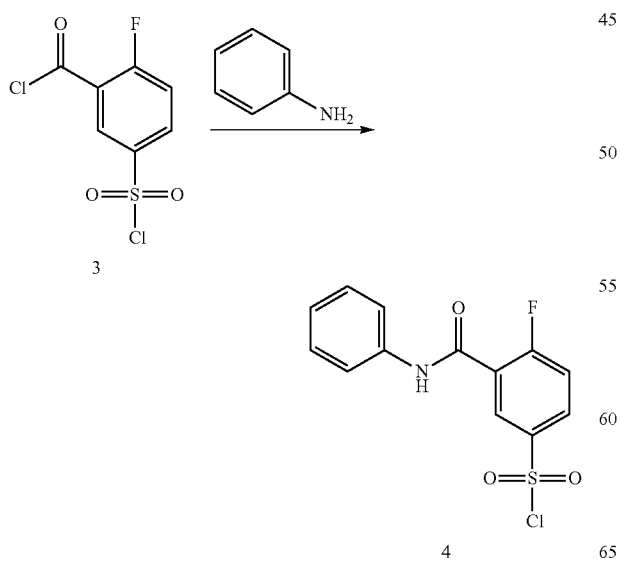

To a boiled solution of compound 3 (5.5 g, 21 mmol) in anhydrous toluene (50 mL) was added a solution of aniline (2.0 mg, 21 mmol). The formed mixture was stirred for another 30 minutes. The mixture was allowed to cool to room temperature, and diluted with EtOAc (50 mL). The mixture was washed with ice-water (20 mL). The organic layer was concentrated to give the desired product, which was used for the next step directly (7.0 g, 67%).

1.4 Preparation of Compound 5

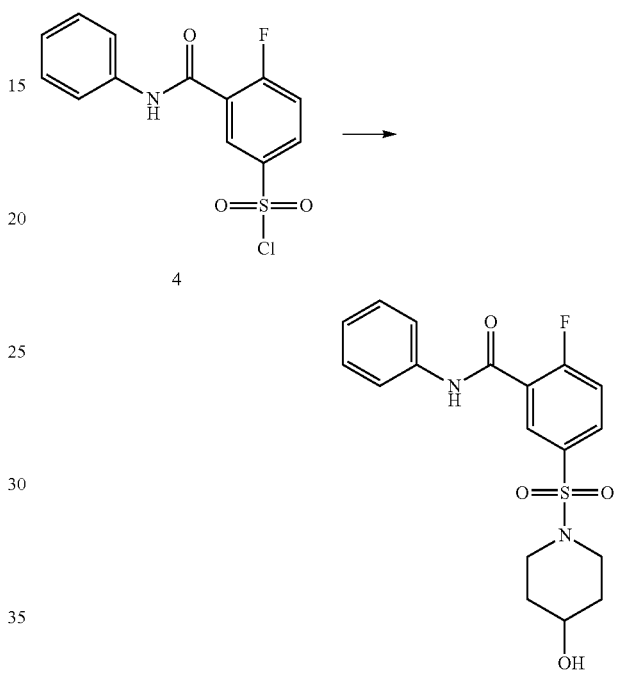

To a solution of Compound 4 (7.0 g, 22 mmol) in dry CH$_2$Cl$_2$ (80 mL) was added piperidin-4-ol (2.2 g, 22 mmol) and Et$_3$N (3 mL) at rt. The formed mixture was stirred overnight. The mixture was diluted with CH$_2$Cl$_2$ (100 mL) and washed with water (50 mL 2). The organic layer was concentrated to give the crude product, which was purified by silica chromatography gel to give the desired product (4.5 g, 53%).

1.5 Preparation of Compound 6

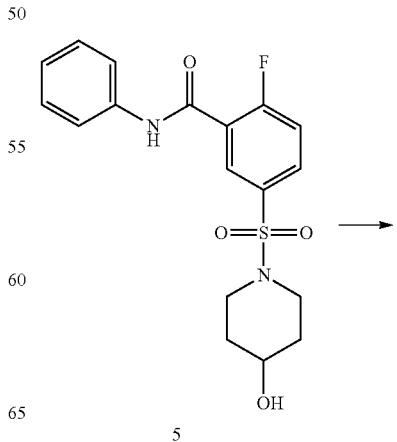

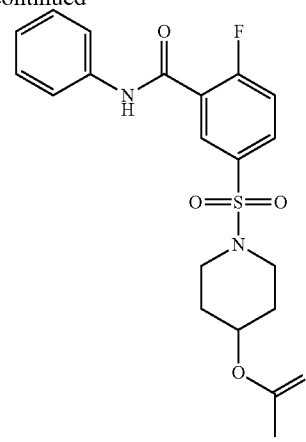

6

To a solution of Compound 5 (4.5 g, 12.1 mmol) in CH$_2$Cl$_2$ (50 mL) was added Et$_3$N (2.5 mL), followed by CH$_3$COCl (1.2 g, 12.1 mmol) at 0° C. The formed mixture was stirred overnight at room temperature. The mixture was washed with aqueous Na$_2$CO$_3$ solution, and the aqueous layer was acidified by 1N HCl. The formed mixture was extracted with CH$_2$Cl$_2$ (100 mL 3). The combined organic layers were concentrated to give crude product which was purified by silica chromatography gel to give the desired product (3.0 g, 60%).

1.6 Preparation of Compound 7

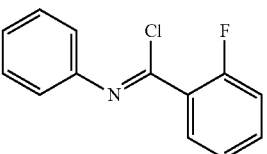

6

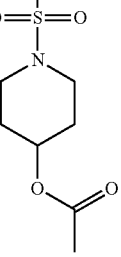

7

A solution of Compound 6 (310 mg, 0.73 mmol) in POCl$_3$ (3.5 mL) was heated to 80° C. for 3 hours. The organic layer was concentrated to give the desired product, which was used for the next step directly (340 mg, crude)

1.7 Preparation of Compound 8

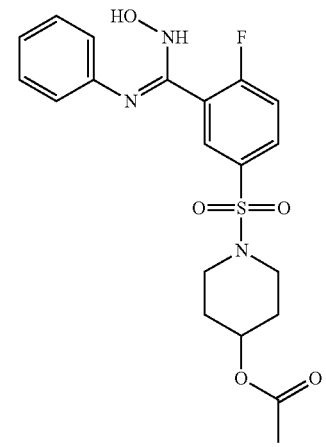

8

To a solution of Compound 7 (340 mg, 0.73 mmol) in anhydrous THF (5 mL) was added O-(trimethylsilyl)hydroxylamine (94 mg, 0.9 mmol) drop-wise at 0° C. The formed mixture was stirred overnight at room temperature. The mixture was washed with 1N HCl solution, and the aqueous layer was acidified by aqueous Na$_2$CO$_3$. The formed mixture was extracted with CH$_2$Cl$_2$ (10 mL 3). The combined organic layers were concentrated to give crude product. (360 mg, crude)

1.8 Preparation of Compound 9

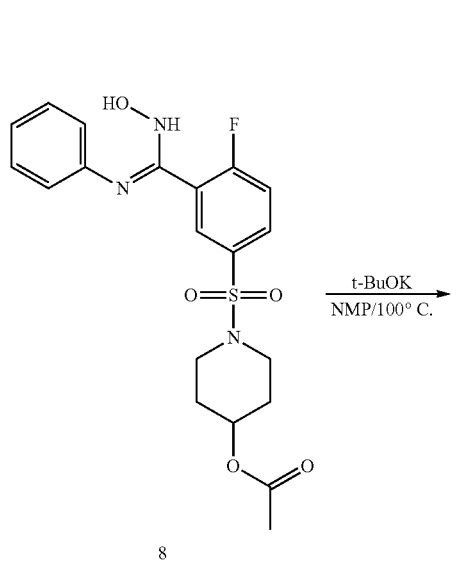

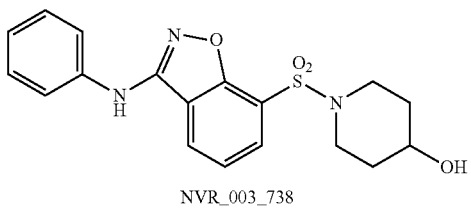

NVR_003_738

A solution of Compound 9 (50 mg, 0.12 mmol), NaOH (10 mg, 0.24 mml), in 1 mL of MeOH and 1 ml of water was stirred at room temperature for 16 hours. The solvent was removed off and purified by Prep-HPLC to afford 20 mg of 738 (20 mg, 40%). LCMS: 374 [M+1].

737 was prepared following the similar procedure with 738.

General Procedure G

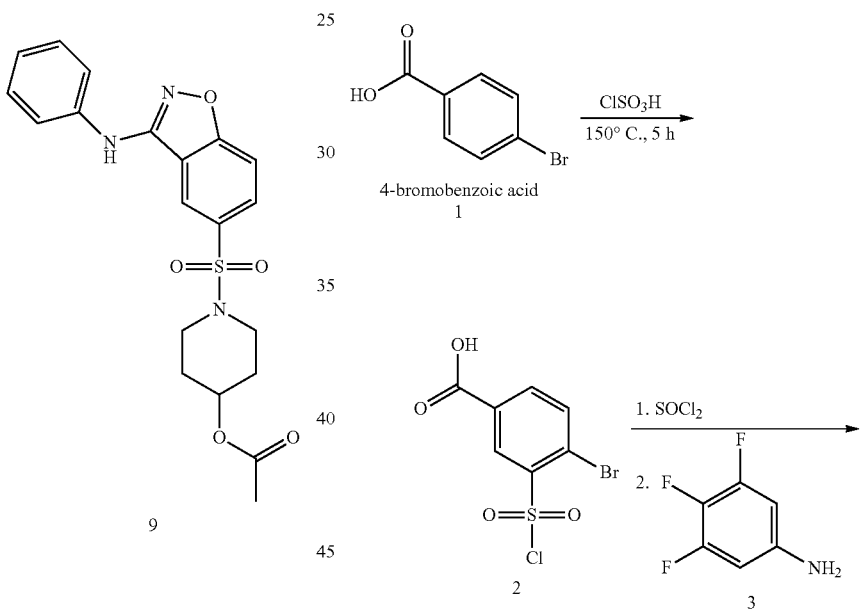

To a solution of Compound 8 (360 mg) in NMP (3 mL) was added t-BuOK (80 mg, 0.71 mmol) at rt, and the mixture was heated to 80° C. for 3 h. The mixture was diluted with EtOAc (20 mL) and washed with water. The organic phase was concentrated in vacuo to give the crude product, which was purified by preparative HPLC to give the desired product. (50 mg, yield: 20%)

1.9 Preparation of 738

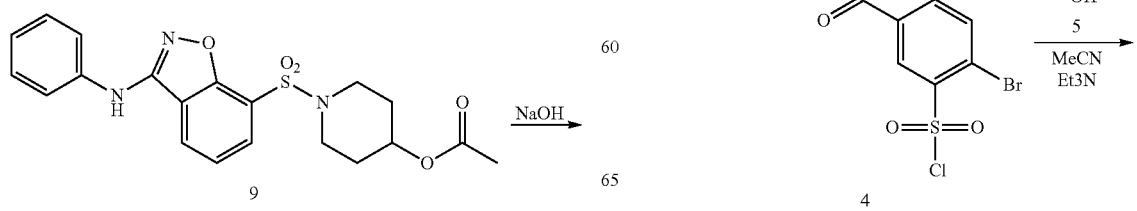

-continued

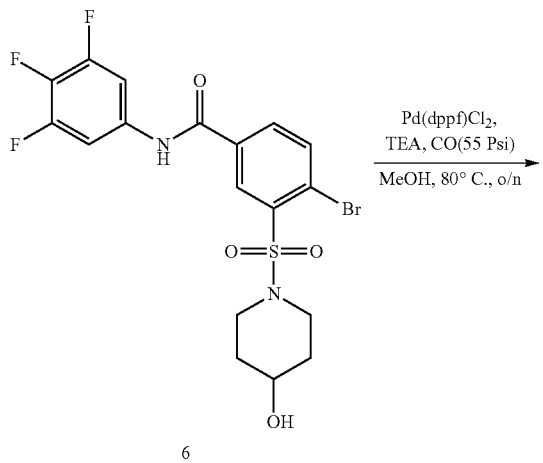

6

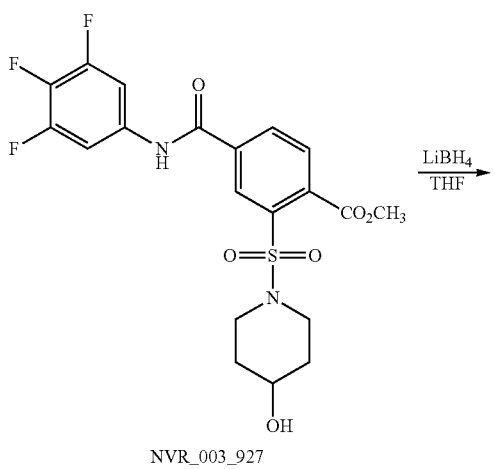

NVR_003_927

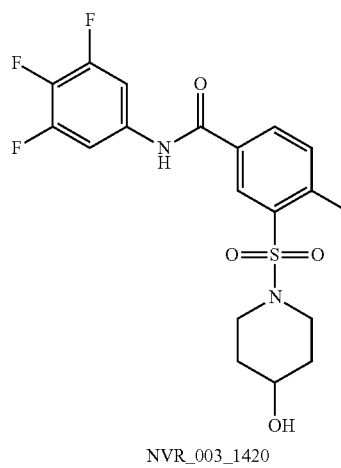

NVR_003_1420

1.1 Preparation of Compound 2

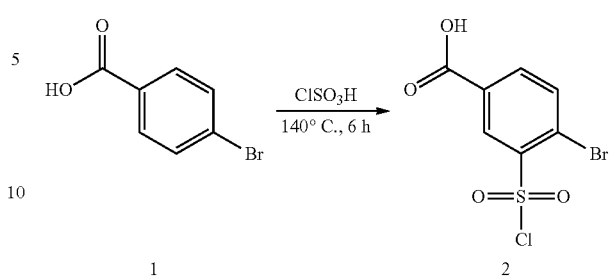

To chlorosulfonic acid (82.4 g, 0.71 mol) cooled to 0° C. was added portionwise Compound 1 (5.0 g, 25 mmol). After complete addition, the yellow solution was warmed to room temperature, then heated to 150° C. for 5 h. The reaction mixture was cooled to room temperature and then added drop-wise to ice (60 g). The white precipitate was filtered, washed with water, and dried in vacuo to afford the desired product as a yellow solid (6.0 g, 80%).

$^1$H NMR (400 MHz, CDCl$_3$): δ ppm: 8.89 (d, J=2.0 Hz 1H), 8.25 (dd, J=2.0, 8.4 Hz, 1H), 8.02 (d, J=8.4 Hz, 1H).

1.2 Preparation of Compound 3

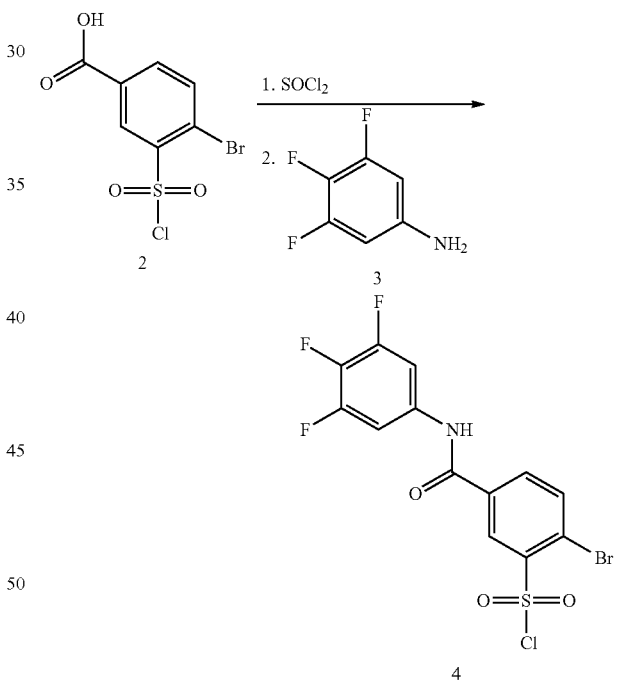

A mixture of Compound 2 (6.0 g, 20.1 mmol) in SOCl$_2$ (60 mL) was heated to reflux for 3 h. The mixture was concentrated to give the crude product, which was used for the next step directly. To a boiled solution of compound 3 (6.4 g, 20.1 mmol) in anhydrous toluene (60 mL) was added 3,4,5-trifluoroaniline (2.9 g, 20.1 mmol). The formed mixture was heated to 100° C. for 6 h. The mixture was allowed to cool to room temperature, and then concentrated to give the desired product, which was used for the next step directly (7.5 g, 87%).

$^1$H NMR (400 MHz, DMSO): δ ppm: 10.78 (s, 1H), 8.45 (d, J=2.0 Hz, 1H), 7.75 (m, 4H).

1.3 Preparation of Compound 6

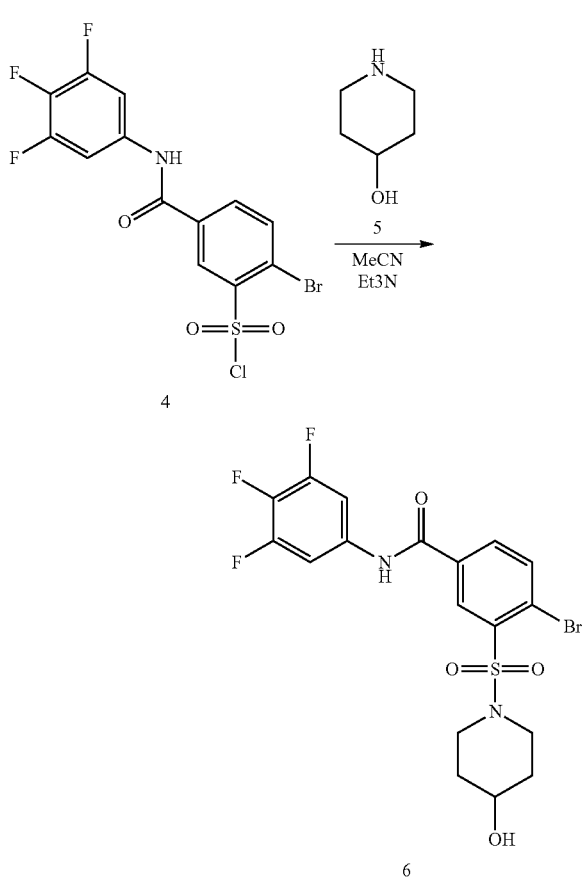 [SMILES: O=C(Nc1cc(F)c(F)c(F)c1)c1ccc(Br)c(S(=O)(=O)Cl)c1 ; OC1CCNCC1 ; O=C(Nc1cc(F)c(F)c(F)c1)c1ccc(Br)c(S(=O)(=O)N2CCC(O)CC2)c1]

To a solution of Compound 4 (2.0 g, 4.7 mmol) in MeCN (20 mL) was added piperidin-4-ol (0.47 g, 4.7 mmol) and Et₃N (1.4 mL) at rt. The formed mixture was stirred for 2 h. The mixture was diluted with EA (150 mL) and washed with water (50 mL 2). The organic layer was concentrated to give the crude product, which was purified by silica chromatography gel to give the desired product (1.7 g, 74%).

1.4 Preparation of 927

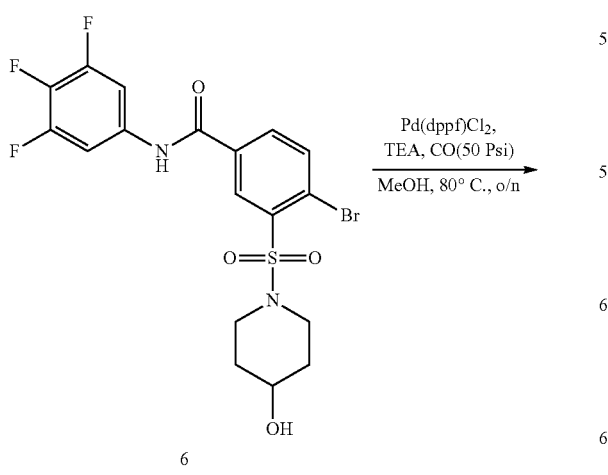

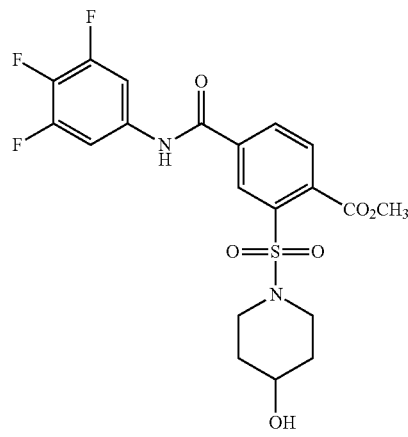

To a solution of Compound 6 (200 mg, 0.41 mmol) in MeOH (10 mL) was added Et₃N (165 mg, 1.62 mmol) and Pd(dppf)Cl₂ (33 mg, 0.04 mmol) under N₂. The formed mixture was stirred at 80° C. under CO of 50 Psi pressure for 12 h. The mixture was allowed to cool to room temperature and filtered. The filtration was concentrated and purified by silica chromatography gel to give the desired product (150 mg, 79%). LCMS: 473.1 [M+1].

$^1$H NMR (400 MHz, DMSO): δ ppm: 10.86 (s, 1H), 8.31 (s, 1H), 8.29 (s, 1H), 7.85 (d, J=7.6 Hz, 1H), 7.72 (t, J=5.0 Hz, 2H), 4.73 (d, J=4.0 Hz, 1H), 3.86 (s, 3H), 3.61 (m, 1H), 3.35 (m, 2H), 2.95 (m, 2H), 1.75 (m, 2H), 1.38 (m, 2H).

1.5 Preparation of 1420

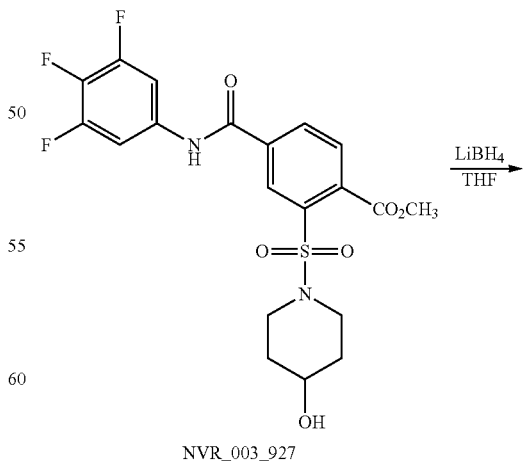

1.2 Preparation of Compound 3

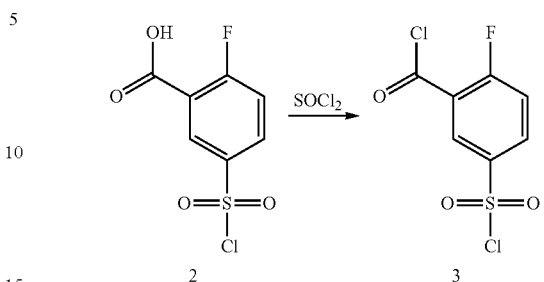

A mixture of Compound 2 (238 mg, 1 mmol) in SOCl₂ (10 mL) was heated at reflux for 12 h. The mixture was concentrated to give the crude product, which was used for the next step directly.

1.3 Preparation of Compound 5

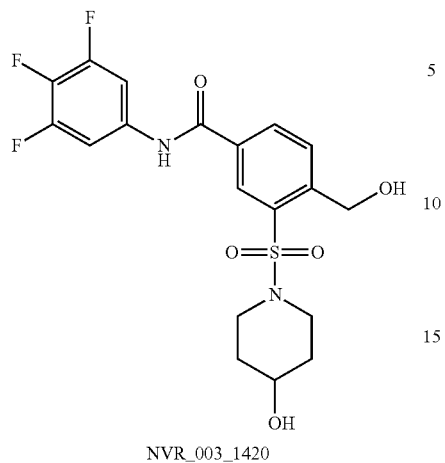

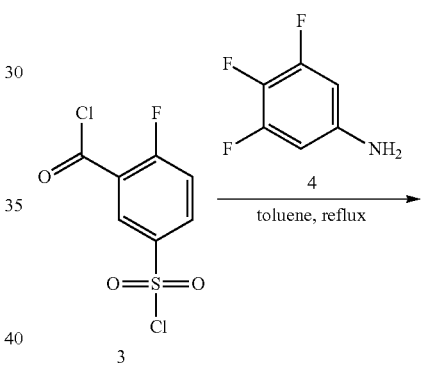

To a solution of Compound 927 (200 mg, 0.42 mmol) in THF (10 mL) was added LiBH₄ (38 mg, 1.72 mmol) under N₂ at 0° C., the formed mixture was stirred at room temperature overnight. The reaction mixture was diluted with EA (100 mL) and washed with brine (50 mL 2). The organic layer were dried over Na₂SO₄, concentrated and purified by silica chromatography gel to give the desired product (45 mg, 24%). LCMS: 445.1 [M+1].

¹H NMR (400 MHz, CD3OD): δ ppm: 8.42 (d, J=2.0 Hz, 1H), 8.21 (dd, J=2.0, 8.4 Hz, 1H), 8.06 (d, J=8.0 Hz, 1H), 7.63 (m, 2H), 5.06 (s, 2H), 3.76 (m, 1H), 3.53 (m, 2H), 3.05 (m, 2H), 1.90 (m, 2H) 1.59 (m, 2H).

Specific Experimental Procedure for Preparation of 777

1.1 Preparation of Compound 2

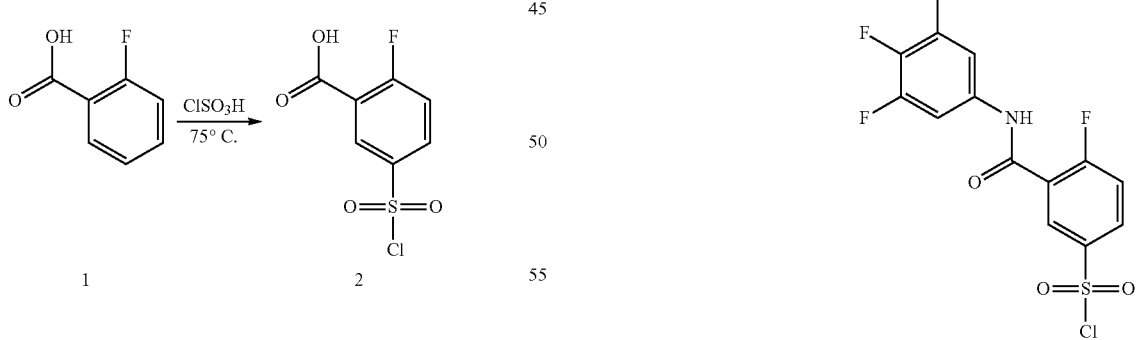

To chlorosulfonic acid (23.8 mL, 350 mmol) was added portionwise 2-fluorobenzoic acid (5 g, 35 mmol) at 0° C. After addition, the yellow solution was allowed to warm to room temperature, and then heated at 75° C. for 12 h. The reaction mixture was cooled to room temperature and then poured onto ice water (150 mL). The white precipitate was filtered, washed with water, and dried in vacuo to afford the desired product (3.37 g, 40.4%).

To a solution of Compound 3 (260 mg, 1 mmol) in refluxing toluene (10 mL) was added Compound 4 (147 mg, 1 mmol). The resulting solution was heated at reflux for 2 h and then concentrated in vacuo to give a solid, which was used for the next step directly without purification.

1.4 Preparation of 777

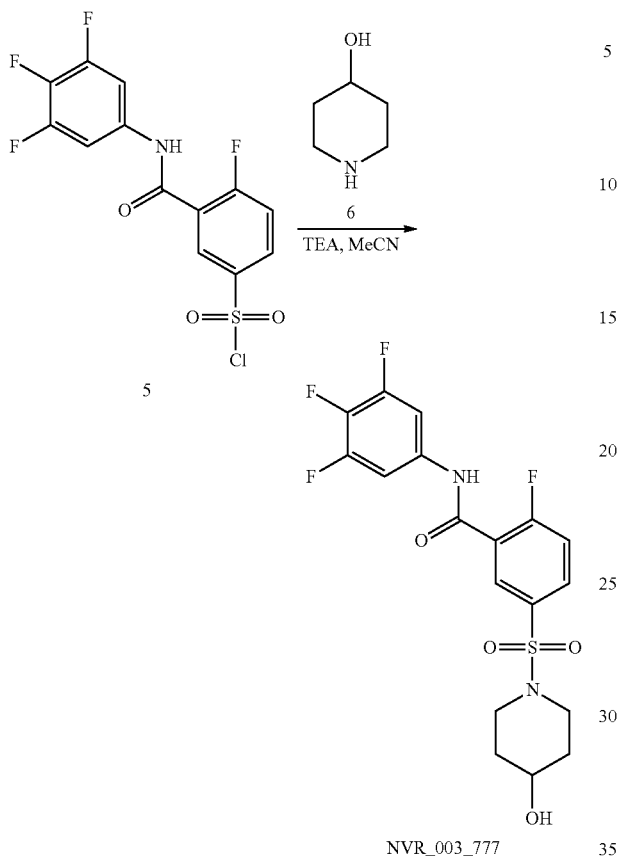

To a solution of crude Compound 5 (370 mg, 1 mmol) and Compound 6 (101 mg, 1 mmol) in MeCN (15 mL) was added Et₃N (150 mg, 1.5 mmol) at room temperature. After addition, the resulting mixture was stirred for 2 h, at which time LCMS indicated the completion of the reaction. The solution was evaporated and the residue was purified by preparative HPLC to give the desired product 777 (251 mg, 61%).

$^1$H NMR (400 MHz, MeOD) δ 8.11-8.14 (m, 1H), 8.00-8.03 (m, 1H), 7.51-7.59 (m, 3H), 3.66-3.71 (m, 1H), 3.36-3.42 (m, 2H), 2.85-2.91 (m, 2H), 1.89-1.94 (m, 2H), 1.15-1.64 (m, 2H). LCMS: 433 [M+1].

Specific Experimental Procedure for Preparation of Compound 890

1.1 Procedure for Preparation of Compound 2

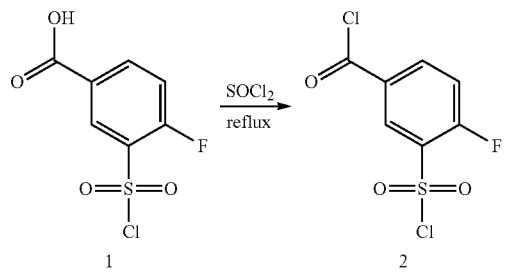

A mixture of Compound 1 (10.0 g, 42.0 mmol) in SOCl₂ (60 mL) was heated to reflux overnight. The mixture was concentrated in vacuo. The residue was dissolved with toluene (30 mL), and concentrated in vacuo to give the crude product, which was used for the next step directly.

1.2 Procedure for Preparation of Compound 3

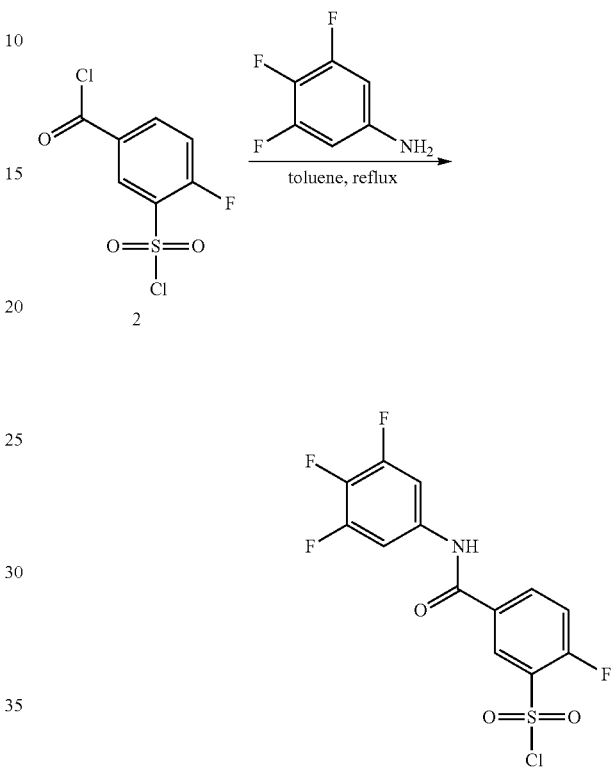

To a boiled solution of crude Compound 2 (42 mmol) in toluene (100 mL) was added a suspension of aniline (6.17 g, 42 mmol) in toluene (40 mL) slowly, and refluxed for 2 h. The mixture was concentrated in vacuo to give a solid, which was used for the next step directly.

1.3 Procedure for Preparation of 890

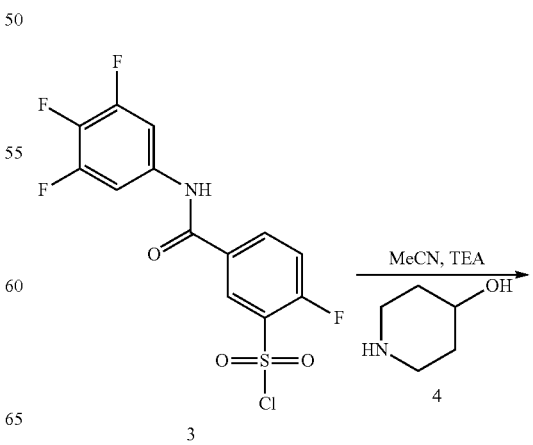

-continued

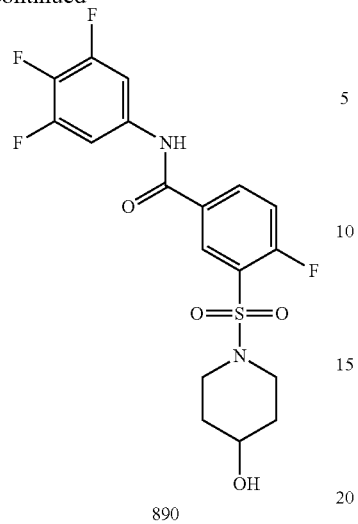

890

To a solution of Compound 3 (42 mmol) in MeCN (250 mL) was added amine 4 (4.3 g, 42 mmol) and Et₃N (6.18 g, 61.2 mmol) at rt, and the mixture was stirred at rt for 3 h. The solution was concentrated in vacuo. The residue was purified by silica gel chromatography to give the desired product as white solid (15.7 g, 86.5%).

H-NMR (Methanol-d4 400 MHz): 8.41-8.39 (dd, J=6.5, 2.4 Hz, 1H), 8.26-8.23 (m, 1H), 7.61-7.50 (m, 3H), 3.74-3.72 (m, 1H), 3.56-3.52 (m, 2H), 3.06-3.01 (m, 2H), 1.91-1.87 (m, 2H), 1.59-1.56 (m, 2H).

LCMS: 433.0 [M+1].

Specific Experimental Procedure for Preparation of 894

1.1 Procedure for Preparation of Compound 2

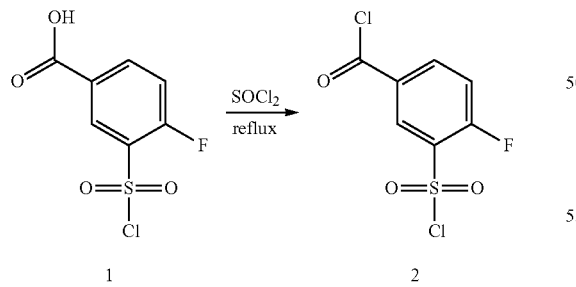

A mixture of Compound 1 (3.0 g, 12.6 mmol) in SOCl₂ (80 mL) was heated to reflux overnight. The mixture was concentrated in vacuo. The residue was re-dissolved with toluene (30 mL), and concentrated in vacuo to give the crude product, which was used for the next step directly.

1.2 Procedure for Preparation of Compound 3

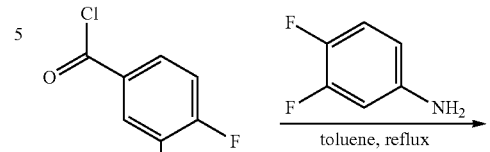

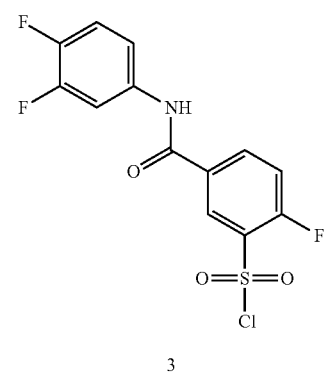

To a solution of crude Compound 2 (12.6 mmol) in refluxing toluene (10 mL) was added 3,4-difluoroaniline (1.6 g, 12.6 mmol). The resulting solution was heated at reflux for 2 h and then concentrated in vacuo to give a solid, which was used for the next step directly without purification.

1.3 Procedure for Preparation of 894

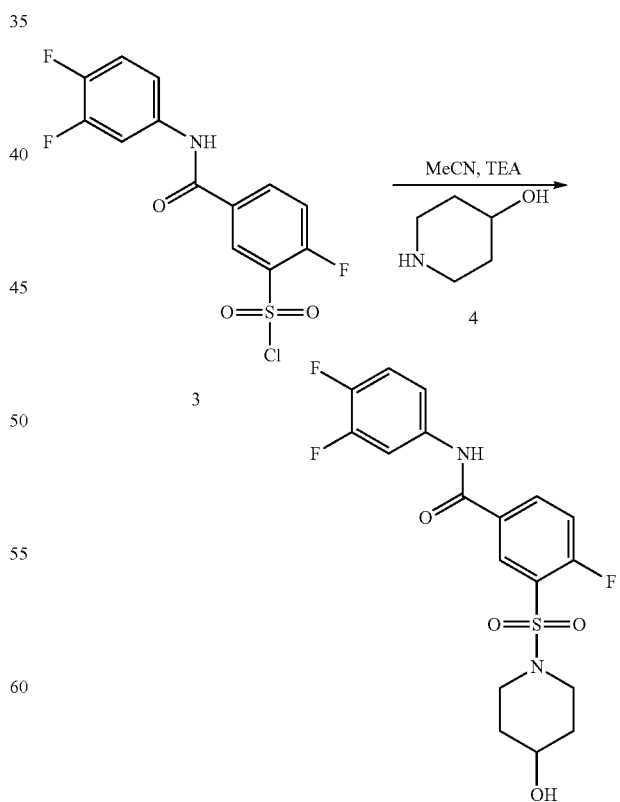

894

To a solution of crude Compound 3 (600 mg, 2.0 mmol) and Compound 4 (203 mg, 2.0 mmol) in MeCN (10 mL) was added Et$_3$N (303 mg, 3.0 mmol) at room temperature. The mixture was stirred at rt for 3 h, at which time LCMS indicated the completion of the reaction. The solution was concentrated in vacuo. The residue was purified by prep-HPLC to give the desired product as white solid (430 mg, 60.3%). H-NMR (Methanol-d4 400 MHz): 8.40-8.42 (m, 1H), 8.23-8.25 (m, 1H), 7.75-7.82 (m, 1H), 7.42-7.52 (m, 2H), 7.25-7.28 (m, 1H), 3.74-3.74 (m, 1H), 3.52-3.56 (m, 2H), 3.01-3.07 (m, 2H), 1.1.87-1.91 (m, 2H), 1.56-1.59 (m, 2H). LCMS: 415.0 [M+1].

Experimental Procedure for Preparation of Compound 891

1.1 Procedure for Preparation of Compound 2

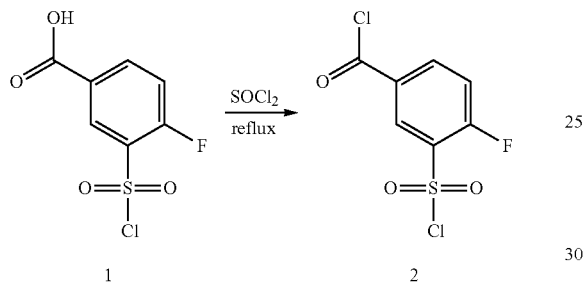

A mixture of Compound 1 (20.0 g, 84.0 mmol) in SOCl$_2$ (120 mL) was heated at reflux for 3 h. The mixture was concentrated in vacuo. The residue was dissolved with toluene (60 mL), and concentrated in vacuo to give the crude product, which was used for the next step directly.

1.2 Procedure for Preparation of Compound 3

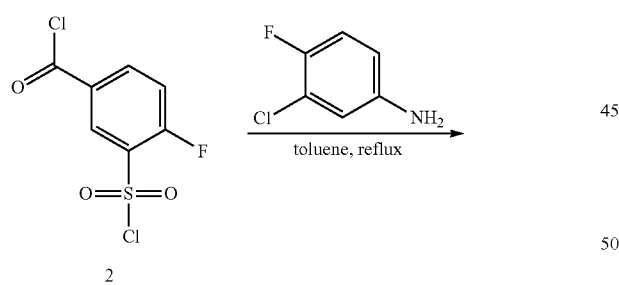

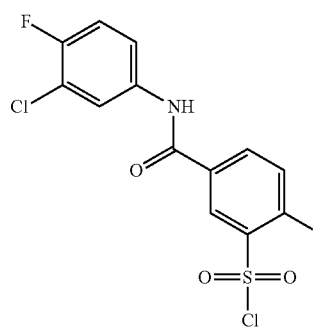

To a solution of crude Compound 2 (84 mmol) in refluxing toluene (200 mL) was added 3-chloro-4-fluoroaniline (12.3 g, 42 mmol). The resulting mixture was refluxed for 5 h. The mixture was concentrated in vacuo to give a solid, which was used for the next step directly.

1.3 Procedure for Preparation of Compound 891

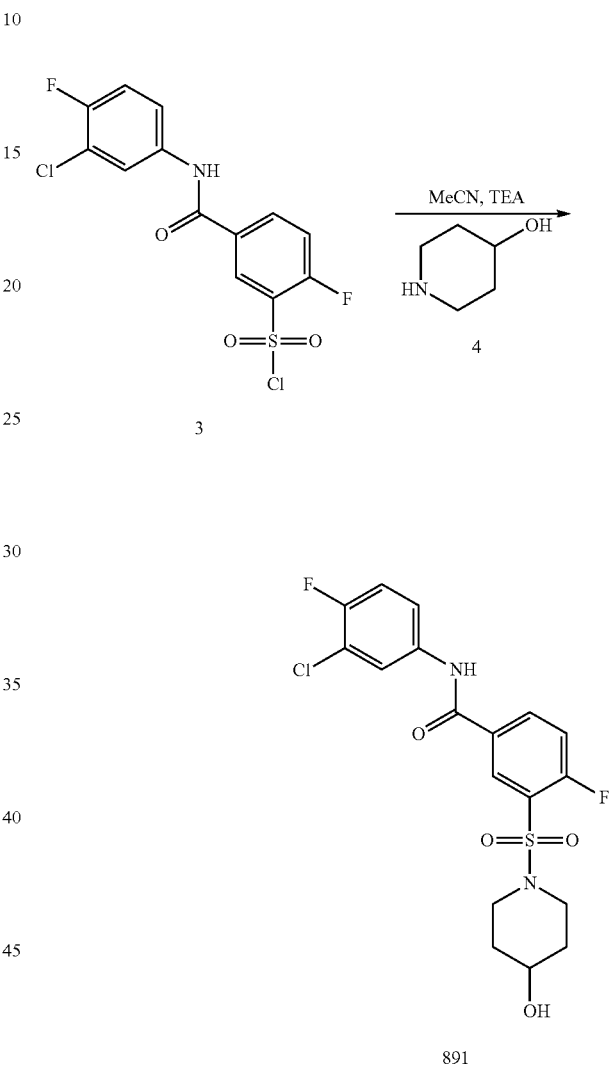

To a solution of crude Compound 3 (2.0 g, 5.5 mmol) and Compound 4 (0.55 g, 5.5 mmol) in MeCN (30 mL) was added Et$_3$N (0.83 g, 8.2 mmol) at rt. The mixture was stirred at rt for 2 h, at which time LCMS indicated the completion of the reaction. The solution was concentrated in vacuo. The residue was purified by silica gel chromatography to give the desired product as white solid (1.41 g, 60.3%). H-NMR (DMSO-d6 400 MHz): 10.66 (s, 1H), 8.37-8.33 (m, 2H), 8.04-8.02 (m, 1H), 7.72-7.62 (m, 2H), 7.47-7.38 (m, 1H), 4.75-4.74 (d, J=4.0 Hz, 1H), 3.65-3.55 (m, 1H), 3.37-3.27 (m, 2H), 2.98-2.88 (m, 2H), 1.75-1.65 (m, 2H), 1.45-1.35 (m, 2H). LCMS: 431.0 [M+1].

Specific Experimental Procedure for Preparation of Compound 903

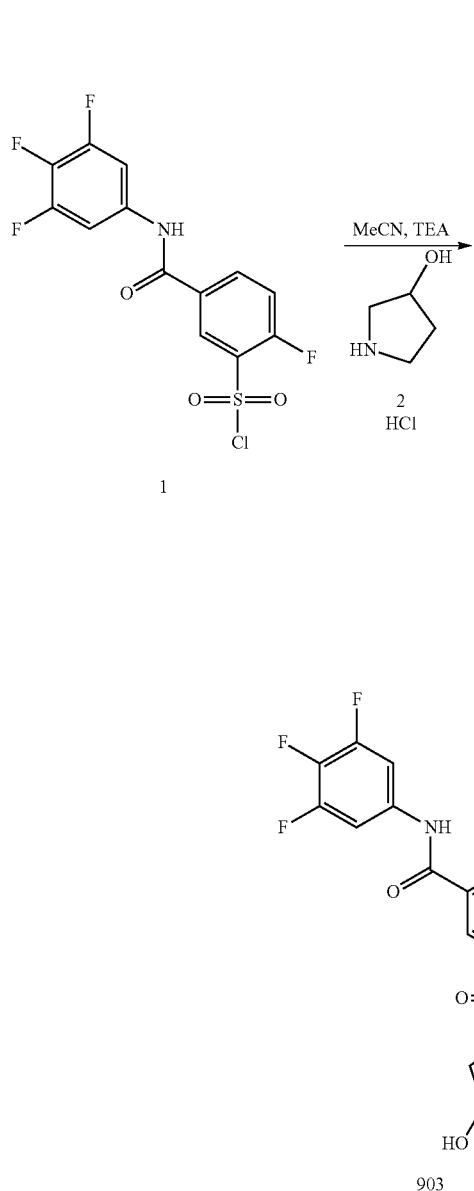

To a solution of Compound 1 (4.5 g, 12.2 mmol) and Compound 2 (1.5 g, 12.2 mmol) in MeCN (70 mL) was added Et₃N (3.1 g, 30.7 mmol) at rt. The mixture was stirred at rt for 2 h, at which time LCMS indicated the completion of the reaction. The solution was concentrated in vacuo. The residue was purified by silica gel chromatography to give the desired product as white solid (2.69 g, 52.7%).

H-NMR (Methanol-d4 400 MHz): 8.59-8.33 (m, 1H), 8.13-8.10 (m, 1H), 7.51-7.42 (m, 2H), 7.41-7.35 (m, 1H), 4.27-4.24 (m, 1H), 3.42-3.37 (m, 3H), 3.25-3.20 (m, 1H), 1.90-1.86 (m, 1H), 1.82-1.78 (m, 1H).

LCMS: 419.0 [M+1].

Experimental Procedure for Preparation of Compound 953

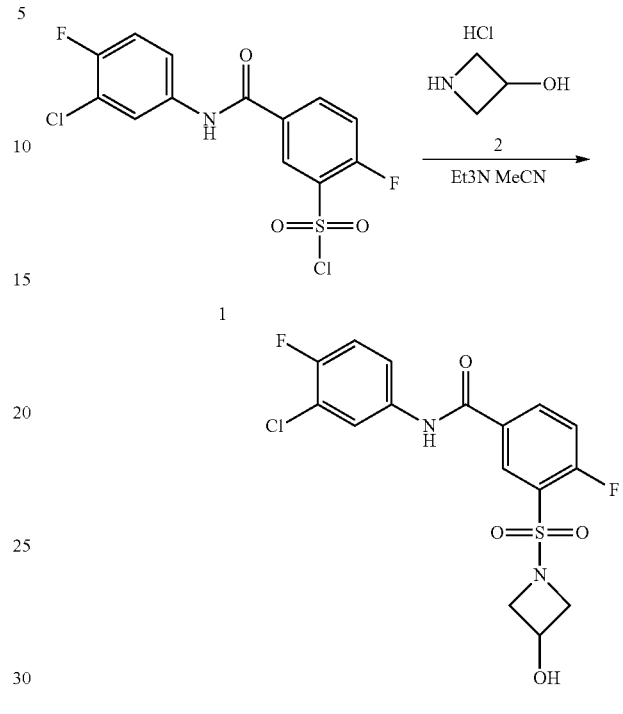

To a solution of Compound 1 (5.5 g, 15.1 mmol) and Compound 2 (1.6 g, 14.7 mmol) in MeCN (80 mL) was added Et₃N (3.8 g, 37.7 mmol) at rt. The mixture was stirred at rt for 2 h, at which time LCMS indicated the completion of the reaction. The solution was concentrated in vacuo. The residue was purified by silica gel chromatography to give the pure product as white solid (1.1 g, 18.3%) and impure product (about 1.0 g).

H-NMR (Methanol-d4 400 MHz): 8.46-8.41 (m, 1H), 8.35-8.25 (m, 1H), 7.99-7.92 (m, 1H), 7.68-7.52 (m, 2H), 7.29-7.24 (t, J=8.4 Hz, 1H), 4.55-4.45 (m, 1H), 4.16-4.12 (m, 2H), 3.76-3.71 (m, 2H). LCMS: 403.0 [M+1].

Experimental Procedure for Preparation of Compound 960_D1 and Compound 960_D2

1.1 Preparation of Compound 2

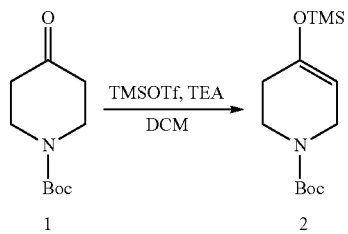

To a solution of Compound 1 (40 g, 188 mmol) in DCM (400 mL) was added TMSOTf (44 g, 198 mmol), followed by Et₃N (38.0 g, 0.377 mol) at room temperature. The reaction mixture was stirred for 1 hour. Then the reaction was concentrated to give the crude product Compound 2 (48.0 g, 88.8%).

¹H NMR (400 MHz, CDCl₃): δ ppm: 4.79 (s, 1H), 3.87 (m, 2H), 3.52 (m, 2H), 2.11 (s, 1H), 1.43 (s, 9H), 0.16 (s, 9H).

1.2 Preparation of Compound 3

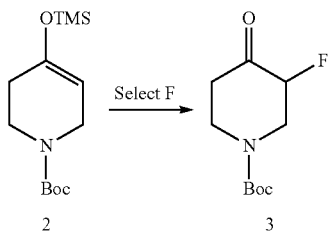

A mixture of Compound 2 (48 g, 167 mmol) and select-F (69 g, 184 mmol) in MeCN (500 mL) was stirred for 4 hours. The mixture was concentrated and purified by column chromatography (PE:AcOEt=5:1) to give the compound 3 (14 g, 36%). ¹H NMR (400 MHz, CDCl₃): δ ppm: 4.10-4.84 (m, 1H), 3.63-3.66 (m, 1H), 3.14-3.21 (m, 1H), 2.48-2.52 (m, 1H), 2.35-2.39 (m, 2H), 1.42 (s, 9H).

1.3 Preparation of Compound 4

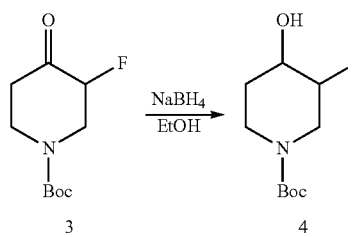

To a solution of Compound 3 (8.6 g, 36.1 mmol) in ethanol (90 mL) was added NaBH₄ (2.13 g, 56.7 mmol) slowly at 0° C. The reaction mixture was stirred at room temperature for 4 hours. The reaction mixture was quenched with aqueous NH₄Cl solution and extracted with AcOEt. The organic layer was dried and concentrated in vacuo. The residue was purified by column chromatography to give the desired product as a mixture of cis and trans isomers (8.3 g, 97.6%).

1.4 Preparation of Compound 5

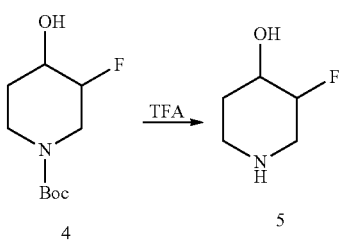 [SMILES: CC(C)(C)OC(=O)N1CCC(O)C(F)C1 ; OC1CCNCC1F ; "TFA"]

To a solution of compound 4 (650 mg, 2.73 mmol) in anhydrous DCM (6 mL) was added TFA (4 mL). The mixture was stirred for 2 h, and concentrated to give the desired product which was used for the next step (300 mg, 80%).

1.5 Preparation of 960_D1

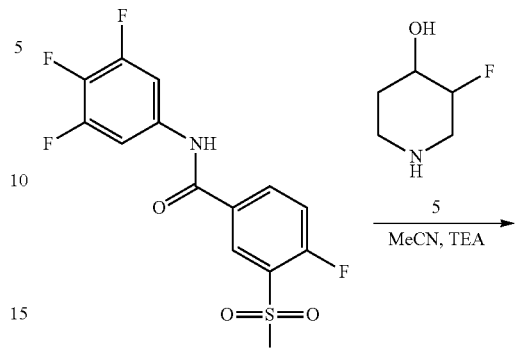

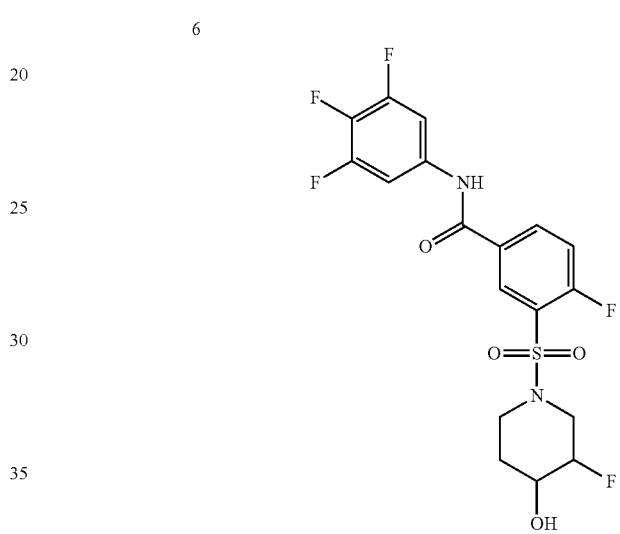

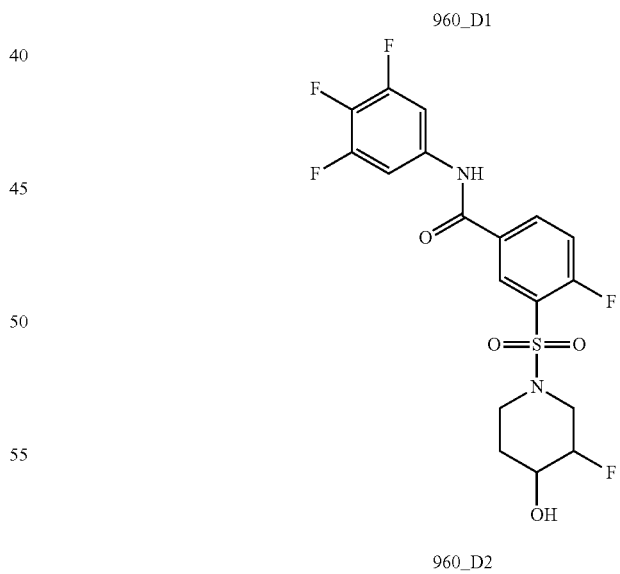

To a solution of Compound 6 (1.54 g, 4.2 mmol) and Compound 5 (500 mg, 4.2 mmol) in MeCN (25 mL) was added Et₃N (848 mg, 8.4 mmol) at rt. The mixture was stirred at rt for 3 h, at which time LCMS indicated the completion of the reaction. The solution was concentrated in vacuo. The residue was purified by preparative HPLC to give the desired product as white solid (580 mg, 42.3%). The first peak in HPLC is named as 960_D1, while the second peak is 960_D2 (12.83 mg, 21.2%).

960_D1: H-NMR (DMSO-d6 400 MHz): 10.79 (s, 1H), 8.37-8.29 (m, 2H), 7.72-7.68 (m, 3H), 5.17-5.16 (d, J=4.0 Hz, 1H), 4.71-4.58 (m, 1H), 3.69-3.53 (m, 3H), 3.200-3.10 (m, 1H), 2.95-2.93 (m, 1H), 1.71-1.66 (m, 2H).

LCMS: 451.1 [M+1].

960_D2: H-NMR (DMSO-d6 400 MHz): 10.82 (s, 1H), 8.38-8.32 (m, 2H), 7.75-7.69 (m, 3H), 5.39-5.38 (d, J=4.0 Hz, 1H), 4.48-4.67 (d, J=4.0 Hz, 1H), 3.71 (s, 1H), 3.35 (s, 2H), 3.23-3.20 (t, J=4.0 Hz, 2H), 1.88-1.85 (m, 1H), 1.56-1.52 (m, 1H).

LCMS: 451.1 [M+1].

Specific Experimental Procedures for Preparation of Compounds 1161/911

1.1 Preparation of Compound 2

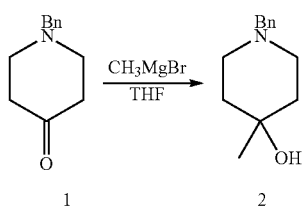

To $CH_3MgBr$ (3 M, 60 mmol) in THF (50 mL) was added a solution of Compound 1 (10.0 g, 53 mmol) in THF (50 mL) slowly at 0-4° C. The resulting mixture was stirred at rt for 1 h. The reaction mixture was quenched by $NH_4Cl$ solution, and extracted with EtOAc (100 mL×3). The organic layer was concentrated to give the crude product, which was purified by column chromatography to give the desired product (2.24 g, Yield: 20.7%). LCMS: 206.0 [M+1].

1.2 Preparation of Compound 3

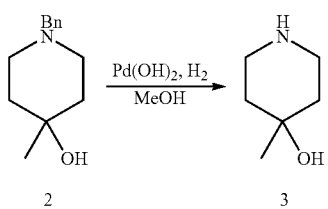

To a solution of Compound 2 (2.26 g, 11 mmol) in MeOH (40 mL) was added $Pd(OH)_2$ (350 mg), and was stirred under $H_2$ at 50 psi for 72 h. The mixture was filtered and the filtrate was concentrated to give the desired product (1.26 g, Yield: 100%).

H-NMR ($CDCl_3$ 400 MHz): 2.85-2.91 (m, 2H), 2.70-2.76 (m, 2H), 2.47-2.51 (m, 4H), 1.18 (s, 3H).

1.3 Procedure for Preparation of Compound 1161

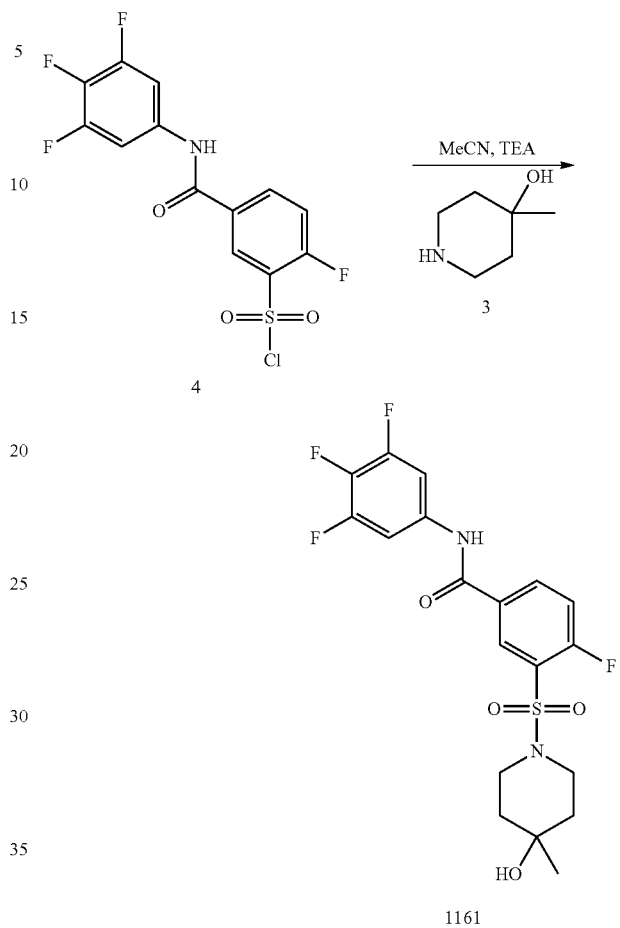

To a solution of Compound 3 (350 mg, 3 mmol) and Compound 4 (1.28 g, 3.5 mmol) in MeCN (15 mL) was added $Et_3N$ (2 mL) at rt. The mixture was stirred at rt for 1 h. The reaction mixture was dissolved with EA (150 mL) and washed with brine (70 mL*2). The organic layer were dried over $Na_2SO_4$, concentrated in vacuo and purified by silica chromatography gel to give the desired product (652 mg, 48.7%). $^1$H NMR (Methanol-d4 400 MHz): 8.43-8.41 (dd, J=6.5, 2.4 Hz, 1H), 8.27-8.25 (m, 1H), 7.65-7.60 (m, 2H), 7.55-7.50 (dd, J=9.8, 8.8 Hz, 1H), 3.60-3.57 (m, 2H), 3.04-2.97 (m, 2H), 1.68-1.63 (m, 4H), 1.22 (s, 3H).

LCMS: 447.0 [M+1].

1.4 Procedure for Preparation of 911

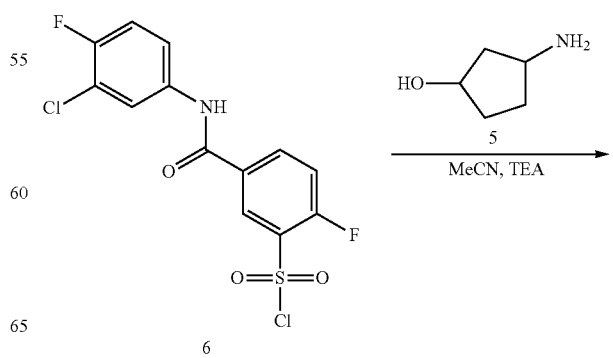

-continued

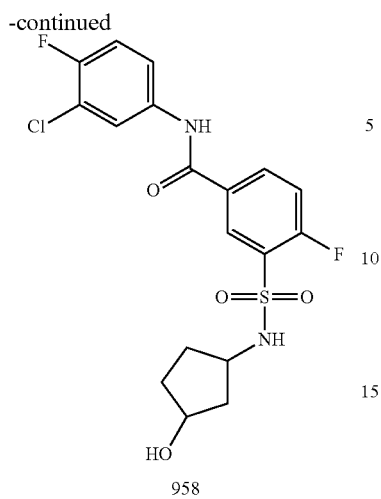

958

To a solution of Compound 3 (335 mg, 2.9 mmol) in MeCN (14 mL) was added Compound 5 (1.22 g, 3.4 mmol) and Et₃N (2 mL) at rt, and the mixture was stirred at rt for 1 h. The reaction mixture was diluted with EA (150 mL) and washed with brine (70 mL*2). The organic layer were dried over Na₂SO₄, concentrated and purified by silica chromatography gel to give the desired product (686 mg, 54.9%).

H-NMR (Methanol-d4 400 MHz): 8.44-8.41 (dd, J=6.5, 2.1 Hz, 1H), 8.28-8.25 (m, 1H), 7.99-7.97 (dd, J=6.8, 2.5 Hz, 1H), 7.65-7.62 (m, 1H), 7.54-7.50 (t, J=9.3 Hz, 1H), 7.29-7.24 (t, J=9.0 Hz, 1H), 3.60-3.57 (m, 2H), 3.04-2.98 (m, 2H), 1.72-1.65 (m, 4H), 1.22 (s, 3H). LCMS: 445.0 [N4+1]/447.0 [M+3].

Experimental Procedure for Preparation of Compound 916

1.1 Preparation of Compound 2

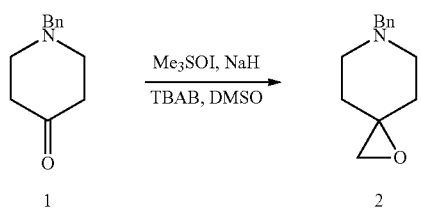 [SMILES: O=C1CCN(Cc2ccccc2)CC1 ; c1ccc(CN2CCC3(CC2)CO3)cc1]

To a solution of Me₃SOI (87.5 g, 396 mmol) in DMSO (400 mL) was added NaH (17 g, 706 mmol) at 0° C., and stirred at room temperature for 1 h. Then Bu₄NBr (8.05 g, 26 mmol) was added to the solution, followed by a solution of Compound 1 (50.0 g, 265 mmol) in DMSO (200 mL), and the mixture was stirred at room temperature for 1.5 h. The mixture was poured into water slowly and extracted with EA. The combined organic phases were washed with brine, dried over Na₂SO₄, and concentrated in vacuo to give the desired product (50.5 g, 93%).

¹H NMR (400 MHz, CDCl₃): δ: 7.28-7.17 (m, 5H), 2.57-2.45 (m, 6H), 1.77-1.74 (m, 2H), 1.50-1.46 (m, 2H), 1.20-1.17 (m, 2H).

1.2 Preparation of Compound 3

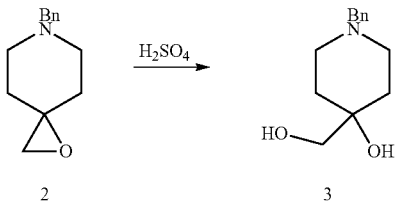

A mixture of Compound 2 (30.5 g, 150 mmol) in H₂SO₄ (37.5 g, 380 mmol, 0.2 M) was stirred at rt overnight. The mixture was neutralized with Na₂CO₃ to pH10 and extracted with EtOAc. The combined organic layers were washed with brine, dried over Na₂SO₄ and concentrated to give the desired product (20.0 g, 58%). ¹H NMR (400 MHz, CD₃OD): δ ppm: 7.29-7.22 (m, 5H), 3.50 (s, 2H), 3.44 (s, 2H), 3.31-3.27 (m, 2H), 2.61-2.58 (m, 2H), 2.41-2.36 (m, 2H), 1.69-1.64 (m, 2H), 1.51-1.49 (m, 2H).

1.3 Preparation of Compound 4

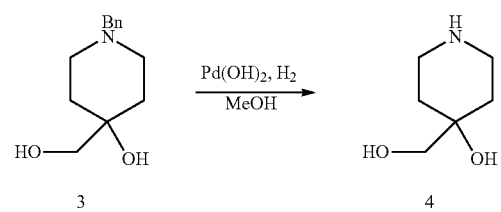 [SMILES: "MeOH" ; OCC1(O)CCN(Cc2ccccc2)CC1 ; OCC1(O)CCNCC1]

To a solution of Compound 3 (20 g, 90 mmol) in CH₃OH (800 mL) was added dry Pd(OH)₂ (2 g). The formed mixture was hydrogenated under H₂ atmosphere of 15 Psi pressure overnight. The catalyst was filtered and the filtrate was concentrated to give the desired product (12 g, 98%).

1.4 Preparation of Compound 916

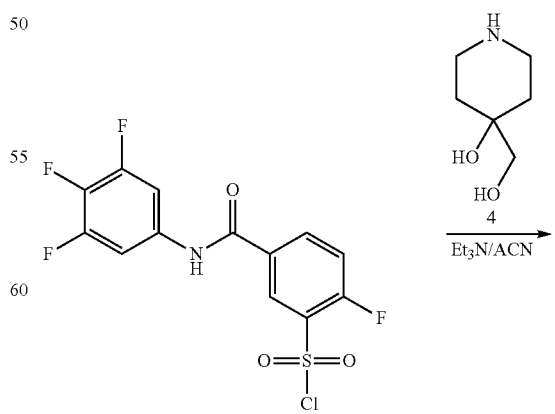

-continued

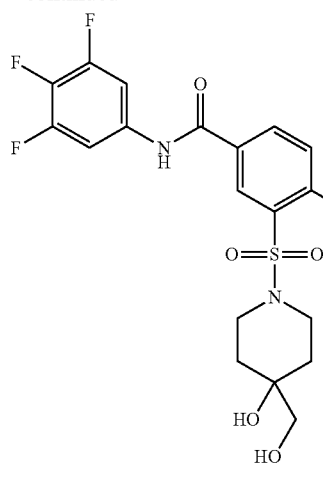

916

To a solution of Compound 5 (7.8 g, 21.2 mmol) in MeCN (100 mL) was added amine 4 (2.8 g, 21.2 mmol) and Et₃N (4.3 g, 42.4 mmol) at rt, and the mixture was stirred at rt for 3 h. The solution was concentrated in vacuo. The residue was purified by silica gel chromatography eluted with PE:EA=from 3:1 to 1:2 to give the desired product as white solid (6.2 g), which was purified by re-crystallization from EA (30 mL) to afford pure product as white solid (4.1 g, yield: 41%).

$^1$H NMR (400 MHz, METHANOL-d4): 8.48-8.39 (m, 1H), 8.33-8.21 (m, 1H), 7.63-7.59 (m, 2H), 7.59-7.52 (m, 1H), 3.72-3.69 (m, 2H), 3.35 (s, 2H), 3.03-2.94 (m, 2H), 1.78-1.67 (m, 2H), 1.63-1.60 (m, 2H)

LCMS: 463.1[M+1].

Specific Experimental Procedure for Preparation of Compounds 826/922

Experimental Data 1.1 Preparation of Compound 2

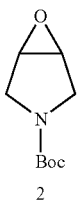

To a solution of Compound 1 (10 g, 0.06 mol) in CH₂Cl₂ (40 mL) was added m-CPBA (9.0 g, 0.66 mol) at room temperature, and the mixture was stirred at rt for 12 hours. The mixture was quenched with Na₂SO₃, washed with NaHCO₃, and concentrated to give the compound 2 (10 g, 90%).

$^1$H NMR (400 MHz, CDCl₃): δ ppm: 3.73-3.75 (m, 2H), 3.59-3.60 (m, 2H), 3.20-3.25 (m, 2H), 1.37 (s, 9H).

1.2 Preparation of Compound 3

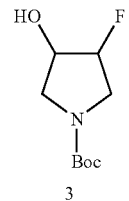

To a solution of Compound 2 (10.0 g, 0.054 mol) in Et₃N (60 mL) was added Py HF (20 mL) at 0° C., and the mixture was heated to 80° C. for 12 hours. Then the mixture was concentrated in vacuo. The residue was diluted with AcOEt, washed with aqueous NH₄Cl solution and brine, dried over Na₂SO₄ and concentrated in vacuo. The residue was purified by column chromatography (PE:EA=4:1) to give the compound 3 (4 g, 36%).

$^1$H NMR (400 MHz, CDCl₃): δ ppm: 4.79-4.90 (m, 1H), 4.31-4.34 (m, 1H), 3.46-3.56 (m, 4H), 2.25 (s, 1H), 1.40 (s, 9H).

1.3 Preparation of Compound 4

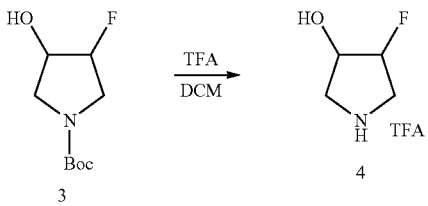

To a solution of compound 3 (2 g, 0.01 mol) in anhydrous DCM (10 mL) was added TFA (10 mL) at 0° C. The formed mixture was stirred for 2 h, and concentrated to give the desired product as a TFA salt which was used for the next step (2.4 g).

1.4 Preparation of 826

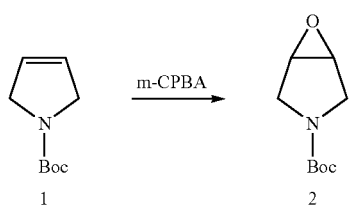 [SMILES: CC(C)(C)OC(=O)N1CC=CC1 ; CC(C)(C)OC(=O)N1CC2OC2C1]

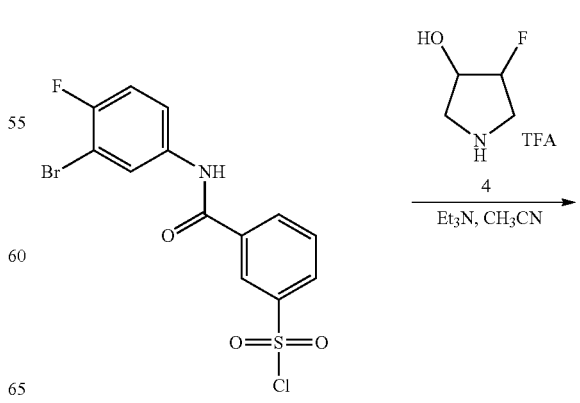

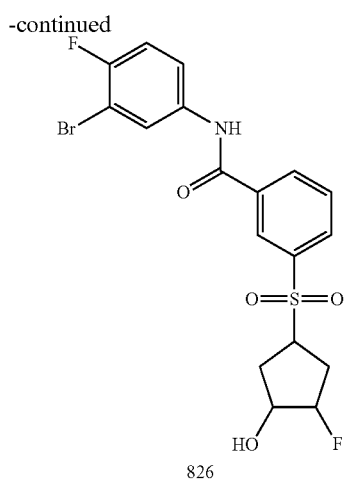

826

To a solution of Compound 5 (900 mg, 2.3 mmol) and Compound 4 (580 mg) in MeCN (50 mL) was added Et₃N (690 mg, 6.9 mmol) at room temperature. The mixture was stirred at rt for 3 hours. The solution was concentrated in vacuo. The residue was purified by silica gel chromatography (PE:EA=3:1) to give 826 as white solid (0.6 g, 60%).

¹H NMR (400 MHz, Methanol-d4): δ ppm: 8.40 (s, 1H), 8.21-8.23 (d, J=7.6 Hz, 1H), 8.06-8.13 (m, 2H), 7.69-8.06 (m, 2H), 4.77-4.88 (m, 1H), 4.23-4.25 (m, 1H), 3.43-3.66 (m, 3H), 3.32-3.33 (m, 1H).

1.5 Preparation of 922

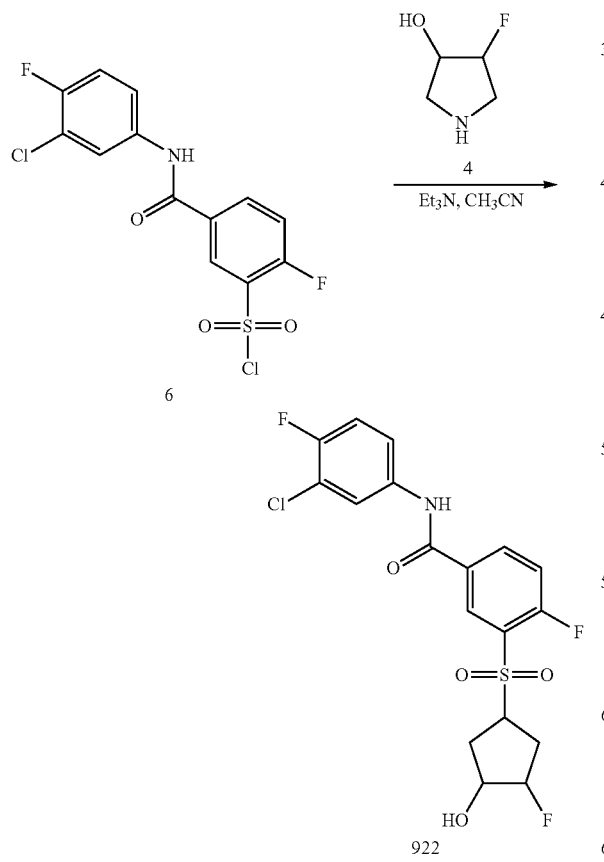

To a solution of Compound 6 (900 mg, 2.47 mmol) and Compound 4 (620 mg) in MeCN (50 mL) was added Et₃N (750 mg, 7.41 mmol) at room temperature. The mixture was stirred at rt for 3 hours. The solution was diluted with AcOEt, washed with water, dried with anhydrous Na₂SO₄ and concentrated in vacuo. The residue was purified by silica gel chromatography (PE:EA=3:1) to give 922 as white solid (0.6 g, 50%).

¹H NMR (400 MHz, DMSO-d6): δ ppm: 8.40 (s, 1H), 10.68 (s, 1H), 8.39-8.42 (m, 2H), 8.03-8.05 (m, 1H), 7.68-7.70 (m, 1H), 7.43-7.48 (m, 1H), 5.61-5.62 (d, J=3.6 Hz 1H), 4.87-5.01 (m, 1H), 4.20-4.22 (m, 1H), 3.57-3.65 (m, 2H), 3.48-3.49 (m, 1H), 3.45-3.47 (m, 1H). LCMS: 435.0[M+1].

Specific Experimental Procedure for Compound 958

1.1 Preparation of Compound 2

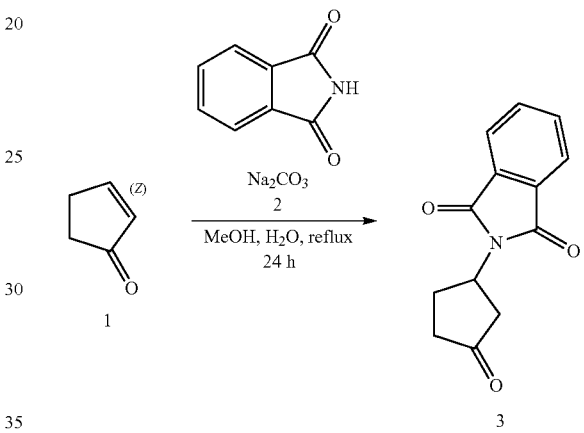

To a slurry of Compound 1 (6.5 g, 79 mmol) and Compound 2 (10.2 g, 69 mmol) in MeOH (100 mL) was added an aqueous Na₂CO₃ (6 mL, 2 N, 12 mmol), and stirred at rt for 24 h. The solid was collected by filtration, washed with MeOH and dried in vacuo, which was used in the next step (14 g, crude).

LCMS: 230.2 [M+1].

1.2 Preparation of Compound 4

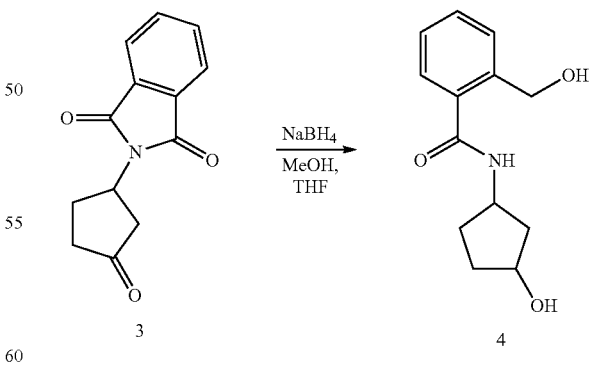

To a mixture of Compound 3 (14 g, 61 mmol) in MeOH/THF (300 mL/50 mL) was added NaBH₄ (3.4 g, 90 mmol) at 0° C., and stirred at rt overnight. 1 N HCl was added slowly to quench the reaction. The resulting mixture was concentrated in vacuo. The residue was dissolve with water and EtOAc. The aqueous phase was extracted with EtOAc (500 mL×2).

The combined organic phase was concentrated to give the crude product, which was purified by column chromatography to give the Compound 4 (8.0 g, 57%). LCMS: 236.1 [M+1].

1.3 Preparation of Compound 5

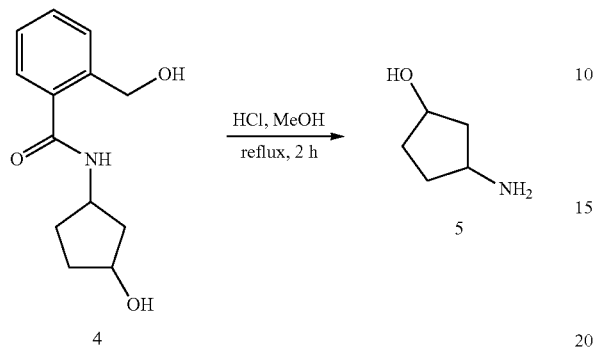

A mixture of Compound 4 (8.0 g, 34 mmol) in MeOH (100 mL) was added concentrated HCl (10 mL), and heated to reflux for 2 h. The mixture was concentrated in vacuo. The residue was dissolved with water and washed with EA. The aqueous phase was concentrated in vacuo to give the desired product with HCl salt (2.8 g, 82%).

$^1$H NMR (400 MHz, CDCl$_3$): δ ppm: 4.33 (bs, 1H), 3.66 (bs, 1H), 2.08-2.16 (m, 2H), 1.74-1.90 (m, 4H).

1.4 Preparation of 958

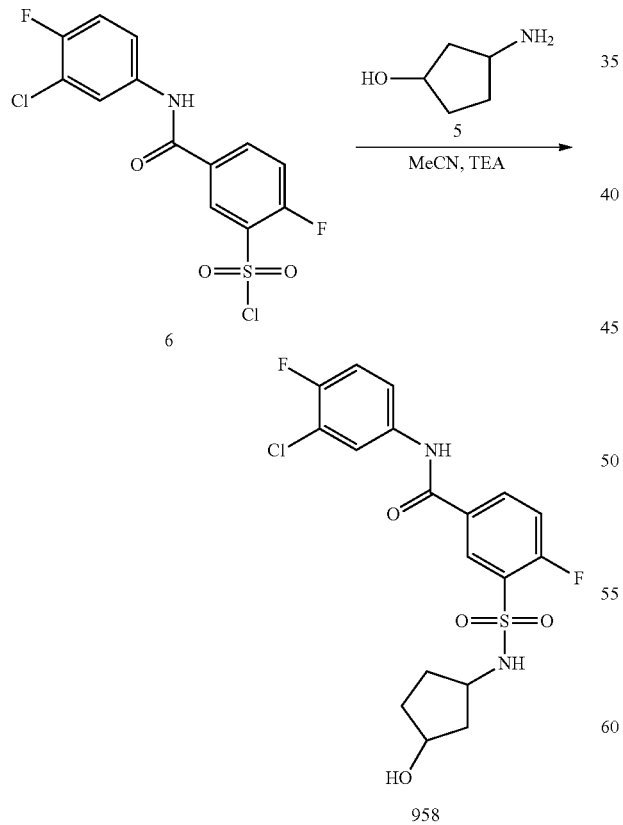

To a solution of Compound 6 (626 mg, 1.72 mmol) and Compound 5 (174 mg, 1.72 mmol) in MeCN (7 mL) was added Et$_3$N (260 mg, 2.58 mmol) at rt, and the mixture was stirred at rt for 2 h. The solution was concentrated in vacuo. The organic phase was concentrated in vacuo to give the crude product, which was purified by prep-HPLC to give the desired product (355 mg, 48%).

H NMR (MeOD-d4 400 MHz): 8.47-8.45 (m, 1H), 8.230-8.22 (m, 1H), 7.98-7.96 (m, 1H), 7.62-7.61 (m, 1H), 7.50-7.48 (m, 1H), 7.46-7.26 (m, 1H), 4.13-4.10 (m, 1H), 3.72-3.68 (m, 1H), 2.10-2.08 (m, 1H), 1.08-1.64 (m, 4H). 1.64-1.43 (m, 1H).

LCMS: 431.0 [M+1].

Example

HBV Assembly Assay

Selected compounds of the invention were assayed in the HBV assembly assay, as described elsewhere herein. The assembly assay was conducted in 96-well plate format. The assembly reactions were carried out in 50 mM Hepes buffer, pH 7.5 and 150 mM NaCl. The compounds were pre-incubated with the HBV CA protein for 15 min, and the assembly reactions were initiated by addition of NaCl. The reaction was allowed to continue for 1 hour at room temperature. The 96-well plate assembly assay consistently had Z' factors greater than 0.7 and were robust and reproducible both from plate-to-plate and day-to-day.

To determine the effect on capsid assembly, each test compound was initially screened at 4 different concentrations: 10 μM, 3 μM, 1 μM and 0.3 μM in duplicates. Primary hits were compounds that show >50% activity in the assembly assay at 10 μM and a representative group of these active compounds is illustrated in Table 2.

TABLE 2

"Activity" represents activity in HBV assembly assay ('+' indicates >50% activity at 10 μM)

| Compound | Activity | Compound | Activity |
|---|---|---|---|
| 065 | + | 078 | + |
| 079 | + | 119 | + |
| 121 | + | 126 | + |
| 129 | + | 148 | + |
| 191 | + | 208 | + |
| 242 | + | 258 | + |
| 282 | + | 318 | + |
| 332 | + | 349 | + |
| 366 | + | 407 | + |
| 419 | + | 451 | + |
| 462 | + | 478 | + |
| 501 | + | 541 | + |
| 553 | + | 595 | + |
| 610D2 | + | 646 | + |
| 659D2 | + | 677R | + |
| 688 | + | 713D2 | + |
| 719D1 | + | 725D1 | + |
| 743D1 | + | 758 | + |
| 765 | + | 775 | + |
| 803 | + | 820D2 | + |
| 824D2 | + | 826 | + |
| 843 | + | 867D2 | + |
| 885 | + | 890 | + |
| 900 | + | 901 | + |
| 903 | + | 914 | + |
| 916 | + | 927 | + |
| 928 | + | 935 | + |
| 946D2 | + | 953 | + |
| 955D1 | + | 955D2 | + |
| 958 | + | 959 | + |
| 960D1 | + | 960D2 | + |
| 989D1 | + | 1042 | + |

TABLE 2-continued

"Activity" represents activity in HBV assembly assay
('+' indicates >50% activity at 10 μM)

| Compound | Activity | Compound | Activity |
|---|---|---|---|
| 1057 | + | 1087 | + |
| 1094S | + | 1099 | + |
| 1106 | + | 1113 | + |
| 1114 | + | 1116 | + |
| 1129 | + | 1130 | + |
| 1134CT2 | + | 1135D1 | + |
| 1149 | + | 1153 | + |
| 1157 | + | 1161 | + |
| 1189 | + | 1283 | + |
| 1338 | + | 1339 | + |
| 1345 | + | 1374CT1 | + |
| 1374CT2 | + | 1378CT2 | + |
| 1379 | + | 1380 | + |
| 1404 | + | 1410 | + |
| 1413 | + | 1420 | + |

Example

Dot-Blot Assay

Selected compounds, which were shown to be active in the HBV assembly assay, were tested for their activity and toxicity in cellular assay. In the first anti-viral assay, the ability of compounds to inhibit HBV replication in an HBV-producing hepatoma cell line using the dot-blot method was evaluated.

Confluent monolayers of HepG2-2.2.15 cells were incubated with complete medium containing various concentrations of a test compound. Three days later, the culture medium was replaced with fresh medium containing the appropriately diluted test compound. Six days following the initial administration of the test compound, the cell culture supernatant was collected, and cell lysis was performed. The samples were applied onto Nylos membranes and DNA was immobilized to the membrane by UV cross-linking. After pre-hybridization, the HBV probe was added and the hybridization was performed overnight. The membranes were exposed to the Kodak films; antiviral activity was calculated from the reduction in HBV DNA levels ($EC_{50}$). The $EC_{50}$ for antiviral activity was calculated from the dose response curves of active compounds. Assay performance over time was monitored by the use of the standard positive control compounds ETV, BAY 41-4109, and HAP-1. Results are illustrated in Table 3.

Cytotoxity ($CC_{50}$) was measured in this same HepG2-2.2.15 cell line using a CellTiter Blue-based cytotoxicity assay employed as recommended by manufacturer (Promega). All compounds in Table 3 demonstrated low toxicity at 5 μM.

TABLE 3

"Activity" represents activity in dot-blot-assay
('+' indicates >50% activity at 10 μM)

| Compound | Activity | Compound | Activity |
|---|---|---|---|
| 065 | + | 078 | + |
| 079 | + | 119 | + |
| 121 | + | 126 | + |
| 129 | + | 148 | + |
| 191 | + | 208 | + |
| 242 | + | 258 | + |
| 282 | + | 318 | + |
| 332 | + | 349 | + |
| 366 | + | 407 | + |
| 419 | + | 451 | + |
| 462 | + | 478 | + |
| 501 | + | 541 | + |
| 553 | + | 595 | + |
| 610D2 | + | 646 | + |
| 659D2 | + | 677R | + |
| 688 | + | 713D2 | + |
| 719D1 | + | 725D1 | + |
| 743D1 | + | 758 | + |
| 765 | + | 775 | + |
| 803 | + | 820D2 | + |
| 826 | + | 843 | + |
| 867D2 | + | 885 | + |
| 890 | + | 900 | + |
| 901 | + | 903 | + |
| 914 | + | 916 | + |
| 927 | + | 928 | + |
| 935 | + | 946D2 | + |
| 953 | + | 955D1 | + |
| 955D2 | + | 958 | + |
| 959 | + | 960D1 | + |
| 960D2 | + | 989D1 | + |
| 1042 | + | 1057 | + |
| 1087 | + | 1094S | + |
| 1099 | + | 1106 | + |
| 1113 | + | 1114 | + |
| 1116 | + | 1129 | + |
| 1130 | + | 1134CT2 | + |
| 1135D1 | + | 1149 | + |
| 1153 | + | 1157 | + |
| 1161 | + | 1189 | + |
| 1283 | + | 1338 | + |
| 1339 | + | 1345 | + |
| 1374CT1 | + | 1374CT2 | + |
| 1378CT2 | + | 1379 | + |
| 1380 | + | 1404 | + |
| 1410 | + | 1413 | + |
| 1420 | + | 824D2 | + |

Example

Prevention of HBV Pre-Genomic RNA (pgRNA) Incorporation

The compounds of the invention were assessed for their ability to suppress both extracellular and intracellular HBV DNA production in two different cell culture models of HBV replication. A particle-gel assay that allows quantitation of intracellular viral capsids, as well as encapsidated pre-genomic RNA and DNA, was performed. The assay relied on agarose gel separation of viral capsid from free capsid/core subunits and viral pg-RNA and DNA.

This assay revealed that the compounds of the invention prevent packaging of pre-genomic RNA into the viral capsid without significant effect on intracellular core particle levels. This effect is consistent with the biochemical activity of the compounds of the invention, which act as allosteric effectors that misdirect in vitro assembly leading to formation of aberrant, non-functional particles. The potent antiviral effect is due to that pg-RNA encapsidation is required for viral DNA synthesis.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and

The invention claimed is:
1. A compound of Formula IVc:

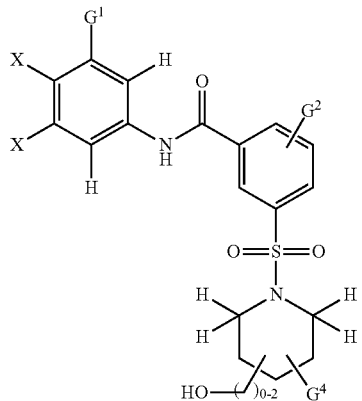
(IVc)

or a pharmaceutically acceptable salt thereof;
wherein X is halo;
$G^1$ is halo;
$G^2$ is $C_1$-$C_4$ alkyl, or halo; and
$G^4$ is H, halo, $C_1$-$C_4$ alkyl, or OH.

2. A pharmaceutical composition comprising a compound according to claim 1, or a salt, solvate or N-oxide-thereof and at least one pharmaceutically acceptable carrier.

3. The compound of claim 1, wherein the compound of Formula IVc is:

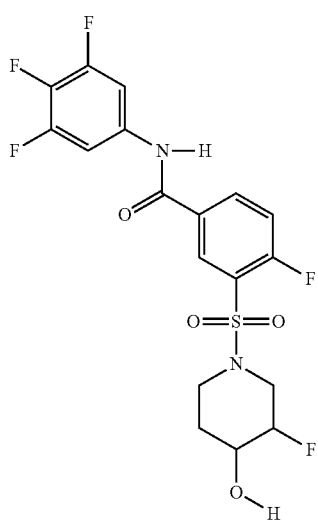

or a pharmaceutically acceptable salt thereof.

4. The compound of claim 1, wherein the compound of Formula IVc is:

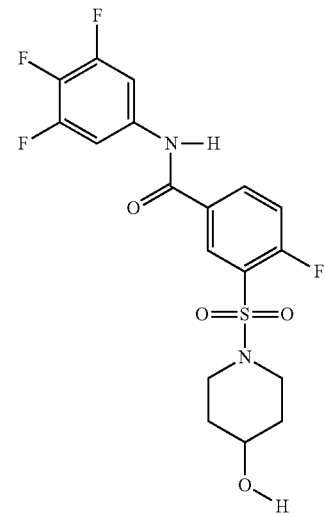 [SMILES: O=C(Nc1cc(F)c(F)c(F)c1)c1ccc(F)c(S(=O)(=O)N2CCC(O)CC2)c1]

or a pharmaceutically acceptable salt thereof.

5. The compound of claim 1, wherein the compound of Formula IVc is:

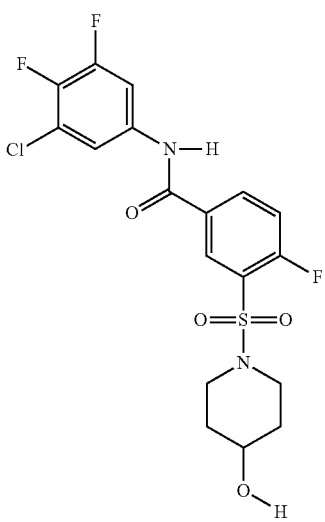 [SMILES: O=C(Nc1cc(F)c(F)c(Cl)c1)c1ccc(F)c(S(=O)(=O)N2CCC(O)CC2)c1]

or a pharmaceutically acceptable salt thereof.

6. The compound of claim 1, wherein the compound of Formula IVc is:

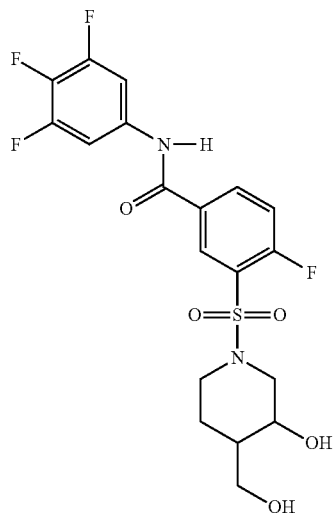 [SMILES: O=C(Nc1cc(F)c(F)c(F)c1)c1ccc(F)c(S(=O)(=O)N2CCC(CO)C(O)C2)c1]

or a pharmaceutically acceptable salt thereof.

7. The compound of claim 1, wherein the compound of Formula IVc is:

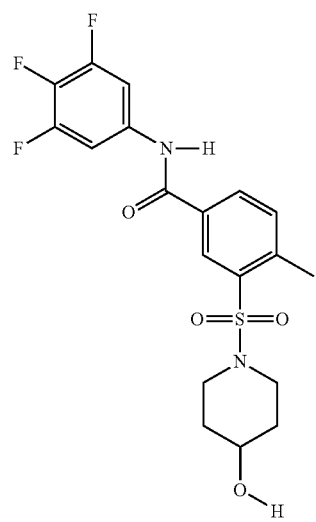 [SMILES: Cc1ccc(C(=O)Nc2cc(F)c(F)c(F)c2)cc1S(=O)(=O)N1CCC(O)CC1]

or a pharmaceutically acceptable salt thereof.

8. The compound of claim 1, wherein the compound of Formula IVc is:

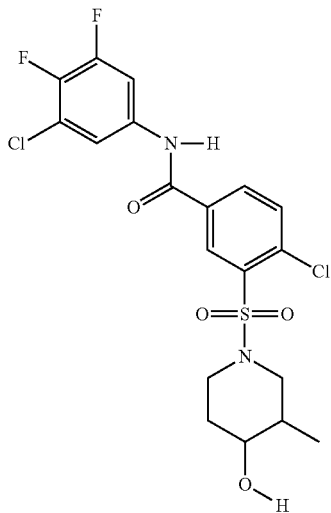 [SMILES: CC1CN(S(=O)(=O)c2cc(C(=O)Nc3cc(F)c(F)c(Cl)c3)ccc2Cl)CCC1O]

or a pharmaceutically acceptable salt thereof.

9. The compound of claim 1, wherein the compound of Formula IVc is:

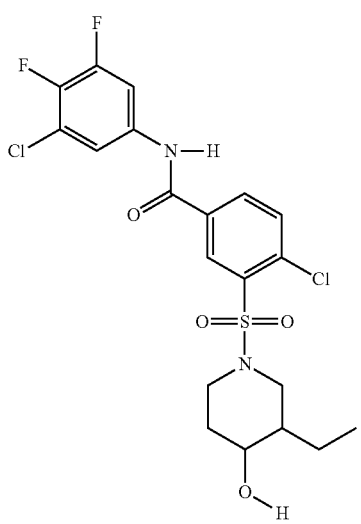 [SMILES: CCC1CN(S(=O)(=O)c2cc(C(=O)Nc3cc(F)c(F)c(Cl)c3)ccc2Cl)CCC1O]

or a pharmaceutically acceptable salt thereof.

10. The compound of claim 1, wherein the compound of Formula IVc is:

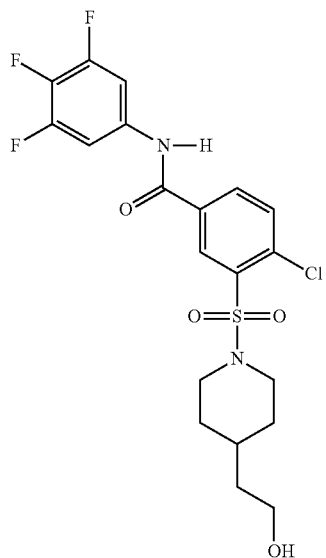 [SMILES: O=C(Nc1cc(F)c(F)c(F)c1)c1ccc(Cl)c(S(=O)(=O)N2CCC(CCO)CC2)c1]

or a pharmaceutically acceptable salt thereof.

11. The compound of claim 1, wherein the compound of Formula IVc is:

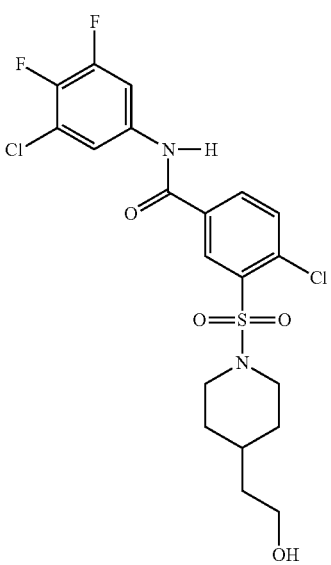 [SMILES: O=C(Nc1cc(F)c(F)c(Cl)c1)c1ccc(Cl)c(S(=O)(=O)N2CCC(CCO)CC2)c1]

or a pharmaceutically acceptable salt thereof.

12. The compound of claim 1, wherein the compound of Formula IVc is:

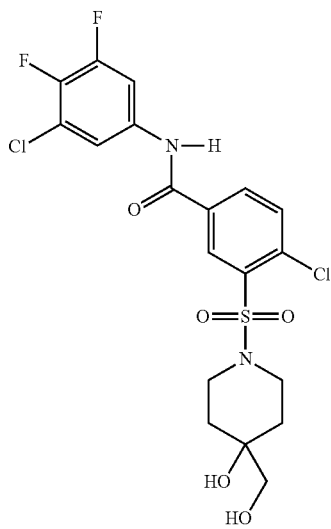 [SMILES: O=C(Nc1cc(F)c(F)c(Cl)c1)c1ccc(Cl)c(S(=O)(=O)N2CCC(O)(CO)CC2)c1]

or a pharmaceutically acceptable salt thereof.

13. The compound of claim 1, wherein the compound of Formula IVc is:

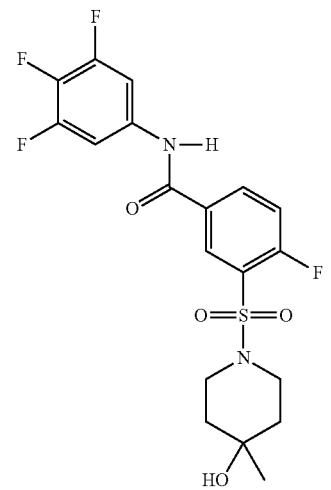 [SMILES: CC1(O)CCN(S(=O)(=O)c2cc(C(=O)Nc3cc(F)c(F)c(F)c3)ccc2F)CC1]

or a pharmaceutically acceptable salt thereof.

14. The compound of claim 1, wherein the compound of Formula IVc is:

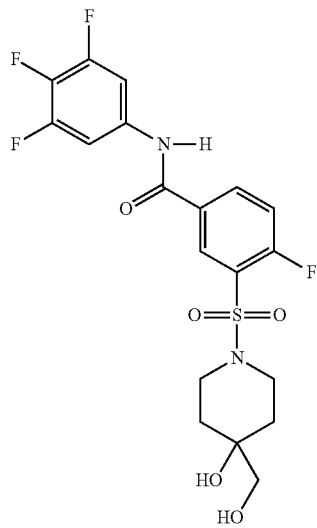 [SMILES: O=C(Nc1cc(F)c(F)c(F)c1)c1ccc(F)c(S(=O)(=O)N2CCC(O)(CO)CC2)c1]

or a pharmaceutically acceptable salt thereof.

15. The compound of claim 1, wherein the compound of Formula IVc is:

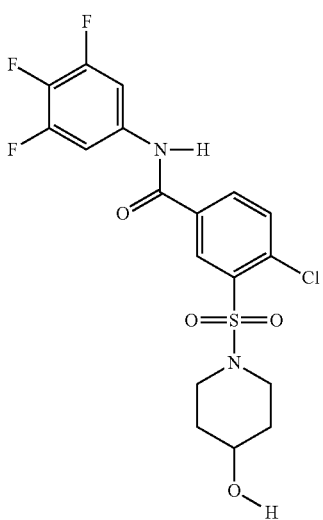 [SMILES: O=C(Nc1cc(F)c(F)c(F)c1)c1ccc(Cl)c(S(=O)(=O)N2CCC(O)CC2)c1]

or a pharmaceutically acceptable salt thereof.

16. The compound of claim 1, wherein the compound of Formula IVc is:

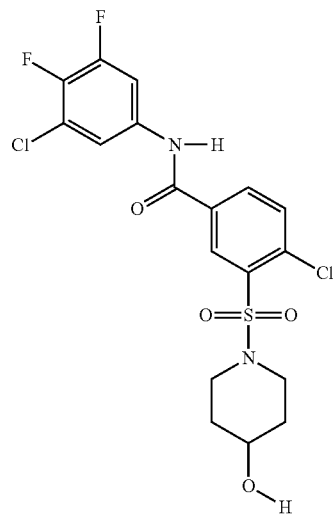 [SMILES: O=C(Nc1cc(F)c(F)c(Cl)c1)c1ccc(Cl)c(S(=O)(=O)N2CCC(O)CC2)c1]

or a pharmaceutically acceptable salt thereof.

17. The compound of claim 1, wherein the compound of Formula IVc is:

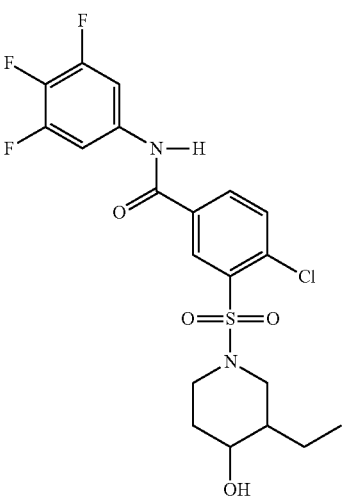 [SMILES: CCC1CN(S(=O)(=O)c2cc(C(=O)Nc3cc(F)c(F)c(F)c3)ccc2Cl)CCC1O]

or a pharmaceutically acceptable salt thereof.

18. The compound of claim 1, wherein the compound of Formula IVc is:

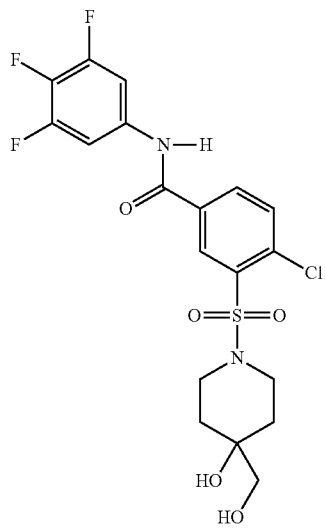 [SMILES: O=C(Nc1cc(F)c(F)c(F)c1)c1ccc(Cl)c(S(=O)(=O)N2CCC(O)(CO)CC2)c1]

or a pharmaceutically acceptable salt thereof.

19. The compound of claim 1, wherein the compound of Formula IVc is:

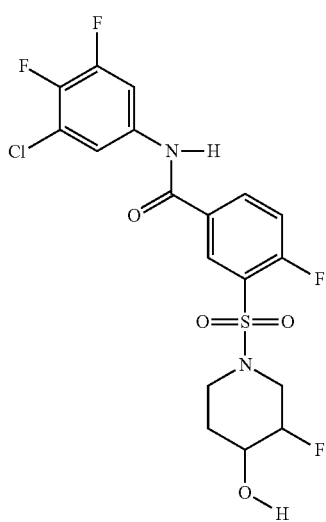

or a pharmaceutically acceptable salt thereof.

20. The compound of claim 1, wherein the compound of Formula IVc is:

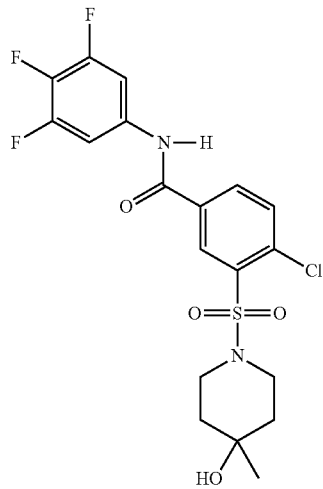 [SMILES: CC1(O)CCN(S(=O)(=O)c2cc(C(=O)Nc3cc(F)c(F)c(F)c3)ccc2Cl)CC1]

or a pharmaceutically acceptable salt thereof.

21. The compound of claim 1, wherein the compound of Formula IVc is:

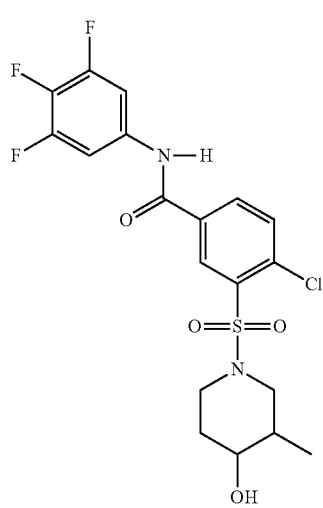 [SMILES: CC1CN(S(=O)(=O)c2cc(C(=O)Nc3cc(F)c(F)c(F)c3)ccc2Cl)CCC1O]

or a pharmaceutically acceptable salt thereof.

22. The compound of claim 1, wherein the compound of Formula IVc is:
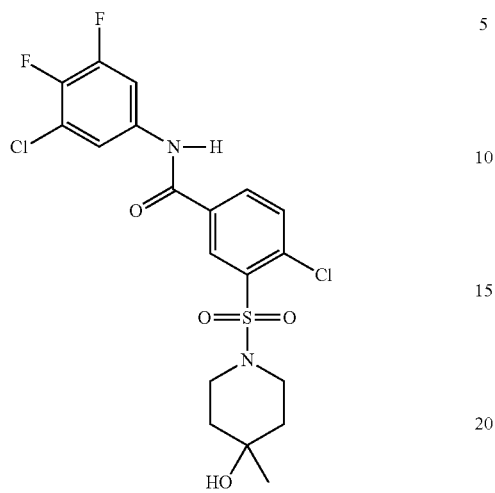
or a pharmaceutically acceptable salt thereof.
* * * * *